US012612416B2

(12) United States Patent
Mccartney et al.

(10) Patent No.: US 12,612,416 B2
(45) Date of Patent: Apr. 28, 2026

(54) MODULATORS OF CYSTIC FIBROSIS TRANSMEMBRANE CONDUCTANCE REGULATOR

(71) Applicant: VERTEX PHARMACEUTICALS INCORPORATED, Boston, MA (US)

(72) Inventors: Jason Mccartney, Cardiff by the Sea, CA (US); Alexander Russell Abela, Escondido, CA (US); Sunny Abraham, San Diego, CA (US); Corey Don Anderson, Brighton, MA (US); Vijayalaksmi Arumugam, San Marcos, CA (US); Jaclyn Chau, San Diego, CA (US); Jeremy Clemens, San Diego, CA (US); Thomas Cleveland, San Marcos, CA (US); Timothy A. Dwight, Quincy, MA (US); Bryan A. Frieman, La Jolla, CA (US); Peter Grootenhuis, Del Mar, CA (US); Sara Sabina Hadida Ruah, La Jolla, CA (US); Yoshihiro Ishihara, San Diego, CA (US); Paul Krenitsky, San Francisco, CA (US); Mark Thomas Miller, Rancho Santa Fe, CA (US); Fabrice Pierre, La Jolla, CA (US); Alina Silina, Needham, MA (US); Jinglan Zhou, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 433 days.

(21) Appl. No.: 18/248,065

(22) PCT Filed: Oct. 6, 2021

(86) PCT No.: PCT/US2021/053853
§ 371 (c)(1),
(2) Date: Apr. 6, 2023

(87) PCT Pub. No.: WO2022/076618
PCT Pub. Date: Apr. 14, 2022

(65) Prior Publication Data

US 2023/0365587 A1 Nov. 16, 2023

Related U.S. Application Data

(60) Provisional application No. 63/088,636, filed on Oct. 7, 2020.

(51) Int. Cl.

| | |
|---|---|
| ***C07D 513/04*** | (2006.01) |
| ***C07D 515/04*** | (2006.01) |
| ***C07D 515/18*** | (2006.01) |

(52) U.S. Cl.
CPC ......... *C07D 513/04* (2013.01); *C07D 515/04* (2013.01); *C07D 515/18* (2013.01)

(58) Field of Classification Search
CPC ... C07D 513/04; C07D 515/04; C07D 515/18
See application file for complete search history.

(56) References Cited

U.S. PATENT DOCUMENTS

| | | | |
|---|---|---|---|
| 7,332,612 | B2 | 2/2008 | Dolitzky et al. |
| 8,586,615 | B2 | 11/2013 | Hadida-Ruah et al. |
| 8,865,902 | B2 | 10/2014 | Morgan |
| 8,883,206 | B2 | 11/2014 | Dokou et al. |
| 9,181,192 | B2 | 11/2015 | Morgan |
| 9,512,079 | B2 | 12/2016 | Morgan |
| 9,663,508 | B2 | 5/2017 | Bregman et al. |

(Continued)

FOREIGN PATENT DOCUMENTS

| | | | |
|---|---|---|---|
| CL | 2019002734 | A1 | 1/2020 |
| CL | 2020000856 | A1 | 8/2020 |

(Continued)

OTHER PUBLICATIONS

"Symdeko in Cystic Fibrosis Patients", ClinicalTrials.gov, Apr. 23, 2018 (Apr. 23, 2018), XP055661778, Retrieved from the Internet: URL:https://clinicaltrials.gov/ct2/show/record/NCT03506061 [retrieved on Jan. 24, 2020].

Bastin, Richard J., et al., "Salt selection and optimization procedures for pharmaceutical new chemical entities," Org. Pro. Res. Dev. 2000, 4(5), 427-435.

Borhade, Sanjay R., et al., "Synthesis of Novel Aryl and Heteroaryl Acyl Sulfonimidamides via Pd-Catalyzed Carbonylation Using a Nongaseous Precursor," Organic Letters, 2013, vol. 15, No. 5, pp. 1056-1059, received Jan. 8, 2013, XP055374206A, © 2013 American Chemical Society, ISSN: 1523-7060, DOI:10.1021/0 4/00049m, published on web Feb. 13, 2013.

Cherepakha, Artem Yu., et al. (2018), "Hetaryl Bromides Bearing the SO2F Group—Versatile Substrates for Palladium-Catalyzed C—C Coupling Reactions," Eur J Org Chem, 47: 6682-6692.

(Continued)

*Primary Examiner* — Daniel R Carcanague

(74) *Attorney, Agent, or Firm* — Finnegan, Henderson, Farabow, Garrett & Dunner, LLP

(57) ABSTRACT

This disclosure provides modulators of Cystic Fibrosis Transmembrane Conductance Regulator (CFTR) having the core structure: pharmaceutical compositions containing at least one such modulator, methods of treatment of cystic fibrosis using such modulators and pharmaceutical compositions, combination therapies, and processes and intermediates for making such modulators.

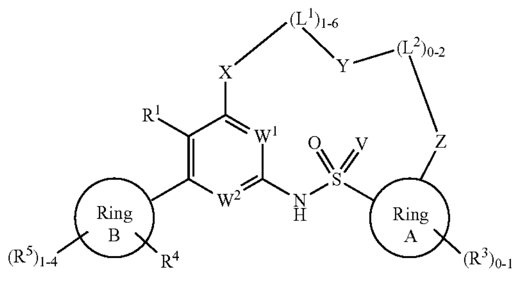

23 Claims, No Drawings

(56) References Cited

U.S. PATENT DOCUMENTS

| | | | |
|---|---|---|---|
| 9,782,408 | B2 | 10/2017 | Miller et al. |
| 9,981,910 | B2 | 5/2018 | Altenbach et al. |
| 10,047,053 | B2 | 8/2018 | Morgan |
| 10,118,916 | B2 | 11/2018 | Altenbach et al. |
| 10,131,670 | B2 | 11/2018 | Strohbach et al. |
| 10,138,227 | B2 | 11/2018 | Altenbach et al. |
| 10,208,053 | B2 | 2/2019 | Strohbach et al. |
| 10,258,624 | B2 | 4/2019 | Miller et al. |
| 10,479,766 | B2 | 11/2019 | Morgan |
| 10,570,115 | B2 | 2/2020 | Alcacio et al. |
| 10,654,829 | B2 | 5/2020 | Dhamankar et al. |
| 10,675,277 | B2 | 6/2020 | Kárpáti et al. |
| 10,738,030 | B2 | 8/2020 | Bear et al. |
| 10,758,534 | B2 | 9/2020 | Miller et al. |
| 10,759,721 | B2 | 9/2020 | Morgan et al. |
| 10,793,547 | B2 | 10/2020 | Abela et al. |
| 10,894,773 | B2 | 1/2021 | Morgan |
| 11,066,417 | B2 | 7/2021 | Clemens et al. |
| 11,179,367 | B2 | 11/2021 | Chu et al. |
| 11,584,761 | B2 | 2/2023 | Angell et al. |
| 11,591,350 | B2 | 2/2023 | Anderson et al. |
| 11,708,331 | B2 | 7/2023 | Lemercier Lewandowski et al. |
| 11,866,450 | B2 * | 1/2024 | Clemens .............. C07D 515/22 |
| 11,873,300 | B2 * | 1/2024 | Shi ...................... C07D 471/08 |
| 12,186,306 | B2 | 1/2025 | Borek et al. |
| 12,319,693 | B2 * | 6/2025 | Shi ...................... C07D 513/22 |
| 2013/0317000 | A1 | 11/2013 | Chowdhury et al. |
| 2013/0317001 | A1 | 11/2013 | Andrez et al. |
| 2018/0099932 | A1 | 4/2018 | Altenbach et al. |
| 2018/0125838 | A1 | 5/2018 | Uttamsingh |
| 2018/0141954 | A1 | 5/2018 | Strohbach et al. |
| 2018/0170938 | A1 | 6/2018 | Strohbach et al. |
| 2018/0244611 | A1 | 8/2018 | Altenbach et al. |
| 2018/0244640 | A1 | 8/2018 | Altenbach et al. |
| 2019/0077784 | A1 | 3/2019 | Altenbach et al. |
| 2019/0153000 | A1 | 5/2019 | Munoz et al. |
| 2022/0041621 | A1 | 2/2022 | Clemens et al. |
| 2022/0047564 | A1 | 2/2022 | Altshuler et al. |
| 2022/0106331 | A1 | 4/2022 | Clemens et al. |
| 2022/0127247 | A1 | 4/2022 | Azimioara et al. |
| 2022/0184049 | A1 | 6/2022 | Borek et al. |
| 2022/0313698 | A1 | 10/2022 | Abela et al. |
| 2022/0372047 | A1 | 11/2022 | Abela et al. |
| 2023/0374038 | A1 * | 11/2023 | Mccartney ........... C07D 515/08 |
| 2023/0382924 | A1 * | 11/2023 | Mccartney ........... C07D 515/04 |
| 2023/0382925 | A1 * | 11/2023 | Mccartney .............. A61P 43/00 |
| 2024/0018161 | A1 * | 1/2024 | Mccartney ........... C07D 515/04 |
| 2024/0150377 | A1 * | 5/2024 | Mccartney .............. A61P 11/00 |
| 2024/0368189 | A1 * | 11/2024 | Clemens ................ A61K 31/47 |
| 2025/0221971 | A1 | 7/2025 | Borek et al. |

FOREIGN PATENT DOCUMENTS

| | | | |
|---|---|---|---|
| CL | 202301016 | | 6/2023 |
| CN | 103833630 | | 6/2014 |
| CO | 12038470 | | 3/2012 |
| EP | 3424534 | B1 | 5/2018 |
| JP | 2014-526500 | A | 10/2014 |
| NC | 2018/0000413 | | 1/2018 |
| NC | 2018/0012171 | | 11/2018 |
| TW | I410423 | B | 10/2013 |
| TW | 201811766 | A | 1/2018 |
| WO | WO 2005/049018 | A1 | 6/2005 |
| WO | WO 2005/075435 | A1 | 8/2005 |
| WO | WO 2006/002421 | A2 | 1/2006 |
| WO | WO 2007/021982 | A2 | 2/2007 |
| WO | WO 2007/053641 | A2 | 5/2007 |
| WO | WO 2007/075946 | A1 | 7/2007 |
| WO | WO 2007/079139 | A2 | 7/2007 |
| WO | WO 2007/087066 | A2 | 8/2007 |
| WO | WO 2007/117715 | A2 | 10/2007 |
| WO | WO 2007/134279 | A2 | 11/2007 |
| WO | WO 2008/127399 | A2 | 10/2008 |
| WO | WO 2009/006315 | A1 | 1/2009 |
| WO | WO 2009/038683 | A2 | 3/2009 |
| WO | WO 2009/073757 | A1 | 6/2009 |
| WO | WO 2009/076142 | A2 | 6/2009 |
| WO | WO 2009/108657 | A2 | 9/2009 |
| WO | WO 2010/019239 | A2 | 2/2010 |
| WO | WO 2010/048526 | A2 | 4/2010 |
| WO | WO 2010/053471 | A1 | 5/2010 |
| WO | WO 2010/054138 | A2 | 5/2010 |
| WO | WO 2010/108162 | A1 | 9/2010 |
| WO | WO 2011/019413 | A1 | 2/2011 |
| WO | WO 2011/029059 | A1 | 3/2011 |
| WO | WO 2011/072241 | A1 | 6/2011 |
| WO | WO 2011/116397 | A1 | 9/2011 |
| WO | WO 2011/119984 | A1 | 9/2011 |
| WO | WO 2011/127241 | A2 | 10/2011 |
| WO | WO 2011/127290 | A2 | 10/2011 |
| WO | WO 2011/133751 | A2 | 10/2011 |
| WO | WO 2011/133951 | A1 | 10/2011 |
| WO | WO 2012/027247 | A2 | 3/2012 |
| WO | WO 2012/027731 | A2 | 3/2012 |
| WO | WO 2012/170061 | A1 | 12/2012 |
| WO | WO 2013/038386 | A1 | 3/2013 |
| WO | WO 2013/070961 | A1 | 5/2013 |
| WO | WO 2013/112804 | A1 | 8/2013 |
| WO | WO 2013/130669 | A1 | 9/2013 |
| WO | WO 2013/158121 | A1 | 10/2013 |
| WO | WO 2013/185112 | A1 | 12/2013 |
| WO | WO 2014/014841 | A1 | 1/2014 |
| WO | WO 2014/071122 | A1 | 5/2014 |
| WO | WO 2014/078842 | A1 | 5/2014 |
| WO | WO 2015/073231 | A1 | 7/2015 |
| WO | WO 2015/160787 | A1 | 10/2015 |
| WO | WO 2016/057572 | A1 | 4/2016 |
| WO | WO 2016/057730 | A1 | 4/2016 |
| WO | WO 2016/081556 | A1 | 5/2016 |
| WO | WO 2016/160945 | A1 | 10/2016 |
| WO | WO 2017/009804 | A1 | 1/2017 |
| WO | WO 2017/053455 | A1 | 3/2017 |
| WO | WO 2017/053711 | A2 | 3/2017 |
| WO | WO 2017/172802 | A1 | 10/2017 |
| WO | WO 2017/173274 | A1 | 10/2017 |
| WO | WO 2017/177124 | A1 | 10/2017 |
| WO | WO 2017/187321 | A1 | 11/2017 |
| WO | WO 2017/208115 | A1 | 12/2017 |
| WO | WO 2017/223188 | A1 | 12/2017 |
| WO | WO 2018/064632 | A1 | 4/2018 |
| WO | WO 2018/080591 | A1 | 5/2018 |
| WO | WO 2018/081377 | A1 | 5/2018 |
| WO | WO 2018/081378 | A1 | 5/2018 |
| WO | WO 2018/081381 | A1 | 5/2018 |
| WO | WO 2018/107100 | A1 | 6/2018 |
| WO | WO 2018/116185 | A1 | 6/2018 |
| WO | WO 2018/127130 | A1 | 7/2018 |
| WO | WO 2018/183367 | A1 | 10/2018 |
| WO | WO 2018/183964 | A1 | 10/2018 |
| WO | WO 2018/201126 | A1 | 11/2018 |
| WO | WO 2018/227049 | A1 | 12/2018 |
| WO | WO 2019/010092 | A1 | 1/2019 |
| WO | WO 2019/014352 | A1 | 1/2019 |
| WO | WO 2019/018353 | A1 | 1/2019 |
| WO | WO 2019/018395 | A1 | 1/2019 |
| WO | WO 2019/028228 | A1 | 2/2019 |
| WO | WO 2019/071078 | A1 | 4/2019 |
| WO | WO 2019/079760 | A1 | 4/2019 |
| WO | WO 2019/109021 | A1 | 6/2019 |
| WO | WO 2019/113089 | A1 | 6/2019 |
| WO | WO 2019/113476 | A2 | 6/2019 |
| WO | WO 2019/152940 | A1 | 8/2019 |
| WO | WO 2019/161078 | A1 | 8/2019 |
| WO | WO 2019/191620 | A1 | 10/2019 |
| WO | WO 2019/195739 | A1 | 10/2019 |
| WO | WO 2019/200246 | A1 | 10/2019 |
| WO | WO 2020/102346 | A1 | 5/2020 |
| WO | WO 2020/128925 | A1 | 6/2020 |
| WO | WO 2020/206080 | A1 | 10/2020 |
| WO | WO 2020/214921 | A1 | 10/2020 |
| WO | WO 2020/242935 | A1 | 12/2020 |
| WO | WO 2021/030552 | A1 | 2/2021 |
| WO | WO 2021/030554 | A1 | 2/2021 |
| WO | WO 2021/030555 | A1 | 2/2021 |

(56) References Cited

FOREIGN PATENT DOCUMENTS

| | | | |
|---|---|---|---|
| WO | WO 2021/030556 | A1 | 2/2021 |
| WO | WO 2021/097054 | A1 | 5/2021 |
| WO | WO 2022/032068 | A1 | 2/2022 |
| WO | WO 2022/036060 | A1 | 2/2022 |
| WO | WO 2022/076620 | A1 | 4/2022 |
| WO | WO 2022/076621 | A1 | 4/2022 |
| WO | WO 2022/076622 | A2 | 4/2022 |
| WO | WO 2022/076624 | A1 | 4/2022 |
| WO | WO 2022/076625 | A1 | 4/2022 |
| WO | WO 2022/076626 | A1 | 4/2022 |
| WO | WO 2022/125826 | A1 | 6/2022 |

OTHER PUBLICATIONS

Clinical Trials Us: "A Phase 2 Study to Evaluate Efficacy and Safety of VX-561 in Subjects Aged 18 Years and Older With Cystic Fibrosis," ClinicalTrials.gov, Apr. 11, 2019 (Apr. 11, 2019), XP055903562, Retrieved from the Internet: URL:https://clinicaltrials.gov/ct2/show/NCT03911713 [retrieved on Mar. 21, 2022].

Clinical Trials Us: "A Study to Evaluate the Safety and Efficacy of VX-121 Combination Therapy in Subjects with Cystic Fibrosis," ClinicalTrials.gov, Apr. 30, 2019 (Apr. 30, 2019), XP55903330, Retrieved from the Internet: URL:https://clinicaltrials.gov/ct2/show/NCT03912233 [retrieved on Mar. 21, 2022].

Donaldson, S.H. et al. (2017) "Tezacaftor/Ivacaftor in Subjects with Cystic Fibrosis and F508del/F508del-CFTR or F508del/G551D-CFTR", *Am. J. Respir. Crit. Care Med.*, 197(2): 214-224.

Eu Clinical Trials Register: "A phase 1/2 study of VX-121 in healthy subjects and in subjects with cystic fibrosis", May 3, 2019 (May 3, 2019). XP055903414, Retrieved from the Internet: URL:https://www.clinicaltrialsregister.eu/ctr-search/trial/2018-000126-55/NL [retrieved on Mar. 21, 2022].

International Patent Application No. PCT/US2021/053853: International Search Report and Written Opinion, mailed Dec. 21, 2021 (12 pages).

Newkome, George R., et al. (1979), "Nicotinic Acid Crown Ethers. Synthesis, Reactions, and Complexation of Nicotinonitrile Macrocycles," J Org Chem, 44(15): 2639-2697.

Nishida, Haruyuki, et al. (2017), "Exploration of pyrrole derivatives to find an effective potassium competitive acid blocker with moderately long-lasting suppression of gastric acid secretion," Bioorg Med Chem, 25(13): 3447-3460.

Notice of Allowance and Fee(s) Due for U.S. Appl. No. 16/992,441, mailed Aug. 25, 2023.

Prashantha, Gunaga, et al. (2017), "Selective IKur Inhibitors for the Potential Treatment of Atrial Fibrillation: Optimization of the Phenyl Quinazoline Series Leading to Clinical Candidate 5 [5-Phenyl-4-(pyridin-2-ylmethylamino)quinazolin-2-yl]pyridine-3-sulfonamide," J Med Chem, 60(9): 3795-3803.

Rewcastle, Gordon W., et al. (1996), "Tyrosine Kinase Inhibitors. 10. Isomeric 4-[(3-Bromophenyl)amino]pyrido[d]-pyrimidines Are Potent ATP Binding Site Inhibitors of the Tyrosine Kinase Function of the Epidermal Growth Factor Receptor," J Med Chem, 39(9): 1823-1835.

U.S. Appl. No. 18/493,667, filed Oct. 24, 2023, by Shi et al.

Davies, J.C. et al. (2018), "VX-659-Tezacaftor-Ivacaftor in Patients with Cystic Fibrosis and One or Two Phe508del Alleles," The New England Journal of Medicine, 379, 17, 1599-1611.

Harbeson, Scott L., et al. "Altering Metabolic Profiles of Drugs by Precision Deuteration 2: Discovery of a Deuterated Analog of Ivacaftor with Differentiated Pharmacokinetics for Clinical Development." The Journal of Pharmacology and Experimental Therapeutics, 2017, 362, 2, 359-367.

Hoppe, Jordana, et al. Vanzacaftor-tezacaftor-deutivacaftor for children aged 6-11 years with cystic fibrosis (Ridgeline Trial VX21-121-105): an analysis from a sing-arm, phase 3 trial. www.thelancet.com/respiratory, vol. Mar. 13, 2025 (12 pages).

International Patent Application No. PCT US2025 014303: International Search Report and Written Opinion, mailed May 22, 2025 (14 pages).

International Patent Application No. PCT/US2025/014740: International Search Report and Written Opinion, mailed Jun. 2, 2025 (15 pages).

Keating, D. et al., "VX-445-Tezacaftor-Ivacaftor in Patients with Cystic Fibrosis and One or Two Phe508del Alleles," The New England Journal of Medicine, 2018, 379, 17, pp. 1612-1620.

Matsuoka, Masakuni, Base & Application of Polymorphic Crystals, popular edition, 1st printing, CMC Publishing Co.,Ltd., Oct. 22, 2010, pp. 105-117, pp. 181-191.

Morissette et al., "High-throughput crystallization: polymorphs, salts, co-crystals and solvates of pharmaceutical solids," Advanced Drug Delivery Reviews, 2004, 56, 275-300.

Taylor-Cousar, Jennifer L. Taylor-Cousar, et al. "Tezacaftor-Ivacaftor in Patients with Cystic Fibrosis Homozygous for Phe508del". The New England Journal of Medicine, 2017, 377, 21, pp. 2013-2023.

Uluer, Ahmet, et al., Safety and efficacy of vanzacaftor-tezacaftor-deutivacaftor in adults with cystic fibrosis: randomised, double-blind, controlled, phase 2 trials, www.thelancet.com/respiratory vol. Jun. 11, 2023 (13 pages).

2021 Vertex to Intitate Phase 3 Development Program for New Once-Daily Triple Combination Regimen in People with Cystic Fibrosis (4 pages).

2024 Vertex Announces Positive Results for Pivotal Trials of Vanzacaftor, Tezacaftor, Deutivacaftor, Next-in-Class Triple Combination Treatment for Cystic Fibrosis (7 pages).

Wang, Xueqing, et al. "Discovery of 4-[(2R,4R)-4-({1-(2,2-Difluoro-1,3-benzodioxol-5-yl)cyclopropyl}carbonyl)amino]-7-(difluoromethoxy)-3,4-dihydro-2H-chromen-2-yl)benzoic Acid (ABBV/GLPG-2222), a Potent Cystic Fibrosis Transmembrane Conductance Regulator (CFTR) Corrector for the Treatment of Cystic Fibrosis." Journal of Medicinal Chemistry, 2018, 61, 1436-1449.

* cited by examiner

MODULATORS OF CYSTIC FIBROSIS TRANSMEMBRANE CONDUCTANCE REGULATOR

This application claims the benefit of priority of U.S. Provisional Application No. 63/088,636, filed Oct. 7, 2020, the contents of which are incorporated by reference herein in their entirety.

The disclosure relates to modulators of Cystic Fibrosis Transmembrane Conductance Regulator (CFTR), pharmaceutical compositions containing the modulators, methods of treatment of CFTR mediated diseases, including cystic fibrosis, using such modulators, combination therapies and combination pharmaceutical compositions employing such modulators, and processes and intermediates for making such modulators.

Cystic fibrosis (CF) is a recessive genetic disease that affects approximately 70,000 children and adults worldwide. Despite progress in the treatment of CF, there is no cure.

Patients with CF have mutations in the CFTR endogenously expressed in respiratory epithelia that lead to reduced apical anion secretion causing an imbalance in ion and fluid transport. The resulting decrease in anion transport contributes to increased mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is reduced among females with cystic fibrosis.

Sequence analysis of the CFTR gene has revealed a variety of disease-causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 2000 mutations in the CF gene have been identified; currently, the CFTR2 database contains information on only 432 of these identified mutations, with sufficient evidence to define 352 mutations as disease causing. The most prevalent disease-causing mutation is a deletion of phenylalanine at position 508 of the CFTR amino acid sequence and is commonly referred to as the F508del mutation. This mutation occurs in many of the cases of cystic fibrosis and is associated with severe disease.

The deletion of residue 508 in CFTR prevents the nascent protein from folding correctly. This results in the inability of the mutant protein to exit the endoplasmic reticulum (ER) and traffic to the plasma membrane. As a result, the number of CFTR channels for anion transport present in the membrane is far less than observed in cells expressing wild-type CFTR, i.e., CFTR having no mutations. In addition to impaired trafficking, the mutation results in defective channel gating. Together, the reduced number of channels in the membrane and the defective gating lead to reduced anion and fluid transport across epithelia. (Quinton, P. M. (1990), FASEB J. 4: 2709-2727). The channels that are defective because of the F508del mutation are still functional, albeit less functional than wild-type CFTR channels. (Dalemans et al. (1991), Nature Lond. 354: 526-528; Pasyk and Foskett (1995), J. Cell. Biochem. 270: 12347-50). In addition to F508del, other disease-causing mutations in CFTR that result in defective trafficking, synthesis, and/or channel gating could be up- or down-regulated to alter anion secretion and modify disease progression and/or severity.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC and CFTR present on the apical membrane and the $Na^+$—$K^+$-ATPase pump and $Cl^-$ channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

A number of CFTR modulating compounds have recently been identified. However, compounds that can treat or reduce the severity of cystic fibrosis and other CFTR mediated diseases, and particularly the more severe forms of these diseases, are still needed.

One aspect of the disclosure provides novel compounds, including compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing.

Formula I encompasses compounds falling within the following structure:

(I)

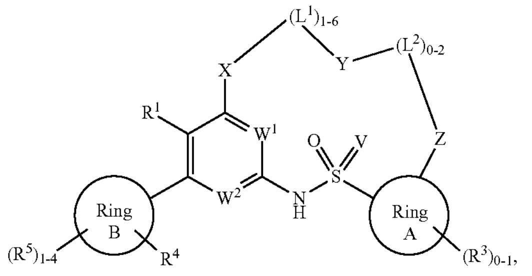

and includes tautomers of those compounds, deuterated derivatives of any of the compounds and tautomers, and pharmaceutically acceptable salts of any of the foregoing, wherein:

Ring A is selected from:

$C_6$-$C_{10}$ aryl, $C_3$-$C_{10}$ cycloalkyl, 3- to 10-membered heterocyclyl, and 5- to 10-membered heteroaryl;

Ring B is selected from:

$C_6$-$C_{10}$ aryl, $C_3$-$C_{10}$ cycloalkyl,
3- to 10-membered heterocyclyl, and
5- to 10-membered heteroaryl;
V is selected from O and NH;
$W^1$ is selected from N and CH;
$W^2$ is selected from N and CH; provided that at least one of $W^1$ and $W^2$ is N;
X is selected from $NR^{XN}$ and $C(R^{XC})_2$;
Y is selected from O, $NR^{YN}$, and $C(R^{YC})_2$;
Z is selected from O, $NR^{ZN}$, and $C(R^{ZC})_2$, provided that when $L^2$ is absent, either Y is $C(R^{YC})_2$ or Z is $C(R^{ZC})_2$.
each $L^1$ is independently selected from $C(R^{L1})_2$ and

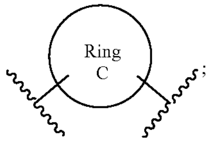

;

each $L^2$ is independently selected from $C(R^{L2})_2$;
Ring C is selected from $C_6$-$C_{10}$ aryl optionally substituted with 1-3 groups independently selected from:
halogen,
$C_1$-$C_6$ alkyl, and
$N(R^N)_2$;
$R^1$ is selected from:
hydrogen,
halogen,
cyano,
$C_1$-$C_6$ alkyl optionally substituted with 1-3 groups independently selected from hydroxyl, oxo, and $N(R^N)_2$,
$C_1$-$C_6$ alkoxy,
$C_1$-$C_6$ fluoroalkyl,
$C_6$-$C_{10}$ aryl optionally substituted with 1-3 groups independently selected from $C_1$-$C_6$ alkoxy,
3- to 10-membered heterocyclyl optionally substituted with 1-3 groups independently selected from $R^N$, and
5- to 10-membered heteroaryl optionally substituted with 1-3 groups independently selected from $C_1$-$C_6$ alkyl;
each $R^3$ is independently selected from:
halogen,
$C_1$-$C_6$ alkyl,
$C_1$-$C_6$ alkoxy,
$C_3$-$C_{10}$ cycloalkyl,
$C_6$-$C_{10}$ aryl optionally substituted with 1-3 groups independently selected from $C_1$-$C_6$ alkyl, and
3- to 10-membered heterocyclyl;
$R^4$ is selected from hydrogen and $C_1$-$C_6$ alkyl;
each $R^5$ is independently selected from:
hydrogen,
halogen,
hydroxyl,
$N(R^N)_2$,
—SO-Me,
—CH═$C(R^Lc)_2$, wherein both $R^{LC}$ are taken together to form a $C_3$-$C_{10}$ cycloalkyl,
$C_1$-$C_6$ alkyl optionally substituted with 1-3 groups independently selected from:
hydroxyl,
$C_1$-$C_6$ alkoxy optionally substituted with 1-3 groups independently selected from $C_1$-$C_6$ alkoxy and $C_6$-$C_{10}$ aryl,
$C_3$-$C_{10}$ cycloalkyl,
—$(O)_{0-1}$—($C_6$-$C_{10}$ aryl) optionally substituted with 1-3 groups independently selected from $C_1$-$C_6$ alkyl and $C_1$-$C_6$ alkoxy,
3- to 10-membered heterocyclyl, and
$N(R^N)_2$,
$C_1$-$C_6$ alkoxy optionally substituted with 1-3 groups independently selected from:
halogen,
$C_6$-$C_{10}$ aryl, and
$C_3$-$C_{10}$ cycloalkyl optionally substituted with 1-3 groups independently selected from $C_1$-$C_6$ fluoroalkyl,
$C_1$-$C_6$ fluoroalkyl,
$C_3$-$C_{10}$ cycloalkyl,
$C_6$-$C_{10}$ aryl, and
3- to 10-membered heterocyclyl;
each $R^{XN}$, $R^{YN}$, and $R^{ZN}$ is independently selected from:
hydrogen,
$C_1$-$C_9$ alkyl optionally substituted with 1-3 groups independently selected from:
hydroxyl,
oxo,
cyano,
$C_1$-$C_6$ alkoxy optionally substituted with 1-3 groups independently selected from halogen and $C_1$-$C_6$ alkoxy,
$N(R^N)_2$,
$SO_2Me$,
$C_3$-$C_{10}$ cycloalkyl optionally substituted with 1-3 groups independently selected from:
hydroxyl,
$C_1$-$C_6$ alkyl optionally substituted with 1-3 groups independently selected from hydroxyl, oxo, $C_1$-$C_6$ alkoxy, $C_6$-$C_{10}$ aryl, and $N(R^N)_2$,
$C_1$-$C_6$ fluoroalkyl,
$C_1$-$C_6$ alkoxy, and
COOH,
$N(R^N)_2$,
$C_6$-$C_{10}$ aryl, and
3- to 10-membered heterocyclyl optionally substituted with 1-3 groups independently selected from oxo and $C_1$-$C_6$ alkyl,
$C_6$-$C_{10}$ aryl optionally substituted with 1-3 groups independently selected from:
halogen,
hydroxyl,
cyano,
$SiMe_3$,
$SO_2Me$,
$SF_5$,
$N(R^N)_2$,
$P(O)Me_2$,
—$(O)_{0-1}$—($C_3$-$C_{10}$ cycloalkyl) optionally substituted with 1-3 groups independently selected from $C_1$-$C_6$ fluoroalkyl,
$C_1$-$C_6$ alkyl optionally substituted with 1-3 groups independently selected from hydroxyl, oxo, $C_1$-$C_6$ alkoxy, 5- to 10-membered heteroaryl, $SO_2Me$, and $N(R^N)_2$,
$C_1$-$C_6$ alkoxy optionally substituted with 1-3 groups independently selected from hydroxyl, oxo, $N(R^N)_2$, and $C_6$-$C_{10}$ aryl,
$C_1$-$C_6$ fluoroalkyl,
3- to 10-membered heterocyclyl optionally substituted with 1-3 groups independently selected from $C_1$-$C_6$ alkyl,
—$(O)_{0-1}$—($C_6$-$C_{10}$ aryl), and —$(O)_{0-1}$-(5- to 10-heteroaryl) optionally substituted with hydroxyl, oxo, $N(R^N)_2$, $C_1$-$C_6$ alkyl, $C_1$-$C_6$ alkoxy, $C_1$-$C_6$ fluoroalkyl, and $C_3$-$C_{10}$ cycloalkyl,
3- to 10-membered heterocyclyl optionally substituted with 1-4 groups independently selected from:
hydroxyl,
oxo,
$N(R^N)_2$,
$C_1$-$C_6$ alkyl (optionally substituted with 1-3 groups independently selected from oxo and $C_1$-$C_6$ alkoxy),
$C_1$-$C_6$ alkoxy,
$C_1$-$C_6$ fluoroalkyl,
$C_6$-$C_{10}$ aryl optionally substituted with 1-3 groups independently selected from halogen, and
5- to 10-membered heteroaryl,
5- to 10-membered heteroaryl optionally substituted with 1-3 groups independently selected from:
hydroxyl,
cyano,
oxo,
halogen,
$B(OH)_2$,
$N(R^N)_2$,
$C_1$-$C_6$ alkyl optionally substituted with 1-3 groups independently selected from hydroxyl, oxo, $C_1$-$C_6$ alkoxy (optionally substituted with 1-3-$SiMe_3$), and $N(R^N)_2$,
$C_1$-$C_6$ alkoxy optionally substituted with 1-3 groups independently selected from hydroxyl, oxo, $C_1$-$C_6$ alkoxy, $N(R^N)_2$, and $C_3$-$C_{10}$ cycloalkyl,
$C_1$-$C_6$ fluoroalkyl,
—$(O)_{0-1}$—($C_3$-$C_{10}$ cycloalkyl) optionally substituted with 1-3 groups independently selected from $C_1$-$C_6$ alkyl,
—$(O)_{0-1}$—($C_6$-$C_{10}$ aryl),
—$(O)_{0-1}$-(3- to 10-membered heterocyclyl) optionally substituted with 1-4 groups independently selected from hydroxyl, oxo, halogen, cyano, $N(R^N)_2$, $C_1$-$C_6$ alkyl (optionally substituted with 1-3 groups independently selected from hydroxyl, oxo, $N(R^N)_2$, and $C_1$-$C_6$ alkoxy), $C_1$-$C_6$ alkoxy, $C_1$-$C_6$ fluoroalkyl, 3- to 10-membered heterocyclyl (optionally substituted with 1-3 groups independently selected from $C_1$-$C_6$ fluoroalkyl), and
5- to 10-membered heteroaryl optionally substituted with 1-4 groups independently selected from $C_1$-$C_6$ alkyl and $C_3$-$C_{10}$ cycloalkyl,
$C_1$-$C_6$ fluoroalkyl,
$C_3$-$C_{10}$ cycloalkyl optionally substituted with 1-3 groups independently selected from:
hydroxyl,
oxo,
halogen,
cyano,
$N(R^N)_2$,
$C_1$-$C_6$ alkyl optionally substituted with 1-3 groups independently selected from:
hydroxyl,
oxo,
$N(R^N)_2$,
$C_1$-$C_6$ alkoxy, and
$C_6$-$C_{10}$ aryl,
$C_1$-$C_6$ alkoxy optionally substituted with 1-3 groups independently selected from halogen, oxo, $C_6$-$C_{10}$ aryl, and $N(R^N)_2$,
halogen,
$C_3$-$C_{10}$ cycloalkyl,
3- to 10-member heterocyclyl optionally substituted with 1-3 groups independently selected from $C_1$-$C_6$ alkyl,
5- to 10-membered heteroaryl optionally substituted with 1-3 groups independently selected from:
hydroxyl,
cyano,
oxo,
halogen,
$N(R^N)_2$,
$C_1$-$C_6$ alkyl optionally substituted with 1-3 groups independently selected from hydroxyl, oxo, $C_1$-$C_6$ alkoxy, and $N(R^N)_2$,
$C_1$-$C_6$ alkoxy optionally substituted with 1-3 groups independently selected from hydroxyl, $C_1$-$C_6$ alkoxy, $N(R^N)_2$, and $C_3$-$C_{10}$ cycloalkyl,
$C_1$-$C_6$ fluoroalkyl,
—$(O)_{0-1}$—($C_3$-$C_{10}$ cycloalkyl) optionally substituted with 1-3 groups independently selected from $C_1$-$C_6$ alkyl,
$C_6$-$C_{10}$ aryl, and
3- to 10-membered heterocyclyl optionally substituted with 1-3 groups independently selected from $C_1$-$C_6$ alkyl,
$C_6$-$C_{10}$ aryl,
3- to 10-membered heterocyclyl optionally substituted with 1-3 groups independently selected from:
oxo,
$C_1$-$C_6$ alkyl optionally substituted with 1-3 groups independently selected from:
oxo,
hydroxyl,
$N(R^N)_2$,
$C_1$-$C_6$ alkoxy optionally substituted with 1-3 groups independently selected from halogen and $C_6$-$C_{10}$ aryl, and
—$(O)_{0-1}$—($C_3$-$C_{10}$ cycloalkyl),
$C_1$-$C_6$ fluoroalkyl,
$C_3$-$C_{10}$ cycloalkyl optionally substituted with 1-3 groups independently selected from halogen, and
3- to 10-membered heterocyclyl,
5- to 10-membered heteroaryl optionally substituted with 1-3 groups independently selected from:
halogen,
$C_1$-$C_6$ alkyl optionally substituted with 1-3 groups independently selected from oxo, $C_1$-$C_6$ alkoxy, and $N(R^N)_2$, and
3- to 10-membered heterocyclyl optionally substituted with 1-3 groups independently selected from $C_1$-$C_6$ alkyl (optionally substituted with 1-3 groups selected from oxo, $C_1$-$C_6$ alkoxy, and $C_6$-$C_{10}$ aryl), and
$R^F$;
each $R^{XC}$, $R^{YC}$, and $R^{ZC}$ is independently selected from:
hydrogen,
$C_1$-$C_6$ alkyl optionally substituted with 1-3 groups independently selected from $C_6$-$C_{10}$ aryl (optionally substituted with 1-3 groups independently selected from $C_1$-$C_6$ alkyl), $C_6$-$C_{10}$ aryl optionally substituted with 1-3 groups independently selected from $C_1$-$C_6$ alkyl, and
$R^F$;
or two $R^{XC}$ are taken together to form a group selected from oxo and $C_3$-$C_{10}$ cycloalkyl;
or two $R^{YC}$ are taken together to form an oxo group;
or two $R^{ZC}$ are taken together to form an oxo group;
each $R^{L1}$ is independently selected from:
hydrogen,
$N(R^N)_2$, provided that two $N(R^N)_2$ are not bonded to the same carbon,
$C_1$-$C_9$ alkyl optionally substituted with 1-3 groups independently selected from:
halogen,
hydroxyl,
oxo,
$N(R^N)_2$,
$C_1$-$C_6$ alkoxy optionally substituted with 1-3 groups independently selected from $C_6$-$C_{10}$ aryl,
$C_3$-$C_{10}$ cycloalkyl optionally substituted with 1-3 groups independently selected from halogen and $C_1$-$C_6$ fluoroalkyl,
$C_6$-$C_{10}$ aryl optionally substituted with 1-3 groups independently selected from $C_1$-$C_6$ alkyl, and
3- to 10-membered heterocyclyl optionally substituted with 1-3 groups independently selected from $C_1$-$C_6$ alkyl (optionally substituted with 1-3 groups independently selected from hydroxyl and oxo),
$C_3$-$C_{10}$ cycloalkyl,
$C_6$-$C_{10}$ aryl optionally substituted with 1-4 groups independently selected from:
halogen,
cyano,
$SiMe_3$,
$POMe_2$,
$C_1$-$C_7$ alkyl optionally substituted with 1-3 groups independently selected from:
hydroxyl,
oxo,
cyano,
$SiMe_3$,
$N(R^N)_2$, and
$C_3$-$C_{10}$ cycloalkyl optionally substituted with 1-3 groups independently selected from $C_1$-$C_6$ fluoroalkyl,
$C_1$-$C_6$ alkoxy optionally substituted with 1-3 groups independently selected from:
$C_3$-$C_{10}$ cycloalkyl optionally substituted with 1-3 groups independently selected from $C_1$-$C_6$ fluoroalkyl, and
$C_1$-$C_6$ alkoxy,
$C_1$-$C_6$ fluoroalkyl,
$C_3$-$C_{10}$ cycloalkyl optionally substituted with 1-3 groups independently selected from $C_1$-$C_6$ alkyl and $C_1$-$C_6$ fluoroalkyl,
$C_6$-$C_{10}$ aryl,
3- to 10-membered heterocyclyl optionally substituted with 1-3 groups independently selected from $C_1$-$C_6$ alkyl, and
5- to 10-membered heteroaryl,
3- to 10-membered heterocyclyl optionally substituted with 1-3 groups independently selected from:
$C_1$-$C_6$ alkyl optionally substituted with 1-3 groups independently selected from:
oxo, and
$C_1$-$C_6$ alkoxy,
5- to 10-membered heteroaryl optionally substituted with 1-3 groups independently selected from:
$C_1$-$C_6$ alkyl optionally substituted with 1-3 groups independently selected from:
$C_3$-$C_{10}$ cycloalkyl optionally substituted with 1-3 groups independently selected from $C_1$-$C_6$ fluoroalkyl, and
$C_6$-$C_{10}$ aryl optionally substituted with 1-3 groups independently selected from $C_1$-$C_6$ alkyl, and
$R^F$;
or two $R^{L1}$ on the same carbon atom are taken together to form an oxo group;
each $R^{L2}$ is independently selected from hydrogen and $R^F$; or two $R^{L2}$ on the same carbon atom are taken together to form an oxo group;
each $R^N$ is independently selected from:
hydrogen,
$C_1$-$C_8$ alkyl optionally substituted with 1-3 groups independently selected from:
oxo,
halogen,
hydroxyl,
$NH_2$,
NHMe,
$NMe_2$,
$C_1$-$C_6$ alkoxy optionally substituted with 1-3 groups independently selected from $C_6$-$C_{10}$ aryl,
$-(O)_{0-1}-(C_3$-$C_{10}$ cycloalkyl),
$C_6$-$C_{10}$ aryl optionally substituted with 1-3 groups independently selected from halogen and $C_1$-$C_6$ alkyl,
3- to 14-membered heterocyclyl optionally substituted with 1-4 groups independently selected from oxo and $C_1$-$C_6$ alkyl, and
5- to 14-membered heteroaryl optionally substituted with 1-4 groups independently selected from oxo and $C_1$-$C_6$ alkyl,
$C_3$-$C_{10}$ cycloalkyl optionally substituted with 1-3 groups independently selected from:
hydroxyl,
$NH_2$,
NHMe,
$C_1$-$C_6$ alkyl optionally substituted with 1-3 groups independently selected from hydroxyl, and
$C_6$-$C_{10}$ aryl, and
3- to 10-membered heterocyclyl;
or two $R^N$ on the same nitrogen atom are taken together with the nitrogen to which they are bonded to form a 3- to 10-membered heterocyclyl optionally substituted with 1-3 groups selected from:
hydroxyl,
oxo,
cyano,
$C_1$-$C_6$ alkyl optionally substituted with 1-3 groups independently selected from oxo, hydroxyl, $C_1$-$C_6$ alkoxy, and $N(R^{N2})_2$, wherein each $R^{N2}$ is independently selected from hydrogen and $C_1$-$C_6$ alkyl,
$C_1$-$C_6$ alkoxy, and
$C_1$-$C_6$ fluoroalkyl;
or one $R^4$ and one $R^{L1}$ are taken together to form a $C_6$-$C_8$ alkylene;
when $R^F$ is present, two $R^F$ taken together with the atoms to which they are bonded form a group selected from:
$C_3$-$C_{10}$ cycloalkyl optionally substituted with 1-3 groups independently selected from $C_1$-$C_6$ alkyl,
$C_6$-$C_{10}$ aryl optionally substituted with 1-3 groups independently selected from:

halogen,
$C_1$-$C_6$ alkyl,
$N(R^N)_2$, and
3- to 10-membered heterocyclyl optionally substituted with 1-3 groups independently selected from hydroxyl,
3- to 11-membered heterocyclyl optionally substituted with 1-3 groups independently selected from:
oxo,
$N(R^N)_2$,
$C_1$-$C_9$ alkyl optionally substituted with 1-4 groups independently selected from:
oxo,
halogen,
hydroxyl,
$N(R^N)_2$,
—$SO_2$—($C_1$-$C_6$ alkyl),
$C_1$-$C_6$ alkoxy optionally substituted with 1-3 groups independently selected from halogen, $C_6$-$C_{10}$ aryl,
$C_6$-$C_{10}$ aryl optionally substituted with 1-3 groups independently selected from hydroxyl, halogen, cyano, $C_1$-$C_6$ alkyl (optionally substituted with 1-3 groups independently selected from oxo and $C_1$-$C_6$ alkoxy), $C_1$-$C_6$ alkoxy (optionally substituted with 1-3 groups independently selected from $C_6$-$C_{10}$ aryl), —$(O)_{0-1}$—($C_1$-$C_6$ fluoroalkyl), and $C_6$-$C_{10}$ aryl (optionally substituted with 1-3 groups independently selected from $C_1$-$C_6$ alkoxy),
—$(O)_{0-1}$—($C_3$-$C_{10}$ cycloalkyl) optionally substituted with 1-4 groups independently selected from hydroxyl, halogen, $N(R^N)_2$, $C_1$-$C_6$ alkyl (optionally substituted with 1-3 groups independently selected from oxo, hydroxyl, and $C_1$-$C_6$ alkoxy), $C_1$-$C_6$ fluoroalkyl, and $C_6$-$C_{10}$ aryl,
3- to 10-membered heterocyclyl optionally substituted with 1-3 groups independently selected from oxo, $C_1$-$C_6$ alkyl (optionally substituted with 1-3 groups independently selected from $C_6$-$C_{10}$ aryl (optionally substituted with 1-3 groups independently selected from halogens)), $C_1$-$C_6$ alkoxy, $C_3$-$C_{10}$ cycloalkyl, and $R^N$,
O-(5- to 12-membered heteroaryl) optionally substituted with 1-3 groups independently selected from $C_6$-$C_{10}$ aryl (optionally substituted with 1-3 groups independently selected from halogen) and $C_1$-$C_6$ alkyl, and
5- to 10-membered heteroaryl optionally substituted with 1-3 groups independently selected from hydroxyl, oxo, $N(R^N)_2$, $C_1$-$C_6$ alkyl (optionally substituted with 1-3 groups independently selected from cyano), $C_1$-$C_6$ alkoxy, —$(O)_{0-1}$—($C_1$-$C_6$ fluoroalkyl), —O—($C_6$-$C_{10}$ aryl), and $C_3$-$C_{10}$ cycloalkyl,
$C_3$-$C_{12}$ cycloalkyl optionally substituted with 1-4 groups independently selected from halogen, $C_1$-$C_6$ alkyl, and $C_1$-$C_6$ fluoroalkyl,
$C_6$-$C_{10}$ aryl,
3- to 10-membered heterocyclyl, and
5- to 10-membered heteroaryl optionally substituted with 1-3 groups independently selected from $C_1$-$C_6$ alkoxy and $C_1$-$C_6$ fluoroalkyl, and
5- to 12-membered heteroaryl optionally substituted with 1-3 groups independently selected from $C_1$-$C_6$ alkyl and $C_1$-$C_6$ fluoroalkyl.

Formula I also includes compounds of Formula Ia:

(Ia)

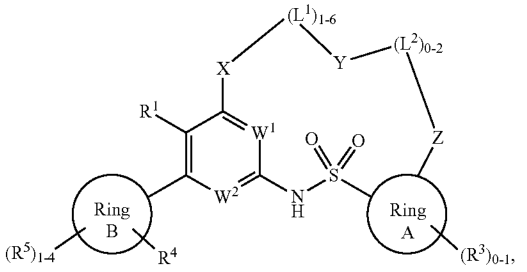

tautomers of those compounds, deuterated derivatives of any of the compounds and tautomers, and pharmaceutically acceptable salts of any of the foregoing, wherein Ring A, Ring B, $W^1$, $W^2$, X, Y, Z, $L^1$, $L^2$, $R^1$, $R^3$, $R^4$, and $R^5$ are as defined for Formula I.

Formula I also includes compounds of Formula IIa:

(IIa)

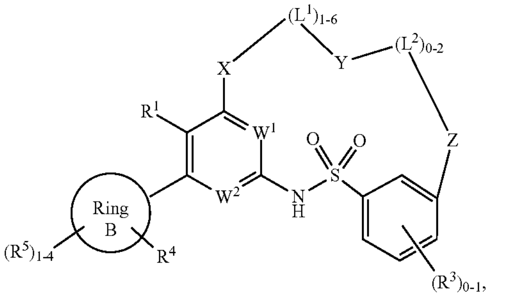

tautomers of those compounds, deuterated derivatives of any of the compounds and tautomers, and pharmaceutically acceptable salts of any of the foregoing, wherein Ring B, $W^1$, $W^2$, X, Y, Z, $L^1$, $L^2$, $R^1$, $R^3$, $R^4$, and $R^5$ are as defined for Formula I.

Formula I also includes compounds of Formula IIb:

(IIb)

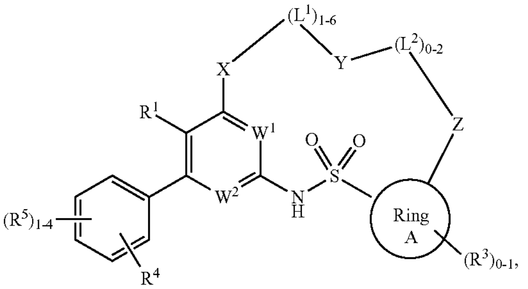

tautomers of those compounds, deuterated derivatives of any of the compounds and tautomers, and pharmaceutically acceptable salts of any of the foregoing, wherein Ring A, $W^1$, $W^2$, X, Y, Z, $L^1$, $L^2$, $R^1$, $R^3$, $R^4$, and $R^5$ are as defined for Formula I.

Formula I also includes compounds of Formula III:

(III)

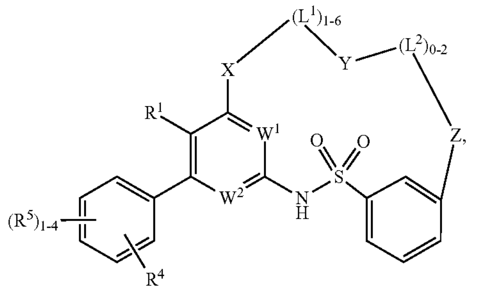

tautomers of those compounds, deuterated derivatives of any of the compounds and tautomers, and pharmaceutically acceptable salts of any of the foregoing, wherein $W^1$, $W^2$, X, Y, Z, $L^1$, $L^2$, $R^1$, $R^4$, and $R^5$ are as defined for Formula I.

Formula I also includes compounds of Formula IV:

(IV)

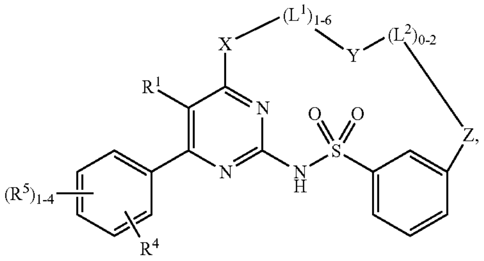

tautomers of those compounds, deuterated derivatives of any of the compounds and tautomers, and pharmaceutically acceptable salts of any of the foregoing, wherein X, Y, Z, $L^1$, $L^2$, $R^1$, $R^4$, and $R^5$ are as defined for Formula I.

Formula I also includes compounds of Formula V:

(V)

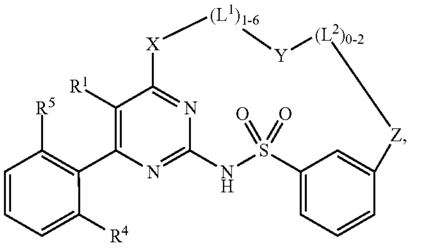

tautomers of those compounds, deuterated derivatives of any of the compounds and tautomers, and pharmaceutically acceptable salts of any of the foregoing, wherein X, Y, Z, $L^1$, $L^2$, $R^1$, $R^4$, and $R^5$ are as defined for Formula I.

Formula I also includes compounds of Formula VIa and Formula VIb:

(VIa)

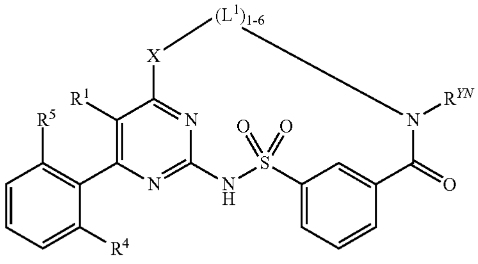

and (VIb)

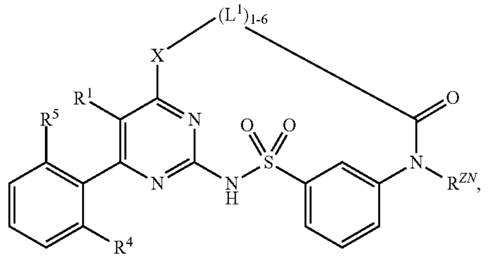

tautomers of those compounds, deuterated derivatives of any of the compounds and tautomers, and pharmaceutically acceptable salts of any of the foregoing, wherein X, $L^1$, $R^1$, $R^4$, $R^5$, $R^{YN}$, and $R^{ZN}$ are as defined for Formula I.

Formula I also includes compounds of Formula VIIa and Formula VIIb:

(VIIa)

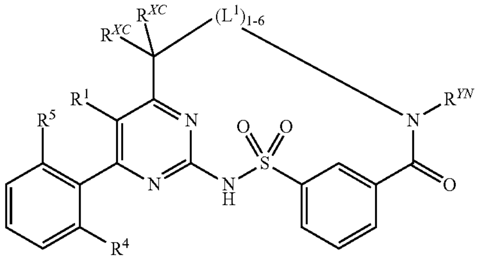

and (VIIb)

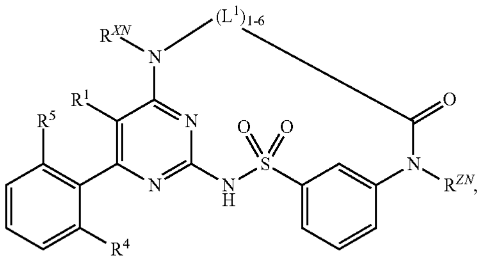

tautomers of those compounds, deuterated derivatives of any of the compounds and tautomers, and pharmaceutically acceptable salts of any of the foregoing, wherein $L^1$, $R^1$, $R^4$, $R^5$, $R^{XC}$, $R^{XN}$, $R^{YN}$, and $R^{ZN}$ are as defined for Formula I.

Another aspect of the disclosure provides at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, optionally in combination with one or more CFTR modulating agents, for use in therapy or for use in the manufacture of a medicament. In some embodiments, the optional one or more CFTR modulating agents are selected from CFTR potentiators. In some embodiments, the one or more additional CFTR modulating agents are selected from CFTR correctors. In some embodiments, the one or more additional CFTR modulating agents are selected from tezacaftor, lumacaftor, ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing.

Another aspect of the disclosure provides pharmaceutical compositions comprising at least one compound chosen from the novel compounds disclosed herein, deuterated derivatives thereof, and pharmaceutically acceptable salts of any of the foregoing, and at least one pharmaceutically acceptable carrier, which compositions may further include at least one additional active pharmaceutical ingredient. In some embodiments, the at least one additional active pharmaceutical ingredient is at least one other CFTR modulator. In some embodiments, the at least one other CFTR modulator is selected from CFTR potentiators and CFTR correctors. Thus, another aspect of the disclosure provides methods of treating the CFTR-mediated disease cystic fibrosis comprising administering at least one of compound chosen from the novel compounds disclosed herein, deuterated derivatives thereof, and pharmaceutically acceptable salts of any of the foregoing, and at least one pharmaceutically acceptable carrier, optionally as part of a pharmaceutical composition comprising at least one additional component, to a subject in need thereof. In some embodiments, the at least one additional active pharmaceutical ingredient is at least one other CFTR modulator. In some embodiments, the at least one other CFTR modulator is selected from CFTR potentiators. In some embodiments, the at least one other CFTR modulator is selected from CFTR correctors. In some embodiments, the at least one other CFTR modulator includes a potentiator and corrector. In some embodiments, the at least one other CFTR modulator is selected from tezacaftor, lumacaftor, ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing.

In certain embodiments, the pharmaceutical compositions of the disclosure comprise at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing. In some embodiments, compositions comprising at least one (i.e., one or more) compound(s) chosen from compounds of Formula I, compounds of any one of Formulae Ia, IIa, IIb, III, IV, V, VIa, VIb, VIIa, and VIIb, tautomers thereof, deuterated derivatives of those compounds and tautomers, and pharmaceutically acceptable salts of any of the foregoing, may optionally further comprise (a) at least one (i.e., one or more) compound(s) chosen from (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (tezacaftor), 3-(6-(1-(2,2-difluorobenzo[d][1,3]dioxol-5-yl)cyclopropane carboxamido)-3-methylpyridin-2-yl)benzoic acid (lumacaftor) and deuterated derivatives and pharmaceutically acceptable salts of tezacaftor and lumacaftor; and/or (b) at least one (i.e., one or more) compound(s) chosen from N-[2,4-bis(1,1-dimethylethyl)-5-hydroxyphenyl]-1,4-dihydro-4-oxoquinoline-3-carboxamide (ivacaftor) or N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (deutivacaftor), (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing.

Another aspect of the disclosure provides methods of treating the CFTR-mediated disease cystic fibrosis that comprise administering to a patient in need thereof at least one compound chosen from the novel compounds disclosed herein, deuterated derivatives thereof, and pharmaceutically acceptable salts of any of the foregoing, and optionally further administering one or more additional CFTR modulating agents. A further aspect of the disclosure provides the pharmaceutical compositions of the disclosure comprising at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing and, optionally, one or more CFTR modulating agents, for use in therapy or for use in the manufacture of a medicament. In some embodiments, the optional one or more additional CFTR modulating agents are selected from CFTR potentiators. In some embodiments, the one or more additional CFTR modulating agents are selected from CFTR correctors. In some embodiments, the one or more additional CFTR modulating agents are selected from tezacaftor, lumacaftor, ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing.

A further aspect of the disclosure provides intermediates and methods for making the compounds and compositions disclosed herein.

Definitions

"Selected from" and "chosen from" are used interchangeably herein.

"Tezacaftor" as used herein, refers to (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, which can be depicted with the following structure:

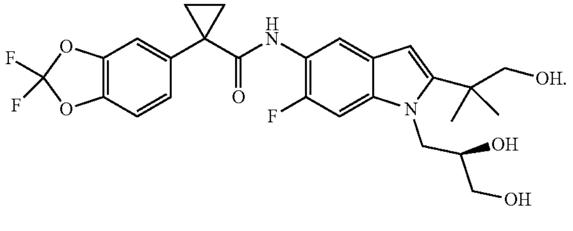 [SMILES: CC(C)(CO)c1cc2cc(NC(=O)C3(c4ccc5c(c4)OC(F)(F)O5)CC3)c(F)cc2n1C[C@@H](O)CO]

Tezacaftor may be in the form of a deuterated derivative or a pharmaceutically acceptable salt, or a pharmaceutically acceptable salt of a deuterated derivative. Tezacaftor and methods of making and using tezacaftor are disclosed in WO 2010/053471, WO 2011/119984, WO 2011/133751, WO 2011/133951, WO 2015/160787, and US 2009/0131492, each of which is incorporated herein by reference.

"Ivacaftor" as used throughout this disclosure refers to N-(2,4-di-tert-butyl-5-hydroxyphenyl)-1,4-dihydro-4-oxo-quinoline-3-carboxamide, which is depicted by the structure:

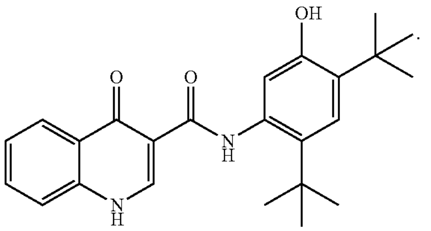 [SMILES: CC(C)(C)c1cc(C(C)(C)C)c(NC(=O)c2c[nH]c3ccccc3c2=O)cc1O]

Ivacaftor may also be in the form of deuterated derivative, a pharmaceutically acceptable salt, or a pharmaceutically acceptable salt of a deuterated derivative. Ivacaftor and methods of making and using ivacaftor are disclosed in WO 2006/002421, WO 2007/079139, WO 2010/108162, and WO 2010/019239, each of which is incorporated herein by reference.

In some embodiments, a specific deuterated derivative of ivacaftor (deutivacaftor) is employed in the compositions and methods disclosed herein. A chemical name for deutivacaftor is N-(2-(tert-butyl)-5-hydroxy-4-(2-(methyl-d3) propan-2-yl-1,1,1,3,3,3-d6)phenyl)-4-oxo-1,4-dihydroquinoline-3-carboxamide, as depicted by the structure:

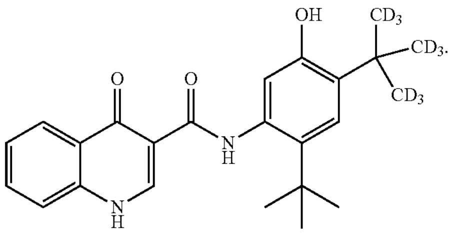 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

Deutivacaftor may be in the form of a further deuterated derivative, a pharmaceutically acceptable salt, or a pharmaceutically acceptable salt of a deuterated derivative. Deutivacaftor and methods of making and using deutivacaftor are disclosed in WO 2012/158885, WO 2014/078842, and U.S. Pat. No. 8,865,902, each of which is incorporated herein by reference.

"Lumacaftor" as used herein, refers to 3-(6-(1-(2,2-difluorobenzo[d][1,3]dioxol-5-yl)cyclopropanecarboxamido)-3-methylpyridin-2-yl)benzoic acid, which is depicted by the chemical structure:

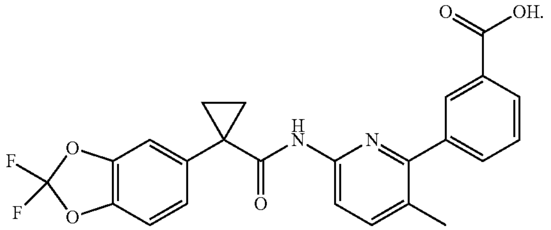 [SMILES: Cc1ccc(NC(=O)C2(c3ccc4c(c3)OC(F)(F)O4)CC2)nc1-c1cccc(C(=O)O)c1]

Lumacaftor may be in the form of a deuterated derivative, a pharmaceutically acceptable salt, or a pharmaceutically acceptable salt of a deuterated derivative. Lumacaftor and methods of making and using Lumacaftor are disclosed in WO 2007/056341, WO 2009/073757, and WO 2009/076142, each of which is incorporated herein by reference.

As used herein, the term "alkyl" refers to a saturated or partially saturated, branched or unbranched aliphatic hydrocarbon containing carbon atoms (such as, for example, 1, 2, 3, 4, 5, 6, 7, 8, 9, 10, 11, 12, 13, 14, 15, 16, 17, 18, 19, or 20 carbon atoms) that may have one or more unsaturated bonds. For example, an alkyl group may contain double (alkenyl) bonds or triple (alkynyl bonds). Alkyl groups may be substituted or unsubstituted.

As used herein, the term "haloalkyl group" refers to an alkyl group substituted with one or more halogen atoms, e.g., fluoroalkyl, wherein the alkyl group is substituted with one or more fluorine atoms.

The term "alkoxy," as used herein, refers to an alkyl or cycloalkyl covalently bonded to an oxygen atom. Alkoxy groups may be substituted or unsubstituted.

As used herein, the term "haloalkoxyl group" refers to an alkoxy group substituted with one or more halogen atoms.

As used herein, "cycloalkyl" refers to a cyclic, bicyclic, tricyclic, or polycyclic non-aromatic hydrocarbon groups having 3 to 12 carbons (such as, for example 3-10 carbons) and may include one or more unsaturated bonds. "Cycloalkyl" groups encompass monocyclic, bicyclic, tricyclic, bridged, fused, and spiro rings, including mono spiro and dispiro rings. Non-limiting examples of cycloalkyl groups are cyclopropyl, cyclobutyl, cyclopentyl, cyclohexyl, adamantyl, norbornyl, dispiro[2.0.2.1]heptane, and spiro[2,3] hexane. Cycloalkyl groups may be substituted or unsubstituted.

The term "aryl," as used herein, is a functional group or substituent derived from an aromatic ring and encompasses monocyclic aromatic rings and bicyclic, tricyclic, and fused ring systems wherein at least one ring in the system is aromatic. Non-limiting examples of aryl groups include phenyl, naphthyl, and 1,2,3,4-tetrahydronaphthalenyl.

The term "heteroaryl ring," as used herein, refers to an aromatic ring comprising at least one ring atom that is a heteroatom, such as O, N, or S. Heteroaryl groups encompass monocyclic rings and bicyclic, tricyclic, bridged, fused, and spiro ring systems (including mono spiro and dispiro rings) wherein at least one ring in the system is aromatic. Non-limiting examples of heteroaryl rings include pyridine, quinoline, indole, and indoline.

As used herein, the term "heterocyclyl ring" refers to a non-aromatic hydrocarbon containing 3 to 12 atoms in a ring (such as, for example, 3-10 atoms) comprising at least one ring atom that is a heteroatom, such as O, N, or S, and may include one or more unsaturated bonds. "Heterocyclyl" rings encompass monocyclic, bicyclic, tricyclic, polycyclic, bridged, fused, and spiro rings, including mono spiro and dispiro rings.

"Substituted," whether preceded by the term "optionally" or not, indicates that at least one hydrogen of the "substituted" group is replaced by a substituent. Unless otherwise indicated, an "optionally substituted" group may have a suitable substituent at each substitutable position of the group, and when more than one position in any given structure may be substituted with more than one substituent chosen from a specified group, the substituent may be either the same or different at each position.

Non-limiting examples of protecting groups for nitrogen include, for example, t-butyl carbamate (Boc), benzyl (Bn), para-methoxybenzyl (PMB), tetrahydropyranyl (THP), 9-fluorenylmethyl carbamate (Fmoc), benzyl carbamate (Cbz), methyl carbamate, ethyl carbamate, 2,2,2-trichloroethyl carbamate (Troc), 2-trimethylsilylethyl carbamate (Teoc), allyl carbamate (Aloc or Alloc), formamide, acetamide, benzamide, allylamine, trifluoroacetamide, triphenylmethylamine, benzylideneamine, and p-toluenesulfonamide. A comprehensive list of nitrogen protecting groups can be found in Wuts, P. G. M. "Greene's Protective Groups in Organic Synthesis: Fifth Edition," 2014, John Wiley and Sons.

As used herein, "deuterated derivative(s)" refers to a compound having the same chemical structure as a reference compound, with one or more hydrogen atoms replaced by a deuterium atom. In chemical structures, deuterium is represented as "D." In some embodiments, the one or more hydrogens replaced by deuterium are part of an alkyl group. In some embodiments, the one or more hydrogens replaced by deuterium are part of a methyl group.

The phrase "and deuterated derivatives and pharmaceutically acceptable salts thereof" is used interchangeably with "and deuterated derivatives and pharmaceutically acceptable salts thereof of any of the forgoing" in reference to one or more specified compounds and refers to deuterated derivatives of the specified compound or compounds as well as pharmaceutically acceptable salts of the specified compound or compounds and pharmaceutically acceptable salts of the deuterated derivative of the specified compound or compounds.

As used herein, "CFTR" means cystic fibrosis transmembrane conductance regulator.

As used herein, the terms "CFTR modulator" and "CFTR modulating agent" are used interchangeably to refer to a compound that increases the activity of CFTR. The increase in activity resulting from a CFTR modulator includes, but is not limited to, compounds that correct, potentiate, stabilize and/or amplify CFTR.

As used herein, the terms "corrector" and "CFTR corrector" are used interchangeably to refer to a compound that facilitates the processing and trafficking of CFTR to increase the amount of CFTR at the cell surface. The novel compounds disclosed herein are CFTR correctors. Other correctors may be used in combination therapies with the novel compounds disclosed herein to treat CFTR mediated diseases, such as cystic fibrosis. Such other correctors include, e.g., tezacaftor, lumacaftor, and their deuterated derivatives and pharmaceutically acceptable salts.

The terms "potentiator" and "CFTR potentiator" are used interchangeably herein to refer to a compound that increases the channel activity of CFTR protein located at the cell surface, resulting in enhanced ion transport. Potentiators may be used in combination with the novel compounds of the disclosure to treat CFTR mediated diseases such as cystic fibrosis. Such potentiators include, e.g., ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and their deuterated derivatives and pharmaceutically acceptable salts.

It will be appreciated that when a description of a combination of a compound selected from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, and other specified CFTR modulating agents is provided herein, typically, but not necessarily, the composition or treatment regime will include at least one potentiator, such as, e.g., a potentiator selected from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts thereof. In some embodiments, a combination of at least one compound selected from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, and other specified CFTR modulating agents, will also include another CFTR corrector, such as, e.g., a corrector compound selected from tezacaftor, lumacaftor, and deuterated derivatives and pharmaceutically acceptable salts thereof.

The term "at least one compound selected from," as used herein, refers to the selection of one or more of the compounds from a specified group.

A reference to "Compounds 1-73" in this disclosure is intended to represent a reference to each of Compounds 1 through 73 individually or a reference to groups of compounds, such as, e.g., Compounds 1-41, Compounds 1-24 and 26-41, Compounds 1-24 and 26-57, Compounds 42-57, Compounds 58-71, and Compounds 72 and 73.

As used herein, the term "active pharmaceutical ingredient" or "therapeutic agent" ("API") refers to a biologically active compound.

The terms "patient" and "subject" are used interchangeably and refer to an animal, including a human.

The terms "effective dose" and "effective amount" are used interchangeably herein and refer to that amount of a compound that produces the desired effect for which it is administered (e.g., improvement in CF or a symptom of CF, or lessening the severity of CF or a symptom of CF). The exact amount of an effective dose will depend on the purpose of the treatment and will be ascertainable by one skilled in the art using known techniques (see, e.g., Lloyd (1999) The Art, Science and Technology of Pharmaceutical Compounding).

As used herein, the terms "treatment," "treating," and the like generally mean the improvement in one or more symptoms of CF or lessening the severity of CF or one or more symptoms of CF in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

It should be understood that references herein to methods of treatment (e.g., methods of treating a CFTR mediated disease or a method of treating cystic fibrosis) using one or more compounds of the disclosure optionally in combination with one or more additional CFTR modulating agents (e.g., a compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, optionally in combination with one or more additional CFTR modulating agents) should also be interpreted as references to:

- one or more compounds (e.g., a compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, optionally in combination with one or more additional CFTR modulating agents) for use in methods of treating, e.g., cystic fibrosis optionally in combination with one or more additional CFTR modulating agents; and/or the use of one or more compounds (e.g., a compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, optionally in combination with one or more additional CFTR modulating agents) in the manufacture of a medicament for treating, e.g., cystic fibrosis.

It should be also understood that references herein to methods of treatment (e.g., methods of treating a CFTR mediated disease or a method of treating cystic fibrosis) using a pharmaceutical composition of the disclosure (e.g., a pharmaceutical composition comprising at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, and optionally further comprising one or more additional CFTR modulating agents) should also be interpreted as references to:

a pharmaceutical composition (e.g., a pharmaceutical composition comprising at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing and optionally further comprising one or more additional CFTR modulating agents) for use in methods of treating, e.g., cystic fibrosis; and/or the use of a pharmaceutical composition (e.g., a pharmaceutical composition comprising at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing and optionally further comprising one or more additional CFTR modulating agents) in the manufacture of a medicament for treating, e.g., cystic fibrosis.

As used herein, the term "in combination with," when referring to two or more compounds, agents, or additional active pharmaceutical ingredients, means the administration of two or more compounds, agents, or active pharmaceutical ingredients to the patient prior to, concurrent with, or subsequent to each other.

The terms "about" and "approximately" may refer to an acceptable error for a particular value as determined by one of skill in the art, which depends in part on how the values are measured or determined. In some embodiments, the terms "about" and "approximately" mean within 20%, 15%, 10%, 5%, 4%, 3%, 2%, 1%, or 0.5% of a given value or range.

As used herein, the term "solvent" refers to any liquid in which the product is at least partially soluble (solubility of product >1 g/l).

As used herein, the term "room temperature" or "ambient temperature" means 15° C. to 30° C.

It will be appreciated that certain compounds of this disclosure may exist as separate stereoisomers or enantiomers and/or mixtures of those stereoisomers or enantiomers.

Certain compounds disclosed herein may exist as tautomers and both tautomeric forms are intended, even though only a single tautomeric structure is depicted. For example, a description of Compound X is understood to include its tautomer Compound Y and vice versa, as well as mixtures thereof:

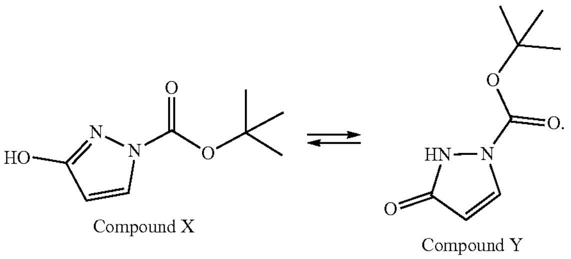

Compound X

Compound Y

As used herein, "minimal function (MF) mutations" refer to CFTR gene mutations associated with minimal CFTR function (little-to-no functioning CFTR protein) and include, for example, mutations associated with severe defects in ability of the CFTR channel to open and close, known as defective channel gating or "gating mutations"; mutations associated with severe defects in the cellular processing of CFTR and its delivery to the cell surface; mutations associated with no (or minimal) CFTR synthesis; and mutations associated with severe defects in channel conductance.

As used herein, the term "pharmaceutically acceptable salt" refers to a salt form of a compound of this disclosure wherein the salt is nontoxic. Pharmaceutically acceptable salts of the compounds of this disclosure include those derived from suitable inorganic and organic acids and bases. A "free base" form of a compound, for example, does not contain an ionically bonded salt.

One of ordinary skill in the art would recognize that, when an amount of "a compound or a pharmaceutically acceptable salt thereof" is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form.

Suitable pharmaceutically acceptable salts are, for example, those disclosed in S. M. Berge, et al. *J. Pharmaceutical Sciences,* 1977, 66, 1-19. For example, Table 1 of that article provides the following pharmaceutically acceptable salts:

TABLE 1

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |

TABLE 1-continued

| | | |
|---|---|---|
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teociate | |
| | Triethiodide | |

Non-limiting examples of pharmaceutically acceptable acid addition salts include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

Methods of Treatment

Any of the novel compounds disclosed herein, such as, for example, compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, can act as a CFTR modulator, i.e., it modulates CFTR activity in the body. Individuals suffering from a mutation in the gene encoding CFTR may benefit from receiving a CFTR modulator. A CFTR mutation may affect the CFTR quantity, i.e., the number of CFTR channels at the cell surface, or it may impact CFTR function, i.e., the functional ability of each channel to open and transport ions. Mutations affecting CFTR quantity include mutations that cause defective synthesis (Class I defect), mutations that cause defective processing and trafficking (Class II defect), mutations that cause reduced synthesis of CFTR (Class V defect), and mutations that reduce the surface stability of CFTR (Class VI defect). Mutations that affect CFTR function include mutations that cause defective gating (Class III defect) and mutations that cause defective conductance (Class IV defect). Some CFTR mutations exhibit characteristics of multiple classes. Certain mutations in the CFTR gene result in cystic fibrosis.

Thus, in some embodiments, the disclosure provides methods of treating, lessening the severity of, or symptomatically treating cystic fibrosis in a patient comprising administering to the patient an effective amount of any of the novel compounds disclosed herein, such as for example, compounds of Formula I, compounds of any one of Formulae Ia, IIa, IIb, III, IV, V, VIa, VIb, VIIa, and VIIb, tautomers thereof, deuterated derivatives of those compounds and tautomers, and pharmaceutically acceptable salts of any of the foregoing, alone or in combination with another active ingredient, such as one or more additional CFTR modulating agents. In some embodiments, the one (or more) CFTR modulating agent is a corrector. In some embodiments, the one (or more) CFTR modulating agent is a potentiator. In some embodiments, the CFTR modulating agents include both a corrector and a potentiator. In some embodiments, the one or more CFTR modulating agents are selected from potentiators: ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing; and correctors: lumacaftor, tezacaftor, and deuterated derivatives and pharmaceutically acceptable salts thereof.

In some embodiments, 5 mg to 500 mg of a compound disclosed herein, a tautomer thereof, a deuterated derivative of the compound or tautomer, or a pharmaceutically acceptable salt of any of the foregoing are administered daily.

In some embodiments, the patient to be treated has an F508del/minimal function (MF) genotype, F508del/F508del genotype (homozygous for the F508del mutation), F508del/gating genotype, or F508del/residual function ($R^F$) genotype. In some embodiments, the patient is heterozygous and has one F508del mutation. In some embodiments, the patient is homozygous for the N1303K mutation.

In some embodiments, the patient to be treated has at least one F508del mutation in the CFTR gene. In some embodiments, the patient has a CFTR gene mutation that is responsive to a compound, tautomer, deuterated derivative, or pharmaceutically acceptable salt of the disclosure based on in vitro data. In some embodiments, the patient is heterozygous and has an F508del mutation on one allele and a mutation on the other allele selected from Table 2:

TABLE 2

| CFTR Mutations | | | | | |
|---|---|---|---|---|---|
| MF Category | Mutation | | | | |
| Nonsense mutations | Q2X | L218X | Q525X | R792X | E1104X |
| | S4X | Q220X | G542X | E822X | W1145X |
| | W19X | Y275X | G550X | W882X | R1158X |
| | G27X | C276X | Q552X | W846X | R1162X |
| | Q39X | Q290X | R553X | Y849X | S1196X |
| | W57X | G330X | E585X | R851X | W1204X |
| | E60X | W401X | G673X | Q890X | L1254X |
| | R75X | Q414X | Q685X | S912X | S1255X |
| | L88X | S434X | R709X | Y913X | W1282X |
| | E92X | S466X | K710X | Q1042X | Q1313X |
| | Q98X | S489X | Q715X | W1089X | Q1330X |
| | Y122X | Q493X | L732X | Y1092X | E1371X |
| | E193X | W496X | R764X | W1098X | Q1382X |
| | W216X | C524X | R785X | R1102X | Q1411X |
| Canonical splice mutations | 185 + 1G→T | 711 + 5G→A | 1717 − 8G→A | 2622 + 1G→A | 3121 − 1G→A |
| | 296 + 1G→A | 712 − 1G→T | 1717 − 1G→A | 2790 − 1G→C | 3500 − 2A→G |
| | 296 + 1G→T | 1248 + 1G→A | 1811 + 1G→C | 3040G→C | 3600 + 2insT |
| | 405 + 1G→A | 1249 − 1G→A | 1811 + 1.6kbA→G | (G970R) | 3850 − 1G→A |
| | 405 + 3A→C | 1341 + 1G→A | 1811 + 1643G→T | 3120G→A | 4005 + 1G→A |
| | 406 − 1G→A | 1525 − 2A→G | 1812 − 1G→A | 3120 + 1G→A | 4374 + 1G→T |
| | 621 + 1G→T | 1525 − 1G→A | 1898 + 1G→A | 3121 − 2A→G | |
| | 711 + 1G→T | | 1898 + 1G→C | | |
| Small (≤3 nucleotide) insertion/deletion (ins/del) frameshift mutations | 182delT | 1078delT | 1677delTA | 2711delT | 3737delA |
| | 306insA | 1119delA | 1782delA | 2732insA | 3791delC |
| | 306delTAGA | 1138insG | 1824delA | 2869insG | 3821delT |
| | 365-366insT | 1154insTC | 1833delT | 2896insAG | 3876delA |
| | 394delTT | 1161delC | 2043delG | 2942insT | 3878delG |
| | 442delA | 1213delT | 2143delT | 2957delT | 3905insT |
| | 444delA | 1259insA | 2183AA→G[a] | 3007delG | 4016insT |
| | 457TAT→G | 1288insTA | 2184delA | 3028delA | 4021dupT |
| | 541delC | 1343delG | 2184insA | 3171delC | 4022insT |
| | 574delA | 1471delA | 2307insA | 3171insC | 4040delA |
| | 663delT | 1497delGG | 2347delG | 3271delGG | 4279insA |
| | 849delG | 1548delG | 2585delT | 3349insT | 4326delTC |
| | 935delA | 1609del CA | 2594delGT | 3659delC | |
| Non-small (>3 nucleotide) insertion/deletion (ins/del) frameshift mutations | CFTRdele1 | | CFTRdele16-17b | | 1461ins4 |
| | CFTRdele2 | | CFTRdele17a, 17b | | 1924del7 |
| | CFTRdele2, 3 | | CFTRdele17a-18 | | 2055del9→A |
| | CFTRdele2-4 | | CFTRdele19 | | 2105-2117del13insAGAAA |
| | CFTRdele3-10, 14b-16 | | CFTRdele19-21 | | 2372del8 |
| | CFTRdele4-7 | | CFTRdele21 | | 2721del11 |
| | CFTRdele4-11 | | CFTRdele22-24 | | 2991del32 |
| | CFTR50kbdel | | CFTRdele22, 23 | | 3667ins4 |
| | CFTRdup6b-10 | | 124del23bp | | 4010del4 |
| | CFTRdele11 | | 602del14 | | 4209TGTT→AA |
| | CFTRdele13, 14a | | 852del22 | | |
| | CFTRdele14b-17b | | 991del5 | | |
| Missense mutations that Are not responsive in vitro to TEZ, IVA, or TEZ/IVA and % PI >50% and $SwCl^-$ >86 mmol/L | A46D | V520F | Y569D | N1303K | |
| | G85E | A559T | L1065P | | |
| | R347P | R560T | R1066C | | |
| | L467P | R560S | L1077P | | |
| | I507del | A561E | M1101K | | |

[a]Also known as 2183delAA→G.

CFTR: cystic fibrosis transmembrane conductance regulator;

IVA: ivacaftor.

SwCl: sweat chloride.

TEZ: tezacaftor.

Source: CFTR2.org [Internet]. Baltimore (MD): Clinical and functional translation of CFTR. The Clinical and Functional Translation of CFTR (CFTR2), US Cystic Fibrosis Foundation, Johns Hopkins University, the Hospital for Sick Children. Available at: http://www.cftr2.org/. Accessed 15 May 2018.

Notes:

% PI: percentage of F508del-CFTR heterozygous patients in the CFTR2 patient registry who are pancreatic insufficient;

SwCl: mean sweat chloride of F508del-CFTR heterozygous patients in the CFTR2 patient registry.

In some embodiments, the disclosure also is directed to methods of treatment using isotope-labelled compounds of the afore-mentioned compounds, or pharmaceutically acceptable salts thereof, wherein the formula and variables of such compounds and salts are each and independently as described above or any other embodiments described above, provided that one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine, and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively.

The isotope-labelled compounds and salts can be used in a number of beneficial ways. They can be suitable for medicaments and/or various types of assays, such as substrate tissue distribution assays. For example, tritium ($^{3}H$)- and/or carbon-14 ($^{14}C$)-labelled compounds are particularly useful for various types of assays, such as substrate tissue distribution assays, due to relatively simple preparation and excellent detectability. For example, deuterium ($^2$H)-labelled ones are therapeutically useful with potential therapeutic advantages over the non-$^2$H-labelled compounds. In general, deuterium ($^2$H)-labelled compounds and salts can have higher metabolic stability as compared to those that are not isotope-labelled owing to the kinetic isotope effect described below. Higher metabolic stability translates directly into an increased in vivo half-life or lower dosages, which could be desired. The isotope-labelled compounds and salts can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds and salts are deuterium (2H)-labelled ones. In some specific embodiments, the isotope-labelled compounds and salts are deuterium ($^2$H)-labelled, wherein one or more hydrogen atoms therein have been replaced by deuterium. The concentration of the isotope(s) (e.g., deuterium) incorporated into the isotope-labelled compounds and salt of the disclosure may be defined by the isotopic enrichment factor. The term "isotopic enrichment factor" as used herein means the ratio between the isotopic abundance and the natural abundance of a specified isotope. In some embodiments, if a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Combination Therapies

One aspect disclosed herein provides methods of treating cystic fibrosis and other CFTR mediated diseases using any of the novel compounds disclosed herein, such as for example, compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, in combination with at least one additional active pharmaceutical ingredient.

In some embodiments, at least one additional active pharmaceutical ingredient is selected from mucolytic agents, bronchodilators, antibiotics, anti-infective agents, and anti-inflammatory agents.

In some embodiments, the additional therapeutic agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In some embodiments, the additional agent is a mucolyte. Exemplary mucolytes useful herein includes Pulmozyme®.

In some embodiments, the additional agent is a bronchodilator. Exemplary bronchodilators include albuterol, metaprotenerol sulfate, pirbuterol acetate, salmeterol, or tetrabuline sulfate.

In some embodiments, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In some embodiments, the additional agent is a nutritional agent. Exemplary nutritional agents include pancrelipase (pancreatic enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In some embodiments, at least one additional active pharmaceutical ingredient is selected from CFTR modulating agents. In some embodiments, the additional active pharmaceutical ingredient is selected from CFTR potentiators. In some embodiments, the potentiator is selected from ivacaftor, deutivacaftor, and (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing. In some embodiments, the additional active pharmaceutical ingredient is chosen from CFTR correctors. In some embodiments, the correctors are selected from lumacaftor, tezacaftor, deuterated derivatives of lumacaftor and tezacaftor, and pharmaceutically acceptable salts of any of the foregoing. In some embodiments, the additional active pharmaceutical ingredient includes both a CFTR potentiator and a CFTR corrector.

In some embodiments, the at least one additional active pharmaceutical ingredient is chosen from (a) tezacaftor, lumacaftor, and deuterated derivatives and pharmaceutically acceptable salts thereof; and (b) ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing. Thus, in some embodiments, the combination therapies provided herein comprise (a) a compound selected from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing; (b) at least one compound selected from tezacaftor, lumacaftor, and deuterated derivatives and pharmaceutically acceptable salts thereof; or (c) at least one compound selected from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing. In some embodiments, the combination therapies provided herein comprise (a) at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing; (b) at least one compound selected from tezacaftor, lumacaftor, and deuterated derivatives and pharmaceutically acceptable salts thereof; and (c) at least one compound selected from ivacaftor, deutivacaftor, (6R,12R)-17-amino-12-methyl-6, 15-bis(trifluoromethyl)-13,19-dioxa-3,4,18-triazatricyclo [12.3.1.12,5]nonadeca-1(18),2,4,14,16-pentaen-6-ol, and deuterated derivatives and pharmaceutically acceptable salts of any of the foregoing.

In some embodiments, at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in combination with at least one compound chosen from tezacaftor and deuterated derivatives and pharmaceutically acceptable salts thereof. In some embodiments, at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in combination with at least one compound chosen from lumacaftor and deuterated derivatives and pharmaceutically acceptable salts thereof. In some embodiments, at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in combination with at least one compound chosen from ivacaftor and deuterated derivatives and pharmaceutically acceptable salts thereof. In some embodiments, at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in combination with at least one compound chosen from deutivacaftor and deuterated derivatives and pharmaceutically acceptable salts thereof. In some embodiments, at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in combination with at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof.

In some embodiments, at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in combination with at least one compound selected from tezacaftor and deuterated derivatives and pharmaceutically acceptable salts thereof, and at least one compound chosen from ivacaftor and deuterated derivatives and pharmaceutically acceptable salts thereof. In some embodiments, at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in combination with at least one compound chosen from tezacaftor and deuterated derivatives and pharmaceutically acceptable salts thereof and at least one compound chosen from deutivacaftor and deuterated derivatives and pharmaceutically acceptable salts thereof. In some embodiments, at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in combination with at least one compound chosen from tezacaftor and deuterated derivatives and pharmaceutically acceptable salts thereof and at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof.

In some embodiments, at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in combination with at least one compound selected from lumacaftor and deuterated derivatives and pharmaceutically acceptable salts thereof, and at least one compound chosen from ivacaftor and deuterated derivatives and pharmaceutically acceptable salts thereof. In some embodiments, at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in combination with at least one compound chosen from lumacaftor and deuterated derivatives and pharmaceutically acceptable salts thereof and at least one compound chosen from deutivacaftor and further deuterated derivatives and pharmaceutically acceptable salts thereof. In some embodiments, at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in combination with at least one compound chosen from lumacaftor and deuterated derivatives and pharmaceutically acceptable salts thereof and at least one compound chosen from (6R,12R)-17-amino-12-methyl-6,15-bis(trifluoromethyl)-13,19-dioxa-3,4,18-triazatricyclo [12.3.1.12,5]nonadeca-1(18),2,4,14,16-pentaen-6-ol and deuterated derivatives and pharmaceutically acceptable salts thereof.

Each of the compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, independently can be administered once daily, twice daily, or three times daily. In some embodiments, at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered once daily. In some embodiments, at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered twice daily.

In some embodiments, at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, and at least one compound chosen from tezacaftor and deuterated derivatives and pharmaceutically acceptable salts thereof are administered once daily. In some embodiments, at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, and at least one compound chosen from tezacaftor and deuterated derivatives and pharmaceutically acceptable salts thereof are administered twice daily.

In some embodiments, (a) at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, (b) and at least one compound chosen from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing are administered once daily. In some embodiments, (a) at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, and (b) at least one compound chosen from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts thereof are administered twice daily.

In some embodiments, (a) at least one compound chosen from compounds of Formula I, compounds of any one of Formulae Ia, I, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, (b) at least one compound chosen from tezacaftor and deuterated derivatives and pharmaceutically acceptable salts thereof, and (c) at least one compound chosen from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts thereof are administered once daily. In some embodiments, (a) at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, (b) at least one compound chosen from tezacaftor and deuterated derivatives and pharmaceutically acceptable salts thereof, and (c) at least one compound chosen from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts thereof are administered twice daily.

In some embodiments, (a) at least one compound of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, (b) at least one compound chosen from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts thereof, and (c) at least one compound chosen from lumacaftor and deuterated derivatives and pharmaceutically acceptable salts thereof, are administered once daily. In some embodiments, (a) at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, (b) at least one compound chosen from lumacaftor and deuterated derivatives and pharmaceutically acceptable salts thereof, and (c) at least one compound chosen from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts thereof are administered twice daily.

In some embodiments, (a) at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, and at least one compound chosen from tezacaftor and deuterated derivatives and pharmaceutically acceptable salts thereof, are administered once daily and (b) at least one compound chosen from ivacaftor and deuterated derivatives and pharmaceutically acceptable salts thereof, are administered twice daily. In some embodiments, (a) at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, and at least one compound chosen from lumacaftor and pharmaceutically acceptable salts thereof, are administered once daily and (b) at least one compound chosen from ivacaftor and deuterated derivatives and pharmaceutically acceptable salts thereof, are administered twice daily.

Compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, in combination with one or more of tezacaftor, lumacaftor, ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of those compounds can be administered in a single pharmaceutical composition or separate pharmaceutical compositions. Such pharmaceutical compositions can be administered once daily or multiple times daily, such as twice daily or three times daily. As used herein, the phrase that a given amount of API (e.g., tezacaftor, lumacaftor, ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, or a deuterated derivative or pharmaceutically acceptable salt thereof) is administered once or twice daily or per day means that said given amount is administered per dosing once or twice daily.

In some embodiments, (a) at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in a first pharmaceutical composition; (b) at least one compound chosen from tezacaftor, lumacaftor, and deuterated derivatives and pharmaceutically acceptable salts thereof is administered in a second pharmaceutical composition; and (c) at least one compound chosen from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts thereof is administered in a third pharmaceutical composition.

In some embodiments, (a) at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in a first pharmaceutical composition; (b) at least one compound chosen from tezacaftor and deuterated derivatives and pharmaceutically acceptable salts thereof is administered in a second pharmaceutical composition; and (c) at least one compound chosen from ivacaftor and deuterated derivatives and pharmaceutically acceptable salts thereof is administered in a third pharmaceutical composition.

In some embodiments, (a) at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in a first pharmaceutical composition; (b) at least one compound chosen from tezacaftor and deuterated derivatives and pharmaceutically acceptable salts thereof is administered in a second pharmaceutical composition; and (c) at least one compound chosen from deutivacaftor and further deuterated derivatives and pharmaceutically acceptable salts thereof is administered in a third pharmaceutical composition.

In some embodiments, (a) at least one compound chosen from compounds of Formula I, compounds of any one of Formulae Ia, I, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in a first pharmaceutical composition; (b) at least one compound chosen from tezacaftor, lumacaftor, and deuterated derivatives and pharmaceutically acceptable salts thereof is administered in a second pharmaceutical composition; (c) at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof is administered in a third pharmaceutical composition.

In some embodiments, (a) at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in a first pharmaceutical composition; and (b) at least one compound chosen from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing is administered in a second pharmaceutical composition.

In some embodiments, (a) at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, is administered in a first pharmaceutical composition; and (b) at least one compound chosen from tezacaftor and pharmaceutically acceptable salts thereof and at least one compound chosen from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts thereof are administered in a second pharmaceutical composition. In some embodiments, the second pharmaceutical composition comprises a half of a daily dose of said at least one compound chosen from ivacaftor and deuterated derivatives and pharmaceutically acceptable salts thereof, and the other half of a daily dose of said at least one compound chosen from ivacaftor and deuterated derivatives and pharmaceutically acceptable salts thereof is administered in a third pharmaceutical composition.

In some embodiments, (a) at least one compound chosen from compounds of Formula I, compounds of any one of Formulae Ia, I, IIb, III, IV, V, VIa, VIb, VIIa, and VIIb, Compounds 1-73, tautomers thereof, deuterated derivatives of those compounds and tautomers, and pharmaceutically acceptable salts of any of the foregoing; (b) at least one compound chosen from tezacaftor and deuterated derivatives and pharmaceutically acceptable salts thereof, and (c) at least one compound chosen from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts thereof are administered in a first pharmaceutical composition. In some embodiments, the first pharmaceutical composition is administered to the patient twice daily. In some embodiments, the first pharmaceutical composition is administered once daily. In some embodiments, the first pharmaceutical composition is administered once daily and a second composition comprising only ivacaftor is administered once daily.

Any suitable pharmaceutical compositions can be used for compounds of Formula I, compounds of any one of Formulae Ia, IIa, IIb, III, IV, V, VIa, VIb, VIIa, and VIIb, Compounds 1-73, tezacaftor, ivacaftor, deutivacaftor, lumacaftor, and tautomers thereof, deuterated derivatives of those compounds and tautomers, and pharmaceutically acceptable salts of any of the foregoing. Some exemplary pharmaceutical compositions for tezacaftor and its pharmaceutically acceptable salts can be found in WO 2011/119984 and WO 2014/014841, both of which are incorporated herein by reference. Some exemplary pharmaceutical compositions for ivacaftor and its pharmaceutically acceptable salts can be found in WO 2007/134279, WO 2010/019239, WO 2011/019413, WO 2012/027731, and WO 2013/130669, all of which are incorporated herein by reference. Some exemplary pharmaceutical compositions for deutivacaftor and its pharmaceutically acceptable salts can be found in U.S. Pat. Nos. 8,865,902, 9,181,192, 9,512,079, WO 2017/053455, and WO 2018/080591, all of which are incorporated herein by reference. Some exemplary pharmaceutical compositions for lumacaftor and its pharmaceutically acceptable salts can be found in WO 2010/037066, WO 2011/127421, and WO 2014/071122, all of which are incorporated herein by reference.

Pharmaceutical Compositions

Another aspect of the disclosure provides a pharmaceutical composition comprising at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, and at least one pharmaceutically acceptable carrier.

In some embodiments, the disclosure provides pharmaceutical compositions comprising at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, in combination with at least one additional active pharmaceutical ingredient. In some embodiments, the at least one additional active pharmaceutical ingredient is a CFTR modulator. In some embodiments, the at least one additional active pharmaceutical ingredient is a CFTR corrector. In some embodiments, the at least one additional active pharmaceutical ingredient is a CFTR potentiator. In some embodiments, the pharmaceutical composition comprises at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, and at least two additional active pharmaceutical ingredients, one of which is a CFTR corrector and one of which is a CFTR potentiator.

In some embodiments, the disclosure provides a pharmaceutical composition comprising (a) at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, (b) at least one compound chosen from tezacaftor, lumacaftor, and deuterated derivatives and pharmaceutically acceptable salts thereof, and (c) at least one pharmaceutically acceptable carrier.

In some embodiments, the disclosure provides a pharmaceutical composition comprising (a) at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, (b) at least one compound chosen from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts thereof, and (c) at least one pharmaceutically acceptable carrier.

In some embodiments, the disclosure provides a pharmaceutical composition comprising (a) at least one compound chosen from compounds of Formula I, compounds of any one of Formulae Ia, I, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, (b) at least one compound chosen from tezacaftor and deuterated derivatives and pharmaceutically acceptable salts thereof, (c) at least one compound chosen from ivacaftor and deuterated derivatives and pharmaceutically acceptable salts thereof, and (d) at least one pharmaceutically acceptable carrier.

In some embodiments, the disclosure provides a pharmaceutical composition comprising (a) at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, (b) at least one compound chosen from tezacaftor and deuterated derivatives and pharmaceutically acceptable salts thereof, (c) at least one compound chosen from deutivacaftor and deuterated derivatives and pharmaceutically acceptable salts thereof, and (d) at least one pharmaceutically acceptable carrier.

In some embodiments, the disclosure provides a pharmaceutical composition comprising (a) at least one compound chosen from compounds of Formula I, compounds of any one of Formulae Ia, IIa, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, (b) at least one compound chosen from tezacaftor and deuterated derivatives and pharmaceutically acceptable salts thereof, (c) at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof, and (d) at least one pharmaceutically acceptable carrier.

In some embodiments, the disclosure provides a pharmaceutical composition comprising (a) at least one compound chosen from compounds of Formula I, compounds of any one of Formulae Ia, I, IIb, III, IV, V, VIa, VIb, VIIa, and VIIb, Compounds 1-73, tautomers thereof, deuterated derivatives of those compounds and tautomers, and pharmaceutically acceptable salts of any of the foregoing, (b) at least one compound chosen from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing, (c) at least one compound chosen from lumacaftor and deuterated derivatives and pharmaceutically acceptable salts thereof, and (d) at least one pharmaceutically acceptable carrier.

Any pharmaceutical composition disclosed herein may comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, and lubricants.

The pharmaceutical compositions described herein are useful for treating cystic fibrosis and other CFTR mediated diseases. The compounds and compositions described herein may be used in the manufacture of medicaments to treat cystic fibrosis and other CFTR mediated diseases.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

Non-Limiting Exemplary Embodiments

A list of non-limiting exemplary embodiments includes:

1. A compound of Formula I:

(I)

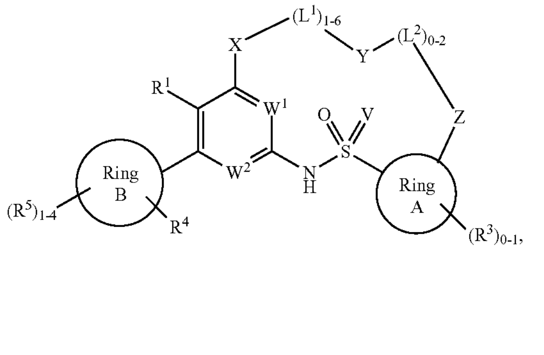

a tautomer thereof, a deuterated derivative of the compound or tautomer, or a pharmaceutically acceptable salt of any of the foregoing, wherein:

Ring A is selected from:
- $C_6$-$C_{10}$ aryl,
- $C_3$-$C_{10}$ cycloalkyl,
- 3- to 10-membered heterocyclyl, and
- 5- to 10-membered heteroaryl;

Ring B is selected from:
- $C_6$-$C_{10}$ aryl,
- $C_3$-$C_{10}$ cycloalkyl,
- 3- to 10-membered heterocyclyl, and
- 5- to 10-membered heteroaryl;

V is selected from O and NH;

$W^1$ is selected from N and CH;

$W^2$ is selected from N and CH, provided that at least one of $W^1$ and $W^2$ is N;

X is selected from $NR^{XN}$ and $C(R^{XC})_2$;

Y is selected from O, $NR^{YN}$, and $C(R^{YC})_2$.

Z is selected from O, $NR^{ZN}$, and $C(R^{ZC})_2$, provided that when $L^2$ is absent, either Y is $C(R^{YC})_2$ or Z is $C(R^{ZC})_2$;

each $L^1$ is independently selected from $C(R^{L1})_2$ and

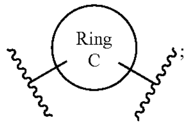;

each $L^2$ is independently selected from $C(R^{L2})_2$;

Ring C is selected from $C_6$-$C_{10}$ aryl optionally substituted with 1-3 groups independently selected from:
- halogen,
- $C_1$-$C_6$ alkyl, and
- $N(R^N)_2$;

$R^1$ is selected from:
- hydrogen,
- halogen,
- cyano,
- $C_1$-$C_6$ alkyl optionally substituted with 1-3 groups independently selected from hydroxyl, oxo, and $N(R^N)_2$,
- $C_1$-$C_6$ alkoxy,
- $C_1$-$C_6$ fluoroalkyl,
- $C_6$-$C_{10}$ aryl optionally substituted with 1-3 groups independently selected from $C_1$-$C_6$ alkoxy,
- 3- to 10-membered heterocyclyl optionally substituted with 1-3 groups independently selected from $R^N$, and
- 5- to 10-membered heteroaryl optionally substituted with 1-3 groups independently selected from $C_1$-$C_6$ alkyl;

each $R^3$ is independently selected from:
- halogen,
- $C_1$-$C_6$ alkyl,
- $C_1$-$C_6$ alkoxy,
- $C_3$-$C_{10}$ cycloalkyl,
- $C_6$-$C_{10}$ aryl optionally substituted with 1-3 groups independently selected from $C_1$-$C_6$ alkyl, and
- 3- to 10-membered heterocyclyl;

$R^4$ is selected from hydrogen and $C_1$-$C_6$ alkyl;

each $R^5$ is independently selected from:
- hydrogen,
- halogen, hydroxyl,
$N(R^N)_2$,
—SO-Me,
—CH═C($R^{LC}$)$_2$, wherein both $R^LC$ are taken together to form a $C_3$-$C_{10}$ cycloalkyl,
$C_1$-$C_6$ alkyl optionally substituted with 1-3 groups independently selected from:
hydroxyl,
$C_1$-$C_6$ alkoxy optionally substituted with 1-3 groups independently selected from $C_1$-$C_6$ alkoxy and $C_6$-$C_{10}$ aryl,
$C_3$-$C_{10}$ cycloalkyl,
—$(O)_{0-1}$—($C_6$-$C_{10}$ aryl) optionally substituted with 1-3 groups independently selected from $C_1$-$C_6$ alkyl and $C_1$-$C_6$ alkoxy,
3- to 10-membered heterocyclyl, and
$N(R^N)_2$,
$C_1$-$C_6$ alkoxy optionally substituted with 1-3 groups independently selected from:
halogen,
$C_6$-$C_{10}$ aryl, and
$C_3$-$C_{10}$ cycloalkyl optionally substituted with 1-3 groups independently selected from $C_1$-$C_6$ fluoroalkyl,
$C_1$-$C_6$ fluoroalkyl,
$C_3$-$C_{10}$ cycloalkyl,
$C_6$-$C_{10}$ aryl, and
3- to 10-membered heterocyclyl;
each $R^{XN}$, $R^{YN}$, and $R^{ZN}$ is independently selected from:
hydrogen,
$C_1$-$C_9$ alkyl optionally substituted with 1-3 groups independently selected from:
hydroxyl,
oxo,
cyano,
$C_1$-$C_6$ alkoxy optionally substituted with 1-3 groups independently selected from halogen and $C_1$-$C_6$ alkoxy,
$N(R^N)_2$,
$SO_2Me$,
$C_3$-$C_{10}$ cycloalkyl optionally substituted with 1-3 groups independently selected from:
hydroxyl,
$C_1$-$C_6$ alkyl optionally substituted with 1-3 groups independently selected from hydroxyl, oxo, $C_1$-$C_6$ alkoxy, $C_6$-$C_{10}$ aryl, and $N(R^N)_2$,
$C_1$-$C_6$ fluoroalkyl,
$C_1$-$C_6$ alkoxy,
COOH,
$N(R^N)_2$,
$C_6$-$C_{10}$ aryl, and
3- to 10-membered heterocyclyl optionally substituted with 1-3 groups independently selected from oxo and $C_1$-$C_6$ alkyl,
$C_6$-$C_{10}$ aryl optionally substituted with 1-3 groups independently selected from:
halogen,
hydroxyl,
cyano,
$SiMe_3$,
$SO_2Me$,
$SF_5$,
$N(R^N)_2$,
$P(O)Me_2$,
—$(O)_{0-1}$—($C_3$-$C_{10}$ cycloalkyl) optionally substituted with 1-3 groups independently selected from $C_1$-$C_6$ fluoroalkyl,
$C_1$-$C_6$ alkyl optionally substituted with 1-3 groups independently selected from hydroxyl, oxo, $C_1$-$C_6$ alkoxy, 5- to 10-membered heteroaryl, $SO_2Me$, and $N(R^N)_2$,
$C_1$-$C_6$ alkoxy optionally substituted with 1-3 groups independently selected from hydroxyl, oxo, $N(R^N)_2$, and $C_6$-$C_{10}$ aryl,
$C_1$-$C_6$ fluoroalkyl,
3- to 10-membered heterocyclyl optionally substituted with 1-3 groups independently selected from $C_1$-$C_6$ alkyl,
—$(O)_{0-1}$—($C_6$-$C_{10}$ aryl), and
—$(O)_{0-1}$-(5- to 10-heteroaryl) optionally substituted with hydroxyl, oxo, $N(R^N)_2$, $C_1$-$C_6$ alkyl, $C_1$-$C_6$ alkoxy, $C_1$-$C_6$ fluoroalkyl, and $C_3$-$C_{10}$ cycloalkyl,
3- to 10-membered heterocyclyl optionally substituted with 1-4 groups independently selected from:
hydroxyl,
oxo,
$N(R^N)_2$,
$C_1$-$C_6$ alkyl optionally substituted with 1-3 groups independently selected from oxo and $C_1$-$C_6$ alkoxy,
$C_1$-$C_6$ alkoxy,
$C_1$-$C_6$ fluoroalkyl,
$C_6$-$C_{10}$ aryl optionally substituted with 1-3 groups independently selected from halogen, and
5- to 10-membered heteroaryl, and
5- to 10-membered heteroaryl optionally substituted with 1-3 groups independently selected from:
hydroxyl,
cyano,
oxo,
halogen,
$B(OH)_2$,
$N(R^N)_2$,
$C_1$-$C_6$ alkyl optionally substituted with 1-3 groups independently selected from hydroxyl, oxo, $C_1$-$C_6$ alkoxy (optionally substituted with 1-3-$SiMe_3$), and $N(R^N)_2$,
$C_1$-$C_6$ alkoxy optionally substituted with 1-3 groups independently selected from hydroxyl, oxo, $C_1$-$C_6$ alkoxy, $N(R^N)_2$, and $C_3$-$C_{10}$ cycloalkyl,
$C_1$-$C_6$ fluoroalkyl,
—$(O)_{0-1}$—($C_3$-$C_{10}$ cycloalkyl) optionally substituted with 1-3 groups independently selected from $C_1$-$C_6$ alkyl,
—$(O)_{0-1}$—($C_6$-$C_{10}$ aryl),
—$(O)_{0-1}$-(3- to 10-membered heterocyclyl) optionally substituted with 1-4 groups independently selected from hydroxyl, oxo, halogen, cyano, $N(R^N)_2$, $C_1$-$C_6$ alkyl (optionally substituted with 1-3 groups independently selected from hydroxyl, oxo, $N(R^N)_2$, and $C_1$-$C_6$ alkoxy), $C_1$-$C_6$ alkoxy, $C_1$-$C_6$ fluoroalkyl, 3- to 10-membered heterocyclyl (optionally substituted with 1-3 groups independently selected from $C_1$-$C_6$ fluoroalkyl), and
5- to 10-membered heteroaryl optionally substituted with 1-4 groups independently selected from $C_1$-$C_6$ alkyl and $C_3$-$C_{10}$ cycloalkyl, $C_1$-$C_6$ fluoroalkyl,
$C_3$-$C_{10}$ cycloalkyl optionally substituted with 1-3 groups independently selected from:
hydroxyl,
oxo,
halogen,
cyano,
$N(R^N)_2$,
$C_1$-$C_6$ alkyl optionally substituted with 1-3 groups independently selected from:
hydroxyl,
oxo,
$N(R^N)_2$,
$C_1$-$C_6$ alkoxy, and
$C_6$-$C_{10}$ aryl,
$C_1$-$C_6$ alkoxy optionally substituted with 1-3 groups independently selected from halogen, oxo, $C_6$-$C_{10}$ aryl, and $N(R^N)_2$,
halogen,
$C_3$-$C_{10}$ cycloalkyl,
3- to 10-member heterocyclyl optionally substituted with 1-3 groups independently selected from $C_1$-$C_6$ alkyl,
5- to 10-membered heteroaryl optionally substituted with 1-3 groups independently selected from:
hydroxyl,
cyano,
oxo,
halogen,
$N(R^N)_2$,
$C_1$-$C_6$ alkyl optionally substituted with 1-3 groups independently selected from hydroxyl, oxo, $C_1$-$C_6$ alkoxy, and $N(R^N)_2$,
$C_1$-$C_6$ alkoxy optionally substituted with 1-3 groups independently selected from hydroxyl, $C_1$-$C_6$ alkoxy, $N(R^N)_2$, and $C_3$-$C_{10}$ cycloalkyl,
$C_1$-$C_6$ fluoroalkyl,
—$(O)_{0-1}$—($C_3$-$C_{10}$ cycloalkyl) optionally substituted with 1-3 groups independently selected from $C_1$-$C_6$ alkyl,
$C_6$-$C_{10}$ aryl, and
3- to 10-membered heterocyclyl optionally substituted with 1-3 groups independently selected from $C_1$-$C_6$ alkyl,
$C_6$-$C_{10}$ aryl,
3- to 10-membered heterocyclyl optionally substituted with 1-3 groups independently selected from:
oxo,
$C_1$-$C_6$ alkyl optionally substituted with 1-3 groups independently selected from:
oxo,
hydroxyl,
$N(R^N)_2$,
$C_1$-$C_6$ alkoxy optionally substituted with 1-3 groups independently selected from halogen and $C_6$-$C_{10}$ aryl, and
—$(O)_{0-1}$—($C_3$-$C_{10}$ cycloalkyl),
$C_1$-$C_6$ fluoroalkyl,
$C_3$-$C_{10}$ cycloalkyl optionally substituted with 1-3 groups independently selected from halogen, and
3- to 10-membered heterocyclyl,
5- to 10-membered heteroaryl optionally substituted with 1-3 groups independently selected from:
halogen, $C_1$-$C_6$ alkyl optionally substituted with 1-3 groups independently selected from oxo, $C_1$-$C_6$ alkoxy, and $N(R^N)_2$, and
3- to 10-membered heterocyclyl optionally substituted with 1-3 groups independently selected from $C_1$-$C_6$ alkyl (optionally substituted with 1-3 groups selected from oxo, $C_1$-$C_6$ alkoxy, and $C_6$-$C_{10}$ aryl), and
$R^F$;
each $R^{XC}$, $R^{YC}$, and $R^{ZC}$ is independently selected from:
hydrogen,
$C_1$-$C_6$ alkyl optionally substituted with 1-3 groups independently selected from $C_6$-$C_{10}$ aryl (optionally substituted with 1-3 groups independently selected from $C_1$-$C_6$ alkyl),
$C_6$-$C_{10}$ aryl optionally substituted with 1-3 groups independently selected from $C_1$-$C_6$ alkyl, and
$R^F$;
or two $R^{XC}$ are taken together to form a group selected from oxo and $C_3$-$C_{10}$ cycloalkyl;
or two $R^{YC}$ are taken together to form an oxo group;
or two $R^{ZC}$ are taken together to form an oxo group;
each $R^{L1}$ is independently selected from:
hydrogen,
$N(R^N)_2$, provided that two $N(R^N)_2$ are not bonded to the same carbon,
$C_1$-$C_9$ alkyl optionally substituted with 1-3 groups independently selected from:
halogen,
hydroxyl,
oxo,
$N(R^N)_2$,
$C_1$-$C_6$ alkoxy optionally substituted with 1-3 groups independently selected from $C_6$-$C_{10}$ aryl,
$C_3$-$C_{10}$ cycloalkyl optionally substituted with 1-3 groups independently selected from halogen and $C_1$-$C_6$ fluoroalkyl,
$C_6$-$C_{10}$ aryl optionally substituted with 1-3 groups independently selected from $C_1$-$C_6$ alkyl, and
3- to 10-membered heterocyclyl optionally substituted with 1-3 groups independently selected from $C_1$-$C_6$ alkyl (optionally substituted with 1-3 groups independently selected from hydroxyl and oxo),
$C_3$-$C_{10}$ cycloalkyl,
$C_6$-$C_{10}$ aryl optionally substituted with 1-4 groups independently selected from:
halogen,
cyano,
$SiMe_3$,
$POMe_2$,
$C_1$-$C_7$ alkyl optionally substituted with 1-3 groups independently selected from:
hydroxyl,
oxo,
cyano,
$SiMe_3$,
$N(R^N)_2$, and
$C_3$-$C_{10}$ cycloalkyl optionally substituted with 1-3 groups independently selected from $C_1$-$C_6$ fluoroalkyl,
$C_1$-$C_6$ alkoxy optionally substituted with 1-3 groups independently selected from:
$C_3$-$C_{10}$ cycloalkyl optionally substituted with 1-3 groups independently selected from $C_1$-$C_6$ fluoroalkyl, and $C_1$-$C_6$ alkoxy,
$C_1$-$C_6$ fluoroalkyl,
$C_3$-$C_{10}$ cycloalkyl optionally substituted with 1-3 groups independently selected from $C_1$-$C_6$ alkyl and $C_1$-$C_6$ fluoroalkyl,
$C_6$-$C_{10}$ aryl,
3- to 10-membered heterocyclyl optionally substituted with 1-3 groups independently selected from $C_1$-$C_6$ alkyl, and
5- to 10-membered heteroaryl,
3- to 10-membered heterocyclyl optionally substituted with 1-3 groups independently selected from:
$C_1$-$C_6$ alkyl optionally substituted with 1-3 groups independently selected from:
oxo, and
$C_1$-$C_6$ alkoxy,
5- to 10-membered heteroaryl optionally substituted with 1-3 groups independently selected from:
$C_1$-$C_6$ alkyl optionally substituted with 1-3 groups independently selected from:
$C_3$-$C_{10}$ cycloalkyl optionally substituted with 1-3 groups independently selected from $C_1$-$C_6$ fluoroalkyl, and
$C_6$-$C_{10}$ aryl optionally substituted with 1-3 groups independently selected from $C_1$-$C_6$ alkyl, and
$R^F$;
or two $R^{L1}$ on the same carbon atom are taken together to form an oxo group;
each $R^{L2}$ is independently selected from hydrogen and $R^F$; or two $R^{L2}$ on the same carbon atom are taken together to form an oxo group;
each $R^N$ is independently selected from:
hydrogen,
$C_1$-$C_8$ alkyl optionally substituted with 1-3 groups independently selected from:
oxo,
halogen,
hydroxyl,
$NH_2$,
NHMe,
$NMe_2$,
$C_1$-$C_6$ alkoxy optionally substituted with 1-3 groups independently selected from $C_6$-$C_{10}$ aryl,
—$(O)_{0-1}$—($C_3$-$C_{10}$ cycloalkyl),
$C_6$-$C_{10}$ aryl optionally substituted with 1-3 groups independently selected from halogen and $C_1$-$C_6$ alkyl,
3- to 14-membered heterocyclyl optionally substituted with 1-4 groups independently selected from oxo and $C_1$-$C_6$ alkyl, and
5- to 14-membered heteroaryl optionally substituted with 1-4 groups independently selected from oxo and $C_1$-$C_6$ alkyl,
$C_3$-$C_{10}$ cycloalkyl optionally substituted with 1-3 groups independently selected from:
hydroxyl,
$NH_2$, and
NHMe, and
$C_1$-$C_6$ alkyl optionally substituted with 1-3 groups independently selected from hydroxyl,
$C_6$-$C_{10}$ aryl, and
3- to 10-membered heterocyclyl;
or two $R^N$ on the same nitrogen atom are taken together with the nitrogen to which they are bonded to form a 3- to 10-membered heterocyclyl optionally substituted with 1-3 groups selected from:
hydroxyl,
oxo,
cyano,
$C_1$-$C_6$ alkyl optionally substituted with 1-3 groups independently selected from oxo, hydroxyl, $C_1$-$C_6$ alkoxy, and $N(R^{N2})_2$, wherein each $R^{N2}$ is independently selected from hydrogen and $C_1$-$C_6$ alkyl,
$C_1$-$C_6$ alkoxy, and
$C_1$-$C_6$ fluoroalkyl;
or one $R^4$ and one $R^{L1}$ are taken together to form a $C_6$-$C_8$ alkylene;
when $R^F$ is present, two $R^F$ taken together with the atoms to which they are bonded form a group selected from:
$C_3$-$C_{10}$ cycloalkyl optionally substituted with 1-3 groups independently selected from $C_1$-$C_6$ alkyl,
$C_6$-$C_{10}$ aryl optionally substituted with 1-3 groups independently selected from:
halogen,
$C_1$-$C_6$ alkyl,
$N(R^N)_2$, and
3- to 10-membered heterocyclyl optionally substituted with 1-3 groups independently selected from hydroxyl,
3- to 11-membered heterocyclyl optionally substituted with 1-3 groups independently selected from:
oxo,
$N(R^N)_2$,
$C_1$-$C_9$ alkyl optionally substituted with 1-4 groups independently selected from:
oxo,
halogen,
hydroxyl,
$N(R^N)_2$,
—$SO_2$—($C_1$-$C_6$ alkyl),
$C_1$-$C_6$ alkoxy optionally substituted with 1-3 groups independently selected from halogen,
$C_6$-$C_{10}$ aryl,
$C_6$-$C_{10}$ aryl optionally substituted with 1-3 groups independently selected from hydroxyl, halogen, cyano, $C_1$-$C_6$ alkyl (optionally substituted with 1-3 groups independently selected from oxo and $C_1$-$C_6$ alkoxy), $C_1$-$C_6$ alkoxy (optionally substituted with 1-3 groups independently selected from $C_6$-$C_{10}$ aryl), —$(O)_{0-1}$—($C_1$-$C_6$ fluoroalkyl), and $C_6$-$C_{10}$ aryl (optionally substituted with 1-3 groups independently selected from $C_1$-$C_6$ alkoxy),
—$(O)_{0-1}$—($C_3$-$C_{10}$ cycloalkyl) optionally substituted with 1-4 groups independently selected from hydroxyl, halogen, $N(R^N)_2$, $C_1$-$C_6$ alkyl (optionally substituted with 1-3 groups independently selected from oxo, hydroxyl, and $C_1$-$C_6$ alkoxy), $C_1$-$C_6$ fluoroalkyl, and $C_6$-$C_{10}$ aryl,
3- to 10-membered heterocyclyl optionally substituted with 1-3 groups independently selected from oxo, $C_1$-$C_6$ alkyl (optionally substituted with 1-3 groups independently selected from $C_6$-$C_{10}$ aryl (optionally substituted with 1-3 groups independently selected from halogens)), $C_1$-$C_6$ alkoxy, $C_3$-$C_{10}$ cycloalkyl, and $R^N$, O-(5- to 12-membered heteroaryl) optionally substituted with 1-3 groups independently selected from $C_6$-$C_{10}$ aryl (optionally substituted with 1-3 groups independently selected from halogen) and $C_1$-$C_6$ alkyl, and
5- to 10-membered heteroaryl optionally substituted with 1-3 groups independently selected from hydroxyl, oxo, $N(R^N)_2$, $C_1$-$C_6$ alkyl (optionally substituted with 1-3 groups independently selected from cyano), $C_1$-$C_6$ alkoxy, —$(O)_{0-1}$—($C_1$-$C_6$ fluoroalkyl), —O—($C_6$-$C_{10}$ aryl), and $C_3$-$C_{10}$ cycloalkyl,
$C_3$-$C_{12}$ cycloalkyl optionally substituted with 1-4 groups independently selected from halogen, $C_1$-$C_6$ alkyl, and $C_1$-$C_6$ fluoroalkyl,
$C_6$-$C_{10}$ aryl,
3- to 10-membered heterocyclyl, and
5- to 10-membered heteroaryl optionally substituted with 1-3 groups independently selected from $C_1$-$C_6$ alkoxy and $C_1$-$C_6$ fluoroalkyl, and
5- to 12-membered heteroaryl optionally substituted with 1-3 groups independently selected from $C_1$-$C_6$ alkyl and $C_1$-$C_6$ fluoroalkyl.

2. The compound, tautomer, deuterated derivative, or pharmaceutically acceptable salt according to embodiment 1, wherein Ring A is selected from selected from $C_6$-$C_{10}$ aryl and 5- to 10-membered heteroaryl.
3. The compound, tautomer, deuterated derivative, or pharmaceutically acceptable salt according to embodiment 1 or 2, wherein Ring A is selected from phenyl and pyridinyl.
4. The compound, tautomer, deuterated derivative, or pharmaceutically acceptable salt according to any one of embodiments 1 to 3, wherein Ring A is phenyl.
5. The compound, tautomer, deuterated derivative, or pharmaceutically acceptable salt according to any one of embodiments 1 to 4, wherein Ring B is selected from $C_6$-$C_{10}$ aryl.
6. The compound, tautomer, deuterated derivative, or pharmaceutically acceptable salt according to any one of embodiments 1 to 5, wherein Ring B is phenyl.
7. The compound, tautomer, deuterated derivative, or pharmaceutically acceptable salt according to any one of embodiments 1 to 6, wherein V is O.
8. The compound, tautomer, deuterated derivative, or pharmaceutically acceptable salt according to any one of embodiments 1 to 7, wherein $W^1$ is N and $W^2$ is N.
9. The compound, tautomer, deuterated derivative, or pharmaceutically acceptable salt according to any one of embodiments 1 to 7, wherein $W^1$ is CH and $W^2$ is N.
10. The compound, tautomer, deuterated derivative, or pharmaceutically acceptable salt according to any one of embodiments 1 to 9, wherein X is $NR^{XN}$.
11. The compound, tautomer, deuterated derivative, or pharmaceutically acceptable salt according to any one of embodiments 1 to 9, wherein X is $C(R^{XC})_2$.
12. The compound, tautomer, deuterated derivative, or pharmaceutically acceptable salt according to any one of embodiments 1 to 11, wherein Z is selected from $NR^{ZN}$, and $C(R^{ZC})_2$, provided that when $L^2$ is absent, either Y is $C(R^{YC})_2$ or Z is $C(R^{ZC})_2$.
13. The compound, tautomer, deuterated derivative, or pharmaceutically acceptable salt according to any one of embodiments 1 to 12, wherein Ring C is a phenyl optionally substituted with 1-3 groups independently selected from:
halogen,
$C_1$-$C_6$ alkyl, and
$N(R^N)_2$.
14. The compound, tautomer, deuterated derivative, or pharmaceutically acceptable salt according to any one of embodiments 1 to 13, wherein $R^1$ is selected from hydrogen, halogen, and $C_1$-$C_6$ alkyl.
15. The compound, tautomer, deuterated derivative, or pharmaceutically acceptable salt according to any one of embodiments 1 to 14, wherein $R^3$ is absent.
16. The compound, tautomer, deuterated derivative, or pharmaceutically acceptable salt according to any one of embodiments 1 to 15, wherein $R^4$ is selected from hydrogen and methyl.
17. The compound, tautomer, deuterated derivative, or pharmaceutically acceptable salt according to any one of embodiments 1 to 16, wherein $R^4$ is methyl.
18. The compound, tautomer, deuterated derivative, or pharmaceutically acceptable salt according to any one of embodiments 1 to 17, wherein each $R^5$ is independently selected from hydrogen and $C_1$-$C_6$ alkyl.
19. The compound, tautomer, deuterated derivative, or pharmaceutically acceptable salt according to any one of embodiments 1 to 18, wherein $R^{XN}$ is selected from:
hydrogen,
$C_1$-$C_9$ alkyl optionally substituted with 1-3 groups independently selected from:
hydroxyl,
$C_6$-$C_{10}$ aryl optionally substituted with 1-3 groups independently selected from $C_1$-$C_6$ alkyl (optionally substituted with 1-3 groups independently selected from hydroxyl), and
5- to 10-membered heteroaryl optionally substituted with 1-3 groups independently selected from $C_1$-$C_6$ alkyl and $C_1$-$C_6$ fluoroalkyl,
$C_3$-$C_{10}$ cycloalkyl optionally substituted with 1-3 groups independently selected from $N(R^N)_2$,
3- to 10-membered heterocyclyl optionally substituted with 1-3 groups independently selected from $C_1$-$C_6$ alkyl (optionally substituted with 1-3 groups independently selected from $C_1$-$C_6$ alkoxy),
5- to 10-membered heteroaryl optionally substituted with 1-3 groups independently selected from $C_1$-$C_6$ alkyl, and
$R^F$.
20. The compound, tautomer, deuterated derivative, or pharmaceutically acceptable salt according to any one of embodiments 1 to 19, wherein $R^{YN}$ is selected from:
hydrogen,
$C_1$-$C_9$ alkyl optionally substituted with 1-3 groups independently selected from:
hydroxyl,
$C_6$-$C_{10}$ aryl optionally substituted with 1-3 groups independently selected from $C_1$-$C_6$ alkyl (optionally substituted with 1-3 groups independently selected from hydroxyl), and
5- to 10-membered heteroaryl optionally substituted with 1-3 groups independently selected from $C_1$-$C_6$ alkyl and $C_1$-$C_6$ fluoroalkyl,
$C_3$-$C_{10}$ cycloalkyl optionally substituted with 1-3 groups independently selected from $N(R^N)_2$,
3- to 10-membered heterocyclyl optionally substituted with 1-3 groups independently selected from $C_1$-$C_6$ alkyl (optionally substituted with 1-3 groups independently selected from $C_1$-$C_6$ alkoxy),
5- to 10-membered heteroaryl optionally substituted with 1-3 groups independently selected from $C_1$-$C_6$ alkyl, and
$R^F$.

21. The compound, tautomer, deuterated derivative, or pharmaceutically acceptable salt according to any one of embodiments 1 to 20, wherein $R^{ZN}$ is selected from:
hydrogen,
$C_1$-$C_9$ alkyl optionally substituted with 1-3 groups independently selected from:
hydroxyl,
$C_6$-$C_{10}$ aryl optionally substituted with 1-3 groups independently selected from $C_1$-$C_6$ alkyl (optionally substituted with 1-3 groups independently selected from hydroxyl), and
5- to 10-membered heteroaryl optionally substituted with 1-3 groups independently selected from $C_1$-$C_6$ alkyl and $C_1$-$C_6$ fluoroalkyl,
$C_3$-$C_{10}$ cycloalkyl optionally substituted with 1-3 groups independently selected from $N(R^N)_2$,
3- to 10-membered heterocyclyl optionally substituted with 1-3 groups independently selected from $C_1$-$C_6$ alkyl (optionally substituted with 1-3 groups independently selected from $C_1$-$C_6$ alkoxy),
5- to 10-membered heteroaryl optionally substituted with 1-3 groups independently selected from $C_1$-$C_6$ alkyl, and
$R^F$.
22. The compound, tautomer, deuterated derivative, or pharmaceutically acceptable salt according to any one of embodiments 1 to 21, wherein $R^{XC}$ is selected from:
hydrogen,
$C_1$-$C_6$ alkyl optionally substituted with 1-3 groups independently selected from $C_6$-$C_{10}$ aryl (optionally substituted with 1-3 groups independently selected from $C_1$-$C_6$ alkyl), and
$C_6$-$C_{10}$ aryl optionally substituted with 1-3 groups independently selected from $C_1$-$C_6$ alkyl, or two $R^{XC}$ are taken together to form a group selected from $C_3$-$C_{10}$ cycloalkyl.
23. The compound, tautomer, deuterated derivative, or pharmaceutically acceptable salt according to any one of embodiments 1 to 21, wherein $R^{YC}$ is selected from:
hydrogen,
$C_1$-$C_6$ alkyl optionally substituted with 1-3 groups independently selected from $C_6$-$C_{10}$ aryl (optionally substituted with 1-3 groups independently selected from $C_1$-$C_6$ alkyl), and
$C_6$-$C_{10}$ aryl optionally substituted with 1-3 groups independently selected from $C_1$-$C_6$ alkyl,
or two $R^{YC}$ are taken together to form an oxo group.
24. The compound, tautomer, deuterated derivative, or pharmaceutically acceptable salt according to any one of embodiments 1 to 21, wherein $R^{ZC}$ is selected from:
hydrogen,
$C_1$-$C_6$ alkyl optionally substituted with 1-3 groups independently selected from $C_6$-$C_{10}$ aryl (optionally substituted with 1-3 groups independently selected from $C_1$-$C_6$ alkyl), and
$C_6$-$C_{10}$ aryl optionally substituted with 1-3 groups independently selected from $C_1$-$C_6$ alkyl,
or two $R^{ZC}$ are taken together to form an oxo group.
25. The compound, tautomer, deuterated derivative, or pharmaceutically acceptable salt according to any one of embodiments 1 to 24, wherein each $R^{L1}$ is independently selected from:
hydrogen,
$C_1$-$C_9$ alkyl optionally substituted with 1-3 groups independently selected from $C_3$-$C_{10}$ cycloalkyl (optionally substituted with 1-3 groups independently selected from $C_1$-$C_6$ fluoroalkyl),
$C_6$-$C_{10}$ aryl optionally substituted with 1-4 groups independently selected from $C_1$-$C_7$ alkyl,
5- to 10-membered heteroaryl optionally substituted with 1-3 groups independently selected from $C_1$-$C_6$ alkyl, and
$R^F$;
or two $R^{L1}$ on the same carbon atom are taken together to form an oxo group.
26. The compound, tautomer, deuterated derivative, or pharmaceutically acceptable salt according to any one of embodiments 1 to 25, wherein each $R^{L2}$ is hydrogen.
27. The compound, tautomer, deuterated derivative, or pharmaceutically acceptable salt according to any one of embodiments 1 to 26, wherein each $R^N$ is independently selected from hydrogen and $C_1$-$C_8$ alkyl.
28. The compound, tautomer, deuterated derivative, or pharmaceutically acceptable salt according to any one of embodiments 1 to 27, wherein when $R^F$ is present, two $R^F$ taken together with the atoms to which they are bonded form a group selected from:
$C_6$-$C_{10}$ aryl, and
5- to 12-membered heteroaryl optionally substituted with 1-3 groups independently selected from $C_1$-$C_6$ alkyl.
29. A compound of Formula Ia:

(Ia)

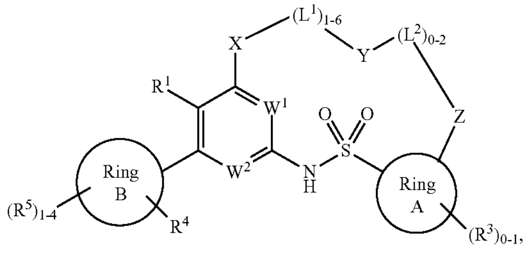

a tautomer thereof, a deuterated derivative of the compound or tautomer, or a pharmaceutically acceptable salt of any of the foregoing, wherein Ring A, Ring B, $W^1$, $W^2$, X, Y, Z, $L^1$, $L^2$, $R^1$, $R^3$, $R^4$, and $R^5$ are defined as according to embodiment 1.
30. The compound, tautomer, deuterated derivative, or pharmaceutically acceptable salt according to embodiment 29, wherein Ring A is selected from selected from $C_6$-$C_{10}$ aryl and 5- to 10-membered heteroaryl.
31. The compound, tautomer, deuterated derivative, or pharmaceutically acceptable salt according to embodiment 29 or 30, wherein Ring A is selected from phenyl and pyridyl.
32. The compound, tautomer, deuterated derivative, or pharmaceutically acceptable salt according to embodiment 30 or 31, wherein Ring A is phenyl.
33. The compound, tautomer, deuterated derivative, or pharmaceutically acceptable salt according to any one of embodiments 30 to 32, wherein Ring B is selected from $C_6$-$C_{10}$ aryl.
34. The compound, tautomer, deuterated derivative, or pharmaceutically acceptable salt according to any one of embodiments 30 to 33, wherein Ring B is phenyl.
35. The compound, tautomer, deuterated derivative, or pharmaceutically acceptable salt according to any one of embodiments 30 to 34, wherein $W^1$ is N and $W^2$ is N.

36. The compound, tautomer, deuterated derivative, or pharmaceutically acceptable salt according to any one of embodiments 30 to 34, wherein $W^1$ is CH and $W^2$ is N.
37. The compound, tautomer, deuterated derivative, or pharmaceutically acceptable salt according to any one of embodiments 30 to 36, wherein X is $NR^{XN}$.
38. The compound, tautomer, deuterated derivative, or pharmaceutically acceptable salt according to any one of embodiments 30 to 36, wherein X is $C(R^{XC})_2$
39. The compound, tautomer, deuterated derivative, or pharmaceutically acceptable salt according to any one of embodiments 30 to 38, wherein Z is selected from $NR^{ZN}$, and $C(R^{ZC})_2$, provided that when $L^2$ is absent, either Y is $C(R^{YC})_2$ or Z is $C(R^{ZC})_2$.
40. The compound, tautomer, deuterated derivative, or pharmaceutically acceptable salt according to any one of embodiments 30 to 39, wherein Ring C is a phenyl optionally substituted with 1-3 groups independently selected from:
    halogen,
    $C_1$-$C_6$ alkyl, and
    $N(R^N)_2$.
41. The compound, tautomer, deuterated derivative, or pharmaceutically acceptable salt according to any one of embodiments 30 to 40, wherein $R^1$ is selected from hydrogen, halogen, and $C_1$-$C_6$ alkyl.
42. The compound, tautomer, deuterated derivative, or pharmaceutically acceptable salt according to any one of embodiments 30 to 41, wherein $R^3$ is absent.
43. The compound, tautomer, deuterated derivative, or pharmaceutically acceptable salt according to any one of embodiments 30 to 42, wherein $R^4$ is selected from hydrogen and methyl.
44. The compound, tautomer, deuterated derivative, or pharmaceutically acceptable salt according to any one of embodiments 30 to 43, wherein $R^4$ is methyl.
45. The compound, tautomer, deuterated derivative, or pharmaceutically acceptable salt according to any one of embodiments 30 to 44, wherein each $R^5$ is independently selected from hydrogen and $C_1$-$C_6$ alkyl.
46. The compound, tautomer, deuterated derivative, or pharmaceutically acceptable salt according to any one of embodiments 30 to 45, wherein $R^{XN}$ is selected from:
    hydrogen,
    $C_1$-$C_9$ alkyl optionally substituted with 1-3 groups independently selected from:
        hydroxyl,
        $C_6$-$C_{10}$ aryl optionally substituted with 1-3 groups independently selected from $C_1$-$C_6$ alkyl (optionally substituted with 1-3 groups independently selected from hydroxyl), and
        5- to 10-membered heteroaryl optionally substituted with 1-3 groups independently selected from $C_1$-$C_6$ alkyl and $C_1$-$C_6$ fluoroalkyl,
    $C_3$-$C_{10}$ cycloalkyl optionally substituted with 1-3 groups independently selected from $N(R^N)_2$,
    3- to 10-membered heterocyclyl optionally substituted with 1-3 groups independently selected from $C_1$-$C_6$ alkyl (optionally substituted with 1-3 groups independently selected from $C_1$-$C_6$ alkoxy),
    5- to 10-membered heteroaryl optionally substituted with 1-3 groups independently selected from $C_1$-$C_6$ alkyl, and
    $R^F$.
47. The compound, tautomer, deuterated derivative, or pharmaceutically acceptable salt according to any one of embodiments 30 to 46, wherein $R^{YN}$ is selected from:
    hydrogen,
    $C_1$-$C_9$ alkyl optionally substituted with 1-3 groups independently selected from:
        hydroxyl,
        $C_6$-$C_{10}$ aryl optionally substituted with 1-3 groups independently selected from $C_1$-$C_6$ alkyl (optionally substituted with 1-3 groups independently selected from hydroxyl), and
        5- to 10-membered heteroaryl optionally substituted with 1-3 groups independently selected from $C_1$-$C_6$ alkyl and $C_1$-$C_6$ fluoroalkyl,
    $C_3$-$C_{10}$ cycloalkyl optionally substituted with 1-3 groups independently selected from $N(R^N)_2$,
    3- to 10-membered heterocyclyl optionally substituted with 1-3 groups independently selected from $C_1$-$C_6$ alkyl (optionally substituted with 1-3 groups independently selected from $C_1$-$C_6$ alkoxy),
    5- to 10-membered heteroaryl optionally substituted with 1-3 groups independently selected from $C_1$-$C_6$ alkyl, and
    $R^F$.
48. The compound, tautomer, deuterated derivative, or pharmaceutically acceptable salt according to any one of embodiments 30 to 47, wherein $R^{ZN}$ is selected from:
    hydrogen,
    $C_1$-$C_9$ alkyl optionally substituted with 1-3 groups independently selected from:
        hydroxyl,
        $C_6$-$C_{10}$ aryl optionally substituted with 1-3 groups independently selected from $C_1$-$C_6$ alkyl (optionally substituted with 1-3 groups independently selected from hydroxyl), and
        5- to 10-membered heteroaryl optionally substituted with 1-3 groups independently selected from $C_1$-$C_6$ alkyl and $C_1$-$C_6$ fluoroalkyl,
    $C_3$-$C_{10}$ cycloalkyl optionally substituted with 1-3 groups independently selected from $N(R^N)_2$,
    3- to 10-membered heterocyclyl optionally substituted with 1-3 groups independently selected from $C_1$-$C_6$ alkyl (optionally substituted with 1-3 groups independently selected from $C_1$-$C_6$ alkoxy),
    5- to 10-membered heteroaryl optionally substituted with 1-3 groups independently selected from $C_1$-$C_6$ alkyl, and
    $R^F$.
49. The compound, tautomer, deuterated derivative, or pharmaceutically acceptable salt according to any one of embodiments 30 to 48, wherein $R^{XC}$ is selected from:
    hydrogen,
    $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and
    $C_6$-$C_{10}$ aryl optionally substituted with 1-3 groups independently selected from $C_1$-$C_6$ alkyl,
    or two $R^{XC}$ are taken together to form a group selected from $C_3$-$C_{10}$ cycloalkyl.
50. The compound, tautomer, deuterated derivative, or pharmaceutically acceptable salt according to any one of embodiments 30 to 49, wherein $R^{YC}$ is selected from:
    hydrogen, $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and $C_6$-$C_{10}$ aryl optionally substituted with 1-3 groups independently selected from $C_1$-$C_6$ alkyl, or two $R^{YC}$ are taken together to form an oxo group.

51. The compound, tautomer, deuterated derivative, or pharmaceutically acceptable salt according to any one of embodiments 30 to 50, wherein $R^{ZC}$ is selected from:

hydrogen, $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and $C_6$-$C_{10}$ aryl optionally substituted with 1-3 groups independently selected from $C_1$-$C_6$ alkyl, or two $R^{ZC}$ are taken together to form an oxo group.

52. The compound, tautomer, deuterated derivative, or pharmaceutically acceptable salt according to any one of embodiments 30 to 51, wherein each $R^{L1}$ is independently selected from:

hydrogen, $C_1$-$C_9$ alkyl optionally substituted with 1-3 groups independently selected from $C_3$-$C_{10}$ cycloalkyl (optionally substituted with 1-3 groups independently selected from $C_1$-$C_6$ fluoroalkyl), $C_6$-$C_{10}$ aryl optionally substituted with 1-4 groups independently selected from $C_1$-$C_7$ alkyl, 5- to 10-membered heteroaryl optionally substituted with 1-3 groups independently selected from $C_1$-$C_6$ alkyl, and $R^F$;

or two $R^{L1}$ on the same carbon atom are taken together to form an oxo group.

53. The compound, tautomer, deuterated derivative, or pharmaceutically acceptable salt according to any one of embodiments 30 to 52, wherein each $R^{L2}$ is hydrogen.

54. The compound, tautomer, deuterated derivative, or pharmaceutically acceptable salt according to any one of embodiments 30 to 53, wherein each $R^N$ is independently selected from hydrogen and $C_1$-$C_8$ alkyl.

55. The compound, tautomer, deuterated derivative, or pharmaceutically acceptable salt according to any one of embodiments 30 to 54, wherein when $R^F$ is present, two $R^F$ taken together with the atoms to which they are bonded form a group selected from:

$C_6$-$C_{10}$ aryl, and 5- to 12-membered heteroaryl optionally substituted with 1-3 groups independently selected from $C_1$-$C_6$ alkyl.

56. A compound of Formula IIa:

(IIa)

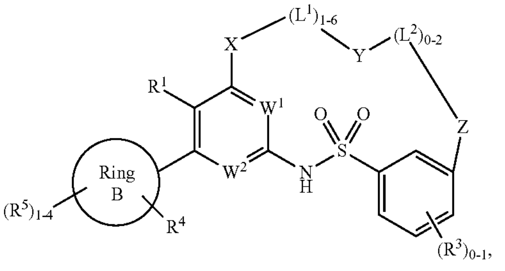

a tautomer thereof, a deuterated derivative of the compound or tautomer, or a pharmaceutically acceptable salt of any of the foregoing, wherein Ring B, $W^1$, $W^2$, X, Y, Z, $L^1$, $L^2$, $R^1$, $R^3$, $R^4$, and $R^5$ are defined as according to embodiment 1.

57. The compound, tautomer, deuterated derivative, or pharmaceutically acceptable salt according to embodiment 56, wherein Ring B is selected from $C_6$-$C_{10}$ aryl.

58. The compound, tautomer, deuterated derivative, or pharmaceutically acceptable salt according to embodiment 56 or 57, wherein Ring B is phenyl.

59. The compound, tautomer, deuterated derivative, or pharmaceutically acceptable salt according to any one of embodiments 56 to 58, wherein $W^1$ is N and $W^2$ is N.

60. The compound, tautomer, deuterated derivative, or pharmaceutically acceptable salt according to any one of embodiments 56 to 58, wherein $W^1$ is CH and $W^2$ is N.

61. The compound, tautomer, deuterated derivative, or pharmaceutically acceptable salt according to any one of embodiments 56 to 60, wherein X is $NR^{XN}$.

62. The compound, tautomer, deuterated derivative, or pharmaceutically acceptable salt according to any one of embodiments 56 to 60, wherein X is $C(R^{XC})_2$.

63. The compound, tautomer, deuterated derivative, or pharmaceutically acceptable salt according to any one of embodiments 56 to 62, wherein Z is selected from $NR^{ZN}$, and $C(R^{ZC})_2$, provided that when $L^2$ is absent, either Y is $C(R^{YC})_2$ or Z is $C(R^{ZC})_2$.

64. The compound, tautomer, deuterated derivative, or pharmaceutically acceptable salt according to any one of embodiments 56 to 63, wherein Ring C is a phenyl optionally substituted with 1-3 groups independently selected from:

halogen, $C_1$-$C_6$ alkyl, and $N(R^N)_2$.

65. The compound, tautomer, deuterated derivative, or pharmaceutically acceptable salt according to any one of embodiments 56 to 64, wherein $R^1$ is selected from hydrogen, halogen, and $C_1$-$C_6$ alkyl.

66. The compound, tautomer, deuterated derivative, or pharmaceutically acceptable salt according to any one of embodiments 56 to 65, wherein $R^3$ is absent.

67. The compound, tautomer, deuterated derivative, or pharmaceutically acceptable salt according to any one of embodiments 56 to 66, wherein $R^4$ is selected from hydrogen and methyl.

68. The compound, tautomer, deuterated derivative, or pharmaceutically acceptable salt according to any one of embodiments 56 to 67, wherein $R^4$ is methyl.

69. The compound, tautomer, deuterated derivative, or pharmaceutically acceptable salt according to any one of embodiments 56 to 68, wherein each $R^5$ is independently selected from hydrogen and $C_1$-$C_6$ alkyl.

70. The compound, tautomer, deuterated derivative, or pharmaceutically acceptable salt according to any one of embodiments 56 to 69, wherein $R^{XN}$ is selected from:

hydrogen, $C_1$-$C_9$ alkyl optionally substituted with 1-3 groups independently selected from:

hydroxyl, $C_6$-$C_{10}$ aryl optionally substituted with 1-3 groups independently selected from $C_1$-$C_6$ alkyl (optionally substituted with 1-3 groups independently selected from hydroxyl), and 5- to 10-membered heteroaryl optionally substituted with 1-3 groups independently selected from $C_1$-$C_6$ alkyl and $C_1$-$C_6$ fluoroalkyl, $C_3$-$C_{10}$ cycloalkyl optionally substituted with 1-3 groups independently selected from $N(R^N)_2$, 3- to 10-membered heterocyclyl optionally substituted with 1-3 groups independently selected from $C_1$-$C_6$ alkyl (optionally substituted with 1-3 groups independently selected from $C_1$-$C_6$ alkoxy), 5- to 10-membered heteroaryl optionally substituted with 1-3 groups independently selected from $C_1$-$C_6$ alkyl, and $R^F$.

71. The compound, tautomer, deuterated derivative, or pharmaceutically acceptable salt according to any one of embodiments 56 to 70, wherein $R^{YN}$ is selected from:

hydrogen, $C_1$-$C_9$ alkyl optionally substituted with 1-3 groups independently selected from:

hydroxyl, $C_6$-$C_{10}$ aryl optionally substituted with 1-3 groups independently selected from $C_1$-$C_6$ alkyl (optionally substituted with 1-3 groups independently selected from hydroxyl), and 5- to 10-membered heteroaryl optionally substituted with 1-3 groups independently selected from $C_1$-$C_6$ alkyl and $C_1$-$C_6$ fluoroalkyl, $C_3$-$C_{10}$ cycloalkyl optionally substituted with 1-3 groups independently selected from $N(R^N)_2$, 3- to 10-membered heterocyclyl optionally substituted with 1-3 groups independently selected from $C_1$-$C_6$ alkyl (optionally substituted with 1-3 groups independently selected from $C_1$-$C_6$ alkoxy), 5- to 10-membered heteroaryl optionally substituted with 1-3 groups independently selected from $C_1$-$C_6$ alkyl, and $R^F$.

72. The compound, tautomer, deuterated derivative, or pharmaceutically acceptable salt according to any one of embodiments 56 to 71, wherein $R^{ZN}$ is selected from:

hydrogen, $C_1$-$C_9$ alkyl optionally substituted with 1-3 groups independently selected from:

hydroxyl, $C_6$-$C_{10}$ aryl optionally substituted with 1-3 groups independently selected from $C_1$-$C_6$ alkyl (optionally substituted with 1-3 groups independently selected from hydroxyl), and 5- to 10-membered heteroaryl optionally substituted with 1-3 groups independently selected from $C_1$-$C_6$ alkyl and $C_1$-$C_6$ fluoroalkyl, $C_3$-$C_{10}$ cycloalkyl optionally substituted with 1-3 groups independently selected from $N(R^N)_2$, 3- to 10-membered heterocyclyl optionally substituted with 1-3 groups independently selected from $C_1$-$C_6$ alkyl (optionally substituted with 1-3 groups independently selected from $C_1$-$C_6$ alkoxy), 5- to 10-membered heteroaryl optionally substituted with 1-3 groups independently selected from $C_1$-$C_6$ alkyl, and $R^F$.

73. The compound, tautomer, deuterated derivative, or pharmaceutically acceptable salt according to any one of embodiments 56 to 72, wherein $R^{XC}$ is selected from:

hydrogen, $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and $C_6$-$C_{10}$ aryl optionally substituted with 1-3 groups independently selected from $C_1$-$C_6$ alkyl, or two $R^{XC}$ are taken together to form a group selected from $C_3$-$C_{10}$ cycloalkyl.

74. The compound, tautomer, deuterated derivative, or pharmaceutically acceptable salt according to any one of embodiments 56 to 73, wherein $R^{YC}$ is selected from:

hydrogen, $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and $C_6$-$C_{10}$ aryl optionally substituted with 1-3 groups independently selected from $C_1$-$C_6$ alkyl, or two $R^{YC}$ are taken together to form an oxo group.

75. The compound, tautomer, deuterated derivative, or pharmaceutically acceptable salt according to any one of embodiments 56 to 74, wherein $R^{ZC}$ is selected from:

hydrogen, $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and $C_6$-$C_{10}$ aryl optionally substituted with 1-3 groups independently selected from $C_1$-$C_6$ alkyl, or two $R^{ZC}$ are taken together to form an oxo group.

76. The compound, tautomer, deuterated derivative, or pharmaceutically acceptable salt according to any one of embodiments 56 to 75, wherein each $R^{L1}$ is independently selected from:

hydrogen, $C_1$-$C_9$ alkyl optionally substituted with 1-3 groups independently selected from $C_3$-$C_{10}$ cycloalkyl (optionally substituted with 1-3 groups independently selected from $C_1$-$C_6$ fluoroalkyl), $C_6$-$C_{10}$ aryl optionally substituted with 1-4 groups independently selected from $C_1$-$C_7$ alkyl, 5- to 10-membered heteroaryl optionally substituted with 1-3 groups independently selected from $C_1$-$C_6$ alkyl, and $R^F$;

or two $R^{L1}$ on the same carbon atom are taken together to form an oxo group.

77. The compound, tautomer, deuterated derivative, or pharmaceutically acceptable salt according to any one of embodiments 56 to 76, wherein each $R^{L2}$ is hydrogen.

78. The compound, tautomer, deuterated derivative, or pharmaceutically acceptable salt according to any one of embodiments 56 to 77, wherein each $R^N$ is independently selected from hydrogen and $C_1$-$C_8$ alkyl.

79. The compound, tautomer, deuterated derivative, or pharmaceutically acceptable salt according to any one of embodiments 56 to 78, wherein when $R^F$ is present, two $R^F$ taken together with the atoms to which they are bonded form a group selected from:

$C_6$-$C_{10}$ aryl, and 5- to 12-membered heteroaryl optionally substituted with 1-3 groups independently selected from $C_1$-$C_6$ alkyl.

80. A compound of Formula IIb:

(IIb)

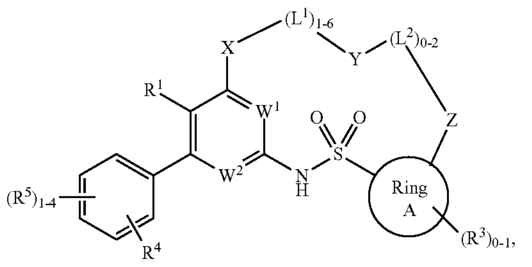

a tautomer thereof, a deuterated derivative of the compound or tautomer, or a pharmaceutically acceptable salt of any of the foregoing, wherein Ring A, $W^1$, $W^2$, X, Y, Z, $L^1$, $L^2$, $R^1$, $R^3$, $R^4$, and $R^5$ are defined as according to embodiment 1.

81. The compound, tautomer, deuterated derivative, or pharmaceutically acceptable salt according to embodiment 80, wherein Ring A is selected from selected from $C_6$-$C_{10}$ aryl and 5- to 10-membered heteroaryl.

82. The compound, tautomer, deuterated derivative, or pharmaceutically acceptable salt according to embodiment 80 or 81, wherein Ring A is selected from phenyl and pyridyl.

83. The compound, tautomer, deuterated derivative, or pharmaceutically acceptable salt according to any one of embodiments 80 to 82, wherein Ring A is phenyl.

84. The compound, tautomer, deuterated derivative, or pharmaceutically acceptable salt according to any one of embodiments 80 to 83, wherein $W^1$ is N and $W^2$ is N.

85. The compound, tautomer, deuterated derivative, or pharmaceutically acceptable salt according to any one of embodiments 80 to 83, wherein $W^1$ is CH and $W^2$ is N.

86. The compound, tautomer, deuterated derivative, or pharmaceutically acceptable salt according to any one of embodiments 80 to 85, wherein X is $NR^{XN}$.

87. The compound, tautomer, deuterated derivative, or pharmaceutically acceptable salt according to any one of embodiments 80 to 85, wherein X is $C(R^{XC})_2$.

88. The compound, tautomer, deuterated derivative, or pharmaceutically acceptable salt according to any one of embodiments 80 to 87, wherein Z is selected from $NR^{ZN}$, and $C(R^{ZC})_2$, provided that when $L^2$ is absent, either Y is $C(R^{YC})_2$ or Z is $C(R^{ZC})_2$.

89. The compound, tautomer, deuterated derivative, or pharmaceutically acceptable salt according to any one of embodiments 80 to 88, wherein Ring C is a phenyl optionally substituted with 1-3 groups independently selected from:
- halogen,
- $C_1$-$C_6$ alkyl, and
- $N(R^N)_2$.

90. The compound, tautomer, deuterated derivative, or pharmaceutically acceptable salt according to any one of embodiments 80 to 89, wherein $R^1$ is selected from hydrogen, halogen, and $C_1$-$C_6$ alkyl.

91. The compound, tautomer, deuterated derivative, or pharmaceutically acceptable salt according to any one of embodiments 80 to 90, wherein $R^3$ is absent.

92. The compound, tautomer, deuterated derivative, or pharmaceutically acceptable salt according to any one of embodiments 80 to 91, wherein $R^4$ is selected from hydrogen and methyl.

93. The compound, tautomer, deuterated derivative, or pharmaceutically acceptable salt according to any one of embodiments 80 to 92, wherein $R^4$ is methyl.

94. The compound, tautomer, deuterated derivative, or pharmaceutically acceptable salt according to any one of embodiments 80 to 93, wherein each $R^5$ is independently selected from hydrogen and $C_1$-$C_6$ alkyl.

95. The compound, tautomer, deuterated derivative, or pharmaceutically acceptable salt according to any one of embodiments 80 to 94, wherein $R^{XN}$ is selected from:
- hydrogen,
- $C_1$-$C_9$ alkyl optionally substituted with 1-3 groups independently selected from:
  - hydroxyl,
  - $C_6$-$C_{10}$ aryl optionally substituted with 1-3 groups independently selected from $C_1$-$C_6$ alkyl (optionally substituted with 1-3 groups independently selected from hydroxyl), and
  - 5- to 10-membered heteroaryl optionally substituted with 1-3 groups independently selected from $C_1$-$C_6$ alkyl and $C_1$-$C_6$ fluoroalkyl,
- $C_3$-$C_{10}$ cycloalkyl optionally substituted with 1-3 groups independently selected from $N(R^N)_2$,
- 3- to 10-membered heterocyclyl optionally substituted with 1-3 groups independently selected from $C_1$-$C_6$ alkyl (optionally substituted with 1-3 groups independently selected from $C_1$-$C_6$ alkoxy),
- 5- to 10-membered heteroaryl optionally substituted with 1-3 groups independently selected from $C_1$-$C_6$ alkyl, and
- $R^F$.

96. The compound, tautomer, deuterated derivative, or pharmaceutically acceptable salt according to any one of embodiments 80 to 95, wherein $R^{YN}$ is selected from:
- hydrogen,
- $C_1$-$C_9$ alkyl optionally substituted with 1-3 groups independently selected from:
  - hydroxyl,
  - $C_6$-$C_{10}$ aryl optionally substituted with 1-3 groups independently selected from $C_1$-$C_6$ alkyl (optionally substituted with 1-3 groups independently selected from hydroxyl), and
  - 5- to 10-membered heteroaryl optionally substituted with 1-3 groups independently selected from $C_1$-$C_6$ alkyl and $C_1$-$C_6$ fluoroalkyl,
- $C_3$-$C_{10}$ cycloalkyl optionally substituted with 1-3 groups independently selected from $N(R^N)_2$,
- 3- to 10-membered heterocyclyl optionally substituted with 1-3 groups independently selected from $C_1$-$C_6$ alkyl (optionally substituted with 1-3 groups independently selected from $C_1$-$C_6$ alkoxy),
- 5- to 10-membered heteroaryl optionally substituted with 1-3 groups independently selected from $C_1$-$C_6$ alkyl, and
- $R^F$.

97. The compound, tautomer, deuterated derivative, or pharmaceutically acceptable salt according to any one of embodiments 80 to 96, wherein $R^{ZN}$ is selected from:
- hydrogen,
- $C_1$-$C_9$ alkyl optionally substituted with 1-3 groups independently selected from:
  - hydroxyl, $C_6$-$C_{10}$ aryl optionally substituted with 1-3 groups independently selected from $C_1$-$C_6$ alkyl (optionally substituted with 1-3 groups independently selected from hydroxyl), and 5- to 10-membered heteroaryl optionally substituted with 1-3 groups independently selected from $C_1$-$C_6$ alkyl and $C_1$-$C_6$ fluoroalkyl, $C_3$-$C_{10}$ cycloalkyl optionally substituted with 1-3 groups independently selected from $N(R^N)_2$, 3- to 10-membered heterocyclyl optionally substituted with 1-3 groups independently selected from $C_1$-$C_6$ alkyl (optionally substituted with 1-3 groups independently selected from $C_1$-$C_6$ alkoxy), 5- to 10-membered heteroaryl optionally substituted with 1-3 groups independently selected from $C_1$-$C_6$ alkyl, and $R^F$.

98. The compound, tautomer, deuterated derivative, or pharmaceutically acceptable salt according to any one of embodiments 80 to 97, wherein $R^{XC}$ is selected from:

hydrogen, $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and $C_6$-$C_{10}$ aryl optionally substituted with 1-3 groups independently selected from $C_1$-$C_6$ alkyl, or two $R^{XC}$ are taken together to form a group selected from $C_3$-$C_{10}$ cycloalkyl.

99. The compound, tautomer, deuterated derivative, or pharmaceutically acceptable salt according to any one of embodiments 80 to 98, wherein $R^{YC}$ is selected from:

hydrogen, $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and $C_6$-$C_{10}$ aryl optionally substituted with 1-3 groups independently selected from $C_1$-$C_6$ alkyl, or two $R^{YC}$ are taken together to form an oxo group.

100. The compound, tautomer, deuterated derivative, or pharmaceutically acceptable salt according to any one of embodiments 80 to 99, wherein $R^{ZC}$ is selected from:

hydrogen, $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and $C_6$-$C_{10}$ aryl optionally substituted with 1-3 groups independently selected from $C_1$-$C_6$ alkyl, or two $R^{ZC}$ are taken together to form an oxo group.

101. The compound, tautomer, deuterated derivative, or pharmaceutically acceptable salt according to any one of embodiments 80 to 100, wherein each $R^{L1}$ is independently selected from:

hydrogen, $C_1$-$C_9$ alkyl optionally substituted with 1-3 groups independently selected from $C_3$-$C_{10}$ cycloalkyl (optionally substituted with 1-3 groups independently selected from $C_1$-$C_6$ fluoroalkyl), $C_6$-$C_{10}$ aryl optionally substituted with 1-4 groups independently selected from $C_1$-$C_7$ alkyl, 5- to 10-membered heteroaryl optionally substituted with 1-3 groups independently selected from $C_1$-$C_6$ alkyl, and $R^F$;

or two $R^{L1}$ on the same carbon atom are taken together to form an oxo group.

102. The compound, tautomer, deuterated derivative, or pharmaceutically acceptable salt according to any one of embodiments 80 to 101, wherein each $R^{L2}$ is hydrogen.

103. The compound, tautomer, deuterated derivative, or pharmaceutically acceptable salt according to any one of embodiments 80 to 102, wherein each $R^N$ is independently selected from hydrogen and $C_1$-$C_8$ alkyl.

104. The compound, tautomer, deuterated derivative, or pharmaceutically acceptable salt according to any one of embodiments 80 to 103, wherein when $R^F$ is present, two $R^F$ taken together with the atoms to which they are bonded form a group selected from:

$C_6$-$C_{10}$ aryl, and 5- to 12-membered heteroaryl optionally substituted with 1-3 groups independently selected from $C_1$-$C_6$ alkyl.

105. A compound of Formula III:

(III)

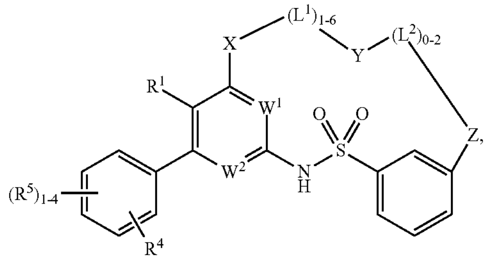

a tautomer thereof, a deuterated derivative of the compound or tautomer, or a pharmaceutically acceptable salt of any of the foregoing, wherein $W^1$, $W^2$, X, Y, Z, $L^1$, $L^2$, $R^1$, $R^4$, and $R^5$ are defined as according to embodiment 1.

106. The compound, tautomer, deuterated derivative, or pharmaceutically acceptable salt according to embodiment 105, wherein $W^1$ is N and $W^2$ is N.

107. The compound, tautomer, deuterated derivative, or pharmaceutically acceptable salt according to embodiment 105, wherein $W^1$ is CH and $W^2$ is N.

108. The compound, tautomer, deuterated derivative, or pharmaceutically acceptable salt according to any one of embodiments 105 to 107, wherein X is $NR^{XN}$.

109. The compound, tautomer, deuterated derivative, or pharmaceutically acceptable salt according to any one of embodiments 105 to 107, wherein X is $C(R^{XC})_2$.

110. The compound, tautomer, deuterated derivative, or pharmaceutically acceptable salt according to any one of embodiments 105 to 109, wherein Z is selected from $NR^{ZN}$, and $C(R^{ZC})_2$, provided that when $L^2$ is absent, either Y is $C(R^{YC})_2$ or Z is $C(R^{ZC})_2$.

111. The compound, tautomer, deuterated derivative, or pharmaceutically acceptable salt according to any one of embodiments 105 to 110, wherein Ring C is a phenyl optionally substituted with 1-3 groups independently selected from:

halogen, $C_1$-$C_6$ alkyl, and $N(R^N)_2$.

112. The compound, tautomer, deuterated derivative, or pharmaceutically acceptable salt according to any one of embodiments 105 to 111, wherein $R^1$ is selected from hydrogen, halogen, and $C_1$-$C_6$ alkyl.

113. The compound, tautomer, deuterated derivative, or pharmaceutically acceptable salt according to any one of embodiments 105 to 112, wherein $R^4$ is selected from hydrogen and methyl.

114. The compound, tautomer, deuterated derivative, or pharmaceutically acceptable salt according to any one of embodiments 105 to 113, wherein $R^4$ is methyl.

115. The compound, tautomer, deuterated derivative, or pharmaceutically acceptable salt according to any one of embodiments 105 to 114, wherein each $R^5$ is independently selected from hydrogen and $C_1$-$C_6$ alkyl.

116. The compound, tautomer, deuterated derivative, or pharmaceutically acceptable salt according to any one of embodiments 105 to 115, wherein $R^{XN}$ is selected from:
hydrogen,
$C_1$-$C_9$ alkyl optionally substituted with 1-3 groups independently selected from:
hydroxyl,
$C_6$-$C_{10}$ aryl optionally substituted with 1-3 groups independently selected from $C_1$-$C_6$ alkyl (optionally substituted with 1-3 groups independently selected from hydroxyl), and
5- to 10-membered heteroaryl optionally substituted with 1-3 groups independently selected from $C_1$-$C_6$ alkyl and $C_1$-$C_6$ fluoroalkyl,
$C_3$-$C_{10}$ cycloalkyl optionally substituted with 1-3 groups independently selected from $N(R^N)_2$,
3- to 10-membered heterocyclyl optionally substituted with 1-3 groups independently selected from $C_1$-$C_6$ alkyl (optionally substituted with 1-3 groups independently selected from $C_1$-$C_6$ alkoxy),
5- to 10-membered heteroaryl optionally substituted with 1-3 groups independently selected from $C_1$-$C_6$ alkyl, and
$R^F$.

117. The compound, tautomer, deuterated derivative, or pharmaceutically acceptable salt according to any one of embodiments 105 to 116, wherein $R^{YN}$ is selected from:
hydrogen,
$C_1$-$C_9$ alkyl optionally substituted with 1-3 groups independently selected from:
hydroxyl,
$C_6$-$C_{10}$ aryl optionally substituted with 1-3 groups independently selected from $C_1$-$C_6$ alkyl (optionally substituted with 1-3 groups independently selected from hydroxyl), and
5- to 10-membered heteroaryl optionally substituted with 1-3 groups independently selected from $C_1$-$C_6$ alkyl and $C_1$-$C_6$ fluoroalkyl,
$C_3$-$C_{10}$ cycloalkyl optionally substituted with 1-3 groups independently selected from $N(R^N)_2$,
3- to 10-membered heterocyclyl optionally substituted with 1-3 groups independently selected from $C_1$-$C_6$ alkyl (optionally substituted with 1-3 groups independently selected from $C_1$-$C_6$ alkoxy),
5- to 10-membered heteroaryl optionally substituted with 1-3 groups independently selected from $C_1$-$C_6$ alkyl, and
$R^F$.

118. The compound, tautomer, deuterated derivative, or pharmaceutically acceptable salt according to any one of embodiments 105 to 117, wherein $R^{ZN}$ is selected from:
hydrogen,
$C_1$-$C_9$ alkyl optionally substituted with 1-3 groups independently selected from:
hydroxyl,
$C_6$-$C_{10}$ aryl optionally substituted with 1-3 groups independently selected from $C_1$-$C_6$ alkyl (optionally substituted with 1-3 groups independently selected from hydroxyl), and
5- to 10-membered heteroaryl optionally substituted with 1-3 groups independently selected from $C_1$-$C_6$ alkyl and $C_1$-$C_6$ fluoroalkyl,
$C_3$-$C_{10}$ cycloalkyl optionally substituted with 1-3 groups independently selected from $N(R^N)_2$,
3- to 10-membered heterocyclyl optionally substituted with 1-3 groups independently selected from $C_1$-$C_6$ alkyl (optionally substituted with 1-3 groups independently selected from $C_1$-$C_6$ alkoxy),
5- to 10-membered heteroaryl optionally substituted with 1-3 groups independently selected from $C_1$-$C_6$ alkyl, and
$R^F$.

119. The compound, tautomer, deuterated derivative, or pharmaceutically acceptable salt according to any one of embodiments 105 to 118, wherein $R^{XC}$ is selected from:
hydrogen,
$C_1$-$C_6$ alkyl optionally substituted with 1-3 groups independently selected from $C_6$-$C_{10}$ aryl (optionally substituted with 1-3 groups independently selected from $C_1$-$C_6$ alkyl), and
$C_6$-$C_{10}$ aryl optionally substituted with 1-3 groups independently selected from $C_1$-$C_6$ alkyl,
or two $R^X$c are taken together to form a group selected from $C_3$-$C_{10}$ cycloalkyl.

120. The compound, tautomer, deuterated derivative, or pharmaceutically acceptable salt according to any one of embodiments 105 to 119, wherein $R^{YC}$ is selected from:
hydrogen,
$C_1$-$C_6$ alkyl optionally substituted with 1-3 groups independently selected from $C_6$-$C_{10}$ aryl (optionally substituted with 1-3 groups independently selected from $C_1$-$C_6$ alkyl), and
$C_6$-$C_{10}$ aryl optionally substituted with 1-3 groups independently selected from $C_1$-$C_6$ alkyl,
or two $R^{YC}$ are taken together to form an oxo group.

121. The compound, tautomer, deuterated derivative, or pharmaceutically acceptable salt according to any one of embodiments 105 to 120, wherein $R^{ZC}$ is selected from:
hydrogen,
$C_1$-$C_6$ alkyl optionally substituted with 1-3 groups independently selected from $C_6$-$C_{10}$ aryl (optionally substituted with 1-3 groups independently selected from $C_1$-$C_6$ alkyl), and
$C_6$-$C_{10}$ aryl optionally substituted with 1-3 groups independently selected from $C_1$-$C_6$ alkyl,
or two $R^{ZC}$ are taken together to form an oxo group.

122. The compound, tautomer, deuterated derivative, or pharmaceutically acceptable salt according to any one of embodiments 105 to 121, wherein each $R^{L1}$ is independently selected from:
hydrogen,
$C_1$-$C_9$ alkyl optionally substituted with 1-3 groups independently selected from $C_3$-$C_{10}$ cycloalkyl (optionally substituted with 1-3 groups independently selected from $C_1$-$C_6$ fluoroalkyl), $C_6$-$C_{10}$ aryl optionally substituted with 1-4 groups independently selected from $C_1$-$C_7$ alkyl, 5- to 10-membered heteroaryl optionally substituted with 1-3 groups independently selected from $C_1$-$C_6$ alkyl, and $R^F$;

or two $R^{L1}$ on the same carbon atom are taken together to form an oxo group.

123. The compound, tautomer, deuterated derivative, or pharmaceutically acceptable salt according to any one of embodiments 105 to 122, wherein each $R^{L2}$ is hydrogen.

124. The compound, tautomer, deuterated derivative, or pharmaceutically acceptable salt according to any one of embodiments 105 to 123, wherein each $R^N$ is independently selected from hydrogen and $C_1$-$C_8$ alkyl.

125. The compound, tautomer, deuterated derivative, or pharmaceutically acceptable salt according to any one of embodiments 105 to 124, wherein when $R^F$ is present, two $R^F$ taken together with the atoms to which they are bonded form a group selected from:

$C_6$-$C_{10}$ aryl, and 5- to 12-membered heteroaryl optionally substituted with 1-3 groups independently selected from $C_1$-$C_6$ alkyl.

126. A compound of Formula IV:

(IV)

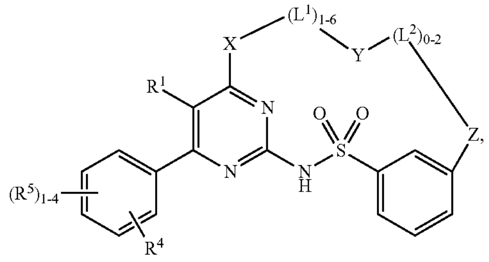

a tautomer thereof, a deuterated derivative of the compound or tautomer, or a pharmaceutically acceptable salt of any of the foregoing, wherein X, Y, Z, $L^1$, $L^2$, $R^1$, $R^4$, and $R^5$ are defined as according to embodiment 1.

127. The compound, tautomer, deuterated derivative, or pharmaceutically acceptable salt according to embodiment 126, wherein X is $NR^{XN}$.

128. The compound, tautomer, deuterated derivative, or pharmaceutically acceptable salt according to embodiment 126 or 127, wherein X is $C(R^{XC})$.

129. The compound, tautomer, deuterated derivative, or pharmaceutically acceptable salt according to any one of embodiments 126 to 128, wherein Z is selected from $NR^{ZN}$, and $C(R^{ZC})_2$, provided that when $L^2$ is absent, either Y is $C(R^{YC})_2$ or Z is $C(R^{ZC})_2$.

130. The compound, tautomer, deuterated derivative, or pharmaceutically acceptable salt according to any one of embodiments 126 to 129, wherein Ring C is a phenyl optionally substituted with 1-3 groups independently selected from:

halogen, $C_1$-$C_6$ alkyl, and $N(R^N)_2$.

131. The compound, tautomer, deuterated derivative, or pharmaceutically acceptable salt according to any one of embodiments 126 to 130, wherein $R^1$ is selected from hydrogen, halogen, and $C_1$-$C_6$ alkyl.

132. The compound, tautomer, deuterated derivative, or pharmaceutically acceptable salt according to any one of embodiments 126 to 131, wherein $R^4$ is selected from hydrogen and methyl.

133. The compound, tautomer, deuterated derivative, or pharmaceutically acceptable salt according to any one of embodiments 126 to 132, wherein $R^4$ is methyl.

134. The compound, tautomer, deuterated derivative, or pharmaceutically acceptable salt according to any one of embodiments 126 to 133, wherein each $R^5$ is independently selected from hydrogen and $C_1$-$C_6$ alkyl.

135. The compound, tautomer, deuterated derivative, or pharmaceutically acceptable salt according to any one of embodiments 126 to 134, wherein $R^{XN}$ is selected from:

hydrogen, $C_1$-$C_9$ alkyl optionally substituted with 1-3 groups independently selected from:

hydroxyl, $C_6$-$C_{10}$ aryl optionally substituted with 1-3 groups independently selected from $C_1$-$C_6$ alkyl (optionally substituted with 1-3 groups independently selected from hydroxyl), and 5- to 10-membered heteroaryl optionally substituted with 1-3 groups independently selected from $C_1$-$C_6$ alkyl and $C_1$-$C_6$ fluoroalkyl, $C_3$-$C_{10}$ cycloalkyl optionally substituted with 1-3 groups independently selected from $N(R^N)_2$, 3- to 10-membered heterocyclyl optionally substituted with 1-3 groups independently selected from $C_1$-$C_6$ alkyl (optionally substituted with 1-3 groups independently selected from $C_1$-$C_6$ alkoxy), 5- to 10-membered heteroaryl optionally substituted with 1-3 groups independently selected from $C_1$-$C_6$ alkyl, and $R^F$.

136. The compound, tautomer, deuterated derivative, or pharmaceutically acceptable salt according to any one of embodiments 126 to 135, wherein $R^{YN}$ is selected from:

hydrogen, $C_1$-$C_9$ alkyl optionally substituted with 1-3 groups independently selected from:

hydroxyl, $C_6$-$C_{10}$ aryl optionally substituted with 1-3 groups independently selected from $C_1$-$C_6$ alkyl (optionally substituted with 1-3 groups independently selected from hydroxyl), and 5- to 10-membered heteroaryl optionally substituted with 1-3 groups independently selected from $C_1$-$C_6$ alkyl and $C_1$-$C_6$ fluoroalkyl, $C_3$-$C_{10}$ cycloalkyl optionally substituted with 1-3 groups independently selected from $N(R^N)_2$, 3- to 10-membered heterocyclyl optionally substituted with 1-3 groups independently selected from $C_1$-$C_6$ alkyl (optionally substituted with 1-3 groups independently selected from $C_1$-$C_6$ alkoxy), 5- to 10-membered heteroaryl optionally substituted with 1-3 groups independently selected from $C_1$-$C_6$ alkyl, and $R^F$.

137. The compound, tautomer, deuterated derivative, or pharmaceutically acceptable salt according to any one of embodiments 126 to 136, wherein $R^{ZN}$ is selected from:

hydrogen, $C_1$-$C_9$ alkyl optionally substituted with 1-3 groups independently selected from:

hydroxyl, $C_6$-$C_{10}$ aryl optionally substituted with 1-3 groups independently selected from $C_1$-$C_6$ alkyl (optionally substituted with 1-3 groups independently selected from hydroxyl), and 5- to 10-membered heteroaryl optionally substituted with 1-3 groups independently selected from $C_1$-$C_6$ alkyl and $C_1$-$C_6$ fluoroalkyl, $C_3$-$C_{10}$ cycloalkyl optionally substituted with 1-3 groups independently selected from $N(R^N)_2$, 3- to 10-membered heterocyclyl optionally substituted with 1-3 groups independently selected from $C_1$-$C_6$ alkyl (optionally substituted with 1-3 groups independently selected from $C_1$-$C_6$ alkoxy), 5- to 10-membered heteroaryl optionally substituted with 1-3 groups independently selected from $C_1$-$C_6$ alkyl, and $R^F$.

138. The compound, tautomer, deuterated derivative, or pharmaceutically acceptable salt according to any one of embodiments 126 to 137, wherein $R^{XC}$ is selected from:

hydrogen, $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and $C_6$-$C_{10}$ aryl optionally substituted with 1-3 groups independently selected from $C_1$-$C_6$ alkyl, or two $R^{XC}$ are taken together to form a group selected from $C_3$-$C_{10}$ cycloalkyl.

139. The compound, tautomer, deuterated derivative, or pharmaceutically acceptable salt according to any one of embodiments 126 to 138, wherein $R^{YC}$ is selected from:

hydrogen, $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and $C_6$-$C_{10}$ aryl optionally substituted with 1-3 groups independently selected from $C_1$-$C_6$ alkyl, or two $R^{YC}$ are taken together to form an oxo group.

140. The compound, tautomer, deuterated derivative, or pharmaceutically acceptable salt according to any one of embodiments 126 to 139, wherein $R^{ZC}$ is selected from:

hydrogen, $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and $C_6$-$C_{10}$ aryl optionally substituted with 1-3 groups independently selected from $C_1$-$C_6$ alkyl, or two $R^{ZC}$ are taken together to form an oxo group.

141. The compound, tautomer, deuterated derivative, or pharmaceutically acceptable salt according to any one of embodiments 126 to 140, wherein each $R^{L1}$ is independently selected from:

hydrogen, $C_1$-$C_9$ alkyl optionally substituted with 1-3 groups independently selected from $C_3$-$C_{10}$ cycloalkyl (optionally substituted with 1-3 groups independently selected from $C_1$-$C_6$ fluoroalkyl), $C_6$-$C_{10}$ aryl optionally substituted with 1-4 groups independently selected from $C_1$-$C_7$ alkyl, 5- to 10-membered heteroaryl optionally substituted with 1-3 groups independently selected from $C_1$-$C_6$ alkyl, and $R^F$;

or two $R^{L1}$ on the same carbon atom are taken together to form an oxo group.

142. The compound, tautomer, deuterated derivative, or pharmaceutically acceptable salt according to any one of embodiments 126 to 141, wherein each $R^{L2}$ is hydrogen.

143. The compound, tautomer, deuterated derivative, or pharmaceutically acceptable salt according to any one of embodiments 126 to 142, wherein each $R^N$ is independently selected from hydrogen and $C_1$-$C_8$ alkyl.

144. The compound, tautomer, deuterated derivative, or pharmaceutically acceptable salt according to any one of embodiments 126 to 143, wherein when $R^F$ is present, two $R^F$ taken together with the atoms to which they are bonded form a group selected from:

$C_6$-$C_{10}$ aryl, and 5- to 12-membered heteroaryl optionally substituted with 1-3 groups independently selected from $C_1$-$C_6$ alkyl.

145. A compound of Formula V:

(V)

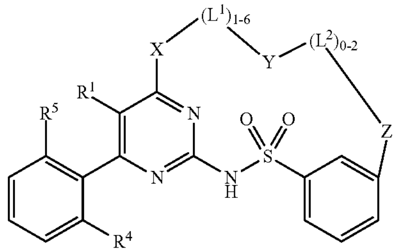

a tautomer thereof, a deuterated derivative of the compound or tautomer, or a pharmaceutically acceptable salt of any of the foregoing, wherein X, Y, Z, $L^1$, $L^2$, $R^1$, $R^4$, and $R^5$ are defined as according to embodiment 1.

146. The compound, tautomer, deuterated derivative, or pharmaceutically acceptable salt according to embodiment 145, wherein X is $NR^{XN}$.

147. The compound, tautomer, deuterated derivative, or pharmaceutically acceptable salt according to embodiment 145 or 146, wherein X is $C(R^{XC})_2$.

148. The compound, tautomer, deuterated derivative, or pharmaceutically acceptable salt according to any one of embodiments 145 to 147, wherein Z is selected from $NR^{ZN}$, and $C(R^{ZC})_2$, provided that when $L^2$ is absent, either Y is $C(R^{YC})_2$ or Z is $C(R^{ZC})_2$.

149. The compound, tautomer, deuterated derivative, or pharmaceutically acceptable salt according to any one of embodiments 145 to 148, wherein Ring C is a phenyl optionally substituted with 1-3 groups independently selected from:

halogen, $C_1$-$C_6$ alkyl, and $N(R^N)_2$.

150. The compound, tautomer, deuterated derivative, or pharmaceutically acceptable salt according to any one of embodiments 145 to 149, wherein $R^1$ is selected from hydrogen, halogen, and $C_1$-$C_6$ alkyl.

151. The compound, tautomer, deuterated derivative, or pharmaceutically acceptable salt according to any one of embodiments 145 to 150, wherein $R^4$ is selected from hydrogen and methyl.

152. The compound, tautomer, deuterated derivative, or pharmaceutically acceptable salt according to any one of embodiments 145 to 151, wherein $R^4$ is methyl.

153. The compound, tautomer, deuterated derivative, or pharmaceutically acceptable salt according to any one of embodiments 145 to 152, wherein each $R^5$ is independently selected from hydrogen and $C_1$-$C_6$ alkyl.

154. The compound, tautomer, deuterated derivative, or pharmaceutically acceptable salt according to any one of embodiments 145 to 153, wherein $R^{XN}$ is selected from:
- hydrogen,
- $C_1$-$C_9$ alkyl optionally substituted with 1-3 groups independently selected from:
  - hydroxyl,
  - $C_6$-$C_{10}$ aryl optionally substituted with 1-3 groups independently selected from $C_1$-$C_6$ alkyl (optionally substituted with 1-3 groups independently selected from hydroxyl), and
  - 5- to 10-membered heteroaryl optionally substituted with 1-3 groups independently selected from $C_1$-$C_6$ alkyl and $C_1$-$C_6$ fluoroalkyl,
- $C_3$-$C_{10}$ cycloalkyl optionally substituted with 1-3 groups independently selected from $N(R^N)_2$,
- 3- to 10-membered heterocyclyl optionally substituted with 1-3 groups independently selected from $C_1$-$C_6$ alkyl (optionally substituted with 1-3 groups independently selected from $C_1$-$C_6$ alkoxy),
- 5- to 10-membered heteroaryl optionally substituted with 1-3 groups independently selected from $C_1$-$C_6$ alkyl, and
- $R^F$.

155. The compound, tautomer, deuterated derivative, or pharmaceutically acceptable salt according to any one of embodiments 145 to 154, wherein $R^{YN}$ is selected from:
- hydrogen,
- $C_1$-$C_9$ alkyl optionally substituted with 1-3 groups independently selected from:
  - hydroxyl,
  - $C_6$-$C_{10}$ aryl optionally substituted with 1-3 groups independently selected from $C_1$-$C_6$ alkyl (optionally substituted with 1-3 groups independently selected from hydroxyl), and
  - 5- to 10-membered heteroaryl optionally substituted with 1-3 groups independently selected from $C_1$-$C_6$ alkyl and $C_1$-$C_6$ fluoroalkyl,
- $C_3$-$C_{10}$ cycloalkyl optionally substituted with 1-3 groups independently selected from $N(R^N)_2$,
- 3- to 10-membered heterocyclyl optionally substituted with 1-3 groups independently selected from $C_1$-$C_6$ alkyl (optionally substituted with 1-3 groups independently selected from $C_1$-$C_6$ alkoxy),
- 5- to 10-membered heteroaryl optionally substituted with 1-3 groups independently selected from $C_1$-$C_6$ alkyl, and
- $R^F$.

156. The compound, tautomer, deuterated derivative, or pharmaceutically acceptable salt according to any one of embodiments 145 to 155, wherein $R^{ZN}$ is selected from:
- hydrogen,
- $C_1$-$C_9$ alkyl optionally substituted with 1-3 groups independently selected from:
  - hydroxyl,
  - $C_6$-$C_{10}$ aryl optionally substituted with 1-3 groups independently selected from $C_1$-$C_6$ alkyl (optionally substituted with 1-3 groups independently selected from hydroxyl), and
  - 5- to 10-membered heteroaryl optionally substituted with 1-3 groups independently selected from $C_1$-$C_6$ alkyl and $C_1$-$C_6$ fluoroalkyl,
- $C_3$-$C_{10}$ cycloalkyl optionally substituted with 1-3 groups independently selected from $N(R^N)_2$,
- 3- to 10-membered heterocyclyl optionally substituted with 1-3 groups independently selected from $C_1$-$C_6$ alkyl (optionally substituted with 1-3 groups independently selected from $C_1$-$C_6$ alkoxy),
- 5- to 10-membered heteroaryl optionally substituted with 1-3 groups independently selected from $C_1$-$C_6$ alkyl, and
- $R^F$.

157. The compound, tautomer, deuterated derivative, or pharmaceutically acceptable salt according to any one of embodiments 145 to 156, wherein $R^{XC}$ is selected from:
- hydrogen,
- $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and
- $C_6$-$C_{10}$ aryl optionally substituted with 1-3 groups independently selected from $C_1$-$C_6$ alkyl,
- or two $R^{XC}$ are taken together to form a group selected from $C_3$-$C_{10}$ cycloalkyl.

158. The compound, tautomer, deuterated derivative, or pharmaceutically acceptable salt according to any one of embodiments 145 to 157, wherein $R^{YC}$ is selected from:
- hydrogen,
- $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and
- $C_6$-$C_{10}$ aryl optionally substituted with 1-3 groups independently selected from $C_1$-$C_6$ alkyl,
- or two $R^{YC}$ are taken together to form an oxo group.

159. The compound, tautomer, deuterated derivative, or pharmaceutically acceptable salt according to any one of embodiments 145 to 158, wherein $R^{ZC}$ is selected from:
- hydrogen,
- $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and
- $C_6$-$C_{10}$ aryl optionally substituted with 1-3 groups independently selected from $C_1$-$C_6$ alkyl,
- or two $R^{ZC}$ are taken together to form an oxo group.

160. The compound, tautomer, deuterated derivative, or pharmaceutically acceptable salt according to any one of embodiments 145 to 159, wherein each $R^{L1}$ is independently selected from:
- hydrogen,
- $C_1$-$C_9$ alkyl optionally substituted with 1-3 groups independently selected from $C_3$-$C_{10}$ cycloalkyl (optionally substituted with 1-3 groups independently selected from $C_1$-$C_6$ fluoroalkyl), $C_6$-$C_{10}$ aryl optionally substituted with 1-4 groups independently selected from $C_1$-$C_7$ alkyl, 5- to 10-membered heteroaryl optionally substituted with 1-3 groups independently selected from $C_1$-$C_6$ alkyl, and $R^F$;

or two $R^{L1}$ on the same carbon atom are taken together to form an oxo group.

161. The compound, tautomer, deuterated derivative, or pharmaceutically acceptable salt according to any one of embodiments 145 to 160, wherein each $R^{L2}$ is hydrogen.

162. The compound, tautomer, deuterated derivative, or pharmaceutically acceptable salt according to any one of embodiments 145 to 161, wherein each $R^N$ is independently selected from hydrogen and $C_1$-$C_8$ alkyl.

163. The compound, tautomer, deuterated derivative, or pharmaceutically acceptable salt according to any one of embodiments 145 to 162, wherein when $R^F$ is present, two $R^F$ taken together with the atoms to which they are bonded form a group selected from:

$C_6$-$C_{10}$ aryl, and 5- to 12-membered heteroaryl optionally substituted with 1-3 groups independently selected from $C_1$-$C_6$ alkyl.

164. A compound of Formula VIa:

(VIa)

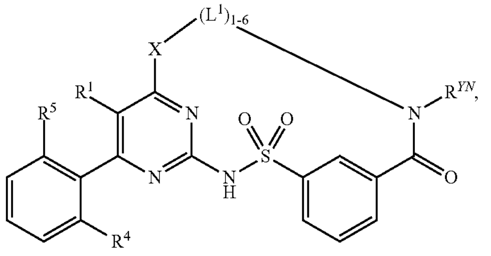

a tautomer thereof, a deuterated derivative of the compound or tautomer, or a pharmaceutically acceptable salt of any of the foregoing, wherein X, $L^1$, $R^1$, $R^4$, $R^5$, and $R^{YN}$ are defined as according to embodiment 1.

165. The compound, tautomer, deuterated derivative, or pharmaceutically acceptable salt according to embodiment 164, wherein X is $NR^{XN}$.

166. The compound, tautomer, deuterated derivative, or pharmaceutically acceptable salt according to embodiment 164 or 165, wherein X is $C(R^{XC})_2$.

167. The compound, tautomer, deuterated derivative, or pharmaceutically acceptable salt according to any one of embodiments 164 to 166, wherein Ring C is a phenyl optionally substituted with 1-3 groups independently selected from:

halogen, $C_1$-$C_6$ alkyl, and $N(R^N)_2$.

168. The compound, tautomer, deuterated derivative, or pharmaceutically acceptable salt according to any one of embodiments 164 to 167, wherein $R^1$ is selected from hydrogen, halogen, and $C_1$-$C_6$ alkyl.

169. The compound, tautomer, deuterated derivative, or pharmaceutically acceptable salt according to any one of embodiments 164 to 168, wherein $R^4$ is selected from hydrogen and methyl.

170. The compound, tautomer, deuterated derivative, or pharmaceutically acceptable salt according to any one of embodiments 164 to 169, wherein $R^4$ is methyl.

171. The compound, tautomer, deuterated derivative, or pharmaceutically acceptable salt according to any one of embodiments 164 to 170, wherein each $R^5$ is independently selected from hydrogen and $C_1$-$C_6$ alkyl.

172. The compound, tautomer, deuterated derivative, or pharmaceutically acceptable salt according to any one of embodiments 164 to 171, wherein $R^{XN}$ is selected from:

hydrogen, $C_1$-$C_9$ alkyl optionally substituted with 1-3 groups independently selected from:

hydroxyl, $C_6$-$C_{10}$ aryl optionally substituted with 1-3 groups independently selected from $C_1$-$C_6$ alkyl (optionally substituted with 1-3 groups independently selected from hydroxyl), and 5- to 10-membered heteroaryl optionally substituted with 1-3 groups independently selected from $C_1$-$C_6$ alkyl and $C_1$-$C_6$ fluoroalkyl, $C_3$-$C_{10}$ cycloalkyl optionally substituted with 1-3 groups independently selected from $N(R^N)_2$, 3- to 10-membered heterocyclyl optionally substituted with 1-3 groups independently selected from $C_1$-$C_6$ alkyl (optionally substituted with 1-3 groups independently selected from $C_1$-$C_6$ alkoxy), 5- to 10-membered heteroaryl optionally substituted with 1-3 groups independently selected from $C_1$-$C_6$ alkyl, and $R^F$.

173. The compound, tautomer, deuterated derivative, or pharmaceutically acceptable salt according to any one of embodiments 164 to 172, wherein $R^{YN}$ is selected from:

hydrogen, $C_1$-$C_9$ alkyl optionally substituted with 1-3 groups independently selected from:

hydroxyl, $C_6$-$C_{10}$ aryl optionally substituted with 1-3 groups independently selected from $C_1$-$C_6$ alkyl (optionally substituted with 1-3 groups independently selected from hydroxyl), and 5- to 10-membered heteroaryl optionally substituted with 1-3 groups independently selected from $C_1$-$C_6$ alkyl and $C_1$-$C_6$ fluoroalkyl, $C_3$-$C_{10}$ cycloalkyl optionally substituted with 1-3 groups independently selected from $N(R^N)_2$, 3- to 10-membered heterocyclyl optionally substituted with 1-3 groups independently selected from $C_1$-$C_6$ alkyl (optionally substituted with 1-3 groups independently selected from $C_1$-$C_6$ alkoxy), 5- to 10-membered heteroaryl optionally substituted with 1-3 groups independently selected from $C_1$-$C_6$ alkyl, and $R^F$.

174. The compound, tautomer, deuterated derivative, or pharmaceutically acceptable salt according to any one of embodiments 164 to 173, wherein $R^{XC}$ is selected from:

hydrogen, $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and $C_6$-$C_{10}$ aryl optionally substituted with 1-3 groups independently selected from $C_1$-$C_6$ alkyl, or two $R^{XC}$ are taken together to form a group selected from $C_3$-$C_{10}$ cycloalkyl.

175. The compound, tautomer, deuterated derivative, or pharmaceutically acceptable salt according to any one of embodiments 164 to 174, wherein each $R^{L1}$ is independently selected from:

hydrogen, $C_1$-$C_9$ alkyl optionally substituted with 1-3 groups independently selected from $C_3$-$C_{10}$ cycloalkyl (optionally substituted with 1-3 groups independently selected from $C_1$-$C_6$ fluoroalkyl), $C_6$-$C_{10}$ aryl optionally substituted with 1-4 groups independently selected from $C_1$-$C_7$ alkyl, 5- to 10-membered heteroaryl optionally substituted with 1-3 groups independently selected from $C_1$-$C_6$ alkyl, and $R^F$;

or two $R^{L1}$ on the same carbon atom are taken together to form an oxo group.

176. The compound, tautomer, deuterated derivative, or pharmaceutically acceptable salt according to any one of embodiments 164 to 175, wherein each $R^N$ is independently selected from hydrogen and $C_1$-$C_8$ alkyl.

177. The compound, tautomer, deuterated derivative, or pharmaceutically acceptable salt according to any one of embodiments 164 to 176, wherein when $R^F$ is present, two $R^F$ taken together with the atoms to which they are bonded form a group selected from:

$C_6$-$C_{10}$ aryl, and 5- to 12-membered heteroaryl optionally substituted with 1-3 groups independently selected from $C_1$-$C_6$ alkyl.

178. A compound of Formula VIb:

(VIb)

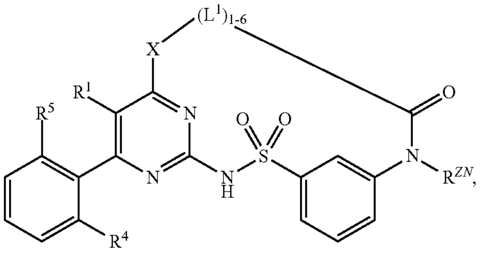

a tautomer thereof, a deuterated derivative of the compound or tautomer, or a pharmaceutically acceptable salt of any of the foregoing, wherein X, $L^1$, $R^1$, $R^4$, $R^5$, and $R^{ZN}$ are defined as according to embodiment 1.

179. The compound, tautomer, deuterated derivative, or pharmaceutically acceptable salt according to embodiment 178, wherein X is $NR^{XN}$.

180. The compound, tautomer, deuterated derivative, or pharmaceutically acceptable salt according to embodiment 178 or 179, wherein X is $C(R^{XC})_2$.

181. The compound, tautomer, deuterated derivative, or pharmaceutically acceptable salt according to any one of embodiments 178 to 180, wherein Ring C is a phenyl optionally substituted with 1-3 groups independently selected from:

halogen, $C_1$-$C_6$ alkyl, and $N(R^N)_2$.

182. The compound, tautomer, deuterated derivative, or pharmaceutically acceptable salt according to any one of embodiments 178 to 181, wherein $R^1$ is selected from hydrogen, halogen, and $C_1$-$C_6$ alkyl.

183. The compound, tautomer, deuterated derivative, or pharmaceutically acceptable salt according to any one of embodiments 178 to 182, wherein $R^4$ is selected from hydrogen and methyl.

184. The compound, tautomer, deuterated derivative, or pharmaceutically acceptable salt according to any one of embodiments 178 to 183, wherein $R^4$ is methyl.

185. The compound, tautomer, deuterated derivative, or pharmaceutically acceptable salt according to any one of embodiments 178 to 184, wherein each $R^5$ is independently selected from hydrogen and $C_1$-$C_6$ alkyl.

186. The compound, tautomer, deuterated derivative, or pharmaceutically acceptable salt according to any one of embodiments 178 to 185, wherein $R^{XN}$ is selected from:

hydrogen, $C_1$-$C_9$ alkyl optionally substituted with 1-3 groups independently selected from:

hydroxyl, $C_6$-$C_{10}$ aryl optionally substituted with 1-3 groups independently selected from $C_1$-$C_6$ alkyl (optionally substituted with 1-3 groups independently selected from hydroxyl), and 5- to 10-membered heteroaryl optionally substituted with 1-3 groups independently selected from $C_1$-$C_6$ alkyl and $C_1$-$C_6$ fluoroalkyl, $C_3$-$C_{10}$ cycloalkyl optionally substituted with 1-3 groups independently selected from $N(R^N)_2$, 3- to 10-membered heterocyclyl optionally substituted with 1-3 groups independently selected from $C_1$-$C_6$ alkyl (optionally substituted with 1-3 groups independently selected from $C_1$-$C_6$ alkoxy), 5- to 10-membered heteroaryl optionally substituted with 1-3 groups independently selected from $C_1$-$C_6$ alkyl, and $R^F$.

187. The compound, tautomer, deuterated derivative, or pharmaceutically acceptable salt according to any one of embodiments 178 to 186, wherein $R^{ZN}$ is selected from:

hydrogen, $C_1$-$C_9$ alkyl optionally substituted with 1-3 groups independently selected from:

hydroxyl, $C_6$-$C_{10}$ aryl optionally substituted with 1-3 groups independently selected from $C_1$-$C_6$ alkyl (optionally substituted with 1-3 groups independently selected from hydroxyl), and 5- to 10-membered heteroaryl optionally substituted with 1-3 groups independently selected from $C_1$-$C_6$ alkyl and $C_1$-$C_6$ fluoroalkyl, $C_3$-$C_{10}$ cycloalkyl optionally substituted with 1-3 groups independently selected from $N(R^N)_2$, 3- to 10-membered heterocyclyl optionally substituted with 1-3 groups independently selected from $C_1$-$C_6$ alkyl (optionally substituted with 1-3 groups independently selected from $C_1$-$C_6$ alkoxy), 5- to 10-membered heteroaryl optionally substituted with 1-3 groups independently selected from $C_1$-$C_6$ alkyl, and $R^F$.

188. The compound, tautomer, deuterated derivative, or pharmaceutically acceptable salt according to any one of embodiments 178 to 187, wherein $R^{XC}$ is selected from:

hydrogen, $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and $C_6$-$C_{10}$ aryl optionally substituted with 1-3 groups independently selected from $C_1$-$C_6$ alkyl, or two $R^{XC}$ are taken together to form a group selected from $C_3$-$C_{10}$ cycloalkyl.

189. The compound, tautomer, deuterated derivative, or pharmaceutically acceptable salt according to any one of embodiments 178 to 188, wherein $R^{YC}$ is selected from:

hydrogen, $C_1$-$C_6$ alkyl optionally substituted with 1-3 groups independently selected from $C_6$-$C_{10}$ aryl (optionally substituted with 1-3 groups independently selected from $C_1$-$C_6$ alkyl), and $C_6$-$C_{10}$ aryl optionally substituted with 1-3 groups independently selected from $C_1$-$C_6$ alkyl, or two $R^{YC}$ are taken together to form an oxo group.

190. The compound, tautomer, deuterated derivative, or pharmaceutically acceptable salt according to any one of embodiments 178 to 189, wherein each $R^{L1}$ is independently selected from:

hydrogen, $C_1$-$C_9$ alkyl optionally substituted with 1-3 groups independently selected from $C_3$-$C_{10}$ cycloalkyl (optionally substituted with 1-3 groups independently selected from $C_1$-$C_6$ fluoroalkyl), $C_6$-$C_{10}$ aryl optionally substituted with 1-4 groups independently selected from $C_1$-$C_7$ alkyl, 5- to 10-membered heteroaryl optionally substituted with 1-3 groups independently selected from $C_1$-$C_6$ alkyl, and $R^F$;

or two $R^{L1}$ on the same carbon atom are taken together to form an oxo group.

191. The compound, tautomer, deuterated derivative, or pharmaceutically acceptable salt according to any one of embodiments 178 to 190, wherein each $R^N$ is independently selected from hydrogen and $C_1$-$C_8$ alkyl.

192. The compound, tautomer, deuterated derivative, or pharmaceutically acceptable salt according to any one of embodiments 178 to 191, wherein when $R^F$ is present, two $R^F$ taken together with the atoms to which they are bonded form a group selected from:

$C_6$-$C_{10}$ aryl, and 5- to 12-membered heteroaryl optionally substituted with 1-3 groups independently selected from $C_1$-$C_6$ alkyl.

193. A compound of Formula VIIa or Formula VIIb:

(VIIa)

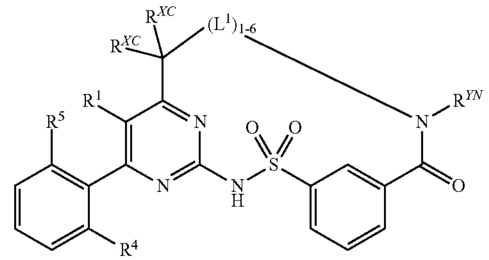

or (VIIb)

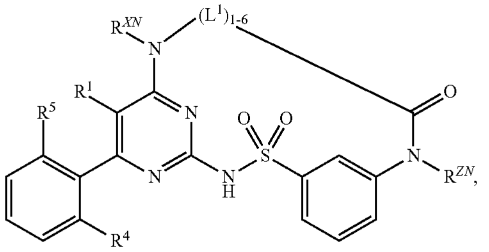

a tautomer thereof, a deuterated derivative of the compound or tautomer, or a pharmaceutically acceptable salt of any of the foregoing, wherein X, $L^1$, $R^1$, $R^4$, $R^5$, $R^{XC}$, $R^{XN}$, $R^{YN}$, and $R^{ZN}$ are defined as according to embodiment 1.

194. The compound, tautomer, deuterated derivative, or pharmaceutically acceptable salt according to any one of embodiments 1 to 193, selected from compounds of any one of Formulae I, Ia, IIa, IIb, III, IV, V, VIa, VIb, VIIa, and VIIb, tautomers thereof, deuterated derivatives of those compounds and tautomers, and pharmaceutically acceptable salts of any of the foregoing.

195. The compound, tautomer, deuterated derivative, or pharmaceutically acceptable salt according to any one of embodiments 1 to 194, selected from Compounds 1-41 (Tables 3, 5, and 8) and 42-57 (Table 7), Compounds 58-71 (Table 11), and Compounds 71 and 72 (Table 12), tautomers thereof, deuterated derivatives of those compounds and tautomers, and pharmaceutically acceptable salts of any of the foregoing.

196. A pharmaceutical composition comprising the compound, tautomer, deuterated derivative, or pharmaceutically acceptable salt according to any one of embodiments 1 to 195, and a pharmaceutically acceptable carrier.

197. The pharmaceutical composition of embodiment 196, further comprising one or more additional therapeutic agent(s).

198. The pharmaceutical composition of embodiment 197, wherein the one or more additional therapeutic agent(s) is selected from mucolytic agents, bronchodilators, antibiotics, anti-infective agents, and anti-inflammatory agents.

199. The pharmaceutical composition of embodiment 197, wherein the one or more additional therapeutic agent(s) is an antibiotic selected from tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

200. The pharmaceutical composition of embodiment 197, wherein the one or more additional therapeutic agent(s) is a CFTR modulator.

201. The pharmaceutical composition of embodiment 200, wherein the CFTR modulator is a potentiator.

202. The pharmaceutical composition of embodiment 200, wherein the CFTR modulator is a corrector.

203. The pharmaceutical composition of embodiment 200, comprising both a CFTR potentiator and a CFTR corrector.

204. The pharmaceutical composition of embodiment 201 or embodiment 203, wherein the CFTR potentiator is selected from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing.

205. The pharmaceutical composition of embodiment 202 or embodiment 203, wherein the CFTR corrector is selected from tezacaftor and lumacaftor.

206. The pharmaceutical composition of embodiment 203, wherein the composition comprises ivacaftor and tezacaftor.

207. The pharmaceutical composition of embodiment 203, wherein the composition comprises deutivacaftor and tezacaftor.

208. The pharmaceutical composition of embodiment 203, wherein the composition comprises (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and tezacaftor.

209. The pharmaceutical composition of embodiment 203, wherein the composition comprises ivacaftor and lumacaftor.

210. The pharmaceutical composition of embodiment 203, wherein the composition comprises deutivacaftor and lumacaftor.

211. The pharmaceutical composition of embodiment 203, wherein the composition comprises (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and lumacaftor.

212. A method of treating cystic fibrosis comprising administering to a patient in need thereof the compound, tautomer, deuterated derivative, or pharmaceutically acceptable salt according to any one of embodiments 1 to 195, or a pharmaceutical composition according to any one of embodiments 196 to 211.

213. The method of embodiment 212, comprising administering to the patient in need thereof the compound, tautomer, deuterated derivative, or pharmaceutically acceptable salt according to any one of embodiments 1 to 195, or a pharmaceutical composition according to embodiment 196, and further administrating one or more additional therapeutic agents prior to, concurrent with, or subsequent to the compound, tautomer, deuterated derivative, or pharmaceutically acceptable salt according to any one of embodiments 1 to 195, or the pharmaceutical composition according to embodiment 196.

214. The method of embodiment 213, wherein the one or more additional therapeutic agents is(are) selected from CFTR modulators.

215. The method of embodiment 214, wherein the CFTR modulator is a potentiator.

216. The method of embodiment 214, wherein the CFTR modulator is a corrector.

217. The method of embodiment 214, comprising administration of both a CFTR potentiator and an additional CFTR corrector.

218. The method of embodiment 215 or embodiment 217, wherein the CFTR potentiator is selected from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing.

219. The method of embodiment 216 or embodiment 217, wherein the CFTR corrector is selected from tezacaftor and lumacaftor.

220. The method of embodiment 214, comprising administration of ivacaftor and tezacaftor.

221. The method of embodiment 214, comprising administration of deutivacaftor and tezacaftor.

222. The method of embodiment 214, comprising administration of (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and tezacaftor.

223. The method of embodiment 214, comprising administration of ivacaftor and lumacaftor.

224. The method of embodiment 214, comprising administration of deutivacaftor and lumacaftor.

225. The method of embodiment 214, comprising administration of (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and lumacaftor.

226. The compound, tautomer, deuterated derivative, or pharmaceutically acceptable salt according to any one of embodiments 1 to 195, or the pharmaceutical composition according to any one of embodiments 196 to 211 for use in the treatment of cystic fibrosis.

227. The compound, tautomer, deuterated derivative, or pharmaceutically acceptable salt according to any one of embodiments 1 to 195, or the pharmaceutical composition according to any one of embodiments 196 to 211 for use in the manufacture of a medicament for the treatment of cystic fibrosis.

228. A compound selected from Compounds 1-72, tautomers thereof, deuterated derivatives of those compounds and tautomers, and pharmaceutically acceptable salts of any of the foregoing.

229. A deuterated derivative of a compound selected from Compounds 1-72.

230. A pharmaceutically acceptable salt of a compound selected from Compounds 1-72.

231. A compound selected from Compounds 1-72.

232. A pharmaceutical composition comprising a compound selected from Compounds 1-72, tautomers thereof, deuterated derivatives of those compounds and tautomers, and pharmaceutically acceptable salts of any of the foregoing and a pharmaceutically acceptable carrier.

233. A pharmaceutical composition comprising a deuterated derivative of a compound selected from Compounds 1-72 and a pharmaceutically acceptable carrier.

234. A pharmaceutical composition comprising a pharmaceutically acceptable salt of a compound selected from Compounds 1-72 and a pharmaceutically acceptable carrier.

235. A pharmaceutical composition comprising a compound selected from Compounds 1-72 and a pharmaceutically acceptable carrier.

236. A pharmaceutical composition comprising (a) a compound selected from Compounds 1-72, tautomers thereof, deuterated derivatives of those compounds and tautomers, and pharmaceutically acceptable salts of any of the foregoing; (b) a CFTR potentiator; and (c) a pharmaceutically acceptable carrier.

237. A pharmaceutical composition composition comprising (a) a deuterated derivative of a compound selected from Compounds 1-72; (b) a CFTR potentiator; and (c) a pharmaceutically acceptable carrier.

238. A pharmaceutical comprising (a) a pharmaceutically acceptable salt of a compound selected from Compounds 1-72; (b) a CFTR potentiator; and (c) a pharmaceutically acceptable carrier.

239. A pharmaceutical composition comprising (a) a compound selected from Compounds 1-72; (b) a CFTR potentiator; and (c) a pharmaceutically acceptable carrier.

240. A pharmaceutical composition comprising (a) a compound selected from Compounds 1-72, tautomers thereof, deuterated derivatives of those compounds and tautomers, and pharmaceutically acceptable salts of any of the foregoing; (b) an additional CFTR corrector; and (c) a pharmaceutically acceptable carrier.

241. A pharmaceutical composition comprising (a) a deuterated derivative of a compound selected from Compounds 1-72; (b) an additional CFTR corrector; and (c) a pharmaceutically acceptable carrier.

242. A pharmaceutical composition comprising (a) a pharmaceutically acceptable salt of a compound selected from Compounds 1-72; (b) an additional CFTR corrector; and (c) a pharmaceutically acceptable carrier.

243. A pharmaceutical composition comprising (a) a compound selected from Compounds 1-72; (b) an additional CFTR corrector; and (c) a pharmaceutically acceptable carrier.

244. A pharmaceutical composition comprising (a) a compound selected from Compounds 1-72, tautomers thereof, deuterated derivatives of those compounds and tautomers, and pharmaceutically acceptable salts of any of the foregoing; (b) an additional CFTR corrector; (c) a CRTR potentiator; and (d) a pharmaceutically acceptable carrier.

245. A pharmaceutical composition comprising (a) a deuterated derivative of a compound selected from Compounds 1-72; (b) an additional CFTR corrector; (c) a CFTR potentiator; and (d) a pharmaceutically acceptable carrier.

246. A pharmaceutical composition comprising (a) a pharmaceutically acceptable salt of a compound selected from Compounds 1-72; (b) an additional CFTR corrector; (c) a CFTR potentiator; and (d) a pharmaceutically acceptable carrier.

247. A pharmaceutical composition comprising (a) a compound selected from Compounds 1-72; (b) an additional CFTR corrector; (c) a CFTR potentiator; and (d) a pharmaceutically acceptable carrier.

248. A compound selected from Compounds 1-72, tautomers thereof, deuterated derivatives of those compounds and tautomers, and pharmaceutically acceptable salts of any of the foregoing for use in a method of treating cystic fibrosis.

249. A deuterated derivative of a compound selected from Compounds 1-72 for use in a method of treating cystic fibrosis.

250. A pharmaceutically acceptable salt of a compound selected from Compounds 1-72 for use in a method of treating cystic fibrosis.

251. A compound selected from Compounds 1-72 for use in a method of treating cystic fibrosis.

252. A pharmaceutical composition comprising a compound selected from Compounds 1-72, tautomers thereof, deuterated derivatives of those compounds and tautomers, and pharmaceutically acceptable salts of any of the foregoing and a pharmaceutically acceptable carrier for use in a method of treating cystic fibrosis.

253. A pharmaceutical composition comprising a deuterated derivative of a compound selected from Compounds 1-72 and a pharmaceutically acceptable carrier for use in a method of treating cystic fibrosis.

254. A pharmaceutical composition comprising a pharmaceutically acceptable salt of a compound selected from Compounds 1-72 and a pharmaceutically acceptable carrier for use in a method of treating cystic fibrosis.

255. A pharmaceutical composition comprising a compound selected from Compounds 1-72 and a pharmaceutically acceptable carrier for use in a method of treating cystic fibrosis.

256. A pharmaceutical composition comprising (a) a compound selected from Compounds 1-72, tautomers thereof, deuterated derivatives of those compounds and tautomers, and pharmaceutically acceptable salts of any of the foregoing; (b) a CFTR potentiator; and (c) a pharmaceutically acceptable carrier for use in a method of treating cystic fibrosis.

257. A pharmaceutical comprising (a) a deuterated derivative of a compound selected from Compounds 1-72; (b) a CFTR potentiator; and (c) a pharmaceutically acceptable carrier for use in a method of treating cystic fibrosis.

258. A pharmaceutical composition comprising (a) a pharmaceutically acceptable salt of a compound selected from Compounds 1-72; (b) a CFTR potentiator; and (c) a pharmaceutically acceptable carrier for use in a method of treating cystic fibrosis.

259. A pharmaceutical composition comprising (a) a compound selected from Compounds 1-72; (b) a CFTR potentiator; and (c) a pharmaceutically acceptable carrier.

260. A pharmaceutical composition comprising (a) a compound selected from Compounds 1-72, tautomers thereof, deuterated derivatives of those compounds and tautomers, and pharmaceutically acceptable salts of any of the foregoing; (b) an additional CFTR corrector; and (c) a pharmaceutically acceptable carrier for use in a method of treating cystic fibrosis.

261. A pharmaceutical composition comprising (a) a deuterated derivative of a compound selected from Compounds 1-72; (b) an additional CFTR corrector; and (c) a pharmaceutically acceptable carrier for use in a method of treating cystic fibrosis.

262. A pharmaceutical composition comprising (a) a pharmaceutically acceptable salt of a compound selected from Compounds 1-72; (b) an additional CFTR corrector; and (c) a pharmaceutically acceptable carrier for use in a method of treating cystic fibrosis.

263. A pharmaceutical composition comprising (a) a compound selected from Compounds 1-72; (b) an additional CFTR corrector; and (c) a pharmaceutically acceptable carrier for use in a method of treating cystic fibrosis.

264. A pharmaceutical composition comprising (a) a compound selected from Compounds 1-72, tautomers thereof, deuterated derivatives of those compounds and tautomers, and pharmaceutically acceptable salts of any of the foregoing; (b) an additional CFTR corrector; (c) a CRTR potentiator; and (d) a pharmaceutically acceptable carrier for use in a method of treating cystic fibrosis.

265. A pharmaceutical composition comprising (a) a deuterated derivative of a compound selected from Compounds 1-72; (b) an additional CFTR corrector; (c) a CFTR potentiator; and (d) a pharmaceutically acceptable carrier for use in a method of treating cystic fibrosis.

266. A pharmaceutical composition comprising (a) a pharmaceutically acceptable salt of a compound selected from Compounds 1-72; (b) an additional CFTR corrector; (c) a CFTR potentiator; and (d) a pharmaceutically acceptable carrier for use in a method of treating cystic fibrosis.

267. A pharmaceutical composition comprising (a) a compound selected from Compounds 1-72; (b) an additional CFTR corrector; (c) a CFTR potentiator; and (d) a pharmaceutically acceptable carrier for use in a method of treating cystic fibrosis.

EXAMPLES

I. Abbreviation List

ACN: Acetonitrile
Boc anhydride ($(Boc)_2O$): Di-tert-butyl dicarbonate
$CDCl_3$: Chloroform-d
CDI: Carbonyl diimidazole
CDMT: 2-Chloro-4,6-dimethoxy-1,3,5-triazine
$CH_2Cl_2$: Dichloromethane
$CH_3CN$: Acetonitrile
COMU: (1-Cyano-2-ethoxy-2-oxoethylidenaminooxy)dimethylamino-morpholino-carbenium hexafluorophosphate
Cmpd: Compound
DABCO: 1,4-Diazabicyclo[2.2.2]octane
DBU: 1,8-Diazabicyclo(5.4.0)undec-7-ene
DCE: 1,2-Dichloroethane
DCM: Dichloromethane
DI: Deionized
DIAD: Diisopropyl azodicarboxylate
DIEA: (DIPEA, DiPEA): N,N-diisopropylethylamine
DMA: N,N-Dimethylacetamide
DMAP: 4-Dimethylaminopyridine
DMF: N,N-Dimethylformamide
DMSO: Dimethyl sulfoxide
DMP: Dess-Martin periodinane
EA: Ethyl acetate
EDC: 1-Ethyl-3-(3-dimethylaminopropyl)carbodiimide
ELSD: Evaporative light scattering detector
ESI-MS: Electrospray ionization mass spectrometry
EtOAc: Ethyl acetate
EtOH: Ethanol
GC: Gas chromatography
Grubbs $1^{st}$ Generation catalyst: Dichloro(benzylidene)bis(tricyclohexylphosphine)ruthenium(II)
Grubbs $2^{nd}$ Generation catalyst: [1,3-Bis(2,4,6-trimethylphenyl)imidazolidin-2-ylidene]-dichloro-[(2-isopropoxyphenyl)methylene]ruthenium
HATU: 1-[Bis(dimethylamino)methylene]-1H-1,2,3-triazolo[4,5-b]pyridinium 3-oxid hexafluorophosphate
HPLC: High-performance liquid chromatography
Hoveyda-Grubbs $2^{nd}$ Generation catalyst: (1,3-Bis-(2,4,6-trimethylphenyl)-2-imidazolidinylidene)dichloro(o-isopropoxyphenylmethylene)ruthenium, Dichloro[1,3-bis(2,4,6-trimethylphenyl)-2-imidazolidinylidene](2-isopropoxyphenylmethylene)ruthenium(II)
IPA: Isopropanol
$KHSO_4$: Potassium bisulfate
LC: Liquid chromatography
LCMS: Liquid chromatography mass spectrometry
LCMS Met.: LCMS method
LCMS Rt: LCMS retention time
LDA: Lithium diisopropylamide
LiOH: Lithium hydroxide
MeCN: Acetonitrile
MeOH: Methanol
$MgSO_4$: Magnesium sulfate
MTBE: Methyl tert-butyl ether
MeTHF or 2-MeTHF: 2-Methyltetrahydrofuran
$NaHCO_3$: Sodium bicarbonate
NaOH: Sodium hydroxide
NMP: N-Methyl-2-pyrrolidone
NMM: N-Methylmorpholine
Pd/C: Palladium on carbon
$Pd_2(dba)_3$: Tris(dibenzylideneacetone)dipalladium(0)
$Pd(dppf)Cl_2$: [1,1'-Bis(diphenylphosphino)ferrocene]dichloropalladium(II)
$Pd(OAc)_2$: Palladium(II) acetate
PTFE: Polytetrafluoroethylene
rt, RT: Room temperature
RuPhos: 2-Dicyclohexylphosphino-2',6'-diisopropoxybiphenyl
SFC: Supercritical fluid chromatography
TBAI: Tetrabutylammonium iodide
TEA: Triethylamine
TFA: Trifluoroacetic acid
THF: Tetrahydrofuran
TLC: Thin layer chromatography
TMS: Trimethylsilyl
TMSCl: Trimethylsilyl chloride
T3P: Propanephosphonic acid anhydride
UPLC: Ultra Performance Liquid Chromatography
XANTPHOS: 4,5-Bis(diphenylphosphino)-9,9-dimethylxanthene
XPhos: 2-Dicyclohexylphosphino-2',4',6'-triisopropylbiphenyl

II. General Methods

Reagents and starting materials were obtained by commercial sources unless otherwise stated and were used without purification.

Proton and carbon NMR spectra were acquired on either a Bruker Biospin DRX 400 MHz FTNMR spectrometer operating at a $^1H$ and $^{13}C$ resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution respectively. All proton and carbon spectra were acquired with temperature control at 30° C. using standard, previously published pulse sequences and routine processing parameters.

NMR (1D & 2D) spectra were also recorded on a Bruker AVNEO 400 MHz spectrometer operating at 400 MHz and 100 MHz respectively equipped with a 5 mm multinuclear Iprobe.

NMR spectra were also recorded on a Varian Mercury NMR instrument at 300 MHz for $^{1}H$ using a 45 degree pulse angle, a spectral width of 4800 Hz and 28860 points of acquisition. FID were zero-filled to 32 k points and a line broadening of 0.3 Hz was applied before Fourier transform. 19F NMR spectra were recorded at 282 MHz using a 30 degree pulse angle, a spectral width of 100 kHz and 59202 points were acquired. FID were zero-filled to 64 k points and a line broadening of 0.5 Hz was applied before Fourier transform.

NMR spectra were also recorded on a Bruker Avance III HD NMR instrument at 400 MHz for $^{1}H$ using a 30 degree pulse angle, a spectral width of 8000 Hz and 128 k points of acquisition. FID were zero-filled to 256 k points and a line broadening of 0.3 Hz was applied before Fourier transform. $^{19}F$ NMR spectra were recorded at 377 MHz using a 30 deg pulse angle, a spectral width of 89286 Hz and 128 k points were acquired. FID were zero-filled to 256 k points and a line broadening of 0.3 Hz was applied before Fourier transform.

NMR spectra were also recorded on a Bruker AC 250 MHz instrument equipped with a: 5 mm QNP(H1/C13/F19/P31) probe (type: 250-SB, s #23055/0020) or on a Varian 500 MHz instrument equipped with a ID PFG, 5 mm, 50-202/500 MHz probe (model/part #99337300).

Final purity of compounds was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 3.0 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C. Final purity was calculated by averaging the area under the curve (AUC) of two UV traces (220 nm, 254 nm). Low-resolution mass spectra were reported as [M+1] species obtained using a single quadrupole mass spectrometer equipped with an electrospray ionization (ESI) source capable of achieving a mass accuracy of 0.1 Da and a minimum resolution of 1000 (no units on resolution) across the detection range. Optical purity of methyl (2S)-2,4-dimethyl-4-nitro-pentanoate was determined using chiral gas chromatography (GC) analysis on an Agilent 7890A/MSD 5975C instrument, using a Restek Rt-βDEXcst (30 m×0.25 mm×0.25 μm_df) column, with a 2.0 mL/min flow rate ($H_2$ carrier gas), at an injection temperature of 220° C. and an oven temperature of 120° C., 15 minutes.

III. General UPLC/HPLC Analytical Methods

LC method A: Analytical reverse phase UPLC using an Acquity UPLC BEH C18 column (50×2.1 mm, 1.7 μm particle) made by Waters (pn: 186002350), and a dual gradient run from 1-99% mobile phase B over 3.0 minutes. Mobile phase A=H2O (0.05% $CF_3CO_2H$). Mobile phase B=$CH_3CN$ (0.035% $CF_3CO_2H$). Flow rate=1.2 mL/min, injection volume=1.5 μL, and column temperature=60° C.

LC method C: Kinetex $C_{18}$ 4.6×50 mm 2.6 μm. Temp: 45° C., Flow: 2.0 mL/min, Run Time: 3 minutes. Mobile phase: Initial 95% water (0.1% formic acid) and 5% acetonitrile (0.1% formic acid) linear gradient to 95% acetonitrile (0.1% formic acid) for 2.0 minutes, then hold at 95% acetonitrile (0.1% formic acid) for 1.0 minute.

LC method D: Acquity UPLC BEH $C_{18}$ column (30×2.1 mm, 1.7 μm particle) made by Waters (pn: 186002349), and a dual gradient run from 1-99% mobile phase B over 1.0 minute. Mobile phase A=$H_2O$ (0.05% $CF_3CO_2H$). Mobile phase B=$CH_3CN$ (0.035% $CF_3CO_2H$). Flow rate=1.5 mL/min, injection volume=1.5 μL, and column temperature=60° C.

LC method K: Kinetex Polar $C_{18}$ 3.0×50 mm 2.6 μm, 3 min, 5-95% ACN in $H_2O$ (0.1% Formic Acid) 1.2 mL/min.

LC method P: Poroshell 120 EC-C18 3.0×50 mm 2.7 μM, Temp: 45° C., Flow: 1.5 mL/min, Run Time: 3 minutes. Mobile phase conditions: Initial. 95% $H_2O$ (0.1% Formic Acid) and 5% $CH_3CN$ (0.1% FA) linear gradient to 95% $CH_3CN$ (0.1% FA) for 1.5 minutes, then hold at 95% $CH_3CN$ (0.1% FA) for 1.5 minutes.

LC method S: Merckmillipore Chromolith SpeedROD $C_{18}$ column (50×4.6 mm) and a dual gradient run from 5-100% mobile phase B over 12 minutes. Mobile phase A=water (0.1% $CF_3CO_2H$). Mobile phase B=acetonitrile (0.1% $CF_3CO_2H$).

LC method T: Merckmillipore Chromolith SpeedROD $C_{18}$ column (50×4.6 mm) and a dual gradient run from 5-100% mobile phase B over 6 minutes. Mobile phase A=water (0.1% $CF_3CO_2H$). Mobile phase B=acetonitrile (0.1% $CF_3CO_2H$).

LC method U: Kinetex Polar $C_{18}$ 3.0×50 mm 2.6 m, 6 min, 5-95% ACN in $H_2O$ (0.1% Formic Acid) 1.2 mL/min.

LC method V: Acquity UPLC BEH $C_{18}$ column (50×2.1 mm, 1.7 μm particle) made by Waters (pn: 186002350), and a dual gradient run from 1-30% mobile phase B over 2.9 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

LC method W: water Cortex 2.7μ $C_{18}$(3.0 mm×50 mm), Temp: 55° C.; Flow: 1.2 mL/min; mobile phase: 100% water with 0.1% trifluoroacetic acid (TFA) then 100% acetonitrile with 0.1% TFA acid, grad: 5% to 100% B over 4 min, with stay at 100% B for 0.5 min, equilibration to 5% B over 1.5 minutes.

IV. Synthesis of Common Intermediates

Example A: Preparation of 3-[[4-Chloro-6-(2,6-dimethylphenyl)pyrimidin-2-yl]sulfamoyl]benzoic acid

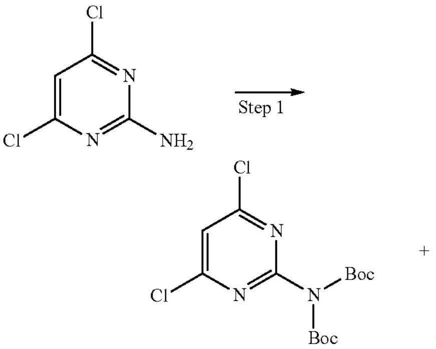

-continued

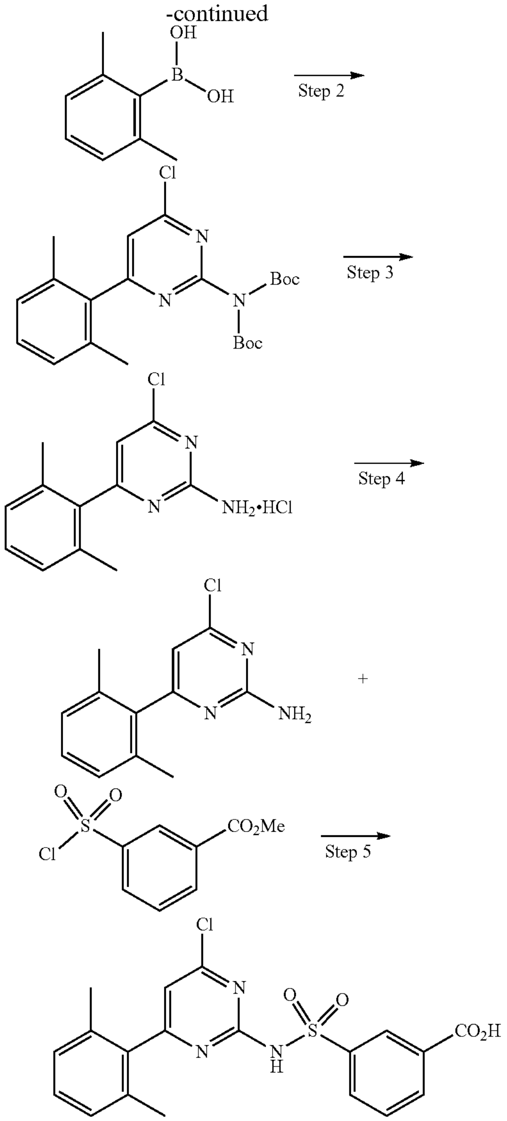

Step 1: tert-Butyl N-tert-butoxycarbonyl-N-(4,6-dichloropyrimidin-2-yl)carbamate

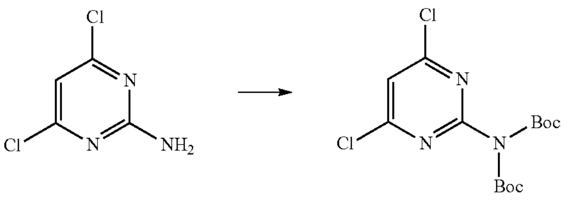 [SMILES: Nc1nc(Cl)cc(Cl)n1 ; CC(C)(C)OC(=O)N(C(=O)OC(C)(C)C)c1nc(Cl)cc(Cl)n1]

To a solution of 4,6-dichloropyrimidin-2-amine (300 g, 1.829 mol) in DCM (2.1 L) was added $(BOC)_2O$ (838 g, 3.840 mol) followed by DMAP (5.6 g, 45.84 mmol). The mixture was stirred at ambient temperature for 6 hours. Additional DMAP (5.6 g, 45.84 mmol) was added and the reaction was continued to stir at ambient temperature for 24 hours. The mixture was diluted with water (2.1 L) and the organic phase separated. The organic phase was washed with water (2.1 L), 2.1 L of brine, dried over magnesium sulfate, filtered over Celite and concentrated in vacuo affording a light orange oil which had a silt in the slurry. The mixture was diluted with ~500 mL of heptane and filtered using an M filter. The precipitate (SM) was washed with 250 mL of heptane. The filtrate was concentrated in vacuo affording a thick orange oil which was seeded with solid from a previous experiment and crystallized on standing, affording a light orange hard solid. tert-butyl N-tert-butoxycarbonyl-N-(4,6-dichloropyrimidin-2-yl)carbamate (645 g, 97%). $^1H$ NMR (400 MHz, DMSO-d6) δ 8.07 (s, 1H), 1.44 (s, 18H). ESI-MS m/z calc. 363.07526, found 364.1 (M+1)+; Retention time: 2.12 minutes (LC method A).

Step 2: tert-Butyl N-tert-butoxycarbonyl-N-[4-chloro-6-(2,6-dimethylphenyl)pyrimidin-2-yl]carbamate

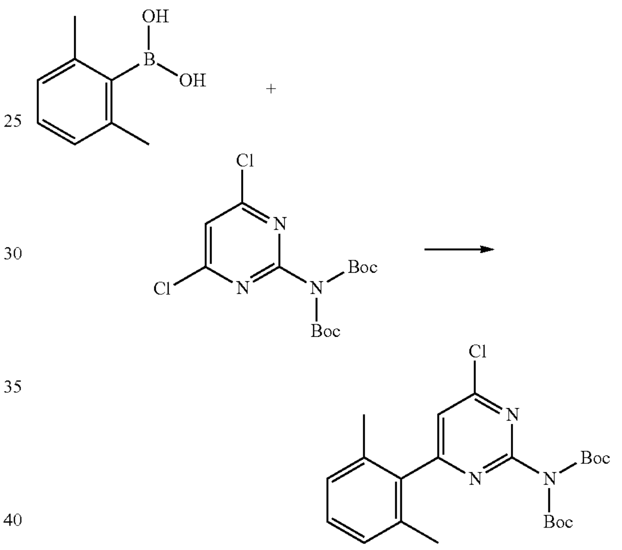

All solvents were degassed prior to use. To a slurry of tert-butyl N-tert-butoxycarbonyl-N-(4,6-dichloropyrimidin-2-yl)carbamate (88 g, 241.6 mmol), (2,6-dimethylphenyl) boronic acid (approximately 36.24 g, 241.6 mmol) and $Cs_2CO_3$ (approximately 196.8 g, 604.0 mmol) in DME (704 mL) and water (176 mL) were added. $Pd(dppf)Cl_2$ (approximately 8.839 g, 12.08 mmol) was added and the mixture was vigorously stirred under nitrogen at 80° C. (reflux) for 1 hour (no starting material remained). The reaction was cooled to ambient temperature and diluted with water (704 mL). The aqueous phase was separated and extracted with EtOAc (704 mL). The organic phase was washed with 700 mL of brine, dried over magnesium sulfate, filtered, and concentrated in vacuo. The crude product was chromatographed on a 1500 g silica gel column eluting with 0-30% EtOAc/hexanes. The product fractions (eluted at 15% EtOAc) were combined and concentrated in vacuo affording the product as a clear oil which crystallized on standing. tert-butyl N-tert-butoxycarbonyl-N-[4-chloro-6-(2,6-dimethylphenyl)pyrimidin-2-yl] carbamate (81.3 g, 78%). $^1H$ NMR (400 MHz, DMSO-d6) δ 7.88 (s, 1H), 7.30 (dd, J=8.2, 7.0 Hz, 1H), 7.21-7.16 (m, 2H), 2.03 (s, 6H), 1.38 (s, 18H). ESI-MS m/z calc. 433.17682, found 434.1 (M+1)+; Retention time: 2.32 minutes (LC method A).

Step 3: 4-Chloro-6-(2,6-dimethylphenyl)pyrimidin-2-amine (hydrochloride Salt)

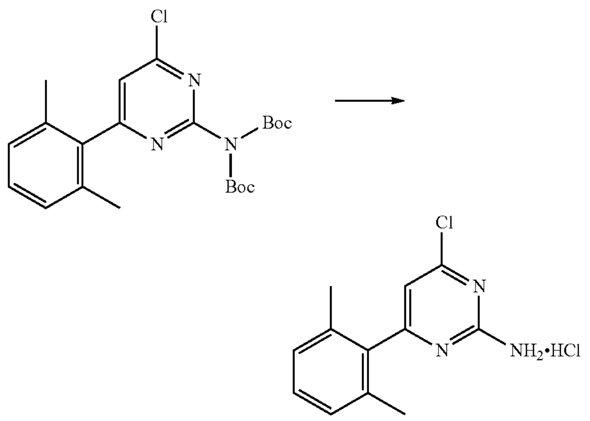

tert-Butyl N-tert-butoxycarbonyl-N-[4-chloro-6-(2,6-dimethylphenyl) pyrimidin-2-yl]carbamate (514.8 g, 915.9 mmol) was dissolved in dichloromethane (4 L). Hydrogen chloride in p-dioxane (1 L, 4 mol) was added and the mixture was stirred overnight at room temperature. The resulting precipitate was collected by vacuum filtration and dried in vacuo to obtain 4-chloro-6-(2,6-dimethylphenyl) pyrimidin-2-amine hydrochloride as a white solid (213.5 g, 82%). $^1$H NMR (250 MHz, DMSO-d6) δ 7.45-6.91 (m, 3H), 6.73 (s, 1H), 2.08 (s, 6H). ESI-MS m/z calc. 233.072, found 234.1 (M+1)+; Retention time: 2.1 minutes (LC Method C).

Step 4: 4-Chloro-6-(2,6-dimethylphenyl)pyrimidin-2-amine

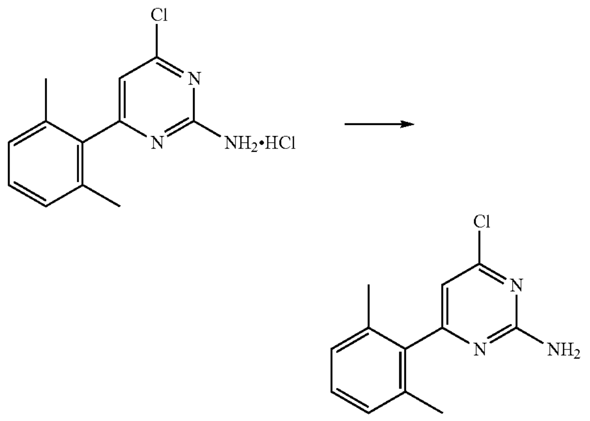

4-Chloro-6-(2,6-dimethylphenyl)pyrimidin-2-amine (hydrochloride salt) (166 g, 614.5 mmol) and 4-chloro-6-(2,6-dimethylphenyl)pyrimidin-2-amine (hydrochloride salt) (30 g, 111.0 mmol) were suspended in DCM (2.5 L), treated with NaOH (725 mL of 1 M, 725.0 mmol) and stirred at room temperature for 1 hour. The mixture was transferred into a separatory funnel and left standing overnight. The DCM phase was separated, and the aqueous phase with insoluble material was extracted twice more with DCM (2×500 mL). The combined brown DCM phases were stirred over magnesium sulfate and charcoal for 1 hour, filtered and the yellow solution concentrated to a volume of ~500 mL. The solution was diluted with heptane (750 mL) and DCM was removed under reduced pressure at 60° C. to give a cream suspension. It was stirred at room temperature for 1 hour, filtered, washed with cold heptane and dried to give 4-chloro-6-(2,6-dimethylphenyl)pyrimidin-2-amine (157 g, 91%) as a cream solid. $^1$H NMR (400 MHz, DMSO-$d_6$) δ 7.28-7.14 (m, 3H), 7.10 (d, J=7.5 Hz, 2H), 6.63 (s, 1H), 2.06 (s, 6H). ESI-MS m/z calc. 233.07198, found 234.0 (M+1)$^+$; Retention time: 1.45 minutes (LC method A).

Step 5: 3-[[4-Chloro-6-(2,6-dimethylphenyl)pyrimidin-2-yl]sulfamoyl]benzoic acid

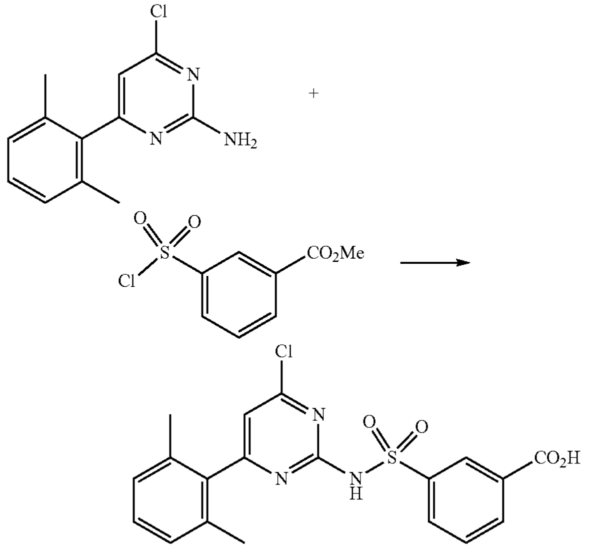

4-Chloro-6-(2,6-dimethylphenyl)pyrimidin-2-amine (235 g, 985.5 mmol) was dissolved in MeTHF (2.3 L) and cooled in an ice bath under stirring and nitrogen. To the cold solution methyl 3-chlorosulfonylbenzoate (347 g, 1.479 mol) was added in one portion (seemed slightly endothermic) and to the cold pale-yellow solution a solution of 2-methyl-butan-2-ol (lithium salt) (875 mL of 3.1 M, 2.712 mol) (in heptane) was added dropwise over 1.25 hours (exothermic, internal temperature from 0 to 10° C.). The ice bath was removed, and the greenish solution was stirred for 4 hours at room temperature. To the greenish solution cold HCl (2 L of 1.5 M, 3.000 mol) was added, the phases separated, and the organic phase was washed once with water (1 L) and once with brine (500 mL). The aqueous phases were back extracted once with MeTHF (350 mL) and the organic phases were combined. This yellow MeTHF solution of methyl 3-[[4-chloro-6-(2,6-dimethylphenyl)pyrimidin-2-yl]sulfamoyl]benzoate (ESI-MS m/z calc. 431.07065, found 432.0 (M+1)$^+$; Retention time: 1.81 minutes) was treated with NaOH (2.3 L of 2 M, 4.600 mol) and stirred at room temperature for 1 hour. The phases were separated and the NaOH phase was washed twice with MeTHF (2×500 mL) and the combined organic phases were extracted once with 2M NaOH (1×250 mL). The combined NaOH phases were combined, stirred in an ice bath and slowly acidified by addition of HCl (416 mL of 36% w/w, 4.929 mol) while keeping the internal temperature between 10 and 20° C. At the end of the addition (pH ~5-6), the final pH was adjusted to 2-3 by the addition of solid citric acid. The formed yellow tacky suspension was stirred at room temperature overnight to give a cream crisp suspension. The solid was collected by filtration, washed with plenty of water, and dried under vacuum for 3 hours. The solid was dried under reduced pressure with a nitrogen leak at 45-50° C. for 120 hours. 3-[[4-chloro-6-(2,6-dimethylphenyl)pyrimidin-2-yl]sulfamoyl]benzoic acid (395 g, 96%) was isolated as an off-white solid. $^1$H NMR (400 MHz, DMSO-$d_6$) δ 13.44 (s, 1H), 12.46 (s, 1H), 8.48-8.39 (m, 1H), 8.25-8.15 (m, 1H), 8.15-8.08 (m, 1H), 7.68 (t, J=7.8 Hz, 1H), 7.31 (s, 1H), 7.28-7.18 (m, 1H), 7.10 (d, J=7.6 Hz, 2H), 1.84 (s, 6H). ESI-MS m/z calc. 417.055, found 418.0 $(M+1)^+$; Retention time: 1.56 minutes. (LC method A).

Example B: Preparation of N-[4-chloro-6-(2,6-dimethylphenyl)pyrimidin-2-yl]-3-nitro-benzenesulfonamide Step 1: N-[4-Chloro-6-(2,6-dimethylphenyl)pyrimidin-2-yl]-3-nitro-benzenesulfonamide

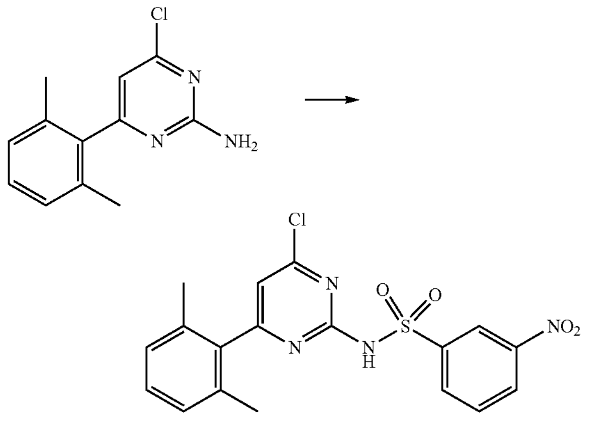

To a suspension of sodium hydride (60% in mineral oil) (4.87 g, 0.122 mol) in anhydrous tetrahydrofuran (30 mL) was added a solution of 4-chloro-6-(2,6-dimethylphenyl) pyrimidin-2-amine (8.13 g, 0.0348 mol) in anhydrous tetrahydrofuran (40 mL) dropwise at 0° C. The reaction mixture was stirred at room temperature for 30 minutes. A solution of 3-nitrobenzenesulfonyl chloride (11.57 g, 52.2 mmol) in anhydrous tetrahydrofuran (40 mL) was added to the reaction mixture dropwise at 0° C. The reaction was stirred at the same temperature for 1 hour. The reaction was quenched with a saturated aqueous solution of sodium bicarbonate (100 mL). The reaction solution was extracted with dichloromethane (3×100 mL). The combined organic layers were washed with water (100 mL), dried over anhydrous sodium sulfate, and then concentrated under vacuum. The residue was purified by silica gel column chromatography using 0 to 10% chloroform-ethyl acetate. The crude product was triturated with a solvent mixture of diethyl ether and hexane (1:5) to furnish N-[4-chloro-6-(2,6-dimethylphenyl)pyrimidin-2-yl]-3-nitro-benzenesulfonamide (5.98 g, 41%) as a white solid. ESI-MS m/z calc. 418.1, found 419.0 (M+1). Retention time: 5.73 minutes. $^1$H NMR (250 MHz, $CDCl_3$) δ (ppm): 9.01 (s, 1H); 8.43 (t, J=10.5 Hz, 2H); 7.682 (t, J=7.8 Hz, 1H); 7.23 (m, 1H); 7.12 (d, J=7.5 Hz, 2H); 6.95 (s, 1H); 1.99 (s, 6H).

Example C: Preparation of N-[4-(2,6-dimethylphenyl)-6-methylsulfonyl-pyrimidin-2-yl]-3-nitro-benzenesulfonamide Step 1: N-[4-(2,6-Dimethylphenyl)-6-methylsulfonyl-pyrimidin-2-yl]-3-nitro-benzenesulfonamide

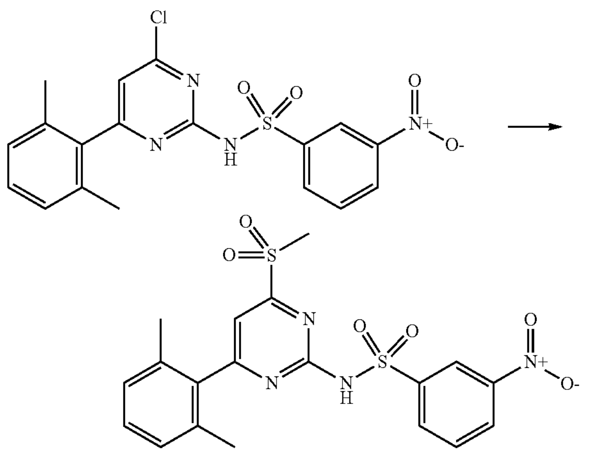

Stage 1: To a 250 mL round-bottomed flask were added N-[4-chloro-6-(2,6-dimethylphenyl)pyrimidin-2-yl]-3-nitro-benzenesulfonamide (14.14 g, 33.76 mmol), sodium thiomethoxide (5.86 g, 83.61 mmol) and NMIP (130 mL). This solution was stirred at 100° C. for 3 hours. The reaction mixture was then cooled to room temperature, quenched with 1 N HCl (300 mL), and extracted with ethyl acetate (3×300 mL). The combined organic extracts were washed with water (300 mL), 3% aqueous hydrogen peroxide solution (300 mL), water (300 mL) and saturated aqueous sodium chloride solution (300 mL), then dried over sodium sulfate, filtered, and evaporated in vacuo. This gave an orange foam (16.71 g, 115% crude product yield) that was carried onto the next reaction.

Stage 2: To a 250 mL round-bottomed flask containing the product from Stage 1, DCM (120 mL) was added, followed by m-CPBA (77% pure, 27.22 g, 121.5 mmol). This solution was stirred at room temperature for 90 minutes. The reaction mixture was quenched by transferring to a 1 L-Erlenmeyer flask containing DCM (400 mL) and solid $Na_2S_2O_3$ (41.15 g, 260.3 mmol). This mixture was stirred at room temperature for 1 hour. The reaction mixture was diluted with DCM (300 mL), then washed with water (3×400 mL) and saturated aqueous sodium chloride solution (300 mL). The organic layer was then dried over sodium sulfate, filtered, and evaporated in vacuo. This solid was then partially dissolved in DCM (100 mL) and filtered in vacuo on a Buchner funnel to remove the m-chlorobenzoic acid waste (this was repeated three times). The remaining solution was then purified by silica gel chromatography (330 g of silica, 0 to 60% gradient of ethyl acetate/hexanes) to give N-[4-(2,6-dimethylphenyl)-6-methylsulfonyl-pyrimidin-2-yl]-3-nitro-benzenesulfonamide (5.881 g, 36%). ESI-MS m z calc. 462.06677, found 463.1 $(M+1)^+$; Retention time: 1.6 minutes; LC method A.

Example D: Preparation of 3-[[4-chloro-6-(2,6-dimethylphenyl)-5-methyl-pyrimidin-2-yl]sulfamoyl] benzoic acid

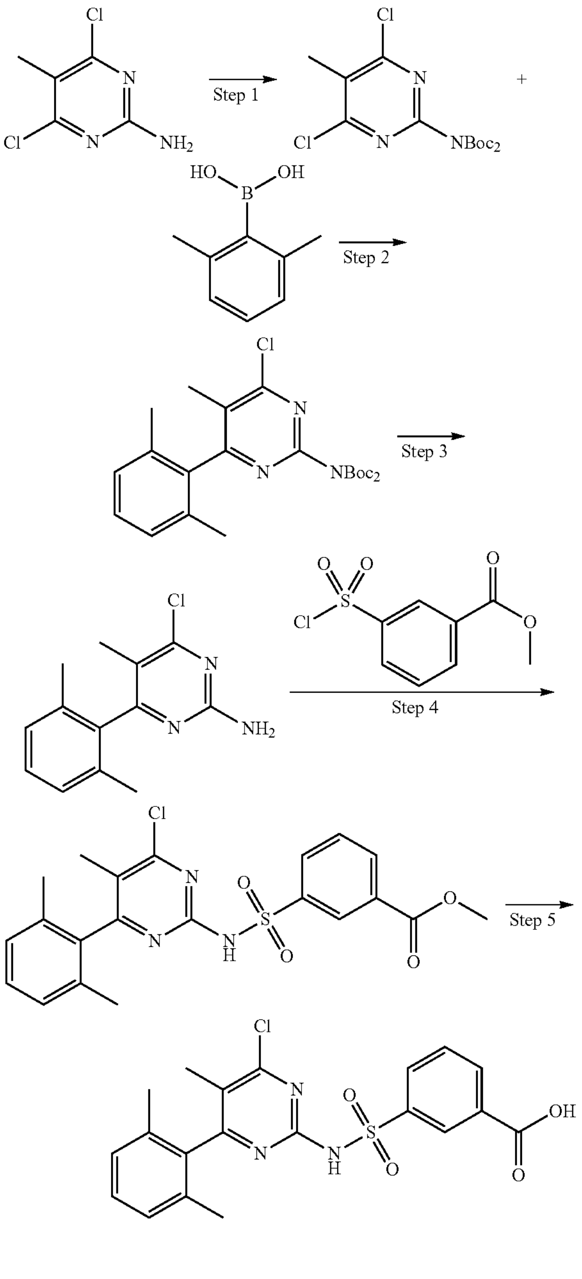

Step 1: tert-Butyl N-tert-butoxycarbonyl-N-(4,6-dichloro-5-methyl-pyrimidin-2-yl)carbamate

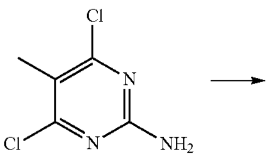

-continued

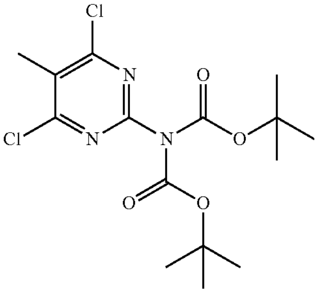

To a solution of 4,6-dichloro-5-methyl-pyrimidin-2-amine (57.85 g, 318.47 mmol) in DCM (580 mL) was added tert-butoxycarbonyl tert-butyl carbonate (159.92 g, 168.34 mL, 710.77 mmol) and DMAP (3.96 g, 32.090 mmol) at room temperature. The reaction was stirred for 3 hours. The reaction mixture was quenched with DI $H_2O$ (250 mL). DCM (100 mL) was added. The layers were separated, and the aqueous layer was extracted with DCM (2×250 mL). The combined organic layers were washed with aqueous saturated NaCl (250 mL), dried over anhydrous sodium sulfate, filtered and concentrated under vacuum. Crude Mass=125.71 g (Yellow Solid). The yellow solid was triturated with hexanes (300 mL, 3 h), filtered through a Type "M" Glass filter by vacuum and the solids were rinsed with Hexanes (2×200 mL). Final Product (101.00 g) was obtained as a yellow solid. tert-butyl N-tert-butoxycarbonyl-N-(4,6-dichloro-5-methyl-pyrimidin-2-yl)carbamate (101.00 g, 80%). $^1H$ NMR (500 MHz, Chloroform-d) δ 2.48 (s, 3H), 1.47 (s, 18H). ESI-MS m/z calc. 377.0909, found 378.0 $(M+1)^+$; Retention time: 3.39 minutes; LC method T.

Step 2: tert-Butyl N-tert-butoxycarbonyl-N-[4-chloro-6-(2,6-dimethylphenyl)-5-methyl-pyrimidin-2-yl]carbamate

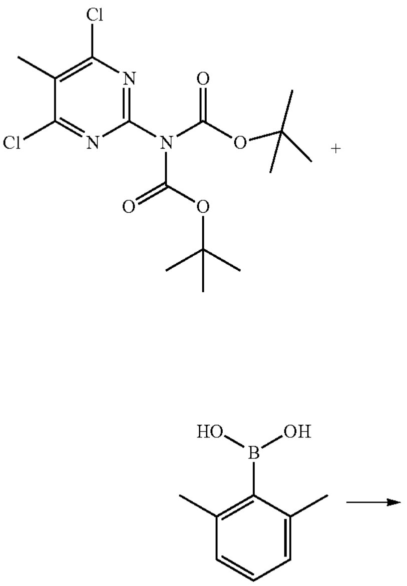

-continued

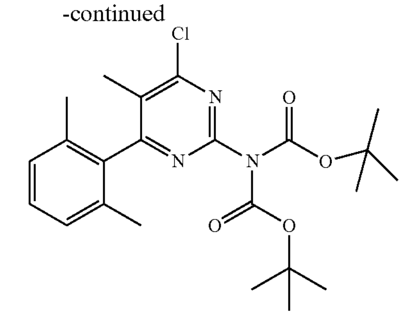

To a solution of tert-butyl N-tert-butoxycarbonyl-N-(4,6-dichloro-5-methyl-pyrimidin-2-yl)carbamate (120.85 g, 319.50 mmol) dissolved in DME (850 mL) and water (120 mL) was added (2,6-dimethylphenyl)boronic acid (57.5 g, 383.38 mmol) and cesium carbonate (271 g, 831.75 mmol) at room temperature. The solution was stirred for 10 minutes while being bubbled with a nitrogen stream. Then Pd(dppf) $Cl_2$ (11.7 g, 15.990 mmol) was added to the solution and heated to 80° C. overnight. The solution was cooled to room temperature before being diluted with water (500 mL) and extracted with ethyl acetate (2×1 L). The combined organic layer was washed with brine (1 L) and dried over sodium sulfate before being concentrated under vacuum. The organic residue was filtered through a pad of silica gel and washed with a solution of 1:3 ethyl acetate-hexanes (3×1 L) to give tert-butyl N-tert-butoxycarbonyl-N-[4-chloro-6-(2,6-dimethylphenyl)-5-methyl-pyrimidin-2-yl]carbamate (100.71 g, 58%). ESI-MS m/z calc. 447.19247, found 448.1 $(M+1)^+$; Retention time: 4.24 minutes; LC method T.

Step 3: 4-Chloro-6-(2,6-dimethylphenyl)-5-methyl-pyrimidin-2-amine

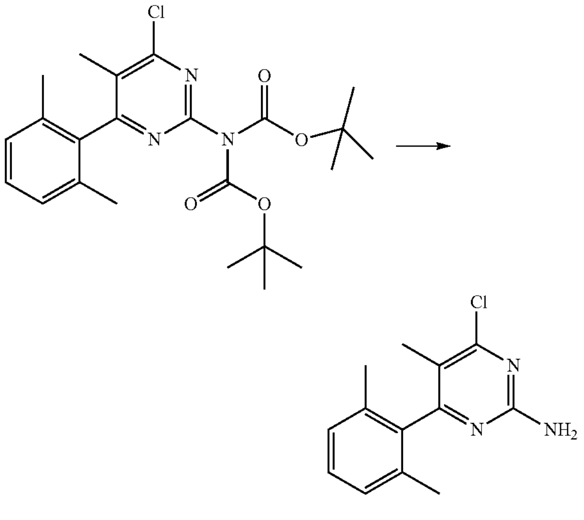

To a solution of tert-butyl N-tert-butoxycarbonyl-N-[4-chloro-6-(2,6-dimethylphenyl)-5-methyl-pyrimidin-2-yl] carbamate (100.71 g, 224.82 mmol) in DCM (500 mL) was added HCl (200 mL of 4 M, 800.00 mmol) in dioxane. The solution was stirred at room temperature overnight before being concentrated under vacuum. The residue was then basified with sodium bicarbonate (500 mL) and extracted with ethyl acetate (1 L). The organic layer was washed with brine (400 mL) and dried over sodium sulfate. The organic phase was concentrated then the residue was triturated with hexanes (2×200 mL) to give 4-chloro-6-(2,6-dimethylphenyl)-5-methyl-pyrimidin-2-amine (54.88 g, 99%) as an off-white solid. ESI-MS m z calc. 247.08763, found 248.2 $(M+1)^+$; Retention time: 2.94 minutes; LC method T.

Step 4: Methyl 3-[[4-chloro-6-(2,6-dimethylphenyl)-5-methyl-pyrimidin-2-yl]sulfamoyl]benzoate

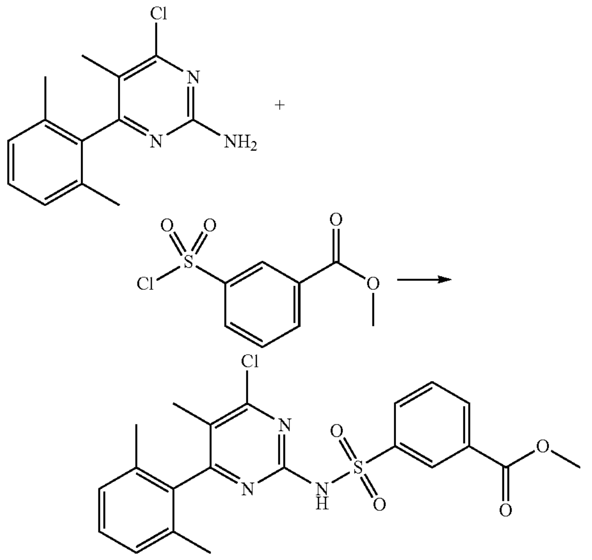

To a solution of 4-chloro-6-(2,6-dimethylphenyl)-5-methyl-pyrimidin-2-amine (35 g, 141.29 mmol) in THF (400 mL) at 0° C. was added methyl 3-chlorosulfonylbenzoate (50 g, 213.08 mmol). Then Lithium tert-amoxide (46.428 g, 159 mL of 40% w/w, 197.40 mmol) was added to the solution dropwise keeping the temperature below 5° C. The solution was allowed to warm to room temperature while it stirred for 3 hours. The solution was acidified with 1 M HCl (200 mL) and extracted with ethyl acetate (3×200 mL). The organic layer was washed with brine (300 mL) and dried over sodium sulfate. The organic layer was then concentrated under vacuum to give methyl 3-[[4-chloro-6-(2,6-dimethylphenyl)-5-methyl-pyrimidin-2-yl]sulfamoyl] benzoate (63.01 g, 100%) as a yellow solid. ESI-MS m/z calc. 445.0863, found 446.2 $(M+1)^+$; Retention time: 3.63 minutes; LC method T.

Step 5: 3-[[4-Chloro-6-(2,6-dimethylphenyl)-5-methyl-pyrimidin-2-yl]sulfamoyl]benzoic acid

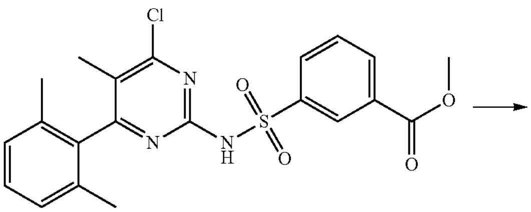

-continued

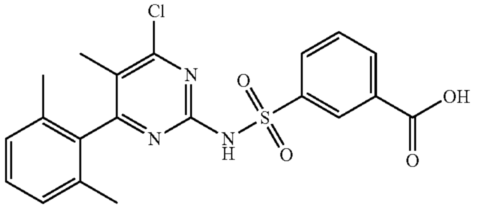

To a solution of methyl 3-[[4-chloro-6-(2,6-dimethylphenyl)-5-methyl-pyrimidin-2-yl]sulfamoyl]benzoate (59.51 g, 133.45 mmol) in THF (500 mL) was added an aqueous solution of NaOH (300 mL of 2 M, 600.00 mmol) and the mixture was stirred for 2 hours at room temperature. The solution was acidified using 3 M HCl (500 mL) and extracted with ethyl acetate (2×500 mL) before being washed with brine (500 mL). The organic layer was dried over sodium sulfate and concentrated under vacuum. The organic residue was then recrystallized with ethanol and filtered to give 3-[[4-chloro-6-(2,6-dimethylphenyl)-5-methyl-pyrimidin-2-yl]sulfamoyl]benzoic acid (34.44 g, 56%) as a white solid. $^1H$ NMR (500 MHz, DMSO-$d_6$) δ 8.43 (t, J=1.8 Hz, 1H), 8.18 (dt, J=7.8, 1.4 Hz, 1H), 8.10 (ddd, J=7.9, 2.0, 1.2 Hz, 1H), 7.66 (t, J=7.8 Hz, 1H), 7.25 (t, J=7.6 Hz, 1H), 7.12 (d, J=7.6 Hz, 2H), 1.85 (s, 3H), 1.74 (s, 6H). ESI-MS m/z calc. 431.07065, found 432.4 $(M+1)^+$; Retention time: 2.43 minutes; LC method T.

Example E: Preparation of (2R)-2-Amino-3-[1-(trifluoromethyl)cyclopropyl] propan-1-ol Step 1: 2-[1-(Trifluoromethyl)cyclopropyl]ethanol

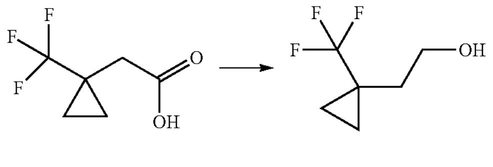 [SMILES: O=C(O)CC1(C(F)(F)F)CC1 ; OCCC1(C(F)(F)F)CC1]

LAH (49.868 g, 1.3139 mol) was added to THF (1700 mL) under nitrogen and the mixture was stirred for 30 minutes before being cooled to 0° C. 2-[1-(trifluoromethyl)cyclopropyl]acetic acid (190.91 g, 1.0107 mol) in THF (500 mL) was added dropwise while controlling the temperature <5° C. The mixture was allowed to warm up to room temperature and stirred for 24 hours. The resulting suspension was cooled to 0° C., water (50 mL) was added very slowly, followed by 15% w/w sodium hydroxide (50 mL) and water (150 mL). The mixture was stirred at 0° C. for 30 minutes, and filtered through Celite pad, the filter cake was washed with THF (2×500 mL). The combined filtrates were evaporated in vacuo to give 2-[1-(trifluoromethyl)cyclopropyl]ethanol (160.27 g, 98%) as amber oil containing ~5% w/w of THF (by NMR). $^1H$ NMR (250 MHz, DMSO-$d_6$) δ 4.57 (t, J=5.2 Hz, 1H), 3.55-3.39 (m, 2H), 1.74 (t, J=7.3 Hz, 2H), 1.00-0.58 (m, 4H).

Step 2: 2-[1-(Trifluoromethyl)cyclopropyl]acetaldehyde

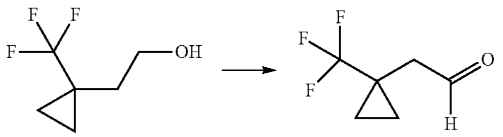 [SMILES: OCCC1(C(F)(F)F)CC1 ; O=CCC1(C(F)(F)F)CC1]

To a solution of 2-[1-(trifluoromethyl)cyclopropyl]ethanol (80 g, 467.1 mmol) in methylene chloride (1.1 L) was stirred at room temperature and treated with Dess-Martin periodinane (250 g, 589.4 mmol) portionwise (exothermic—cooled in ice bath and kept T<15° C.). To the mixture was added water (12 mL, 666.1 mmol) slowly added over 0.5 hours (exothermic during addition up to 33° C., kept between 20 and 33° C. by cooling with cold water) giving a thick suspension. After the addition, the pale-yellow fine suspension was stirred at room temperature for 18 hours. The yellow suspension was diluted with diethylether (500 mL) (yellow suspension) and stirred for 30 minutes. The slurry was filtered over Celite and the precipitate washed with 100 mL of Diethylether. The organic phase was carefully treated with a saturated aqueous solution of sodium carbonate (500 ml, strong gas evolution, pH ~10 at the end). The three-phase mixture was stirred at room temperature for 1 hour, and the solid was removed by filtration (large glass frit). The phases (yellow cloudy Diethylether phase, colorless water phase) were separated and the organic phase was washed once more with a saturated aqueous solution of sodium carbonate (250 mL), once with 1 M sodium thiosulfate (250 mL) and once with brine (250 mL). The aqueous phases were back extracted once with diethyl ether (150 mL) and the combined organic phases were dried, filtered and evaporated to give 2-[1-(trifluoromethyl)cyclopropyl]acetaldehyde (40 g, 56%) as a yellow liquid.

Step 3: 2-[[(1R)-1-Phenylethyl]amino]-3-[1-(trifluoromethyl)cyclopropyl]propanenitrile

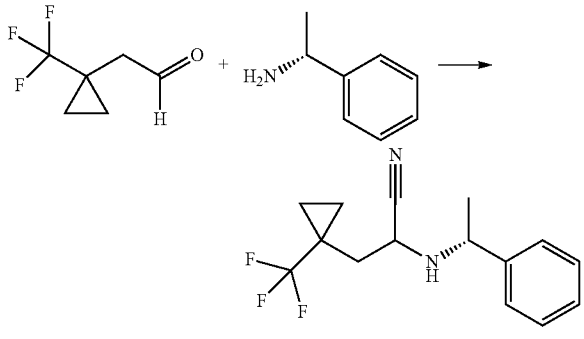

3:1 mixture of diastereomers

2-[1-(Trifluoromethyl)cyclopropyl]acetaldehyde (102 g, 670.5 mmol) in MeOH (700 mL) was treated with (1R)-1-phenylethanamine (86 mL, 667.1 mmol) and cooled in an ice bath. The solution was treated with acetic acid (38 mL, 668.2 mmol), stirred for 20 minutes in the ice bath, then solid NaCN (33 g, 673.4 mmol) was added in one portion and the suspension was stirred in the melting ice bath for 14 hours. The solution was concentrated under reduced pressure (the exhaust from the pump was running through a bleach trap) and the residue was extracted with MTBE (1000 mL) and saturated sodium carbonate/water 1:1 (1000 mL) and washed with brine (350 mL). The aqueous phases were back extracted once with MTBE (250 mL) and the combined organic phases were dried, filtered and evaporated to give 2-[[(1R)-1-phenylethyl]amino]-3-[1-(trifluoromethyl)cyclopropyl]propanenitrile (180.8 g, 96%) as 3:1 mixture of diastereomers. ESI-MS m/z calc. 282.13437, found 283.0 $(M+1)^+$; Retention time: 1.69 minutes (major isomer) and 1.62 minutes (minor isomer), LC method A.

Step 4: (2R)-2-[[(1R)-1-Phenylethyl]amino]-3-[1-(trifluoromethyl)cyclopropyl]propenamide

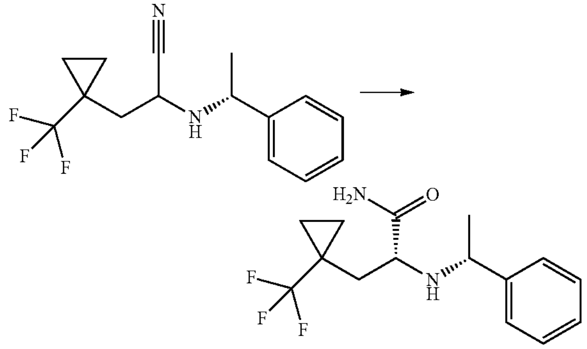

In a 2 L flask equipped with mechanical stirring and a temperature probe, sulfuric acid (285 mL of 18 M, 5.130 mol) was added it was cooled in an ice bath. At an internal temperature of 5° C., a solution of 2-[[(1R)-1-phenylethyl]amino]-3-[1-(trifluoromethyl)cyclopropyl]propanenitrile (180.8 g, 640.4 mmol, 3:1 mixture of diastereomers) in DCM (900 mL) was added dropwise over 20 minutes. The ice bath was removed, and the deep orange emulsion was stirred at room temperature for 18 hours and at 30-40° C. for 2 hours. The deep orange emulsion was carefully added to a mixture of ice and water (2.2 L) under mechanical stirring to give a yellow three phase mixture, which was basified by slow addition of ammonium hydroxide (1.33 L of 30% w/w, 10.25 mol) under ice cooling (very exothermic, internal temperature kept between 10 and 25° C. by adding ice). The yellow emulsion was stirred for 10 minutes at room temperature (pH ~10), diluted with DCM (500 mL) and the phases were separated. The aqueous phase was washed twice more with DCM (400 and 200 mL) and the combined organic phases were washed once with water/brine 1:1 (500 mL). The DCM phase was dried, filtered, and evaporated to give crude 2-[[(1R)-1-phenylethyl]amino]-3-[1-(trifluoromethyl)cyclopropyl]propanamide (189.5 g, 99%) as a yellow-orange oil. ESI-MS m z calc. 300.14496, found 301.0 $(M+1)^+$; Retention time: 1.40 minutes (major isomer) and 1.50 minutes (minor isomer) (3:1 mixture of diastereomers). The product was dissolved in ethanol (1.5 L) and it was treated quickly with HCl (240 mL of 4 M, 960.0 mmol) (4 M in dioxane) and the resulting thick suspension was stirred at room temperature overnight under mechanical stirring. The solid was collected by filtration, washed with cold ethanol and dried under vacuum with a nitrogen bleed at 40-45° C. to give (2R)-2-[[(1R)-1-phenylethyl]amino]-3-[1-(trifluoromethyl)cyclopropyl]propanamide (hydrochloride salt) (147 g, 68%). $^1$H NMR (499 MHz, DMSO-$d_6$) δ 9.74 (d, J=67.9 Hz, 2H), 8.16-7.94 (m, 1H), 7.86 (s, 1H), 7.64-7.51 (m, 2H), 7.51-7.34 (m, 3H), 4.22 (s, 1H), 3.46-3.37 (m, 1H), 2.45 (d, J=15.9 Hz, 1H), 1.85 (dd, J 15.1, 10.4 Hz, 1H), 1.58 (d, J=6.7 Hz, 3H), 0.89 (pd, J=9.6, 9.2, 4.3 Hz, 2H), 0.84-0.66 (m, 2H). ESI-MS m/z calc. 300.14496, found 301.0 $(M+1)^+$; Retention time: 1.40 minutes (major isomer) and 1.40 minutes (minor isomer), 97:3 mixture of diastereomers (LC method V).

Step 5: (2R)-2-[[(1R)-1-Phenylethyl]amino]-3-[1-(trifluoromethyl)cyclopropyl]propanoic acid

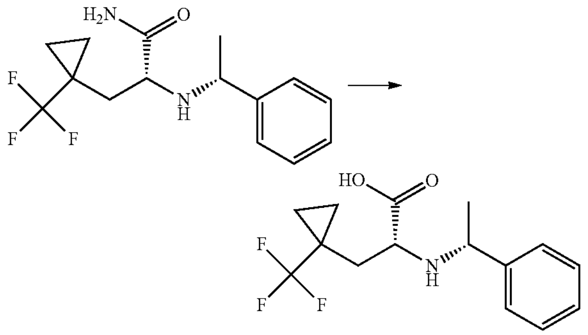

In a 5 L flask equipped with mechanical stirring, (2R)-2-[[(1R)-1-phenylethyl]amino]-3-[1-(trifluoromethyl)cyclopropyl]propanamide (hydrochloride salt) (147 g, 436.5 mmol) was added to acetic acid (735 mL) under stirring and the thick colorless suspension was treated with HCl (1.3 L of 12 M, 15.60 mol). The colorless suspension was carefully heated to 60-65° C. (strong foaming, acetic acid (145 mL) was added) and the suspension was stirred at 60-65° C. for 16 hours. The suspension was then slowly heated to 100° C. (over 4 hours, strong foaming) and the resulting solution was stirred at 100° C. for another 20 hours. The pale-yellow solution was concentrated under reduced pressure at 65° C. to a semisolid mass and it was treated with water (1.5 L). The thick suspension was heated to 70-80° C. and left to cool to room temperature under stirring for 2 hours. The solid was collected by filtration, washed with water and sucked dry overnight. The wet solid was further dried under reduced pressure at 50-60° C. for 4 hours to give (2R)-2-[[(1R)-1-phenylethyl]amino]-3-[1-(trifluoromethyl)cyclopropyl] propanoic acid (hydrochloride salt) (135 g, 92%) as an off-white solid. ESI-MS m/z calc. 301.12897, found 302.0 $(M+1)^+$; Retention time: 1.82 minutes; (LC method V).

Step 6: (2R)-2-[[(1R)-1-phenylethyl]amino]-3-[1-(trifluoromethyl)cyclopropyl]propan-1-ol

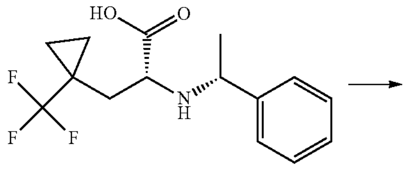

-continued

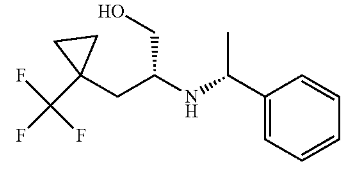

In a 5 L flask equipped with mechanical stirring and under dry nitrogen atmosphere, (2R)-2-[[(1R)-1-phenylethyl] amino]-3-[1-(trifluoromethyl)cyclopropyl] propanoic acid (hydrochloride salt) (135 g, 399.7 mmol) was suspended in THF (2 L) (thick suspension). It was heated to 35-40° C. and LAH (47.3 g, 1.214 mol) (pellets) was slowly added over 1 hour, while keeping the internal temperature between 30 and 40° C. by external cooling. The mixture was stirred for 1 hour at 30-40° C. (almost no hydrogen evolution anymore, grey suspension, most starting material in solution) and it was heated at 50-55° C. for 1 hour. The grey suspension was left stirring in the cooling heating mantel overnight. The grey suspension was cooled in an ice bath and quenched by careful addition of water (44 mL, 2.442 mol), NaOH (41 mL of 6 M, 246.0 mmol) and water (44 mL, 2.442 mol) (high exotherm with first water addition, kept between 5° C. and 30° C. by cooling). The grey suspension was heated to 50-55° C. for 1 hour, by which time a colorless suspension was obtained. The warm suspension was filtered over a pad of Celite covered over magnesium sulfate. The solids were washed with hot THF and evaporated to give crude (2R)-2-[[(1R)-1-phenylethyl]amino]-3-[1-(trifluoromethyl)cyclopropyl]propan-1-ol (121 g, 105%) as an oil. The crude was dissolved in diethyl ether (1 L, clear solution) and slowly treated with HCl (101 mL of 4 M, 404.0 mmol) (4 M in dioxane) under cooling. The resulting thick suspension was stirred at room temperature for 1 hour, the solid collected by filtration, washed with diethyl ether and dried under reduced pressure at 40-45° C. with a nitrogen bleed to give (2R)-2-[[(1R)-1-phenylethyl]amino]-3-[1-(trifluoromethyl)cyclopropyl]propan-1-ol (hydrochloride salt) (126.6 g, 98%) as an off-white solid. $^{1}H$ NMR (500 MHz, DMSO-$d_6$) δ 9.34 (s, 2H), 7.66 (d, J=7.4 Hz, 2H), 7.43 (dt, J=25.1, 7.4 Hz, 3H), 5.59 (s, 1H), 4.58 (q, J=6.6 Hz, 1H), 3.83 (d, J=12.6 Hz, 1H), 3.62-3.54 (m, 1H), 2.89 (s, 1H), 2.33-2.24 (m, 1H), 1.67-1.51 (m, 4H), 0.97-0.81 (m, 3H), 0.71 (s, 1H). ESI-MS m/z calc. 287.1497, found 288.0 $(M+1)^+$; Retention time: 0.99 minutes (LC method A).

Step 7: (2R)-2-Amino-3-[1-(trifluoromethyl)cyclopropyl]propan-1-ol

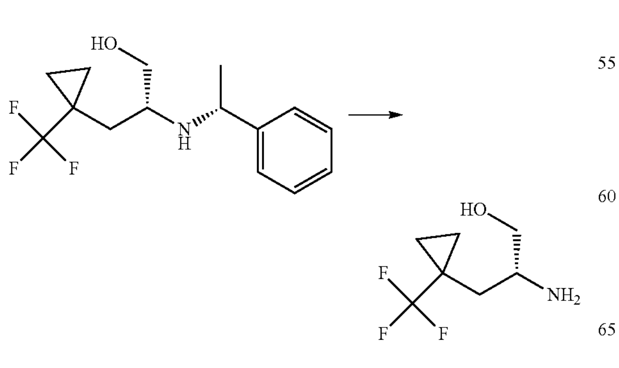

In a 1 L hydrogenation reactor, (2R)-2-[[(1R)-1-phenylethyl]amino]-3-[1-(trifluoromethyl)cyclopropyl]propan-1-ol (hydrochloride salt) (63.3 g, 195.5 mmol) was dissolved in EtOH (630 mL) (under warming), and it was treated with Pd/C (6.3 g of 10% w/w, 5.920 mmol) (12.5 g of 50% water wet) and the reaction was stirred under 2 bar of hydrogen at 40° C. for 24 hours. The reaction mixture was filtered over Celite. The pad was washed with ethanol and the colorless filtrate was evaporated to a solid mass, which was triturated with diethyl ether. The suspension was stirred at room temperature for 1 hour. The solid was filtered, washed with plenty of diethyl ether and dried to give (2R)-2-amino-3-[1-(trifluoromethyl)cyclopropyl]propan-1-ol (hydrochloride salt) (41.8 g, 97%) as an off-white solid. $^{1}H$ NMR (500 MHz, DMSO-$d_6$) δ 8.18 (s, 3H), 5.45 (t, J=4.9 Hz, 1H), 3.71 (dt, J 11.6, 3.9 Hz, 1H), 3.55 (dt, J=11.2, 5.4 Hz, 1H), 3.24 (h, J=4.7 Hz, 1H), 2.08 (dd, J=15.1, 5.4 Hz, 1H), 1.69 (dd, J=15.1, 9.4 Hz, 1H), 0.97 (h, J=6.5, 5.9 Hz, 2H), 0.86 (s, 2H). ESI-MS m/z calc. 183.0871, found 184.0 $(M+1)^+$; Retention time: 0.65 minutes; LC method A.

Example F: Preparation of 6-[[4-chloro-6-(2,6-dimethylphenyl)pyrimidin-2-yl]sulfamoyl]pyridine-2-carboxylic acid Step 1: Methyl 6-benzylsulfanylpyridine-2-carboxylate

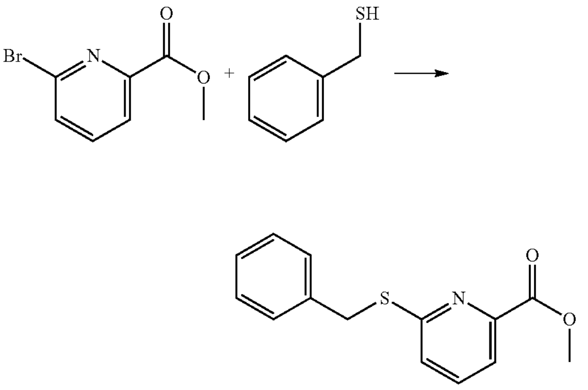

To a solution of phenylmethanethiol (28.408 g, 26.800 mL, 228.72 mmol) in THF (600 mL) was added NaH (11.200 g, 60% w/w, 280.03 mmol) in a few portions at 0° C. The slurry was warmed to room temperature and stirred for 30 minutes, then methyl 6-bromopyridine-2-carboxylate (50 g, 231.45 mmol) was added as a single portion. After 3 hours, the reaction was diluted with ether (800 mL) and quenched with water (400 mL) and saturated sodium bicarbonate (50 mL). The layers were separated, and the organic layer was washed with brine, dried over sodium sulfate, and concentrated under reduced pressure to yield methyl 6-benzylsulfanylpyridine-2-carboxylate (56.35 g, 89%) as a yellow oil. $^{1}H$ NMR (500 MHz, DMSO-$d_6$) δ 7.84-7.77 (m, 1H), 7.77-7.73 (m, 1H), 7.52 (m, 1H), 7.48 (d, J=7.8 Hz, 2H), 7.28 (t, J=7.2, 7.2 Hz, 2H), 7.24-7.18 (m, 1H), 4.44 (s, 2H), 3.90 (d, J=1.2 Hz, 3H). ESI-MS m/z calc. 259.0667, found 260.1 $(M+1)^+$; Retention time: 3.2 minutes; LC method T.

Step 2: Methyl 6-chlorosulfonylpyridine-2-carboxylate

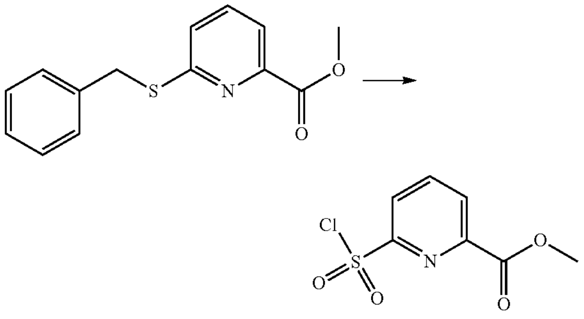

A solution of methyl 6-benzylsulfanylpyridine-2-carboxylate (121.62 g, 431.47 mmol) in DCM (950 mL) and DI water (300 mL) was cooled in a −1-0° C. ice bath and, with vigorous stirring, sulfuryl chloride (228.14 g, 140 mL, 1.6396 mol) was added dropwise while the temperature was maintained below 5° C. After the addition, the organic phase was separated, washed with DI water (2×500 mL), dried over anhydrous sodium sulfate, filtered and concentrated under vacuum. The residue was dissolved in DCM (500 mL). Hexanes (1000 mL) was added and the DCM was slowly evaporated off. The white precipitate was filtered by vacuum and the solids were washed with Hexanes (2×500 mL). The filtered solids were collected. The residue solids in the filtrate were filtered and dissolved in DCM (500 mL). The DCM solution was transferred to a 1 L round-bottom flask and concentrated under vacuum. The residue was dissolved in DCM (200 mL). Hexanes (600 mL) was added and the DCM was slowly evaporated off. The white precipitation was filtered by vacuum and the solids were washed with hexanes (2×500 mL) After drying, methyl 6-chlorosulfonylpyridine-2-carboxylate (56.898 g, 55%) was isolated. $^1$H NMR (500 MHz, Chloroform-d) δ 8.48 (dd, J=7.8, 1.1 Hz, 1H), 8.31 (dd, J=7.9, 1.1 Hz, 1H), 8.25 (t, J=7.8 Hz, 1H), 4.08 (s, 3H). ESI-MS m/z calc. 234.97061, found 236.1 (M+1)$^+$; Retention time: 1.74 minutes; LC method T.

Step 3: Methyl 6-[[4-chloro-6-(2,6-dimethylphenyl)pyrimidin-2-yl]sulfamoyl]pyridine-2-carboxylate

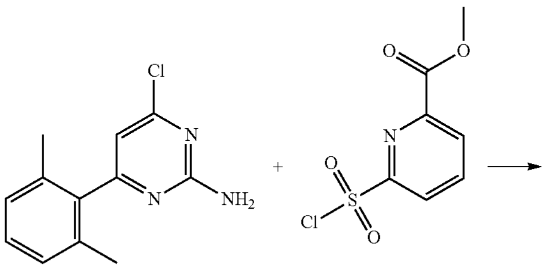

-continued

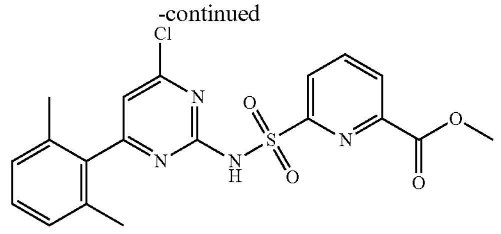

A solution of 4-chloro-6-(2,6-dimethylphenyl)pyrimidin-2-amine (16.63 g, 71.161 mmol) and methyl 6-chlorosulfonylpyridine-2-carboxylate (16.8 g, 71.294 mmol) dissolved in anhydrous THF (680 mL) was cooled to −78° C. Then Lithium bis(trimethylsilyl)amide (143 mL of 1 M, 143.00 mmol) in solution in THF was added dropwise. The mixture was allowed to warm up to 0° C. slowly and then 1 M aqueous HCl (146 mL) was added, followed by DI water (680 mL). The THF was evaporated and the aqueous phase was extracted with chloroform (3×250 mL). The combined organic layers were washed with saturated aqueous NaCl (300 mL), dried over anhydrous sodium sulfate, filtered, and concentrated under vacuum. The crude was recrystallized in 10% Acetone in Hexanes (500 mL). The white precipitate was filtered and rinsed with acetone (2×100 mL) to give methyl 6-[[4-chloro-6-(2,6-dimethylphenyl)pyrimidin-2-yl] sulfamoyl] pyridine-2-carboxylate (15.79 g, 50%). ESI-MS m/z calc. 432.06592, found 433.3 (M+1)$^+$; Retention time: 5.5 minutes; LC method S.

Step 4: 6-[[4-Chloro-6-(2,6-dimethylphenyl)pyrimidin-2-yl]sulfamoyl]pyridine-2-carboxylic acid

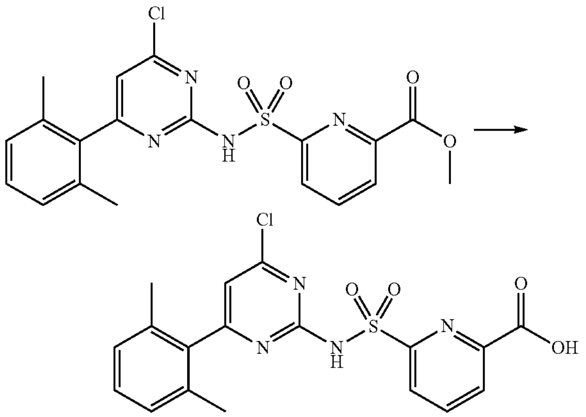

To a solution of methyl 6-[[4-chloro-6-(2,6-dimethylphenyl)pyrimidin-2-yl]sulfamoyl]pyridine-2-carboxylate (15.79 g, 36.477 mmol) in THF (180 mL) was added aqueous sodium hydroxide (182 mL of 1 M, 182.00 mmol). The reaction was stirred at room temperature for 1 hour. The THF was evaporated, and the aqueous layer was washed with diethyl ether (2×200 mL). The aqueous layer was acidified to pH 2 with 1 M Aqueous HCl (250 mL). The precipitate was filtered and the white solid were rinsed with DI water (2×250 mL). The solids were dried under vacuum to give 6-[[4-chloro-6-(2,6-dimethylphenyl) pyrimidin-2-yl] sulfamoyl]pyridine-2-carboxylic acid (14.3444 g, 93%). $^1$H NMR (250 MHz, DMSO-d$_6$) δ 8.14-7.99 (m, 3H), 7.21-7.11 (m, 1H), 7.03 (d, J=7.7 Hz, 2H), 6.92 (s, 1H), 1.78 (s, 6H).

ESI-MS m/z calc. 418.05026, found 419.1 $(M+1)^+$; Retention time: 2.61 minutes; LC method T.

Example G: Preparation of 3-[[4-Chloro-6-(2,6-dimethylphenyl)-2-pyridyl]sulfamoyl]benzoic acid Step 1: 4-Chloro-6-(2,6-dimethylphenyl)pyridin-2-amine

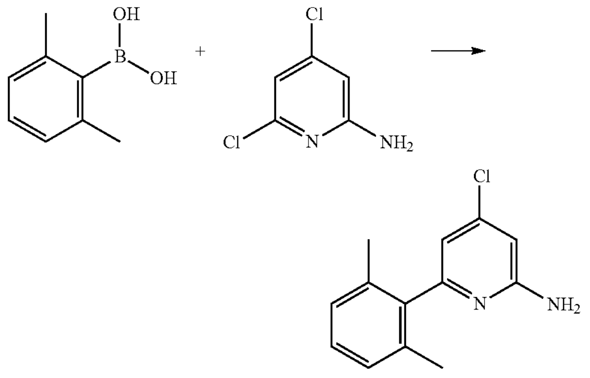

To a stirring solution of (2,6-dimethylphenyl)boronic acid (11.515 g, 76.775 mmol) and 4,6-dichloropyridin-2-amine (12.513 g, 76.765 mmol) in Toluene (425 mL) and EtOH (213 mL) was added an aqueous solution of Sodium carbonate (115 mL of 2 M, 230.00 mmol) and the reaction mixture was degassed with nitrogen gas for 45 minutes. $Pd(dppf)Cl_2$ (6.271 g, 7.6791 mmol) was then added with degassing continuing for an additional 15 minutes. Then the reaction vial was sealed, and the mixture heated to 100° C. and stirred at that temperature for 24 hours. After this time, volatiles were removed under reduced pressure and the residue was extracted with ethyl acetate (3×200 mL). The combined organic layers were washed with brine, dried over anhydrous sodium sulfate and concentrated under reduced pressure. The crude product was purified by silica gel column chromatography (0-25% EtOAc in Hexanes) and triturated with Hexanes to afford 4-chloro-6-(2,6-dimethylphenyl)pyridin-2-amine (6.469 g, 34%) as an off-white solid. ESI-MS m/z calc. 232.07672, found 233.1 $(M+1)^+$; Retention time: 2.31 minutes; (LC method T).

Step 2: Methyl 3-[[4-chloro-6-(2,6-dimethylphenyl)-2-pyridyl]sulfamoyl]benzoate

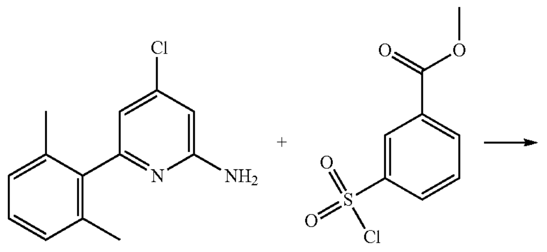

-continued

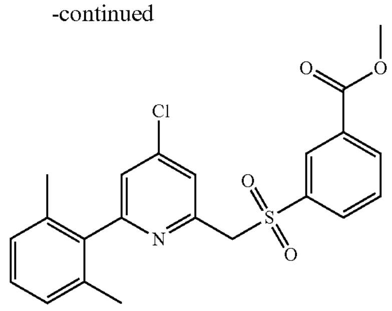

To a solution of 4-chloro-6-(2,6-dimethylphenyl)pyridin-2-amine (4.9 g, 20.635 mmol) and methyl 3-chlorosulfonylbenzoate (4.9 g, 20.046 mmol) in THF (200 mL) was added dropwise Lithium bis(trimethylsilyl)amide (45 mL of 1 M, 45.000 mmol) at −78° C. under nitrogen. The reaction mixture was stirred for 30 minutes at −78° C.; then warmed up to 0° C. and stirred for 2 hours at 0° C. The reaction was quenched with cold 1.0 M Hydrochloric acid (50 mL) and diluted with water (200 mL). The mixture was extracted with ethyl acetate (2×400 mL). The organic layers were combined, washed with brine (500 mL), dried over sodium sulfate, filtered and concentrated. The residue was purified by chromatography using 0-20% ethyl acetate in hexanes to afford methyl 3-[[4-chloro-6-(2,6-dimethylphenyl)-2-pyridyl]sulfamoyl]benzoate (6.2 g, 68%) as a white solid. ESI-MS m/z calc. 430.0754, found 431.5 $(M+1)^+$; Retention time: 3.65 minutes; (LC method T).

Step 3: 3-[[4-Chloro-6-(2,6-dimethylphenyl)-2-pyridyl]sulfamoyl]benzoic acid

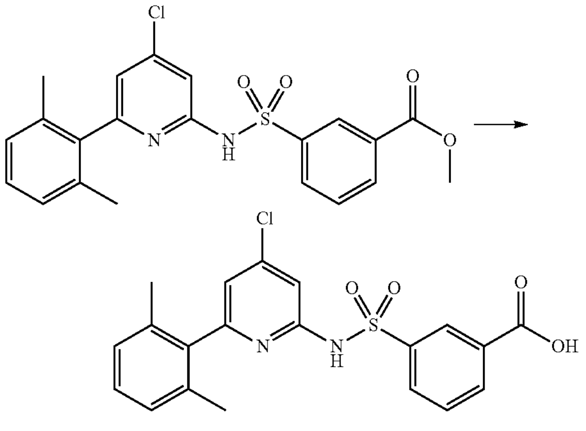

To a stirring solution of 3-[4-chloro-6-(2,6-dimethyl-phenyl)-pyridin-2-ylsulfamoyl]-benzoic acid methyl ester (5.3 g, 12.3 mmol) in a mixture of tetrahydrofuran (80 mL) and water (80 mL) at room temperature was added lithium hydroxide monohydrate (1.55 g, 36.9 mmol) and the reaction mixture was stirred at 45 C for 2 hours. Tetrahydrofuran was removed under vacuum and the residue was diluted with water (100 mL). The aqueous layer was washed with diethyl ether (2×50 mL), hexanes (50 mL) and acidified with 1.0 M hydrochloric acid to pH=2-3. The precipitated product was collected by filtration and dried in a vacuum oven at 75° C. to constant weight to afford 3-[4-chloro-6-(2,6-dimethylphenyl)-pyridin-2-ylsulfamoyl]-benzoic acid (4.8 g, 93%) as a white solid. $^1H$ NMR (250 MHz, DMSO-$d_6$) δ (ppm): 8.32 (d, J=1.9 Hz, 1H), 8.14 (d, J=7.7 Hz, 1H), 8.03 (d, J=8.0 Hz, 1H), 7.63 (t, J=7.8 Hz, 1H), 7.28-6.96 (m, 5H), 1.77 (s, 6H). ESI-MS m/z calc. 416.8, found 417.0 (M+1). Retention time: 5.11 minutes.

Example H: Preparation of (1R,2R)-2-Amino-1-(4-tert-butylphenyl)propan-1-ol

Step 1: tert-Butyl N-[(1R)-1-methyl-2-oxo-ethyl] carbamate

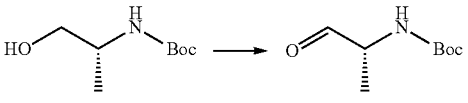

To a solution of tert-butyl N-[(1R)-2-hydroxy-1-methyl-ethyl] carbamate (200 g, 1.141 mol) in DCM (3 L) was added Dess-Martin periodinane (625 g, 1.474 mol) (fine suspension, most into solution, started exotherm, controlled with ice-bath). To the mixture was added water (28 mL, 1.554 mol), which was slowly added over 0.5 hours (exothermic during addition up to 33° C., kept between 20 and 33° C. by cooling with cold water), giving a colorless thick suspension. The suspension was stirred at room temperature for 16 hours. The solid was removed by filtration over Celite and washed 3× with 100 mL of DCM. The solvent was removed in vacuo affording an off-white slurry, which was diluted with MTBE (750 mL). The slurry was cooled with an ice-bath and filtered over Celite. The filtrate was washed 3× with saturated sodium bicarbonate, brine, dried over magnesium sulfate, filtered and concentrated in vacuo. The semi-solid was re-dissolved in MTBE (300 mL) and diluted with heptane (750 mL). The solution was concentrated in vacuo until a cloud point occurred. The slurry was stirred at ambient temperature for 0.5 hours. The precipitate was collected, washed with cold heptane and dried in vacuo at ambient temperature (this solid was product and was therefore kept aside). The filtrate was further concentrated in vacuo until a cloud point occurred. The solution was allowed to stand for 48 hours affording a thick off-white slurry. The slurry was filtered, and the filter cake was washed with −50 mL of cold heptane. The filter cake was combined with the solid kept aside earlier and air-dried for 4 hours. Product contained approximately 9% residual heptane by $^1H$ NMR. tert-Butyl N-[(1R)-1-methyl-2-oxo-ethyl]carbamate (95.6 g, 48%), $^1H$ NMR (500 MHz, DMSO-$d_6$) δ 9.43 (s, 1H), 7.35 (d, J=6.8 Hz, 1H), 3.86 (t, J=7.2 Hz, 1H), 1.40 (s, 9H), 1.13 (d, J=7.3 Hz, 3H).

Step 2: tert-Butyl N-[(1R,2R)-2-(4-tert-butylphenyl)-2-hydroxy-1-methyl-ethyl]carbamate

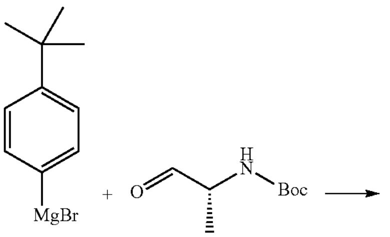

-continued

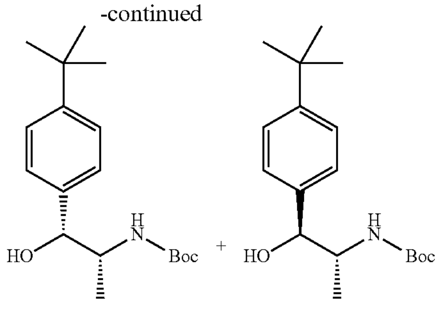

(major) (minor)

A solution of tert-butyl N-[(1R)-1-methyl-2-oxo-ethyl] carbamate (101.73 g, 587.3 mmol) in MeTHF (500 mL) was added slowly over 1 hour to bromo-(4-tert-butylphenyl) magnesium (1300 mL of 1 M, 1.300 mol) (1 M in MeTHF) in a −35° C. cold bath at a rate which maintained an internal temperature between −2° C. and −15° C. After the addition was complete, the mixture was stirred for 5 minutes, then the mixture was removed from the cold bath and transferred to a room temperature water bath, then stirred for 2.5 hours. The mixture was cooled to 0° C., then saturated ammonium chloride (1700 mL) was added (large exotherm) at a rate which maintained an internal temperature of 5° C. Water (500 mL) was added, the organic layer was separated and washed with brine (500 mL), dried over magnesium sulfate, then concentrated under vacuum to give a light yellow oil, tert-butyl N-[(1R,2R)-2-(4-tert-butylphenyl)-2-hydroxy-1-methyl-ethyl]carbamate (266 g, >100% yield), which was used in the next step without further purification. ESI-MS m/z calc. 307.21475, found 308.1 $(M+1)^+$; Retention time: 1.86 minutes; LC method A.

Step 3: (1R,2R)-2-Amino-1-(4-tert-butylphenyl) propan-1-ol (hydrochloride Salt)

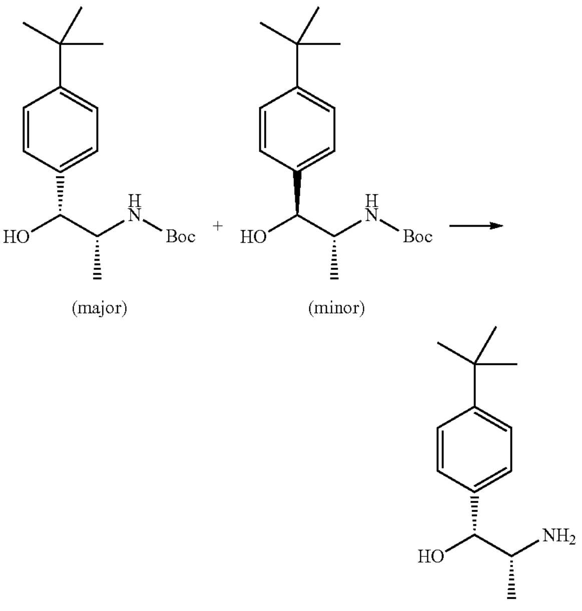

A solution of tert-butyl N-[(1R,2R)-2-(4-tert-butylphenyl)-2-hydroxy-1-methyl-ethyl]carbamate (180.6 g, 587.5 mmol) in MeOH (250 mL) was added dropwise over 50 minutes to HCl in dioxane (478 mL of 4 M, 1.912 mol), maintaining a temperature between 18° C. and 23° C., then stirred at room temperature for 2 hours. The mixture was concentrated under vacuum to give 267.5 g of residue. This was recrystallized from dioxane, the product was collected by filtration, then rinsed with MeTHF until all the color was removed, giving 75.4 g of product. This was further recrystallized from MeOH/dioxane, which gave (1R,2R)-2-amino-1-(4-tert-butylphenyl)propan-1-ol (hydrochloride salt) (62.65 g, 44%); $^1$H NMR (500 MHz, DMSO-$d_6$) δ 8.10 (s, 3H), 7.39 (d, J=8.2 Hz, 2H), 7.28 (d, J=8.1 Hz, 2H), 6.12 (d, J=3.8 Hz, 1H), 4.50-4.34 (m, 1H), 3.28-3.12 (m, 1H), 1.27 (s, 9H), 0.96 (d, J=6.6 Hz, 3H). ESI-MS m/z calc. 207.16231, found 208.2 $(M+1)^+$; Retention time: 1.01 minutes; LC method A.

Example I: Preparation of (1S,2R)-2-[Benzyl(methyl)amino]-1-(5-tert-butyl-2-pyridyl)-4-methyl-pentan-1-ol Step 1: (2R)-2-[Benzyl(methyl)amino]-N-methoxy-N,4-dimethyl-pentanamide

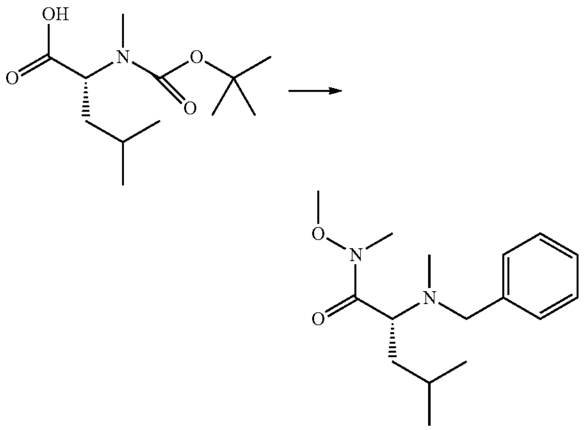

Stage 1: In a 1-L round-bottomed flask, (2R)-2-[tert-butoxycarbonyl(methyl) amino]-4-methyl-pentanoic acid (21.46 g, 82.23 mmol), DCM (110 mL), DMF (110 mL), N-methoxymethanamine (hydrochloride salt) (11.50 g, 117.9 mmol), DIPEA (68 mL, 390.4 mmol), HOBt (15.97 g, 118.2 mmol), and EDCI (hydrochloride salt) (27.05 g, 118.6 mmol) were added in this order. This solution was stirred at room temperature for 4 hours, after which it was diluted with ethyl acetate (1 L). This mixture was washed with 1N NaOH solution (400 mL), 1N HCl solution (2×400 mL), water (400 mL) and saturated aqueous sodium chloride solution (400 mL), then dried over sodium sulfate, filtered, and evaporated in vacuo to give a slightly yellow liquid, corresponding to the Weinreb amide intermediate (~27 g, >100% yield), ESI-MS m/z calc. 288.2049, found 289.3 $(M+1)^+$; Retention time: 1.64 minutes; LC method A.

Stage 2: In a 250-mL round-bottomed flask, the crude product from Stage 1 was dissolved in dioxane (25 mL) and cooled to 0° C. This solution was treated with a dioxane solution of HCl (75 mL of 4.0 M, 300.0 mmol), and the resulting mixture was warmed to room temperature over 4 hours. Evaporation of the resulting slurry in vacuo provided an off-white solid, corresponding to the deprotected intermediate (~28 g, >100% yield).

Stage 3: In a 250-mL round-bottomed flask, the crude product from Stage 2 was dissolved in EtOH (100 mL) and water (25 mL), to which potassium carbonate (35.0 g, 253.2 mmol) and benzyl bromide (11.0 mL, 92.48 mmol) were added. This slurry was stirred at room temperature for 69 hours, after which it was filtered over Celite, using MeOH (50 mL) to rinse the potassium carbonate and Celite. The filtrate was evaporated in vacuo and this slurry was taken up in DCM (100 mL), filtered over Celite and evaporated in vacuo. The resulting yellow liquid was then purified by silica gel chromatography (330 g of silica) using a gradient eluent of 1 to 5% MeOH in DCM, then filtered under a flow of nitrogen to give a colorless viscous liquid: (2R)-2-[benzyl(methyl)amino]-N-methoxy-N,4-dimethyl-pentanamide (12.0617 g, 53%); $^1$H NMR (400 MHz, dimethylsulfoxide-$d_6$) δ 7.33-7.25 (m, 4H), 7.25-7.19 (m, 1H), 4.06-3.73 (m, 1H), 3.66 (AB quartet, 2H), 3.59 (s, 3H), 3.11 (s, 3H), 2.21 (s, 3H), 1.68-1.53 (m, 2H), 1.53-1.41 (m, 1H), 0.88 (dd, J=6.7 Hz, 1H). ESI-MS m/z calc. 278.19943, found 279.3 $(M+1)^+$; Retention time: 0.88 minutes; LC method A.

Step 2: (2R)-2-[Benzyl(methyl)amino]-1-(5-tert-butyl-2-pyridyl)-4-methyl-pentan-1-one

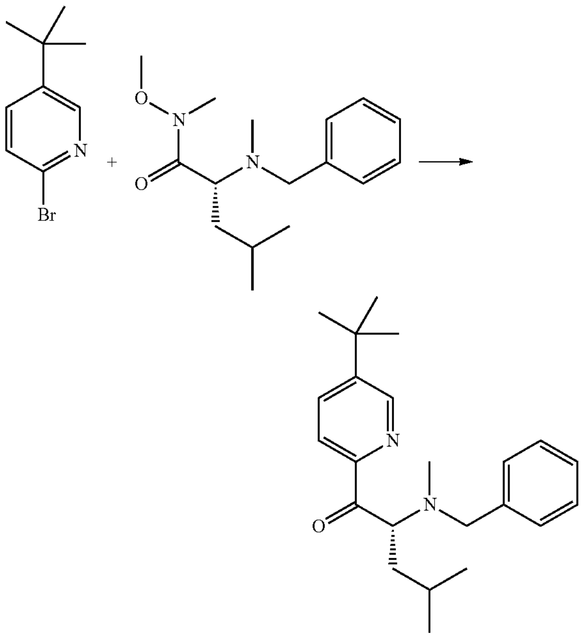

In a 20-mL microwave vial, 2-bromo-5-tert-butyl-pyridine (350 mg, 1.635 mmol) was dissolved in anhydrous THF (8 mL) and cooled to −78° C. A hexanes solution of nBuLi (700 µL of 2.5 M, 1.750 mmol) was added in one portion, and this mixture was stirred at −78° C. for 10 minutes. A solution of (2R)-2-[benzyl(methyl)amino]-N-methoxy-N,4-dimethyl-pentanamide (455.3 mg, 1.635 mmol) in anhydrous THF (2 mL) was then added dropwise. This solution was stirred at −78° C. for 5 minutes and warmed to room temperature over 2 hours. The reaction mixture was then quenched with 0.5 N HCl (20 mL) and extracted with ethyl acetate (3×20 mL). The combined organic extracts was washed with water (50 mL) and saturated aqueous sodium chloride solution (50 mL), then dried over sodium sulfate, filtered, and evaporated in vacuo. The resulting yellow oil was purified by silica gel chromatography (40 g of silica) using a gradient eluent of 0 to 40% ethyl acetate in hexanes to give the product as a yellow oil: (2R)-2-[benzyl(methyl)amino]-1-(5-tert-butyl-2-pyridyl)-4-methyl-pentan-1-one (339.0 mg, 59%) $^1$H NMR (400 MHz, dimethylsulfoxide-$d_6$) δ 8.80 (dd, J=2.4, 0.8 Hz, 1H), 8.03 (dd, J=8.2, 2.4 Hz, 1H), 7.92 (dd, J=8.3, 0.8 Hz, 1H), 7.28-7.22 (m, 2H), 7.22-7.17 (m, 1H), 7.18-7.14 (m, 2H), 5.11 (t, J=7.1 Hz, 1H), 3.65 (s, 2H), 2.15 (s, 3H), 1.70-1.55 (m, 3H), 1.36 (s, 9H), 0.90 (d, J=6.0 Hz, 6H) ESI-MS m/z calc. 352.25146, found 353.4 $(M+1)^+$; Retention time: 1.5 minutes; LC method A.

Step 3: (1S,2R)-2-[Benzyl(methyl)amino]-1-(5-tert-butyl-2-pyridyl)-4-methyl-pentan-1-ol

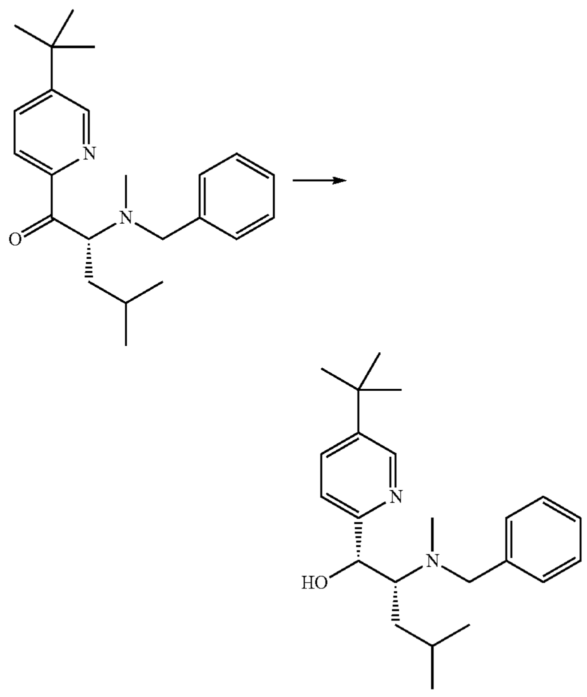

In a 20-mL vial, (2R)-2-[benzyl(methyl)amino]-1-(5-tert-butyl-2-pyridyl)-4-methyl-pentan-1-one (333.9 mg, 0.9472 mmol) was dissolved in MeOH (2.0 mL), to which sodium borohydride (45.3 mg, 1.197 mmol) was added. This mixture was stirred at room temperature for 10 minutes, after which it was quenched with 0.5 N HCl solution (5 mL). The mixture was neutralized with 0.5 N NaOH (~4 mL), then extracted with ethyl acetate (4×5 mL). The combined organic extracts was washed with water (10 mL) and saturated aqueous sodium chloride solution (10 mL), then dried over sodium sulfate, filtered, and evaporated in vacuo to give a slightly yellow viscous gum, (1S,2R)-2-[benzyl(methyl)amino]-1-(5-tert-butyl-2-pyridyl)-4-methyl-pentan-1-ol (303.1 mg, 90%) $^1$H NMR (400 MHz, dimethylsulfoxide-$d_6$) δ 8.52 (d, J=2.1 Hz, 1H), 7.79 (dd, J=8.3, 2.6 Hz, 1H), 7.41 (dd, J=8.3, 0.7 Hz, 1H), 7.28-7.15 (m, 3H), 7.14-7.00 (m, 2H), 5.45-4.88 (bs, 1H), 4.70-4.51 (m, 1H), 3.70 (AB quartet, $\Delta\delta_{AB}$=0.13 ppm, $J_{AB}$=13.2 Hz, 2H), 3.11-2.84 (m, 1H), 2.19 (s, 3H), 1.59-1.26 (m, 3H), 1.32 (s, 9H), 0.78 (d, J=6.5 Hz, 3H), 0.72 (d, J=6.3 Hz, 3H) ESI-MS m/z calc. 354.26712, found 355.4 $(M+1)^+$; Retention time: 1.3 minutes; LC method A.

V. Synthesis of Compounds 1-73

Example 1: Preparation of Compound 1

Step 1: 6-[6-(2,6-Dimethylphenyl)-2-[(3-nitrophenyl)sulfonylamino]pyrimidin-4-yl]hexanoic acid

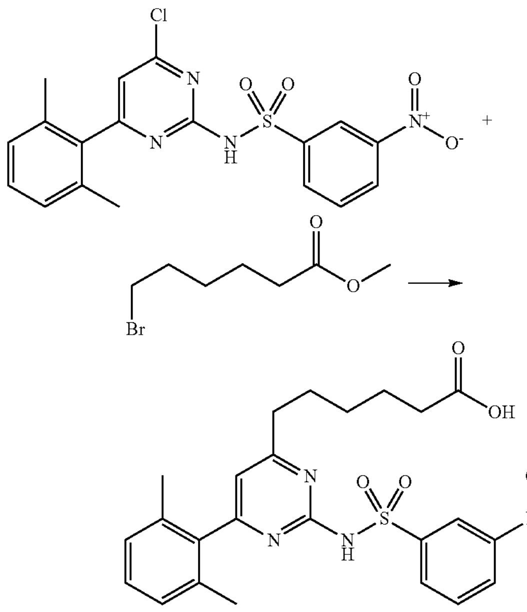

Stage 1: A 10 mL microwave vial equipped with a stir bar was placed under high vacuum then flushed with nitrogen. LiCl (318.1 mg, 7.503 mmol) was added, and the vessel was placed under high vacuum and heated with a heat gun for 3 minutes. The vial was allowed to cool to room temperature, after which it was filled with nitrogen. A THF solution of $ZnCl_2$ (4.3 mL of 0.7 M, 3.010 mmol) and Mg (183 mg, 7.529 mmol) were added, and this mixture was allowed to stir under nitrogen for 5 minutes. Then, methyl 6-bromohexanoate (627.5 mg, 3.001 mmol) was added in one portion, and this mixture was allowed to stir at room temperature for 4 hours. After this time, stirring was stopped until all the solids settled at the bottom of the vial. Another 10 mL microwave vial equipped with a stir bar was placed under high vacuum then flushed with nitrogen; N-[4-chloro-6-(2,6-dimethylphenyl)pyrimidin-2-yl]-3-nitro-benzenesulfonamide (161.8 mg, 0.3863 mmol) was added, followed by 4.0 mL of the organozine reagent prepared above. This mixture was stirred at room temperature under nitrogen for 5 minutes, after which PEPPSI-SIPr (4.1 mg, 0.006008 mmol) was added. The microwave vial was tightly capped, and the mixture was stirred at 60° C. for 30 minutes, then cooled to room temperature over 17 hours. This mixture was quenched with saturated aqueous ammonium chloride solution (6 mL), then extracted with ethyl acetate (3×10 mL). The combined organic extracts was washed with water (10 mL) and saturated aqueous sodium chloride solution (10 mL), then dried over sodium sulfate, filtered, and evaporated in vacuo.

Stage 2: In a 20 mL vial, the crude product from Stage 1 was dissolved in THF (4 mL) and water (4 mL), to which LiOH (30.8 mg, 1.286 mmol) was added. This solution was stirred at 60° C. for 20 minutes. The reaction mixture was cooled to room temperature, quenched with 1 N HCl (5 mL), then was extracted with ethyl acetate (3×6 mL). The combined organic extracts was washed with water (10 mL) and saturated aqueous sodium chloride solution (10 mL), then dried over sodium sulfate, filtered, and evaporated in vacuo. This crude product was purified by a silica gel plug (1 g of silica, 30 mL 1:1 ethyl acetate:hexanes) to give 6-[6-(2,6-dimethylphenyl)-2-[(3-nitrophenyl)sulfonylamino] pyrimidin-4-yl]hexanoic acid (16.7 mg, 9%) ESI-MS m/z calc. 498.15732, found 499.4 $(M+1)^+$; Retention time: 0.59 minutes; LC method D.

Step 2: 6-(2,6-dimethylphenyl)-2,2-dioxo-2 λ6-thia-3,5,15,21-tetrazatricyclo[14.3.1.14,8]henicosa-1(20), 4(21),5,7,16,18-hexaen-14-one (Compound 1)

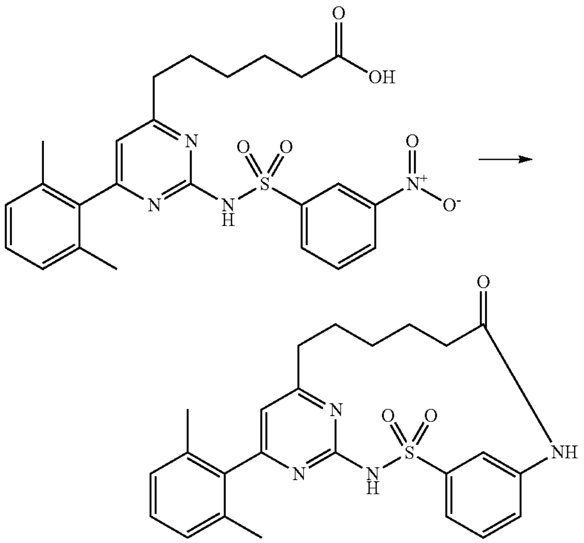

Stage 1: In a 10 mL microwave vial equipped with a magnetic stir bar, 6-[6-(2,6-dimethylphenyl)-2-[(3-nitrophenyl)sulfonylamino]pyrimidin-4-yl]hexanoic acid (16.7 mg, 0.03350 mmol) was dissolved in EtOH (1.0 mL). This solution was sparged with a balloon of hydrogen gas for 5 minutes. The cap was briefly removed, and 10% $Pd(OH)_2/C$ (3.0 mg, 0.002136 mmol) was added. This reaction mixture was stirred under hydrogen (2 L, 79.37 mmol) at 60° C. for 1 hour, after which it was cooled to room temperature, filtered through Celite and rinsed with methanol (3.0 mL). This solution was evaporated in vacuo to give 16.8 mg of crude product that was not purified at this stage.

Stage 2: The product from Stage 1 was dissolved in DMF (1.0 mL) and treated with DIPEA (30 μL, 0.1722 mmol) and HATU (20.9 mg, 0.05497 mmol). This mixture was stirred at room temperature for 5 minutes, after which it was filtered and purified by reverse phase HPLC (1-70% acetonitrile in water using HCl as a modifier) to give a white powder, 6-(2,6-dimethylphenyl)-2,2-dioxo-2$\lambda^6$-thia-3,5,15,21-tetrazatricyclo[14.3.1.14,8]henicosa-1(20),4(21),5,7,16,18-hexaen-14-one (6.1 mg, 40%); $^1H$ NMR (400 MHz, dimethylsulfoxide-$d_6$) δ 11.55 (s, 1H, $D_2O$ exchangeable), 10.27 (s, 1H, $D_2O$ exchangeable), 8.75 (s, 1H), 7.61-7.44 (m, 3H), 7.20 (t, J=7.7 Hz, 1H), 7.09 (d, J=7.6 Hz, 2H), 6.92 (s, 1H), 2.70-2.60 (m, 2H), 2.35-2.26 (m, 2H), 1.93 (s, 6H), 1.82-1.71 (m, 2H), 1.66-1.54 (m, 2H), 1.47-1.35 (m, 2H). ESI-MS m/z calc. 450.17255, found 451.5 $(M+1)^+$; Retention time: 1.47 minutes; LC method A.

Example 2: Preparation of Compound 2

Step 1: Methyl 3-[(4,4,5,5-tetramethyl-1,3,2-dioxaborolan-2-yl)methyl]benzoate

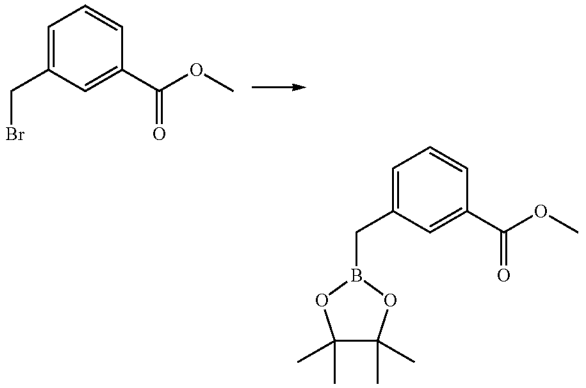

A heterogeneous solution consisting of 4,4,5,5-tetramethyl-2-(4,4,5,5-tetramethyl-1,3,2-dioxaborolan-2-yl)-1,3,2-dioxaborolane (8 g, 31.50 mmol), methyl 3-(bromomethyl)benzoate (6 g, 26.19 mmol), tetrakis (triphenylphosphine)palladium(0) (1.52 g, 1.32 mmol), and potassium carbonate (10.90 g, 78.87 mmol) in dioxane (105 mL) was heated to 90° C. in a sealed vessel for 16 hours. The reaction mixture was diluted with diethyl ether and filtered through Celite. The filtrate was concentrated in vacuo. The crude residue was separated by flash column chromatography on silica gel (10% ethyl acetate in hexanes) which afforded methyl 3-[(4,4,5,5-tetramethyl-1,3,2-dioxaborolan-2-yl)methyl]benzoate (5.4 g, 27%) as a white solid. $^1H$ NMR (400 MHz, Chloroform-d) δ 7.86 (td, J=1.8, 0.6 Hz, 1H), 7.80 (dt, J=7.6, 1.5 Hz, 1H), 7.47-7.16 (m, 3H), 3.90 (s, 3H), 2.34 (s, 2H), 1.23 (s, 12H).

Step 2: 5-(2,6-Dimethylphenyl)-9 λ6-thia-6,8,15,23-tetraazatetracyclo [15.3.1.13,7.110,14]tricosa-1(21), 3(23),4,6,10,12,14(22),17,19-nonaene-9,9,16-trione (Compound 2)

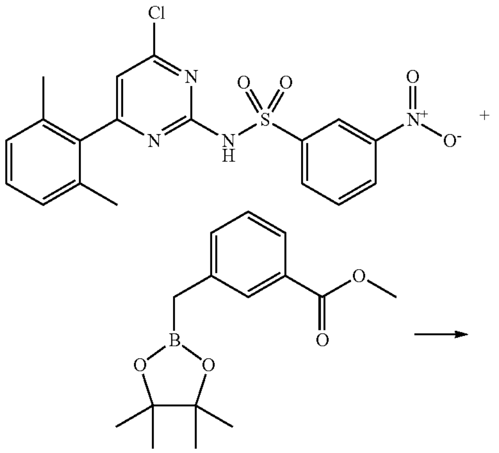

-continued

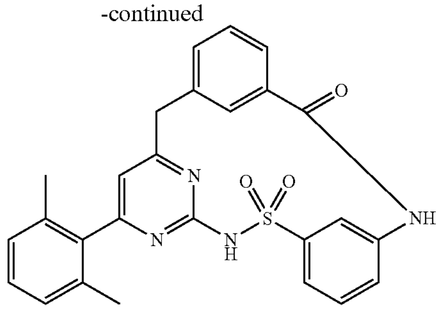

Stage 1: In a 10 mL microwave vial, N-[4-chloro-6-(2,6-dimethylphenyl)pyrimidin-2-yl]-3-nitro-benzenesulfonamide (180.2 mg, 0.4302 mmol), methyl 3-[(4,4,5,5-tetramethyl-1,3,2-dioxaborolan-2-yl)methyl]benzoate (180.5 mg, 0.6537 mmol), and $Pd(dppf)Cl_2$-DCM (44.8 mg, 0.05486 mmol) were dissolved in dioxane (3.0 mL), to which an aqueous solution of sodium carbonate (1.0 mL of 2.0 M, 2.000 mmol) was added. This mixture was sparged with a balloon of nitrogen gas for 15 minutes under sonication. It was then stirred at 80° C. for 14 hours, after which it was cooled to room temperature. LiOH (86.0 mg, 3.591 mmol) and water (2.0 mL) were added, and this mixture was stirred at 80° C. for 40 minutes. The reaction mixture was then cooled to room temperature, quenched with 1 N HCl (8 mL), and extracted with ethyl acetate (3×8 mL). The combined organic extracts was washed with water (15 mL) and saturated aqueous sodium chloride solution (15 mL), then dried over sodium sulfate, filtered, and evaporated in vacuo. This crude product was purified by silica gel chromatography (24 g of silica, 0 to 40% gradient of ethyl acetate/hexanes) to give 91.5 mg of 66% pure product.

Stage 2: In a 10 mL microwave vial, the product from Stage 1 was dissolved in EtOH (3.0 mL). This solution was sparged with a balloon of hydrogen gas for 5 minutes. The cap was briefly removed, and 10% $Pd(OH)_2/C$ (23.1 mg, 0.0164 mmol) was added. This reaction mixture was stirred under hydrogen (2 L, 79.37 mmol) at room temperature for 19 hours, after which it was filtered through Celite and rinsed with methanol (5.0 mL). This solution was evaporated in vacuo, then purification by reverse phase HPLC (1-70% acetonitrile in water using HCl as a modifier) gave a white powder, 3-[[2-[(3-aminophenyl)sulfonylamino]-6-(2,6-dimethylphenyl)pyrimidin-4-yl]methyl]benzoic acid (hydrochloride salt) (41.3 mg, 18%) ESI-MS m/z calc. 488.15182, found 489.3 $(M+1)^+$; Retention time: 1.43 minutes; LC method A.

Stage 3: The product from Stage 2 (41.0 mg, 0.0781 mmol) was dissolved in DMF (0.9 mL) and treated with DIPEA (50 μL, 0.29 mmol) and HATU (59.7 mg, 0.157 mmol). This mixture was stirred at room temperature for 5 minutes, after which it was filtered and purified by reverse phase HPLC (1-70% acetonitrile in water using HCl as a modifier) to give 5-(2,6-dimethylphenyl)-9$\lambda^6$-thia-6,8,15,23-tetraazatetracyclo[15.3.1.13,7.110,14]tricosa-1(21),3(23),4,6,10,12,14(22),17,19-nonaene-9,9,16-trione (27.9 mg, 14%) $^1H$ NMR (400 MHz, dimethylsulfoxide-$d_6$) δ 11.86-11.45 (bs, 1H, $D_2O$ exchangeable), 10.44 (s, 1H, $D_2O$ exchangeable), 7.60 (dt, J=7.7, 1.5 Hz, 1H), 7.52 (d, J=5.1 Hz, 1H), 7.49 (dd, J=7.7, 5.3 Hz, 1H), 7.42-7.30 (m, 3H), 7.24 (t, J=7.6 Hz, 1H), 7.13 (d, J=7.6 Hz, 2H), 7.11-7.03 (m, 2H), 7.01 (t, J=2.0 Hz, 1H), 4.06 (s, 2H), 2.01 (s, 6H) ESI-MS m/z calc. 470.14127, found 471.3 $(M+1)^+$; Retention time: 1.44 minutes; LC method A.

Example 3: Preparation of Compound 3

Step 1: tert-Butyl N-[(1R)-1-[methoxy(methyl)carbamoyl]-3-methyl-butyl]carbamate

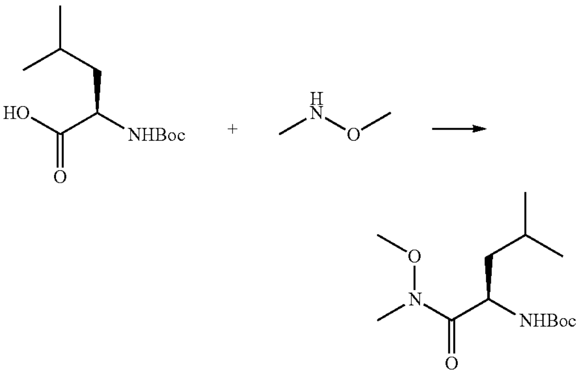

(2R)-2-(tert-Butoxycarbonylamino)-4-methyl-pentanoic acid (20 g, 86.472 mmol) was dissolved in DCM (200 mL) and stirred at −10° C. Then HOBt (11.7 g, 86.588 mmol) and 1-(3-dimethylaminopropyl)-3-ethylcarbodiimide (20.171 g, 23 mL, 129.93 mmol) were added. The reaction was stirred for 30 minutes. N-methoxymethanamine (hydrochloride salt) (8.6 g, 88.166 mmol) and DIPEA (28.196 g, 38 mL, 218.16 mmol) were added to the reaction mixture. The reaction was stirred at this temperature for 30 minutes, then allowed to warm to room temperature and stirred overnight. The reaction was quenched with 1 M HCl (aq.) (200 mL). Two layers were separated, and the organic layer was washed with saturated sodium bicarbonate (200 mL), and brine (200 mL), dried over sodium sulfate and concentrated under vacuum to give tert-butyl N-[(1R)-1-[methoxy(methyl)carbamoyl]-3-methyl-butyl]carbamate (23.95 g, 101%) as a yellow oil. ESI-MS m/z calc. 274.18927, found 275.3 $(M+1)^+$; Retention time: 3.02 minutes; LC method T.

Step 2: tert-Butyl N-[(1R)-1-ethynyl-3-methyl-butyl]carbamate

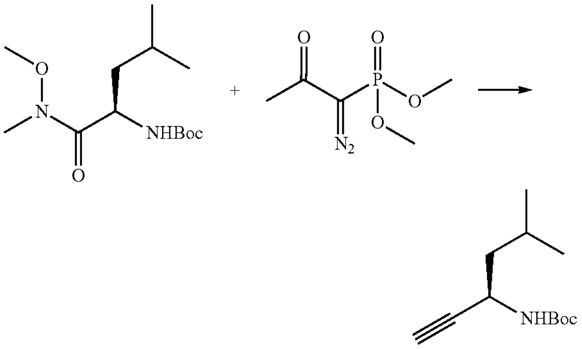

Into a solution of tert-butyl N-[(1R)-1-[methoxy(methyl)carbamoyl]-3-methyl-butyl]carbamate (253 mg, 0.9222 mmol) in anhydrous DCM (10 mL) was added DIBAL-H (2.8 mL of 1 M, 2.8000 mmol) in toluene at −78° C. The reaction was stirred at the same temperature for 30 minutes. Excess of DIBAL-H was quenched with MeOH (10 mL), and the reaction was slowly raised to 0° C. Potassium carbonate (391 mg, 2.8291 mmol) and a solution of dimethyl (1-diazo-2-oxopropyl)phosphonate (384.00 mg, 0.3 mL, 1.9884 mmol) in MeOH (10 mL) was added to the reaction. The reaction was stirred at 0° C. for 1 hour, then slowly raised to room temperature and stirred overnight. The reaction was quenched with Rochelles's salt (20 mL) and diluted with DCM (20 mL). The reaction was stirred for 10 minutes until both layers were clear. Two layers were separated. The aqueous layer was extracted with DCM (2×25 mL). The combined organic layers were washed with brine (25 mL), dried over anhydrous sodium sulfate, and concentrated under vacuum. The crude product was purified by silica gel chromatography using 0 to 20% ethyl acetate in hexane to furnish tert-butyl N-[(1R)-1-ethynyl-3-methyl-butyl]carbamate (134 mg, 69%) as a clear liquid. $^1$H NMR (250 MHz, Chloroform-d) δ 4.68 (s, 1H), 4.50-4.29 (m, 1H), 2.24 (d, J=2.3 Hz, 1H), 1.87-1.66 (m, 1H), 1.50 (t, J=7.5 Hz, 2H), 1.43 (s, 9H), 0.91 (dd, J=6.6, 2.4 Hz, 6H).

Step 3: Methyl 3-[[4-[(3R)-3-(tert-butoxycarbonylamino)-5-methyl-hex-1-ynyl]-6-(2,6-dimethylphenyl)-2-pyridyl]sulfamoyl]benzoate

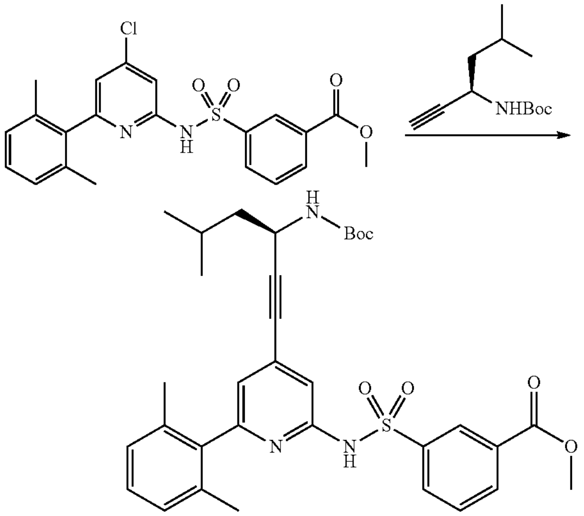

Methyl 3-[[4-chloro-6-(2,6-dimethylphenyl)-2-pyridyl]sulfamoyl]benzoate (900 mg, 2.0469 mmol), palladium diacetate (50 mg, 0.2183 mmol), XPhos (200 mg, 0.4111 mmol), and cesium carbonate (2 g, 6.1384 mmol) were suspended in 1,4-dioxane (18 mL), and stirred for 20 minutes at room temperature. tert-butyl N-[(1R)-1-ethynyl-3-methyl-butyl]carbamate (650 mg, 3.0147 mmol) was then added, and the resulting solution was stirred for 13 hours at 105° C. The mixture (combined with another batch) was diluted with EtOAc (200 mL)/water (200 mL). The aqueous layer was extracted with EtOAc (2×100 mL). The combined organic layer was washed by brine, dried over sodium sulfate, and concentrated. The crude residue was purified by silica-gel column chromatography using 0-20% ethyl acetate in hexanes to afford methyl 3-[[4-[(3R)-3-(tert-butoxycarbonylamino)-5-methyl-hex-1-ynyl]-6-(2,6-dimethylphenyl)-2-pyridyl]sulfamoyl]benzoate (1.42 g, 112%). (here including other batches). ESI-MS m/z calc. 605.256, found 606.7 (M+1)$^+$; Retention time: 4.24 minutes, LC method T.

Step 4: Methyl 3-[[4-[(3S)-3-(tert-butoxycarbonylamino)-5-methyl-hexyl]-6-(2,6-dimethylphenyl)-2-pyridyl]sulfamoyl]benzoate

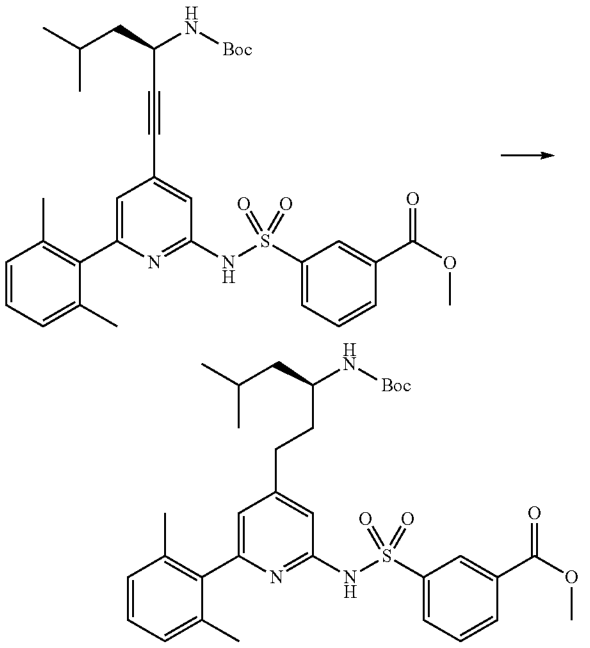

Into a solution of methyl 3-[[4-[(3R)-3-(tert-butoxycarbonylamino)-5-methyl-hex-1-ynyl]-6-(2,6-dimethylphenyl)-2-pyridyl]sulfamoyl]benzoate (1.42 g, 2.2973 mmol) in ethanol (100 mL) was added Pd (1 g, 0.9397 mmol) on carbon. The mixture was in a Parr shaker at 60 psi of hydrogen for 40 minutes. The reaction mixture was filtered through a Celite pad. The filtrate was concentrated under vacuum to give methyl 3-[[4-[(3S)-3-(tert-butoxycarbonylamino)-5-methyl-hexyl]-6-(2,6-dimethylphenyl)-2-pyridyl]sulfamoyl]benzoate (1.25 g, 85%). ESI-MS m/z calc. 609.2873, found 610.7 (M+1)$^+$; Retention time: 4.06 minutes, LC method T.

Step 5: -[[4-[(3S)-3-Amino-5-methyl-hexyl]-6-(2,6-dimethylphenyl)-2-pyridyl]sulfamoyl]benzoate

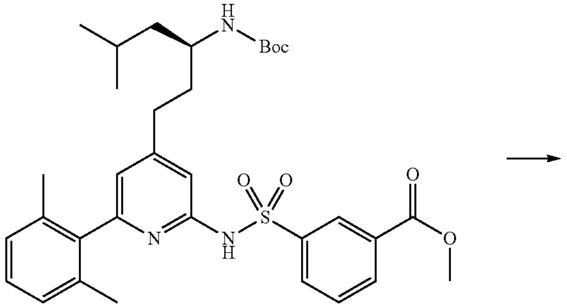

-continued

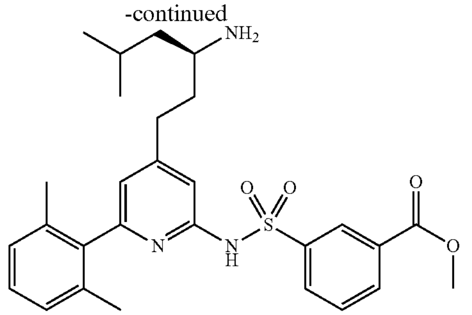

Into a solution of methyl 3-[[4-[(3S)-3-(tert-butoxycarbonylamino)-5-methyl-hexyl]-6-(2,6-dimethylphenyl)-2-pyridyl]sulfamoyl]benzoate (1.25 g, 1.9474 mmol) in DCM (30 mL) was added HCl (24 mL of 4 M, 96.000 mmol) in dioxane. The reaction was stirred at room temperature for 1 hour. The mixture was concentrated and washed with ether to give methyl 3-[[4-[(3S)-3-amino-5-methyl-hexyl]-6-(2,6-dimethylphenyl)-2-pyridyl]sulfamoyl]benzoate (hydrochloride salt) (0.99 g, 88%). ESI-MS m/z calc. 509.2348, found 510.5 $(M+1)^+$; Retention time: 4.66 minutes, (LC method S).

Step 6: Methyl 3-[[6-(2,6-dimethylphenyl)-4-[(3S)-5-methyl-3-(spiro[2.3]hexan-5-ylamino)hexyl]-2-pyridyl]sulfamoyl]benzoate

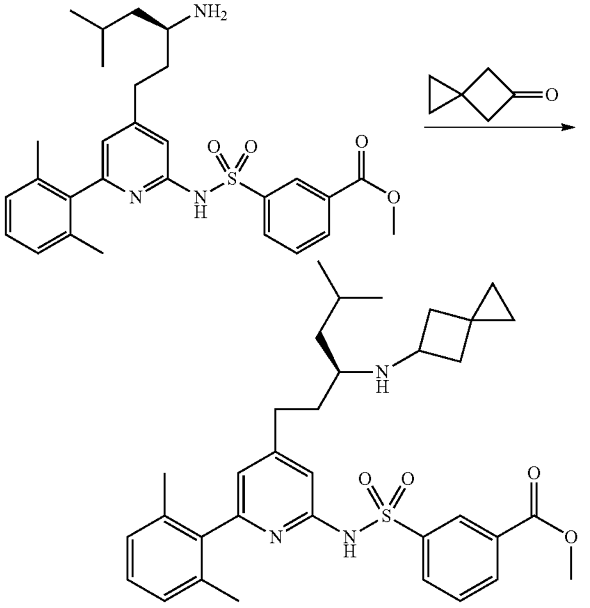

Into a solution of spiro[2.3]hexan-5-one (50 mg, 0.5097 mmol) and methyl 3-[[4-[(3S)-3-amino-5-methyl-hexyl]-6-(2,6-dimethylphenyl)-2-pyridyl]sulfamoyl]benzoate (hydrochloride salt) (170 mg, 0.2957 mmol) in TEA (36.300 mg, 50 μL, 0.3587 mmol) and DCE (2 mL) was added sodium triacetoxyborohydride (150 mg, 0.7077 mmol) and HOAc (31.680 mg, 30 μL, 0.5275 mmol). The reaction mixture was stirred at room temperature for 22 hours. The reaction mixture was quenched by adding sodium bicarbonate and extracted with EtOAc (2×50 mL). The organic layer was concentrated to give crude methyl 3-[[6-(2,6-dimethylphenyl)-4-[(3S)-5-methyl-3-(spiro[2.3]hexan-5-ylamino)hexyl]-2-pyridyl]sulfamoyl]benzoate (185 mg, 95%). ESI-MS m/z calc. 589.2974, found 590.6 $(M+1)^+$; Retention time: 3.17 minutes, LC method T.

Step 7: 3-[[6-(2,6-Dimethylphenyl)-4-[(3S)-5-methyl-3-(spiro[2.3]hexan-5-ylamino)hexyl]-2-pyridyl]sulfamoyl]benzoic acid

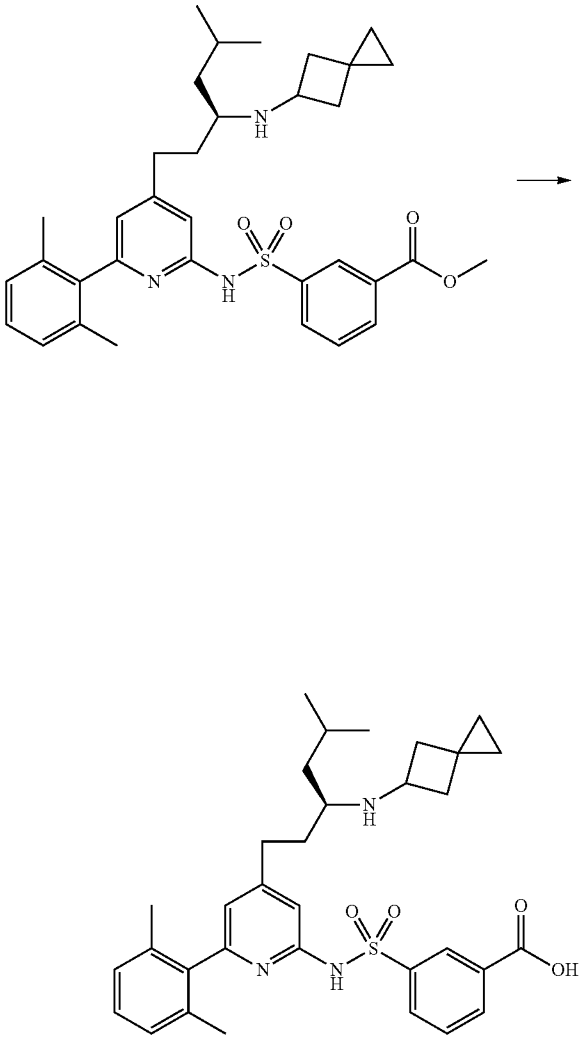

The solution of methyl 3-[[6-(2,6-dimethylphenyl)-4-[(3S)-5-methyl-3-(spiro[2.3]hexan-5-ylamino)hexyl]-2-pyridyl]sulfamoyl]benzoate (185 mg, 0.2823 mmol) in NaOH (10 mL of 2 M, 20.000 mmol) and MeOH (10 mL) was stirred at room temperature for 2 hours. After removing MeOH, the aqueous solution was washed with EtOEt (2×30 mL) and adjusted to pH=1, then EtOAc (2×100 mL) was added for extraction. The organic layer was washed with brine, dried over sodium sulfate, and concentrated to afford 3-[[6-(2,6-dimethylphenyl)-4-[(3S)-5-methyl-3-(spiro[2.3]hexan-5-ylamino)hexyl]-2-pyridyl]sulfamoyl]benzoic acid (hydrochloride salt) (170 mg, 93%). ESI-MS m/z calc. 575.2818, found 576.6 $(M+1)^+$; Retention time: 4.84 minutes, LC method S.

Step 8: (11S)-6-(2,6-Dimethylphenyl)-11-isobutyl-2,2-dioxo-12-spiro[2.3]hexan-5-yl-2 λ6-thia-3,5,12-triazatricyclo[12.3.1.14,8]nonadeca-1(18),4(19),5,7,14,16-hexaen-13-one (Compound 3)

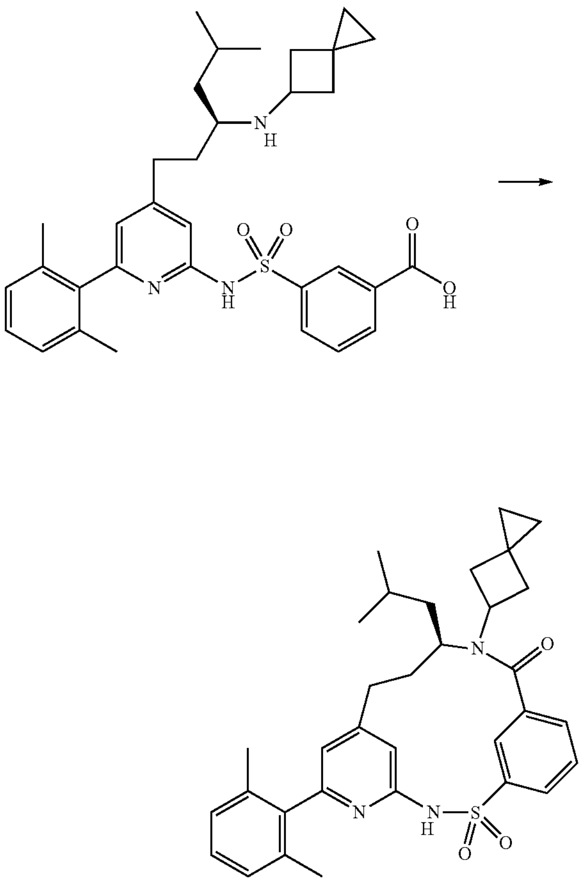

Into a solution of 3-[[6-(2,6-dimethylphenyl)-4-[(3S)-5-methyl-3-(spiro[2.3]hexan-5-ylamino)hexyl]-2-pyridyl]sulfamoyl]benzoic acid (97 mg, 0.1600 mmol) and DIEA (111.30 mg, 150 μL, 0.8612 mmol) in anhydrous DMF (3 mL) was dropwise added to a solution of HATU (100 mg, 0.2604 mmol) and DIEA (111.30 mg, 150 μL, 0.8612 mmol) in DMF (3 mL). The reaction mixture was stirred at room temperature for 15 minutes. The reaction mixture was purified by reverse phase HPLC using 0 to 100% acetonitrile in water (5 mM HCl in water) to furnish (11S)-6-(2,6-dimethylphenyl)-11-isobutyl-2,2-dioxo-12-spiro[2.3]hexan-5-yl-2$\lambda^6$-thia-3,5,12-triazatricyclo[12.3.1.14,8]nonadeca-1(18),4(19),5,7,14,16-hexaen-13-one (17.8 mg, 19%) as a white powder. $^1$H NMR (500 MHz, DMSO-$d_6$) δ 7.87-7.74 (m, 2H), 7.62 (t, J=7.7 Hz, 1H), 7.54 (d, J=7.6 Hz, 1H), 7.31 (s, 1H), 7.16 (t, J=7.7 Hz, 1H), 7.05 (s, 2H), 6.76 (s, 1H), 4.16 (p, J=8.6 Hz, 1H), 3.33 (t, J=9.3 Hz, 3H), 3.00 (d, J=15.5 Hz, 1H), 2.33-2.16 (m, 2H), 2.07 (t, J=8.8 Hz, 1H), 1.97 (dd, J=19.9, 11.0 Hz, 4H), 1.63 (s, 3H), 1.43 (t, J=12.8 Hz, 1H), 1.22 (ddd, J=11.9, 8.0, 5.0 Hz, 1H), 1.12 (d, J=13.7 Hz, 1H), 0.74 (d, J=6.6 Hz, 3H), 0.50 (dq, J=11.4, 4.3, 3.8 Hz, 2H), 0.47-0.40 (m, 2H), 0.10 (d, J=6.2 Hz, 3H). ESI-MS m/z calc. 557.2712, found 558.4 $(M+1)^+$; Retention time: 3.26 minutes, LC method W.

Example 4: Preparation of Compound 4

Step 1: 2-Amino-5-fluoro-pyrimidine-4,6-diol

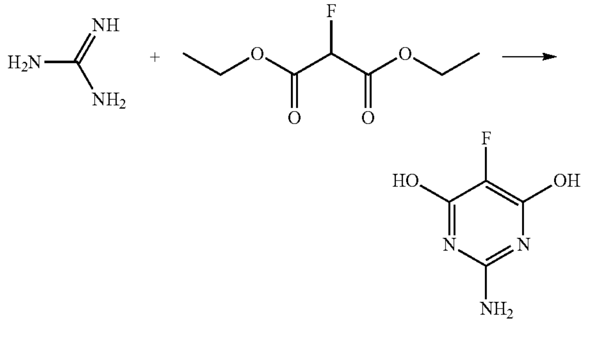

To a 2 L flask charged with ethanol (750 mL), solid chunks of sodium metal (21.5 g, 935.20 mmol) were added gradually and carefully and the mixture was stirred until completely dissolved. Once cooled back to room temperature guanidine (hydrochloride salt) (34.5 g, 361.14 mmol) and diethyl 2-fluoropropanedioate (50 g, 280.65 mmol) were successively added and the reaction was heated at 80° C. for 17 hours. Once cooled to room temperature, the crude mixture was concentrated under reduced pressure to remove most of the ethanol. Water was added to complete dissolution, the resulting solution was cooled in an ice bath and acidified to pH of 1-2 using concentrated HCl. The solids were filtered and washed with water (2×200 mL) then with acetone (2×50 mL) and dried under high vacuum to provide 2-amino-5-fluoro-pyrimidine-4,6-diol hydrate (41.8 g, 91%) as a pink solid. $^1$H NMR (300 MHz, DMSO-$d_6$) ppm 6.53 (br. s., 1H), 10.97 (br. s., 1H). 19F NMR (282 MHz, DMSO-$d_6$) ppm −196.1 (br. s., 1F). ESI-MS m/z calc. 145.0288, found 146.1 $(M+1)^+$; Retention time: 0.2 minutes (LC method P).

Step 2: 4,6-Dichloro-5-fluoro-pyrimidin-2-amine

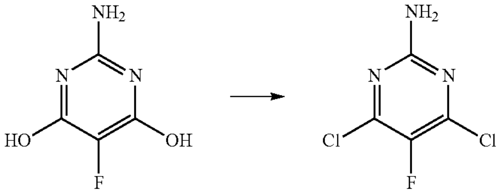 [SMILES: Nc1nc(O)c(F)c(O)n1 ; Nc1nc(Cl)c(F)c(Cl)n1]

A solution of 2-amino-5-fluoro-pyrimidine-4,6-diol hydrate (21.09 g, 126.46 mmol) in phosphorus oxychloride (101.99 g, 62 mL, 665.16 mmol) was heated to 90° C. and N,N-diethylaniline (25.326 g, 27 mL, 169.71 mmol) was added slowly. The reaction was then heated for 3 hours at 105° C. The solution was poured in water and neutralized to pH ~5 with 50% aqueous sodium hydroxide solution and refluxed for 1 hour. The solution was cooled on ice and the precipitate was filtered and dried. The solid was triturated in dichloromethane (~150 mL), filtered and dried. The solid obtained was then triturated in a mix of acetone/heptanes (1:1, 40 mL), filtered, and dried to provide the desired 4,6-dichloro-5-fluoro-pyrimidin-2-amine (13.75 g, 59%) as a yellow solid. $^1$H NMR (300 MHz, DMSO-$d_6$) δ 7.44 (br.

s., 2H). $^{19}F$ NMR (282 MHz, DMSO-$d_6$) δ−149.01 (s, 1F). ESI-MS m/z calc. 180.961, found 182.0 $(M+1)^+$; Retention time: 2.17 minutes. LC method U.

Step 3: tert-Butyl N-(4,6-dichloro-5-fluoro-pyrimidin-2-yl)carbamate

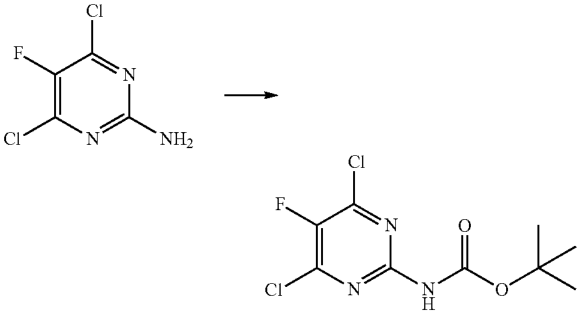

To a stirring solution of 4,6-dichloro-5-fluoro-pyrimidin-2-amine (5.153 g, 27.495 mmol) and Boc anhydride (8.43 g, 38.626 mmol) in anhydrous THF (100 mL) at −78° C. under nitrogen was dropwise added a solution of LiHMDS (50 mL of 1.3 M, 65.000 mmol) in THF. After the addition was complete, the reaction mixture was stirred at this temperature for 2 hours. The reaction was quenched cold with saturated aqueous ammonium chloride (20 mL) and allowed to warm up to room temperature. The product was extracted with ethyl acetate (3×30 mL). The combined organic layers were washed with brine (30 mL), dried over anhydrous sodium sulfate, and concentrated. The crude was purified by silica gel chromatography using 0-15% ethyl acetate in hexane to afford tert-butyl N-(4,6-dichloro-5-fluoro-pyrimidin-2-yl)carbamate (6.632 g, 86%) as a white solid. $^1H$ NMR (500 MHz, DMSO-$d_6$) δ 10.74 (s, 1H), 1.45 (s, 9H).

Step 4: tert-Butyl N-[4-chloro-6-(2,6-dimethylphenyl)-5-fluoro-pyrimidin-2-yl]carbamate

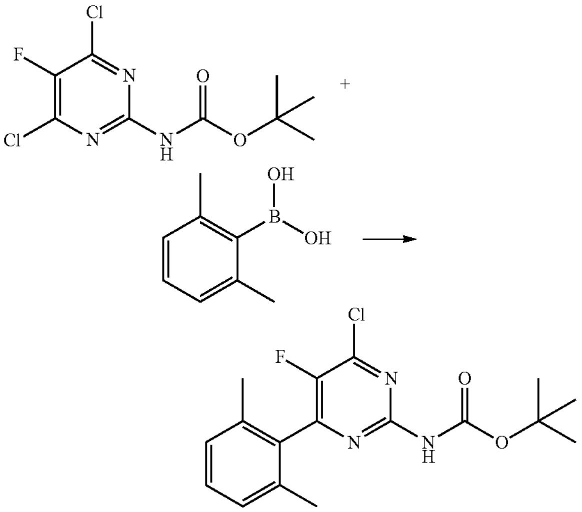

A stirring solution of tert-butyl N-(4,6-dichloro-5-fluoro-pyrimidin-2-yl)carbamate (6.815 g, 22.467 mmol) and (2,6-dimethylphenyl)boronic acid (3.06 g, 20.402 mmol) in a mixture of 1,2-dimethoxyethane (55 mL) and water (15 mL) at room temperature was degassed with nitrogen for 30 minutes. Under nitrogen, cesium carbonate (18.3 g, 56.166 mmol) and [1,1'-bis(diphenylphosphino)ferrocene]dichloropalladium(II) (1.65 g, 2.2550 mmol) were added. The reaction mixture was heated to 80° C. for 4 hours. After cooling to room temperature, water (150 mL) was added and the product was extracted with ethyl acetate (3×150 mL). The combined organic layers were washed with brine (50 mL), dried over anhydrous sodium sulfate, and concentrated. The crude was purified by silica gel chromatography using 0-5% hexanes-ethyl acetate to afford tert-butyl N-[4-chloro-6-(2,6-dimethylphenyl)-5-fluoro-pyrimidin-2-yl]carbamate (2.43 g, 29%) as white solid. ESI-MS m/z calc. 351.115, found 352.4 $(M+1)^+$; Retention time: 6.51 minutes, LC method S.

Step 5: 4-Chloro-6-(2,6-dimethylphenyl)-5-fluoro-pyrimidin-2-amine

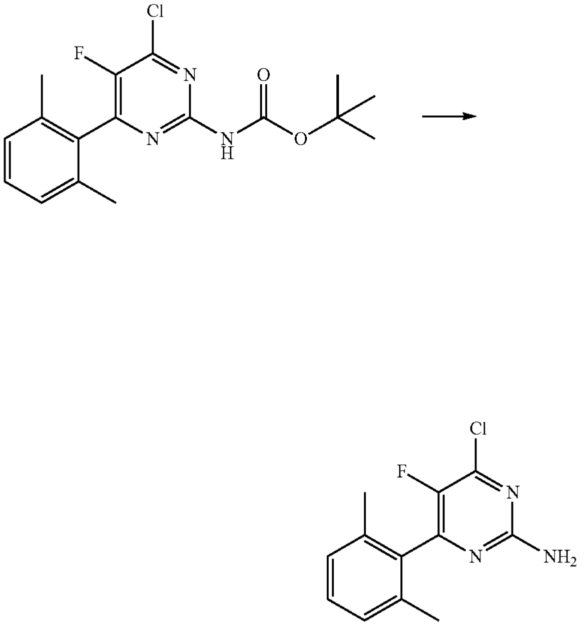

To a stirring solution of tert-butyl N-[4-chloro-6-(2,6-dimethylphenyl)-5-fluoro-pyrimidin-2-yl]carbamate (2.43 g, 6.4238 mmol) in DCM (23 mL) at room temperature was added a solution of HCl (6.5 mL of 4 M, 26.000 mmol) in 1,4-dioxane. The reaction mixture was stirred at this temperature for 2 hours. The reaction mixture was evaporated to dryness. The obtained white solid was resuspended in saturated aqueous sodium bicarbonate (100 mL) and stirred at room temperature for 15 minutes. The product was extracted with ethyl acetate (3×100 mL). The combined organic layers were washed with brine (50 mL), dried over anhydrous sodium sulfate, and concentrated. The crude was purified by silica gel chromatography using 0-15% hexanes-ethyl acetate to afford 4-chloro-6-(2,6-dimethylphenyl)-5-fluoro-pyrimidin-2-amine (1.42 g, 83%) as white solid. ESI-MS m/z calc. 251.0626, found 252.3 $(M+1)^+$; Retention time: 5.06 minutes, LC method S.

Step 6: Methyl 3-[[4-chloro-6-(2,6-dimethylphenyl)-5-fluoro-pyrimidin-2-yl]sulfamoyl]benzoate

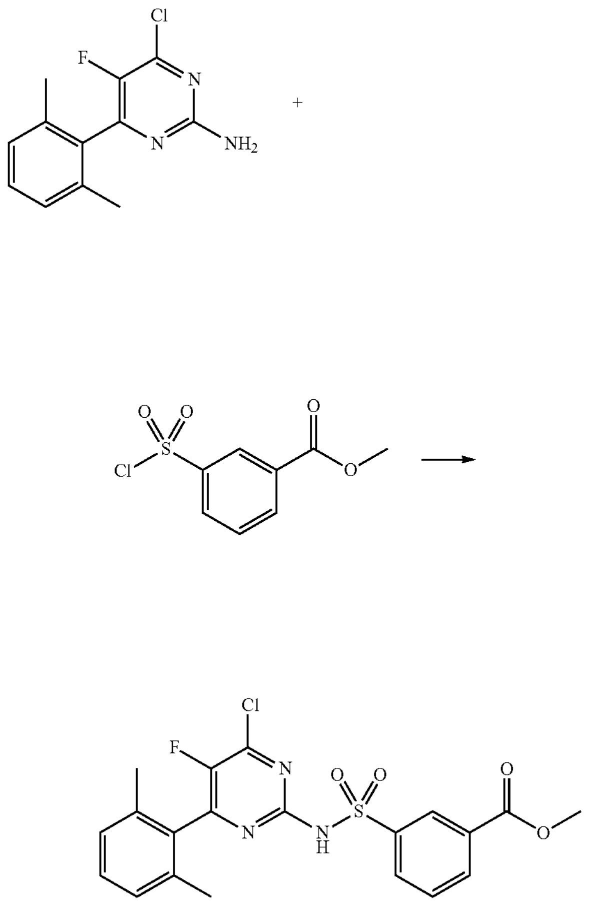

To a stirring solution of 4-chloro-6-(2,6-dimethylphenyl)-5-fluoro-pyrimidin-2-amine (2.54 g, 10.092 mmol) and methyl 3-chlorosulfonylbenzoate (4.25 g, 18.112 mmol) in anhydrous THF (70 mL) at 0° C. under nitrogen was dropwise added a solution of lithium tert-amoxide (5.8400 g, 20 mL of 40% w/w, 24.830 mmol) in heptanes. After the addition was complete, the reaction mixture was stirred at this temperature for 1 hour. The reaction was quenched cold with 1 M aqueous HCl (180 mL) and then allowed to warm up to room temperature. Volatiles were removed under vacuum and the product was extracted with ethyl acetate (3×100 mL). The combined organic layers were washed with brine (60 mL), dried over anhydrous sodium sulfate, and concentrated. The crude was purified by silica gel chromatography using 0-20% hexanes-ethyl acetate. The obtained product was triturated with hexanes (100 mL), collected by filtration, and dried under vacuum to afford methyl 3-[[4-chloro-6-(2,6-dimethylphenyl)-5-fluoro-pyrimidin-2-yl]sulfamoyl]benzoate (4.381 g, 93%) as white solid. ESI-MS m/z calc. 449.0612, found 450.1 $(M+1)^+$; Retention time: 2.72 minutes, LC method T. $^1H$ NMR (500 MHz, DMSO-$d_6$) δ 12.49 (s, 1H), 8.43 (t, J=1.8 Hz, 1H), 8.21 (dt, J=7.8, 1.4 Hz, 1H), 8.14 (dt, J=8.0, 1.5 Hz, 1H), 7.73 (t, J=7.8 Hz, 1H), 7.32 (t, J=7.6 Hz, 1H), 7.14 (d, J=7.6 Hz, 2H), 3.82 (s, 3H), 1.85 (s, 6H).

Step 7: Methyl 3-[[4-[(3R)-3-(tert-butoxycarbonylamino)-5-methyl-hex-1-ynyl]-6-(2,6-dimethylphenyl)-5-fluoro-pyrimidin-2-yl]sulfamoyl]benzoate

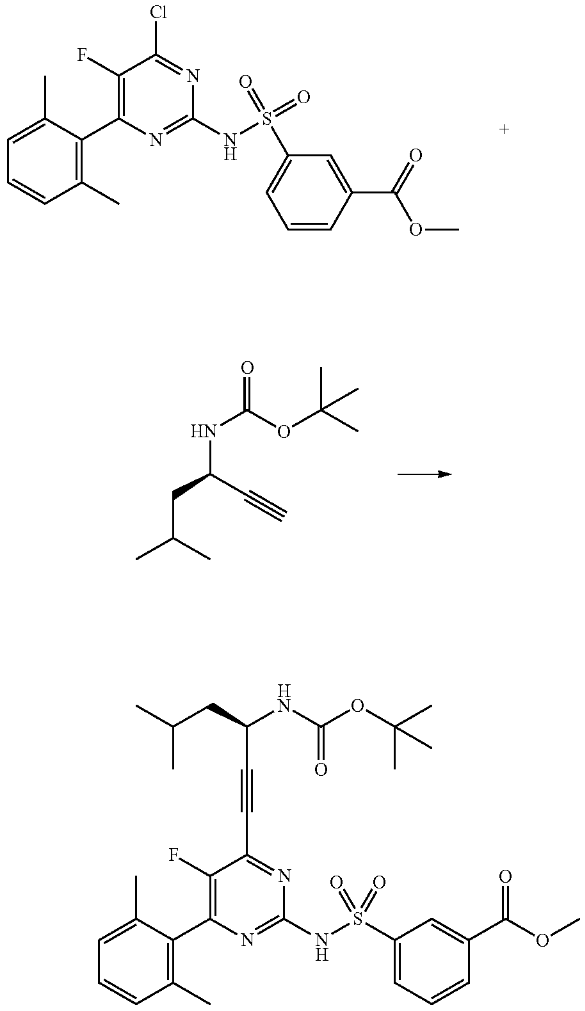

Methyl 3-[[4-chloro-6-(2,6-dimethylphenyl)-5-fluoro-pyrimidin-2-yl]sulfamoyl]benzoate (20 mg, 0.0445 mmol), tert-butyl N-[(1R)-1-ethynyl-3-methyl-butyl]carbamate (16 mg, 0.0757 mmol), XPhos (5 mg, 0.0105 mmol), cesium carbonate (46 mg, 0.1412 mmol) and palladium diacetate (1 mg, 0.0045 mmol), and dioxane (0.5 mL) were all added to a microwave vial, which was purged with nitrogen and irradiated in a microwave for 1.5 hours at 100° C. The reaction was diluted with water (5 mL), EtOAc (5 mL) and brine (2 mL) The layers were separated, and the aqueous layer was extracted three times with EtOAc (5 mL). The organic layer was dried over sodium sulfate and concentrated. The crude residue was dry loaded on to silica gel and purified by flash column chromatography using 0-40% EtOAc in hexanes. The appropriate fractions were collected to give methyl 3-[[4-[(3R)-3-(tert-butoxycarbonylamino)-5-methyl-hex-1-ynyl]-6-(2,6-dimethylphenyl)-5-fluoro-pyrimidin-2-yl]sulfamoyl]benzoate (20.5 mg, 63%) as a yellow oil. ESI-MS m/z calc. 624.2418, found 625.7 $(M+1)^+$; Retention time: 4.07 minutes, LC method T.

Step 8: Methyl 3-[[4-[(3S)-3-(tert-butoxycarbonylamino)-5-methyl-hexyl]-6-(2,6-dimethylphenyl)-5-fluoro-pyrimidin-2-yl]sulfamoyl]benzoate

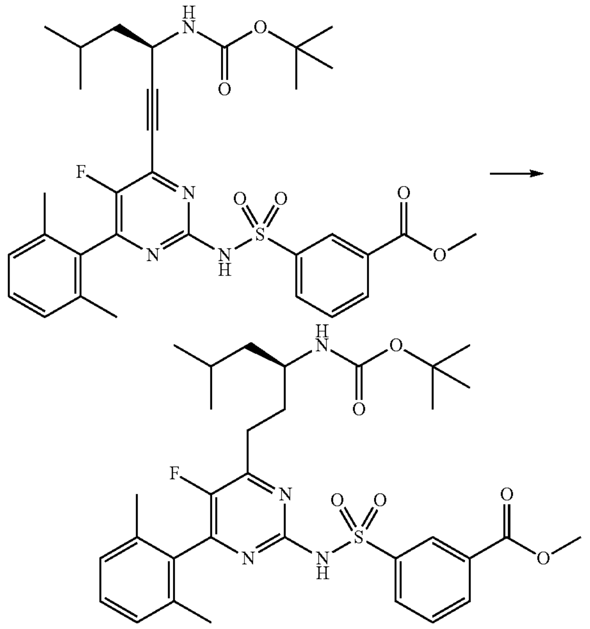

Methyl 3-[[4-[(3R)-3-(tert-butoxycarbonylamino)-5-methyl-hex-1-ynyl]-6-(2,6-dimethylphenyl)-5-fluoro-pyrimidin-2-yl]sulfamoyl]benzoate (178.1 mg, 0.2851 mmol) was dissolved in EtOH (4.4525 mL) and added to a parr vessel charged with 10% Pd on carbon (126 mg, 0.1184 mmol). The mixture was shaken on a parr shaker under hydrogen (30 Psi) for 1 hour. Then Celite (200 mg) was added to the mixture and the reaction stirred for 5 minutes, and the solids were filtered off and the crude residue was concentrated to give methyl 3-[[4-[(3S)-3-(tert-butoxycarbonylamino)-5-methyl-hexyl]-6-(2,6-dimethylphenyl)-5-fluoro-pyrimidin-2-yl]sulfamoyl]benzoate (164.3 mg, 87%) as a brown oil. ESI-MS m/z calc. 628.2731, found 629.5 $(M+1)^+$; Retention time: 4.07 minutes ESI-MS m/z calc. 628.2731, found 629.5 $(M+1)^+$; Retention time: 4.07 minutes, LC method T.

Step 9: 3-[[4-[(3S)-3-(tert-Butoxycarbonylamino)-5-methyl-hexyl]-6-(2,6-dimethylphenyl)-5-fluoro-pyrimidin-2-yl]sulfamoyl]benzoic acid

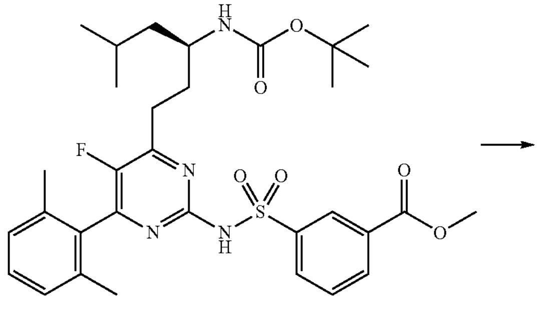

-continued

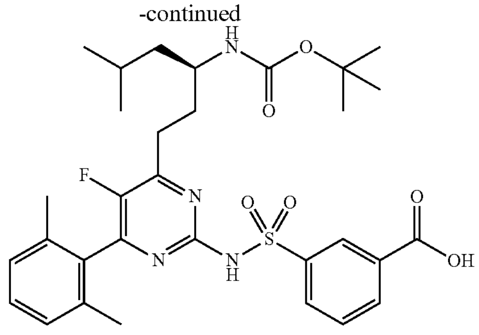

Methyl 3-[[4-[(3S)-3-(tert-butoxycarbonylamino)-5-methyl-hexyl]-6-(2,6-dimethylphenyl)-5-fluoro-pyrimidin-2-yl]sulfamoyl]benzoate (164.3 mg, 0.2613 mmol) was dissolved in THF (1 mL) then NaOH (1.1 mL of 1 M, 1.1000 mmol) was added and the reaction stirred at room temperature for 3 hours. The reaction was acidified with 2M HCl (2 mL), and the aqueous layer was extracted three times with EtOAc (3×5 mL). The organic layer was washed with brine (5 mL), then dried over sodium sulfate and concentrated to give 3-[[4-[(3S)-3-(tert-butoxycarbonylamino)-5-methyl-hexyl]-6-(2,6-dimethylphenyl)-5-fluoro-pyrimidin-2-yl]sulfamoyl]benzoic acid (152.5 mg, 85%) as a light brown oil. ESI-MS m/z calc. 614.2574, found 615.5 $(M+1)^+$; Retention time: 3.69 minutes, LC method T.

Step 10: 3-[[4-[(3S)-3-Amino-5-methyl-hexyl]-6-(2,6-dimethylphenyl)-5-fluoro-pyrimidin-2-yl]sulfamoyl]benzoic acid

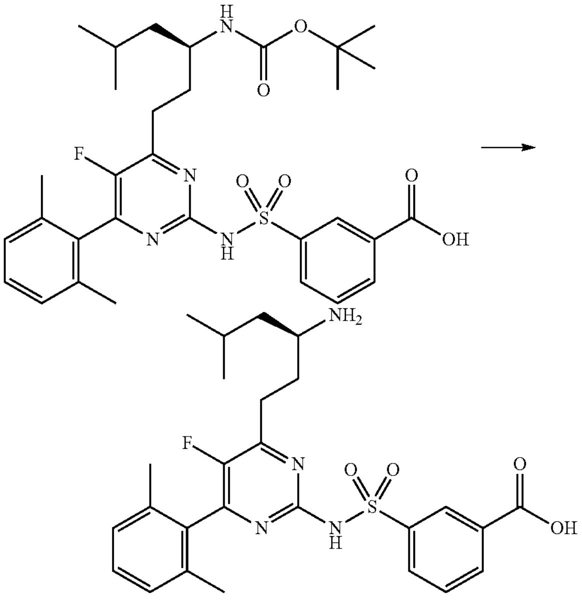

3-[[4-[(3S)-3-(tert-butoxycarbonylamino)-5-methyl-hexyl]-6-(2,6-dimethylphenyl)-5-fluoro-pyrimidin-2-yl]sulfamoyl]benzoic acid (152.5 mg, 0.2481 mmol) was dissolved in DCM (1 mL), then HCl in dioxane (0.25 mL of 4 M, 1.0000 mmol) was added and the reaction stirred overnight. The reaction was incomplete by LCMS and HCl in dioxane (0.25 mL of 4 M, 1.0000 mmol) was added. The reaction was stirred for another 3 hours and the volatiles were removed to give 3-[[4-[(3S)-3-amino-5-methyl-hexyl]-6-(2,6-dimethylphenyl)-5-fluoro-pyrimidin-2-yl]sulfamoyl] benzoic acid (hydrochloride salt) (140 mg, 92%) as an off-white solid. ESI-MS m/z calc. 514.205, found 515.6 $(M+1)^+$; Retention time: 2.58 minutes, LC method T.

Step 11: 3-[[4-(2,6-Dimethylphenyl)-5-fluoro-6-[(3S)-5-methyl-3-(spiro[2.3]hexan-5-ylamino)hexyl] pyrimidin-2-yl]sulfamoyl]benzoic acid

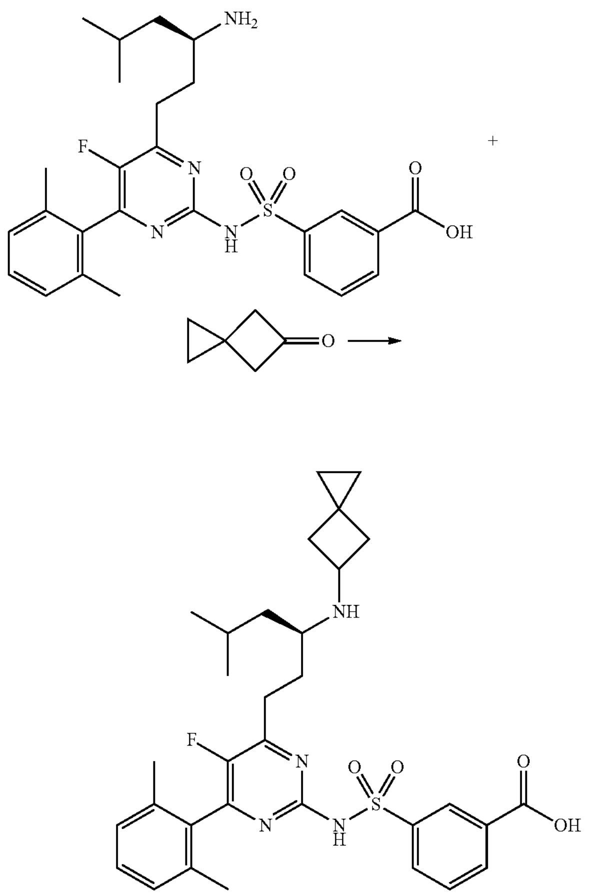

3-[[4-[(3S)-3-Amino-5-methyl-hexyl]-6-(2,6-dimethylphenyl)-5-fluoro-pyrimidin-2-yl]sulfamoyl]benzoic acid (140 mg, 0.2720 mmol) was dissolved in DCM (4 mL) and spiro[2.3]hexan-5-one (36 mg, 0.3745 mmol) was added. Next, sodium triacetoxyborohydride (83 mg, 0.3916 mmol) was added in a single portion and the reaction stirred overnight at room temperature. The reaction was incomplete by LCMS, so more spiro[2.3]hexan-5-one (31 mg, 0.3225 mmol) and sodium triacetoxyborohydride (94 mg, 0.4435 mmol) were added sequentially. After 5 hours, the volatiles were removed, and the crude residue was dry loaded on to silica gel. The residue was purified by flash column chromatography using 0-10% DCM:MeOH. The appropriate fractions were collected to give 3-[[4-(2,6-dimethylphenyl)-5-fluoro-6-[(3S)-5-methyl-3-(spiro[2.3]hexan-5-ylamino) hexyl]pyrimidin-2-yl]sulfamoyl]benzoic acid (90 mg, 53%) as a yellow foam. ESI-MS m/z calc. 594.2676, found 595.7 $(M+1)^+$; Retention time: 2.9 minutes, LC method T.

Step 12: (11S)-6-(2,6-Dimethylphenyl)-7-fluoro-11-isobutyl-2,2-dioxo-12-spiro[2.3]hexan-5-yl-2 λ6-thia-3,5,12,19-tetrazatricyclo[12.3.1.14,8]nonadeca-1(18),4(19),5,7,14,16-hexaen-13-one (Compound 4)

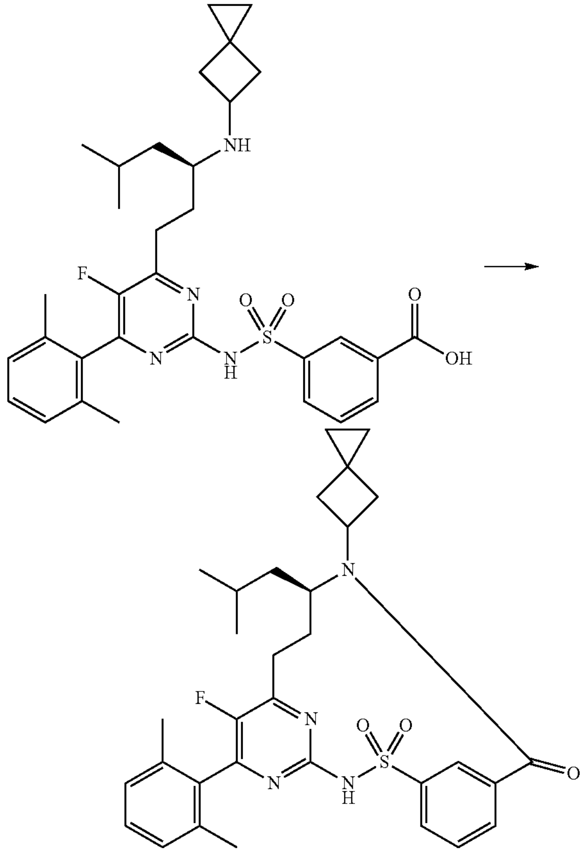

3-[[4-(2,6-Dimethylphenyl)-5-fluoro-6-[(3S)-5-methyl-3-(spiro[2.3]hexan-5-ylamino)hexyl]pyrimidin-2-yl]sulfamoyl]benzoic acid (90 mg, 0.1513 mmol) was dissolved in anhydrous NMP (1.5 mL) then HATU (90 mg, 0.2367 mmol) and DIEA (81.620 mg, 0.11 mL, 0.6315 mmol) were added. The reaction was stirred at room temperature for 4 hours, then more HATU (84 mg, 0.2209 mmol) was added. The reaction was stirred overnight at room temperature, then quenched with a small amount of water (1 mL). The reaction mixture was purified by reverse phase HPLC using 0 to 100% acetonitrile in water (buffered with 0.1% TFA) to furnish (11S)-6-(2,6-dimethylphenyl)-7-fluoro-11-isobutyl-2,2-dioxo-12-spiro[2.3]hexan-5-yl-2$\lambda^6$-thia-3,5,12,19-tetrazatricyclo[12.3.1.14,8]nonadeca-1(18),4(19),5,7,14,16-hexaen-13-one (27.5 mg, 30%) as a white powder. ESI-MS m/z calc. 576.257, found 577.6 $(M+1)^+$; Retention time: 3.38 minutes, LC method W. $^1$H NMR (500 MHz, DMSO-$d_6$) δ 11.89 (s, 1H), 8.31 (t, J=1.8 Hz, 1H), 7.97 (dt, J=7.3, 1.7 Hz, 1H), 7.79-7.70 (m, 2H), 7.27 (t, J=7.6 Hz, 1H), 7.17 (d, J 7.6 Hz, 1H), 7.11 (d, J=7.6 Hz, 1H), 4.21 (p, J=8.6 Hz, 1H), 3.43-3.31 (m, 3H), 3.08-2.89 (m, 2H), 2.61-2.53 (m, 1H), 2.22 (t, J=12.6 Hz, 1H), 2.09 (d, J=8.8 Hz, 1H), 2.05 (s, 3H), 1.99 (t, J=9.1 Hz, 1H), 1.75 (s, 3H), 1.52 (ddd, J=14.1, 10.8, 2.9 Hz, 1H), 1.20 (dtd, J=13.0, 6.5, 6.0, 2.6 Hz, 1H), 0.91 (ddd, J=14.0, 10.1, 3.3 Hz, 1H), 0.66 (d, J=6.7 Hz, 3H), 0.52 (dd, J=9.4, 6.7 Hz, 2H), 0.46 (dq, J=9.0, 4.4, 4.0 Hz, 2H), 0.06 (s, 3H).

Example 5: Preparation of Compound 5

Step 1: 3-(4-tert-Butylphenyl)prop-2-yn-1-ol

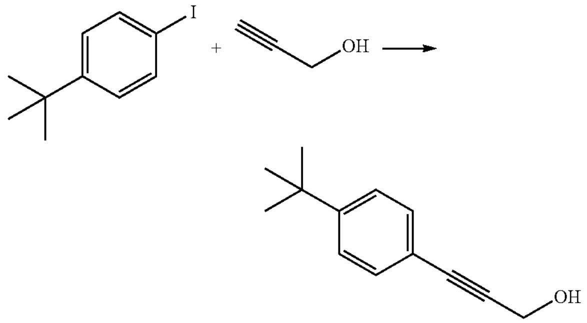

A solution of 1-tert-butyl-4-iodo-benzene (5.21 g, 20.030 mmol), prop-2-yn-1-ol (3.4164 g, 3.6 mL, 60.938 mmol), and $Pd(PPh_3)_4$ (1.16 g, 1.0038 mmol) in TEA (100 mL) was purged with argon for 5 minutes, then CuI (191 mg, 1.0029 mmol) was added. The resulting solution was stirred at ambient temperature for 18 hours. The solution was diluted with ethyl acetate, filtered through Celite, washed with ethyl acetate and filtrate was concentrated under reduced pressure. The crude product obtained was purified by flash chromatography (dry loading) (220 g silica gel, eluting 0 to 25% ethyl acetate in hexane) to afford 3-(4-tert-butylphenyl) prop-2-yn-1-ol (3.4 g, 90%) as a brown solid. ESI-MS m/z calc. 188.1201, found 189.4 $(M+1)^+$; Retention time: 5.76 minutes; $^1H$ NMR (250 MHz, $CDCl_3$) δ 7.46-7.30 (m, 4H), 4.50 (s, 2H), 1.63 (s, 1H), 1.32 (s, 9H). LC method S.

Step 2: (Z)-3-(4-tert-Butylphenyl)-3-iodo-prop-2-en-1-ol

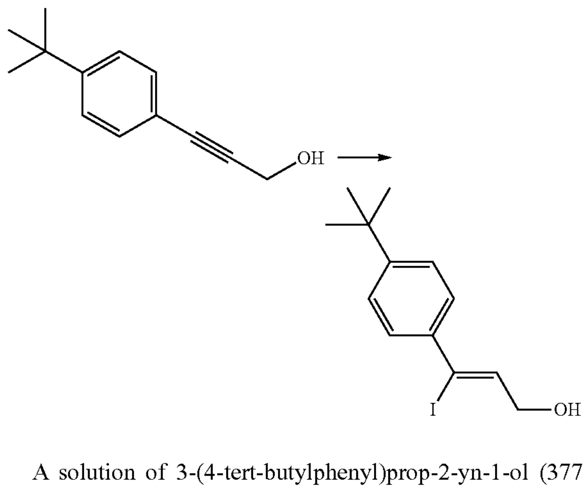

A solution of 3-(4-tert-butylphenyl)prop-2-yn-1-ol (377 mg, 2.0025 mmol) in anhydrous 2-MeTHF (2.5 mL) was purged with argon for 1 minute, then the solution was cooled to 0-30° C. and Red-Al (880.6 mg, 0.8500 mL of 60% w/w, 2.6136 mmol) in toluene was added dropwise. The solution was stirred at this temperature for 30 minutes, then anhydrous ethyl acetate (2.2550 g, 2.5 mL, 25.594 mmol) was added followed by iodine (1.0165 g, 0.2062 mL, 4.0050 mmol). The resulting solution continued to stir for 30 minutes while the temperature was raised to 10° C. The reaction was quenched with saturated Rochelle's salt solution (30 mL), and ethyl acetate (100 mL) was added. The organic layer was separated, washed with aqueous sodium thiosulfate (10%, 30 mL), brine (30 mL), dried over anhydrous sodium sulfate, filtered and concentrated under reduced pressure. The crude product was purified by flash chromatography (dry loading) (80 g silica gel, eluting 0 to 30% ethyl acetate in hexane) to afford (Z)-3-(4-tert-butylphenyl)-3-iodo-prop-2-en-1-ol (450 mg, 69%) as a pale-yellow liquid. $^1H$ NMR (500 MHz, Chloroform-d) δ 7.45-7.40 (m, 2H), 7.36-7.31 (m, 2H), 6.24 (t, J=5.7 Hz, 1H), 4.40 (d, J=5.7 Hz, 2H), 1.67 (s, 1H), 1.33 (s, 9H). ESI-MS m/z calc. 316.0324, Retention time: 5.49 minutes (no ionization detected); LC method S.

Step 3: (Z)-3-(4-tert-butylphenyl)-3-trimethylstannyl-prop-2-en-1-ol

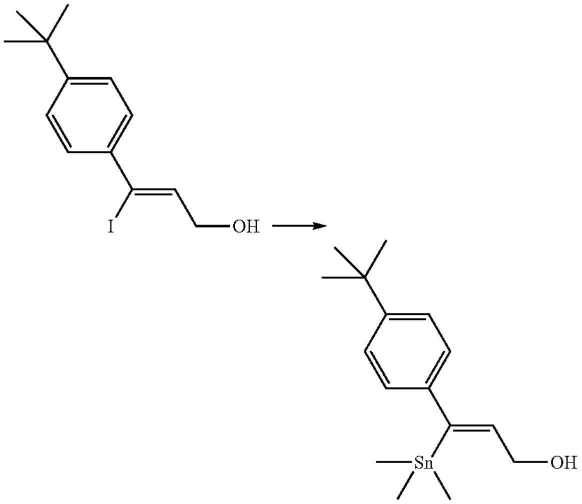

The solution of (Z)-3-(4-tert-butylphenyl)-3-iodo-prop-2-en-1-ol (2.97 g, 9.0177 mmol) in anhydrous 1,4-Dioxane (90 mL) was purged with argon for 1 minute, then $Pd(PPh_3)_4$ (521 mg, 0.4509 mmol) was added, followed by hexamethyldistananne (5.9088 g, 3.7397 mL, 18.035 mmol). The resulting solution was further purged with argon for 1 minute, then sealed and heated at 80° C. under argon for 19 hours. The reaction solution was cooled to ambient temperature, diluted with ether (150 mL), washed with potassium fluoride solution (10%, 50 mL), brine (40 mL) and dried over anhydrous sodium sulfate. The solution was filtered and concentrated under reduced pressure. The crude product obtained was purified by flash chromatography (loaded with DCM) (80 g silica gel, eluting 0 to 25% ethyl acetate in hexane) to afford (Z)-3-(4-tert-butylphenyl)-3-trimethylstannyl-prop-2-en-1-ol (782 mg, 25%) as a brown oil. $^1H$ NMR (500 MHz, Chloroform-d) δ 7.35-7.29 (m, 2H), 7.08-6.92 (m, 2H), 6.43 (t, J=6.3 Hz, 1H), 4.29 (t, J=5.9 Hz, 2H), 1.32 (s, 9H), 0.23 (s, 9H). ESI-MS m/z calc. 354.10056, Retention time: 4.38 minutes (no ionization detected), LC method S.

Step 4: tert-Butyl-[(Z)-3-(4-tert-butylphenyl)-3-trimethylstannyl-allyloxy]-dimethyl-silane

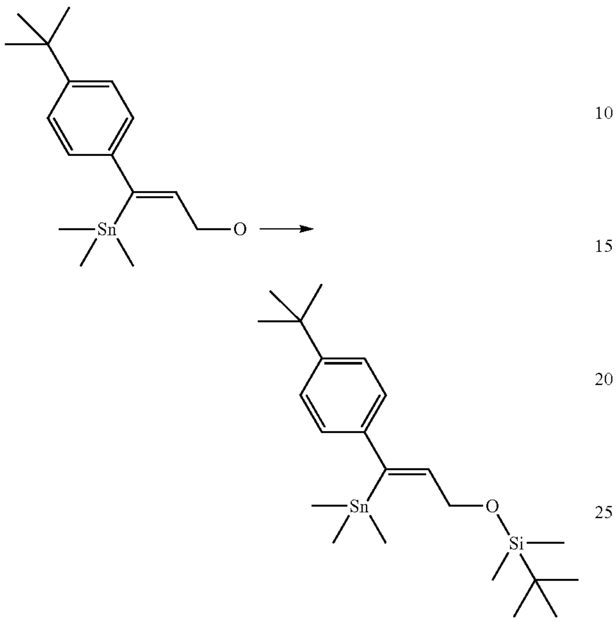

To a solution of (Z)-3-(4-tert-butylphenyl)-3-trimethylstannyl-prop-2-en-1-ol (776 mg, 2.1978 mmol) in anhydrous DCM (20 mL) was added imidazole (375 mg, 5.5084 mmol) followed by tert-butyldimethylsilyl chloride (663 mg, 4.3988 mmol). The resulting solution was stirred at ambient temperature for 2 hours. The reaction was diluted with dichloromethane (150 mL), washed with brine (2×30 mL), dried over anhydrous sodium sulfate, filtered and concentrated under reduced pressure. Residue obtained was purified by flash chromatography (loaded with DCM) (80 g silica gel, eluting 0 to 20% dichloromethane in hexane) to afford tert-butyl-[(Z)-3-(4-tert-butylphenyl)-3-trimethylstannyl-allyloxy]-dimethyl-silane (886 mg, 86%) as a colorless liquid. $^{1}$H NMR (500 MHz, Chloroform-d) δ 7.32-7.28 (m, 2H), 7.05-6.98 (m, 2H), 6.34 (t, J=6.1 Hz, 1H), 4.31 (d, J=6.1 Hz, 2H), 1.32 (s, 9H), 0.92 (s, 9H), 0.22 (s, 9H), 0.11 (s, 6H).

Step 5: Methyl 3-[[4-chloro-6-(2,6-dimethylphenyl)pyrimidin-2-yl]-(methoxymethyl)sulfamoyl]benzoate

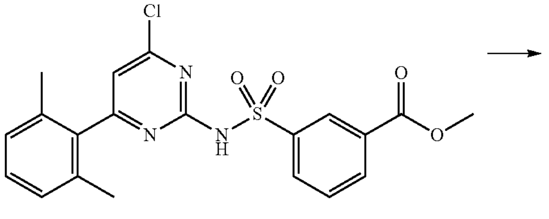

-continued

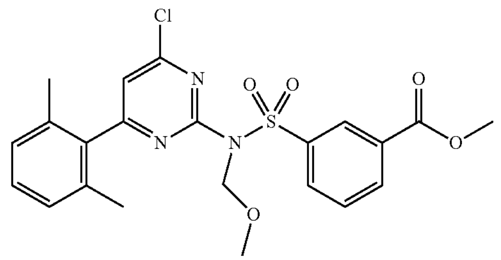

To a solution of methyl 3-[[4-chloro-6-(2,6-dimethylphenyl)pyrimidin-2-yl]sulfamoyl]benzoate (35.04 g, 81.131 mmol) in Acetonitrile (525 mL) and 1,2-dichloroethane (525 mL) was added potassium carbonate (16.8 g, 121.56 mmol) followed by Chloromethyl methyl ether (7.5260 g, 7.1 mL, 93.475 mmol). The reaction mixture was stirred at room temperature for overnight. The solvent was evaporated, and the resulting material was partitioned between water (300 mL) and EtOAc (300 mL). The aqueous layer was extracted with EtOAc (2×200 mL). The combined organic layers were washed with water (300 mL) and brine (300 mL), dried over anhydrous sodium sulfate, and concentrated under vacuum. The residue was purified by silica gel chromatography using 0 to 40% EtOAc in Hexane to afford methyl 3-[[4-chloro-6-(2,6-dimethylphenyl)pyrimidin-2-yl]-(methoxymethyl)sulfamoyl]benzoate (30.95 g, 80%) as clear gel. ESI-MS m/z calc. 475.0969, found 476.3 $(M+1)^{+}$; Retention time: 3.96 minutes, LC method T.

Step 6: Methyl 3-[[4-[(Z)-3-[tert-butyl(dimethyl)silyl]oxy-1-(4-tert-butylphenyl)prop-1-enyl]-6-(2,6-dimethylphenyl)pyrimidin-2-yl]-(methoxymethyl)sulfamoyl]benzoate

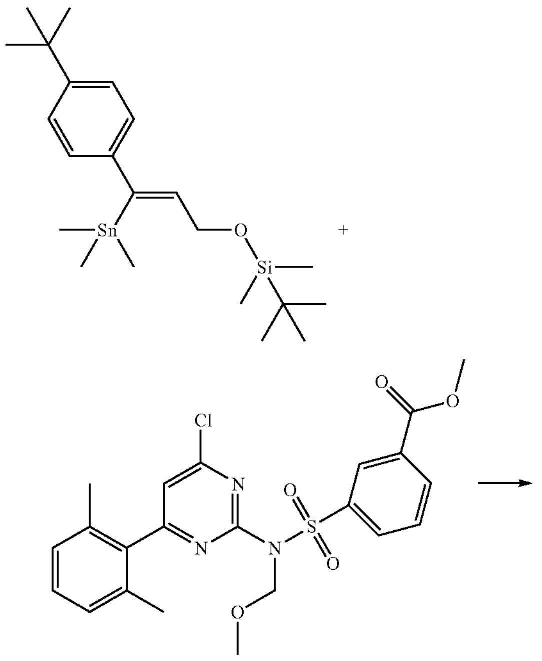

-continued

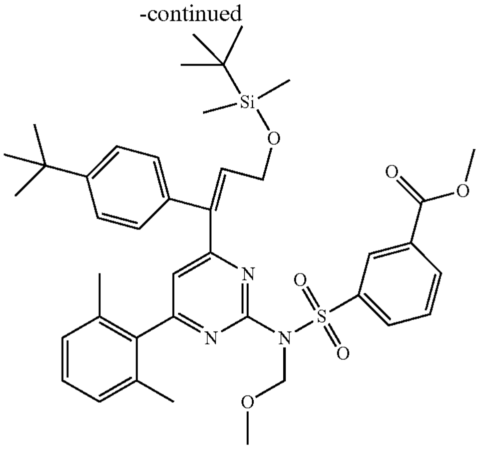

To a solution of tert-butyl-[(Z)-3-(4-tert-butylphenyl)-3-trimethylstannyl-allyloxy]-dimethyl-silane (945 mg, 2.0220 mmol) and methyl 3-[[4-chloro-6-(2,6-dimethylphenyl)pyrimidin-2-yl]-(methoxymethyl)sulfamoyl]benzoate (1.25 g, 2.6264 mmol) in anhydrous NMP (15 mL) were added CuI (39 mg, 0.2048 mmol) and $Pd(PPh_3)_4$ (118 mg, 0.1021 mmol). The solution was purged with argon for 1 minute, then heated at 90° C. under argon for 20 hours. The reaction solution was cooled to ambient temperature, diluted with ether (200 mL), washed with aqueous KF solution (10%, 2×25 mL), water (2×25 mL), and brine (50 mL). The organic layer was dried over anhydrous sodium sulfate, filtered, and concentrated under reduced pressure. The crude product obtained was purified by flash chromatography (load with DCM) (120 g silica gel, eluting 0 to 20% ethyl acetate in hexane) to afford methyl 3-[[4-[(Z)-3-[tert-butyl(dimethyl)silyl]oxy-1-(4-tert-butylphenyl)prop-1-enyl]-6-(2,6-dimethylphenyl)pyrimidin-2-yl]-(methoxymethyl)sulfamoyl]benzoate (747 mg, 50%) as a sticky brown liquid. ESI-MS m/z calc. 743.3424, found 744.0 $(M+1)^+$; Retention time: 9.75 minutes; $^1H$ NMR (500 MHz, Chloroform-d) δ 8.61 (t, J=1.8 Hz, 1H), 8.11 (ddt, J=7.2, 5.7, 1.4 Hz, 2H), 7.33-7.29 (m, 3H), 7.19 (t, J=7.6 Hz, 1H), 7.12-7.07 (m, 2H), 7.04 (d, J=7.6 Hz, 2H), 6.67 (s, 1H), 6.28 (t, J 5.7 Hz, 1H), 5.79 (s, 2H), 4.62 (d, J=5.7 Hz, 2H), 3.79 (s, 3H), 3.43 (s, 3H), 1.85 (s, 6H), 1.31 (s, 9H), 0.90 (s, 9H), 0.07 (s, 6H). LC method S.

Step 7: Methyl 3-[[4-[(Z)-1-(4-tert-butylphenyl)-3-hydroxy-prop-1-enyl]-6-(2,6-dimethylphenyl)pyrimidin-2-yl]-(methoxymethyl)sulfamoyl]benzoate

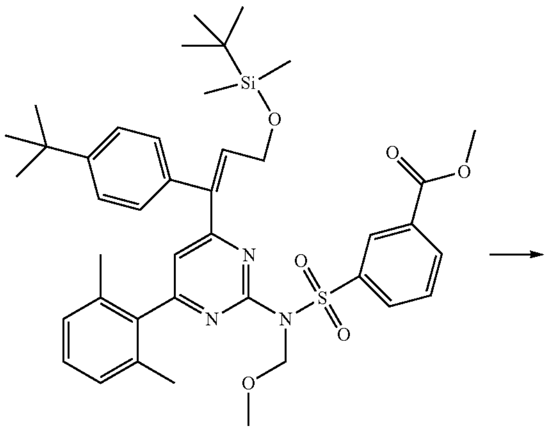

-continued

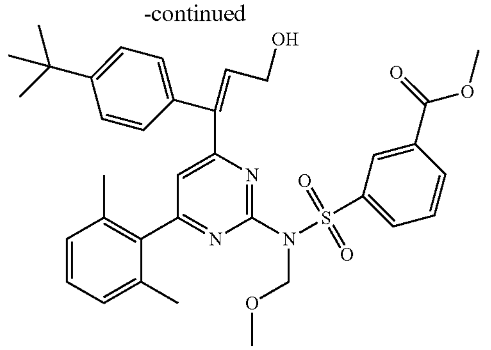

To a solution of methyl 3-[[4-[(Z)-3-[tert-butyl(dimethyl)silyl]oxy-1-(4-tert-butylphenyl)prop-1-enyl]-6-(2,6-dimethylphenyl)pyrimidin-2-yl]-(methoxymethyl)sulfamoyl]benzoate (631 mg, 0.8481 mmol) in THF (8.5 mL) at 0° C. was added TBAF (1.3 mL of 1 M, 1.3000 mmol). The resulting solution was stirred at this temperature for 1 hour. The reaction solution was diluted with ethyl acetate (150 mL), washed with saturated ammonium chloride aqueous solution (30 mL) and brine (30 mL). The organic layer was dried over anhydrous sodium sulfate, filtered, and concentrated under reduced pressure. The crude product obtained was purified by flash chromatography (load with DCM) (40 g silica gel, eluting 0 to 40% ethyl acetate in hexane) to afford methyl 3-[[4-[(Z)-1-(4-tert-butylphenyl)-3-hydroxy-prop-1-enyl]-6-(2,6-dimethylphenyl)pyrimidin-2-yl]-(methoxymethyl)sulfamoyl]benzoate (475 mg, 88%) as a white foam solid. ESI-MS m/z calc. 629.256, found 630.2 $(M+1)^+$; Retention time: 7.54 minutes, LC method S.

Step 8: Methyl 3-[[4-[1-(4-tert-butylphenyl)-3-hydroxy-propyl]-6-(2,6-dimethylphenyl)pyrimidin-2-yl]-(methoxymethyl)sulfamoyl]benzoate

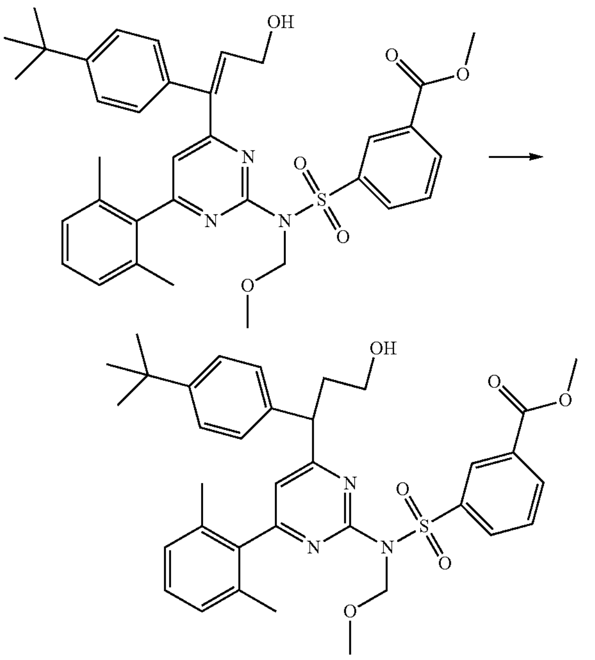

To a solution of methyl 3-[[4-[(Z)-1-(4-tert-butylphenyl)-3-hydroxy-prop-1-enyl]-6-(2,6-dimethylphenyl)pyrimidin-2-yl]-(methoxymethyl)sulfamoyl]benzoate (475 mg, 0.7467 mmol) in MeOH (30 mL) in a hydrogenation vessel was added $Pd(OH)_2$ on carbon (90 mg, 0.1282 mmol) (20 wt %). The reaction vessel was hydrogenated under 60 Psi in Parr-Shaker for 3 hours. The reaction solution was filtered through Celite, washed with methanol and filtrate was removed under reduced pressure. Toluene (2×20 mL) was added, and concentrated under reduced pressure to remove trace amount of methanol to afford methyl 3-[[4-[1-(4-tert-butylphenyl)-3-hydroxy-propyl]-6-(2,6-dimethylphenyl)pyrimidin-2-yl]-(methoxymethyl)sulfamoyl]benzoate (472 mg, 80%) as a white solid. The crude product obtained was used directly in next step. ESI-MS m/z calc. 631.2716, found 632.3 $(M+1)^+$; Retention time: 7.17 minutes, LC method S.

Step 9: Methyl 3-[[4-[3-azido-1-(4-tert-butylphenyl) propyl]-6-(2,6-dimethylphenyl)pyrimidin-2-yl]-(methoxymethyl)sulfamoyl]benzoate

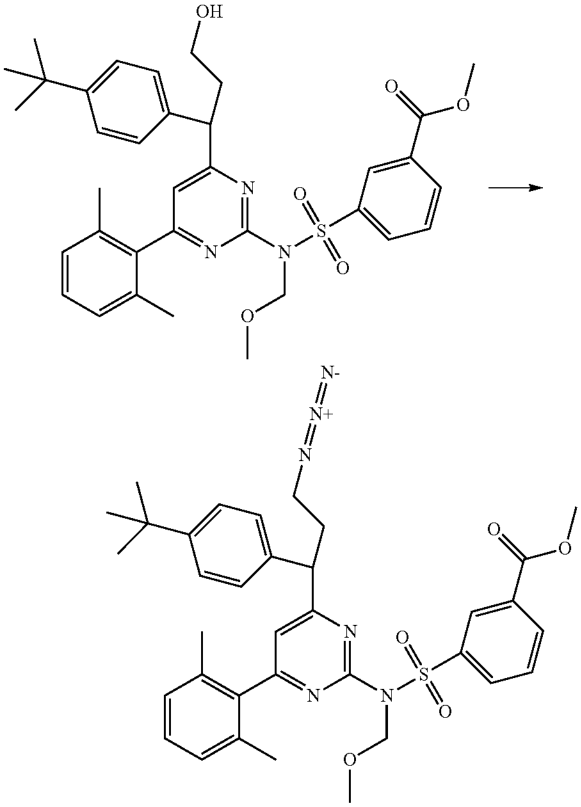

To a solution of methyl 3-[[4-[1-(4-tert-butylphenyl)-3-hydroxy-propyl]-6-(2,6-dimethylphenyl)pyrimidin-2-yl]-(methoxymethyl)sulfamoyl]benzoate (773 mg, 0.7341 mmol) and DBU (407.20 mg, 0.4 mL, 2.6748 mmol) in anhydrous Toluene (3 mL) at 0° C. under argon was added DPPA (510.80 mg, 0.4 mL, 1.8561 mmol). The resulting solution was then stirred at ambient temperature for 1 hour, then heated at 80° C. for 2 hours. The reaction solution was cooled to ambient temperature and purified by flash chromatography (loaded with DCM) (80 g silica gel, eluting 0 to 20% ethyl acetate in hexane) to afford methyl 3-[[4-[3-azido-1-(4-tert-butylphenyl)propyl]-6-(2,6-dimethylphenyl)pyrimidin-2-yl]-(methoxymethyl)sulfamoyl]benzoate (286 mg, 56%) as a white foam solid. ESI-MS m/z calc. 656.2781, found 657.5 $(M+1)^+$; Retention time: 8.34 minutes; $^1$H NMR (500 MHz, Chloroform-d) δ 8.70 (t, J=1.8 Hz, 1H), 8.27-8.15 (m, 2H), 7.45 (t, J=7.9 Hz, 1H), 7.28-7.27 (m, 1H), 7.26-7.24 (m, 1H), 7.19 (t, J=7.6 Hz, 1H), 7.07-7.01 (m, 4H), 6.67 (s, 1H), 5.83 (d, J=1.6 Hz, 2H), 4.00 (dd, J=8.2, 7.1 Hz, 1H), 3.85 (s, 3H), 3.41 (s, 3H), 3.27-3.11 (m, 2H), 2.42-2.26 (m, 1H), 2.18-2.05 (m, 1H), 1.84 (s, 6H), 1.28 (s, 9H). LC method S.

Step 10: Methyl 3-[[4-[3-(tert-butoxycarbonylamino)-1-(4-tert-butylphenyl)propyl]-6-(2,6-dimethylphenyl)pyrimidin-2-yl]-(methoxymethyl)sulfamoyl]benzoate

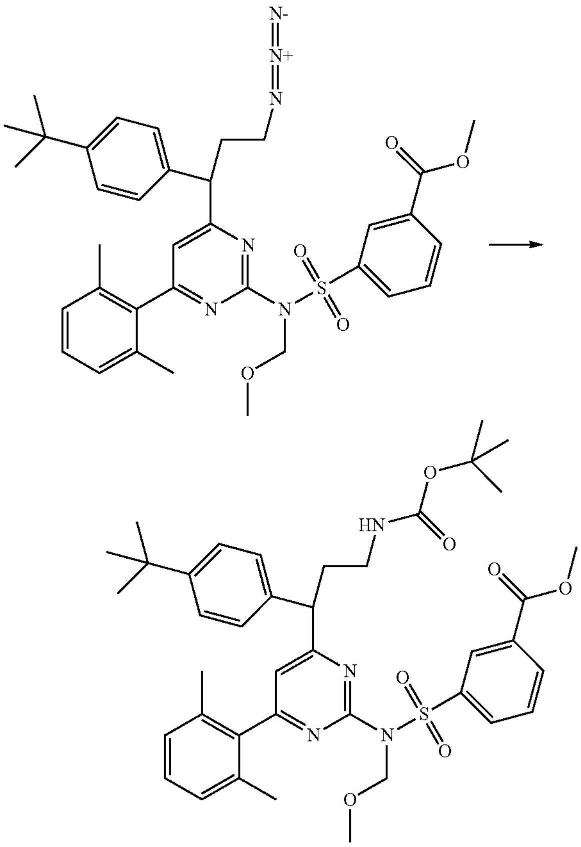

To a solution of methyl 3-[[4-[3-azido-1-(4-tert-butylphenyl)propyl]-6-(2,6-dimethylphenyl)pyrimidin-2-yl]-(methoxymethyl) sulfamoyl]benzoate (284 mg, 0.4108 mmol) in MeOH (20 mL) was added Boc anhydride (310 mg, 1.4204 mmol) followed by 10% Pd/C (97 mg, 0.9115 mmol). The resulting solution was then hydrogenated under 50 Psi in a Parr-Shaker for 19 hours. The reaction solution was filtered through Celite, washed with methanol and filtrate was concentrated under reduced pressure. The crude product obtained was purified by flash chromatography (load with DCM) (40 g silica gel, eluting 0 to 20% ethyl acetate in hexane) to afford methyl 3-[[4-[3-(tert-butoxycarbonylamino)-1-(4-tert-butylphenyl)propyl]-6-(2,6-dimethylphenyl)pyrimidin-2-yl]-(methoxymethyl)sulfamoyl]benzoate (241 mg, 80%) as a white foam solid. ESI-MS m/z calc. 730.34, found 731.5 $(M+1)^+$; Retention time: 8.19 minutes, LC method S.

Step 11: 3-[[4-[3-(tert-Butoxycarbonylamino)-1-(4-tert-butylphenyl)propyl]-6-(2,6-dimethylphenyl) pyrimidin-2-yl]-(methoxymethyl)sulfamoyl]benzoic acid

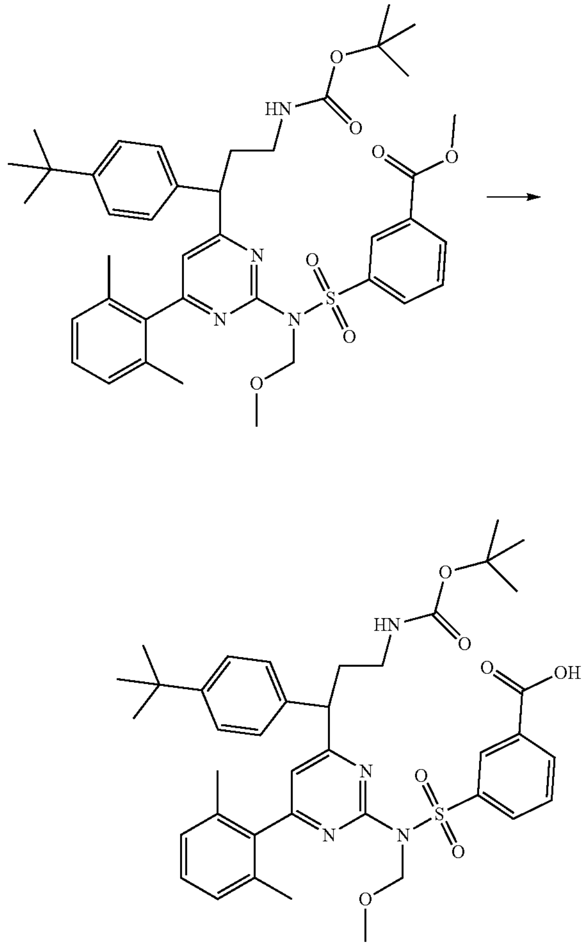

To a solution of methyl 3-[[4-[3-(tert-butoxycarbonylamino)-1-(4-tert-butylphenyl)propyl]-6-(2,6-dimethylphenyl)pyrimidin-2-yl]-(methoxymethyl)sulfamoyl]benzoate (225 mg, 0.3078 mmol) in THF (4 mL) was added aqueous solution of NaOH (1.3 mL of 1 M, 1.3000 mmol). The resulting solution was stirred at ambient temperature for 20 hours. Then reaction was quenched with aqueous HCl (20 mL, 1N) and extracted with ethyl acetate (3×50 mL). The combined organic layers were washed with brine (2×20 mL), dried over anhydrous sodium sulfate, filtered, and concentrated under reduced pressure to afford crude product. The 3-[[4-[3-(tert-butoxycarbonylamino)-1-(4-tert-butylphenyl)propyl]-6-(2,6-dimethylphenyl)pyrimidin-2-yl]-(methoxymethyl)sulfamoyl]benzoic acid (225 mg, 99%) obtained was used directly in next step. ESI-MS m/z calc. 716.3244, found 717.3 $(M+1)^+$; Retention time: 7.45 minutes, LC method S.

Step 12: 3-[[4-[3-Amino-1-(4-tert-butylphenyl)propyl]-6-(2,6-dimethylphenyl)pyrimidin-2-yl]sulfamoyl]benzoic acid

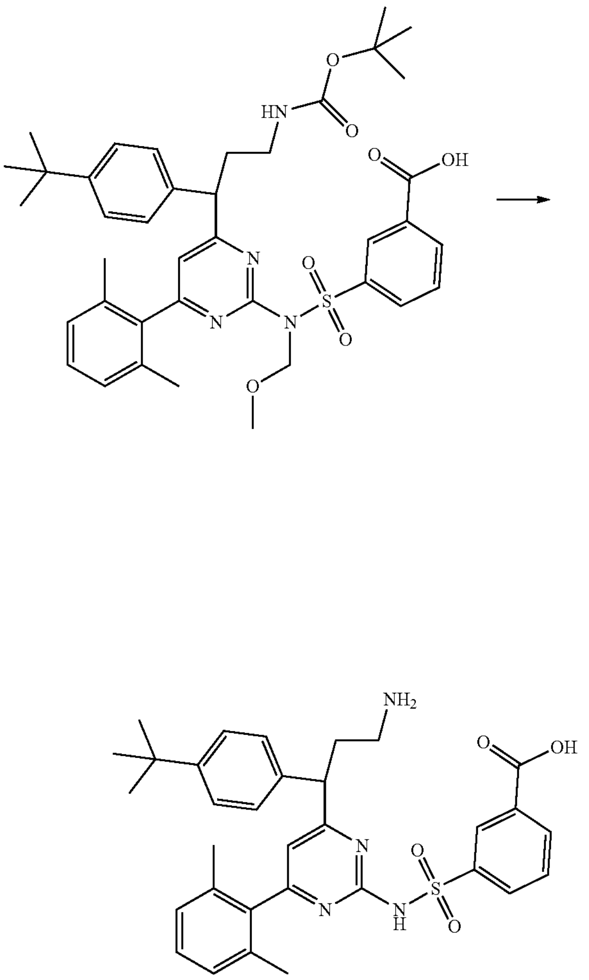

To a vial containing 3-[[4-[3-(tert-butoxycarbonylamino)-1-(4-tert-butylphenyl)propyl]-6-(2,6-dimethylphenyl)pyrimidin-2-yl]-(methoxymethyl)sulfamoyl]benzoic acid (236 mg, 0.3292 mmol) was added HCl (5 mL of 4 M, 20.000 mmol) in 1,4-dioxane. The resulting solution was stirred at ambient temperature for 45 minutes. All solvents were removed under reduced pressure. Solid obtained was purified by reverse HPLC (20% to 80% $CH_3CN$ in water buffed with 5 mM HCl). Pure fractions were dried using speed vacuum Savant at room temperature to afford 3-[[4-[3-amino-1-(4-tert-butylphenyl)propyl]-6-(2,6-dimethylphenyl)pyrimidin-2-yl]sulfamoyl]benzoic acid (hydrochloride salt) (160 mg, 77%) as a white solid. ESI-MS m/z calc. 572.2457, found 573.4 $(M+1)^+$; Retention time: 2.17 minutes; $^1H$ NMR (500 MHz, DMSO-$d_6$) δ 13.49 (s, 1H), 12.03 (s, 1H), 8.48 (t, J=1.9 Hz, 1H), 8.22 (ddt, J=13.7, 7.8, 1.4 Hz, 2H), 7.92 (s, 2H), 7.73 (t, J=7.8 Hz, 1H), 7.25 (d, J=8.3 Hz, 2H), 7.21 (d, J 7.6 Hz, 1H), 7.09 (d, J=7.6 Hz, 2H), 7.05 (d, J=7.9 Hz, 2H), 6.97 (s, 1H), 4.14 (t, J=7.7 Hz, 1H), 2.69 (s, 1H), 2.59 (s, 1H), 2.28 (dq, J=14.0, 6.9 Hz, 1H), 2.19 (q, J=8.5 Hz, 1H), 1.84 (s, 6H), 1.24 (s, 9H). LC method W.

Step 13: 9-(4-tert-Butylphenyl)-6-(2,6-dimethylphenyl)-2,2-dioxo-2 λ6-thia-3,5,12,19-tetrazatricyclo [12.3.1.14,8]nonadeca-1(18),4(19),5,7,14,16-hexaen-13-one (Compound 5)

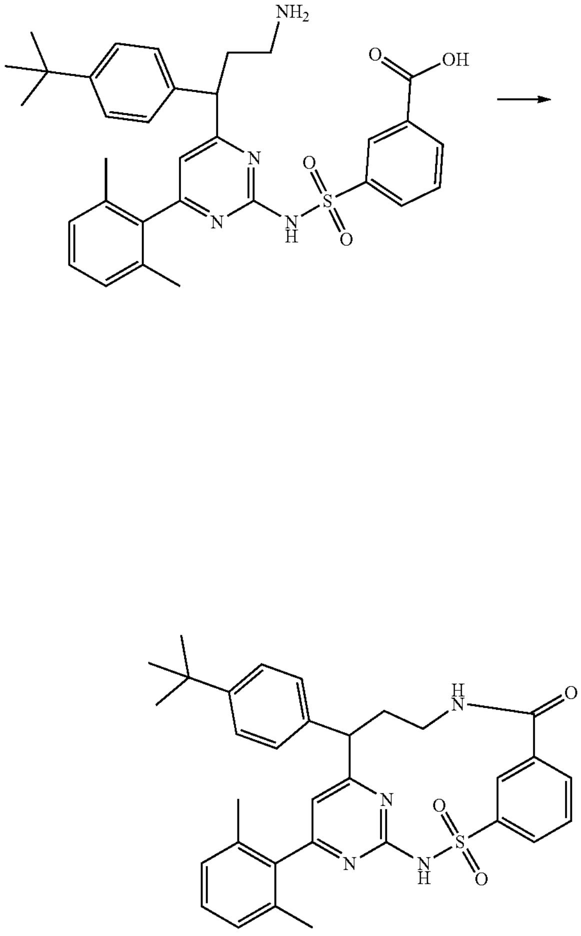

To a solution of HATU (61 mg, 0.1604 mmol) in anhydrous DMF (7 mL) was added the solution of 3-[[4-[3-amino-1-(4-tert-butylphenyl)propyl]-6-(2,6-dimethylphenyl)pyrimidin-2-yl]sulfamoyl]benzoic acid (hydrochloride salt) (75 mg, 0.1161 mmol) and DIEA (63.812 mg, 0.086 mL, 0.4937 mmol) in anhydrous DMF (3 mL) dropwise. After the addition was completed, the resulting solution was stirred at ambient temperature for 21 hours. Then HCl (1N, 20 mL) was added, followed by ethyl acetate (50 mL). The solution was filtered, and white solid was collected. White solid was washed with water, ethyl acetate and dried to afford 9-(4-tert-butylphenyl)-6-(2,6-dimethyl phenyl)-2,2-dioxo-2λ$^6$-thia-3,5,12,19-tetrazatricyclo[12.3.1.14,8]nonadeca-1(18),4(19), 5,7,14,16-hexaen-13-one (26.8 mg, 40%). ESI-MS m/z calc. 554.2352, found 555.4 $(M+1)^+$; Retention time: 2.82 minutes; $^1$H NMR (500 MHz, DMSO-$d_6$) δ 11.84 (s, 1H), 8.65 (s, 1H), 8.11 (s, 1H), 8.03 (d, J=7.5 Hz, 1H), 7.76 (d, J=11.7 Hz, 2H), 7.35 (d, J=7.9 Hz, 2H), 7.27 (d, J=8.0 Hz, 2H), 7.18 (t, J=7.4 Hz, 1H), 7.06 (d, J=7.6 Hz, 2H), 6.92 (s, 1H), 4.16 (d, J=11.5 Hz, 1H), 3.03 (s, 1H), 2.95-2.81 (m, 2H), 2.18-1.98 (m, 1H), 1.81 (s, 6H), 1.25 (s, 9H), LC method W.

Example 6: Preparation of Compound 6

Step 1: 3-[[4-[(3R)-3-(tert-Butoxycarbonylamino)-5-methyl-hex-1-ynyl]-6-(2,6-dimethylphenyl)pyrimidin-2-yl]sulfamoyl]benzoic acid

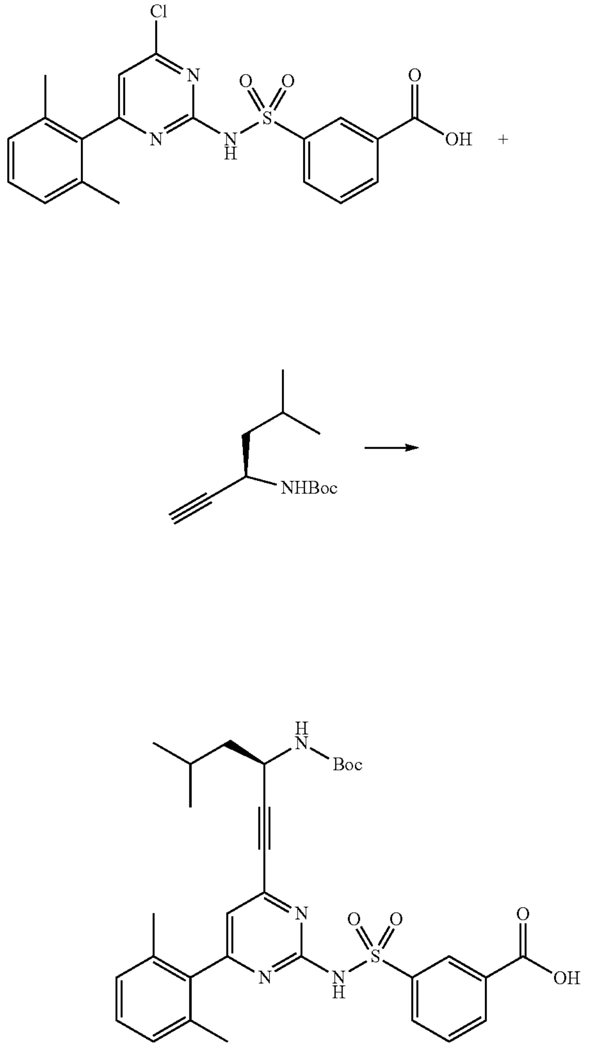

Into a microwavable vial was charged with a solution of 3-[[4-chloro-6-(2,6-dimethylphenyl)pyrimidin-2-yl]sulfamoyl]benzoic acid (102 mg, 0.2441 mmol), tert-butyl N-[(1R)-1-ethynyl-3-methyl-butyl]carbamate (59 mg, 0.2792 mmol) and TEA (123.42 mg, 0.17 mL, 1.2197 mmol) in DMSO (1.0 mL). The solution of purged with argon for 1 minute, then $Pd(PPh_3)_4$ (17 mg, 0.0147 mmol) and CuI (5 mg, 0.0263 mmol) were added. The reaction was irradiated in a microwave reactor for 3 hours at 80° C. The reaction mixture was worked up with another reaction crude from a reaction run on the same scale to furnish 3-[[4-[(3R)-3-(tert-butoxycarbonylamino)-5-methyl-hex-1-ynyl]-6-(2,6-dimethylphenyl)pyrimidin-2-yl]sulfamoyl]benzoic acid (102 mg, 49% corrected yield) as a yellow solid. ESI-MS m/z calc. 592.23553, found 593.2 $(M+1)^+$; Retention time: 6.02 minutes; LC method S.

Step 2: 3-[[4-[(3S)-3-(tert-Butoxycarbonylamino)-5-methyl-hexyl]-6-(2,6-dimethylphenyl)pyrimidin-2-yl]sulfamoyl]benzoic acid

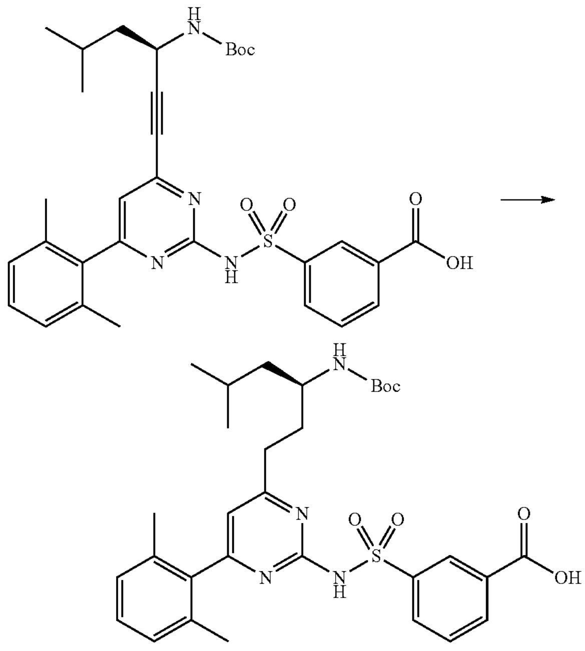

Into a solution of 3-[[4-[(3R)-3-(tert-butoxycarbonylamino)-5-methyl-hex-1-ynyl]-6-(2,6-dimethylphenyl) pyrimidin-2-yl]sulfamoyl]benzoic acid (3.117 g, 3.6813 mmol) in ethanol (100 mL) was added 10% Pd (1.69 g, 1.5880 mmol) on carbon. The reaction was purged with nitrogen, then it was stirred at room temperature under 1 atm of hydrogen for 16 hours. The catalyst was removed by filtration. The filtrate was concentrated under vacuum to furnish 3-[[4-[(3S)-3-(tert-butoxycarbonylamino)-5-methyl-hexyl]-6-(2,6-dimethylphenyl)pyrimidin-2-yl]sulfamoyl] benzoic acid (2.81 g, 98%) as a yellow oil. ESI-MS m/z calc. 596.26685, found 597.3 $(M+1)^+$; Retention time: 5.78 minutes; LC method S.

Step 3: 3-[[4-[(3S)-3-Amino-5-methyl-hexyl]-6-(2,6-dimethylphenyl)pyrimidin-2-yl]sulfamoyl]benzoic acid

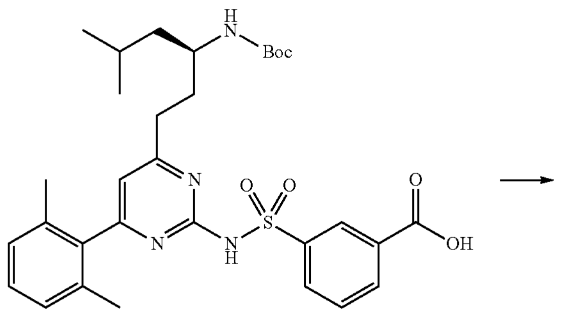

-continued

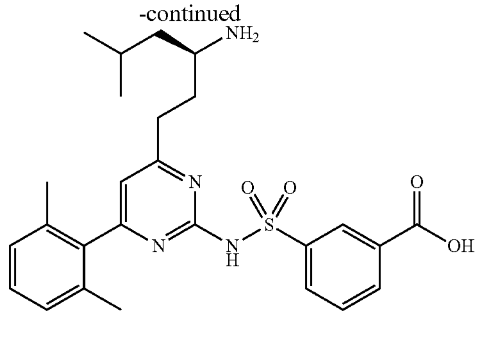

Into a solution of 3-[[4-[(3S)-3-(tert-butoxycarbonylamino)-5-methyl-hexyl]-6-(2,6-dimethylphenyl)pyrimidin-2-yl]sulfamoyl]benzoic acid (255 mg, 0.3846 mmol) in DCM (5 mL) was added HCl (5 mL of 4 M, 20.000 mmol) in dioxane. The reaction mixture was stirred at room temperature for 1 hour, then it was concentrated under vacuum to furnish 3-[[4-[(3S)-3-amino-5-methyl-hexyl]-6-(2,6-dimethylphenyl)pyrimidin-2-yl]sulfamoyl]benzoic acid (hydrochloride salt) (212 mg, 93%) as a yellow oil. ESI-MS m/z calc. 496.2144, found 497.3 (M+1)+; Retention time: 4.13 minutes. The product was used in the next step reaction without further purification. ESI-MS m/z calc. 496.21442, found 497.3 $(M+1)^+$; Retention time: 4.13 minutes; LC method S.

Step 4: 3-[[4-(2,6-Dimethylphenyl)-6-[(3S)-5-methyl-3-(spiro[2.3]hexan-5-ylamino)hexyl]pyrimidin-2-yl]sulfamoyl]benzoic acid

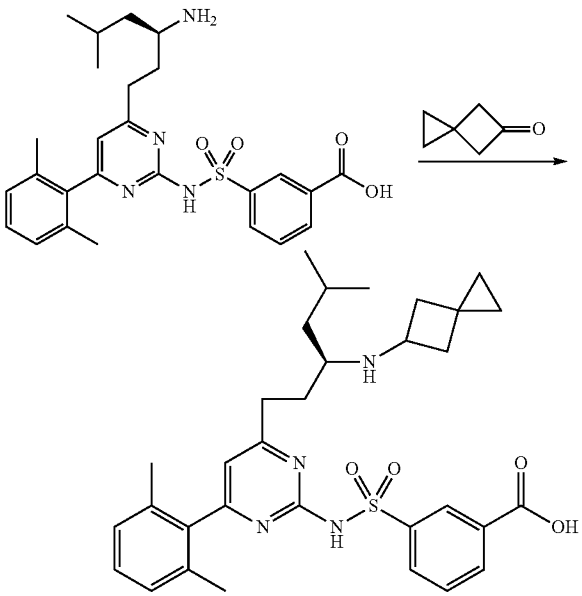

Into a solution of spiro[2.3]hexan-5-one (9 mg, 0.0936 mmol) and 3-[[4-[(3S)-3-amino-5-methyl-hexyl]-6-(2,6-dimethylphenyl)pyrimidin-2-yl]sulfamoyl]benzoic acid (hydrochloride salt) (54 mg, 0.0938 mmol) in DCM (1 mL) was added sodium triacetoxyborohydride (30 mg, 0.1415 mmol). The reaction mixture was stirred at room temperature for 2 days. The reaction was worked up with another reaction mixture to furnish 3-[[4-(2,6-dimethylphenyl)-6-[(3S)-5-methyl-3-(spiro[2.3]hexan-5-ylamino)hexyl]pyrimidin-2- yl]sulfamoyl]benzoic acid (23.6 mg, 44%) as a yellow solid. $^1$H NMR (250 MHz, Chloroform-d) δ 9.08 (s, 1H), 8.30 (d, J=7.6 Hz, 1H), 7.73 (d, J=7.7 Hz, 1H), 7.44 (t, J=7.9 Hz, 1H), 7.29-7.15 (m, 1H), 7.08 (d, J=7.6 Hz, 2H), 6.70 (s, 1H), 4.40-4.06 (m, 1H), 3.16-2.64 (m, 4H), 2.63-2.37 (m, 1H), 2.37-2.18 (m, 2H), 2.01 (s, 6H), 1.88-1.47 (m, 4H), 0.87 (t, J=6.9 Hz, 6H), 0.60-0.17 (m, 4H). ESI-MS m/z calc. 576.27704, found 577.4 (M+1)$^+$; Retention time: 4.83 minutes; LC method S.

Step 5: (11S)-6-(2,6-Dimethylphenyl)-11-isobutyl-2,2-dioxo-12-spiro[2.3]hexan-5-yl-2 λ6-thia-3,5,12,19-tetrazatricyclo[12.3.1.14,8]nonadeca-1(18),4(19),5,7,14,16-hexaen-13-one (Compound 6)

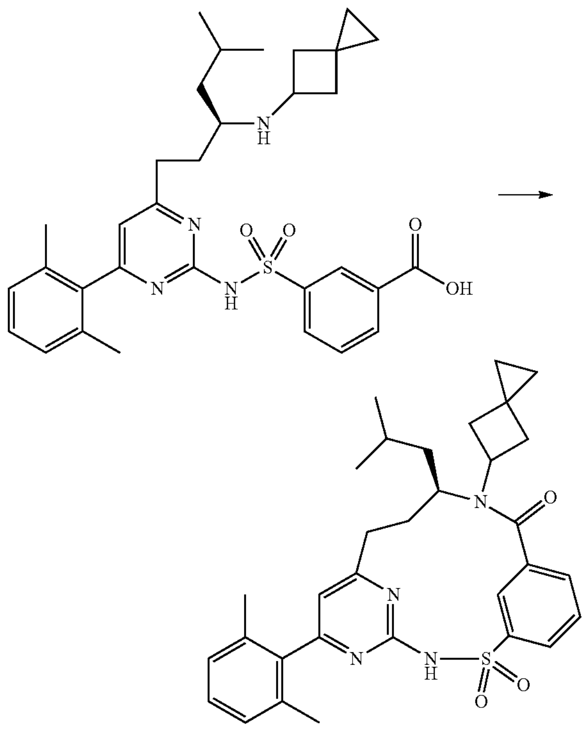

Into a solution of 3-[[4-(2,6-dimethylphenyl)-6-[(3S)-5-methyl-3-(spiro[2.3]hexan-5-ylamino)hexyl]pyrimidin-2-yl]sulfamoyl]benzoic acid (73 mg, 0.1266 mmol) in anhydrous NMP (1 mL) was added HATU (72 mg, 0.1894 mmol) and DIEA (65.296 mg, 0.088 mL, 0.5052 mmol). The reaction mixture was stirred at room temperature for 2 hours. The reaction mixture was purified by reverse phase HPLC using 0 to 100% acetonitrile in water (buffered with 0.1% TFA) to furnish (11S)-6-(2,6-dimethylphenyl)-11-isobutyl-2,2-dioxo-12-spiro[2.3]hexan-5-yl-2λ$^6$-thia-3,5,12,19-tetrazatricyclo[12.3.1.14,8]nonadeca-1(18),4(19),5,7,14,16-hexaen-13-one (35.9 mg, 50%) as a beige solid. $^1$H NMR (500 MHz, DMSO-d$_6$) δ 11.69 (s, 1H), 8.31 (d, J=1.9 Hz, 1H), 7.99-7.90 (m, 1H), 7.71 (d, J=7.6 Hz, 2H), 7.21 (t, J=7.6 Hz, 1H), 7.09 (d, J=7.6 Hz, 2H), 7.04 (s, 1H), 4.21 (p, J=8.6 Hz, 1H), 3.34 (ddt, J=20.0, 13.2, 6.7 Hz, 3H), 3.08-2.97 (m, 1H), 2.83 (dd, J=16.0, 12.1 Hz, 1H), 2.57 (ddt, J=13.3, 9.0, 4.0 Hz, 1H), 2.19-2.04 (m, 2H), 1.98 (t, J=9.5 Hz, 1H), 1.88 (s, 6H), 1.48 (t, J=11.8 Hz, 1H), 1.20 (dd, J=12.7, 6.8 Hz, 1H), 1.05 (t, J=12.3 Hz, 1H), 0.68 (d, J=6.6 Hz, 3H), 0.57-0.39 (m, 4H), −0.06 (s, 3H). ESI-MS m/z calc. 558.2665, found 559.3 (M+1)$^+$; Retention time: 3.21 minutes; LC method W.

Example 7: Preparation of Compound 7

Step 1: tert-Butyl N-[(1R)-1-(hydroxymethyl)-2-[1-(trifluoromethyl)cyclopropyl]ethyl]carbamate

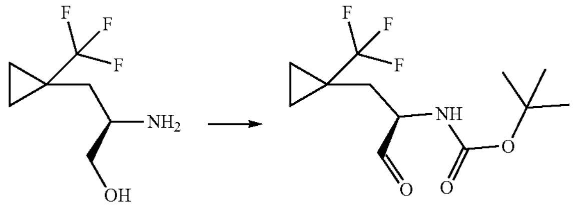 [SMILES: N[C@@H](CO)CC1(C(F)(F)F)CC1 ; CC(C)(C)OC(=O)N[C@@H](C=O)CC1(C(F)(F)F)CC1]

A slurry of (2R)-2-amino-3-[1-(trifluoromethyl)cyclopropyl]propan-1-ol (hydrochloride salt) (24.5 g, 111.55 mmol) and TEA (28.2 g, 38.843 mL, 278.68 mmol) in THF (500 mL) was prepared. The mixture was cooled in an ice water bath, then BOC-OSu (25.2 g, 117.10 mmol) was added and the ice bath was removed. The mixture was stirred at room temperature for three hours, then it was extracted with 0.5M NaOH (4×250 mL). The aqueous phases were discarded, and the organic phase was dried over sodium sulfate and concentrated in vacuo to obtain tert-butyl N-[(1R)-1-(hydroxymethyl)-2-[1-(trifluoromethyl)cyclopropyl]ethyl]carbamate (31.5 g, 95%). ESI-MS m/z calc. 283.1395, found 284.4 (M+1)+; Retention time: 4.64 minutes (LC method S).

Step 2: tert-Butyl N-[(1R)-1-formyl-2-[1-(trifluoromethyl)cyclopropyl]ethyl]carbamate

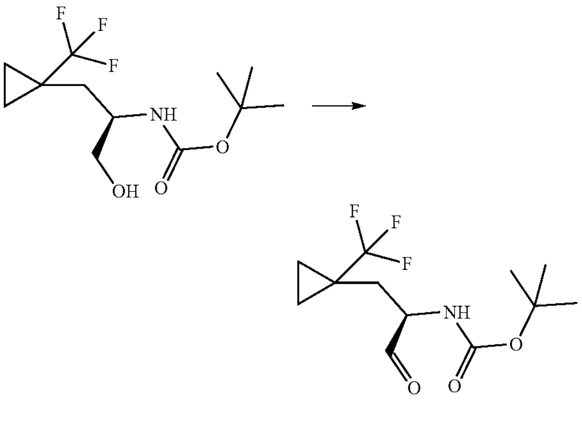

A solution of tert-butyl N-[(1R)-1-(hydroxymethyl)-2-[1-(trifluoromethyl)cyclopropyl]ethyl]carbamate (500 mg, 1.7650 mmol) in DCM (10 mL) was chilled in an ice water bath, then Dess-Martin periodinane (786 mg, 1.8532 mmol) was added and the resulting mixture was stirred at 0° C. for fifteen minutes, then at room temperature for four hours. LCMS analysis showed complete consumption of starting material to obtain tert-butyl N-[(1R)-1-formyl-2-[1-(trifluoromethyl)cyclopropyl]ethyl]carbamate (500 mg, 96%). ESI-MS m/z calc. 281.12387, found 282.7 (M+1)$^+$; Retention time: 4.84 minutes; LC method S.

Step 3: tert-Butyl N-[(1R)-1-[[1-(trifluoromethyl) cyclopropyl]methyl]prop-2-ynyl]carbamate

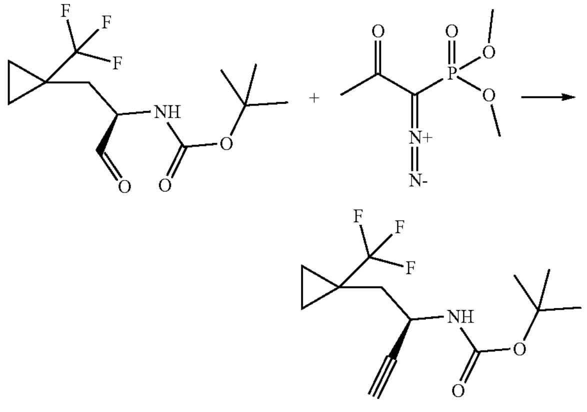

A solution of tert-butyl N-[(1R)-1-formyl-2-[1-(trifluoromethyl)cyclopropyl]ethyl]carbamate (500 mg, 1.7776 mmol) and potassium carbonate (491 mg, 3.5527 mmol) in MeOH (7 mL) was chilled in an ice water bath, then 1-diazo-1-dimethoxyphosphoryl-propan-2-one (410 mg, 2.1342 mmol) was added and the resulting mixture stirred at 0° C. for two hours. LCMS analysis showed the starting material was consumed and the product has the expected MW: tert-butyl N-[(1R)-1-[[1-(trifluoromethyl)cyclopropyl] methyl]prop-2-ynyl]carbamate (400 mg, 77%) ESI-MS m/z calc. 277.129, found 278.3 (M+1)+; Retention time: 5.94 minutes. ESI-MS m/z calc. 277.12897, found 278.3 $(M+1)^+$; Retention time: 5.94 minutes; LC method S.

Step 4: Methyl 3-[[4-[(3R)-3-(tert-butoxycarbonylamino)-4-[1-(trifluoromethyl)cyclopropyl]but-1-ynyl]-6-(2,6-dimethylphenyl)pyrimidin-2-yl]sulfamoyl]benzoate

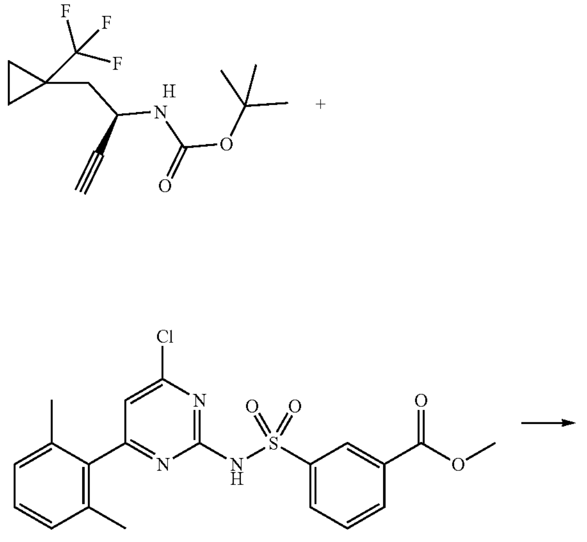

-continued

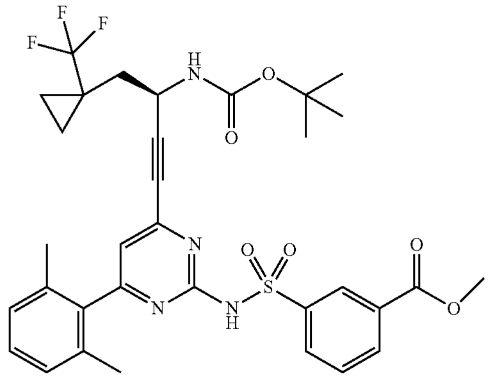

A mixture of methyl 3-[[4-chloro-6-(2,6-dimethylphenyl) pyrimidin-2-yl]sulfamoyl]benzoate (2 g, 4.6308 mmol), triphenylphosphine (122 mg, 0.1078 mL, 0.4651 mmol), $Pd(PPh_3)_2Cl_2$ (163 mg, 0.2322 mmol), CuI (88 mg, 0.4621 mmol), and TEA (3.6 g, 4.9587 mL, 35.577 mmol) in THF (3 mL) was prepared. The resulting solution was degassed in vacuo, then tert-butyl N-[(1R)-1-[[1-(trifluoromethyl)cyclopropyl] methyl]prop-2-ynyl]carbamate (1.9 g, 6.8522 mmol) was added and the mixture heated to 80° C. in a heating block for two hours. The mixture was concentrated in vacuo to obtain a dark red oil that was combined with the product from a second batch and purified by silica gel chromatography (0-30% ethyl acetate-hexane) to obtain methyl 3-[[4-[(3R)-3-(tert-butoxycarbonylamino)-4-[1-(trifluoromethyl)cyclopropyl]but-1-ynyl]-6-(2,6-dimethylphenyl)pyrimidin-2-yl]sulfamoyl]benzoate (650 mg, 20% combined yield). ESI-MS m/z calc. 672.22296, found 673.8 $(M+1)^+$; Retention time: 7.55 minutes; LC method S.

Step 5: Methyl 3-[[4-[(3S)-3-(tert-butoxycarbonylamino)-4-[1-(trifluoromethyl)cyclopropyl]butyl]-6-(2,6-dimethylphenyl)pyrimidin-2-yl]sulfamoyl] benzoate

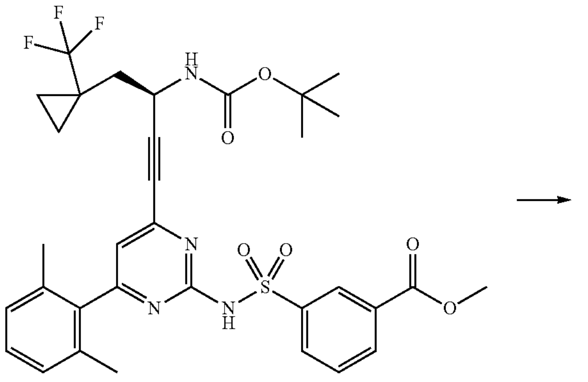

-continued

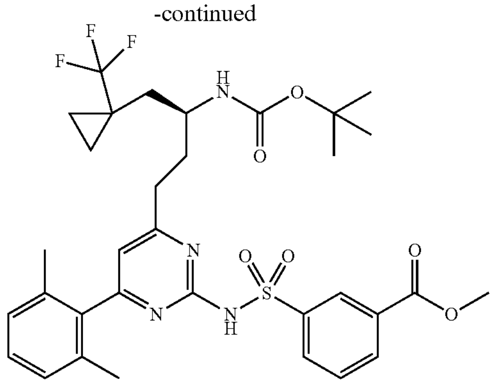

A solution of methyl 3-[[4-[(3R)-3-(tert-butoxycarbonylamino)-4-[1-(trifluoromethyl)cyclopropyl]but-1-ynyl]-6-(2,6-dimethylphenyl)pyrimidin-2-yl]sulfamoyl]benzoate (3.3 g, 4.9055 mmol) in ethanol (600 mL) was prepared, then Palladium on carbon (5.2 g, 10% w/w, 4.8863 mmol) was added. The resulting mixture was stirred under hydrogen (60 PSI) overnight, then was filtered through a pad of Celite. The solids were discarded, and the filtrate was concentrated in vacuo to obtain methyl 3-[[4-[(3S)-3-(tert-butoxycarbonylamino)-4-[1-(trifluoromethyl)cyclopropyl]butyl]-6-(2,6-dimethylphenyl)pyrimidin-2-yl]sulfamoyl]benzoate (3.6 g, 98%) as a yellow oil. ESI-MS m z calc. 676.2542, found 677.5 $(M+1)^+$; Retention time: 7.15 minutes (LC method S).

Step 6: 3-[[4-[(3S)-3-(tert-Butoxycarbonylamino)-4-[1-(trifluoromethyl)cyclopropyl]butyl]-6-(2,6-dimethylphenyl)pyrimidin-2-yl]sulfamoyl]benzoic acid

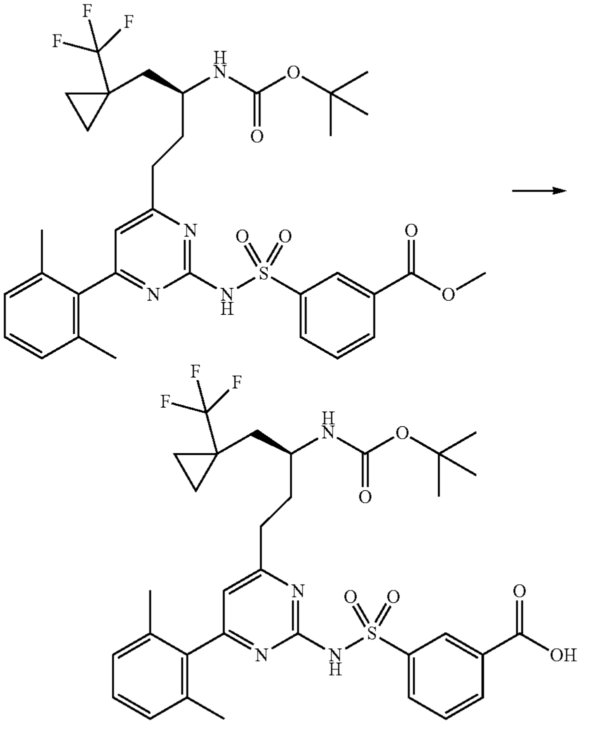

A solution of methyl 3-[[4-[(3S)-3-(tert-butoxycarbonylamino)-4-[1-(trifluoromethyl)cyclopropyl]butyl]-6-(2,6-dimethylphenyl)pyrimidin-2-yl]sulfamoyl]benzoate (3.6 g, 5.3196 mmol) in a mixture of MeOH (27 mL) and water (9 mL) was prepared. NaOH (1.1 g, 27.502 mmol) was then added, and the resulting solution was stirred at room temperature for two hours. LCMS analysis showed clean hydrolysis of the ester. The pH of the reaction mixture was adjusted to 3-4 using 1M HCl, and was then diluted with 50 mL of water and extracted with DCM (2×25 mL). The aqueous phase was discarded, and the organic phase was concentrated in vacuo to obtain 3-[[4-[(3S)-3-(tert-butoxycarbonylamino)-4-[1-(trifluoromethyl)cyclopropyl]butyl]-6-(2,6-dimethylphenyl)pyrimidin-2-yl]sulfamoyl]benzoic acid (2.2 g, 59%) as an orange solid. ESI-MS m/z calc. 662.2386, found 663.7 $(M+1)^+$; Retention time: 6.42 minutes; LC method S.

Step 7: 3-[[4-[(3S)-3-Amino-4-[1-(trifluoromethyl)cyclopropyl]butyl]-6-(2,6-dimethylphenyl)pyrimidin-2-yl]sulfamoyl]benzoic acid

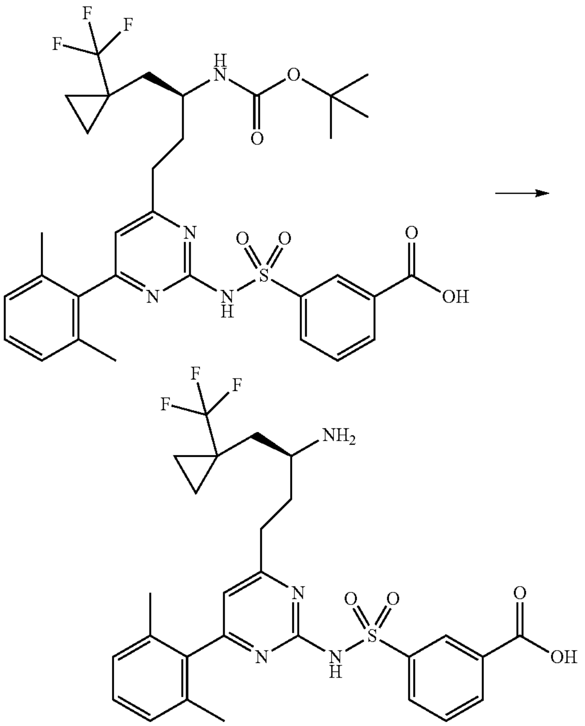

HCl in 1,4-dioxane (9 mL of 4 M, 36.000 mmol) was added to a solution of 3-[[4-[(3S)-3-(tert-butoxycarbonylamino)-4-[1-(trifluoromethyl)cyclopropyl]butyl]-6-(2,6-dimethylphenyl)pyrimidin-2-yl]sulfamoyl]benzoic acid (2.1 g, 3.1688 mmol) in DCM (5 mL). The resulting mixture was stirred at room temperature overnight, then concentrated in vacuo. The resulting oil was triturated with a small amount of diethyl ether, and the resulting solid was collected by vacuum filtration and dried in vacuo to obtain 3-[[4-[(3S)-3-amino-4-[1-(trifluoromethyl)cyclopropyl]butyl]-6-(2,6-dimethylphenyl)pyrimidin-2-yl]sulfamoyl]benzoic acid (hydrochloride salt) (1.95 g, 98%). ESI-MS m/z calc. 562.18616, found 563.6 $(M+1)^+$; Retention time: 4.39 minutes; LC method S.

Step 8: 3-[[4-(2,6-Dimethylphenyl)-6-[(3S)-3-(spiro[2.3]hexan-5-ylamino)-4-[1-(trifluoromethyl)cyclopropyl]butyl]pyrimidin-2-yl]sulfamoyl]benzoic acid

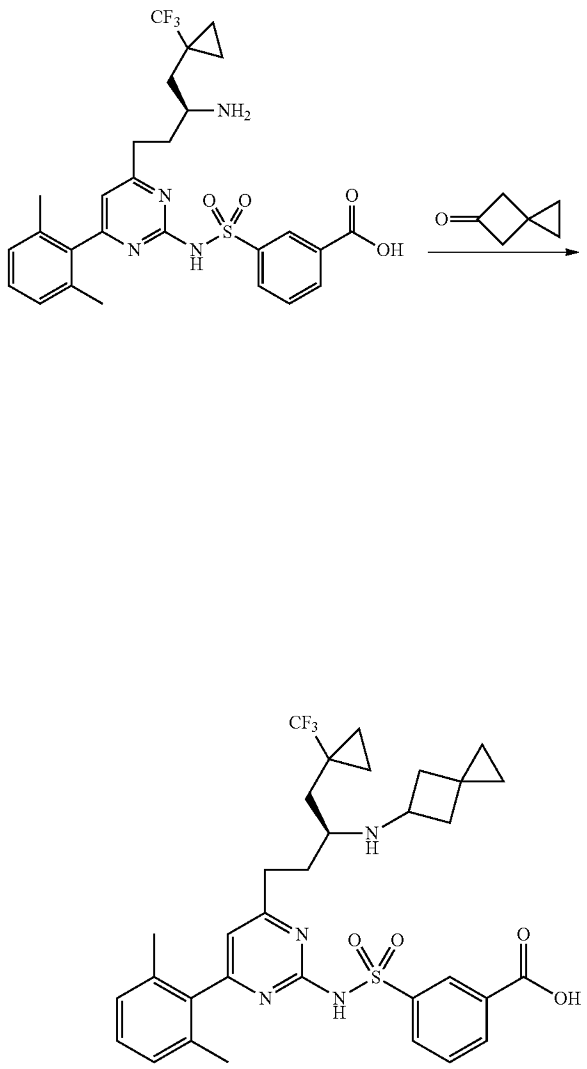

Into a solution of 3-[[4-[(3S)-3-amino-4-[1-(trifluoromethyl) cyclopropyl]butyl]-6-(2,6-dimethylphenyl)pyrimidin-2-yl]sulfamoyl]benzoic acid (hydrochloride salt) (100 mg, 0.1669 mmol) and spiro[2.3]hexan-5-one (36 mg, 0.3745 mmol) in anhydrous DCE (2 mL) was added sodium triacetoxyborohydride (88 mg, 0.4152 mmol). The reaction mixture was stirred at room temperature for 2 days. The reaction was quenched with 1 N HCl (aq.) (15 mL), and the aqueous layer was extracted with ethyl acetate (3×15 mL). The combined organic layers were washed with brine (15 mL), dried over anhydrous sodium sulfate, and concentrated under vacuum to furnish 3-[[4-(2,6-dimethylphenyl)-6-[(3S)-3-(spiro[2.3]hexan-5-ylamino)-4-[1-(trifluoro methyl) cyclopropyl]butyl]pyrimidin-2-yl]sulfamoyl]benzoic acid (hydrochloride salt) (103 mg, 80%) as a yellow oil. ESI-MS m/z calc. 642.2488, found 643.3 $(M+1)^+$; Retention time: 5.45 minutes; LC method S.

Step 9: (11S)-6-(2,6-Dimethylphenyl)-2,2-dioxo-12-spiro[2.3]hexan-5-yl-11-[[1-(trifluoromethyl)cyclopropyl]methyl]-2 λ6-thia-3,5,12,19-tetrazatricyclo[12.3.1.14,8]nonadeca-1(18),4(19),5,7,14,16-hexaen-13-one (Compound 7)

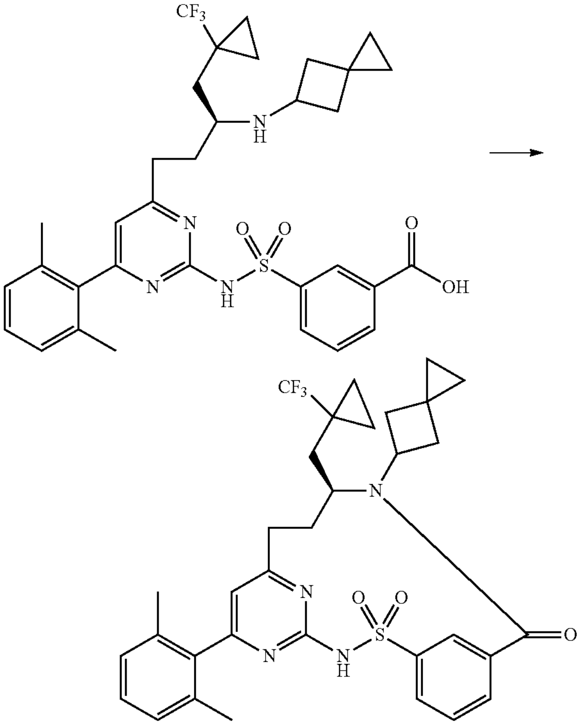

Into a solution of 3-[[4-(2,6-dimethylphenyl)-6-[(3S)-3-(spiro[2.3]hexan-5-ylamino)-4-[1-(trifluoromethyl)cyclopropyl]butyl]pyrimidin-2-yl]sulfamoyl]benzoic acid (hydrochloride salt) (103 mg, 0.1342 mmol) and DIEA (74.200 mg, 0.1 mL, 0.5741 mmol) in anhydrous NMP (5 mL) was added HATU (77 mg, 0.2025 mmol). The reaction was stirred at room temperature for 16 hours. The reaction was quenched with 10% citric acid (10 mL). The product was extracted from the aqueous solution using ethyl acetate (3×10 mL). The combined organic layers were washed with brine (3×10 mL), dried over anhydrous sodium sulfate, and concentrated under vacuum. The residue was purified by silica gel chromatography using 0 to 50% acetone in hexane. The corrected fractions were combined and concentrated under vacuum. The residue was further purified by reverse phase HPLC using 0 to 100% acetonitrile in water (buffered with 0.1% TFA) to furnish (11S)-6-(2,6-dimethylphenyl)-2,2-dioxo-12-spiro[2.3]hexan-5-yl-11-[[1-(trifluoro methyl) cyclopropyl]methyl]-2λ$^6$-thia-3,5,12,19-tetrazatricyclo[12.3.1.14,8]nonadeca-1(18),4(19),5,7,14,16-hexaen-13-one (19.1 mg, 22%) as a white solid. $^1$H NMR (500 MHz, DMSO-$d_6$) δ 11.73 (s, 1H), 8.34 (t, J=1.8 Hz, 1H), 7.93 (d, J=7.1 Hz, 1H), 7.73-7.61 (m, 2H), 7.21 (t, J=7.6 Hz, 1H), 7.09 (d, J=7.6 Hz, 2H), 6.99 (s, 1H), 4.17 (p, J=8.7 Hz, 1H), 3.51 (t, J=9.1 Hz, 2H), 3.30 (t, J=9.4 Hz, 1H), 2.97 (dt, J=25.9, 13.0 Hz, 2H), 2.47 (s, 1H), 2.14-2.02 (m, 2H), 2.02-1.95 (m, 2H), 1.92 (s, 6H), 1.49 (dd, J=16.2, 9.4 Hz, 1H), 0.81-0.72 (m, 1H), 0.64 (q, J=7.1, 5.8 Hz, 2H), 0.54-0.33 (m, 5H). ESI-MS m/z calc. 624.2382, found 625.4 $(M+1)^+$; Retention time: 2.57 minutes; LC method W.

Example 8: Preparation of Compound 8

Step 1: 3-[[4-[(3S)-3-[[2-(tert-Butoxycarbonylamino)spiro[3.3]heptan-6-yl]amino]-5-methyl-hexyl]-6-(2,6-dimethylphenyl)pyrimidin-2-yl]sulfamoyl]benzoic acid

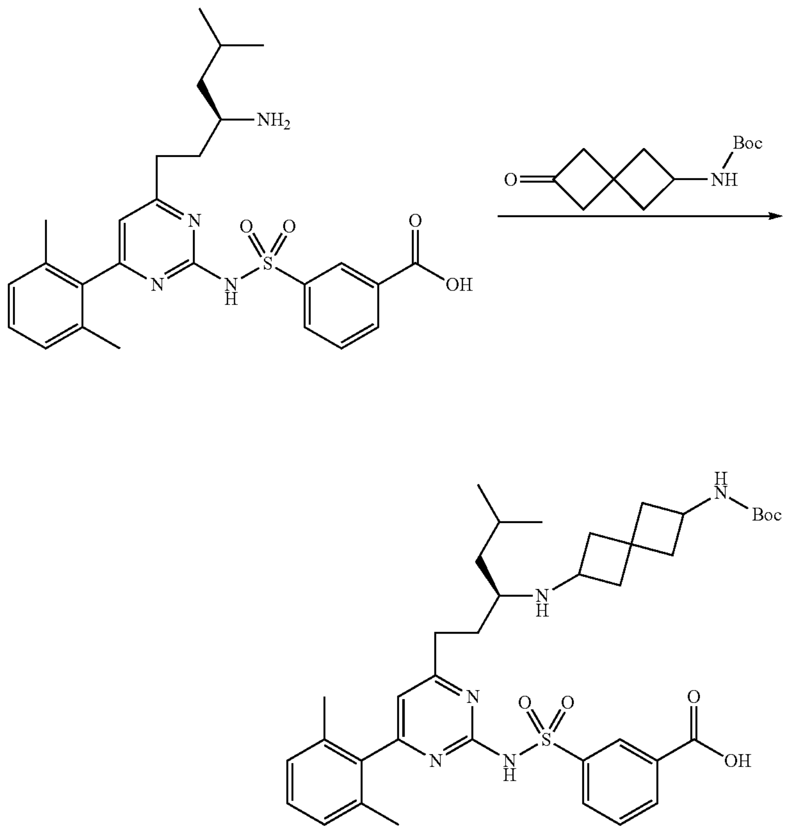

Into a solution of 3-[[4-[(3S)-3-amino-5-methyl-hexyl]-6-(2,6-dimethylphenyl)pyrimidin-2-yl]sulfamoyl]benzoic acid (hydrochloride salt) (302 mg, 0.5665 mmol) and tert-butyl N-(2-oxospiro[3.3]heptan-6-yl)carbamate (207 mg, 0.9188 mmol) in DCM (6 mL) was added sodium triacetoxyborohydride (300 mg, 1.4155 mmol). The reaction was stirred at room temperature for 16 hours. LCMS indicated starting material was not fully consumed. Another batch of tert-butyl N-(2-oxospiro[3.3]heptan-6-yl)carbamate (207 mg, 0.9188 mmol) and sodium triacetoxyborohydride (300 mg, 1.4155 mmol) was added. The reaction was stirred for another 8 hours, and then it was poured into 10% citric acid (aq.) (30 mL). The reaction was extracted with DCM (3x30 mL). The combined organic layers were washed with brine (30 mL), dried over anhydrous sodium sulfate, and concentrated under vacuum. The residue was purified by silica gel chromatography using 0 to 10% methanol in DCM to furnish 3-[[4-[(3S)-3-[[2-(tert-butoxycarbonylamino)spiro[3.3]heptan-6-yl]amino]-5-methyl-hexyl]-6-(2,6-dimethylphenyl)pyrimidin-2-yl]sulfamoyl]benzoic acid (331 mg, 83%) as a white solid. ESI-MS m/z calc. 705.356, found 706.4 $(M+1)^+$; Retention time: 5.53 minutes; LC method S.

Step 2: tert-Butyl N-[2-[(11S)-6-(2,6-dimethylphenyl)-11-isobutyl-2,2,13-trioxo-2 λ6-thia-3,5,12,19-tetrazatricyclo[12.3.1.14,8]nonadeca-1(18),4(19),5,7,14,16-hexaen-12-yl]spiro[3.3]heptan-6-yl]carbamate

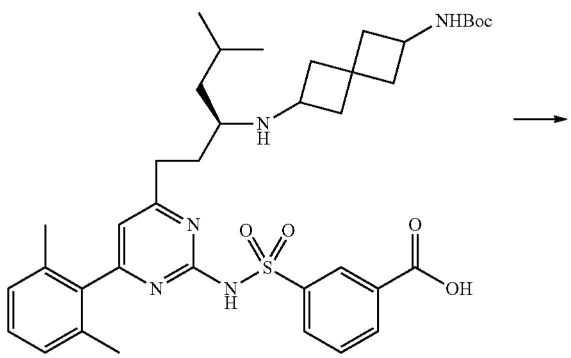

-continued

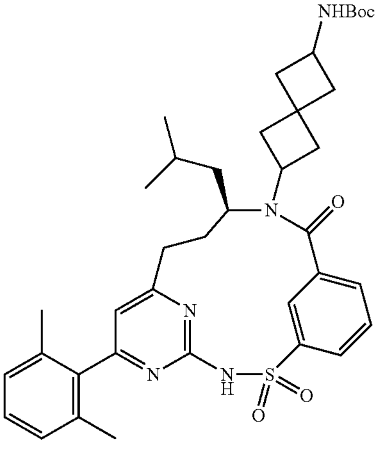

Into a solution of 3-[[4-[(3S)-3-[[2-(tert-butoxycarbonylamino)spiro[3.3]heptan-6-yl]amino]-5-methyl-hexyl]-6-(2,6-dimethylphenyl)pyrimidin-2-yl]sulfamoyl]benzoic acid (386 mg, 0.5468 mmol) in NMP (20 mL) was added DIEA (296.80 mg, 0.4 mL, 2.2964 mmol) and HATU (312 mg, 0.8206 mmol). The reaction was stirred at room temperature for 2 hours. The reaction was poured into a 10% aqueous citric acid solution (30 mL), and diluted with ethyl acetate (30 mL). Two layers were separated and the aqueous layer was extracted with ethyl acetate (2×30 mL). The combined organic layers were washed with brine (3×30 mL), dried over anhydrous sodium sulfate, and concentrated under vacuum. The residue was purified by silica gel chromatography using 0 to 35% acetone in hexane to furnish tert-butyl N-[2-[(11S)-6-(2,6-dimethylphenyl)-11-isobutyl-2,2,13-trioxo-2λ$^6$-thia-3,5,12,19-tetrazatricyclo[12.3.1.14,8]nonadeca-1(18),4(19),5,7,14,16-hexaen-12-yl]spiro[3.3]heptan-6-yl]carbamate (331 mg, 88%) as a white solid. ESI-MS m/z calc. 687.34546, found 688.6 (M+1)$^+$; Retention time: 7.02 minutes; LC method S.

Step 3: (11S)-12-(6-Aminospiro[3.3]heptan-2-yl)-6-(2,6-dimethylphenyl)-11-isobutyl-2,2-dioxo-2 λ6-thia-3,5,12,19-tetrazatricyclo[12.3.1.14,8]nonadeca-1(18),4(19),5,7,14,16-hexaen-13-one

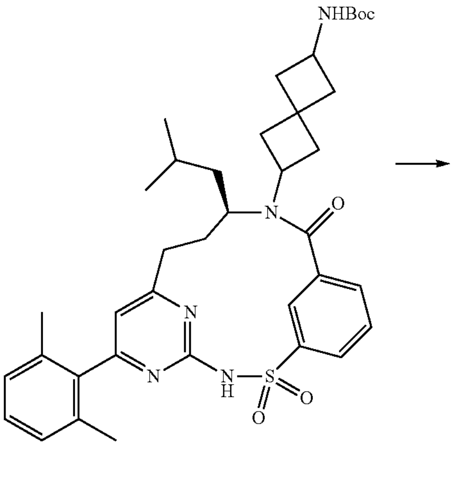

-continued

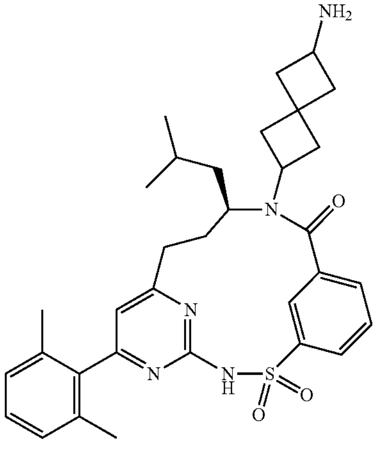

Into a solution of tert-butyl N-[2-[(11S)-6-(2,6-dimethylphenyl)-11-isobutyl-2,2,13-trioxo-2λ$^6$-thia-3,5,12,19-tetrazatricyclo[12.3.1.14,8]nonadeca-1(18),4(19),5,7,14,16-hexaen-12-yl]spiro[3.3]heptan-6-yl]carbamate (331 mg, 0.4812 mmol) in DCM (5 mL) was added HCl (5 mL of 4 M, 20.000 mmol) in dioxane at 0° C. The reaction was stirred at room temperature for 3 hours. All volatiles were removed under vacuum to furnish (11S)-12-(6-aminospiro[3.3]heptan-2-yl)-6-(2,6-dimethyl phenyl)-11-isobutyl-2,2-dioxo-2λ$^6$-thia-3,5,12,19-tetrazatricyclo[12.3.1.14,8]nonadeca-1(18),4(19),5,7,14,16-hexaen-13-one (hydrochloride salt) (402 mg, 134%) as a clear oil. ESI-MS m/z calc. 587.293, found 588.1 (M+1)$^+$; Retention time: 4.92 minutes; LC method S.

Step 4: (11S)-12-[2-(Dimethylamino)spiro[3.3]heptan-6-yl]-6-(2,6-dimethylphenyl)-11-isobutyl-2,2-dioxo-2 λ6-thia-3,5,12,19-tetrazatricyclo[12.3.1.14,8]nonadeca-1(18),4(19),5,7,14,16-hexaen-13-one (Compound 8)

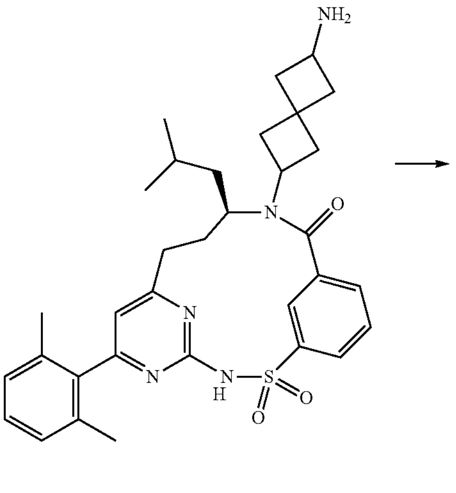

-continued

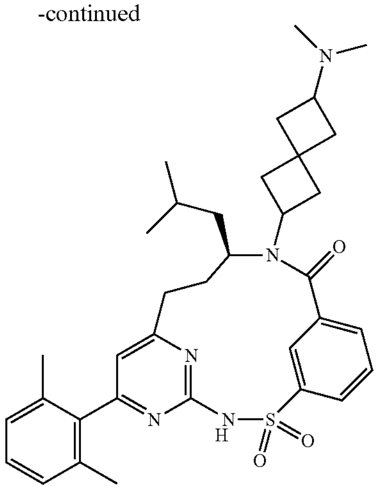

Into a solution of (11S)-12-(6-aminospiro[3.3]heptan-2-yl)-6-(2,6-dimethylphenyl)-11-isobutyl-2,2-dioxo-2λ$^6$-thia-3,5,12,19-tetrazatricyclo[12.3.1.14,8] nonadeca-1(18),4(19),5,7,14,16-hexaen-13-one (hydrochloride salt) (402 mg, 0.6440 mmol) in formic acid (6 mL) was added formaldehyde (6 mL) (37% aqueous solution). The reaction was stirred at 95° C. for 6 hours. The reaction was diluted with water (10 mL) and extracted with chloroform (3×30 mL).

The combined chloroform layers were concentrated under vacuum and purified by reverse phase HPLC using 0 to 100% acetonitrile in water (buffered with 0.1% HCl). The correct fractions were combined and further purified by silica gel chromatography using 0 to 10% methanol in chloroform to furnish (11S)-12-[2-(dimethylamino)spiro[3.3]heptan-6-yl]-6-(2,6-dimethylphenyl)-11-isobutyl-2,2-dioxo-2λ$^6$-thia-3,5,12,19-tetrazatricyclo[12.3.1.14,8]nonadeca-1(18),4(19),5,7,14,16-hexaen-13-one (hydrochloride salt) (11.3 mg, 3%) as a white solid. $^1$H NMR (500 MHz, DMSO-$d_6$) δ 8.29 (s, 1H), 7.97-7.92 (m, 1H), 7.69 (d, J=4.7 Hz, 2H), 7.21 (t, J=7.7 Hz, 1H), 7.09 (d, J=7.6 Hz, 2H), 7.02 (s, 1H), 3.99-3.90 (m, 1H), 3.51 (t, J=8.3 Hz, 1H), 3.06 (m, 5H), 2.99 (s, 1H), 2.81 (t, J=14.6 Hz, 1H), 2.58 (m, 7H), 2.48-2.40 (m, 1H), 2.30 (t, J=7.2 Hz, 4H), 2.08 (d, J=11.6 Hz, 1H), 1.87 (s, 6H), 1.44 (dt, J=25.1, 12.8 Hz, 1H), 1.03 (t, J=12.4 Hz, 1H), 0.75-0.66 (m, 3H), −0.06 (s, 3H). ESI-MS m/z calc. 615.32434, found 616.4 (M+1)$^+$; Retention time: 2.21 minutes; LC method W.

Example 9: Preparation of Compound 9

Step 1: 3-[[4-[(3S)-3-[(7-tert-Butoxycarbonyl-7-azaspiro[3.5]nonan-2-yl)amino]-5-methyl-hexyl]-6-(2,6-dimethylphenyl)pyrimidin-2-yl]sulfamoyl]benzoic acid

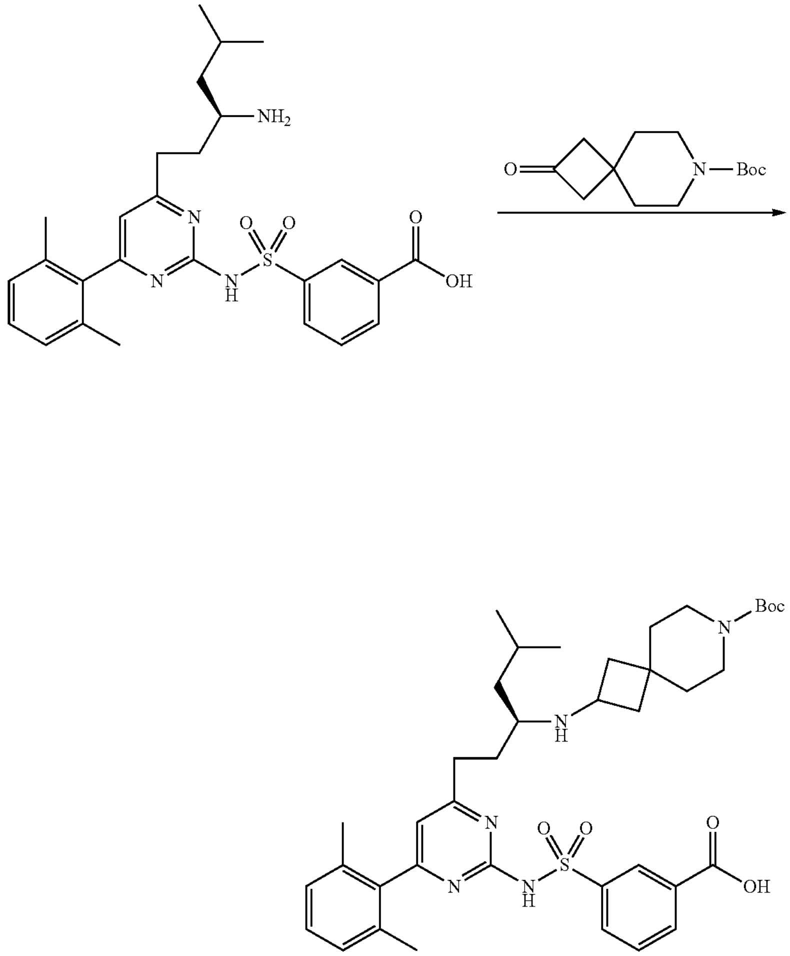

Into a solution of 3-[[4-[(3S)-3-amino-5-methyl-hexyl]-6-(2,6-dimethylphenyl)pyrimidin-2-yl]sulfamoyl]benzoic acid (hydrochloride salt) (147 mg, 0.2758 mmol) and tert-butyl 2-oxo-7-azaspiro[3.5]nonane-7-carboxylate (105 mg, 0.4388 mmol) in DCM (2.5 mL) was added sodium triacetoxyborohydride (122 mg, 0.5756 mmol). The reaction mixture was stirred at room temperature for 2 days. LCMS indicated there is still unreacted starting material. Another portion of tert-butyl 2-oxo-7-azaspiro[3.5]nonane-7-carboxylate (105 mg, 0.4388 mmol) and sodium triacetoxyborohydride (122 mg, 0.5756 mmol) were added. The reaction was stirred at room temperature for another 24 hours. The reaction was concentrated under vacuum. The residue was purified by silica gel chromatography using 0 to 10% methanol in dichloromethane to furnish 3-[[4-[(3S)-3-[(7-tert-butoxycarbonyl-7-azaspiro[3.5]nonan-2-yl)amino]-5-methyl-hexyl]-6-(2,6-dimethylphenyl)pyrimidin-2-yl]sulfamoyl]benzoic acid (143 mg, 71%) as a light-yellow solid. ESI-MS m/z calc. 719.37164, found 720.5 $(M+1)^+$; Retention time: 5.62 minutes; LC method S.

Step 2: tert-Butyl 2-[(11S)-6-(2,6-dimethylphenyl)-11-isobutyl-2,2,13-trioxo-2 λ6-thia-3,5,12,19-tetrazatricyclo[12.3.1.14,8]nonadeca-1(18),4(19),5,7,14,16-hexaen-12-yl]-7-azaspiro[3.5]nonane-7-carboxylate

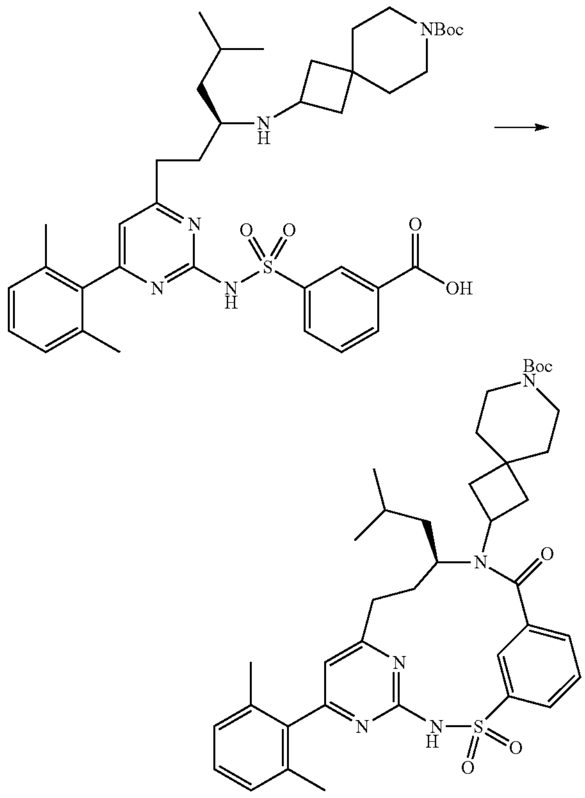

Into a solution of 3-[[4-[(3S)-3-[(7-tert-butoxycarbonyl-7-azaspiro[3.5]nonan-2-yl)amino]-5-methyl-hexyl]-6-(2,6-dimethylphenyl)pyrimidin-2-yl]sulfamoyl]benzoic acid (143 mg, 0.1947 mmol) in anhydrous NMP (2 mL) was added DIEA (103.88 mg, 0.14 mL, 0.8038 mmol) and HATU (111 mg, 0.2919 mmol). The reaction was stirred at room temperature for 2 hours. The reaction was poured into a 10% citric acid aqueous solution (15 mL), and extracted with ethyl acetate (3×15 mL). The combined organic layers were washed with brine (3×10 mL), dried over anhydrous sodium sulfate, and concentrated under vacuum. The residue was purified by silica gel chromatography using 0 to 50% acetone in hexane to furnish tert-butyl 2-[(11S)-6-(2,6-dimethylphenyl)-11-isobutyl-2,2,13-trioxo-2$\lambda^6$-thia-3,5,12,19-tetrazatricyclo[12.3.1.14,8]nonadeca-1(18),4(19),5,7,14,16-hexaen-12-yl]-7-azaspiro[3.5]nonane-7-carboxylate (95 mg, 68%) as a clear gel. ESI-MS m/z calc. 701.3611, found 702.5 $(M+1)^+$; Retention time: 7.49 minutes; LC method S.

Step 3: (11S)-12-(7-Azaspiro[3.5]nonan-2-yl)-6-(2,6-dimethylphenyl)-11-isobutyl-2,2-dioxo-2%6-thia-3,5,12,19-tetrazatricyclo[12.3.1.14,8]nonadeca-1(18),4(19),5,7,14,16-hexaen-13-one

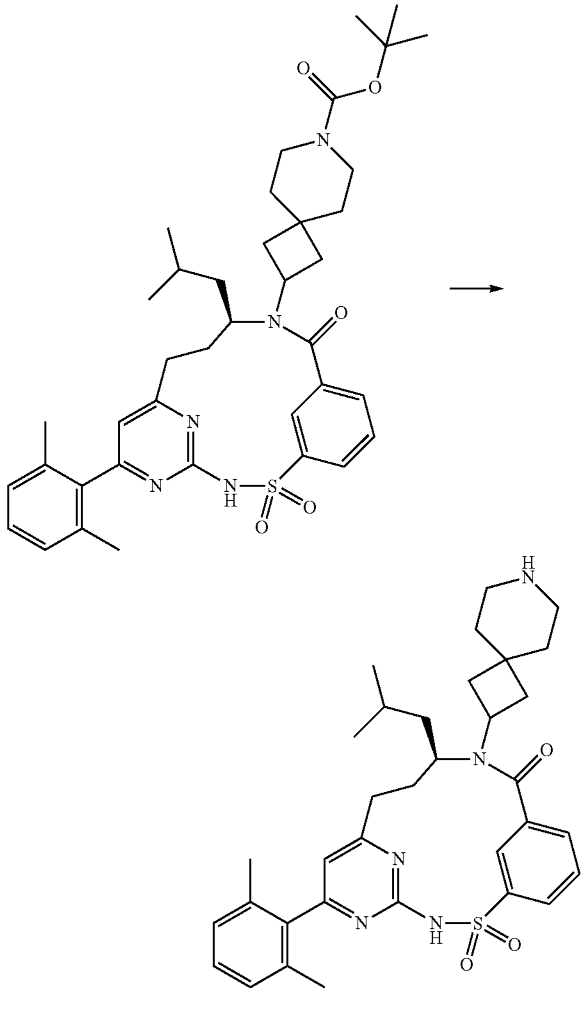

Into a solution of tert-butyl 2-[(11S)-6-(2,6-dimethylphenyl)-11-isobutyl-2,2,13-trioxo-2$\lambda^6$-thia-3,5,12,19-tetrazatricyclo[12.3.1.14,8]nonadeca-1(18),4(19),5,7,14,16-hexaen-12-yl]-7-azaspiro[3.5]nonane-7-carboxylate (95 mg, 0.1326 mmol) in anhydrous DCM (2.5 mL) was added HCl (2.5 mL of 4 M, 10.000 mmol) in dioxane at 0° C. The reaction mixture was stirred at room temperature for 3 hours. All the volatiles were removed under vacuum to furnish (11S)-12-

(7-azaspiro[3.5]nonan-2-yl)-6-(2,6-dimethylphenyl)-11-isobutyl-2,2-dioxo-2λ$^6$-thia-3,5,12,19-tetrazatricyclo[12.3.1.14,8]nonadeca-1(18),4(19),5,7,14,16-hexaen-13-one (hydrochloride salt) (80 mg, 95%) as a white solid. ESI-MS m/z calc. 601.30865, found 602.3 $(M+1)^+$; Retention time: 5.0 minutes; LC method S.

Step 4: (11S)-6-(2,6-Dimethylphenyl)-11-isobutyl-12-[7-(2-methoxyethyl)-7-azaspiro[3.5]nonan-2-yl]-2,2-dioxo-2λ6-thia-3,5,12,19-tetrazatricyclo[12.3.1.14,8]nonadeca-1(18),4(19),5,7,14,16-hexaen-13-one (Compound 9)

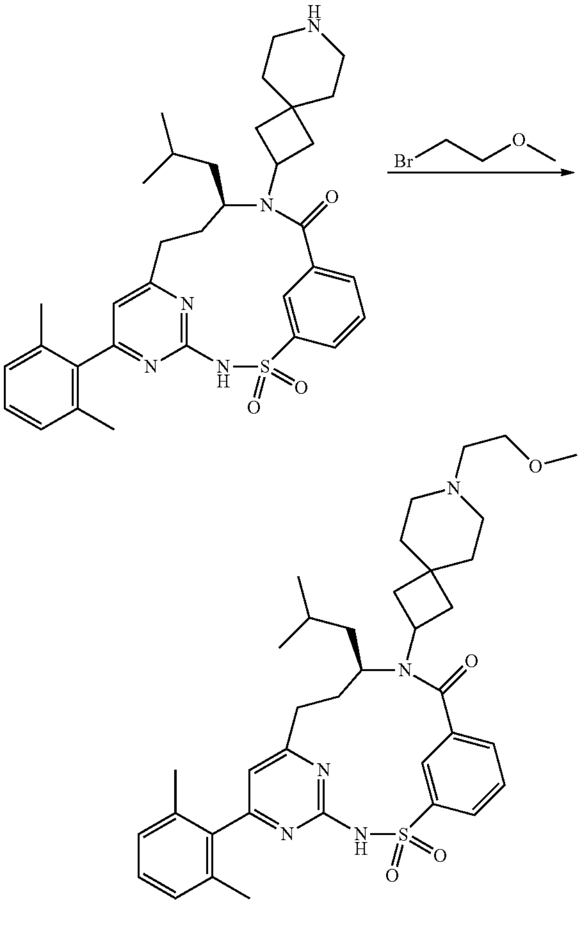

Into a solution of (11S)-12-(7-azaspiro[3.5]nonan-2-yl)-6-(2,6-dimethylphenyl)-11-isobutyl-2,2-dioxo-2λ$^6$-thia-3,5,12,19-tetrazatricyclo[12.3.1.14,8]nonadeca-1(18),4(19),5,7,14,16-hexaen-13-one (hydrochloride salt) (80 mg, 0.1253 mmol) and triethylamine (87.120 mg, 0.12 mL, 0.8610 mmol) in acetonitrile (1.2 mL) was added 1-bromo-2-methoxy-ethane (25.137 mg, 18 μL, 0.1718 mmol). The reaction mixture was heated at 55° C. for 20 hours. The reaction was cooled to room temperature and then it was quenched with 1 N HCl (aq.) (10 mL). The product was extracted with DCM (3×10 mL). The combined organic layers were washed with brine (10 mL), dried over anhydrous sodium sulfate, and concentrated under vacuum. The residue was dissolved in DMSO (2 mL) and purified by reverse phase HPLC using 0 to 100% acetonitrile in water (buffered with 0.1% HCl) to furnish (11S)-6-(2,6-dimethylphenyl)-11-isobutyl-12-[7-(2-methoxyethyl)-7-azaspiro[3.5]nonan-2-yl]-2,2-dioxo-2λ$^6$-thia-3,5,12,19-tetrazatricyclo[12.3.1.14,8]nonadeca-1(18),4(19),5,7,14,16-hexaen-13-one (hydrochloride salt) (23 mg, 25%) as a white solid. $^1H$ NMR (500 MHz, DMSO-$d_6$) δ 8.31 (s, 1H), 8.03-7.90 (m, 1H), 7.70 (d, J=4.7 Hz, 2H), 7.21 (t, J=7.6 Hz, 1H), 7.16-6.99 (m, 3H), 4.07 (q, J=8.9 Hz, 1H), 3.70 (t, J=5.0 Hz, 2H), 3.46 (s, 2H), 3.32 (s, 3H), 3.28 (s, 1H), 3.24 (d, J=10.3 Hz, 2H), 3.11-2.72 (m, 6H), 2.55 (d, J=2.2 Hz, 1H), 2.28-1.99 (m, 5H), 1.88 (s, 9H), 1.45 (t, J=12.7 Hz, 1H), 1.19 (s, 1H), 1.03 (t, J=11.2 Hz, 1H), 0.70 (d, J=6.6 Hz, 3H), 0.02 (m, 3H). ESI-MS m/z calc. 659.3505, found 660.5 $(M+1)^+$; Retention time: 2.2 minutes; LC method W.

Example 10: Preparation of Compound 10

Step 1: Methyl 3-[[4-(2,6-dimethylphenyl)-6-[(E)-3-hydroxy-1-methyl-prop-1-enyl]pyrimidin-2-yl]-(methoxymethyl)sulfamoyl]benzoate

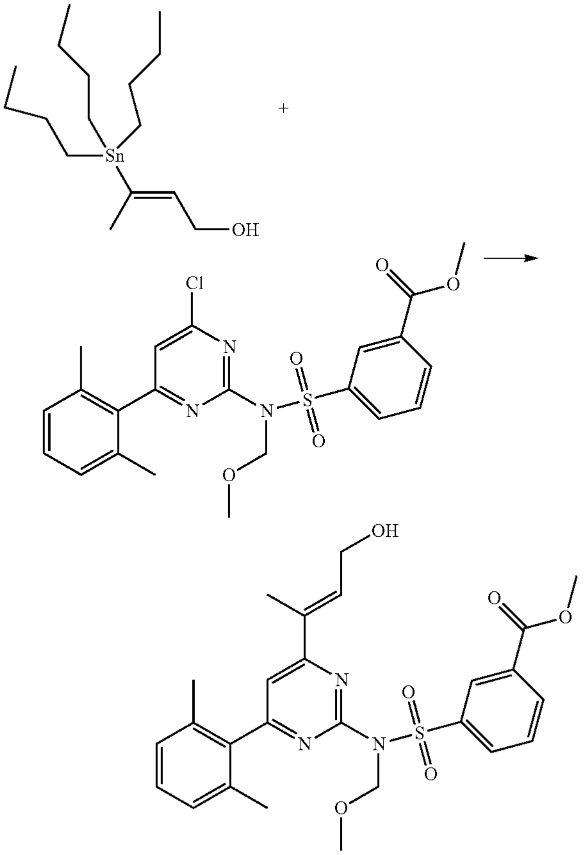

To a solution of (E)-3-tributylstannylbut-2-en-1-ol (4.85 g, 13.429 mmol) and methyl 3-[[4-chloro-6-(2,6-dimethylphenyl)pyrimidin-2-yl]-(methoxymethyl)sulfamoyl]benzoate (6.38 g, 13.405 mmol) in anhydrous NMP (130 mL) were added CuI (258 mg, 1.3547 mmol) and $Pd(PPh_3)_4$ (776 mg, 0.6715 mmol). The solution was purged with argon for 5 minutes, then heated at 90° C. under argon for 23 hours. The reaction solution was cooled to ambient temperature, diluted with ether (700 mL), washed with water (100 mL), aqueous KF solution (10%, 100 mL), and brine (100 mL). Organic layer was dried over anhydrous sodium sulfate, filtered, and concentrated under reduced pressure. Crude product obtained was purified by flash chromatography (loaded with DCM) (120 g silica gel, eluting 0 to 50% ethyl acetate in hexane) to afford methyl 3-[[4-(2,6-dimethylphenyl)-6-[(E)-3-hydroxy-1-methyl-prop-1-enyl]pyrimidin-2-yl]-(methoxymethyl)sulfamoyl]benzoate (7.4 g, 91%) as a brown liquid. ESI-MS m/z calc. 511.1777, found 512.3 $(M+1)^+$; Retention time: 5.86 minutes; LC method S.

Step 2: Methyl 3-[[4-(2,6-dimethylphenyl)-6-(3-hydroxy-1-methyl-propyl)pyrimidin-2-yl]-(methoxymethyl)sulfamoyl]benzoate

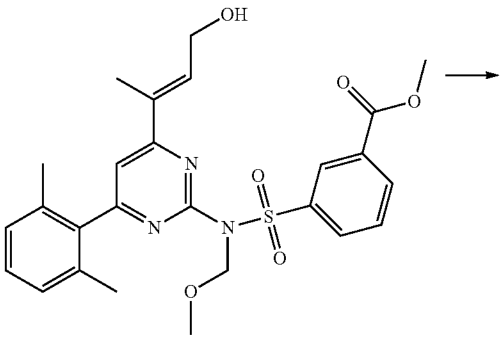

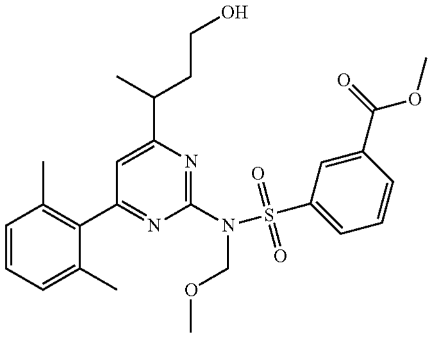

To a solution of methyl 3-[[4-(2,6-dimethylphenyl)-6-[(E)-3-hydroxy-1-methyl-prop-1-enyl]pyrimidin-2-yl]-(methoxymethyl)sulfamoyl]benzoate in MeOH (10 mL) in a hydrogenation vessel was added 10% Pd/C (36 mg, 0.3383 mmol). The resulting solution was hydrogenated in Parr-Shaker under 65 psi for 19 hours. The reaction solution was filtered through Celite, washed with methanol and dichloromethane. Filtrate was concentrated under reduced pressure. Residue obtained was added toluene (3×15 mL), and toluene was removed under reduced pressure to remove trace amount of methanol to afford methyl 3-[[4-(2,6-dimethylphenyl)-6-(3-hydroxy-1-methyl-propyl)pyrimidin-2-yl]-(methoxymethyl)sulfamoyl]benzoate (598 mg, 88%) as a white foam solid. ESI-MS m/z calc. 513.19336, found 514.2 $(M+1)^+$; Retention time: 5.72 minutes; LC method S.

Step 3: Methyl 3-[[4-(3-azido-1-methyl-propyl)-6-(2,6-dimethylphenyl)pyrimidin-2-yl]-(methoxymethyl)sulfamoyl]benzoate

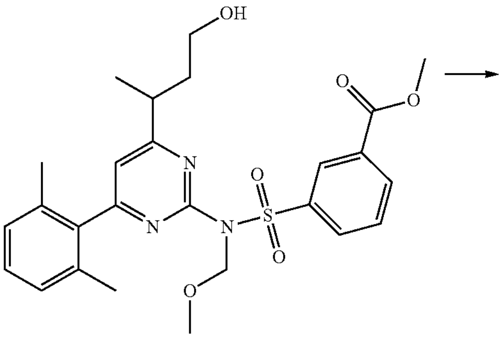

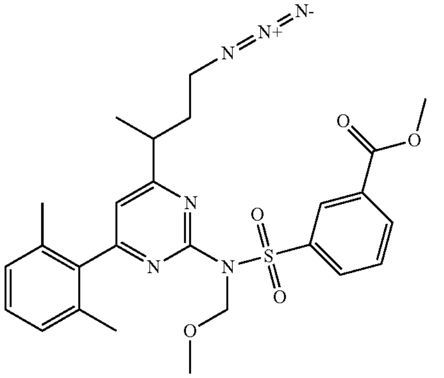

To a solution of methyl 3-[[4-(2,6-dimethylphenyl)-6-(3-hydroxy-1-methyl-propyl)pyrimidin-2-yl]-(methoxymethyl)sulfamoyl]benzoate (1.216 g, 2.3676 mmol) in anhydrous toluene (8 mL) at 0° C. was added DBU (1.3234 g, 1.3 mL, 8.6930 mmol) followed by DPPA (1.5324 g, 1.2 mL, 5.5683 mmol). The resulting solution was then warmed up to ambient temperature and stirred for 2 hours, then heated at 80° C. for 2.5 hours. The reaction solution was cooled to ambient temperature and purified by flash chromatography (load with DCM) (40 g silica gel, eluting 0 to 20% ethyl acetate in hexane) to afford methyl 3-[[4-(3-azido-1-methyl-propyl)-6-(2,6-dimethylphenyl)pyrimidin-2-yl]-(methoxymethyl)sulfamoyl]benzoate (1.012 g, 79%) as a colorless sticky oil. ESI-MS m/z calc. 538.1998, found 539.2 $(M+1)^+$; Retention time: 7.04 minutes; LC method S.

Step 4: Methyl 3-[[4-[3-(tert-butoxycarbonylamino)-1-methyl-propyl]-6-(2,6-dimethylphenyl)pyrimidin-2-yl]-(methoxymethyl)sulfamoyl]benzoate

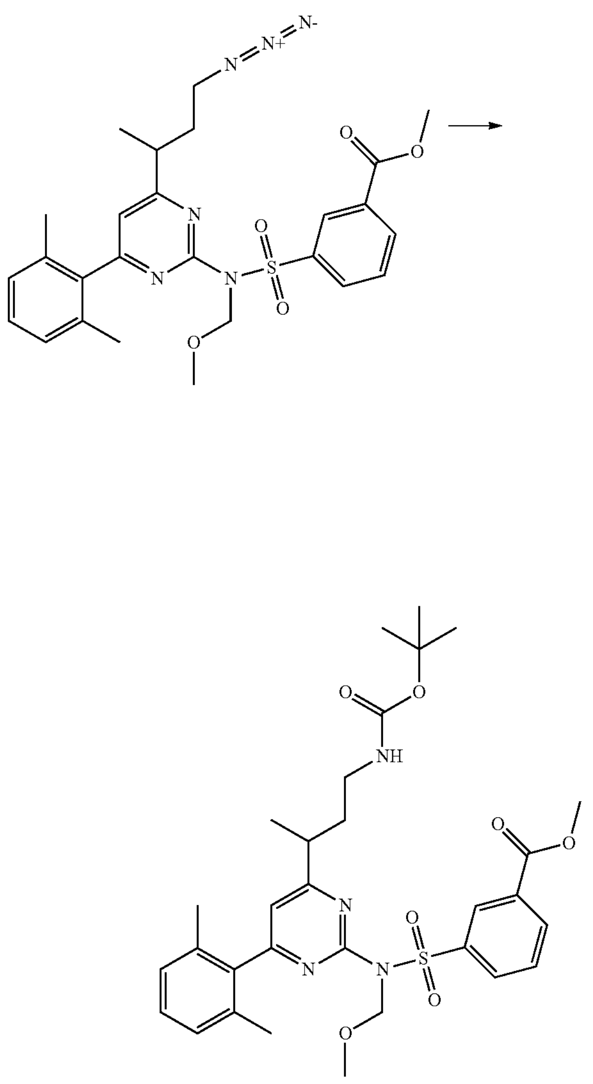

To a solution of methyl 3-[[4-(3-azido-1-methyl-propyl)-6-(2,6-dimethylphenyl)pyrimidin-2-yl]-(methoxymethyl)sulfamoyl]benzoate (380 mg, 0.7055 mmol) in MeOH (20 mL) was added Boc anhydride (540 mg, 2.4743 mmol) followed by 10% Pd/C (180 mg, 1.6914 mmol). The resulting solution was then hydrogenated under 60 PSI in a Parr-Shaker for 5 hours. The reaction solution was filtered through Celite, washed with methanol, and the filtrate was concentrated under reduced pressure. Crude product obtained was purified by flash chromatography (loaded with DCM) (40 g silica gel, eluting 0 to 25% ethyl acetate in hexane) to afford methyl 3-[[4-[3-(tert-butoxycarbonylamino)-1-methyl-propyl]-6-(2,6-dimethylphenyl)pyrimidin-2-yl]-(methoxymethyl)sulfamoyl]benzoate (399 mg, 90%) as a colorless sticky oil. ESI-MS m/z calc. 612.2618, found 613.3 $(M+1)^+$; Retention time: 6.98 minutes; LC method S.

Step 5: Methyl 3-[[4-(3-amino-1-methyl-propyl)-6-(2,6-dimethylphenyl)pyrimidin-2-yl]sulfamoyl]benzoate

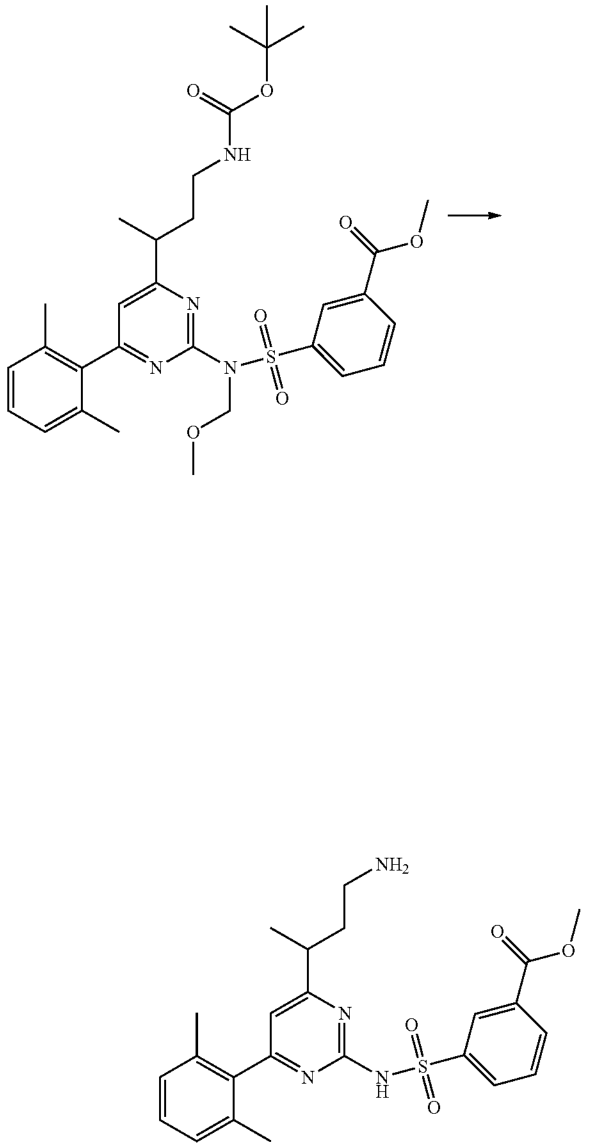

To a round-bottom flask containing methyl 3-[[4-[3-(tert-butoxycarbonylamino)-1-methyl-propyl]-6-(2,6-dimethylphenyl)pyrimidin-2-yl]-(methoxymethyl)sulfamoyl]benzoate (2.278 g, 3.8048 mmol) was added HCl (30 mL of 4 M, 120.00 mmol) in 1,4-dioxane. The resulting solution was stirred at ambient temperature for 1 hour. All solvents were removed under reduced pressure. Then dichloromethane and hexane were added. Solvents were removed. This process was repeated twice. Crude product was high vacuumed to afford crude product methyl 3-[[4-(3-amino-1-methyl-propyl)-6-(2,6-dimethylphenyl)pyrimidin-2-yl]sulfamoyl]benzoate (hydrochloride salt) (1.946 g, 100%) as a pale yellow solid. ESI-MS m z calc. 468.18314, found 469.4 $(M+1)^+$; Retention time: 3.83 minutes; LC method S.

Step 6: Methyl 3-[[4-[3-(tert-butoxycarbonylamino)-1-methyl-propyl]-6-(2,6-dimethylphenyl)pyrimidin-2-yl]sulfamoyl]benzoate

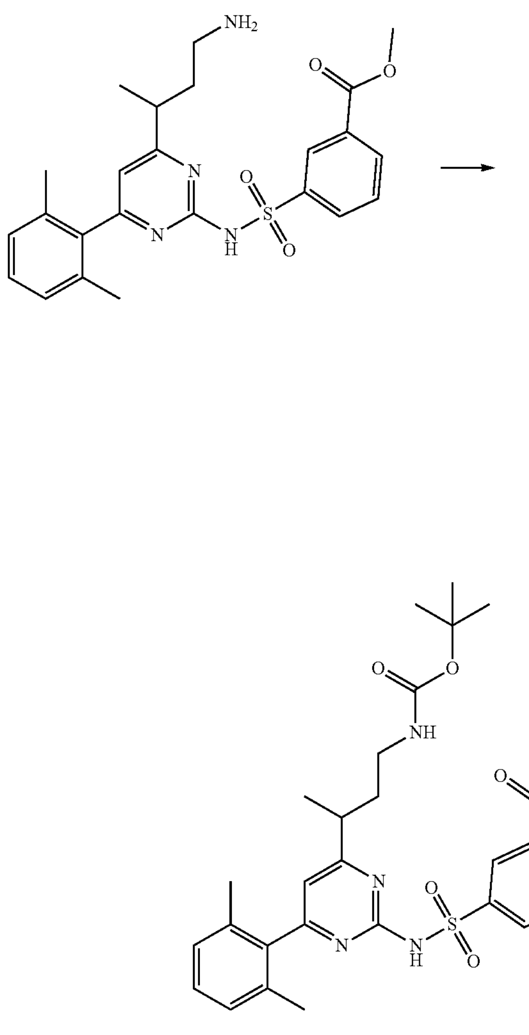

To a solution of methyl 3-[[4-(3-amino-1-methyl-propyl)-6-(2,6-dimethylphenyl)pyrimidin-2-yl]sulfamoyl]benzoate (hydrochloride salt) (1.946 g, 3.8532 mmol) in the mixture of THF (20 mL) and saturated sodium bicarbonate aqueous solution (20 mL) was added Boc anhydride (1.09 g, 1.1474 mL, 4.9943 mmol). The resulting solution was stirred at ambient temperature for 2 days. The reaction solution was carefully acidified to pH=5 using HCl aqueous solution (6 N). The reaction solution was extracted with ethyl acetate (3x50 mL). Organic layers were combined and dried over anhydrous sodium sulfate, filtered, and concentrated under reduced pressure. Crude product obtained was purified by flash chromatography (load with DCM) (80 g silica gel, eluting 0 to 50% ethyl acetate in hexane) to afford methyl 3-[[4-[3-(tert-butoxycarbonylamino)-1-methyl-propyl]-6-(2,6-dimethylphenyl)pyrimidin-2-yl]sulfamoyl]benzoate (1.947 g, 80%) as a white solid. ESI-MS m/z calc. 568.23553, found 569.6 $(M+1)^+$; Retention time: 6.82 minutes; LC method S.

Step 7: 3-[[4-[3-(tert-Butoxycarbonylamino)-1-methyl-propyl]-6-(2,6-dimethylphenyl)pyrimidin-2-yl]sulfamoyl]benzoic acid

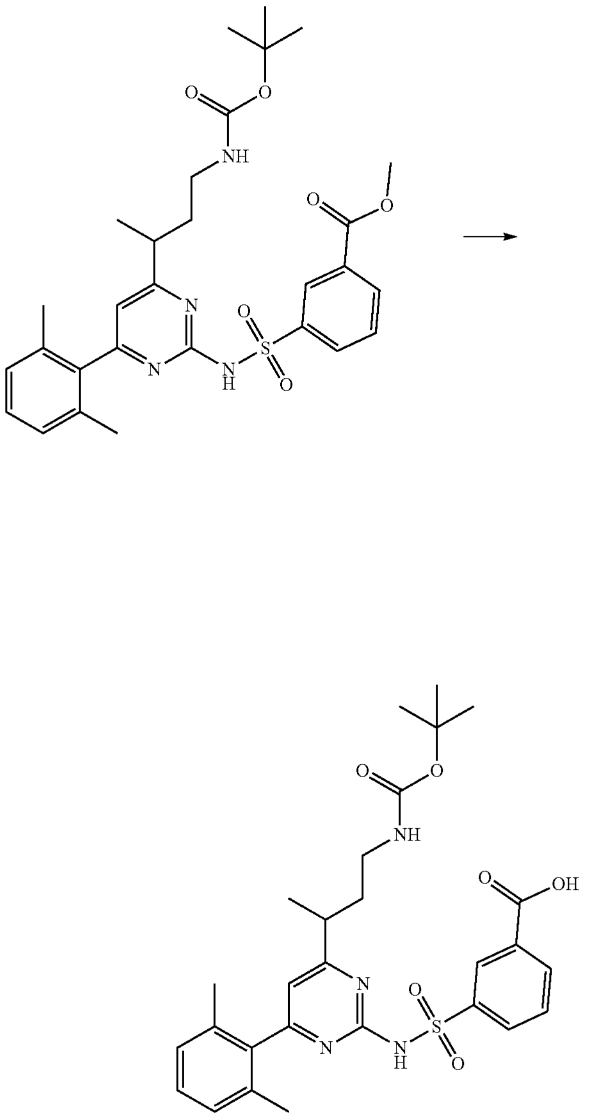

To a solution of methyl 3-[[4-[3-(tert-butoxycarbonylamino)-1-methyl-propyl]-6-(2,6-dimethylphenyl)pyrimidin-2-yl]sulfamoyl]benzoate (1.947 g, 3.2525 mmol) in the mixture of THF (20 mL) and MeOH (5 mL) was added aqueous solution of NaOH (7 mL of 2 M, 14.000 mmol). The resulting solution was stirred at ambient temperature for 1 hour. The reaction was diluted with ethyl acetate (50 mL), and HCl aqueous solution (30 mL, 1N) was added. Aqueous layer was extracted with ethyl acetate (2x50 mL). Combined organic layer was washed with brine (30 mL), dried over anhydrous sodium sulfate, filtered and concentrated under reduced pressure. Crude product obtained was high vacuumed to afford 3-[[4-[3-(tert-butoxycarbonylamino)-1-methyl-propyl]-6-(2,6-dimethylphenyl)pyrimidin-2-yl]sulfamoyl]benzoic acid (2.225 g, 100%) as a white foam solid which was used directly in next step. ESI-MS m/z calc. 554.2199, found 555.4 $(M+1)^+$; Retention time: 5.25 minutes; LC method S.

Step 8: 3-[[4-(3-Amino-1-methyl-propyl)-6-(2,6-dimethylphenyl)pyrimidin-2-yl]sulfamoyl]benzoic acid

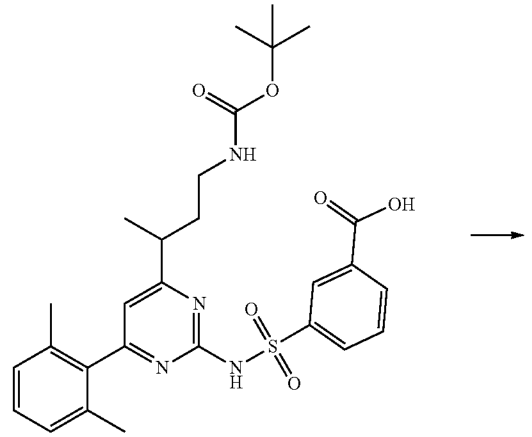

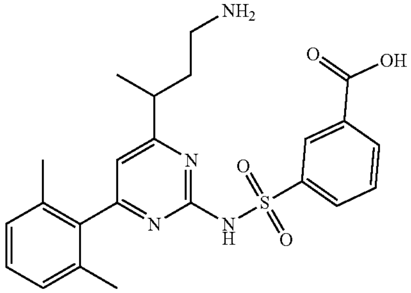

To a round-bottom flask containing 3-[[4-[3-(tert-butoxycarbonylamino)-1-methyl-propyl]-6-(2,6-dimethylphenyl) pyrimidin-2-yl]sulfamoyl]benzoic acid (2.225 g, 3.2493 mmol) was added HCl (25 mL of 4 M, 100.00 mmol) in 1,4-dioxane. The resulting solution was stirred at ambient temperature for 1 hour. All solvents were removed under reduced pressure. Crude product was added to dichloromethane, sonicated, filtered, washed with hexane to afford 3-[[4-(3-amino-1-methyl-propyl)-6-(2,6-dimethylphenyl) pyrimidin-2-yl]sulfamoyl]benzoic acid (hydrochloride salt) (1.569 g, 93%). $^1H$ NMR (500 MHz, DMSO-$d_6$) δ 8.49 (s, 1H), 8.21-8.14 (m, 2H), 8.12-7.87 (m, 3H), 7.71 (t, J=7.8 Hz, 1H), 7.23 (t, J=7.5 Hz, 1H), 7.11 (d, J=7.4 Hz, 2H), 7.03-6.98 (m, 1H), 2.97-2.87 (m, 1H), 2.77-2.58 (m, 2H), 1.89 (m, 7H), 1.84-1.75 (m, 1H), 1.11 (d, J=6.9 Hz, 3H). ESI-MS m/z calc. 454.16748, found 455.2 $(M+1)^+$; Retention time: 1.47 minutes; LC method W.

Step 9: 3-[[4-(2,6-Dimethylphenyl)-6-[3-[(4-methoxy-4-oxo-butyl)amino]-1-methyl-propyl]pyrimidin-2-yl]sulfamoyl]benzoic acid

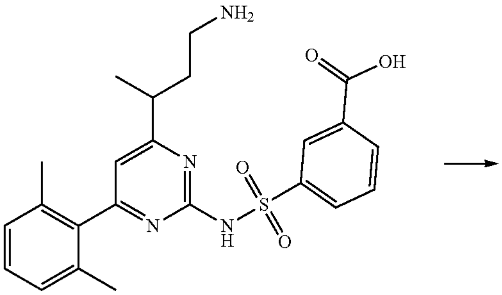

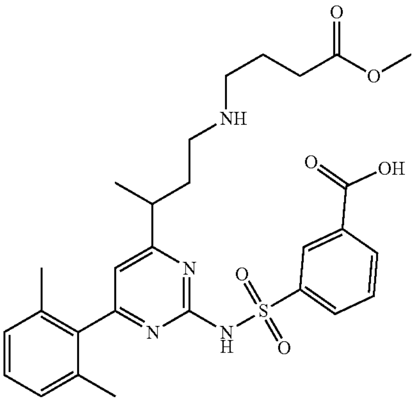

To a solution of 3-[[4-(3-amino-1-methyl-propyl)-6-(2,6-dimethylphenyl)pyrimidin-2-yl]sulfamoyl]benzoic acid (hydrochloride salt) (150 mg, 0.2924 mmol) and 4-oxobutanoic acid methyl ester (40.7 mg, 0.3155 mmol) in anhydrous 1,2-dichloroethane (3 mL) was added DIEA (38.584 mg, 0.052 mL, 0.2985 mmol) followed by sodium triacetoxyborohydride (93 mg, 0.4388 mmol). The resulting solution was stirred at ambient temperature for 19 hours. The reaction was quenched with aqueous HCl solution (1 N, 20 mL) and extracted with chloroform (4×40 mL). Combined organic layer was dried over anhydrous sodium sulfate, filtered and concentrated under reduced pressure. Crude product obtained was purified by flash chromatography (load with DCM) (40 g silica gel, eluting 0 to 8% methanol in DCM) to afford 3-[[4-(2,6-dimethylphenyl)-6-[3-[(4-methoxy-4-oxo-butyl)amino]-1-methyl-propyl]pyrimidin-2-yl]sulfamoyl]benzoic acid (hydrochloride salt) (68 mg, 35%) as a white solid. ESI-MS m/z calc. 554.2199, found 555.3 $(M+1)^+$; Retention time: 3.82 minutes; LC method S.

Step 10: Methyl 4-[6-(2,6-dimethylphenyl)-9-methyl-2,2,13-trioxo-2 λ6-thia-3,5,12,19-tetrazatricyclo[12.3.1.14,8]nonadeca-1(18),4(19),5,7,14,16-hexaen-12-yl]butanoate

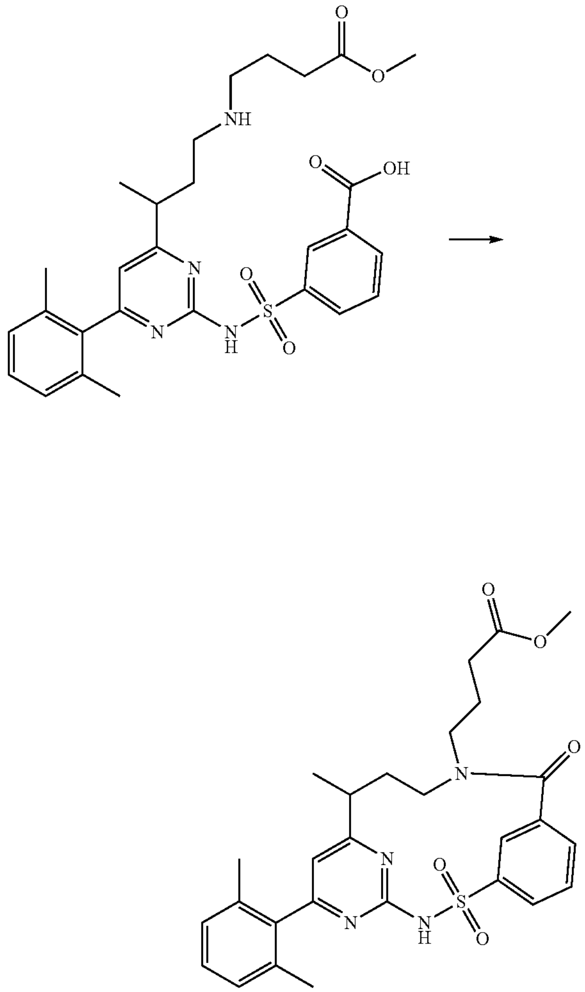

To a solution of HATU (55 mg, 0.1446 mmol) and DIEA (57.134 mg, 0.077 mL, 0.4421 mmol) in anhydrous NMP (3 mL) at ambient temperature was added a solution of 3-[[4-(2,6-dimethylphenyl)-6-[3-[(4-methoxy-4-oxo-butyl)amino]-1-methyl-propyl]pyrimidin-2-yl]sulfamoyl]benzoic acid (68 mg, 0.1103 mmol) in anhydrous NMP (2 mL). The resulting solution was stirred at ambient temperature for 15 hours. The reaction was quenched with aqueous HCl solution (1 mL, 1N) and water (20 mL). Solution was extracted with ethyl acetate (4×30 mL). Combined organic layer was washed with water (2×20 mL), brine (20 mL), dried over anhydrous sodium sulfate, filtered and concentrated under reduced pressure. Crude product obtained was purified by flash chromatography (load with DCM) (25 g silica gel, eluting 0 to 60% ethyl acetate in hexane) to afford methyl 4-[6-(2,6-dimethylphenyl)-9-methyl-2,2,13-trioxo-2λ$^6$-thia-3,5,12,19-tetrazatricyclo[12.3.1.14,8]nonadeca-1(18),4(19),5,7,14,16-hexaen-12-yl]butanoate (53.4 mg, 90%) as a white solid. ESI-MS m/z calc. 536.20935, found 537.1 $(M+1)^+$; Retention time: 5.13 minutes; LC method S.

Step 11: 6-(2,6-Dimethylphenyl)-12-(4-hydroxy-4-methyl-pentyl)-9-methyl-2,2-dioxo-2λ6-thia-3,5,12,19-tetrazatricyclo[12.3.1.14,8]nonadeca-1(18),4(19),5,7,14,16-hexaen-13-one (Compound 10)

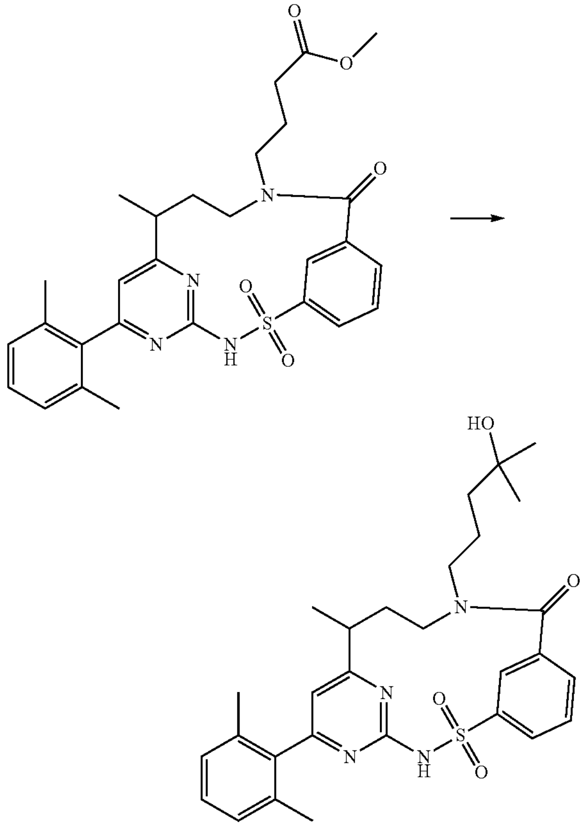

To a stirred solution of methyl 4-[6-(2,6-dimethylphenyl)-9-methyl-2,2,13-trioxo-2λ$^6$-thia-3,5,12,19-tetrazatricyclo[12.3.1.14,8]nonadeca-1(18),4(19),5,7,14,16-hexaen-12-yl]butanoate (53 mg, 0.0988 mmol) in anhydrous THF (2 mL) was added methyl magnesium bromide (0.7 mL of 1.4 M, 0.9800 mmol) solution in THF: toluene(1:3) at 0° C., then the reaction was warmed up to ambient temperature and stirred for 1 hour. The reaction was quenched with saturated ammonium chloride aqueous solution (15 mL) followed by aqueous HCl solution (10 mL). The solution was extracted with ethyl acetate (4×30 mL). Combined organic layer was washed with brine (2×20 mL), dried over anhydrous sodium sulfate, filtered, and concentrated under reduced pressure. Crude product obtained was purified by reverse HPLC (gradient of 20%-85% acetonitrile in water buffered with 0.1% TFA) to afford 6-(2,6-dimethylphenyl)-12-(4-hydroxy-4-methyl-pentyl)-9-methyl-2,2-dioxo-2λ$^6$-thia-3,5,12,19-tetrazatricyclo[12.3.1.14,8]nonadeca-1(18),4(19),5,7,14,16-hexaen-13-one (33 mg, 60%) as a white solid. $^1$H NMR (500 MHz, DMSO-$d_6$) δ 11.70 (s, 1H), 8.41 (d, J=1.9 Hz, 1H), 7.98-7.93 (m, 1H), 7.74-7.65 (m, 2H), 7.21 (t, J=7.6 Hz, 1H), 7.10 (d, J=7.6 Hz, 2H), 6.97 (s, 1H), 3.61-3.52 (m, 1H), 3.35-3.25 (m, 1H), 3.01-2.87 (m, 3H), 2.45-2.36 (m, 1H), 2.25-2.15 (m, 1H), 1.92 (s, 6H), 1.73-1.59 (m, 2H), 1.44-1.31 (m, 2H), 1.25 (d, J=7.0 Hz, 3H), 1.11 (s, 6H). ESI-MS m/z calc. 536.2457, found 537.7 $(M+1)^+$; Retention time: 2.23 minutes; LC method W.

Example 11: Preparation of Compound 11

Step 1: 3-[[4-(2,6-Dimethylphenyl)-6-[1-methyl-3-(spiro[2.3]hexan-5-ylamino)propyl]pyrimidin-2-yl]sulfamoyl]benzoic acid

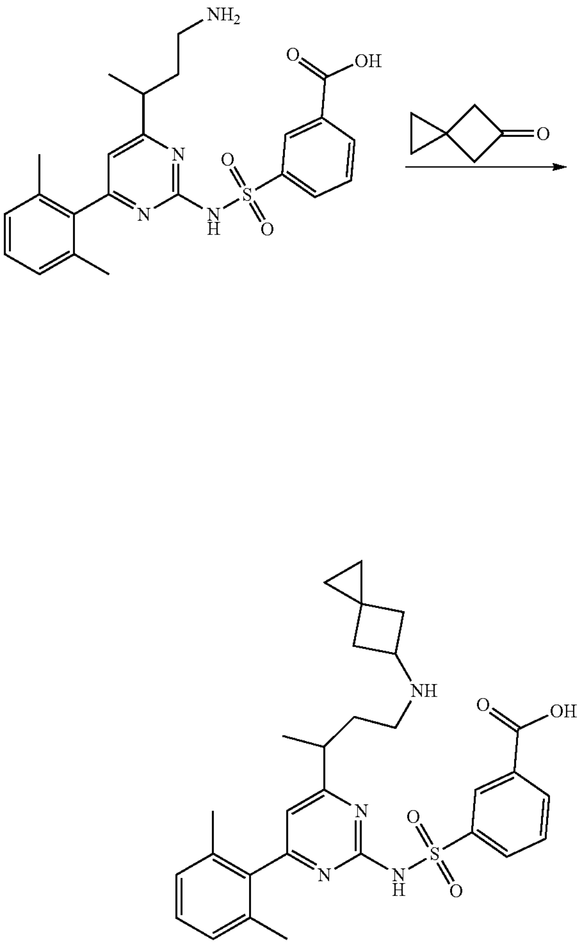

To a solution of 3-[[4-(3-amino-1-methyl-propyl)-6-(2,6-dimethylphenyl)pyrimidin-2-yl]sulfamoyl]benzoic acid (hydrochloride salt) (122 mg, 0.1988 mmol) and spiro[2.3]hexan-5-one (27 mg, 0.2809 mmol) in anhydrous 1,2-dichloroethane (1.2 mL) was added DIEA (25.970 mg, 0.035 mL, 0.2009 mmol). The mixed solution was stirred at ambient temperature for 10 minutes, then sodium triacetoxyborohydride (75 mg, 0.3539 mmol) was added. The resulting solution was stirred at ambient temperature for 21 hours. Then reaction was quenched with aqueous HCl solution (20 mL, 1N), and extracted with chloroform (4×40 mL). Combined organic layer was dried over anhydrous sodium sulfate, filtered, and concentrated under reduced pressure. Crude product was purified by flash chromatography (load with DCM) (24 g silica gel, eluting 0 to 10% methanol in dichloromethane) to afford 3-[[4-(2,6-dimethylphenyl)-6-[1-methyl-3-(spiro[2.3]hexan-5-ylamino)propyl]pyrimidin-2-yl]sulfamoyl]benzoic acid (hydrochloride salt) (59.3 mg, 51%) as a white solid. ESI-MS m/z calc. 534.2301, found 535.2 $(M+1)^+$; Retention time: 4.14 minutes; LC method S.

Step 2: 6-(2,6-Dimethylphenyl)-9-methyl-2,2-dioxo-12-spiro[2.3]hexan-5-yl-2a6-thia-3,5,12,19-tetrazatricyclo[12.3.1.14,8]nonadeca-1(18),4(19),5,7,14,16-hexaen-13-one (Compound 11)

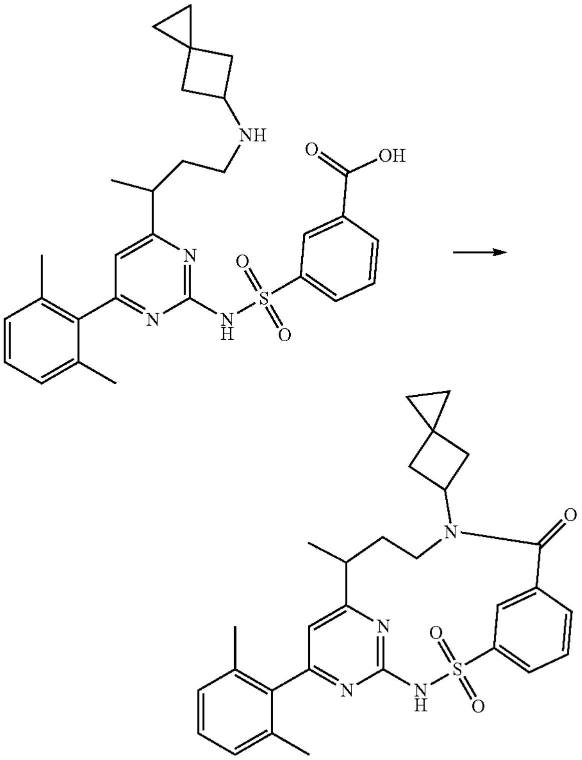

To a solution of HATU (50 mg, 0.1315 mmol) in anhydrous NMP (3 mL) was added DIEA (53.424 mg, 0.072 mL, 0.4134 mmol), then 3-[[4-(2,6-dimethylphenyl)-6-[1-methyl-3-(spiro[2.3]hexan-5-ylamino)propyl]pyrimidin-2-yl]sulfamoyl]benzoic acid (hydrochloride salt) (59.3 mg, 0.1007 mmol) in anhydrous NMP (2 mL) was added dropwise. The reaction was stirred at ambient temperature for 16 hours. Then aqueous HCl solution (1 mL, 1N) and water (10 mL) were added. The solution was extracted with ethyl acetate (3×30 mL). Combined organic layer was washed with brine (10 mL), dried over anhydrous sodium sulfate, filtered and concentrated under reduced pressure. Crude product obtained was purified by reverse HPLC (25% to 85% acetonitrile in water buffered with 0.1% TFA). Desired fractions were dried to afford 6-(2,6-dimethylphenyl)-9-methyl-2,2-dioxo-12-spiro[2.3]hexan-5-yl-2$\lambda^6$-thia-3,5,12,19-tetrazatricyclo[12.3.1.14,8]nonadeca-1(18),4(19),5,7,14,16-hexaen-13-one (44.8 mg, 86%). $^1$H NMR (500 MHz, DMSO-$d_6$) δ 11.69 (s, 1H), 8.42 (d, J=2.1 Hz, 1H), 7.95 (dt, J=6.7, 2.1 Hz, 1H), 7.71-7.64 (m, 2H), 7.21 (t, J=7.6 Hz, 1H), 7.10 (d, J=7.6 Hz, 2H), 6.94 (s, 1H), 4.71 (p, J 8.6 Hz, 1H), 3.15-3.05 (m, 1H), 3.01-2.91 (m, 1H), 2.90-2.81 (m, 1H), 2.78-2.70 (m, 1H), 2.61 (dd, J=11.9, 9.0 Hz, 1H), 2.50-2.44 (m, 1H), 2.28-2.19 (m, 2H), 2.05 (d, J=13.0 Hz, 1H), 1.91 (s, 6H), 1.24 (d, J=7.0 Hz, 3H), 0.58-0.51 (m, 2H), 0.49-0.40 (m, 2H). ESI-MS m/z calc. 516.2195, found 517.1 $(M+1)^+$; Retention time: 2.82 minutes; LC method W.

Example 12: Characterization of Compounds 12-23
The compounds in the Tables 3 and 4 were prepared in a manner analogous to that described above using commercially available reagents and intermediates described herein.
TABLE 3
| Compound number | Structure | LCMS Rt (min) | Calc. mass | M + 1 | LCMS Method |
|---|---|---|---|---|---|
| 12 | 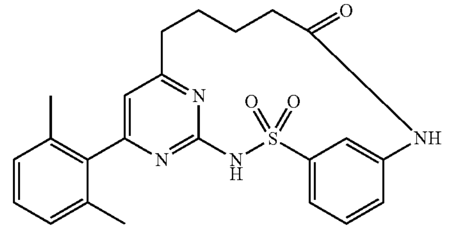 [SMILES: Cc1cccc(C)c1-c1cc2nc(n1)NS(=O)(=O)c1cccc(c1)NC(=O)CCCC2] | 1.38 | 436.157 | 437.4 | A |
| 13 | 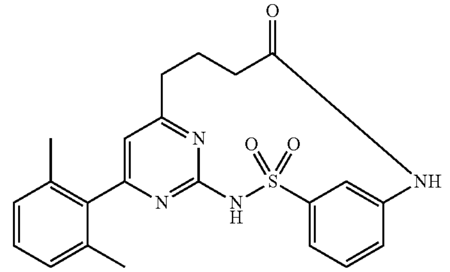 [SMILES: Cc1cccc(C)c1-c1cc2nc(n1)NS(=O)(=O)c1cccc(c1)NC(=O)CCC2] | 1.25 | 422.141 | 423.3 | A |
| 14 | 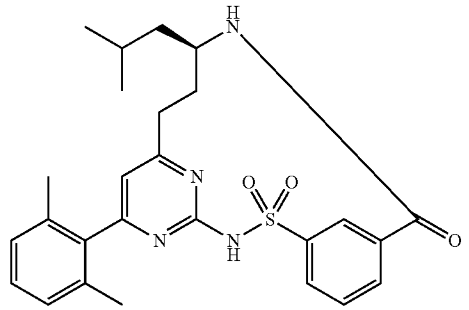 [SMILES: Cc1cccc(C)c1-c1cc2nc(n1)NS(=O)(=O)c1cccc(c1)C(=O)N[C@H](CC(C)C)CC2] | 2.33 | 478.204 | 479.2 | W |
| 15 | 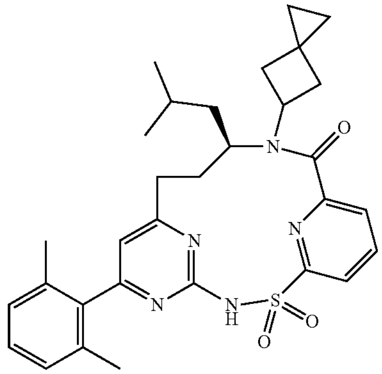 [SMILES: Cc1cccc(C)c1-c1cc2nc(n1)NS(=O)(=O)c1cccc(n1)C(=O)N(C1CC3(CC3)C1)[C@H](CC(C)C)CC2] | 3.03 | 559.262 | 560.2 | W |

TABLE 3-continued
| Compound number | Structure | LCMS Rt (min) | Calc. mass | M + 1 | LCMS Method |
|---|---|---|---|---|---|
| 16 | 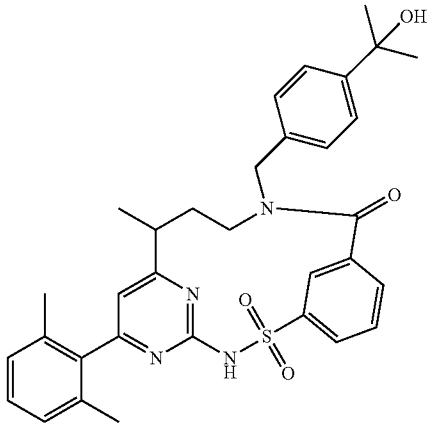 [SMILES: Cc1cccc(C)c1-c1cc2nc(n1)NS(=O)(=O)c1cccc(c1)C(=O)N(Cc1ccc(C(C)(C)O)cc1)CCC2C] | 2.52 | 584.246 | 585.5 | W |
| 17 | 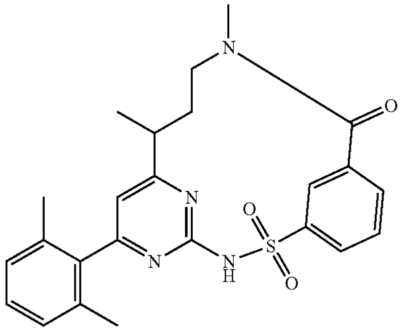 [SMILES: Cc1cccc(C)c1-c1cc2nc(n1)NS(=O)(=O)c1cccc(c1)C(=O)N(C)CCC2C] | 2.19 | 450.173 | 451.3 | W |
| 18 | 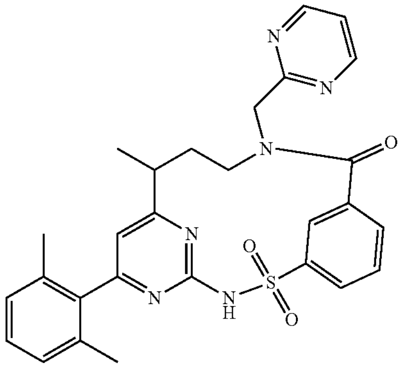 [SMILES: Cc1cccc(C)c1-c1cc2nc(n1)NS(=O)(=O)c1cccc(c1)C(=O)N(Cc1ncccn1)CCC2C] | 2.09 | 528.194 | 529.3 | W |
| 19 | 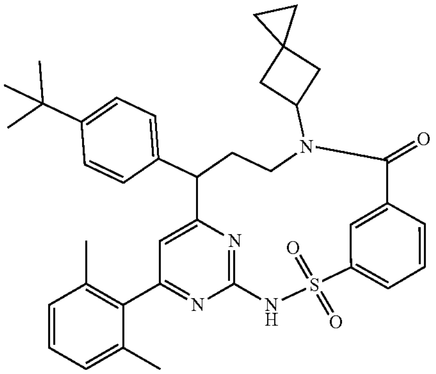 [SMILES: Cc1cccc(C)c1-c1cc2nc(n1)NS(=O)(=O)c1cccc(c1)C(=O)N(C1CC3(CC3)C1)CCC2c1ccc(C(C)(C)C)cc1] | 3.63 | 634.298 | 635.6 | W |

TABLE 3-continued
| Compound number | Structure | LCMS Rt (min) | Calc. mass | M + 1 | LCMS Method |
|---|---|---|---|---|---|
| 20 | 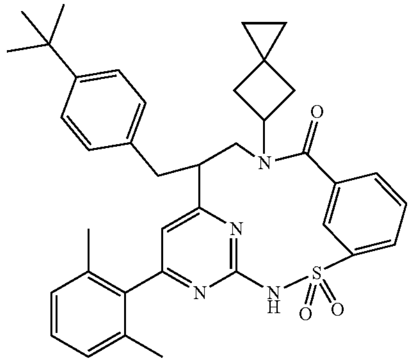 [SMILES: Cc1cccc(C)c1-c1cc2nc(n1)NS(=O)(=O)c1cccc(c1)C(=O)N(C1CC3(CC3)C1)CC2Cc1ccc(C(C)(C)C)cc1] | 3.47 | 634.298 | 635.3 | W |
| 21 | 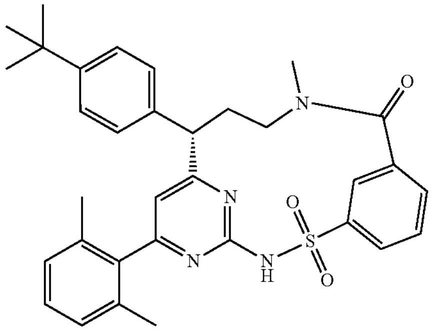 [SMILES: Cc1cccc(C)c1-c1cc2nc(n1)NS(=O)(=O)c1cccc(c1)C(=O)N(C)CC[C@H]2c1ccc(C(C)(C)C)cc1] | 3.01 | 568.251 | 569 | I |
| 22 | 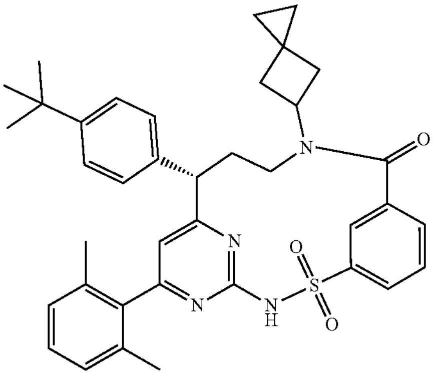 [SMILES: Cc1cccc(C)c1-c1cc2nc(n1)NS(=O)(=O)c1cccc(c1)C(=O)N(C1CC3(CC3)C1)CC[C@H]2c1ccc(C(C)(C)C)cc1] | 2.46 | 634.298 | 635 | A |
| 23 | 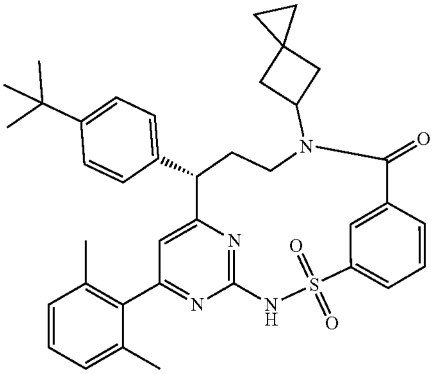 [SMILES: Cc1cccc(C)c1-c1cc2nc(n1)NS(=O)(=O)c1cccc(c1)C(=O)N(C1CC3(CC3)C1)CC[C@H]2c1ccc(C(C)(C)C)cc1] | 2.46 | 634.298 | 635 | A |

TABLE 4

| Compound number | NMR |
|---|---|
| 13 | $^1$H NMR (400 MHz, dimethylsulfoxide-$d_6$) δ 12.21-11.31 (bs, 1H, D2O exchangeable), 9.93 (s, 1H, $D_2O$ exchangeable), 8.28 (t, J = 2.0 Hz, 1H), 7.72 (d, J = 7.9 Hz, 1H), 7.60 (t, J = 7.9 Hz, 1H), 7.32 (d, J = 7.8 Hz, 1H), 7.21 (dd, J = 8.2, 6.9 Hz, 1H), 7.10 (d, J = 7.6 Hz, 2H), 6.95 (s, 1H), 3.04 (t, J = 5.7 Hz, 2H), 2.35-2.26 (m, 2H), 2.11-2.01 (m, 2H), 1.96 (s, 6H) |
| 14 | $^1$H NMR (500 MHz, DMSO-$d_6$) δ 11.71 (s, 1H), 8.49 (s, 1H), 8.01-7.94 (m, 1H), 7.88 (d, J = 10.2 Hz, 1H), 7.71 (d, J = 4.6 Hz, 2H), 7.21 (t, J = 7.6 Hz, 1H), 7.10 (d, J = 7.6 Hz, 2H), 7.03 (s, 1H), 3.05-2.80 (m, 3H), 2.56 (d, J = 14.5 Hz, 1H), 1.90 (s, 6H), 1.75 (td, J = 9.9, 5.0 Hz, 1H), 1.36 (ddt, J = 13.4, 6.6, 4.0 Hz, 1H), 1.32-1.20 (m, 1H), 1.17-1.05 (m, 1H), 0.61 (d, J = 6.6 Hz, 3H), 0.10 (d, J = 6.5 Hz, 3H). |
| 15 | $^1$H NMR (500 MHz, DMSO-$d_6$) δ 11.78 (s, 1H), 8.21 (d, J = 8.2 Hz, 1H), 8.10 (d, J = 7.9 Hz, 1H), 7.81 (d, J = 7.7 Hz, 1H), 7.21 (t, J = 7.6 Hz, 1H), 7.09 (d, J = 7.6 Hz, 2H), 6.99 (s, 1H), 4.24 (p, J = 8.6 Hz, 1H), 3.42 (dd, J = 17.4, 8.9 Hz, 2H), 3.18 (s, 1H), 3.00-2.88 (m, 2H), 2.74 (t, J = 15.6 Hz, 1H), 2.08 (t, J = 9.5 Hz, 1H), 2.03-1.78 (m, 8H), 1.48 (t, J = 12.9 Hz, 1H), 1.29-1.17 (m, 1H), 1.05-0.95 (m, 1H), 0.71 (d, J = 6.7 Hz, 3H), 0.57-0.40 (m, 4H), 0.05--0.02 (m, 3H). |
| 16 | $^1$H NMR (500 MHz, DMSO-$d_6$) δ 8.56 (s, 1H), 7.87 (d, J = 7.6 Hz, 1H), 7.64-7.50 (m, 2H), 7.48-7.41 (m, 2H), 7.26 (d, J = 8.1 Hz, 2H), 7.14 (t, J = 7.6 Hz, 1H), 7.03 (d, J = 7.6 Hz, 2H), (6.54, 6.29) (s, 1H, isomers), 5.01-4.91 (m, 2H), 4.50 (d, J = 15.1 Hz, 1H), 3.23-3.28 (m, 1H), 2.88-2.77 (m, 1H), 2.72 2.58 (m, 1H), 2.46-2.36 (m, 1H), 2.19-2.05 (m, 1H), 1.91 (s, 6H), 1.41 (s, 6H), 1.16 (d, J = 6.8 Hz, 3H). |
| 17 | (500 MHz, DMSO-$d_6$) δ 11.72 (s, 1H), 8.42 (d, J = 1.9 Hz, 1H), 8.01-7.89 (m, 1H), 7.71 (d, J = 7.6 Hz, 2H), 7.22 (t, J = 7.6 Hz, 1H), 7.10 (d, J = 7.6 Hz, 2H), 6.99 (s, 1H), 3.07-3.02 (m, 4H), 2.95-2.81 (m, 2H), 2.45-2.32 (m, 1H), 2.30-2.18 (m, 1H), 1.92 (s, 6H), 1.26 (d, J = 7.0 Hz, 3H) |
| 18 | $^1$H NMR (500 MHz, DMSO-$d_6$) δ 11.75 (s, 1H), 8.80 (d, J = 4.9 Hz, 2H), 8.60 (s, 1H), 8.04-7.97 (m, 1H), 7.76-7.68 (m, 2H), 7.41 (t, J = 4.9 Hz, 1H), 7.21 (t, J = 7.6 Hz, 1H), 7.10 (d, J = 7.6 Hz, 2H), 7.02-6.95 (d, J = 15.1 Hz, 1H), 4.95 (d, J = 16.9 Hz, 1H), 4.84 (d, J = 16.9 Hz, 1H), 3.25-3.08 (m, 2H), 2.91-2.83 (m, 1H), 2.58-2.52 (m, 1H), 2.24-2.14 (m, 1H), 1.93 (s, 6H), 1.21 (d, J = 7.0 Hz, 3H). |
| 19 | $^1$H NMR (500 MHz, DMSO-$d_6$) δ 11.82 (s, 1H), 8.57 (s, 1H), 7.99 (s, 1H), 7.71 (d, J = 4.6 Hz, 2H), 7.37-7.31 (m, 2H), 7.28 (d, J = 8.3 Hz, 2H), 7.18 (t, J = 7.6 Hz, 1H), 7.06 (d, J = 7.6 Hz, 2H), 6.93 (s, 1H), 4.71 (p, J = 8.5 Hz, 1H), 4.20 (d, J = 11.3 Hz, 1H), 3.30 (d, J = 13.8 Hz, 1H), 2.98 (d, J = 10.3 Hz, 2H), 2.73 (t, J = 9.8 Hz, 1H), 2.57 (t, J = 9.7 Hz, 1H), 2.24-2.10 (m, 3H), 1.80 (s, 6H), 1.25 (s, 9H), 0.51 (td, J = 7.3, 6.8, 3.9 Hz, 2H), 0.41 (ddd, J = 12.0, 9.2, 5.1 Hz, 2H). |
| 20 | $^1$H NMR (500 MHz, DMSO-$d_6$) δ (11.92, 10.71, 8.88) (rotamers, 1H), 8.09-7.78 (m, 1H), 7.78-7.48 (m, 2H), 7.21 (t, J = 7.7 Hz, 0.5H), 7.19-7.14 (m, 3H), 7.13 (d, J = 7.6 Hz, 0.5H), 7.09 (d, J = 7.5 Hz, 1H), 7.01 (d, J = 7.6 Hz, 1H), 6.94 (d, J = 7.9 Hz, 2H), 6.42 (s, 1H), (5.0-4.93, 4.55-4.50, 3.92 3.78) (rotamers, m, 1H), 3.54-3.37 (m, 2H), 3.29-3.14 (m, 1H), 3.14-2.87 (m, 2H), 2.87-2.56 (m, 1H), 2.49-2.29 (m, 3H), 1.98-1.51 (m, 6H), (1.23, 1.18) (rotamers, 9H), 0.69-0.24 (m, 4H). |
| 21 | $^1$H NMR (400 MHz, DMSO-$d_6$) δ 11.82 (s, 1H), 8.57 (s, 1H), 7.95 (s, 1H), 7.66 (s, 2H), 7.43-7.24 (m, 3H), 7.15 (s, 1H), 7.03 (s, 2H), 6.52 (s, 1H), 4.02 (s, 3H), 3.02 (s, 4H), 2.88 (s, 1H), 1.78 (s, 6H), 1.24 (s, 9H). |
| 22 | $^1$H NMR (400 MHz, DMSO-$d_6$) δ 11.73 (s, 1H), 8.56 (s, 1H), 7.98 (s, 1H), 7.68 (d, J = 4.8 Hz, 2H), 7.39-7.21 (m, 4H), 7.16 (s, 1H), 7.04 (d, J = 7.6 Hz, 2H), 6.85 (s, 1H), 4.70 (d, J = 17.0 Hz, 1H), 4.17 (d, J = 10.5 Hz, 1H), 3.29 (s, 1H), 2.99 (s, 2H), 2.71 (s, 1H), 2.57 (s, 1H), 2.19 (d, J = 18.0 Hz, 3H), 1.79 (s, 6H), 1.24 (s, 9H), 0.50 (s, 2H), 0.41 (s, 2H). |
| 23 | $^1$H NMR (400 MHz, DMSO-$d_6$) δ 11.79 (s, 1H), 8.56 (s, 1H), 7.97 (s, 1H), 7.69 (d, J = 4.4 Hz, 2H), 7.34 (d, J = 8.3 Hz, 2H), 7.27 (d, J = 8.3 Hz, 2H), 7.17 (s, 1H), 7.05 (d, J = 7.6 Hz, 2H), 6.89 (s, 1H), 4.70 (s, 1H), 4.18 (d, J = 11.1 Hz, 1H), 2.94 (s, 2H), 2.72 (s, 1H), 2.57 (d, J = 19.9 Hz, 2H), 2.14 (d, J = 26.3 Hz, 3H), 1.79 (s, 6H), 1.24 (s, 9H), 0.56-0.30 (m, 4H). |

Example 13: Preparation of Compound 24

Step 1: 3-[[4-(2-Aminoethoxy)-6-(2,6-dimethylphenyl)-5-methyl-pyrimidin-2-yl]sulfamoyl]benzoic acid

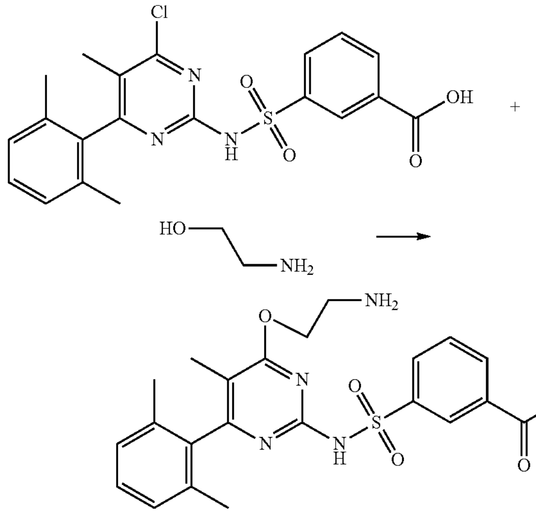

3-[[4-Chloro-6-(2,6-dimethylphenyl)-5-methyl-pyrimidin-2-yl]sulfamoyl]benzoic acid (753 mg, 1.743 mmol) and 2-aminoethanol (115 μL, 1.905 mmol) were combined in THF (3.5 mL) and sodium tert-butoxide (703 mg, 7.315 mmol) was added. The reaction was stirred at room temperature for 10 minutes. The reaction was partitioned between ethyl acetate (10 mL) and a 1M HCl solution (10 mL). The product crashed out as a white solid and was collected by vacuum filtration. The product was further dried to give 3-[[4-(2-aminoethoxy)-6-(2,6-dimethylphenyl)-5-methyl-pyrimidin-2-yl]sulfamoyl]benzoic acid (hydrochloride salt) (487.6 mg, 57%). ESI-MS m/z calc. 456.14673, found 457.0 $(M+1)^+$; Retention time: 0.38 minutes, LC method D.

Step 2: 6-(2,6-Dimethylphenyl)-7-methyl-9-oxa-2%6-thia-3,5,12,19-tetraazatricyclo[12.3.1.14,8]nonadeca-1(18),4,6,8(19),14,16-hexaene-2,2,13-trione, and 6-(2,6-dimethylphenyl)-7-methyl-12-oxa-2 λ6-thia-3,5,9,19-tetraazatricyclo[12.3.1.14,8]nonadeca-1(18),4,6,8(19),14,16-hexaene-2,2,13-trione, (Compound 24)

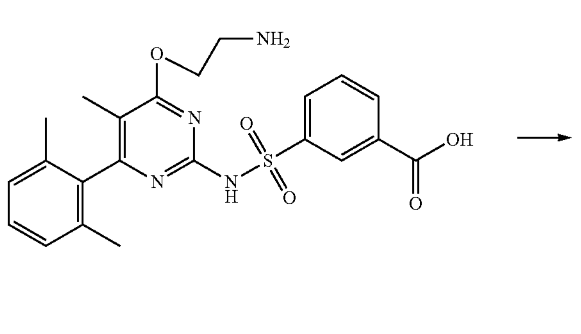

-continued

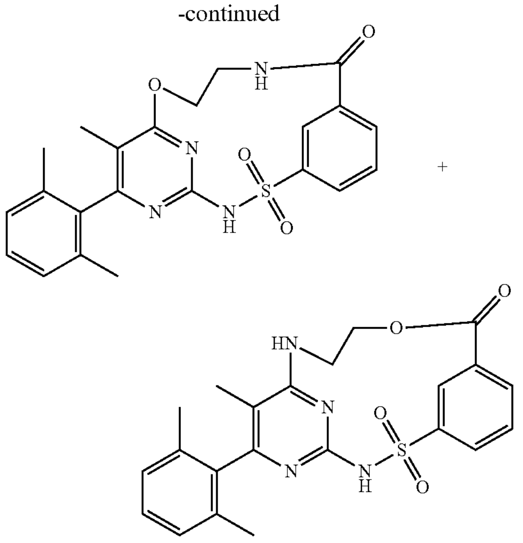

3-[[4-(2-Aminoethoxy)-6-(2,6-dimethylphenyl)-5-methyl-pyrimidin-2-yl]sulfamoyl]benzoic acid (hydrochloride salt) (25 mg, 0.05071 mmol) and HATU (19.9 mg, 0.05234 mmol) were dissolved in DMF (1 mL) and DIEA (45 μL, 0.2584 mmol) was added. The reaction mixture was stirred at room temperature for 1 hour. The reaction mixture was filtered and purified by LC/MS utilizing a gradient of 1-99% acetonitrile in 5 mM aqueous HCl to yield two products: 6-(2,6-Dimethylphenyl)-7-methyl-9-oxa-$2\lambda^6$-thia-3,5,12,19-tetraazatricyclo[12.3.1.14,8]nonadeca-1(18),4,6,8(19),14,16-hexaene-2,2,13-trione (5.4 mg, 23%) as a white solid ESI-MS m/z calc. 438.13617, found 439.1 $(M+1)^+$; Retention time: 1.19 minutes (LC method A); and 6-(2,6-dimethylphenyl)-7-methyl-12-oxa-$2\lambda^6$-thia-3,5,9,19-tetraazatricyclo[12.3.1.14,8]nonadeca-1(18),4,6,8(19),14,16-hexaene-2,2,13-trione (5.2 mg, 23%) as a white solid ESI-MS m/z calc. 438.13617, found 439.1 $(M+1)^+$; Retention time: 1.54 minutes (LC method A).

Example 14: Preparation of Compound 25

Step 1: 1-Bromo-4-tert-butyl-2-iodo-benzene

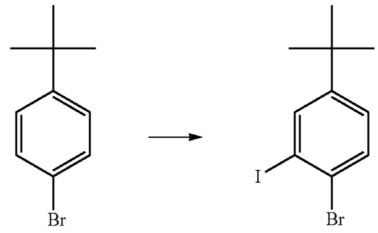

To a solution of 1-bromo-4-tert-butyl-benzene (100 g, 469.23 mmol) in TFA (1.5000 L) was added NIS (110.85 g, 492.69 mmol) portion-wise at room temperature. The reaction was allowed to stir for 4 hours before the volatiles were removed under reduced pressure. The crude residue was diluted with water (500 mL) and EtOAc (500 mL). The aqueous layer was extracted three times with EtOAc (3×1 L). The combined organic layers were washed with sodium bicarbonate (1 L), water (1 L), and brine (1 L), then dried over sodium sulfate and concentrated under vacuum. This crude residue was dissolved in hexanes and passed through a pad of silica gel. The pad of silica gel was washed three times with hexanes (3×500 mL); this residue was concentrated to give 1-bromo-4-tert-butyl-2-iodo-benzene (158.86 g, 98%). $^1$H NMR (250 MHz, $CDCl_3$) δ 7.84 (s, 1H), 7.58-7.40 (m, 1H), 7.29-7.08 (m, 1H), 1.28 (s, 9H).

Step 2: tert-Butyl N-[(1R)-1-[methoxy(methyl)carbamoyl]-3-methyl-butyl]carbamate

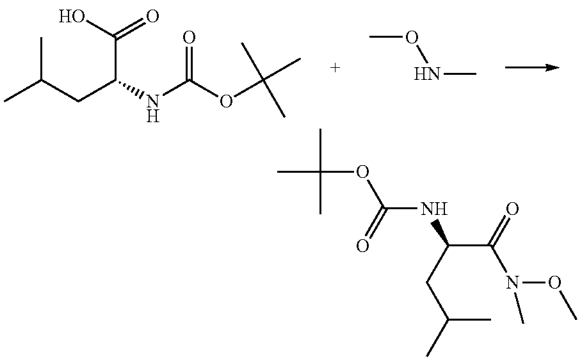

(2R)-2-(tert-Butoxycarbonylamino)-4-methyl-pentanoic acid (20 g, 86.472 mmol) EDC (24.866 g, 129.71 mmol) and HOBt (17.527 g, 129.71 mmol) were dissolved in DCM (200 mL) and cooled to 0° C. Next, N-methoxymethanamine (7.9231 g, 129.71 mmol) and DIPEA (22.351 g, 30.123 mL, 172.94 mmol) were added. The reaction was allowed to stir at room temperature overnight and was quenched with water (100 mL). The layers were separated and the aqueous layer was extracted three times with DCM (50 mL) and the combined organic layers were dried over sodium sulfate and concentrated. The residue was purified by flash column chromatography using 0-50% hexanes:diethylether as an eluent to give tert-butyl N-[(1R)-1-[methoxy(methyl)carbamoyl]-3-methyl-butyl]carbamate (15.62 g, 63%) as a colorless oil. ESI-MS m/z calc. 274.1893, found 275.3 $(M+1)^+$; Retention time: 3.04 minutes, LC method T.

Step 3: 2-Bromo-5-tert-butyl-benzaldehyde

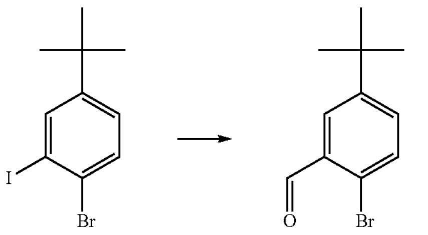

To a solution of 1-bromo-4-tert-butyl-2-iodo-benzene (235.93 g, 695.94 mmol) in dry THF (2 L) was added i-PrMgBr (1.6 L of 1 M, 1.6000 mol) dropwise at −78° C. The solution was stirred at this temperature for 4.5 hours. DMF (203.48 g, 215.55 mL, 2.7838 mol) was added to the solution at −78° C. and the reaction was stirred for 2 hours at this temperature before being allowed to warm to room temperature overnight. The solution was quenched with water (1 L) and the aqueous layer separated and extracted with diethyl ether (3×1 L). The organic layers were washed with brine (1 L) and dried over sodium sulfate. The organic residue was purified by silica gel chromatography eluting 0-2% hexanes-diethyl ether to give 2-bromo-5-tert-butyl-benzaldehyde (122.09 g, 73%). $^1$H NMR (250 MHz, $CDCl_3$) δ 10.36 (s, 1H), 7.94 (d, J=2.5 Hz, 1H), 7.57 (d, J=8.4 Hz, 1H), 7.50 (d, J=2.5 Hz, 1H), 1.33 (s, 9H). ESI-MS m/z calc. 240.01498, Retention time: 3.34 minutes; LC method T.

Step 4: tert-Butyl N-[(1R)-1-formyl-3-methyl-butyl]carbamate

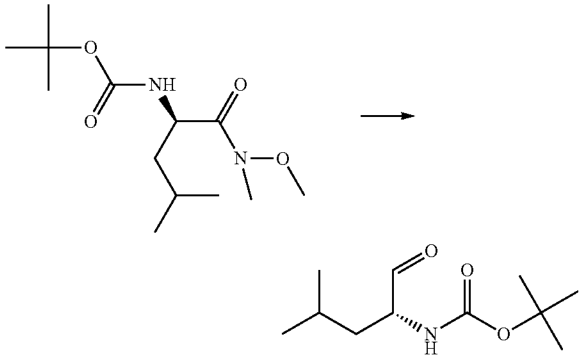

tert-Butyl N-[(1R)-1-[methoxy(methyl)carbamoyl]-3-methyl-butyl]carbamate (31.881 g, 116.20 mmol) was dissolved in THF (750 mL) and cooled to 0° C. Next, LAH (2.6462 g, 69.720 mmol) was added slowly. The reaction was stirred at 0° C. for 2 hours then quenched with 200 mL saturated Rochelle's salt solution. The reaction was allowed to stir overnight until the mixture became biphasic and the aqueous layer was slightly cloudy. The layers were separated and the aqueous layer extracted twice with diethylether (200 mL). The combined organic layers were dried over sodium sulfate and concentrated. The crude residue was dry loaded on silica gel and purified by flash column chromatography (0-15% hexanes:diethylether). Analysis of the fractions by TLC ($KMnO_4$ stain) revealed the appropriate factions to collect to give tert-butyl N-[(1R)-1-formyl-3-methyl-butyl]carbamate (15 g, 48%) as a colorless oil. $^1$H NMR (250 MHz, $CDCl_3$) δ 9.58 (s, 1H), 5.02-4.87 (m, 1H), 4.33-4.12 (m, 1H), 1.92-1.54 (m, 3H), 1.44 (s, 9H), 0.96 (dd, J=6.5, 1.5 Hz, 6H).

Step 5: 2-(2-Bromo-5-tert-butyl-phenyl)-1,3-dioxolane

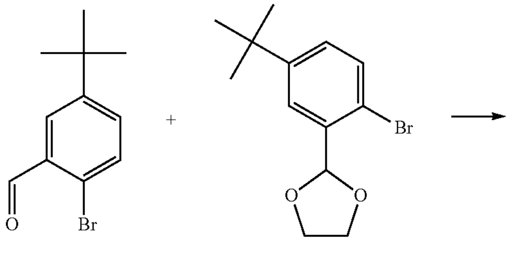

-continued

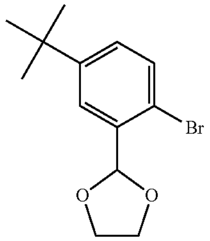

To a mixture of 2-(2-bromo-5-tert-butyl-phenyl)-1,3-dioxolane and 2-bromo-5-tert-butyl-benzaldehyde (49.29 g, 204.42 mmol) in EtOH (492.90 mL) was added sodium borohydride (9.2803 g, 9.8204 mL, 245.30 mmol) at 0° C. The reaction was stirred at this temperature for 1 hour before being quenched with slow addition of water. The solution was concentrated under vacuum to remove solvent before being extracted with DCM (3×300 mL). The combined organic layers were washed with brine (500 mL) before being dried over sodium sulfate and concentrated. The organic residue was purified by silica gel chromatography eluting 0-4% hexanes-diethyl ether to give 2-(2-bromo-5-tert-butyl-phenyl)-1,3-dioxolane (26.68 g, 46%) as a yellow oil ESI-MS m/z calc. 284.0412, found 285.0 $(M+1)^+$; Retention time: 3.32 minutes. $^1H$ NMR (250 MHz, $CDCl_3$) δ 7.61 (d, J=2.6 Hz, 1H), 7.48 (d, J=8.4 Hz, 1H), 7.35-7.09 (m, 1H), 6.07 (s, 1H), 4.38-4.13 (m, 2H), 4.13-3.99 (m, 2H), 1.31 (s, 9H). ESI-MS m/z calc. 284.0412, found 285.0 $(M+1)^+$; Retention time: 3.32 minutes; LC method T.

Step 6: tert-butyl N-[(1R)-1-[(R)-[4-tert-butyl-2-(1,3-dioxolan-2-yl)phenyl]-hydroxy-methyl]-3-methyl-butyl]carbamate, and tert-butyl N-[(1R)-1-[(S)-[4-tert-butyl-2-(1,3-dioxolan-2-yl)phenyl]-hydroxy-methyl]-3-methyl-butyl]carbamate

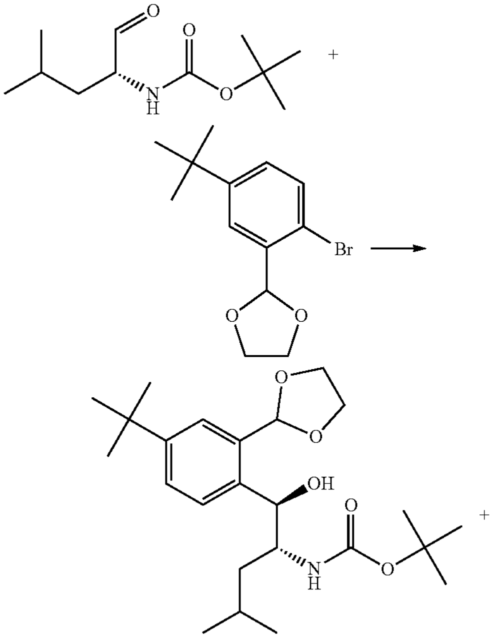

-continued

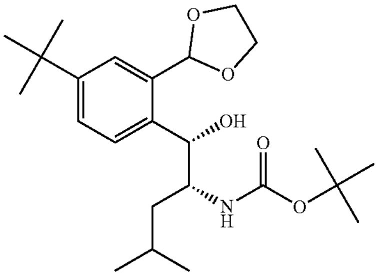

2-(2-Bromo-5-tert-butyl-phenyl)-1,3-dioxolane (26.6 g, 93.275 mmol) was dissolved in THF (80 mL) and magnesium (2.7205 g, 111.93 mmol) was added. The reaction was refluxed for 5 hours. The reaction was then cooled to room temperature and stirred overnight. The dark brown mixture was cooled to 0° C. and cannulated into a solution of tert-butyl N-[(1R)-1-formyl-3-methyl-butyl]carbamate (8.0324 g, 37.31 mmol) in THF (80 mL) which was cooled to 0° C. The reaction was allowed to stir for 2 hours and was cooled to 0° C. and quenched with ammonium chloride (150 mL). The layers were separated, and the aqueous layer was extracted twice with diethylether (100 mL). The combined organic layers were washed with water (50 mL) and brine (50 mL), dried over magnesium sulfate, and concentrated. The crude residue was dry loaded on to silica gel and purified by flash column chromatography using 0-50% hexanes:diethylether as an eluent to give two products: tert-Butyl N-[(1R)-1-[(R)-[4-tert-butyl-2-(1,3-dioxolan-2-yl)phenyl]-hydroxy-methyl]-3-methyl-butyl]carbamate (3.57 g, 20%) was collected as a yellow foam. $^1H$ NMR (250 MHz, $CDCl_3$) δ 7.63-7.33 (m, 3H), 5.96 (s, 1H), 4.99 (s, 1H), 4.78 (d, J=9.5 Hz, 1H), 4.23-3.94 (m, 4H), 1.62-1.44 (m, 2H), 1.30 (s, 18H), 0.97-0.84 (m, 6H) LCMS retention time: 3.90 minutes (LC method T) and tert-butyl N-[(1R)-1-[(S)-[4-tert-butyl-2-(1,3-dioxolan-2-yl)phenyl]-hydroxy-methyl]-3-methyl-butyl]carbamate (3.2 g, 17%), which was collected a yellow oil. $^1H$ NMR (250 MHz, $CDCl_3$) δ 7.60-7.38 (m, 3H), 6.01 (s, 1H), 5.20 (s, 1H), 5.03 (d, J=5.7 Hz, 1H), 4.83 (d, J=9.3 Hz, 1H), 4.26-3.95 (m, 4H), 1.65-1.43 (m, 2H), 1.30 (s, 18H), 1.03-0.78 (m, 6H), LCMS retention time: 3.90 minutes (LC method T).

Step 7: tert-Butyl (3R,4S)-7-tert-butyl-4-hydroxy-3-isobutyl-3,4-dihydro-1H-isoquinoline-2-carboxylate

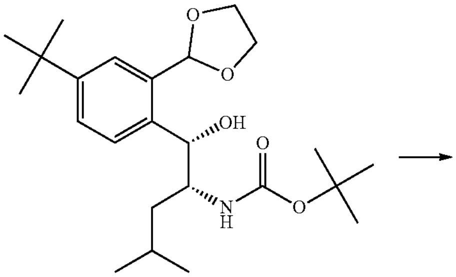

-continued

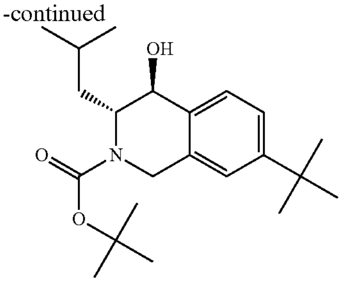

tert-Butyl N-[(1R)-1-[(S)-[4-tert-butyl-2-(1,3-dioxolan-2-yl)phenyl]-hydroxy-methyl]-3-methyl-butyl]carbamate (3.788 g, 8.9855 mmol) was dissolved in HCl (4M in dioxanes) (22.5 mL of 4 M, 90.000 mmol) and stirred for 1 hour. The volatiles were removed in vacuo. The crude residue was dissolved in EtOH (70 mL) and cooled to 0° C. Then sodium triacetoxyborohydride (3.82 g, 18.024 mmol) was added to the reaction in portions. After 1 hour, the volatiles were removed, and the reaction was diluted with ammonium chloride and EtOAc. The aqueous phase was extracted three times with EtOAc, dried over sodium sulfate, and concentrated. The crude residue was dissolved in THF (70 mL) and 3.75 M NaOH solution (70 mL). Boc anhydride (3.95 g, 18.099 mmol) was added and the reaction stirred for 1 hour. The layers were separated, and the aqueous layer was extracted three times with EtOAc (20 mL). The combined organic layers were dried over sodium sulfate and concentrated. The crude residue was dry loaded on to silica gel and purified by flash column chromatography using 0-40% hexanes:diethylether as an eluent (220 nm monitor). The appropriate fractions (visualized by TLC/$KMnO_4$ stain) were collected to give tert-butyl (3R,4S)-7-tert-butyl-4-hydroxy-3-isobutyl-3,4-dihydro-1H-isoquinoline-2-carboxylate (668 mg, 20%) as a light yellow oil. ESI-MS m/z calc. 361.2617, found 362.4 $(M+1)^+$; Retention time: 3.33 minutes, (LC method W). $^1H$ NMR (500 MHz, DMSO-$d_6$) δ 7.41 (d, J=8.0 Hz, 1H), 7.24 (d, J=8.2 Hz, 1H), 7.12 (d, J=9.7 Hz, 1H), 5.63 (d, J=5.4 Hz, 1H), 4.76 (dd, J=24.6, 17.5 Hz, 1H), 4.68-4.59 (m, 1H), 4.53-4.33 (m, 1H), 4.05 (dd, J=60.7, 17.6 Hz, 1H), 1.42 (s, 9H), 1.39 (dd, J=8.1, 4.5 Hz, 1H), 1.25 (s, 9H), 1.09-0.95 (m, 2H), 0.95-0.78 (m, 6H).

Step 8: (16S,24R)-20-tert-Butyl-12-(2,6-dimethylphenyl)-24-(2-methylpropyl)-15-oxa-8λ6-thia-1,9,11,25-tetraazapentacyclo[14.7.1.13,7.110,14.017,22]hexacosa-3,5,7(26),10,12,14(25),17,19,21-nonaene-2,8,8-trione, and (16R,24R)-20-tert-butyl-12-(2,6-dimethylphenyl)-24-(2-methylpropyl)-15-oxa-8λ6-thia-1,9,11,25-tetraazapentacyclo[14.7.1.13,7.110,14.017,22]hexacosa-3,5,7(26),10,12,14(25),17,19,21-nonaene-2,8,8-trione, and (16S,24R)-20-tert-butyl-4-(2,6-dimethylphenyl)-24-(2-methylpropyl)-15-oxa-8 λ6-thia-1,5,7,26-tetraazapentacyclo[14.7.1.12,6.19,13.017,22]hexacosa-2(26),3,5,9(25),10,12,17,19,21-nonaene-8,8,14-trione, (Compound 25)

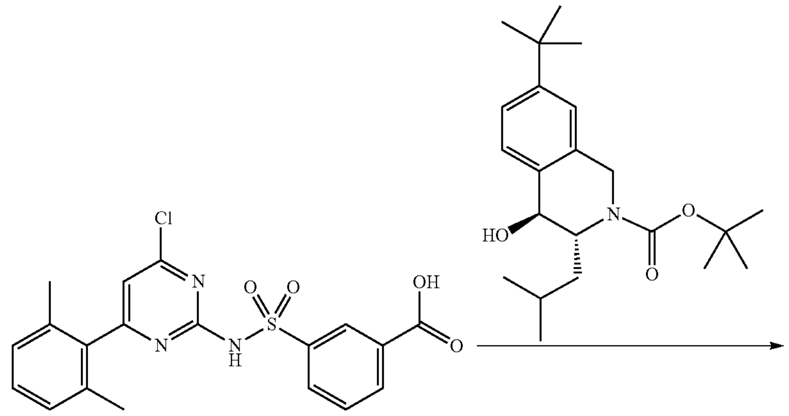

+

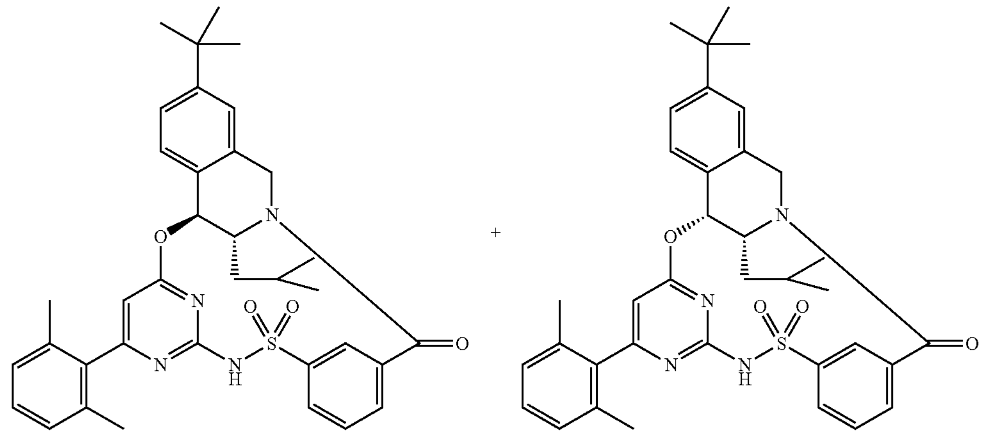

+

-continued

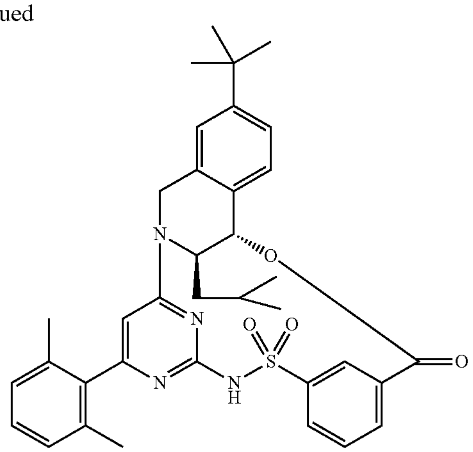

In a 20-mL vial, tert-butyl (3R,4S)-7-tert-butyl-4-hydroxy-3-isobutyl-3,4-dihydro-1H-isoquinoline-2-carboxylate (260.7 mg, 0.7211 mmol) was dissolved in dioxane (3.0 mL), to which a dioxane solution of HCl (3.0 mL of 4.0 M, 12.00 mmol) was added. This mixture was stirred at room temperature for 4.5 hours. This mixture was then evaporated to dryness in vacuo to give 224.6 mg (>100% yield) of a yellow solid. In a 20-mL vial, the product was mixed with THF (3.0 mL), to which NaOtBu (512.2 mg, 5.330 mmol) was added. This mixture was stirred at room temperature for 10 min, after which it was cooled to 0° C. Then, 3-[[4-chloro-6-(2,6-dimethylphenyl)pyrimidin-2-yl]sulfamoyl]benzoic acid (349.1 mg, 0.8354 mmol) was added, and this mixture was stirred at 0° C. for 1 hour, and at room temperature for 1 hour. In a separate 20-mL vial, a solution of HATU (845.2 mg, 2.223 mmol) in DMF (6.0 mL) was prepared. The above-prepared reaction mixture was added dropwise onto this HATU solution, and the resulting mixture was stirred at room temperature for 15 minutes. This mixture was then quenched with 1 N HCl solution (30 mL) and diluted with ethyl acetate (120 mL). The layers were separated, and the organic layer was washed with 1 N HCl solution (40 mL), water (40 mL) and saturated aqueous sodium chloride solution (40 mL), then dried over sodium sulfate, filtered, and evaporated in vacuo to give a yellow solid. Purification by silica gel chromatography (24 g of silica column) using a gradient eluent of 1 to 70% ethyl acetate in hexanes gave 2 batches of product (80 mg of 70% pure material and 125 mg of 60% pure material). These were dissolved separately in warm DMSO (2 mL each) and purified by reverse phase preparative chromatography using a $C_{18}$ column and a gradient eluent of 1 to 99% acetonitrile in water containing 5 mM hydrochloric acid to give: major product, (16S,24R)-20-tert-butyl-12-(2,6-dimethylphenyl)-24-(2-methylpropyl)-15-oxa-8$\lambda^6$-thia-1,9,11,25-tetraazapentacyclo[14.7.1.13,7.110,14.017,22]hexacosa-3,5,7(26),10,12,14(25),17,19,21-nonaene-2,8,8-trione (122.5 mg, 27%) $^1$H NMR (400 MHz, DMSO-$d_6$) δ 12.17-11.55 (bs, 1H), 8.44 (t, J=1.8 Hz, 1H), 7.89 (d, J=7.7 Hz, 1H), 7.69 (d, J=7.6 Hz, 1H), 7.64 (t, J=7.6 Hz, 1H), 7.58 (d, J=8.1 Hz, 1H), 7.45 (d, J=2.0 Hz, 1H), 7.44-7.39 (m, 1H), 7.41 (s, 1H), 7.25 (t, J=7.6 Hz, 1H), 7.13 (d, J=7.6 Hz, 2H), 5.53 (s, 1H), 5.48 (d, J=18.1 Hz, 1H), 4.25 (d, J=18.1 Hz, 1H), 3.48-3.30 (m, 1H, hidden under water peak), 2.08-1.72 (bs, 6H), 1.44-1.19 (m, 3H), 1.33 (s, 9H), 0.56 (d, J=6.3 Hz, 3H), 0.44 (d, J=6.3 Hz, 3H) ESI-MS m/z calc. 624.27704, found 625.5 $(M+1)^+$; Retention time: 2.13 minutes (LC method A); and minor product, (16R,24R)-20-tert-butyl-12-(2,6-dimethylphenyl)-24-(2-methylpropyl)-15-oxa-8$\lambda^6$-thia-1,9,11,25-tetraazapentacyclo[14.7.1.13,7.110,14.017,22]hexacosa-3,5,7(26),10,12,14(25),17,19,21-nonaene-2,8,8-trione (5.9 mg, 1%) $^1$H NMR (400 MHz, DMSO-$d_6$) δ 12.22-11.61 (bs, 1H), 8.45 (s, 1H), 7.89 (d, J=7.7 Hz, 1H), 7.73-7.58 (m, 3H), 7.50 (dd, J=8.2, 2.1 Hz, 1H), 7.48 (s, 1H), 7.25 (t, J=7.6 Hz, 1H), 7.13 (d, J=7.6 Hz, 2H), 5.52 (s, 1H), 5.40 (d, J=18.1 Hz, 1H), 4.22 (d, J=18.1 Hz, 1H), 3.48-3.30 (m, 1H, hidden under water peak), 2.11-1.81 (bs, 6H), 1.43-1.15 (m, 3H), 1.30 (s, 9H), 0.55 (d, J=6.2 Hz, 3H), 0.44 (d, J=6.3 Hz, 3H) ESI-MS m/z calc. 624.27704, found 625.5 $(M+1)^+$; Retention time: 2.1 minutes (LC method A); and side product, (16S,24R)-20-tert-butyl-4-(2,6-dimethylphenyl)-24-(2-methylpropyl)-15-oxa-8$\lambda^6$-thia-1,5,7,26-tetraazapentacyclo[14.7.1.12,6.19,13.017,22]hexacosa-2(26),3,5,9(25),10,12,17,19,21-nonaene-8,8,14-trione (16.3 mg, 4%) ESI-MS m/z calc. 624.27704, found 625.5 $(M+1)^+$; Retention time: 2.22 minutes (LC method A).

Example 15: Preparation of Compound 26

Step 1: 2-(2-Tetrahydropyran-4-ylethylamino)-4-[1-(trifluoromethyl)cyclopropyl]butanenitrile

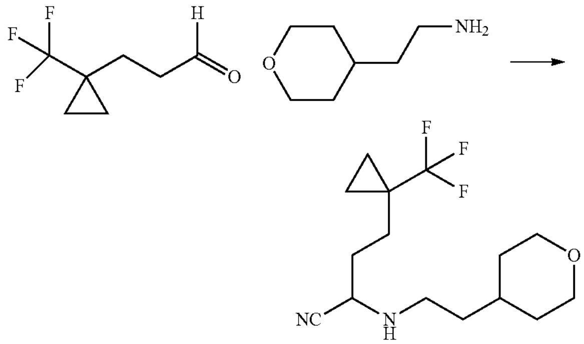

To a stirring solution of 3-[1-(trifluoromethyl)cyclopropyl]propanal (821.9 mg, 4.947 mmol) in acetonitrile (48.19 mL) under nitrogen atmosphere was added 2-tetrahydropyran-4-ylethanamine (639 mg, 4.946 mmol) and trimethylsilylformonitrile (791.4 µL, 5.935 mmol). bromo(dimethyl) sulfonium bromide (109.8 mg, 0.4947 mmol) was then added and the mixture was stirred for 90 minutes. The mixture was diluted with water (48.19 mL), then ~½ of the acetonitrile was removed by rotary evaporation. The resulting mixture was extracted with EtOAc (3×), combined organic phases, dried (sodium sulfate), filtered, and concentrated to light tan oil, 2-(2-tetrahydropyran-4-ylethylamino)-4-[1-(trifluoromethyl)cyclopropyl]butanenitrile (1.3 g, 86%) ESI-MS m/z calc. 304.17624, found 305.0 $(M+1)^+$; Retention time: 0.39 minutes (LC method D).

Step 2: 2-(2-Tetrahydropyran-4-ylethylamino)-4-[1-(trifluoromethyl)cyclopropyl]butanoic acid

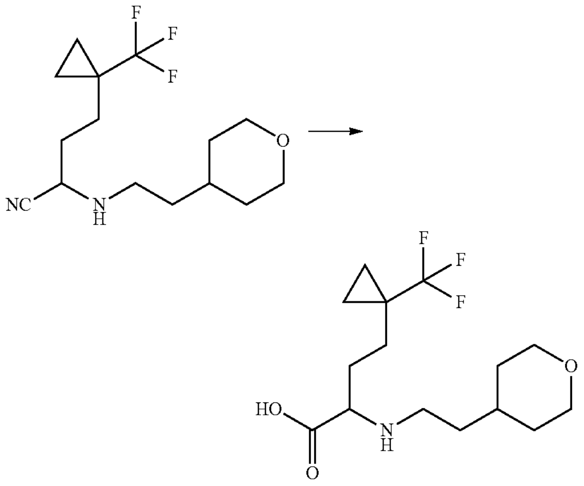

To a stirring solution of 2-(2-tetrahydropyran-4-ylethylamino)-4-[1-(trifluoromethyl)cyclopropyl]butanenitrile (1.3 g, 4.271 mmol) in acetic acid (813.7 μL, 14.31 mmol) in a vial was added HCl (8.123 mL of 37% w/v, 82.43 mmol) and the vial was capped. The mixture was stirred and heated in an aluminum block at 95° C. for 16 hours. The mixture was transferred to a round bottom flask using MeOH and was concentrated by rotary evaporation, including treatment with diethyl ether and removing the solvents three times to give 2-(2-tetrahydropyran-4-ylethylamino)-4-[1-(trifluoromethyl)cyclopropyl]butanoic acid as a light tan solid that was dried thoroughly on the high vacuum pump then taken directly to the next step (1.576 g, 100%). ESI-MS m/z calc. 323.17084, found 324.0 $(M+1)^+$; Retention time: 0.33 minutes, LC method D.

Step 3: 2-(2-Tetrahydropyran-4-ylethylamino)-4-[1-(trifluoromethyl)cyclopropyl]butan-1-ol

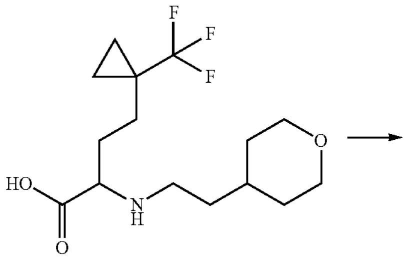

-continued

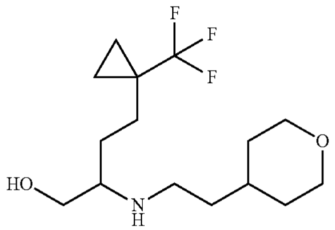

To a stirring solution of 2-(2-tetrahydropyran-4-ylethylamino)-4-[1-(trifluoromethyl)cyclopropyl]butanoic acid (1.576 g, 4.265 mmol) in THF (27.58 mL) under nitrogen atmosphere at 0° C. was slowly added LAH (664.7 mg, 17.06 mmol) and the resulting mixture was stirred at 0° C. for 2 minutes, then allowed to warm to room temperature and was stirred for 75 minutes. The mixture was cooled to 0° C. and quenched by the addition of water (1.279 mL, 71.00 mmol), then KOH (1.279 mL of 15% w/v, 3.419 mmol) then water (2.556 mL, 141.9 mmol). The mixture was warmed to room temperature, Celite was added and stirred for 5 minutes then filtered over Celite eluting with ether. The ethereal filtrate was then dried (magnesium sulfate), filtered and concentrated the filtrate by rotary evaporation to an orange oil, 2-(2-tetrahydropyran-4-ylethylamino)-4-[1-(trifluoromethyl)cyclopropyl]butan-1-ol (1.225 g, 93%) ESI-MS m/z calc. 309.19156, found 310.0 $(M+1)^+$; Retention time: 0.34 minutes, LC method D.

Step 4: 3-[[4-(2,6-Dimethylphenyl)-6-[2-(2-tetrahydropyran-4-ylethylamino)-4-[1-(trifluoromethyl)cyclopropyl]butoxy]pyrimidin-2-yl]sulfamoyl]benzoic acid

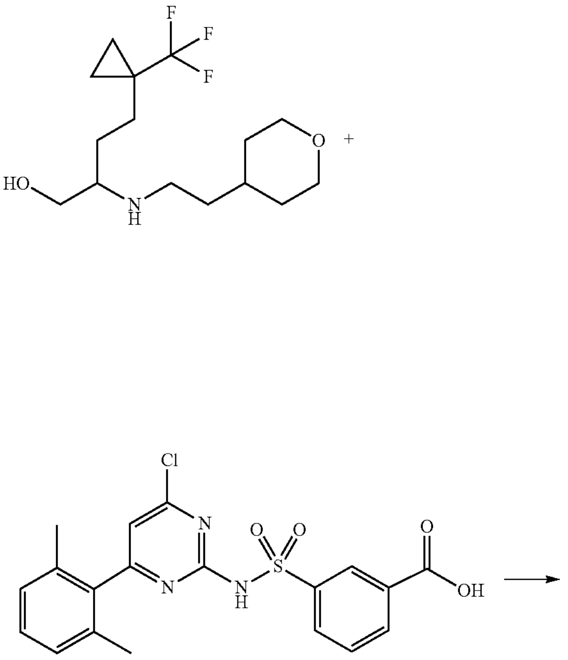

-continued

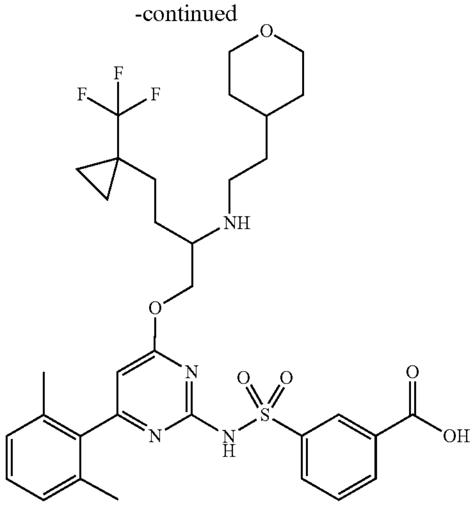

To a stirring solution of 3-[[4-chloro-6-(2,6-dimethylphenyl)pyrimidin-2-yl]sulfamoyl]benzoic acid (675.3 mg, 1.616 mmol) and 2-(2-tetrahydropyran-4-ylethylamino)-4-[1-(trifluoromethyl)cyclopropyl]butan-1-ol (500 mg, 1.616 mmol) in THF (11 mL) at 0° C. was added KOtBu (804.1 μL, 6.464 mmol) and the mixture was stirred at 50° C. for 20 minutes, then removed the acetonitrile by rotary evaporation, dissolved the residue in DMSO, filtered and chromatographed on a 275 g Reverse Phase Column eluting with 20-100% ACN/Water giving 3-[[4-(2,6-dimethylphenyl)-6-[2-(2-tetrahydropyran-4-ylethylamino)-4-[1-(trifluoromethyl)cyclopropyl]butoxy]pyrimidin-2-yl]sulfamoyl]benzoic acid (330 mg, 30%) ESI-MS m/z calc. 690.2699, found 691.1 $(M+1)^+$; Retention time: 0.51 minutes, LC method D.

Step 5: 6-(2,6-dimethylphenyl)-2,2-dioxo-12-(2-tetrahydropyran-4-ylethyl)-11-[2-[1-(trifluoromethyl)cyclopropyl]ethyl]-9-oxa-2λ6-thia-3,5,12,19-tetrazatricyclo[12.3.1.14,8]nonadeca-1(18),4(19),5,7,14,16-hexaen-13-one, and 6-(2,6-dimethylphenyl)-2,2-dioxo-9-(2-tetrahydropyran-4-ylethyl)-10-[2-[1-(trifluoromethyl)cyclopropyl]ethyl]-12-oxa-2λ6-thia-3,5,9,19-tetrazatricyclo[12.3.1.14,8]nonadeca-1(18),4(19),5,7,14,16-hexaen-13-one (Compound 26)

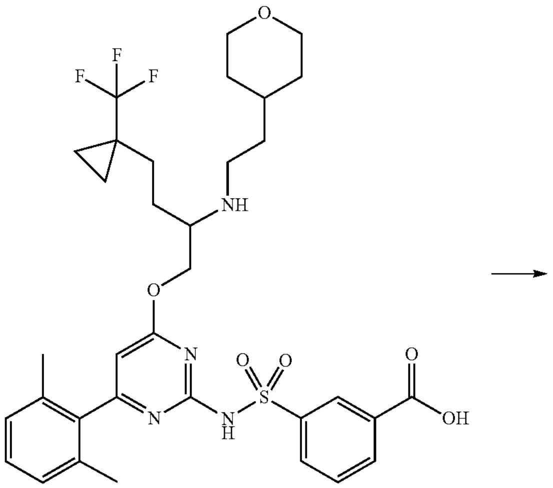

-continued

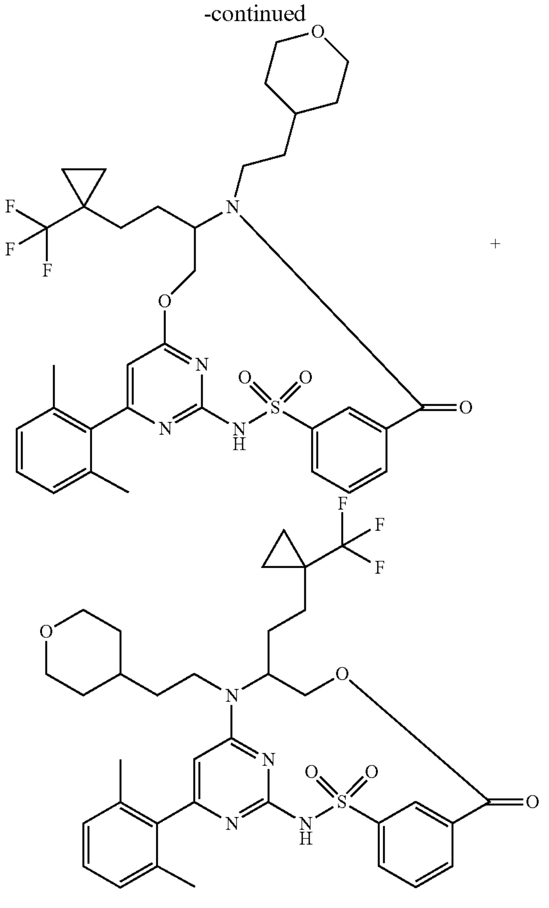

3-[[4-(2,6-dimethylphenyl)-6-[2-(2-tetrahydropyran-4-ylethylamino)-4-[1-(trifluoromethyl)cyclopropyl]butoxy]pyrimidin-2-yl]sulfamoyl]benzoic acid (325 mg, 0.4705 mmol) was combined with HATU (232.5 mg, 0.6115 mmol) in DMF (19.5 mL), and DIPEA (246 μL, 1.412 mmol) was added. The mixture was stirred at room temperature overnight, then diluted with EtOAc and washed with saturated aqueous ammonium chloride (2×), saturated aqueous sodium bicarbonate (2×) and brine (1×), then dried (magnesium sulfate), filtered and concentrated to an orange oil which was chromatographed on a 275 g Reverse Phase Column eluting with 20-100% ACN/Water giving the intended lactam product still contaminated with the lactone side product. Fractions containing product were concentrated, filtered, and purified using a reverse phase HPLC-MS method using a Luna $C_{18}$ (2) column (75×30 mm, 5 m particle size) sold by Phenomenex (pn: 00C-4252-U0-AX), and a dual gradient run from 50-99% mobile phase B over 15.0 minutes (mobile phase A=water (5 mM HCl), mobile phase B=acetonitrile, flow rate=50 mL/min, injection volume=950 μL and column temperature=25° C.) giving the intended lactam product, 6-(2,6-dimethylphenyl)-2,2-dioxo-12-(2-tetrahydropyran-4-ylethyl)-11-[2-[1-(trifluoromethyl)cyclopropyl]ethyl]-9-oxa-2$\lambda^6$-thia-3,5,12,19-tetrazatricyclo[12.3.1.14,8]nonadeca-1(18),4(19),5,7,14,16-hexaen-13-one as a white solid (71.7 mg, 23%)$^1$H NMR (400 MHz, Chloroform-d) δ 8.50 (t, J=1.8 Hz, 1H), 8.12 (d, J=7.8 Hz, 1H), 7.74 (dt, J=7.7, 1.4 Hz, 1H), 7.62 (t, J=7.8 Hz, 1H), 7.21 (t, J=7.6 Hz, 1H), 7.00 (d, J=7.6 Hz, 2H), 6.14 (s, 1H), 5.28 (dd, J=10.7, 3.9 Hz, 1H), 4.08-3.93 (m, 3H), 3.93-3.75 (m, 2H), 3.47-3.35 (m, 2H), 2.98 (d, J=2.9 Hz, 1H), 1.92 (d, J=30.5 Hz, 6H), 1.84-1.74 (m, 1H), 1.69 (dt, J=15.0, 7.5 Hz, 4H), 1.53 (d, J=3.8 Hz, 1H), 1.47-1.34 (m, 3H), 0.99 (d, J=3.3 Hz, 1H), 0.95-0.84 (m, 2H), 0.49-0.39 (m, 2H). ESI-MS m/z calc. 672.25934, found 673.1 $(M+1)^+$; Retention time: 1.85 minutes (LC method A). The reverse phase HPLC also provided 6-(2,6-dimethylphenyl)-2,2-dioxo-9-(2-tetrahydropyran-4-ylethyl)-10-[2-[1-(trifluoromethyl)cyclopropyl] ethyl]-12-oxa-2$\lambda^6$-thia-3,5,9,19-tetrazatricyclo [12.3.1.14,8]nonadeca-1(18),4(19),5,7,14,16-hexaen-13-one as a white solid (5.49 mg, 2Co) ES-MS m/z calc. 672.25934, found 673.1 (M+1); Retention time: 1.79 minutes (LC method A).

Example 16: Characterization of Compounds 27-36

The compounds in Tables 5 and 6 were prepared in a manner analogous to that described above using commercially available reagents and intermediates described herein.

TABLE 5

| Compound number | Structure | LCMS Rt (min) | Calc. mass | M + 1 | LCMS Method |
|---|---|---|---|---|---|
| 27 | 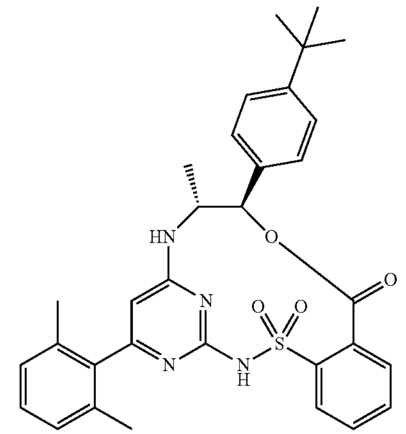 [SMILES: Cc1cccc(C)c1-c1cc2nc(n1)NS(=O)(=O)c1ccccc1C(=O)O[C@H](c1ccc(C(C)(C)C)cc1)[C@@H](C)N2] | 20.6 | 570.23 | 571 | A |
| 28 | 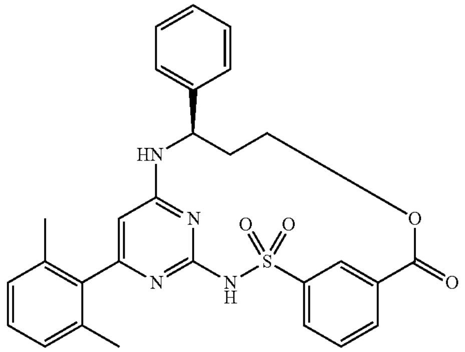 [SMILES: Cc1cccc(C)c1-c1cc2nc(n1)NS(=O)(=O)c1cccc(c1)C(=O)OCC[C@H](c1ccccc1)N2] | 1.6 | 514.167 | 515.3 | A |
| 29 | 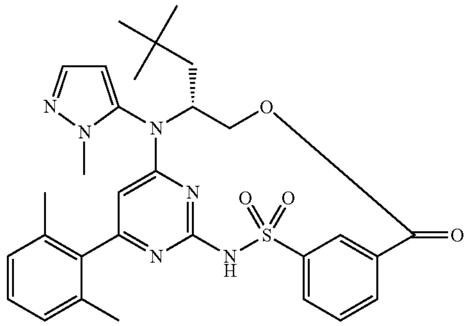 [SMILES: Cc1cccc(C)c1-c1cc2nc(n1)NS(=O)(=O)c1cccc(c1)C(=O)OC[C@@H](CC(C)(C)C)N2c1ccnn1C] | 1.74 | 574.236 | 575.3 | A |

TABLE 5-continued
| Compound number | Structure | LCMS Rt (min) | Calc. mass | M + 1 | LCMS Method |
|---|---|---|---|---|---|
| 30 | 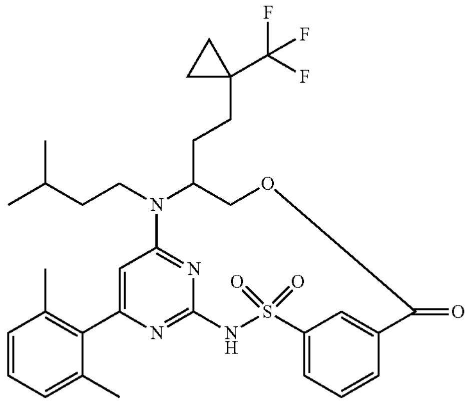 [SMILES: Cc1cccc(C)c1-c1cc2nc(n1)NS(=O)(=O)c1cccc(c1)C(=O)OCC(CCC1(C(F)(F)F)CC1)N2CCC(C)C] | 2.1 | 630.249 | 631.3 | A |
| 31 | 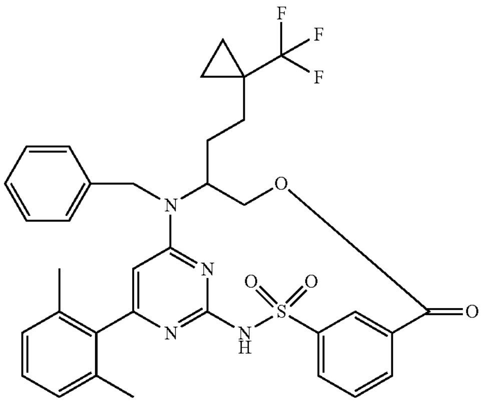 [SMILES: Cc1cccc(C)c1-c1cc2nc(n1)NS(=O)(=O)c1cccc(c1)C(=O)OCC(CCC1(C(F)(F)F)CC1)N2Cc1ccccc1] | 1.99 | 650.217 | 651.4 | A |
| 32 | 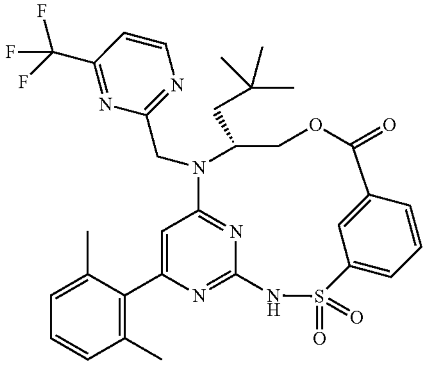 [SMILES: Cc1cccc(C)c1-c1cc2nc(n1)NS(=O)(=O)c1cccc(c1)C(=O)OC[C@@H](CC(C)(C)C)N2Cc1nccc(C(F)(F)F)n1] | 1.72 | 654.224 | 655.2 | A |
| 33 | 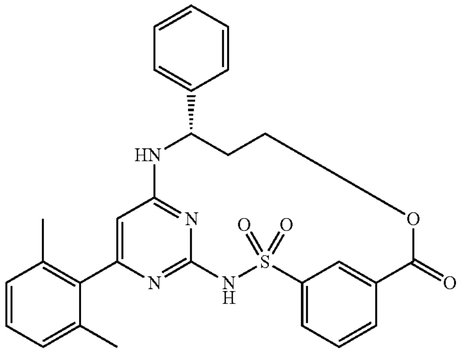 [SMILES: Cc1cccc(C)c1-c1cc2nc(n1)NS(=O)(=O)c1cccc(c1)C(=O)OCC[C@@H](c1ccccc1)N2] | 1.58 | 514.167 | 515.3 | A |

TABLE 5-continued
| Compound number | Structure | LCMS Rt (min) | Calc. mass | M + 1 | LCMS Method |
|---|---|---|---|---|---|
| 34 | 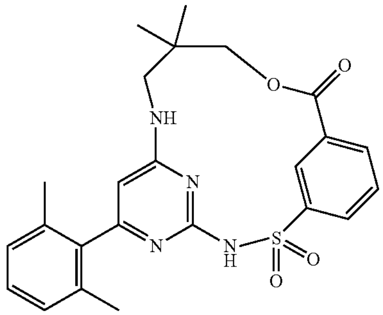 [SMILES: Cc1cccc(C)c1-c1cc2nc(n1)NS(=O)(=O)c1cccc(c1)C(=O)OCC(C)(C)CN2] | 1.41 | 466.167 | 467.3 | A |
| 35 | 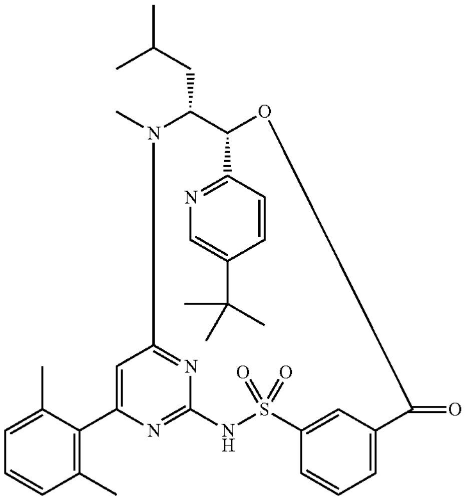 [SMILES: Cc1cccc(C)c1-c1cc2nc(n1)NS(=O)(=O)c1cccc(c1)C(=O)O[C@H](c1ccc(C(C)(C)C)cn1)[C@@H](CC(C)C)N2C] | 1.92 | 627.288 | 628.5 | A |
| 36 | 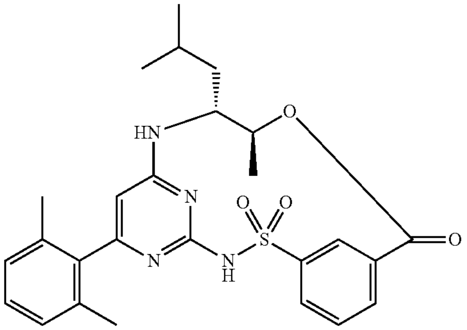 [SMILES: Cc1cccc(C)c1-c1cc2nc(n1)NS(=O)(=O)c1cccc(c1)C(=O)O[C@@H](C)[C@@H](CC(C)C)N2] | 1.5 | 494.199 | 495.4 | A |
TABLE 6
| Compound number | NMR |
|---|---|
| 29 | $^1$H NMR (400 MHz, Methanol-$d_4$) δ 8.79 (s, 1H), 7.96 (d, J = 7.8 Hz, 1H), 7.82 (d, J = 7.5 Hz, 1H), 7.61 (t, J = 7.8 Hz, 1H), 7.49 (d, J = 2.1 Hz, 1H), 7.08 (d, J = 8.0 Hz, 1H), 6.96 (s, 2H), 6.32 (s, 1H), 6.14 (s, 1H), 5.70 (s, 1H), 4.98 (s, 1H), 4.03 (s, 1H), 3.58 (s, 2H), 3.25 (s, 7H), 1.93 (s, 6H), 1.47 (s, 2H), 1.19 (s, 0H), 1.03 (s, 10H), 0.81 (s, 1H). |
| 34 | $^1$H NMR (400 MHz, $CDCl_3$) δ 9.67 (s, 2H), 8.13 (t, J = 1.7 Hz, 1H), 7.99 (ddd, J = 7.8, 1.9, 1.1 Hz, 1H), 7.83 (dt, J = 7.8, 1.3 Hz, 1H), 7.55 (t, J = 7.7 Hz, 1H), 7.29 (dd, J = 8.1, 7.1 Hz, 1H), 7.18-7.11 (m, 2H), 5.70 (s, 1H), 3.97 (s, 2H), 3.87 (s, 2H), 2.28 (s, 6H), 1.31 (s, 6H). |

Example 17: Preparation of Compound 37

Step 1: 3-[[4-[(2-Amino-4-methyl-pentyl)amino]-6-(2,6-dimethylphenyl)pyrimidin-2-yl]sulfamoyl]benzoic acid

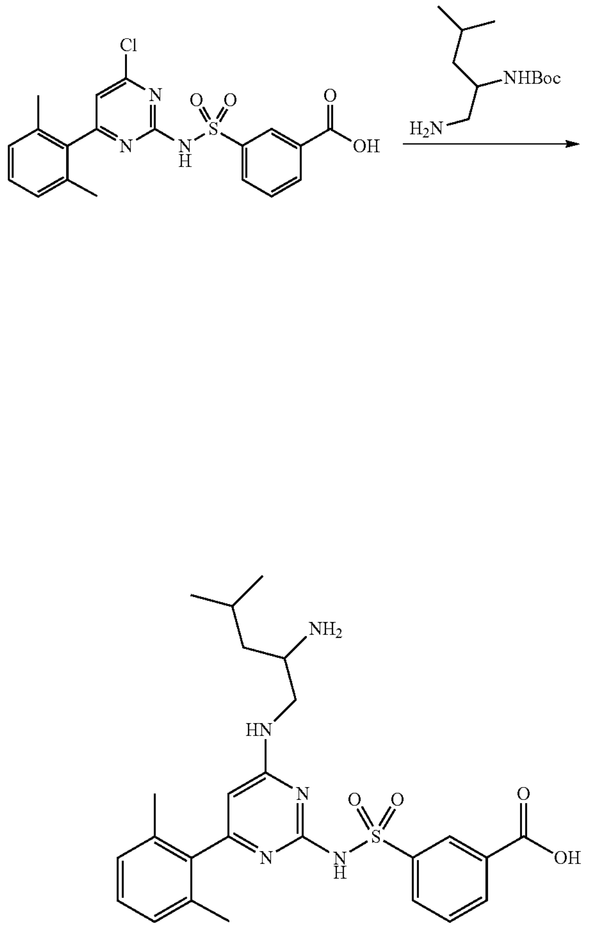

3-[[4-Chloro-6-(2,6-dimethylphenyl)pyrimidin-2-yl]sulfamoyl]benzoic acid (100 mg, 0.2393 mmol), tert-butyl N-[1-(aminomethyl)-3-methyl-butyl]carbamate (62.6 mg, 0.2894 mmol), and potassium carbonate (130 mg, 0.9406 mmol) were combined in THF (1 mL) and heated at 65° C. for 16 hours. The reaction was partitioned between ethyl acetate and a 1M HCl solution. The organics were washed with brine, dried over sodium sulfate, and evaporated. The rude product was dissolved in HCl in dioxane (2 μL of 4 M, 0.008000 mmol) and stirred for 20 minutes. The reaction was evaporated and the crude material was purified by LC/MS utilizing a gradient of 1-99% acetonitrile in 5 mM aqueous HCl to yield 3-[[4-[(2-amino-4-methyl-pentyl)amino]-6-(2,6-dimethylphenyl)pyrimidin-2-yl]sulfamoyl]benzoic acid (hydrochloride salt) (50.7 mg, 40%). ESI-MS m/z calc. 497.2097, found 498.4 $(M+1)^+$; Retention time: 0.46 minutes; LC method D.

Step 2: 6-(2,6-Dimethylphenyl)-11-isobutyl-2,2-dioxo-2 λ6-thia-3,5,9,12,19-pentazatricyclo[12.3.1.14,8]nonadeca-1(18),4(19),5,7,14,16-hexaen-13-one (Compound 37)

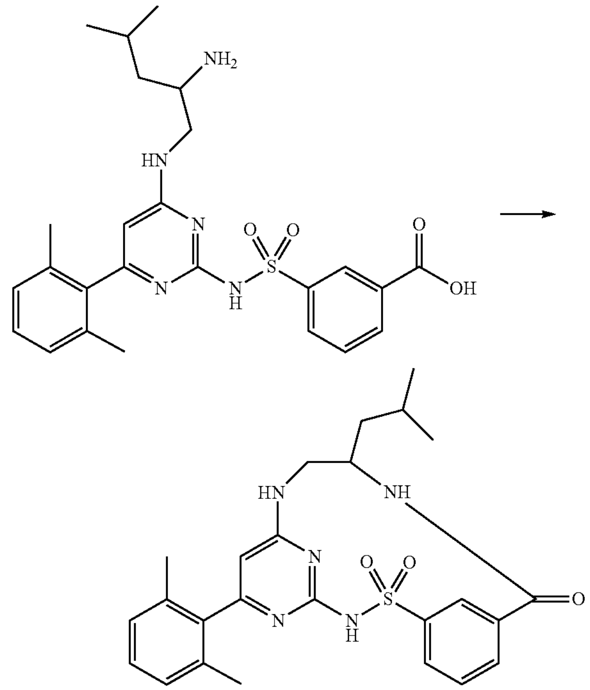

3-[[4-[(2-amino-4-methyl-pentyl)amino]-6-(2,6-dimethylphenyl)pyrimidin-2-yl]sulfamoyl]benzoic acid (hydrochloride salt) (27 mg, 0.05056 mmol), HATU (21 mg, 0.05523 mmol), and triethylamine (31 μL, 0.2224 mmol) were combined in DMF (1 mL) and stirred for 30 minutes. The reaction was filtered and purified by LC/MS utilizing a gradient of 1-99% acetonitrile in 5 mM aqueous HCl to yield 6-(2,6-dimethylphenyl)-11-isobutyl-2,2-dioxo-2$\lambda^6$-thia-3,5,9,12,19-pentazatricyclo[12.3.1.14,8]nonadeca-1(18),4(19),5,7,14,16-hexaen-13-one (16.2 mg, 67%). ESI-MS m/z calc. 479.1991, found 480.4 $(M+1)^+$; Retention time: 1.51 minutes; LC method A.

Example 18: Preparation of Compound 38

Step 1: tert-Butyl N-[(1R)-2-(benzylamino)-1-methyl-ethyl]carbamate

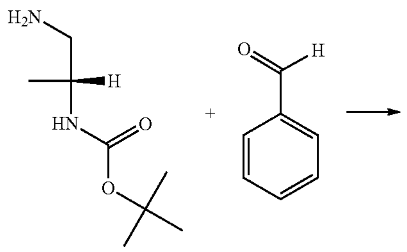

-continued

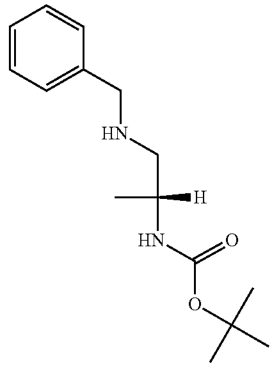

tert-Butyl N-[(1R)-2-amino-1-methyl-ethyl]carbamate (hydrochloride salt) (100 mg, 0.4746 mmol), benzaldehyde (50 μL, 0.4919 mmol), and sodium triacetoxyborohydride (106 mg, 0.5001 mmol) were combined in DCE (1 mL) and stirred at room temperature for 16 hours. The reaction was partitioned between ethyl acetate and a saturated sodium bicarbonate solution. The organics were separated, washed with brine, dried over sodium sulfate, and evaporated. The crude material was purified by LC/MS utilizing a gradient of 1-70% acetonitrile in 5 mM aqueous HCl to yield tert-butyl N-[(1R)-2-(benzylamino)-1-methyl-ethyl]carbamate (hydrochloride salt) (43 mg, 30%) ESI-MS m/z calc. 264.18378, found 265.3 $(M+1)^+$; Retention time: 0.36 minutes; LC method D.

Step 2: 3-[[4-[[(2R)-2-Aminopropyl]-benzyl-amino]-6-(2,6-dimethylphenyl)pyrimidin-2-yl]sulfamoyl]benzoic acid, and 3-[[4-[[(1R)-2-(benzylamino)-1-methyl-ethyl]amino]-6-(2,6-dimethylphenyl)pyrimidin-2-yl]sulfamoyl]benzoic acid

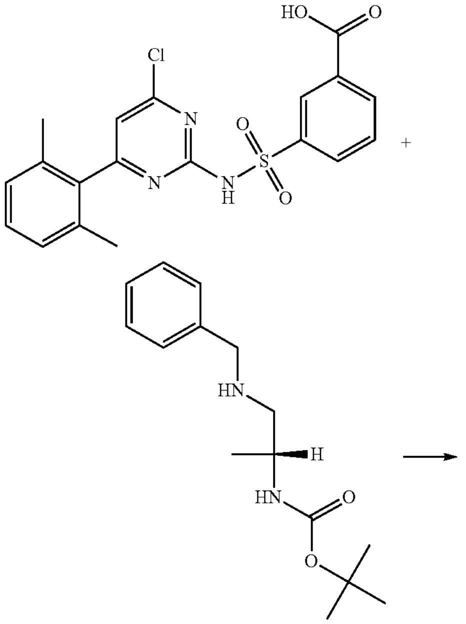

-continued

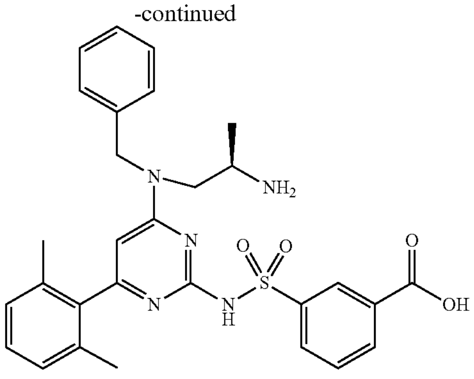

+

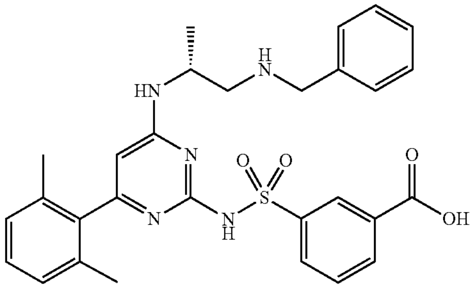

3-[[4-Chloro-6-(2,6-dimethylphenyl)pyrimidin-2-yl]sulfamoyl]benzoic acid (59.71 mg, 0.1429 mmol), 2-methylpropan-2-olate (sodium salt) (54.93 mg, 0.5716 mmol), and tert-butyl N-[(1R)-2-(benzylamino)-1-methyl-ethyl]carbamate (hydrochloride salt) (43 mg, 0.1429 mmol) were combined in THF (0.5 mL) and stirred at 60° C. for 16 hours. The reaction gave a mixture of products. The reaction mixture was partitioned between ethyl acetate and a 1M HCl solution. The organics were separated, washed with brine, dried over sodium sulfate, and evaporated. The crude material was purified by LC/MS utilizing a gradient of 1-99% acetonitrile in 5 mM aqueous HCl to yield the two Boc-protected regioisomers. The two isolated products were treated with 4 M HCl in dioxane (1 mL) and stirred for 30 minutes. The reaction was evaporated to dryness to give 3-[[4-[[(2R)-2-aminopropyl]-benzyl-amino]-6-(2,6-dimethylphenyl)pyrimidin-2-yl]sulfamoyl]benzoic acid (hydrochloride salt) (25.9 mg, 31%) ESI-MS m/z calc. 545.20966, found 546.4 $(M+1)^+$; Retention time: 0.43 minutes—major product, (LC method D); and 3-[[4-[[(1R)-2-(benzylamino)-1-methyl-ethyl]amino]-6-(2,6-dimethylphenyl)pyrimidin-2-yl]sulfamoyl]benzoic acid (hydrochloride salt) (11 mg, 13%) ESI-MS m/z calc. 545.20966, found 546.4 $(M+1)^+$; Retention time: 0.45 minutes (LC method D).

Step 3: (11R)-9-benzyl-6-(2,6-dimethylphenyl)-11-methyl-2,2-dioxo-2λ6-thia-3,5,9,12,19-pentazatricyclo[12.3.1.14,8]nonadeca-1(18),4(19),5,7,14,16-hexaen-13-one (Compound 38)

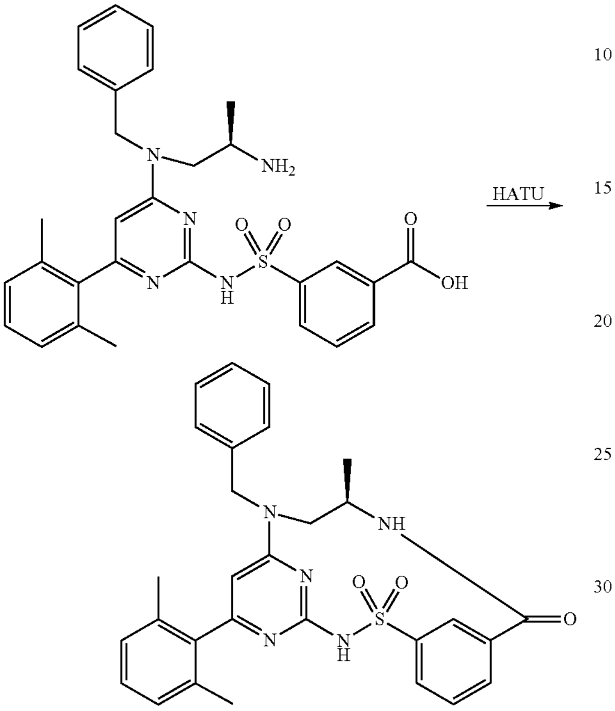

3-[[4-[[(2R)-2-Aminopropyl]-benzyl-amino]-6-(2,6-dimethylphenyl)pyrimidin-2-yl]sulfamoyl]benzoic acid (hydrochloride salt) (26 mg, 0.04466 mmol), HATU (17 mg, 0.04471 mmol), and triethylamine (20 μL, 0.1435 mmol) were combined in DMF (1 mL) and stirred at room temperature for 16 hours. The reaction mixture was filtered and purified by LC/MS utilizing a gradient of 1-99% acetonitrile in 5 mM aqueous HCl to yield (11R)-9-benzyl-6-(2,6-dimethylphenyl)-11-methyl-2,2-dioxo-2$\lambda^6$-thia-3,5,9,12,19-pentazatricyclo[12.3.1.14,8]nonadeca-1(18),4(19),5,7,14,16-hexaen-13-one (5.5 mg, 23%). ESI-MS m/z calc. 527.1991, found 528.4 $(M+1)^+$; Retention time: 1.37 minutes; LC method A.

Example 19: Preparation of Compound 39

Step 1: tert-Butyl N-[2-(isobutylamino)ethyl]carbamate

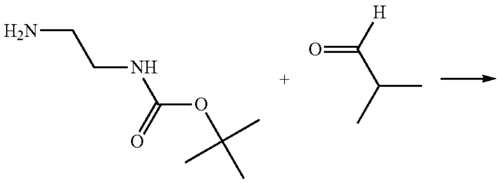

-continued

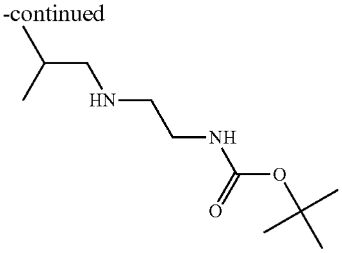

tert-Butyl N-(2-aminoethyl)carbamate (180 mg, 1.123 mmol), 2-methylpropanal (81 mg, 1.123 mmol), and sodium triacetoxyborohydride (245 mg, 1.156 mmol) were combined in DCE (4 mL) and stirred at room temperature for 4 hours. The reaction was quenched with methanol and evaporated. The crude material was purified by LC/MS utilizing a gradient of 1-99% acetonitrile in 5 mM aqueous HCl to yield tert-butyl N-[2-(isobutylamino)ethyl]carbamate (93 mg, 38%). $^1$H NMR (400 MHz, DMSO-$d_6$) δ 8.82 (s, 1H), 7.09 (s, 1H), 3.28 (q, J=6.2 Hz, 2H), 2.90 (t, J=6.5 Hz, 2H), 2.72 (d, J=7.1 Hz, 2H), 1.99 (hept, J=6.8 Hz, 1H), 1.39 (s, 9H), 0.94 (d, J=6.7 Hz, 6H).

Step 2: 3-[[4-[2-Aminoethyl(isobutyl)amino]-6-(2,6-dimethylphenyl)pyrimidin-2-yl]sulfamoyl]benzoic acid

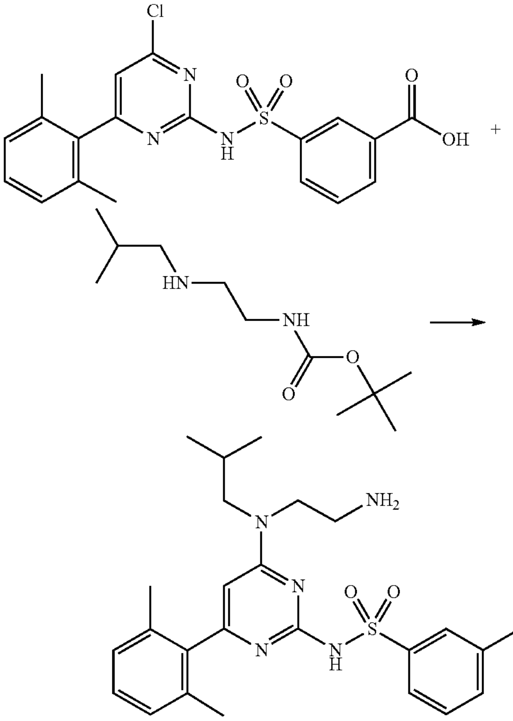

3-[[4-Chloro-6-(2,6-dimethylphenyl)pyrimidin-2-yl]sulfamoyl]benzoic acid (93 mg, 0.2226 mmol), tert-butyl N-[2-(isobutylamino)ethyl]carbamate (96 mg, 0.4438 mmol), and potassium carbonate (97 mg, 0.7019 mmol) were combined in DMSO (0.5 mL) and heated at 130° C. for 16 hours. The reaction mixture was cooled, diluted with methanol (1.5 mL), filtered, and purified by LC/MS utilizing a gradient of 1-99% acetonitrile in 5 mM aqueous HCl to yield 3-[[4-[2-

(tert-butoxycarbonylamino)ethyl-isobutyl-amino]-6-(2,6-dimethylphenyl)pyrimidin-2-yl]sulfamoyl]benzoic acid (20 mg, 14%). 3-[[4-[2-(tert-Butoxycarbonylamino)ethyl-isobutyl-amino]-6-(2,6-dimethylphenyl)pyrimidin-2-yl]sulfamoyl]benzoic acid (20 mg) was dissolved in 4 M HCl in dioxane (1 mL of 4 M, 4.000 mmol) and stirred for 20 minutes. The reaction mixture was evaporated and the crude material was purified by LC/MS utilizing a gradient of 1-99% acetonitrile in 5 mM aqueous HCl to yield 3-[[4-[2-aminoethyl(isobutyl)amino]-6-(2,6-dimethylphenyl)pyrimidin-2-yl]sulfamoyl]benzoic acid (12.6 mg, 11%) ESI-MS m/z calc. 497.2097, found 498.4 $(M+1)^+$; Retention time: 0.43 minutes; LC method D.

Step 3: 6-(2,6-Dimethylphenyl)-9-isobutyl-2,2-dioxo-2 λ6-thia-3,5,9,12,19-pentazatricyclo[12.3.1.14,8]nonadeca-1(18),4(19),5,7,14,16-hexaen-13-one (Compound 39)

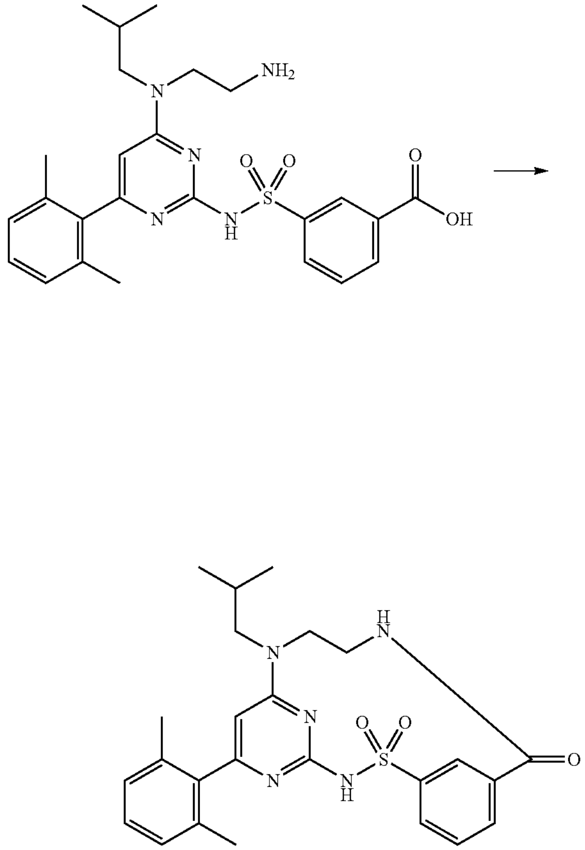

3-[[4-[2-Aminoethyl(isobutyl)amino]-6-(2,6-dimethylphenyl)pyrimidin-2-yl]sulfamoyl]benzoic acid (12.6 mg, 0.02532 mmol), HATU (10 mg, 0.02630 mmol), and triethylamine (20 μL, 0.1435 mmol) were combined in DMF (1 mL) and stirred at room temperature for 30 minutes. The reaction mixture was filtered and purified by LC/MS utilizing a gradient of 1-99% acetonitrile in 5 mM aqueous HCl to yield 6-(2,6-dimethylphenyl)-9-isobutyl-2,2-dioxo-2$\lambda^6$-thia-3,5,9,12,19-pentazatricyclo[12.3.1.14,8]nonadeca-1(18),4(19),5,7,14,16-hexaen-13-one (4.3 mg, 35%) ESI-MS m/z calc. 479.1991, found 480.4 $(M+1)^+$; Retention time: 1.29 minutes; LC method A.

Example 20: Preparation of Compound 40

Step 1: 3-[[4-[[1-(Aminomethyl)cyclohexyl]methylamino]-6-(2,6-dimethylphenyl)pyrimidin-2-yl]sulfamoyl]benzoic acid

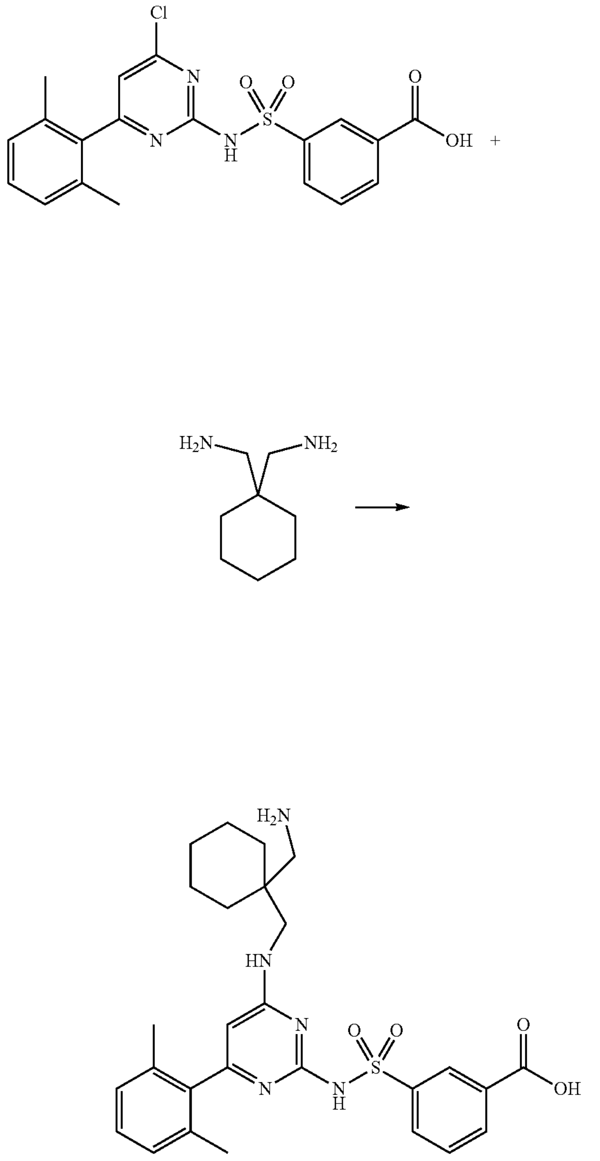

3-[[4-Chloro-6-(2,6-dimethylphenyl)pyrimidin-2-yl]sulfamoyl]benzoic acid (55 mg, 0.1316 mmol), [1-(aminomethyl)cyclohexyl]methanamine (75 mg, 0.5273 mmol), and potassium carbonate (77 mg, 0.5571 mmol) were combined in THF (0.5 μL) and heated at 65° C. for 16 hours. The reaction mixture was filtered and purified by LC/MS utilizing a gradient of 1-70% acetonitrile in 5 mM aqueous HCl to yield 3-[[4-[[1-(aminomethyl)cyclohexyl]methylamino]-6-(2,6-dimethylphenyl)pyrimidin-2-yl]sulfamoyl]benzoic acid (hydrochloride salt) (34.5 mg, 47%) ESI-MS m/z calc. 523.22534, found 524.3 $(M+1)^+$; Retention time: 0.48 minutes; LC method D.

Step 2: 6-(2,6-Dimethylphenyl)-2,2-dioxo-spiro[2λ6-thia-3,5,9,13,20-pentazatricyclo[13.3.1.14,8]icosa-1(19),4(20),5,7,15,17-hexaene-11,1'-cyclohexane]-14-one (Compound 40)

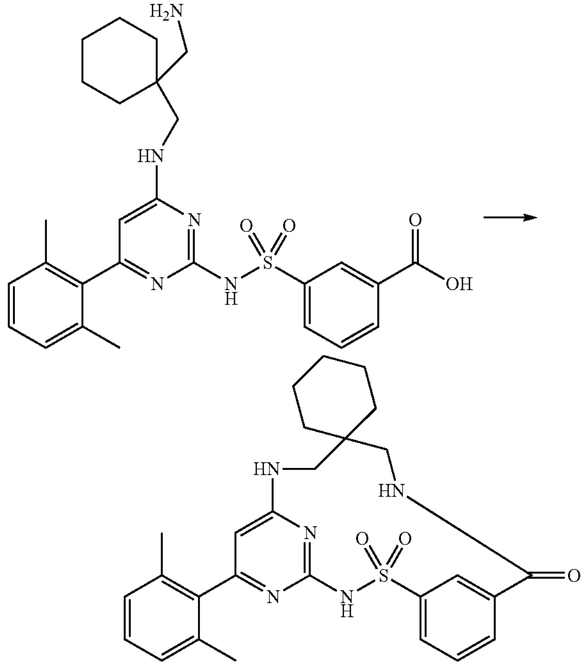

3-[[4-[[1-(Aminomethyl)cyclohexyl]methylamino]-6-(2,6-dimethylphenyl)pyrimidin-2-yl]sulfamoyl]benzoic acid (hydrochloride salt) (33 mg, 0.05892 mmol), HATU (23 mg, 0.06049 mmol), and triethylamine (40 μL, 0.2870 mmol) were combined in DMF (1 mL) and stirred for 30 minutes. The reaction was filtered and purified by LC/MS utilizing a gradient of 1-99% acetonitrile in 5 mM aqueous HCl to yield 6-(2,6-dimethylphenyl)-2,2-dioxo-spiro[2λ$^6$-thia-3,5,9,13,20-pentazatricyclo[13.3.1.14,8]icosa-1(19),4(20),5,7,15,17-hexaene-11,1'-cyclohexane]-14-one (9.7 mg, 33%) ESI-MS m/z calc. 505.21475, found 506.4 $(M+1)^+$; Retention time: 1.33 minutes; LC method A.

Example 21: Preparation of Compound 41

Step 1: 2-(3-Tributylstannylbut-3-enyl)isoindoline-1,3-dione

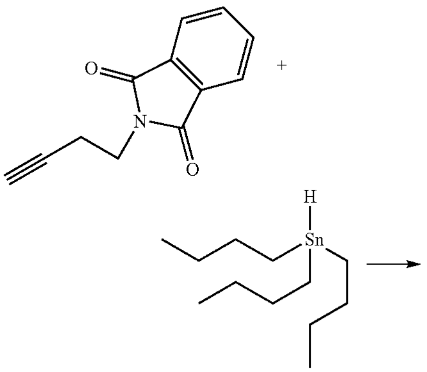

-continued

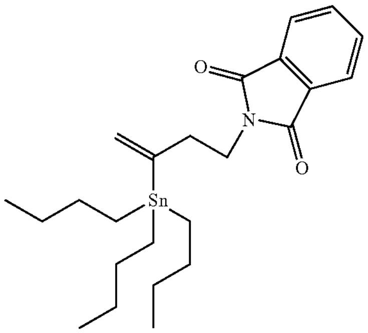

A solution of 2-but-3-ynylisoindoline-1,3-dione (8.9 g, 44.678 mmol) and tributylstannane (14.066 g, 13.0 mL, 48.327 mmol) in anhydrous DCM (125 mL) was degassed by vacuum-backfilling with nitrogen (3×) and added slowly (over 1 hour) into stirred degassed solution of [Cp*Ru(MeCN)3]$PF_6$ (500 mg, 0.9912 mmol) in anhydrous DCM (20 mL) at ambient temperature. The resulting mixture was stirred for 1 hour until reaction completion (LCMS) and concentrated to about 20-30 mL. The dark oil was directly loaded on silica gel (220 g) and purified by chromatography, eluent hexanes-EtOAc 100:0 to 80:20 gradient to afford 2-(3-tributylstannylbut-3-enyl)isoindoline-1,3-dione (17.31 g, 75%) as a light yellow oil. ESI-MS m/z calc. 491.1846, found 434.5 $(M+H-C_4H_{10})^+$; Retention time: 5.15 minutes (LC method T).

Step 2: Methyl 3-[[4-(2,6-dimethylphenyl)-6-[3-(1,3-dioxoisoindolin-2-yl)-1-methylene-propyl]pyrimidin-2-yl]-(methoxymethyl)sulfamoyl]benzoate

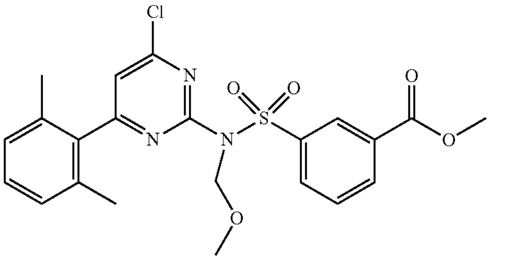

+

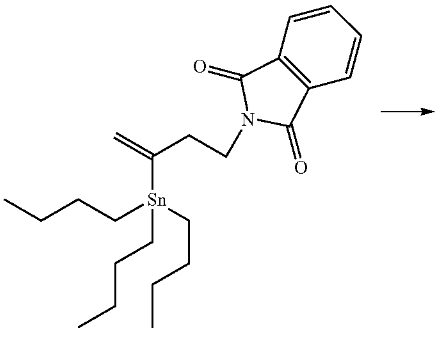

-continued

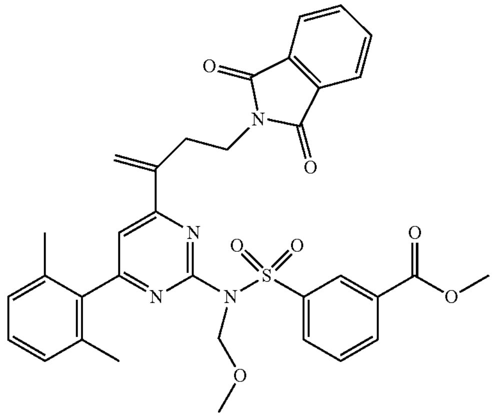

Methyl 3-[[4-chloro-6-(2,6-dimethylphenyl)pyrimidin-2-yl]-(methoxymethyl)sulfamoyl]benzoate (3 g, 6.3032 mmol, 2-(3-tributylstannylbut-3-enyl)isoindoline-1,3-dione (3.4 g, 6.9350 mmol), and anhydrous NMP (30 mL) were degassed by vacuum-backfilling with nitrogen (3×). CuI (0.12 g, 0.6301 mmol) and $Pd(PPh_3)_4$ (0.36 g, 0.3115 mmol) were added, and the solution was degassed again (3×), stirred under nitrogen at 90-100° C. for 1 day. The mixture was diluted with ether (150 mL), washed with aqueous KF (10%, 30 mL), water (30 mL), and brine (30 mL), dried over sodium sulfate, filtered, concentrated, and purified by chromatography on silica gel (120 g), eluent hexanes-ethyl acetate 100:0 to 0:100 gradient to afford methyl 3-[[4-(2,6-dimethylphenyl)-6-[3-(1,3-dioxoisoindolin-2-yl)-1-methylene-propyl]pyrimidin-2-yl]-(methoxymethyl)sulfamoyl] benzoate (2.91 g, 70%) as an off-white foam. $^1H$ NMR (250 MHz, $CDCl_3$) δ 8.64 (t, J=1.4, 1.4 Hz, 1H), 8.15 (t, J=9.3, 9.3 Hz, 2H), 7.80 (dd, J=5.6, 3.1 Hz, 2H), 7.71 (dd, J=5.5, 3.1 Hz, 2H), 7.39 (t, J=7.8, 7.8 Hz, 1H), 7.23 (dd, J=9.3, 7.4 Hz, 1H), 7.12-7.00 (m, 3H), 5.92 (s, 1H), 5.89 (s, 2H), 5.47 (s, 1H), 3.92-3.76 (m, 5H), 3.46 (s, 3H), 2.90 (t, J=7.0, 7.0 Hz, 2H), 1.90 (s, 6H). ESI-MS m/z calc. 640.19916, found 641.5 (M+H)*; Retention time: 3.69 minutes; LC method T.

Step 3: Methyl 3-[[4-(2,6-dimethylphenyl)-6-[1-[2-(1,3-dioxoisoindolin-2-yl)ethyl]cyclopropyl]pyrimidin-2-yl]-(methoxymethyl)sulfamoyl]benzoate -continued

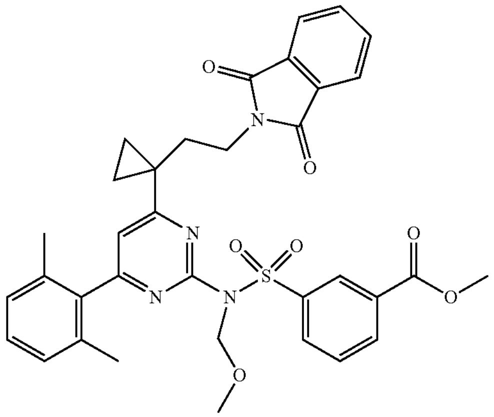

Methyl 3-[[4-(2,6-dimethylphenyl)-6-[3-(1,3-dioxoisoindolin-2-yl)-1-methylene-propyl]pyrimidin-2-yl]-(methoxymethyl)sulfamoyl]benzoate (400 mg, 0.6243 mmol) and $Pd(OAc)_2$ (7 mg, 0.0312 mmol) were dissolved in DCM (4 mL) and the solution cooled with ice bath. A solution of diazomethane (12 mL of 1 M, 12.000 mmol) in diethyl ether was added in small portions over 1-2 hours until reaction completion. The mixture was concentrated and purified by chromatography on silica gel (40 g, load in DCM), eluent hexanes-ethyl acetate 100:0 to 0:100 gradient to afford methyl 3-[[4-(2,6-dimethylphenyl)-6-[1-[2-(1,3-dioxoisoindolin-2-yl)ethyl]cyclopropyl]pyrimidin-2-yl]-(methoxymethyl)sulfamoyl]benzoate (304 mg, 71%) as an off-white foam. $^1H$ NMR (250 MHz, Chloroform-d) δ ppm 8.64 (s, 1H) 8.17 (t, J=7.25 Hz, 2H) 7.81 (dd, J=5.16, 3.19 Hz, 2H) 7.70 (dd, J=5.20, 3.20 Hz, 2H) 7.42 (t, J=7.58 Hz, 1H) 7.22 (d, J=7.69 Hz, 1H) 7.02-7.15 (m, 2H) 6.95 (s, 1H) 5.84 (s, 2H) 3.85 (s, 3H) 3.70-3.82 (m, 2H) 3.45 (s, 4H) 1.82-2.04 (m, 8H) 1.12 (br. s., 2H) 0.97 (br. s., 2H). ESI-MS m/z calc. 654.21484, found 655.7 $(M+H)^+$; Retention time: 3.83 minutes; LC method T.

Step 4: 3-[[4-[1-(2-Aminoethyl)cyclopropyl]-6-(2,6-dimethylphenyl)pyrimidin-2-yl]-(methoxymethyl) sulfamoyl]benzoic acid

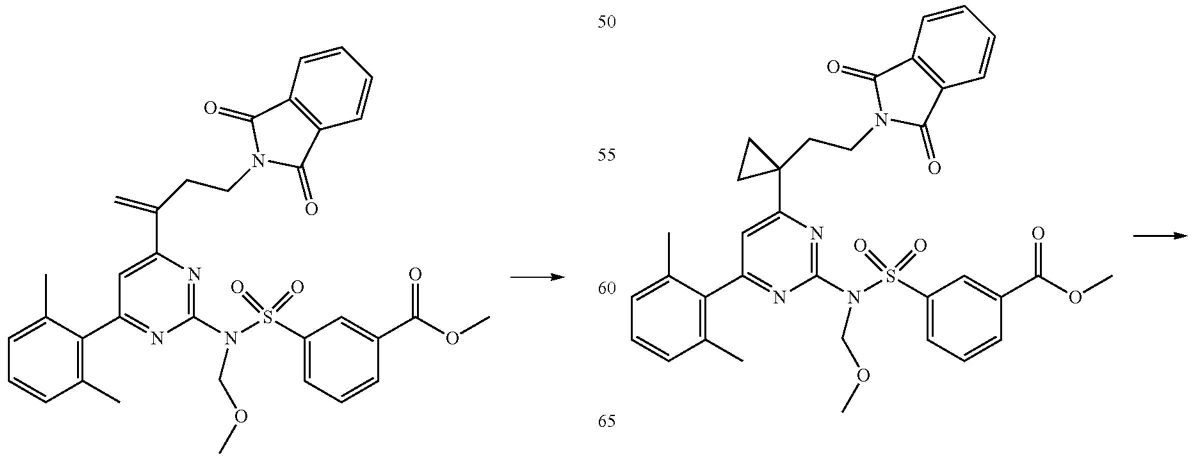

-continued

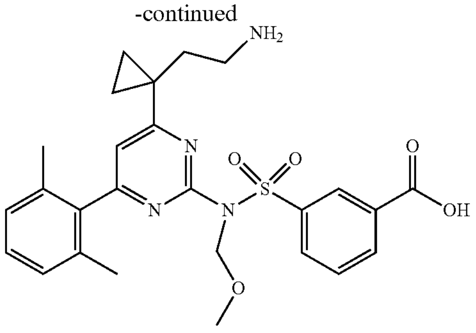

Methyl 3-[[4-(2,6-dimethylphenyl)-6-[1-[2-(1,3-dioxoisoindolin-2-yl)ethyl]cyclopropyl]pyrimidin-2-yl]-(methoxymethyl)sulfamoyl]benzoate (298 mg, 0.4551 mmol) was dissolved in MeOH (10 mL), hydrazine hydrate (114.24 mg, 0.112 mL, 2.2820 mmol) was added and the solution was stirred in a vial at 65° C. for 3 hours. Lithium hydroxide hydrate (190.98 mg, 4.5510 mmol) and water (3 mL) were added to the reaction mixture and stirred at ambient temperature for 18 hours. The mixture was concentrated to dryness under vacuum, the solid residue was extracted with DCM (2 mL), sonicated, filtered from solids, washed with DCM (2×2 mL), and concentrated to afford 3-[[4-[1-(2-aminoethyl)cyclopropyl]-6-(2,6-dimethylphenyl)pyrimidin-2-yl]-(methoxymethyl)sulfamoyl]benzoic acid (273 mg, 100%). ESI-MS m/z calc. 510.1937, found 511.6 $(M+H)^+$; Retention time: 2.45 minutes; LC method T.

Step 5: 3-[[4-(2,6-Dimethylphenyl)-6-[1-[2-(spiro[2.3]hexan-5-ylamino)ethyl]cyclopropyl]pyrimidin-2-yl]-(methoxymethyl)sulfamoyl]benzoic acid

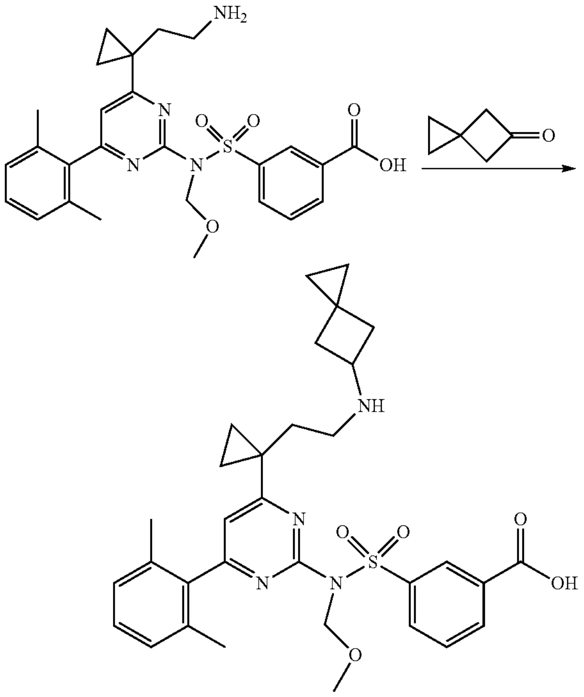

3-[[4-[1-(2-Aminoethyl)cyclopropyl]-6-(2,6-dimethylphenyl)pyrimidin-2-yl]-(methoxymethyl)sulfamoyl]benzoic acid (100 mg, 0.1958 mmol) was dissolved in DCM (2 mL), spiro[2.3]hexan-5-one (26 mg, 0.2705 mmol) was added followed by Sodium Triacetoxyborohydride (83 mg, 0.3916 mmol), and the mixture was stirred at ambient temperature for 1 d. Additional amount of spiroketone (13 mg) was added, stirred for 2 hours, then sodium triacetoxyborohydride (42 mg) was added, and the mixture was stirred for 3 days. Saturated aqueous sodium bicarbonate (2 mL) was added, the organic layer separated, the aqueous layer was extracted with DCM (2×2 mL), organic extracts were washed with brine (2 mL) and concentrated to afford 3-[[4-(2,6-dimethylphenyl)-6-[1-[2-(spiro[2.3]hexan-5-ylamino)ethyl]cyclopropyl]pyrimidin-2-yl]-(methoxymethyl)sulfamoyl]benzoic acid (0.13 g, 101%) as a light-yellow foam. ESI-MS m/z calc. 590.2563, found 591.3 $(M+H)^+$; Retention time: 2.9 minutes; LC method T.

Step 6: 6-(2,6-Dimethylphenyl)-2,2-dioxo-12-spiro[2.3]hexan-5-yl-spiro[2λ6-thia-3,5,12,19-tetrazatricyclo[12.3.1.14,8]nonadeca-1(18),4(19),5,7,14,16-hexaene-9,1'-cyclopropane]-13-one (Compound 41)

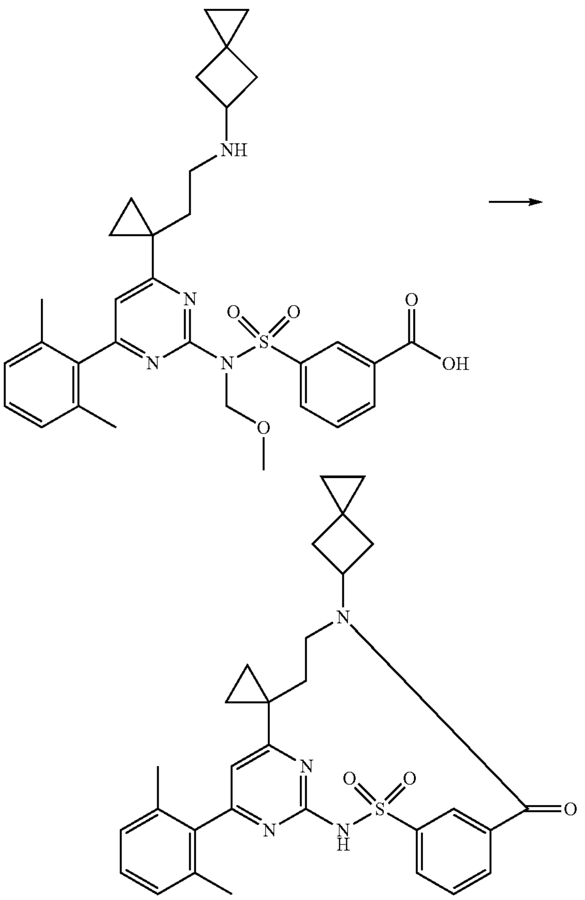

3-[[4-(2,6-Dimethylphenyl)-6-[1-[2-(spiro[2.3]hexan-5-ylamino)ethyl]cyclopropyl]pyrimidin-2-yl]-(methoxymethyl)sulfamoyl]benzoic acid (115.19 mg, 0.195 mmol) and HATU (89 mg, 0.2341 mmol) were dissolved in anhydrous DMF (2 mL), DIPEA (126.14 mg, 0.17 mL, 0.9760 mmol) was added (solution turned yellow), and the mixture was stirred at ambient temperature until reaction completion (15 min). Concentrated HCl (0.5 mL of 10 M, 5.0000 mmol)

was added, and the solution was vigorously stirred for 16 hours, then heated to 40° C. for 1 hour to complete the hydrolysis. The reaction mixture was concentrated under vacuum, diluted with DMSO, and purified by preparative HPLC to afford 6-(2,6-dimethylphenyl)-2,2-dioxo-12-spiro[2.3]hexan-5-yl-spiro[2λ$^6$-thia-3,5,12,19-tetrazatricyclo[12.3.1.14,8]nonadeca-1(18),4(19),5,7,14,16-hexaene-9,1'-cyclopropane]-13-one (20.1 mg, 19%) as a white powder. $^1$H NMR (500 MHz, DMSO-$d_6$) δ 11.73 (s, 1H), 8.60 (d, J=1.9 Hz, 1H), 7.99-7.92 (m, 1H), 7.71 (d, J=6.9 Hz, 2H), 7.24-7.17 (m, 1H), 7.09 (d, J=7.6 Hz, 2H), 6.52 (s, 1H), 4.67-4.56 (m, 1H), 3.24-3.21 (m, 2H), 2.67 (t, J=10.3, 2H), 2.26-2.18 (m, 2H), 1.95 (m, 8H), 1.19 (m, 4H), 0.57-0.47 (m, 2H), 0.47-0.38 (m, 2H). ESI-MS m/z calc. 528.2195, found 529.3 (M+H)$^+$; Retention time: 2.92 minutes; LC method W.

Example 22: Compounds 42 to 57

Compounds 42 to 57, depicted in Table 7 below can be prepared following the procedures described above for Compounds 1-41, and CFTR modulating activity can be assessed using one or more of the assays outlined below.

TABLE 7

| Compound Number | Structure |
|---|---|
| 42 | 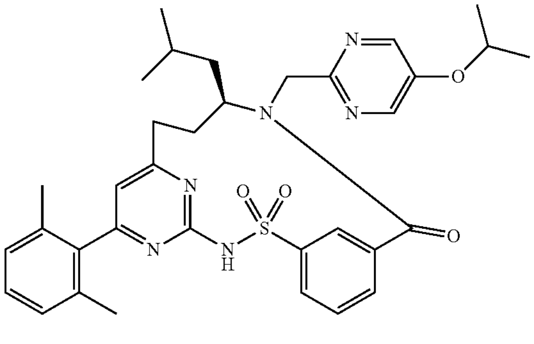 [SMILES: Cc1cccc(C)c1-c1cc2nc(n1)NS(=O)(=O)c1cccc(c1)C(=O)N(Cc1ncc(OC(C)C)cn1)[C@H](CC(C)C)CC2] |
| 43 | 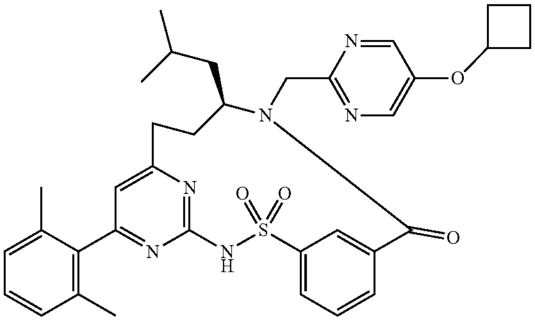 [SMILES: Cc1cccc(C)c1-c1cc2nc(n1)NS(=O)(=O)c1cccc(c1)C(=O)N(Cc1ncc(OC3CCC3)cn1)[C@H](CC(C)C)CC2] |
| 44 | 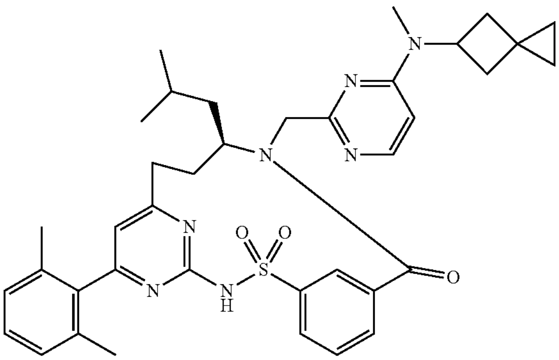 [SMILES: Cc1cccc(C)c1-c1cc2nc(n1)NS(=O)(=O)c1cccc(c1)C(=O)N(Cc1nccc(N(C)C3CC4(CC4)C3)n1)[C@H](CC(C)C)CC2] |

TABLE 7-continued
| Compound Number | Structure |
|---|---|
| 45 | 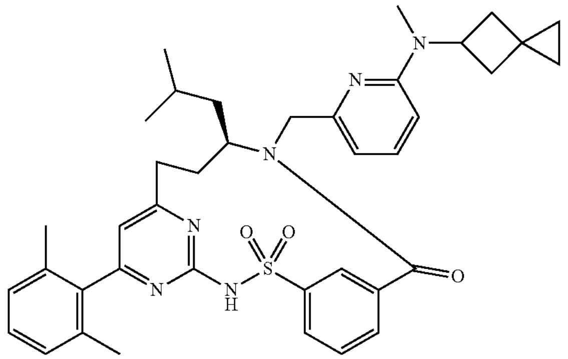 [SMILES: Cc1cccc(C)c1-c1cc2nc(n1)NS(=O)(=O)c1cccc(c1)C(=O)N(Cc1cccc(N(C)C3CC4(CC4)C3)n1)[C@H](CC(C)C)CC2] |
| 46 | 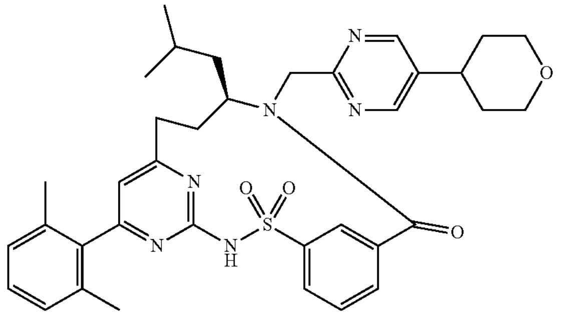 [SMILES: Cc1cccc(C)c1-c1cc2nc(n1)NS(=O)(=O)c1cccc(c1)C(=O)N(Cc1ncc(C3CCOCC3)cn1)[C@H](CC(C)C)CC2] |
| 47 | 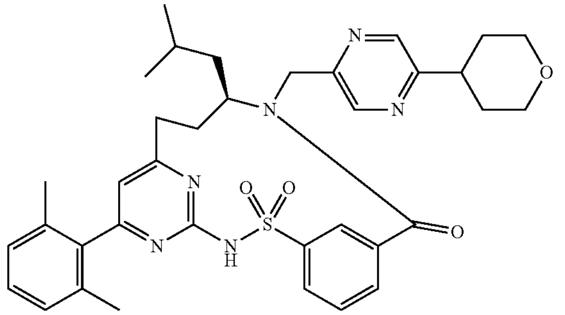 [SMILES: Cc1cccc(C)c1-c1cc2nc(n1)NS(=O)(=O)c1cccc(c1)C(=O)N(Cc1cnc(C3CCOCC3)cn1)[C@H](CC(C)C)CC2] |
| 48 | 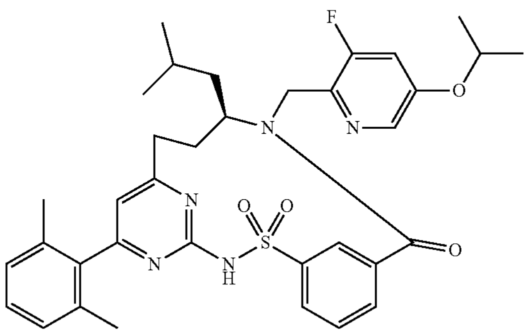 [SMILES: Cc1cccc(C)c1-c1cc2nc(n1)NS(=O)(=O)c1cccc(c1)C(=O)N(Cc1ncc(OC(C)C)cc1F)[C@H](CC(C)C)CC2] |

TABLE 7-continued
| Compound Number | Structure |
| --- | --- |
| 49 | 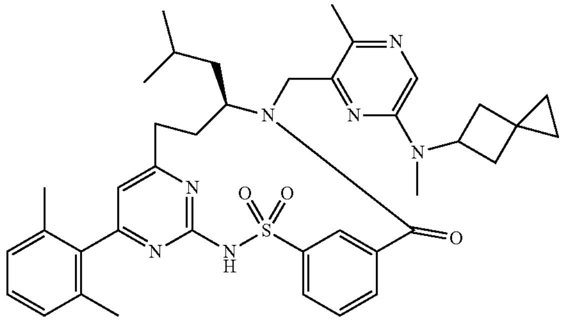 [SMILES: Cc1cccc(C)c1-c1cc2nc(n1)NS(=O)(=O)c1cccc(c1)C(=O)N(Cc1nc(N(C)C3CC4(CC4)C3)cnc1C)[C@H](CC(C)C)CC2] |
| 50 | 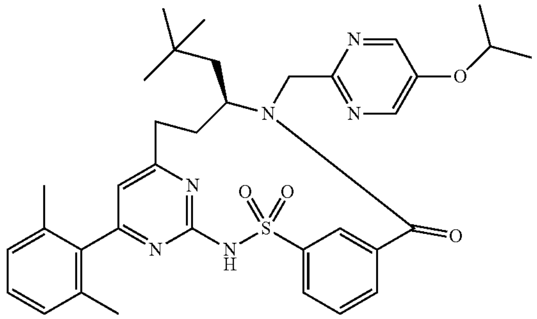 [SMILES: Cc1cccc(C)c1-c1cc2nc(n1)NS(=O)(=O)c1cccc(c1)C(=O)N(Cc1ncc(OC(C)C)cn1)[C@H](CC(C)(C)C)CC2] |
| 51 | 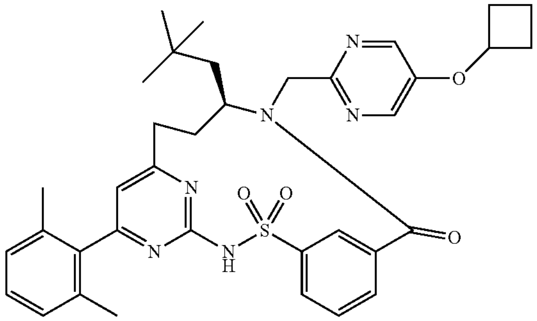 [SMILES: Cc1cccc(C)c1-c1cc2nc(n1)NS(=O)(=O)c1cccc(c1)C(=O)N(Cc1ncc(OC3CCC3)cn1)[C@H](CC(C)(C)C)CC2] |
| 52 | 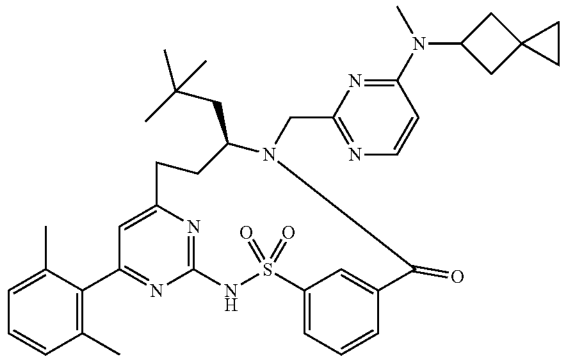 [SMILES: Cc1cccc(C)c1-c1cc2nc(n1)NS(=O)(=O)c1cccc(c1)C(=O)N(Cc1nccc(N(C)C3CC4(CC4)C3)n1)[C@H](CC(C)(C)C)CC2] |

TABLE 7-continued
| Compound Number | Structure |
|---|---|
| 53 | 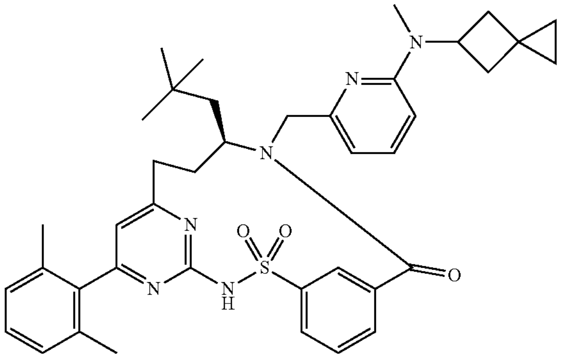 [SMILES: Cc1cccc(C)c1-c1cc2nc(n1)NS(=O)(=O)c1cccc(c1)C(=O)N(Cc1cccc(N(C)C3CC4(CC4)C3)n1)[C@H](CC(C)(C)C)CC2] |
| 54 | 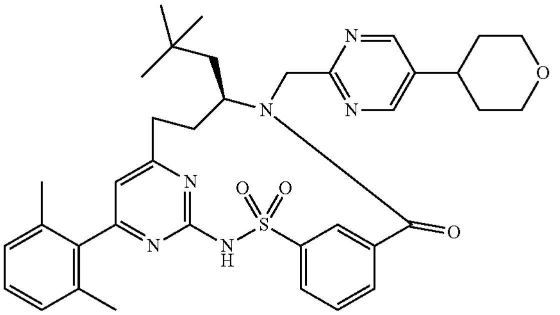 [SMILES: Cc1cccc(C)c1-c1cc2nc(n1)NS(=O)(=O)c1cccc(c1)C(=O)N(Cc1ncc(C3CCOCC3)cn1)[C@H](CC(C)(C)C)CC2] |
| 55 | 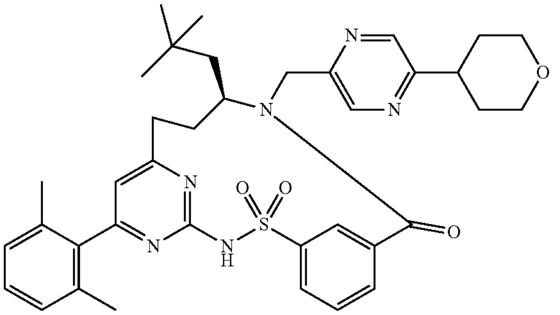 [SMILES: Cc1cccc(C)c1-c1cc2nc(n1)NS(=O)(=O)c1cccc(c1)C(=O)N(Cc1cnc(C3CCOCC3)cn1)[C@H](CC(C)(C)C)CC2] |
| 56 | 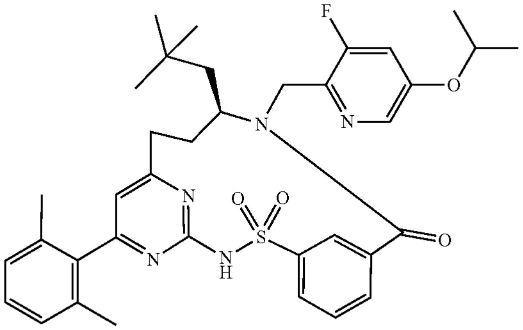 [SMILES: Cc1cccc(C)c1-c1cc2nc(n1)NS(=O)(=O)c1cccc(c1)C(=O)N(Cc1ncc(OC(C)C)cc1F)[C@H](CC(C)(C)C)CC2] |

TABLE 7-continued

| Compound Number | Structure |
|---|---|
| 57 | 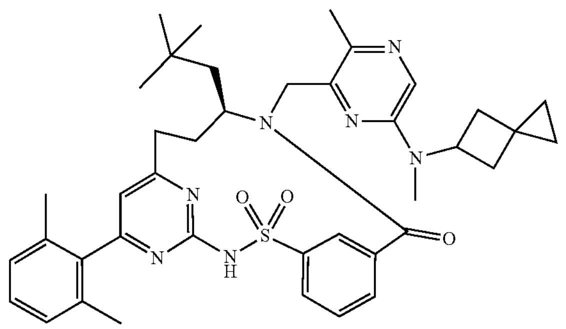 [SMILES: Cc1cccc(C)c1-c1cc2nc(n1)NS(=O)(=O)c1cccc(c1)C(=O)N(Cc1nc(N(C)C3CC4(CC4)C3)cnc1C)[C@H](CC(C)(C)C)CC2] |

VI. Bioactivity Data for Compounds 1-57

Any of the compounds disclosed herein, including Compounds 1-41 and 42-57 can be assayed ofr CFTR modulating activity according to the assays described below.

3T3 Assay

1. Membrane Potential Optical Methods for Assaying F508del Modulation Properties of Compounds The assay utilizes fluorescent voltage sensing dyes to measure changes in membrane potential using a fluorescent plate reader (e.g., FLIPR III, Molecular Devices, Inc.) as a readout for increase in functional F508del in NIH 3T3 cells. The driving force for the response is the creation of a chloride ion gradient in conjunction with channel activation by a single liquid addition step after the cells have previously been treated with compounds and subsequently loaded with a voltage sensing dye.

2. Identification of Corrector Compounds

To identify correctors of F508del, a single-addition HTS assay format was developed. This HTS assay utilizes fluorescent voltage sensing dyes to measure changes in membrane potential on the FLIPR III as a measurement for increase in gating (conductance) of F508del in F508del NIH 3T3 cells. The F508del NIH 3T3 cell cultures were incubated with the corrector compounds at a range of concentrations for 18-24 hours at 37° C., and subsequently loaded with a redistribution dye. The driving force for the response is a $Cl^-$ ion gradient in conjunction with channel activation with forskolin in a single liquid addition step using a fluorescent plate reader such as FLIPR III. The efficacy and potency of the putative F508del correctors was compared to that of the known corrector, lumacaftor, in combination with acutely added 300 nM Ivacaftor.

3. Solutions

Bath Solution #1: (in mM) NaCl 160, KCl 4.5, $CaCl_2$) 2, $MgCl_2$ 1, HEPES 10, pH 7.4 with NaOH.

Chloride-free bath solution: Chloride salts in Bath Solution #1 (above) are substituted with gluconate salts.

4. Cell Culture

NIH3T3 mouse fibroblasts stably expressing F508del are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, b-ME, 1×pen/strep, and 25 mM HEPES in 175 $cm^2$ culture flasks. For all optical assays, the cells were seeded at ~20,000/well in 384-well Matrigel-coated plates. For the correction assays, the cells are cultured at 37° C. with and without compounds for 16-24 hours.

Enteroid Assay

5. Solutions

Base medium (ADF+++) consisted of Advanced DMEM/Ham's F12, 2 mM Glutamax, 10 mM HEPES, 1 μg/mL penicillin/streptomycin.

Intestinal enteroid maintenance medium (IEMM) consisted of ADF+++, 1×B27 supplement, 1×N2 supplement, 1.25 mM N-acetyl cysteine, 10 mM Nicotinamide, 50 ng/mL hEGF, 10 nM Gastrin, 1 μg/mL hR-spondin-1, 100 ng/mL hNoggin, TGF-b type 1 inhibitor A-83-01, 100 μg/mL Primocin, 10 μM P38 MAPK inhibitor SB202190.

Bath 1 Buffer consisted of 1 mM $MgCl_2$, 160 mM NaCl, 4.5 mM KCl, 10 mM HEPES, 10 mM Glucose, 2 mM $CaCl_2$).

Chloride Free Buffer consisted of 1 mM Magnesium Gluconate, 2 mM Calcium Gluconate, 4.5 mM Potassium Gluconate, 160 mM Sodium Gluconate, 10 mM HEPES, 10 mM Glucose.

BathI Dye Solution consisted of Bath 1 Buffer, 0.04% Pluronic F127, 20 μM Methyl Oxonol, 30 μM CaCCinh-A01, 30 μM Chicago Sky Blue.

Chloride Free Dye Solution consisted of Chloride Free Buffer, 0.04% Pluronic F127, 20 μM Methyl Oxonol, 30 μM CaCCinh-A01, 30 μM Chicago Sky Blue.

Chloride Free Dye Stimulation Solution consisted of Chloride Free Dye Solution, 10 μM forskolin, 100 μM IBMX, and 300 nM Compound III.

6. Cell Culture

Human intestinal epithelial enteroid cells were obtained from the Hubrecht Institute for Developmental Biology and Stem Cell Research, Utrecht, The Netherlands and expanded in T-Flasks as previously described (Dekkers J F, Wiegerinck C L, de Jonge H R, Bronsveld I, Janssens H M, de Winter-de Groot K M, Brandsma A M, de Jong N W M, Bijvelds M J C, Scholte B J, Nieuwenhuis E E S, van den Brink S, Clevers H, van der Ent C K, Middendorp S and M Beekman J M. A functional CFTR assay using primary cystic fibrosis intestinal organoids. Nat Med. 2013 July; 19(7):939-45.).

7. Enteroid Cell Harvesting and Seeding

Cells were recovered in cell recovery solution, collected by centrifugation at 650 rpm for 5 minutes at 4° C., resuspended in TrypLE and incubated for 5 minutes at 37° C. Cells were then collected by centrifugation at 650 rpm for 5 minutes at 4° C. and resuspended in IEMM containing 10 μM ROCK inhibitor (RI). The cell suspension was passed through a 40 μm cell strainer and resuspended at $1\times10^6$ cells/mL in IEMM containing 10 μM RI. Cells were seeded at 5000 cells/well into multi-well plates and incubated for overnight at 37° C., 95% humidity and 5% $CO_2$ prior to assay.

8. Membrane Potential Dye, Enteroid Assay A

Enteroid cells were incubated with test compound in IEMM for 18-24 hours at 37° C., 95% humidity and 5% $C_{02}$. Following compound incubations, a membrane potential dye assay was employed using a FLIPR Tetra to directly measure the potency and efficacy of the test compound on CFTR-mediated chloride transport following acute addition of 10 μM forskolin and 300 nM N-[2,4-bis(1,1-dimethylethyl)-5-hydroxyphenyl]-1,4-dihydro-4-oxoquinoline-3-carboxamide. Briefly, cells were washed 5 times in Bath 1 Buffer. Bath 1 Dye Solution was added, and the cells were incubated for 25 minutes at room temperature. Following dye incubation, cells were washed 3 times in Chloride Free Dye Solution. Chloride transport was initiated by addition of Chloride Free Dye Stimulation Solution and the fluorescence signal was read for 15 minutes. The CFTR-mediated chloride transport for each condition was determined from the AUC of the fluorescence response to acute forskolin and 300 nM N-[2,4-bis(1,1-dimethylethyl)-5-hydroxyphenyl]-1,4-dihydro-4-oxoquinoline-3-carboxamide stimulation. Chloride transport was then expressed as a percentage of the chloride transport following treatment with 3 μM (S)—N-((6-aminopyridin-2-yl)sulfonyl)-6-(3-fluoro-5-isobutoxyphenyl)-2-(2,2,4-trimethylpyrrolidin-1-yl)nicotinamide, 3 μM (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide and 300 nM acute N-[2,4-bis(1,1-dimethylethyl)-5-hydroxyphenyl]-1,4-dihydro-4-oxoquinoline-3-carboxamide triple combination control (% Activity).

9. Membrane Potential Dye, Enteroid Assay B

Enteroid cells were incubated with test compound in IEMM for 18-24 hours at 37° C., 95% humidity, and 5% $C_{02}$. Following compound incubations, a membrane potential dye assay was employed using a FLIPR Tetra to directly measure the potency and efficacy of the test compound on CFTR-mediated chloride transport following acute addition of 10 μM forskolin and 300 nM N-[2,4-bis(1,1-dimethylethyl)-5-hydroxyphenyl]-1,4-dihydro-4-oxoquinoline-3-carboxamide. Briefly, cells were washed 5 times in Bath 1 Buffer. Bath 1 Dye Solution was added and the cells were incubated for 25 minutes at room temperature. Following dye incubation, cells were washed 3 times in Chloride Free Dye Solution. Chloride transport was initiated by addition of Chloride Free Dye Stimulation Solution and the fluorescence signal was read for 15 minutes. The CFTR-mediated chloride transport for each condition was determined from the AUC of the fluorescence response to acute forskolin and 300 nM N-[2,4-bis(1,1-dimethylethyl)-5-hydroxyphenyl]-1,4-dihydro-4-oxoquinoline-3-carboxamide stimulation. Chloride transport was then expressed as a percentage of the chloride transport following treatment with 1 μM (14S)-8-[3-(2-{Dispiro[2.0.2.1]heptan-7-yl}ethoxy)-1H-pyrazol-1-yl]-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione, 3 μM (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide and 300 nM acute N-[2,4-bis(1,1-dimethylethyl)-5-hydroxyphenyl]-1,4-dihydro-4-oxoquinoline-3-carboxamide triple combination control (% Activity).

C. Biological Activity

Table 8 provides CFTR modulating activity for representative compounds of the disclosure generated using one or more of the assays disclosed herein ($EC_{50}$: +++ is <1 μM; ++ is 1-<3 μM; + is 3-<30 μM; and ND is "not detected in this assay." % Activity: +++ is >60%; ++ is 30-60%; + is <30%).

TABLE 8

| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 1 | 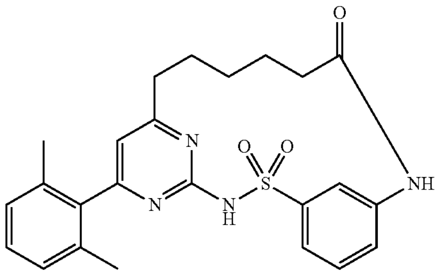 [SMILES: Cc1cccc(C)c1-c1cc2nc(n1)NS(=O)(=O)c1cccc(c1)NC(=O)CCCCC2] | +++ | +++ | | | | |
| 2 | 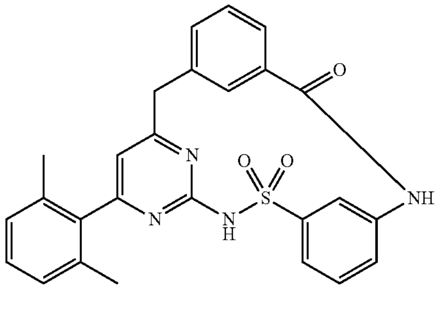 [SMILES: Cc1cccc(C)c1-c1cc2nc(n1)NS(=O)(=O)c1cccc(c1)NC(=O)c1cccc(c1)C2] | ++ | +++ | | | | |

TABLE 8-continued
| Cmpd No. | Structure | 3T3 EC50 (μM) | 3T3 Max Activity (%) | Ent. A EC50 (μM) | Ent. A Max Activity (%) | Ent. B EC50 (μM) | Ent. B Max Activity (%) |
|---|---|---|---|---|---|---|---|
| 3 | 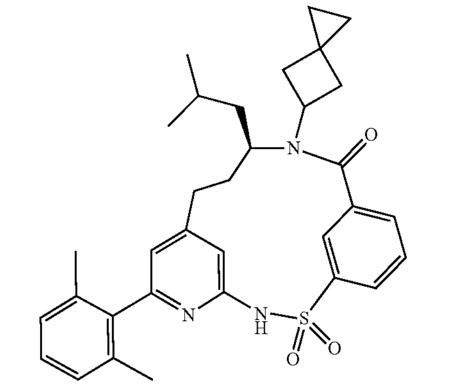 [SMILES: Cc1cccc(C)c1-c1cc2cc(n1)NS(=O)(=O)c1cccc(c1)C(=O)N(C1CC3(CC3)C1)[C@H](CC(C)C)CC2] | | | | | +++ | +++ |
| 4 | 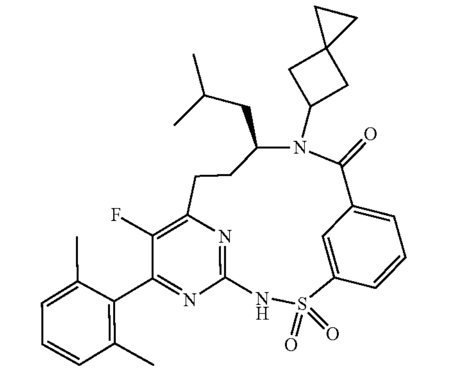 [SMILES: Cc1cccc(C)c1-c1nc2nc(c1F)CC[C@@H](CC(C)C)N(C1CC3(CC3)C1)C(=O)c1cccc(c1)S(=O)(=O)N2] | | | | | +++ | +++ |
| 5 | 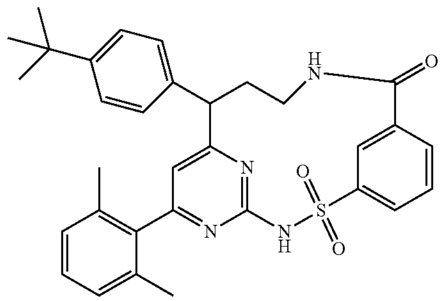 [SMILES: Cc1cccc(C)c1-c1cc2nc(n1)NS(=O)(=O)c1cccc(c1)C(=O)NCCC2c1ccc(C(C)(C)C)cc1] | | | | | +++ | +++ |
| 6 | 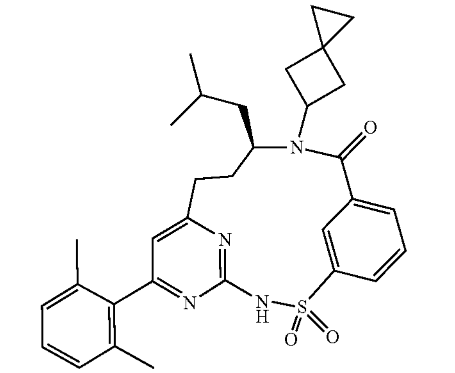 [SMILES: Cc1cccc(C)c1-c1cc2nc(n1)NS(=O)(=O)c1cccc(c1)C(=O)N(C1CC3(CC3)C1)[C@H](CC(C)C)CC2] | | | | | +++ | +++ |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
| --- | --- | --- | --- | --- | --- | --- | --- |
| 7 | 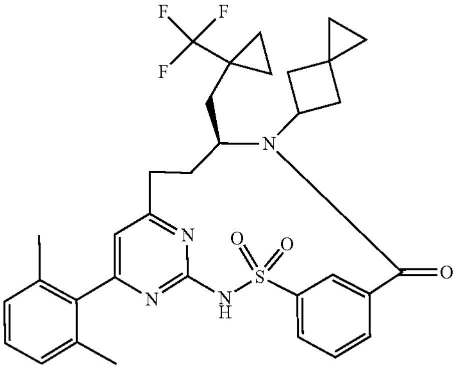 [SMILES: Cc1cccc(C)c1-c1cc2nc(n1)NS(=O)(=O)c1cccc(c1)C(=O)N(C1CC3(CC3)C1)[C@H](CC1(C(F)(F)F)CC1)CC2] | | | | | +++ | +++ |
| 8 | 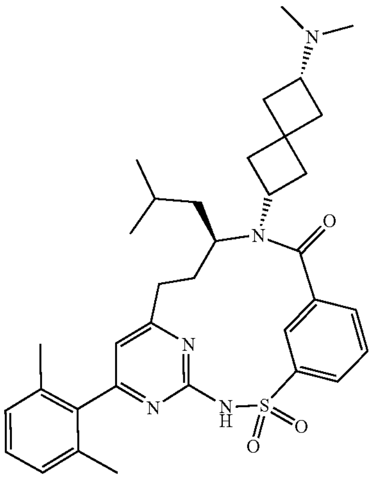 | | | | | | |
| 9 | 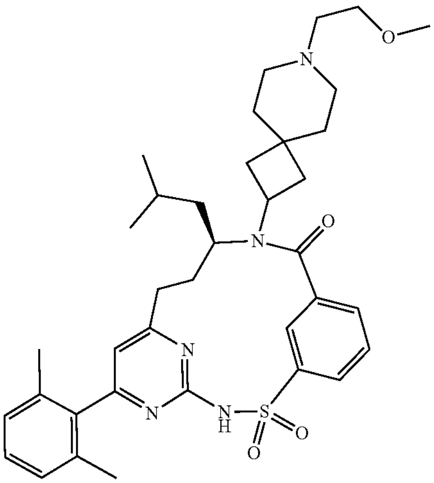 [SMILES: COCCN1CCC2(CC1)CC(N1C(=O)c3cccc(c3)S(=O)(=O)Nc3nc(cc(-c4c(C)cccc4C)n3)CC[C@H]1CC(C)C)C2] | | | | | +++ | +++ |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 10 | 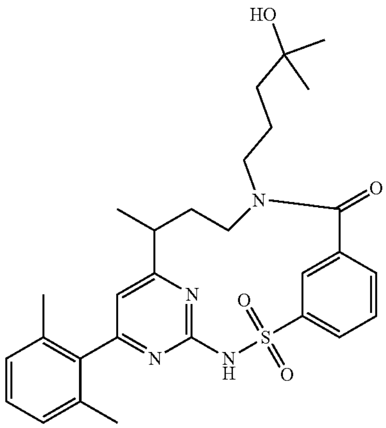 [SMILES: Cc1cccc(C)c1-c1cc2nc(n1)NS(=O)(=O)c1cccc(c1)C(=O)N(CCCC(C)(C)O)CCC2C] | | | | | ++ | +++ |
| 11 | 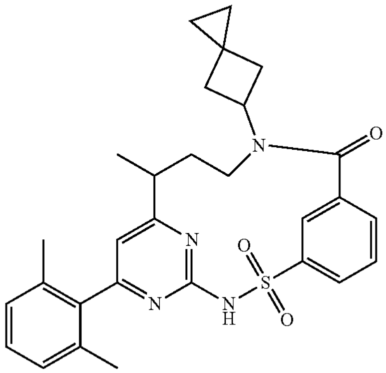 [SMILES: Cc1cccc(C)c1-c1cc2nc(n1)NS(=O)(=O)c1cccc(c1)C(=O)N(C1CC3(CC3)C1)CCC2C] | | | | | ++ | +++ |
| 12 | 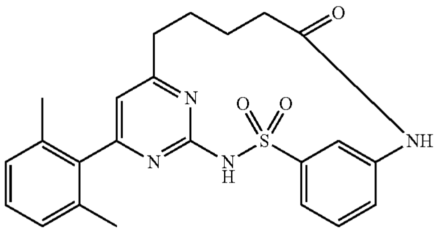 [SMILES: Cc1cccc(C)c1-c1cc2nc(n1)NS(=O)(=O)c1cccc(c1)NC(=O)CCCC2] | ++ | +++ | | | | |
| 13 | 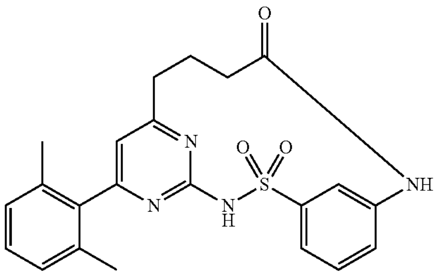 [SMILES: Cc1cccc(C)c1-c1cc2nc(n1)NS(=O)(=O)c1cccc(c1)NC(=O)CCC2] | ++ | +++ | | | | |

TABLE 8-continued
| Cmpd No. | Structure | 3T3 EC$_{50}$ (μM) | 3T3 Max Activity (%) | Ent. A EC$_{50}$ (μM) | Ent. A Max Activity (%) | Ent. B EC$_{50}$ (μM) | Ent. B Max Activity (%) |
|---|---|---|---|---|---|---|---|
| 14 | 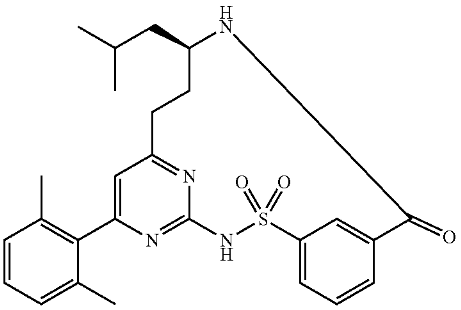 [SMILES: Cc1cccc(C)c1-c1cc2nc(n1)NS(=O)(=O)c1cccc(c1)C(=O)N[C@H](CC(C)C)CC2] | | | | | +++ | +++ |
| 15 | 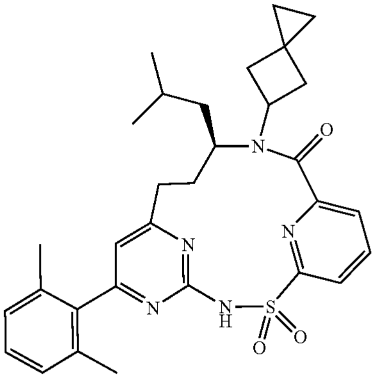 [SMILES: Cc1cccc(C)c1-c1cc2nc(n1)NS(=O)(=O)c1cccc(n1)C(=O)N(C1CC3(CC3)C1)[C@H](CC(C)C)CC2] | | | | | +++ | ++ |
| 16 | 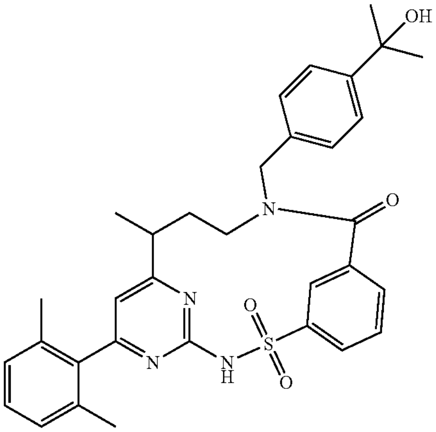 [SMILES: Cc1cccc(C)c1-c1cc2nc(n1)NS(=O)(=O)c1cccc(c1)C(=O)N(Cc1ccc(C(C)(C)O)cc1)CCC2C] | | | | | +++ | +++ |
| 17 | 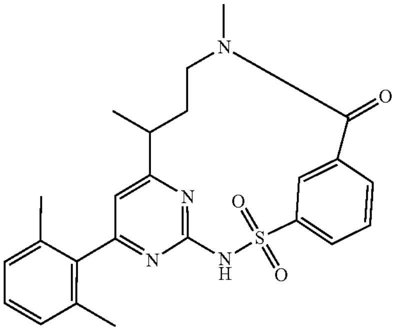 [SMILES: Cc1cccc(C)c1-c1cc2nc(n1)NS(=O)(=O)c1cccc(c1)C(=O)N(C)CCC2C] | | | | | ++ | +++ |

TABLE 8-continued
| Cmpd No. | Structure | 3T3 EC$_{50}$ (μM) | 3T3 Max Activity (%) | Ent. A EC$_{50}$ (μM) | Ent. A Max Activity (%) | Ent. B EC$_{50}$ (μM) | Ent. B Max Activity (%) |
|---|---|---|---|---|---|---|---|
| 18 | 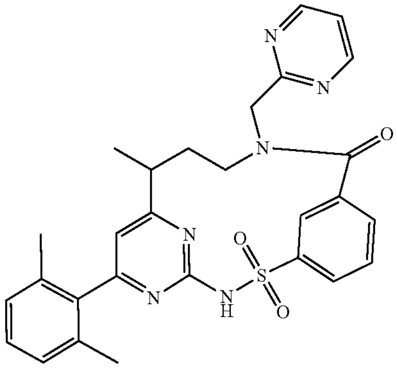 [SMILES: Cc1cccc(C)c1-c1cc2nc(n1)NS(=O)(=O)c1cccc(c1)C(=O)N(Cc1ncccn1)CCC2C] | | | | | ++ | +++ |
| 19 | 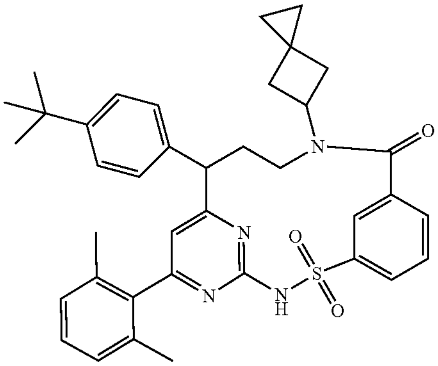 [SMILES: Cc1cccc(C)c1-c1cc2nc(n1)NS(=O)(=O)c1cccc(c1)C(=O)N(C1CC3(CC3)C1)CCC2c1ccc(C(C)(C)C)cc1] | | | | | +++ | ++ |
| 20 | 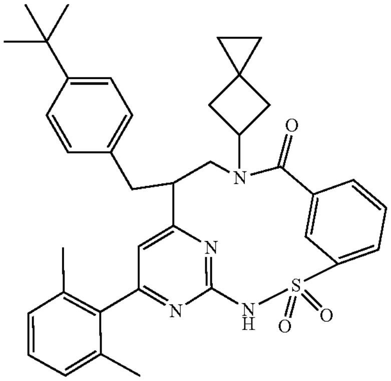 [SMILES: Cc1cccc(C)c1-c1cc2nc(n1)NS(=O)(=O)c1cccc(c1)C(=O)N(C1CC3(CC3)C1)CC2Cc1ccc(C(C)(C)C)cc1] | | | | | +++ | ++ |
| 21 | 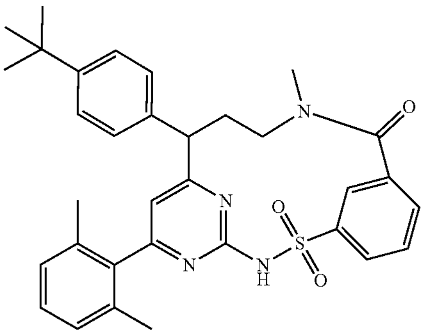 [SMILES: Cc1cccc(C)c1-c1cc2nc(n1)NS(=O)(=O)c1cccc(c1)C(=O)N(C)CCC2c1ccc(C(C)(C)C)cc1] | | | | | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 22 | 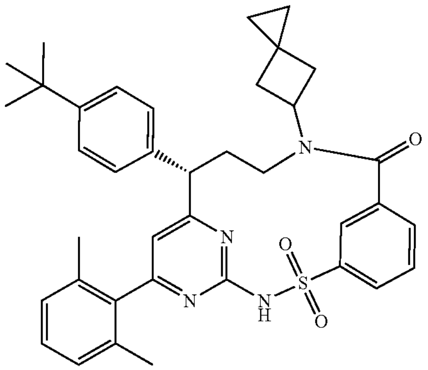 [SMILES: Cc1cccc(C)c1-c1cc2nc(n1)NS(=O)(=O)c1cccc(c1)C(=O)N(C1CC3(CC3)C1)CC[C@H]2c1ccc(C(C)(C)C)cc1] | | | | | +++ | ++ |
| 23 | 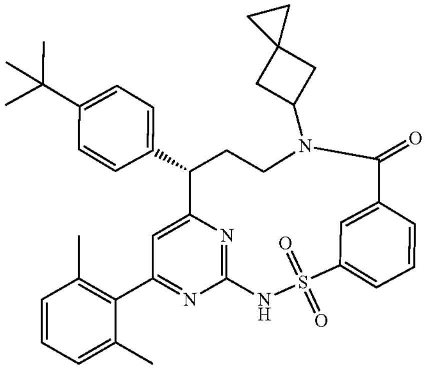 [SMILES: Cc1cccc(C)c1-c1cc2nc(n1)NS(=O)(=O)c1cccc(c1)C(=O)N(C1CC3(CC3)C1)CC[C@H]2c1ccc(C(C)(C)C)cc1] | | | | | +++ | ++ |
| 24 | 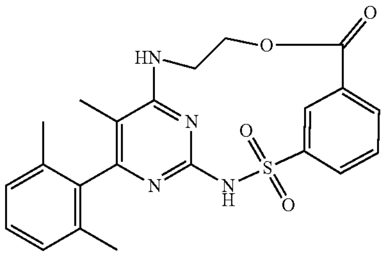 [SMILES: Cc1cccc(C)c1-c1nc2nc(c1C)NCCOC(=O)c1cccc(c1)S(=O)(=O)N2] | | | | | ND | + |
| 25 | 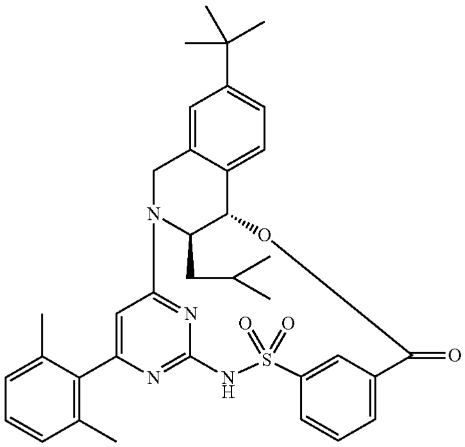 [SMILES: Cc1cccc(C)c1-c1cc2nc(n1)NS(=O)(=O)c1cccc(c1)C(=O)O[C@H]1c3ccc(C(C)(C)C)cc3CN2[C@@H]1CC(C)C] | | | | | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 26 | 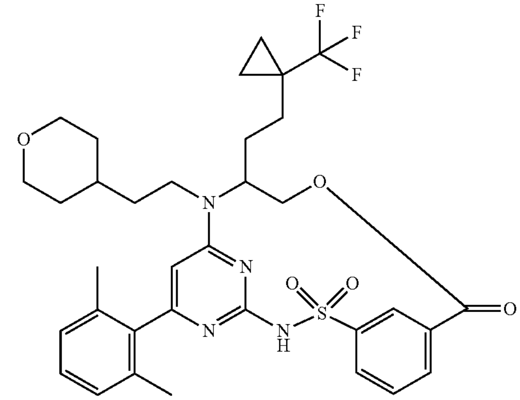 [SMILES: Cc1cccc(C)c1-c1cc2nc(n1)NS(=O)(=O)c1cccc(c1)C(=O)OCC(CCC1(C(F)(F)F)CC1)N2CCC1CCOCC1] | | | ++ | +++ | | |
| 27 | 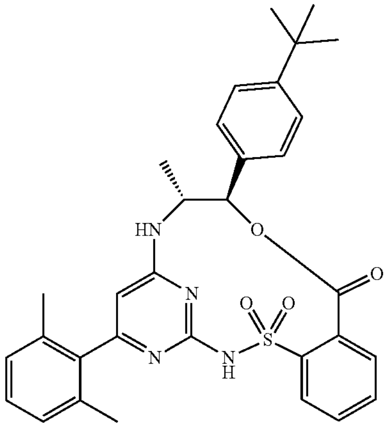 [SMILES: Cc1cccc(C)c1-c1cc2nc(n1)NS(=O)(=O)c1ccccc1C(=O)O[C@H](c1ccc(C(C)(C)C)cc1)[C@@H](C)N2] | | | ND | + | | |
| 28 | 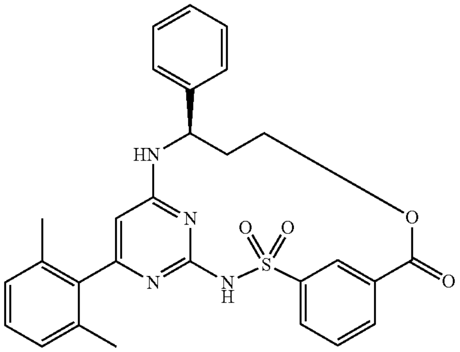 [SMILES: Cc1cccc(C)c1-c1cc2nc(n1)NS(=O)(=O)c1cccc(c1)C(=O)OCC[C@H](c1ccccc1)N2] | | | ++ | ++ | | |
| 29 | 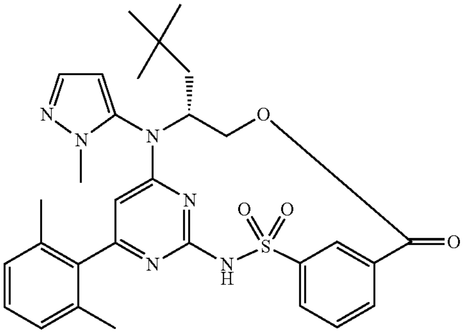 [SMILES: Cc1cccc(C)c1-c1cc2nc(n1)NS(=O)(=O)c1cccc(c1)C(=O)OC[C@@H](CC(C)(C)C)N2c1ccnn1C] | | | | | ND | + |

TABLE 8-continued
| Cmpd No. | Structure | 3T3 EC$_{50}$ (μM) | 3T3 Max Activity (%) | Ent. A EC$_{50}$ (μM) | Ent. A Max Activity (%) | Ent. B EC$_{50}$ (μM) | Ent. B Max Activity (%) |
|---|---|---|---|---|---|---|---|
| 30 | 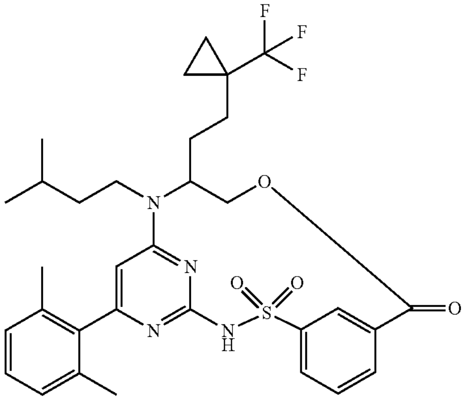 [SMILES: Cc1cccc(C)c1-c1cc2nc(n1)NS(=O)(=O)c1cccc(c1)C(=O)OCC(CCC1(C(F)(F)F)CC1)N2CCC(C)C] | | | ND | + | | |
| 31 | 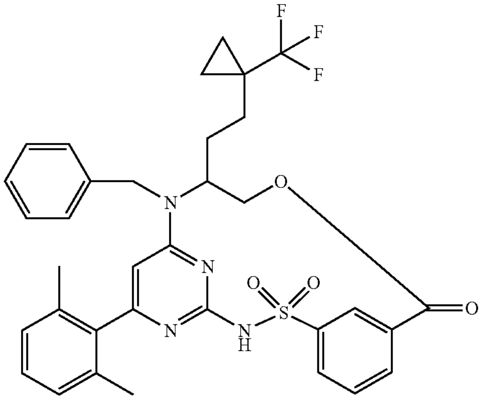 [SMILES: Cc1cccc(C)c1-c1cc2nc(n1)NS(=O)(=O)c1cccc(c1)C(=O)OCC(CCC1(C(F)(F)F)CC1)N2Cc1ccccc1] | | | ++ | ++ | | |
| 32 | 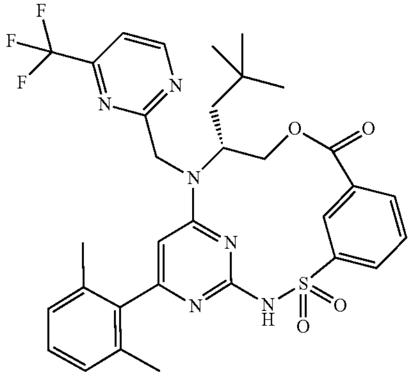 [SMILES: Cc1cccc(C)c1-c1cc2nc(n1)NS(=O)(=O)c1cccc(c1)C(=O)OC[C@@H](CC(C)(C)C)N2Cc1nccc(C(F)(F)F)n1] | | | | | ND | + |
| 33 | 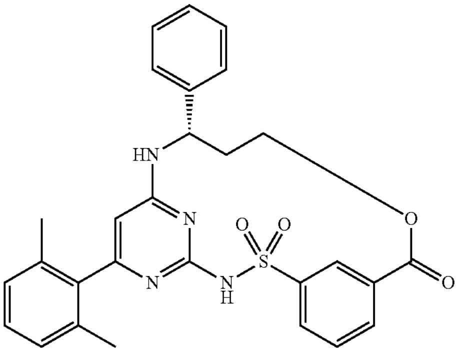 | | | ++ | +++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 34 | 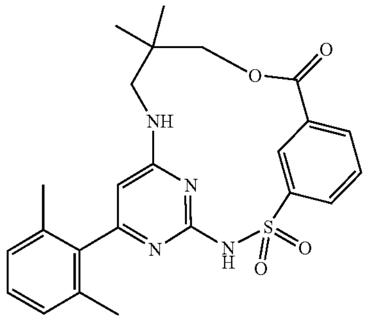 [SMILES: Cc1cccc(C)c1-c1cc2nc(n1)NS(=O)(=O)c1cccc(c1)C(=O)OCC(C)(C)CN2] | | | ND | + | | |
| 35 | 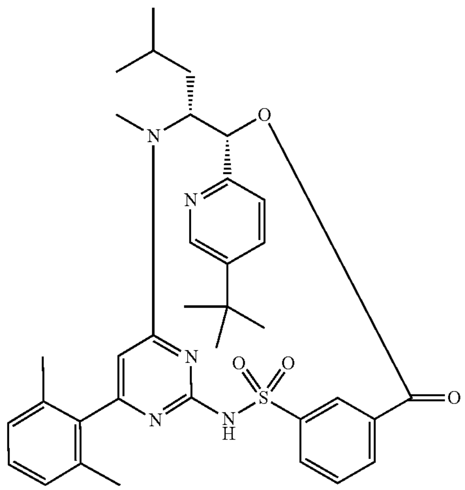 [SMILES: Cc1cccc(C)c1-c1cc2nc(n1)NS(=O)(=O)c1cccc(c1)C(=O)O[C@H](c1ccc(C(C)(C)C)cn1)[C@@H](CC(C)C)N2C] | +++ | +++ | ++ | ++ | | |
| 36 | 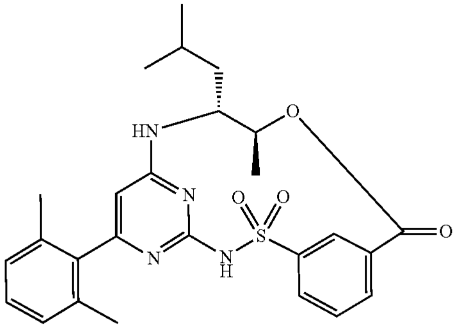 [SMILES: Cc1cccc(C)c1-c1cc2nc(n1)NS(=O)(=O)c1cccc(c1)C(=O)O[C@@H](C)[C@@H](CC(C)C)N2] | | | ND | + | | |
| 37 | 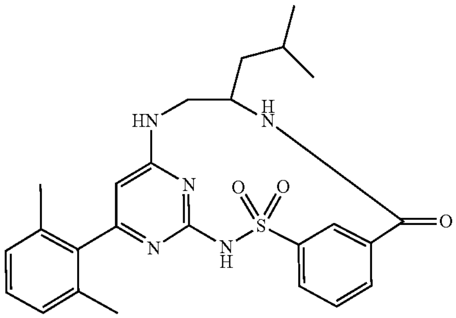 [SMILES: Cc1cccc(C)c1-c1cc2nc(n1)NS(=O)(=O)c1cccc(c1)C(=O)NC(CC(C)C)CN2] | | | ND | + | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 38 | 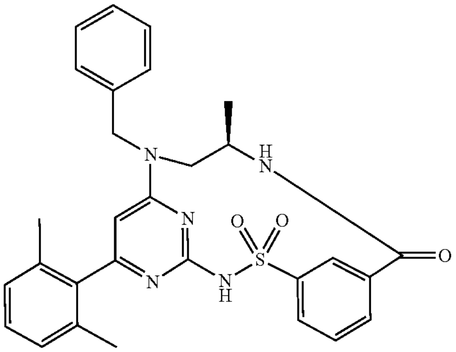 [SMILES: Cc1cccc(C)c1-c1cc2nc(n1)NS(=O)(=O)c1cccc(c1)C(=O)N[C@H](C)CN2Cc1ccccc1] | | | ND | + | | |
| 39 | 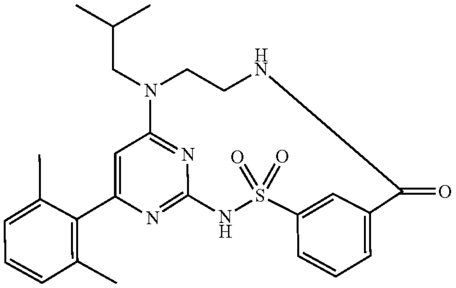 [SMILES: Cc1cccc(C)c1-c1cc2nc(n1)NS(=O)(=O)c1cccc(c1)C(=O)NCCN2CC(C)C] | | | ND | + | | |
| 40 | 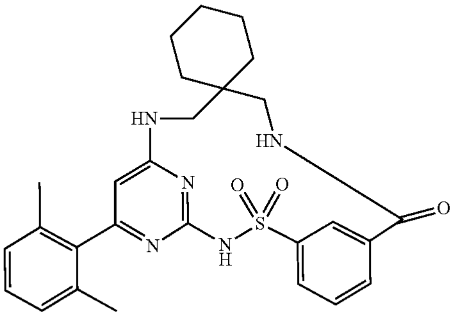 [SMILES: Cc1cccc(C)c1-c1cc2nc(n1)NS(=O)(=O)c1cccc(c1)C(=O)NCC1(CCCCC1)CN2] | | | ++ | + | | |
| 41 | 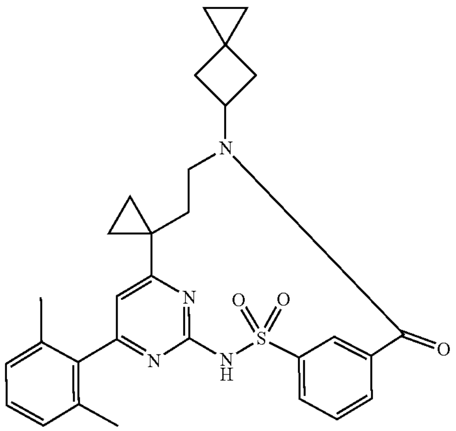 [SMILES: Cc1cccc(C)c1-c1cc2nc(n1)NS(=O)(=O)c1cccc(c1)C(=O)N(C1CC3(CC3)C1)CCC21CC1] | | | | | +++ | ++ |

VII. Preparation of Compounds 58-71

A. Synthesis of Common Intermediates

Preparation of 3-[[4-chloro-6-(2,6-dimethylphenyl)-5-methoxy-pyrimidin-2-yl]sulfamoyl]benzoic acid

Step 1: tert-Butyl N-tert-butoxycarbonyl-N-(4,6-dichloro-5-methoxy-pyrimidin-2-yl)carbamate

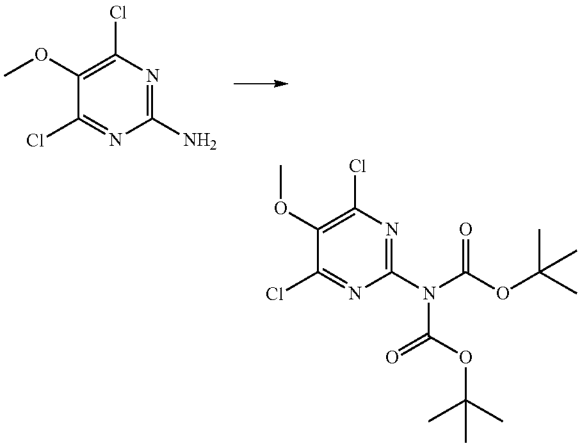

To a solution of 4,6-dichloro-5-methoxy-pyrimidin-2-amine (11.73 g, 60.458 mmol) in DCM (200 mL) was added DMAP (591 mg, 4.8376 mmol) and $Boc_2O$ (27.7 g, 29.158 mL, 126.92 mmol). The reaction was stirred for 3 hours at room temperature before being washed with brine (200 mL) and water (200 mL). The organic layer was concentrated in vacuum and dried over sodium sulfate to give tert-butyl N-tert-butoxycarbonyl-N-(4,6-dichloro-5-methoxy-pyrimidin-2-yl)carbamate (21.55 g, 90%). ESI-MS m/z calc. 393.08582, found 394.0 $(M+1)^+$; Retention time: 3.44 minutes; LC method T.

Step 2: tert-Butyl N-tert-butoxycarbonyl-N-[4-chloro-6-(2,6-dimethylphenyl)-5-methoxy-pyrimidin-2-yl]carbamate

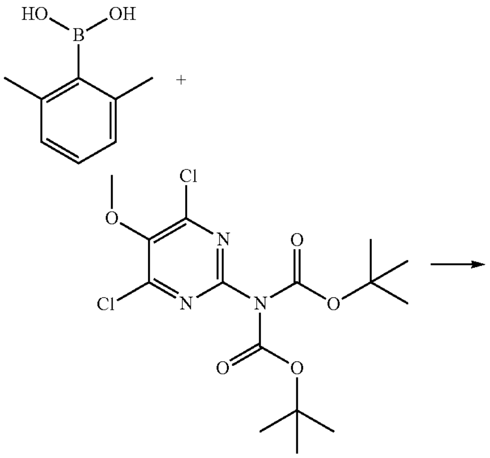

-continued

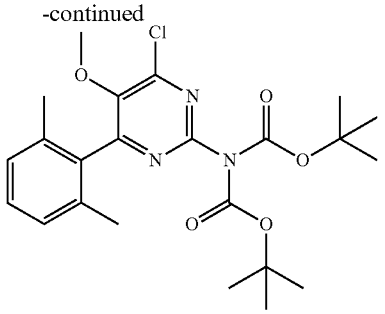

To a solution of tert-butyl N-tert-butoxycarbonyl-N-(4,6-dichloro-5-methoxy-pyrimidin-2-yl)carbamate (31.58 g, 80.101 mmol) dissolved in DME (225 mL) and water (31 mL) was added (2,6-dimethylphenyl)boronic acid (16.5 g, 110.01 mmol) and cesium carbonate (68 g, 208.71 mmol) at room temperature. The solution was stirred for 10 min while being bubbled with a nitrogen stream. Then $Pd(dppf)Cl_2$ (5.86 g, 8.0087 mmol) was added to the solution and heated to 80° C. overnight. The solution was cooled to room temperature before being diluted with water (250 mL) and extracted with ethyl acetate (2×300 mL). The combined organic layer was washed with brine (400 mL) and dried over sodium sulfate before being concentrated under vacuum. The organic residue was purified by silica gel chromatography eluting 0-60% ethyl acetate-hexanes to give tert-butyl N-tert-butoxycarbonyl-N-[4-chloro-6-(2,6-dimethylphenyl)-5-methoxy-pyrimidin-2-yl]carbamate (50.35 g, 135%). ESI-MS m/z calc. 463.1874, found 464.2 $(M+1)^+$; Retention time: 3.68 minutes; LC method T.

Step 3: 4-Chloro-6-(2,6-dimethylphenyl)-5-methoxy-pyrimidin-2-amine

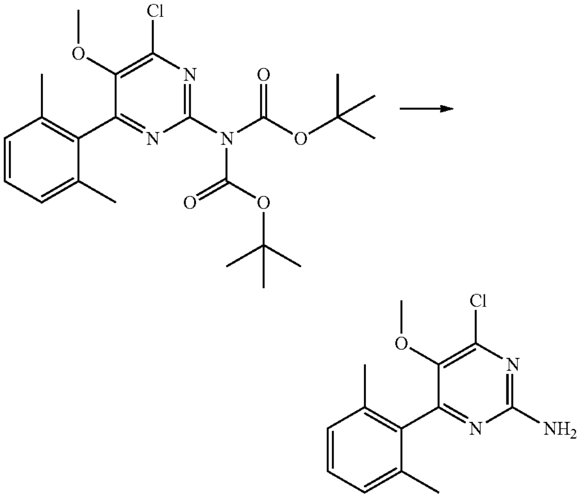

To a solution of tert-butyl N-tert-butoxycarbonyl-N-[4-chloro-6-(2,6-dimethylphenyl)-5-methoxy-pyrimidin-2-yl]carbamate (50.35 g, 108.52 mmol) in DCM (500 mL) was added HCl (100 mL of 4 M, 400.00 mmol) in dioxane. The solution was stirred at room temperature overnight before being concentrated in vacuum. The residue was then basified with sodium bicarbonate (400 mL) and extracted with ethyl acetate (500 mL). The organic layer was washed with brine (500 mL) and dried over sodium sulfate. The organic phase was concentrated then triturated with hexanes (2×50 mL) to give 4-chloro-6-(2,6-dimethylphenyl)-5-methoxy-pyrimidin-2-amine (10.16 g, 36%). ESI-MS m/z calc. 263.08255, found 264.1 $(M+1)^+$; Retention time: 2.73 minutes; LC method T.

Step 4: Methyl 3-[[4-chloro-6-(2,6-dimethylphenyl)-5-methoxy-pyrimidin-2-yl]sulfamoyl]benzoate

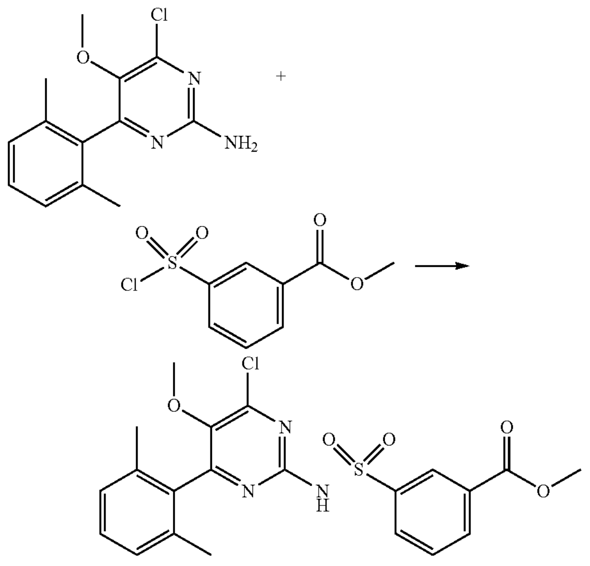

To a solution of 4-chloro-6-(2,6-dimethylphenyl)-5-methoxy-pyrimidin-2-amine (223 mg, 0.8456 mmol) in THF (6 mL) at 0° C. was added methyl 3-chlorosulfonylbenzoate (496 mg, 2.1137 mmol). Then Lithium tert-amoxide (584.00 mg, 2 mL of 40% w/w, 2.4830 mmol) was added to the solution dropwise keeping the temperature below 5° C. The solution was allowed to warm to room temperature while it stirred for 3 hours. The solution was acidified with 1M HCl (5 mL) and extracted with ethyl acetate (20 mL). The organic layer was washed with brine (20 mL) and dried over sodium sulfate. The organic layer was then concentrated in vacuum to give methyl 3-[[4-chloro-6-(2,6-dimethylphenyl)-5-methoxy-pyrimidin-2-yl]sulfamoyl]benzoate (386 mg, 99%) of a yellow solid. ESI-MS m/z calc. 461.0812, found 462.1 $(M+1)^+$; Retention time: 3.18 minutes; LC method T.

Step 5: 3-[[4-Chloro-6-(2,6-dimethylphenyl)-5-methoxy-pyrimidin-2-yl]sulfamoyl]benzoic acid

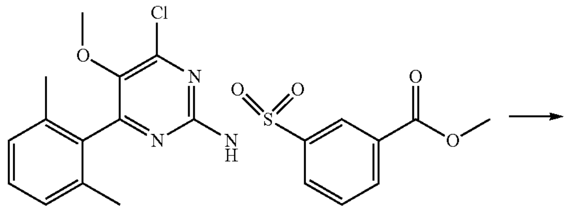

-continued

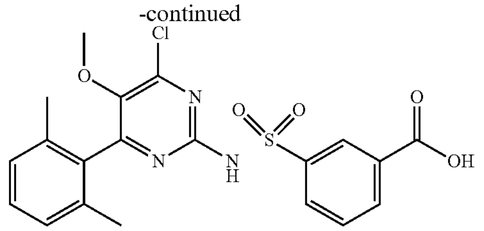

To a solution of methyl 3-[[4-chloro-6-(2,6-dimethylphenyl)-5-methoxy-pyrimidin-2-yl]sulfamoyl]benzoate (386 mg, 0.8356 mmol) in THF (10 mL) was added an aqueous solution of NaOH (5 mL of 1 M, 5.0000 mmol) and stirred for 1 hour at room temperature. The solution was acidified using 1M HCl (5 mL) and extracted with ethyl acetate (2×20 mL) before being washed with brine (20 mL). The organic layer was dried over sodium sulfate and concentrated in vacuum to give 3-[[4-chloro-6-(2,6-dimethylphenyl)-5-methoxy-pyrimidin-2-yl]sulfamoyl]benzoic acid (314 mg, 84%) as a white solid. ESI-MS m/z calc. 447.06558, found 448.1 $(M+1)^+$; Retention time: 2.9 minutes; LC method T.

B. Synthesis Compounds 58-73

Preparation of Compound 60

Step 1: Methyl 4-[isopropyl(methyl)amino]pyrimidine-2-carboxylate

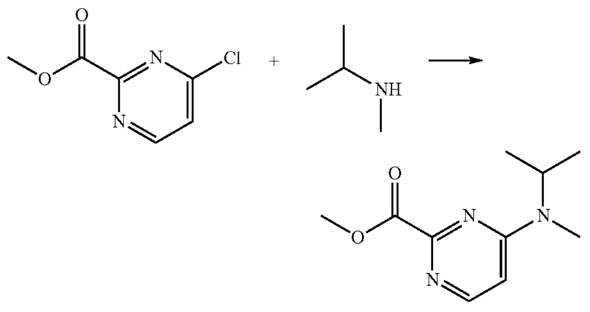

A tube was charged with methyl 4-chloropyrimidine-2-carboxylate (1 g, 5.7948 mmol) p-toluenesulfonic acid monohydrate (1.1 g, 5.7829 mmol) and dioxane (12.5 mL). N-methylpropan-2-amine (840.00 mg, 1.2 mL, 11.485 mmol) was added, then the tube was sealed and the reaction was stirred overnight at 80° C. The reaction was cooled down to room temperature then quenched with a saturated aqueous solution of ammonium chloride (30 mL) and the aqueous layer was extracted with ethyl acetate (4×20 mL). The combined organic extracts were washed with brine (50 mL) and water (50 mL), dried over sodium sulfate, filtered and concentrated under reduced pressure to afford methyl 4-[isopropyl(methyl)amino]pyrimidine-2-carboxylate (1.114 g, 88%) as a brown oil which was used in the next Step without further purification. $^1H$ NMR (400 MHz, $CDCl_3$) δ 8.27 (d, J=6.1 Hz, 1H), 6.48 (d, J=5.9 Hz, 1H), 3.98 (s, 3H), 2.93 (br. s, 3H), 1.70 (br. s, 1H), 1.21 (d, J=6.6 Hz, 6H). ESI-MS m/z calc. 209.11642, found 210.1 $(M+1)^+$; Retention time: 1.23 minutes; LC method K.

Step 2: [4-[Isopropyl(methyl)amino]pyrimidin-2-yl] methanol

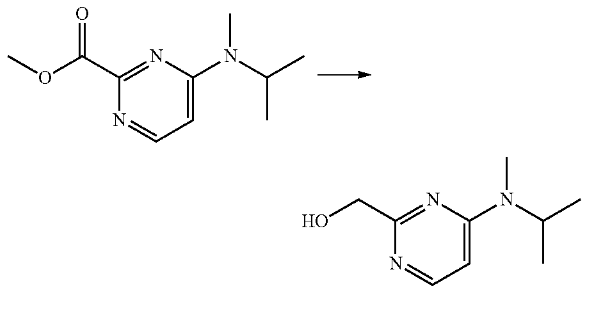

To a solution of methyl 4-[isopropyl(methyl)amino]pyrimidine-2-carboxylate (5.698 g, 25.597 mmol) in MeOH (85 mL) at 0° C. was added sodium borohydride (3.880 g, 102.56 mmol) and the mixture was allowed to warm up to room temperature and stirred for 1 h. The reaction was then quenched with water and extracted with ethyl acetate (3×80 mL). The combined organic layers were washed with brine, dried over anhydrous sodium sulfate and concentrated under reduced pressure to afford [4-[isopropyl(methyl)amino]pyrimidin-2-yl]methanol (4.868 g, 102%) as a dark brown oil. ESI-MS m/z calc. 181.1215, found 182.2 $(M+1)^+$; Retention time: 1.55 minutes; LC method T.

Step 3: 4-[Isopropyl(methyl)amino]pyrimidine-2-carbaldehyde

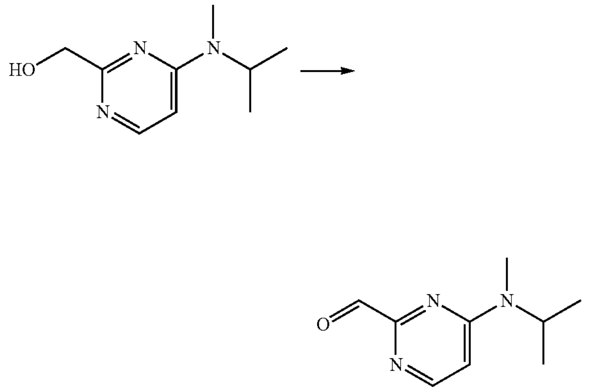

To a solution of [4-[isopropyl(methyl)amino]pyrimidin-2-yl]methanol (4.703 g, 25.950 mmol) in anhydrous DCM (195 mL) was added DMP (11.551 g, 27.234 mmol) at 0° C. The mixture was allowed to warm up to room temperature and stirred for 2 h. The precipitated solids were removed by filtration through a pad of Celite and the filtrate was concentrated under reduced pressure. The crude product was purified by silica gel column chromatography (0-100% EtOAc in Hexanes) to afford 4-[isopropyl(methyl)amino] pyrimidine-2-carbaldehyde (2.5 g, 52%) as a yellow oil. $^1H$ NMR (500 MHz, Chloroform-d) δ 9.89 (s, 1H), 8.35 (d, J=6.1 Hz, 1H), 6.54-6.42 (m, 1H), 2.93 (s, 4H), 1.31-1.15 (m, 6H).

Step 4: 3-[[4-(2,6-Dimethylphenyl)-6-[(3S)-3-[[4-[isopropyl(methyl)amino]pyrimidin-2-yl]methylamino]-5-methyl-hexyl]pyrimidin-2-yl]sulfamoyl] benzoic acid

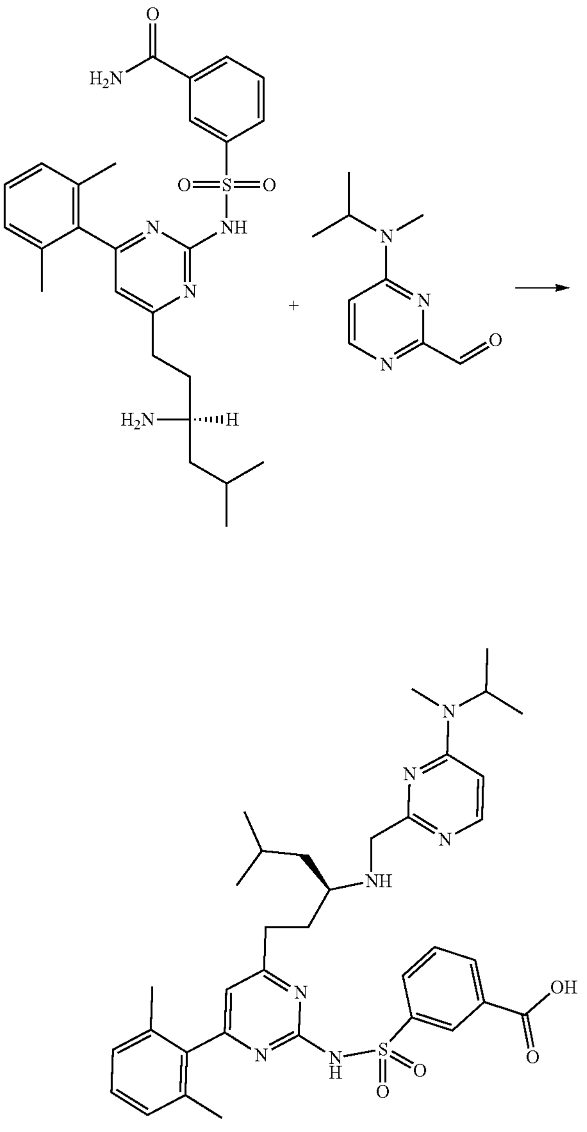

3-[[4-[(3S)-3-amino-5-methyl-hexyl]-6-(2,6-dimethylphenyl)pyrimidin-2-yl]sulfamoyl]benzoic acid (Trifluoroacetate salt) (29.5 mg, 0.04831 mmol), 4-[isopropyl(methyl) amino]pyrimidine-2-carbaldehyde (12.4 mg, 0.06919 mmol), and sodium triacetoxyborohydride (30.5 mg, 0.1439 mmol) were combined in DCM (300 μL) and stirred at room temperature for 2 h. The reaction was quenched with aqueous HCl (25 μL of 6 M, 0.1500 mmol) and diluted with methanol. The mixture was filtered and purified by LC/MS utilizing a gradient of 1-99% acetonitrile in 5 mM aqueous HCl to yield 3-[[4-(2,6-dimethylphenyl)-6-[(3S)-3-[[4-[isopropyl(methyl)amino]pyrimidin-2-yl]methylamino]-5-methyl-hexyl]pyrimidin-2-yl]sulfamoyl]benzoic acid (Hydrochloride salt) (18.8 mg, 26%). ESI-MS m/z calc. 659.3254, found 660.5 $(M+1)^+$; Retention time: 0.54 minutes; LC method D.

Step 5: (11S)-6-(2,6-Dimethylphenyl)-11-isobutyl-2-[[4-[isopropyl(methyl)amino]pyrimidin-2-yl]methyl]-2,2-dioxo-2 λ6-thia-3,5,12,19-tetrazatricyclo[12.3.1.14,8]nonadeca-1(18),4(19),5,7,14,16-hexaen-13-one

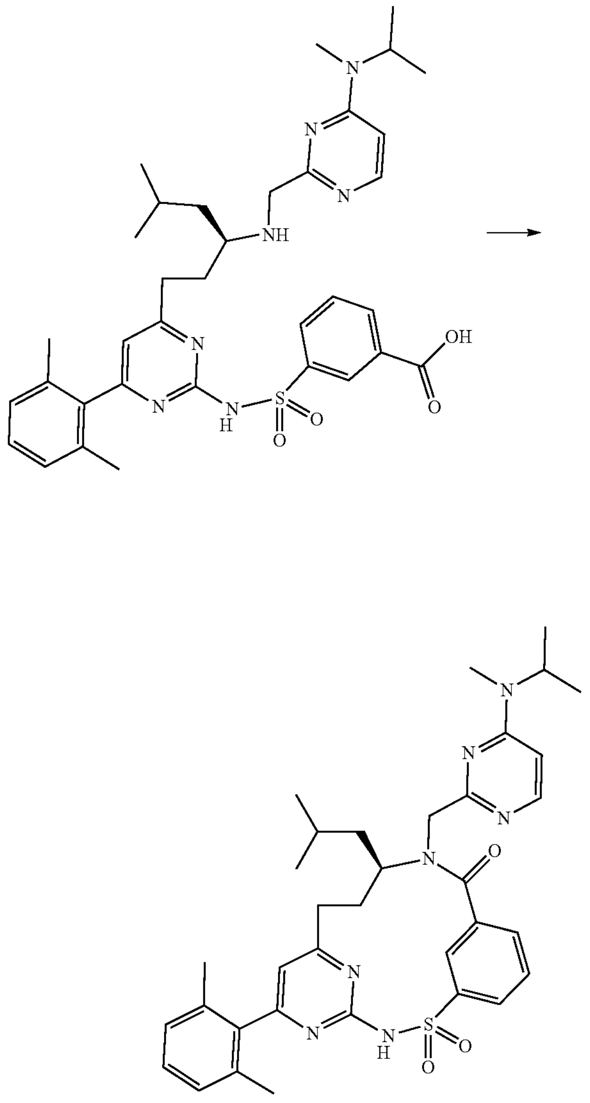

3-[[4-(2,6-Dimethylphenyl)-6-[(3S)-3-[[4-[isopropyl(methyl)amino]pyrimidin-2-yl]methylamino]-5-methyl-hexyl]pyrimidin-2-yl]sulfamoyl]benzoic acid (Hydrochloride salt) (18.8 mg, 0.01242 mmol), HATU (11.2 mg, 0.02946 mmol), and DIEA (20 μL, 0.1148 mmol) were combined in DMF (1 mL) and stirred at room temperature for 2 h. The reaction was filtered and purified by LC/MS utilizing a gradient of 1-99% acetonitrile in 5 mM aqueous HCl to yield (11S)-6-(2,6-dimethylphenyl)-11-isobutyl-12-[[4-[isopropyl(methyl)amino]pyrimidin-2-yl]methyl]-2,2-dioxo-2$\lambda^6$-thia-3,5,12,19-tetrazatricyclo[12.3.1.14,8]nonadeca-1(18),4(19),5,7,14,16-hexaen-13-one (Hydrochloride salt) (4.2 mg, 49%) as a white solid. ESI-MS m/z calc. 641.3148, found 642.6 $(M+1)^+$; Retention time: 1.4 minutes; LC method A.

Preparation of Compound 65 and Compound 66

Step 1: tert-Butyl N-[(1R)-1-[methoxy(methyl)carbamoyl]-3,3-dimethyl-butyl]carbamate

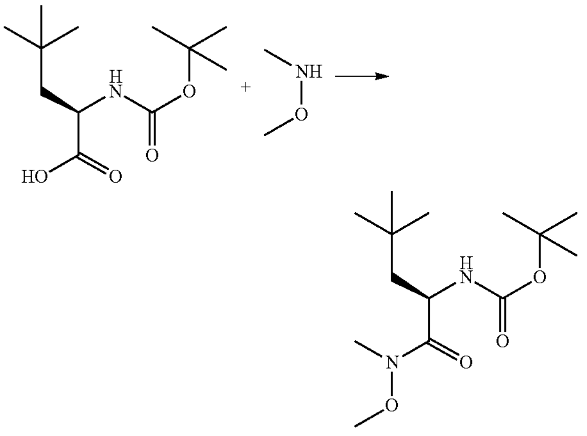

A solution of (2R)-2-(tert-butoxycarbonylamino)-4,4-dimethyl-pentanoic acid (29.6 g, 120.66 mmol) in DCM (450 mL) and stirred at −10° C. Then HOBt (17.3 g, 128.03 mmol) and 1-(3-dimethylaminopropyl)-3-ethylcarbodiimide (hydrochloride salt) (34.6 g, 180.49 mmol) were added. The reaction was stirred for 15 minutes at −10° C. and N-methoxymethanamine (hydrochloride salt) (12.15 g, 124.56 mmol) was added in one portion followed by dropwise addition of DIPEA (38.955 g, 52.5 mL, 301.41 mmol) over 15 min. (internal temp. -9° C.). The bath was −15° C. The reaction was warmed to rt over 16 hours. The reaction treated with was quenched with HCl (270 mL of 1 M, 270.00 mmol) until pH=3. The mixture was filtered, and the two layers of filtrate were separated. The organic layer was washed with saturated sodium bicarbonate (500 mL), brine (100 mL), dried over anhydrous magnesium sulfate and concentrated under vacuum to furnish tert-butyl N-[(1R)-1-[methoxy(methyl)carbamoyl]-3,3-dimethyl-butyl]carbamate (33.52 g, 87%) as a colorless wax. $^1$H NMR (500 MHz, Chloroform-d) δ 5.10-4.92 (m, 1H), 4.85-4.69 (m, 1H), 3.79 (s, 3H), 3.19 (s, 3H), 1.56 (dd, J=14.3, 3.0 Hz, 2H), 1.42 (s, 9H), 0.97 (s, 9H). ESI-MS m/z calc. 288.2049, found 289.3 $(M+1)^+$; Retention time: 4.95 minutes; LC method S.

Step 2: tert-Butyl N-[(1R)-1-ethynyl-3,3-dimethyl-butyl]carbamate

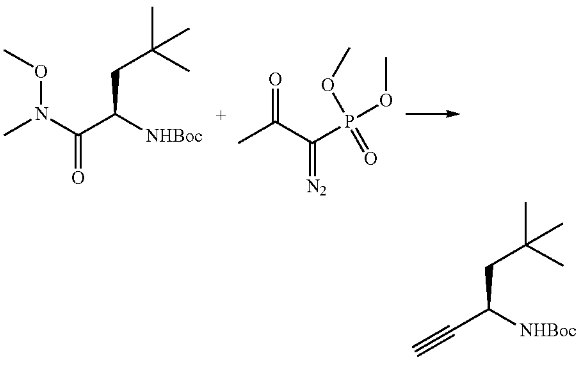

A solution of tert-butyl N-[(1R)-1-[methoxy(methyl)carbamoyl]-3,3-dimethyl-butyl]carbamate (21.25 g, 73.687 mmol) in anhydrous DCM (550.00 mL) was treated with DIBAL-H (184 mL of 1 M, 184.00 mmol) in toluene dropwise over 80 min. at −72° C. (internal temperature). The reaction was stirred at the same temperature for 2 h. Excess of DIBAL-H was quenched with MeOH (400 mL), over 70 minutes. The reaction was slowly raised to 0° C. over 70 minutes. Then the solution was treated with potassium carbonate (30.5 g, 220.69 mmol) in one portion and a solution of 1-dimethoxyphosphoryl-1-(imino-$\lambda^4$-azanylidene)propan-2-one (29.440 g, 23 mL, 152.45 mmol) in MeOH (400 mL) was added to the reaction (0° C. internal) over 2 h and 30 minutes. The bath was warmed slowly to room temperature over 18 h. The reaction was quenched with saturated aqueous Rochells's salt (700 mL) and the reaction was stirred for 60 minutes. The majority of the DCM and MeOH was removed in vacuo and the reaction mixture was extracted with EtOAc (400 mL). The aqueous layer was extracted with EtOAc (3×150 mL). The combined organic layers were washed with brine (2×100 mL), dried over anhydrous sodium sulfate and concentrated under vacuum gave a yellow liquid crude product. The crude residue was purified by flash chromatography (Combiflash 330 g $SiO_2$, liquid loaded, eluted with 0-20% $Et_2O$ in hexanes over a 10 column volume gradient). The pure fractions were combined and the solvent was evaporated in vacuo to obtain the product, tert-butyl N-[(1R)-1-ethynyl-3,3-dimethyl-butyl]carbamate (9.3 g, 50%), as a clear liquid. $^1$H NMR (500 MHz, Chloroform-d) δ 4.64 (m, 1H), 4.47 (m, 1H), 2.27 (d, J=2.3 Hz, 1H), 1.72-1.65 (m, 1H), 1.57 (dd, J=13.8, 6.3 Hz, 1H), 1.44 (s, 9H), 0.98 (s, 9H). ESI-MS m/z calc. 225.17288, found 226.5 $(M+1)^+$; Retention time: 5.43 minutes; LC method S.

Step 3: 3-[[4-[(3R)-3-(tert-Butoxycarbonylamino)-5,5-dimethyl-hex-1-ynyl]-6-(2,6-dimethylphenyl)pyrimidin-2-yl]sulfamoyl]benzoic acid

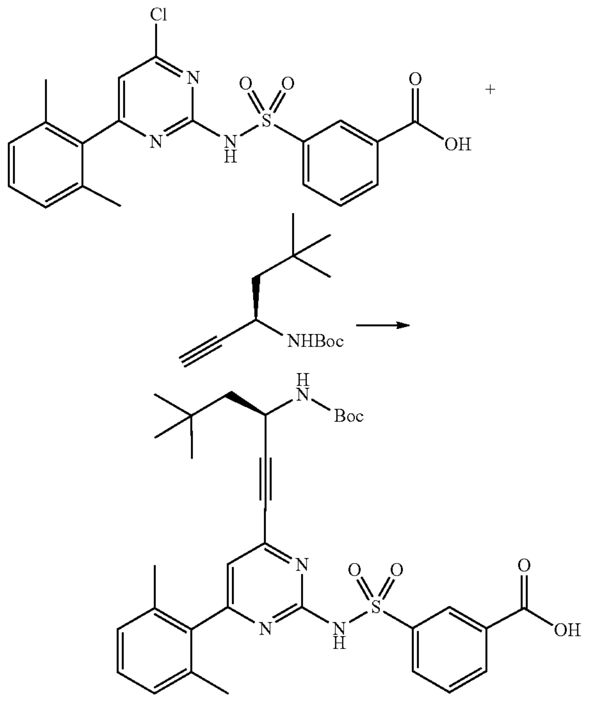

A flask was charged with 3-[[4-chloro-6-(2,6-dimethylphenyl)pyrimidin-2-yl]sulfamoyl]benzoic acid (11.5 g, 27.521 mmol), and tert-butyl N-[(1R)-1-ethynyl-3,3-dimethyl-butyl]carbamate (7.86 g, 34.883 mmol) and purged with argon for 2 h, then the solids were treated with DMSO (115 mL) and degassed an additional 2 h. Then the solution was treated with, Pd(PPh3)4 (1.59 g, 1.3760 mmol) and CuI (522 mg, 2.7409 mmol) and the reaction sparged with argon for an additional 1 h and 30 minutes. Then the solution was treated with TEA (23.232 g, 32 mL, 229.59 mmol), heated in an oil bath at 80° C. for 4 h and 30 minutes. Then the reaction was treated with tert-butyl N-[(1R)-1-ethynyl-3-methyl-butyl]carbamate (1.1 g, 5.2058 mmol) in DMSO (4 mL) at 80° C. and heated at this temperature for an additional 45 min., and then cooled to RT. The reaction mixture was diluted with water (1.2 L) and diethyl ether (800 mL) and washed an additional time with $Et_2O$ (400 mL). The two layers were separated and the ether layer was set aside. The aqueous phase was diluted with EtOAC (400 mL) and acidified to pH 4 with aqueous citric acid (10% wt/vol). The layers were separated and then aqueous phase was extracted with ethyl acetate (3×250 mL). The combined organic layers were washed with brine (4×100 mL), dried over anhydrous sodium sulfate and concentrated under vacuum. The crude residue was purified by flash chromatography (Combiflash 330 g $SiO_2$, dry loaded, eluted with 20-40% acetone in hexanes (buffered with 0.3% acetic acid) over a 10 column volume gradient). The appropriate fractions were combined and concentrated in vacuo. The residue was triturated with hexane (500 mL) to furnish 3-[[4-[(3R)-3-(tert-butoxycarbonylamino)-5,5-dimethyl-hex-1-ynyl]-6-(2,6-dimethylphenyl)pyrimidin-2-yl]sulfamoyl]benzoic acid (11 g, 64%) as a yellow solid. $^1$H NMR (500 MHz, Chloroform-d) δ 9.12 (m, 1H), 8.27 (m, 2H), 7.55 (t, J=7.8 Hz, 1H), 7.21 (t, J=7.6 Hz, 1H), 7.08 (d, J=7.6 Hz, 2H), 6.86 (s, 1H), 4.95 (d, J=9.1 Hz, 1H), 4.85-4.75 (m, 1H), 1.97 (s, 6H), 1.81 (m, 1H), 1.68 (m, 1H), 1.53-1.45 (m, 9H), 1.02 (s, 9H). ESI-MS m/z calc. 606.2512, found 607.3 $(M+1)^+$; Retention time: 6.73 minutes; LC method S.

Step 4: 3-[[4-[(3S)-3-(tert-Butoxycarbonylamino)-5,5-dimethyl-hexyl]-6-(2,6-dimethylphenyl)pyrimidin-2-yl]sulfamoyl]benzoic acid

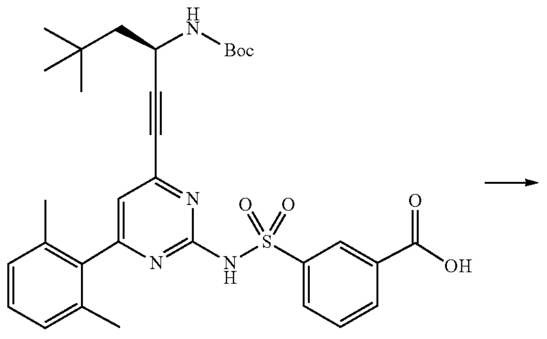

-continued

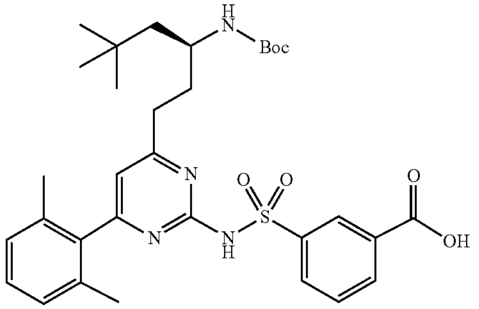

A solution of 3-[[4-[(3R)-3-(tert-butoxycarbonylamino)-5,5-dimethyl-hex-1-ynyl]-6-(2,6-dimethylphenyl)pyrimidin-2-yl]sulfamoyl]benzoic acid (11 g, 17.586 mmol) in ethanol (380 mL) was treated with 10% Pd/C (2.75 g, 2.5841 mmol) on carbon. The reaction was purged with nitrogen, then H2 gas was bubbled through the suspension and the reaction was stirred at room temperature under 1 atm of hydrogen for 3 hour. The catalyst was removed by filtration. The filtrate was concentrated under vacuum to furnish 3-[[4-[(3S)-3-(tert-butoxycarbonylamino)-5,5-dimethyl-hexyl]-6-(2,6-dimethylphenyl)pyrimidin-2-yl]sulfamoyl]benzoic acid (10.71 g, 99%) as a yellow solid. $^1$H NMR (500 MHz, Chloroform-d) δ 9.13 (s, 1H), 8.30-8.16 (m, 2H), 7.57 (t, J=7.7 Hz, 1H), 7.20 (t, J=7.6 Hz, 1H), 7.07 (d, J=7.6 Hz, 2H), 6.75 (s, 1H), 4.49 (d, J=9.5 Hz, 1H), 3.84-3.76 (m, 1H), 2.89-2.61 (m, 2H), 1.98 (s, 6H), 1.79 (m, 2H), 1.45 (m, 10H), 1.35-1.27 (m, 1H), 0.95 (s, 9H). ESI-MS m/z calc. 610.28253, found 611.5 (M+1)$^+$; Retention time: 6.61 minutes; LC method S.

Step 5: 3-[[4-[(3S)-3-Amino-5,5-dimethyl-hexyl]-6-(2,6-dimethylphenyl)pyrimidin-2-yl]sulfamoyl]benzoic acid

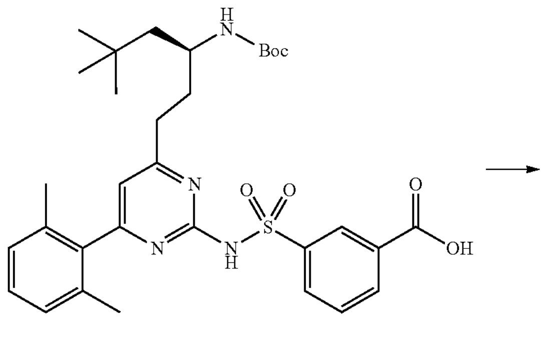

-continued

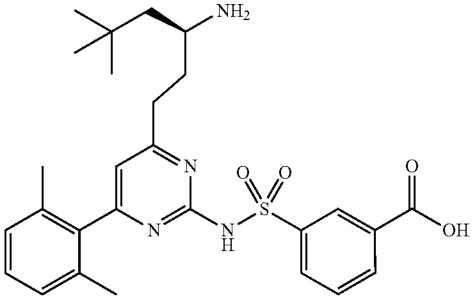

A solution of 3-[[4-[(3S)-3-(tert-butoxycarbonylamino)-5,5-dimethyl-hexyl]-6-(2,6-dimethylphenyl)pyrimidin-2-yl]sulfamoyl]benzoic acid (10.71 g, 17.360 mmol) in DCM (45 mL) was treated with HCl in dioxane (25 mL of 4 M, 100.00 mmol) over 5 min. at RT. The reaction was stirred at rt for 2 h and the solvent was removed under reduced pressure. The residue was triturated with TBME (60 mL), filtered, and rinsed with TBME (30 mL), and the solids were dried in vacuo to obtain the target the target, 3-[[4-[(3S)-3-amino-5,5-dimethyl-hexyl]-6-(2,6-dimethylphenyl)pyrimidin-2-yl]sulfamoyl]benzoic acid (hydrochloride salt) (9.7794 g, 100%), as a light yellow powder. $^1$H NMR (500 MHz, DMSO-d$_6$) δ 13.38 (s, 1H), 11.91 (s, 1H), 8.47 (s, 1H), 8.16 (d, J=7.8 Hz, 2H), 8.01 (s, 3H), 7.68 (t, J=7.8 Hz, 1H), 7.22 (t, J=7.6 Hz, 1H), 7.10 (d, J=7.6 Hz, 2H), 7.02 (s, 1H), 3.11-3.04 (m, 1H), 2.89-2.75 (m, 2H), 1.97-1.86 (m, 2H), 1.85 (s, 6H), 1.50-1.39 (m, 2H), 0.81 (s, 9H). ESI-MS m/z calc. 510.23007, found 511.6 (M+1)$^+$; Retention time: 2.03 minutes; LC method W.

Step 6: 3-[[4-(2,6-Dimethylphenyl)-6-[(3S)-3-[(6-methoxycarbonylspiro[3.3]heptan-2-yl)amino]-5,5-dimethyl-hexyl]pyrimidin-2-yl]sulfamoyl]benzoic acid

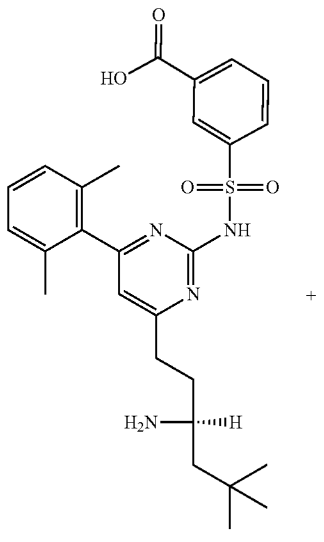

-continued

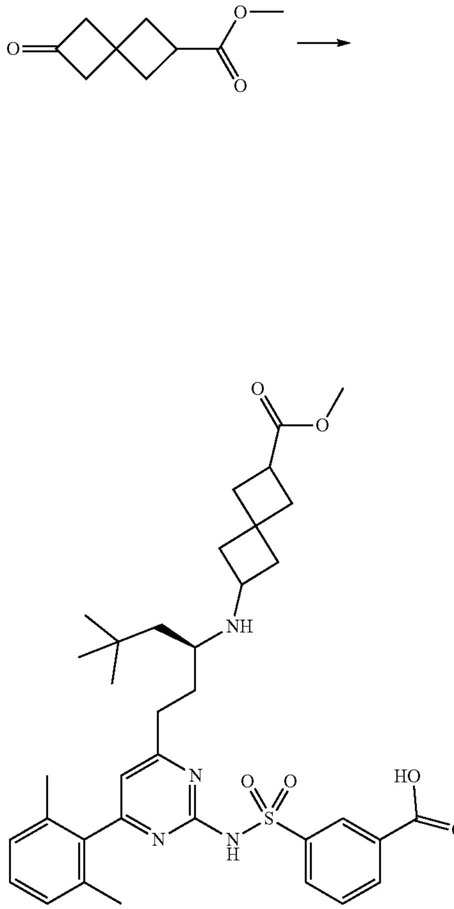

A 4 mL vial was charged under nitrogen with 3-[[4-[(3S)-3-amino-5,5-dimethyl-hexyl]-6-(2,6-dimethylphenyl)pyrimidin-2-yl]sulfamoyl]benzoic acid (Hydrochloride salt) (130 mg, 0.2376 mmol), methyl 2-oxospiro[3.3]heptane-6-carboxylate (48 mg, 0.2854 mmol) and DCM (600 μL). The mixture was stirred at room temperature for 30 min. triacetoxyborohydride (Sodium salt) (77 mg, 0.3633 mmol) was added and and the mixture was stirred at room temperature for 30 min. More triacetoxyborohydride (Sodium salt) (150 mg, 0.7077 mmol) was added and the reaction was stirred at rt for 18 h. The reaction was quenched with a few drops of 1N aqueous HCl. Methanol and DMSO were added (2 mL total volume). After filtration, the product was subjected to reverse phase HPLC (1-99% acetonitrile/5 mM aqueous HCl over 15 min) to give 3-[[4-(2,6-dimethylphenyl)-6-[(3S)-3-[(6-methoxycarbonylspiro[3.3]heptan-2-yl)amino]-5,5-dimethyl-hexyl]pyrimidin-2-yl]sulfamoyl]benzoic acid (Hydrochloride salt) (74.8 mg, 45%) as an off-white solid. ESI-MS m/z calc. 662.3138, found 663.66 (M+1)$^+$; Retention time: 0.58 minutes; LC method D.

Step 7: Methyl 2-[(11S)-6-(2,6-dimethylphenyl)-11-(2,2-dimethylpropyl)-2,2,13-trioxo-2λ6-thia-3,5,12,19-tetrazatricyclo[12.3.1.14,8]nonadeca-1(18),4(19),5,7,14,16-hexaen-12-yl]spiro[3.3]heptane-6-carboxylate

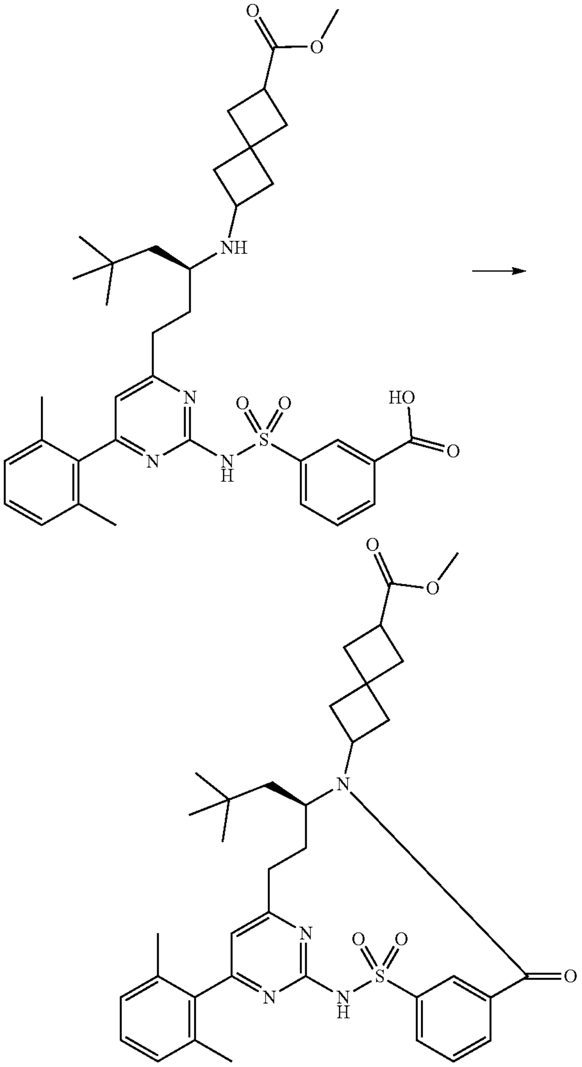

3-[[4-(2,6-Dimethylphenyl)-6-[(3S)-3-[(6-methoxycarbonylspiro[3.3]heptan-2-yl)amino]-5,5-dimethyl-hexyl]pyrimidin-2-yl]sulfamoyl]benzoic acid (hydrochloride salt) (74.8 mg, 0.1070 mmol) was combined in a 4 mL vial under nitrogen with CDMT (29 mg, 0.1652 mmol) and DMF (2.2 mL). The solution was stirred at 0° C. 4-Methyl-morpholine (60 μL, 0.5457 mmol) was added and the mixture was stirred in the cooling bath that was allowed to warm to room temperature for 18 h. The reaction was filtered. Purification by reverse phase HPLC (1-99% acetonitrile/5 mM aqueous HCl over 15 min) gave methyl 2-[(11S)-6-(2,6-dimethylphenyl)-11-(2,2-dimethylpropyl)-2,2,13-trioxo-2$\lambda^6$-thia-3,5,12,19-tetrazatricyclo[12.3.1.14,8]nonadeca-1(18),4(19),5,7,14,16-hexaen-12-yl]spiro[3.3]heptane-6-carboxylate (54.9 mg, 80%) as an off-white solid (1:1 mixture of diastereomers). ESI-MS m z calc. 644.3032, found 645.56 (M+1)$^+$; Retention time: 2.03 minutes, second isomer, found 645.51 $(M+1)^+$, 2.05 minutes; LC method A.

Step 8: (11S)-6-(2,6-Dimethylphenyl)-11-(2,2-dimethylpropyl)-12-[6-(1-hydroxy-1-methyl-ethyl)spiro[3.3]heptan-2-yl]-2,2-dioxo-2λ6-thia-3,5,12,19-tetrazatricyclo[12.3.1.14,8]nonadeca-1(18),4,6,8(19),14,16-hexaen-13-one, diastereomer 1, Compound 65, and (11S)-6-(2,6-dimethylphenyl)-11-(2,2-dimethylpropyl)-12-[6-(1-hydroxy-1-methyl-ethyl)spiro[3.3]heptan-2-yl]-2,2-dioxo-2 λ6-thia-3,5,12,19-tetrazatricyclo[12.3.1.14,8]nonadeca-1(18),4,6,8(19),14,16-hexaen-13-one, diastereomer 2, Compound 66

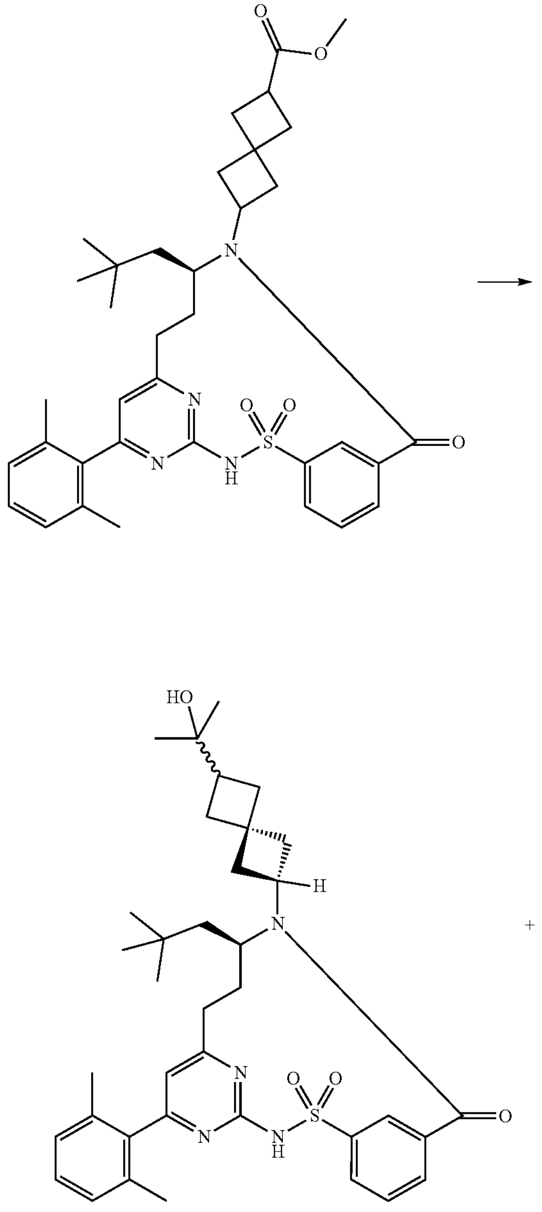

diastereomer 1

-continued

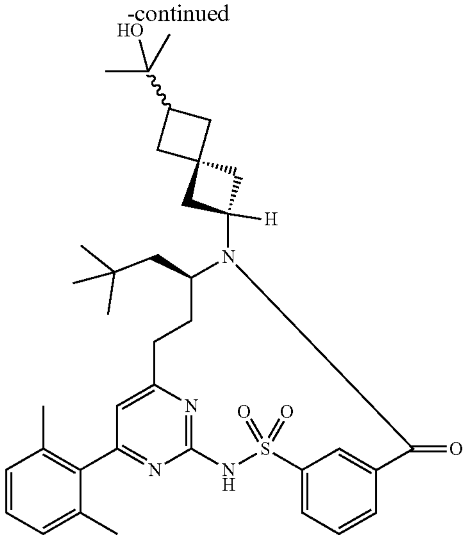

diastereomer 2

A 4 mL vial was charged under nitrogen with methyl 2-[(11S)-6-(2,6-dimethylphenyl)-11-(2,2-dimethylpropyl)-2,2,13-trioxo-2$\lambda^6$-thia-3,5,12,19-tetrazatricyclo[12.3.1.14,8]nonadeca-1(18),4(19),5,7,14,16-hexaen-12-yl]spiro[3.3]heptane-6-carboxylate (54.9 mg, 0.08514 mmol) (isomer ratio 1:1), anhydrous THF (0.70 mL) and the solution was cooled down in an ice bath. MeMgBr (0.09 mL of 3 M, 0.2700 mmol)(3M solution in diethyl ether) was added dropwise. The reaction mixture was stirred in the ice bath for 5 min, then it was stirred at room temperature for 19 h. The mixture was cooled down in ice and quenched by adding an aqueous saturated solution of ammonium chloride (0.2 mL), water (a few drops) and DMSO (3 mL). The mixture was filtered and subjected to purification by reverse phase HPLC (1-99% acetonitrile/5 mM aqueous HCl over 45 min) to give two isomers: More polar, first to elute isomer, diastereomer 1 (11S)-6-(2,6-dimethylphenyl)-11-(2,2-dimethylpropyl)-12-[6-(1-hydroxy-1-methyl-ethyl)spiro[3.3]heptan-2-yl]-2,2-dioxo-2$\lambda^6$-thia-3,5,12,19-tetrazatricyclo[12.3.1.14,8]nonadeca-1(18),4,6,8(19),14,16-hexaen-13-one (15.6 mg, 56%), $^1$H NMR (400 MHz, DMSO-$d_6$) δ 11.73 (s, 1H), 8.37 (s, 1H), 7.94 (d, J=7.4 Hz, 1H), 7.76-7.58 (m, 2H), 7.19 (t, J=7.6 Hz, 1H), 7.11-6.91 (m, 3H), 3.97 (s, 1H), 3.85 (p, J=8.8 Hz, 1H), 3.46 (s, 1H), 3.14-2.96 (m, 3H), 2.88 (t, J=15.0 Hz, 1H), 2.28-2.19 (m, 1H), 2.17-2.06 (m, 2H), 2.04-1.68 (m, 12H), 1.40 (dd, J=15.2, 9.4 Hz, 1H), 1.28-1.16 (m, 1H), 0.97 (d, J 2.3 Hz, 6H), 0.41 (s, 9H). ESI-MS m/z calc. 644.3396, found 645.81 $(M+1)^+$; Retention time: 1.99 minutes, and a less polar, second to elute isomer, diastereomer 2 (11S)-6-(2,6-dimethylphenyl)-11-(2,2-dimethylpropyl)-12-[6-(1-hydroxy-1-methyl-ethyl)spiro[3.3]heptan-2-yl]-2,2-dioxo-2$\lambda^6$-thia-3,5,12,19-tetrazatricyclo[12.3.1.14,8]nonadeca-1(18),4,6,8(19),14,16-hexaen-13-one (16 mg, 58%), $^1$H NMR (400 MHz, DMSO-$d_6$) δ 11.73 (s, 1H), 8.36 (s, 1H), 7.94 (d, J=7.1 Hz, 1H), 7.74-7.62 (m, 2H), 7.20 (t, J=7.6 Hz, 1H), 7.12-6.91 (m, 3H), 3.98 (s, 1H), 3.85 (p, J=8.8 Hz, 1H), 3.45 (s, 1H), 3.18 (t, J=9.5 Hz, 1H), 3.10-2.80 (m, 3H), 2.24 (td, J=9.5, 8.9, 3.8 Hz, 1H), 2.17-1.70 (m, 14H), 1.43 (dd, J=15.1, 9.5 Hz, 1H), 1.22 (d, J=15.0 Hz, 1H), 1.07-0.90 (m, 6H), 0.42 (s, 9H). ESI-MS m/z calc. 644.3396, found 645.81 $(M+1)^+$; Retention time: 2.04 minutes; LC method A.

Preparation of Compound 62

Step 1: 2-Chloro-5-isopropoxy-pyrimidine

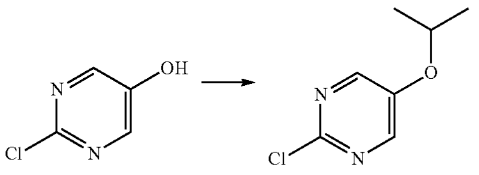

To a solution of 2-chloropyrimidin-5-ol (15 g, 114.91 mmol) in DMF (150 mL) was added potassium carbonate (32 g, 231.54 mmol) then 2-iodopropane (29.803 g, 17.5 mL, 175.32 mmol) and the mixture was heated at 50° C. for 1 h. The reaction was cooled to room temperature and diluted with $Et_2O$ (1500 mL), washed with a mixture of brine (300 mL) and water (300 mL), then brine (2×300 mL) again. The organics were dried over sodium sulfate, filtered and concentrated in vacuo to provide 2-chloro-5-isopropoxy-pyrimidine (18.5 g, 91%) as flaky white crystals. $^1H$ NMR (500 MHz, Chloroform-d) δ 8.25 (s, 2H), 4.59 (hept, J=6.1 Hz, 1H), 1.38 (d, J=6.1 Hz, 6H). ESI-MS m/z calc. 172.04034, found 173.4 $(M+1)^+$; Retention time: 2.2 minutes; LC method T.

Step 2: Methyl 5-isopropoxypyrimidine-2-carboxylate

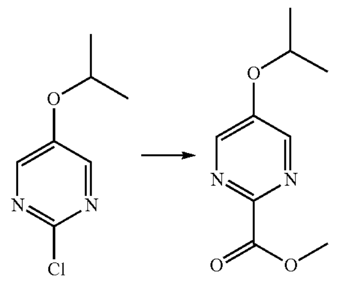

A stirred mixture of 2-chloro-5-isopropoxy-pyrimidine (40 g, 220.15 mmol) and $Pd(dppf)_2Cl_2$·DCM (10 g, 12.245 mmol) in DMF (200 mL)/MeOH (200 mL)/TEA (400.00 mL) in a 2 L steel bomb with an overhead mechanical stirrer was purged with carbon monoxide three times. The reaction mixture was heated to 120° C. with 120 psi of CO and retained at this temperature for one hour. Heating was turned off and the reaction mixture was allowed to cool to rt. Methanol and triethylamine were evaporated in vacuo. Water (1 L) was added and the suspendsion filtered to remove catalyst residue. The cake was washed with water. The filtrate was extracted with DCM (3×700 mL). The combined organic layer was washed with brine, dried over sodium sulfate, filtered and concentrated in vacuo. The resulting brown oil was purified by flash chromatography ($SiO_2$, 220 g, loaded in DCM, eluted with 25% ethyl acetate in hexanes) to give a greenish oil, which was triturated with hexanes and filtered. The cake was washed with hexanes and dried in vacuo to give methyl 5-isopropoxypyrimidine-2-carboxylate (30.1 g, 66%) as a beige solid. ESI-MS m/z calc. 196.0848, found 197.4 $(M+1)^+$; Retention time: 3.15 minutes; LC method S.

Step 3: 5-Isopropoxypyrimidine-2-carbaldehyde

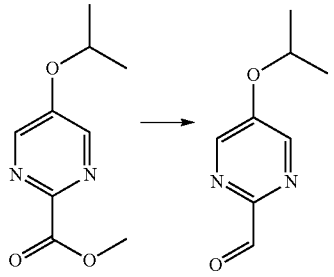

To a stirred solution of methyl 5-isopropoxypyrimidine-2-carboxylate (32.6 g, 157.85 mmol) in THF (1 L) was added DIBAL in toluene (240 mL of 1 M, 240.00 mmol) at −78° C. over 30 minutes and the reaction was stirred for 1 h. The reaction mixture was quenched with methanol (500 mL) and water (250 mL). The dry ice bath was removed, and the reaction mixture was allowed to warm to rt. The mixture was concentrated in vacuo to remove THF and methanol. DCM (2 L) was added, and the suspension was filtered. The organic layer from the filtrate was separated and the aqueous layer was extracted with DCM (2×1 L). The combined organic layer was dried over sodium sulfate, filtered, and concentrated in vacuo. The resulting yellow solid was triturated with hexanes and filtered. The cake was washed with hexanes and dried to give 5-isopropoxypyrimidine-2-carbaldehyde (23.3 g, 88%) as an off-white solid. $^1H$ NMR (500 MHz, DMSO-$d_6$) δ 9.89 (s, 1H), 8.75 (s, 2H), 4.99 (hept, J=6.0 Hz, 1H), 1.34 (d, J=6.0 Hz, 6H). ESI-MS m/z calc. 166.07423, found 167.2 $(M+1)^+$; Retention time: 1.13 minutes; LC method W.

Step 4: 3-[[4-(2,6-Dimethylphenyl)-6-[(3S)-3-[(5-isopropoxypyrimidin-2-yl)methylamino]-5,5-dimethyl-hexyl]pyrimidin-2-yl]sulfamoyl]benzoic acid

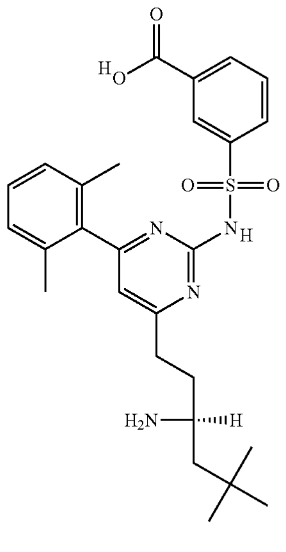

+

-continued

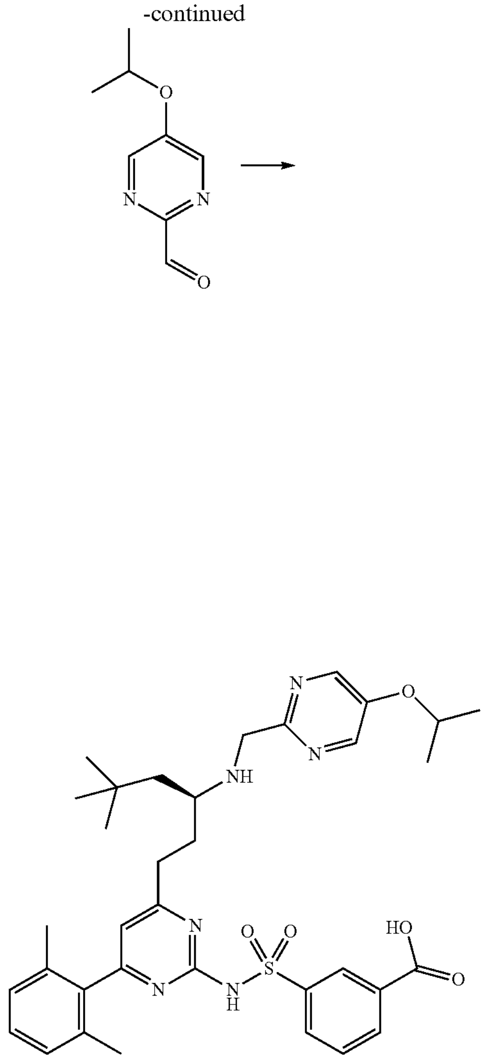

A 4 mL vial was charged under nitrogen with 3-[[4-[(3S)-3-amino-5,5-dimethyl-hexyl]-6-(2,6-dimethylphenyl)pyrimidin-2-yl]sulfamoyl]benzoic acid (Hydrochloride salt) (67.9 mg, 0.1241 mmol), 5-isopropoxypyrimidine-2-carbaldehyde (25 mg, 0.1504 mmol) and DCM (300 μL). The mixture was stirred at room temperature for 15 min. triacetoxyborohydride (Sodium salt) (40 mg, 0.1887 mmol) was added and and the mixture was stirred at room temperature for 1 h. The reaction was quenched with a few drops of 1N aqueous HCl. Methanol and DMSO were added (2 mL total volume). After filtration, the product was subjected to reverse phase HPLC (1-99% acetonitrile/5 mM aqueous HCl over 15 min) to give 3-[[4-(2,6-dimethylphenyl)-6-[(3S)-3-[(5-isopropoxypyrimidin-2-yl)methylamino]-5,5-dimethyl-hexyl]pyrimidin-2-yl]sulfamoyl]benzoic acid (Hydrochloride salt) (43.1 mg, 50%) as an off-white solid. ESI-MS m/z calc. 660.3094, found 661.57 $(M+1)^+$; Retention time: 1.47 minutes; LC method A.

Step 5: (11S)-6-(2,6-Dimethylphenyl)-11-(2,2-dimethylpropyl)-12-[(5-isopropoxypyrimidin-2-yl)methyl]-2,2-dioxo-2 λ6-thia-3,5,12,19-tetrazatricyclo[12.3.1.14,8]nonadeca-1(18),4(19),5,7,14,16-hexaen-13-one

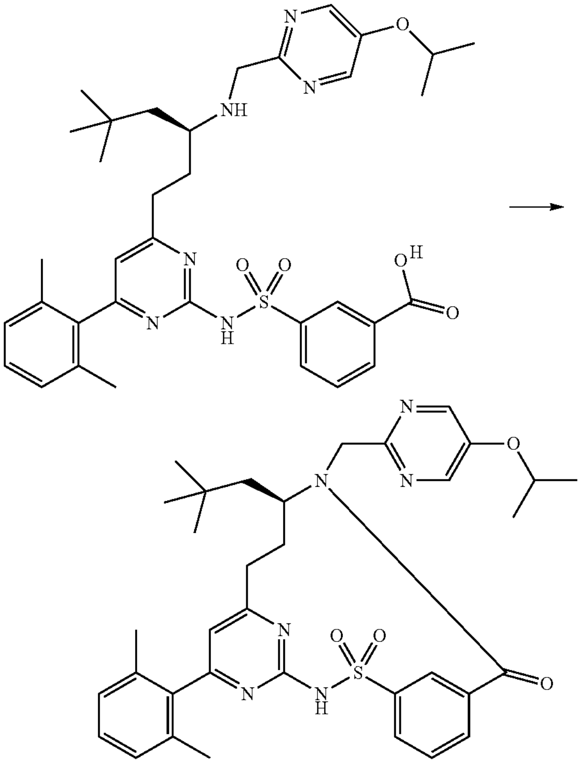

3-[[4-(2,6-Dimethylphenyl)-6-[(3S)-3-[(5-isopropoxypyrimidin-2-yl)methylamino]-5,5-dimethyl-hexyl]pyrimidin-2-yl]sulfamoyl]benzoic acid (hydrochloride salt) (43.1 mg, 0.06181 mmol) was combined in a 4 mL vial under nitrogen with CDMT (17 mg, 0.09683 mmol) and DMF (1.3 mL). The solution was stirred at 0° C. 4-Methyl-morpholine (34 μL, 0.3093 mmol) was added and the mixture was stirred in the cooling bath that was allowed to warm to room temperature for 18 h. The reaction was diluted with DMSO and filtered. Purification by reverse phase HPLC (1-99% acetonitrile/5 mM aqueous HCl over 15 min) gave (11S)-6-(2,6-dimethylphenyl)-11-(2,2-dimethylpropyl)-12-[(5-isopropoxypyrimidin-2-yl)methyl]-2,2-dioxo-2$\lambda^6$-thia-3,5,12,19-tetrazatricyclo[12.3.1.14,8]nonadeca-1(18),4(19),5,7,14,16-hexaen-13-one (31.5 mg, 79%) as an off-white solid. $^1$H NMR (400 MHz, DMSO-$d_6$) δ 11.75 (s, 1H), 8.71-8.64 (m, 1H), 8.52 (s, 2H), 8.05-7.95 (m, 1H), 7.72 (s, 2H), 7.21 (t, J=7.5 Hz, 1H), 7.09 (d, J=7.9 Hz, 3H), 4.87-4.74 (m, 2H), 4.53 (d, J=16.7 Hz, 1H), 3.86-3.70 (m, 1H), 3.04 (d, J=14.5 Hz, 1H), 2.96-2.73 (m, 2H), 2.02-1.73 (m, 7H), 1.59 (dd, J=15.2, 10.0 Hz, 1H), 1.31 (d, J=3.2 Hz, 3H), 1.29 (d, J=3.2 Hz, 3H), 1.26 (d, J=14.5 Hz, 1H), 0.49 (s, 9H). ESI-MS m/z calc. 642.2988, found 643.58 $(M+1)^+$; Retention time: 1.94 minutes; LC method A.

Preparation of Compound 68

Step 1: Methyl 6-[cyclobutyl(methyl)amino]pyrazine-2-carboxylate

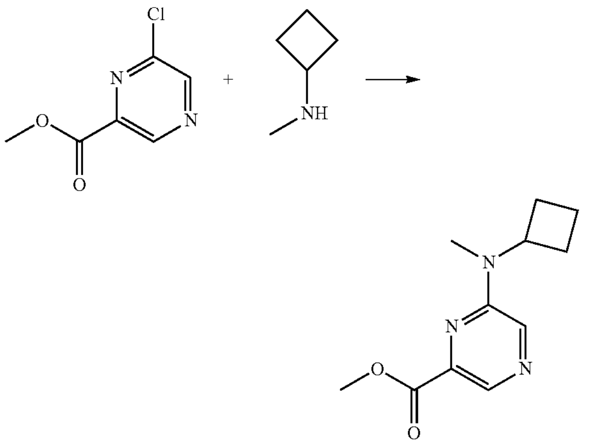

To a stirring solution of methyl 6-chloropyrazine-2-carboxylate (10.5 g, 60.845 mmol) and N-methylcyclobutanamine (hydrochloride salt) (9.46 g, 73.901 mmol) in anhydrous DMSO (150 mL) under nitrogen was added anhydrous sodium carbonate (20 g, 188.70 mmol) in one portion at room temperature. The resulting black mixture was stirred at 90° C. overnight. After cooling to room temperature, water (1000 mL) was added and the resulting solution was extracted with EtOAc (3×300 mL). The combined organic solutions were washed with water (2×300 mL), followed by brine (300 mL), dried over anhydrous sodium sulfate, and filtered. The solvent was removed by rotary evaporation and the residue was dried in vacuo overnight yielding methyl 6-[cyclobutyl(methyl)amino]pyrazine-2-carboxylate (7.77 g, 58%) as an amber oil. The crude was used in the next Step without further purification. $^1$H NMR (500 MHz, $CDCl_3$) δ 8.48 (s, 1H), 8.14 (s, 1H), 4.76-4.65 (m, 1H), 3.96 (s, 3H), 3.11 (s, 3H), 2.37-2.27 (m, 2H), 2.26-2.14 (m, 2H), 1.82-1.70 (m, 2H). ESI-MS m/z calc. 221.11642, found 222.2 $(M+1)^+$; Retention time: 2.43 minutes; LC method T.

Step 2: [6-[Cyclobutyl(methyl)amino]pyrazin-2-yl]methanol

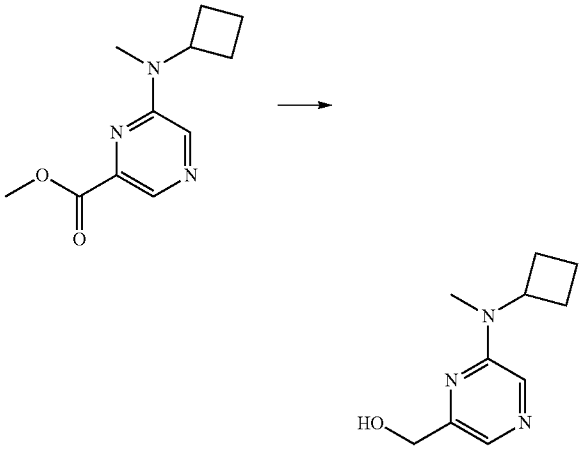

A solution of methyl 6-[cyclobutyl(methyl)amino]pyrazine-2-carboxylate (7.77 g, 35.118 mmol) in MeOH (200 mL) was cooled to 0° C. using an ice bath. Sodium borohydride (13.3 g, 351.55 mmol) was then added in portions over 15 min at the same temperature. The reaction mixture was stirred for 1 h and then warmed to room temperature and stirred for 7 h. The reaction mixture was quenched with water (100 mL). MeOH was removed by rotary evaporation and the remaining aqueous layer was further diluted with water (200 mL), saturated with sodium chloride, and extracted with DCM (100 mL×5). The combined organic solutions were dried over anhydrous sodium sulfate and filtered. The solvent was removed by rotary evaporation and the residue was dried in vacuo for 5 h yielding [6-[cyclobutyl(methyl)amino]pyrazin-2-yl]methanol (5.45 g, 79%) as a yellow oil. The crude was used in the next Step without further purification. ESI-MS m/z calc. 193.1215, found 194.1 $(M+1)^+$; Retention time: 1.41 minutes; LC method T.

Step 3: 6-[Cyclobutyl(methyl)amino]pyrazine-2-carbaldehyde

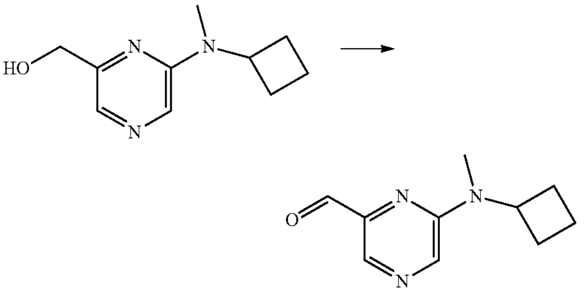

A solution of [6-[cyclobutyl(methyl)amino]pyrazin-2-yl]methanol (5.45 g, 27.638 mmol) in anhydrous DCM (250 mL) was added with DMP (14.2 g, 33.479 mmol) in portions over 5 min under nitrogen. The resulting amber solution was stirred at room temperature overnight. LCMS indicated incomplete oxidation. More DMP (3.6 g, 8.4877 mmol) was added and stirring was continued for 3 h. The reaction mixture was added with a saturated aqueous sodium bicarbonate solution (200 mL) and stirred for 15 min. The organic layer was separated and washed further with saturated aqueous sodium bicarbonate solution (2×200 mL). The organic layer was dried over anhydrous sodium sulfate and filtered. The solvent was removed by rotary evaporation and the crude aldehyde was purified by silica flash chromatography (330 g, dry loaded, eluting from 0 to 40% EtOAc in hexanes over a 70 min gradient). The fractions were combined and concentrated under reduced pressure and the residue was further dried in vacuo overnight yielding 6-[cyclobutyl(methyl)amino]pyrazine-2-carbaldehyde (3.7 g, 67%) as an orange liquid. $^1$H NMR (500 MHz, DMSO-$d_6$) δ 9.90 (s, 1H), 8.40 (s, 1H), 8.27 (s, 1H), 4.89-4.80 (m, 1H), 3.08 (s, 3H), 2.26-2.16 (m, 4H), 1.75-1.61 (m, 2H). ESI-MS m/z calc. 191.10587, found 192.1 $(M+1)^+$; Retention time: 2.19 minutes; LC method W.

Step 4: 3-[[4-[(3R)-3-(tert-Butoxycarbonylamino)-5,5-dimethyl-hex-1-ynyl]-6-(2,6-dimethylphenyl)-5-methoxy-pyrimidin-2-yl]sulfamoyl]benzoic acid

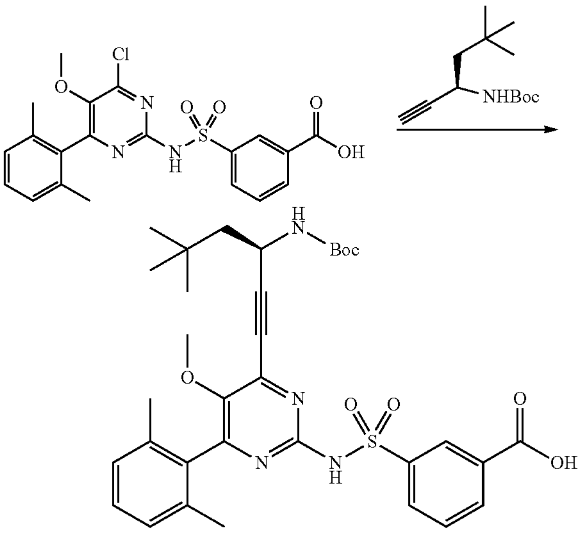

A flask equipped with a reflux condenser was charged with 3-[[4-chloro-6-(2,6-dimethylphenyl)-5-methoxy-pyrimidin-2-yl]sulfamoyl]benzoic acid (3.5 g, 7.8144 mmol), and tert-butyl N-[(1R)-1-ethynyl-3,3-dimethyl-butyl]carbamate (2.81 g, 10.916 mmol) and purged with argon. Then solids were treated with DMSO (38 mL) and degassed an additional 4 h with argon. Then the solution was treated with $Pd(PPh_3)_4$ (994 mg, 0.8602 mmol) and CuI (195 mg, 1.0239 mmol). Then argon was bubbled through the reaction solution for 60 minutes. The reaction was treated with TEA (7.9860 g, 11 mL, 78.921 mmol) at RT, heated in an oil bath at 75° C. for 5 h and 15 min, and cooled to rt for 12 h. Then the reaction was treated with more tert-butyl N-[(1R)-1-ethynyl-3-methyl-butyl]carbamate (0.94 g, 4.4486 mmol) and sparged with argon for 60 minutes. $Pd(PPh_3)_4$ (271 mg, 0.2345 mmol), CuI (30 mg, 0.1575 mmol) were added and then sparged with argon for 60 min and then treated with TEA (3.6300 g, 5 mL, 35.873 mmol). The reaction was heated an additional 5 h at 75° C. The reaction mixture was cooled to rt and poured into water (375 mL) and diluted with $Et_2O$ (250 mL). The two layers were separated. The ether layer was back extracted with 1M NaOH (10 mL). The ether layer was discarded. The combined aqueous phase was acidified with aqueous 10% w/v citric acid to until pH=4 and extracted with ethyl acetate (3×100 mL). The combined organic layers were washed with brine (3×125 mL), dried over anhydrous sodium sulfate and concentrated under vacuum to give a brown crude mixture (7 g). The crude residue was purified by flash chromatography (120 g SiO2, dry loaded, eluted with 0 to 35% acetone in hexane (buffered with 0.3% acetic acid) over a 30 min. gradient). The appropriate fractions were combined and concentrated in vacuo. The residue was diluted with Et2O and concentrated in vacuo, this cycle was repeated 3 times to obtain the target, 3-[[4-[(3R)-3-(tert-butoxycarbonylamino)-5,5-dimethyl-hex-1-ynyl]-6-(2,6-dimethylphenyl)-5-methoxy-pyrimidin-2-yl]sulfamoyl]benzoic acid (2.87 g, 55%), as a brittle yellow solid. $^1H$ NMR (500 MHz, DMSO-$d_6$) δ 13.36 (s, 1H), 11.93 (s, 1H), 8.36 (s, 1H), 8.15 (d, J=7.8 Hz, 1H), 8.10 (d, J=8.0 Hz, 1H), 7.63 (t, J=7.8 Hz, 1H), 7.55 (d, J=8.6 Hz, 1H), 7.23 (t, J=7.6 Hz, 1H), 7.08 (d, J=7.6 Hz, 2H), 4.59 (q, J=7.2 Hz, 1H), 3.45 (s, 3H), 1.78 (s, 6H), 1.75-1.64 (m, 2H), 1.39 (s, 9H), 0.95 (s, 9H). ESI-MS m/z calc. 636.2618, found 637.6 $(M+1)^+$; Retention time: 6.63 minutes; LC method S.

Step 5: 3-[[4-[(3S)-3-(tert-Butoxycarbonylamino)-5,5-dimethyl-hexyl]-6-(2,6-dimethylphenyl)-5-methoxy-pyrimidin-2-yl]sulfamoyl]benzoic acid

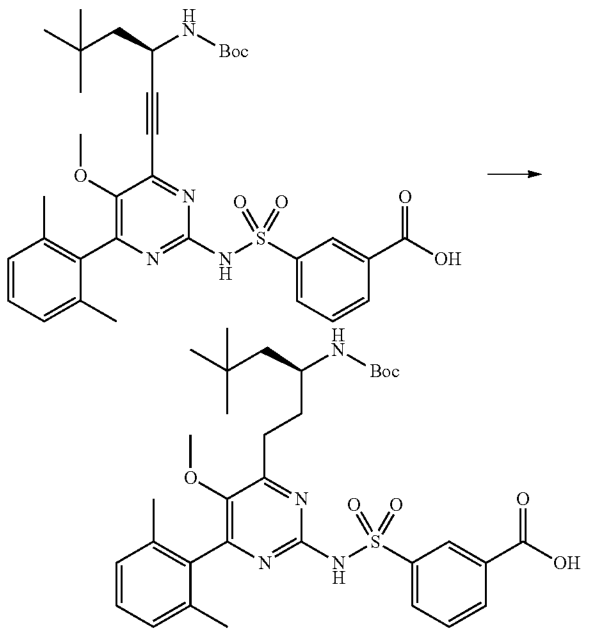

A solution of 3-[[4-[(3R)-3-(tert-butoxycarbonylamino)-5,5-dimethyl-hex-1-ynyl]-6-(2,6-dimethylphenyl)-5-methoxy-pyrimidin-2-yl]sulfamoyl]benzoic acid (2.29 g, 3.4165 mmol) in AcOH (35 mL) was charged with Pd/C (800 mg, 10% w/w, 0.7517 mmol) and sparged with $N_2$ for 6 times to a pressure of 40 psi. Then the vessel was charged with H2 (60 PSI) 6 times and held at 60 PSI. The reaction was stirred at room temperature for 20 h in a Parr shaker. The reaction was treated with additional Pd/C (800 mg, 10% w/w, 0.7517 mmol) and charged with $H_2$ g (60 psi) in the same fashion. The pressure was reduced $H_2$ g (20 psi). The reaction was stirred at room temperature for 20 h in a Parr shaker. The pressure was increased to (60 PSI) $H_2$. The reaction was stirred at room temperature for 20 h. The reaction was filtered through celite and washed with MeOH (500 mL). The reaction was concentrated in vacuo to give an orange solid. The material was again dissolved in AcOH (35 mL), treated with Pd/C (800 mg, 10% w/w, 0.7517 mmol) sparged with $N_2$ for 6 times to a pressure of 40 psi. Then the vessel was charged with $H_2$ (60 PSI) 6 times and held at 60 PSI. The reaction was stirred at room temperature for 33 h in a Parr shaker. The reaction was filtered through celite and washed with MeOH (500 mL). The filtrates were collected and concentrated under reduced pressure to obtain the crude mixture of the target, 3-[[4-[(3S)-3-(tert-butoxycarbonylamino)-5,5-dimethyl-hexyl]-6-(2,6-dimethylphenyl)-5-methoxy-pyrimidin-2-yl]sulfamoyl]benzoic acid (2.37 g, 97%), as an orange solid. $^1H$ NMR (500 MHz, Chloroform-d) δ 9.17-9.01 (m, 1H), 8.32-8.15 (m, 2H), 7.58 (t, J=7.9, 7.9

Hz, 1H), 7.23 (t, J=7.6, 7.6 Hz, 1H), 7.09 (t, J=7.3, 7.3 Hz, 2H), 4.54 (d, J 9.8 Hz, 1H), 3.91-3.63 (m, 1H), 3.28 (s, 3H), 2.93-2.67 (m, 2H), 2.04 (s, 3H), 1.99 (s, 3H), 1.89-1.68 (m, 2H), 1.52-1.43 (m, 9H), 1.41-1.23 (m, 2H), 0.99-0.93 (m, 9H). ESI-MS m/z calc. 640.2931, found 641.5 $(M+1)^+$; Retention time: 6.61 minutes; LC method S.

Step 6: 3-[[4-[(3S)-3-Amino-5,5-dimethyl-hexyl]-6-(2,6-dimethylphenyl)-5-methoxy-pyrimidin-2-yl]sulfamoyl]benzoic acid

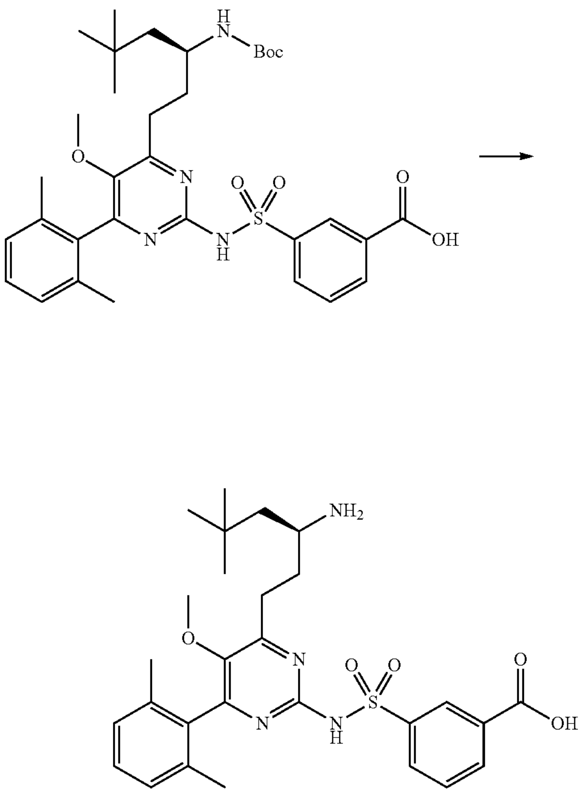

A flask charged with 3-[[4-[(3S)-3-(tert-butoxycarbonylamino)-5,5-dimethyl-hexyl]-6-(2,6-dimethylphenyl)-5-methoxy-pyrimidin-2-yl]sulfamoyl]benzoic acid (2.37 g, 3.2991 mmol) was purged with argon. The solids were treated with TFA (9.5 mL) at RT. The reaction was stirred at room temperature for 30 minutes. The solvent was removed in vacuo to give the target compound as a dark orange viscous residue (3.21 g). The residue was dissolved into TBME (9 mL) and added dropwise into n-hexanes (200 mL) and the precipitate was rapidly collected by filtration and dried in vacuo to give the target, 3-[[4-[(3S)-3-amino-5,5-dimethyl-hexyl]-6-(2,6-dimethylphenyl)-5-methoxy-pyrimidin-2-yl]sulfamoyl]benzoic acid (Trifluoroacetic Acid (1)) (2.1938 g, 97%), as a light yellow orange powder. $^1H$ NMR (500 MHz, DMSO-$d_6$) δ 13.46 (s, 1H), 11.79 (s, 1H), 8.45 (t, J=1.8 Hz, 1H), 8.17 (dt, J=7.8, 1.4 Hz, 1H), 8.13 (dt, J=8.0, 1.5 Hz, 1H), 7.78 (s, 3H), 7.67 (t, J=7.8 Hz, 1H), 7.25 (t, J=7.6 Hz, 1H), 7.11 (d, J=7.6 Hz, 2H), 3.28-3.21 (m, 4H), 2.93-2.76 (m, 2H), 1.94-1.79 (m, 8H), 1.53-1.42 (m, 2H), 0.90 (s, 9H). ESI-MS m/z calc. 540.24066, found 541.3 $(M+1)^+$; Retention time: 2.01 minutes; LC method W.

Step 7: 3-[[4-[(3S)-3-[[6-[Cyclobutyl(methyl)amino]pyrazin-2-yl]methylamino]-5,5-dimethyl-hexyl]-6-(2,6-dimethylphenyl)-5-methoxy-pyrimidin-2-yl]sulfamoyl]benzoic acid

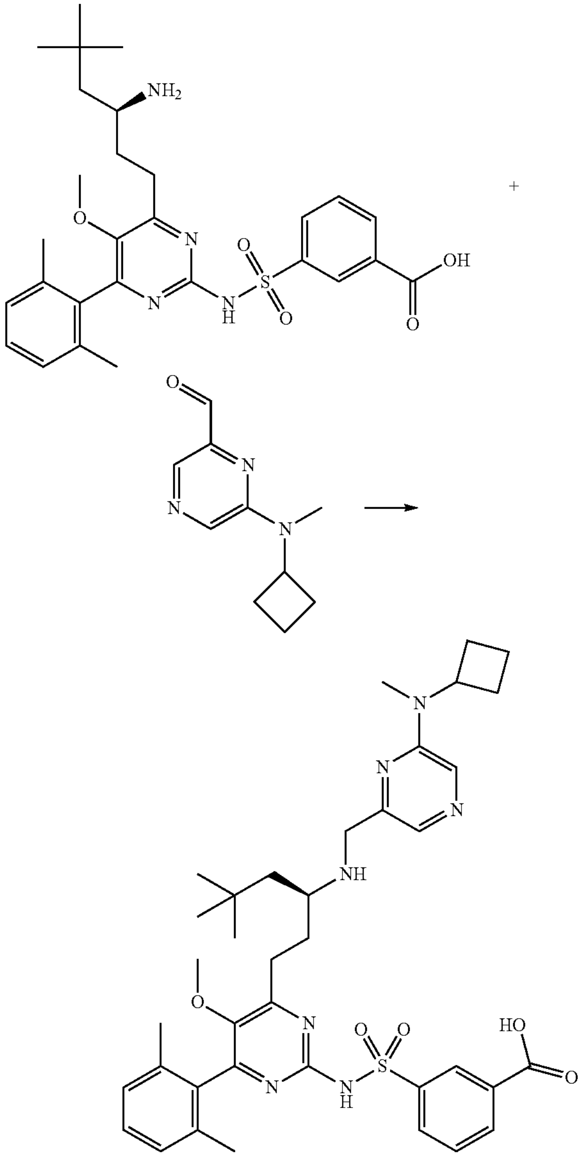

A 20 mL vial was charged under nitrogen with 3-[[4-[(3S)-3-amino-5,5-dimethyl-hexyl]-6-(2,6-dimethylphenyl)-5-methoxy-pyrimidin-2-yl]sulfamoyl]benzoic acid (500 mg, 0.9248 mmol), 6-[cyclobutyl(methyl)amino]pyrazine-2-carbaldehyde (195.6 mg, 1.023 mmol), anhydrous DCM (4.2 mL), and acetic acid (0.08 mL, 1.407 mmol). The mixture was cooled down in an ice bath. DIEA (0.34 mL, 1.952 mmol) was added, followed by sodium triacetoxyborohydride (Sodium salt) (1.506 g, 7.106 mmol), and the reaction was vigorously stirred at 0° C. for 4 h. The reaction was quenched with 3 N aqueous HCl, diluted with MeOH and DMSO, and the resulting solution was filtered. Purification by reverse phase HPLC (1-99% acetonitrile/5 mM aqueous HCl over 15 min) provided 3-[[4-[(3S)-3-[[6-[cyclobutyl(methyl)amino]pyrazin-2-yl]methylamino]-5,5-dimethyl-hexyl]-6-(2,6-dimethylphenyl)-5-methoxy-pyrimidin-2-yl]sulfamoyl]benzoic acid (hydrochloride salt) (68 mg, 10%) as a yellow solid. ESI-MS m/z calc. 715.35156, found 716.0 $(M+1)^+$; Retention time: 1.65 minutes; LC method A.

Step 8: (11S)-12-[[6-[Cyclobutyl(methyl)amino]pyrazin-2-yl]methyl]-6-(2,6-dimethylphenyl)-11-(2,2-dimethylpropyl)-7-methoxy-2,2-dioxo-2%6-thia-3,5,12,19-tetrazatricyclo[12.3.1.14,8]nonadeca-1(18),4(19),5,7,14,16-hexaen-13-one

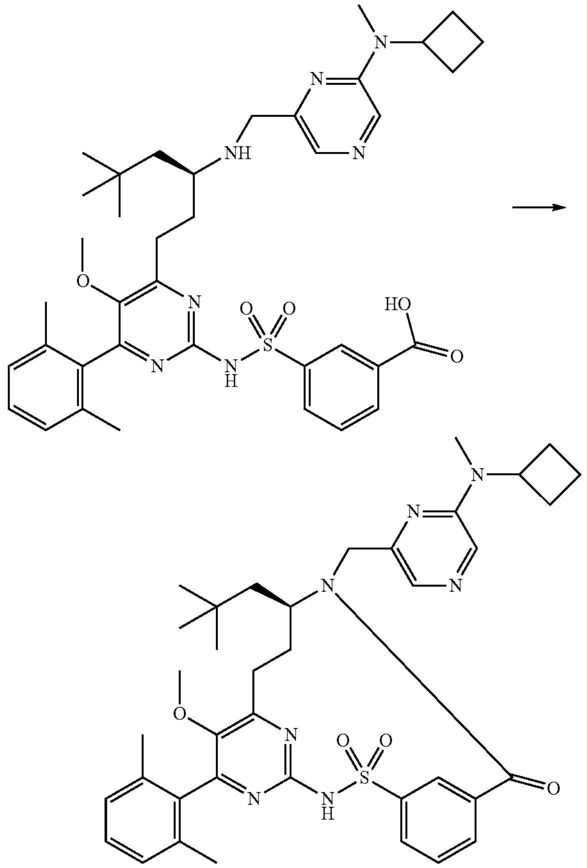

3-[[4-[(3S)-3-[[6-[Cyclobutyl(methyl)amino]pyrazin-2-yl]methylamino]-5,5-dimethyl-hexyl]-6-(2,6-dimethylphenyl)-5-methoxy-pyrimidin-2-yl]sulfamoyl]benzoic acid (Hydrochloride salt) (68 mg, 0.09038 mmol) was combined with CDMT (18.9 mg, 0.1076 mmol) in DMF (6.8 mL) and cooled to 0° C. N-methylmorpholine (0.06 mL, 0.5457 mmol) was added by syringe and the reaction was stirred at 0° C. for 30 minutes. The ice bath was then removed and stirring was continued for an additional 72 hours at room temperature. The reaction mixture was then partitioned between 50 mL 1M HCl and 50 mL ethyl acetate. The layers were separated, and the aqueous layer was extracted with an additional 50 mL ethyl acetate. The combined organic layers were washed 2×50 mL with brine, dried over sodium sulfate, filtered, and concentrated. The crude residue was diluted with DMSO (1 mL), filtered, and purified by reverse phase HPLC (1-99% acetonitrile/5 mM aqueous HCl over 25 min) to give (11S)-12-[[6-[cyclobutyl(methyl)amino]pyrazin-2-yl]methyl]-6-(2,6-dimethylphenyl)-11-(2,2-dimethylpropyl)-7-methoxy-2,2-dioxo-2$\lambda^6$-thia-3,5,12,19-tetrazatricyclo[12.3.1.14,8]nonadeca-1(18),4(19),5,7,14,16-hexaen-13-one (22 mg, 33%) as a white-yellow solid. $^1H$ NMR (400 MHz, $CDCl_3$) δ 8.92 (s, 1H), 8.08 (d, J=1.6 Hz, 1H), 7.93-7.86 (m, 3H), 7.62 (t, J=7.8 Hz, 1H), 7.22 (t, J=7.6 Hz, 1H), 7.11 (d, J=7.6 Hz, 1H), 7.05 (d, J=7.6 Hz, 1H), 5.05 (d, J=15.7 Hz, 1H), 4.68-4.58 (m, 1H), 4.17-4.03 (m, 2H), 3.32-3.21 (m, 4H), 3.11 (s, 3H), 3.08-3.01 (m, 1H), 2.86-2.79 (m, 1H), 2.32-2.13 (m, 4H), 2.10 (s, 3H), 2.08-1.95 (m, 2H), 1.88 (s, 3H), 1.76-1.66 (m, 2H), 1.30-1.24 (m, 1H), 0.55 (s, 9H). ESI-MS m/z calc. 697.341, found 698.2 $(M+1)^+$; Retention time: 1.915 minutes; LC method A.

Preparation of Compound 64

Step 1: 2-Chloro-5-(cyclobutoxy)pyrimidine

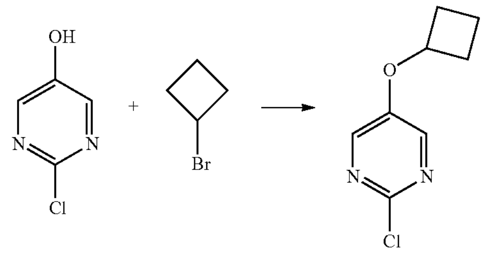 [SMILES: Oc1cnc(Cl)nc1 ; BrC1CCC1 ; Clc1ncc(OC2CCC2)cn1]

A stirred mixture of 2-chloropyrimidin-5-ol (42.6 g, 326.36 mmol), bromocyclobutane (58 g, 429.62 mmol) and potassium carbonate (113 g, 817.62 mmol) in DMF (400 mL) was heated at 80° C. for 2 h. The reaction mixture was allowed to cool to rt and poured onto water (1 L). The solids were filtered, washed with water, and dissolved in DCM (1 L). The DCM layer was dried over sodium sulfate, filtered and concentrated in vacuo to give 2-chloro-5-(cyclobutoxy)pyrimidine (42.3 g, 63%) as a white solid. $^1H$ NMR (500 MHz, DMSO-$d_6$) δ 8.42 (s, 2H), 4.84 (p, J=6.8 Hz, 1H), 2.48-2.42 (m, 2H), 2.10-2.00 (m, 2H), 1.84-1.76 (m, 1H), 1.68-1.55 (m, 1H). ESI-MS m/z calc. 184.04034, found 185.5 $(M+1)^+$; Retention time: 3.72 minutes; LC method S.

Step 2: Methyl 5-(cyclobutoxy)pyrimidine-2-carboxylate

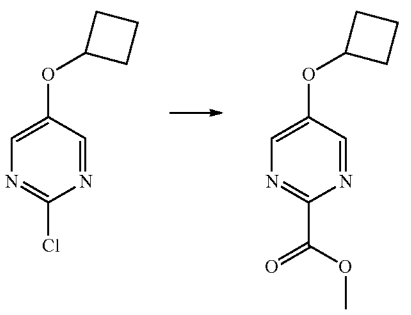

A mixture of 2-chloro-5-(cyclobutoxy)pyrimidine (23.4 g, 114.07 mmol) and $Pd(dppf)_2Cl_2CH_2Cl_2$ (6.5 g, 7.9595 mmol) in DMF (240 mL)/TEA (240 mL)/MeOH (240 mL) in a 2 L steel bomb with overhead mechanical stirrer was purged with carbon monoxide three times. The reaction mixture was heated to 100° C. with 120 psi of CO over one hour and retained at this temperature for one hour. Heating was turned off and the reaction mixture was allowed to cool to rt. Methanol and triethylamine was evaporated in vacuo. Water (500 mL) was added and filtered to remove catalyst residue. The cake was washed with water. The filtrate was extracted with DCM (3×500 mL). The combined organic layer was washed with brine, dried over sodium sulfate, filtered and concentrated in vacuo. The resulting brown oil was purified by flash chromatography ($SiO_2$, 120 g, loaded in DCM, eluted with 25% ethyl acetate in hexanes) to give methyl 5-(cyclobutoxy)pyrimidine-2-carboxylate (11.9 g, 48%) as a beige solid. ESI-MS m z calc. 208.0848, found 209.1 $(M+1)^+$; Retention time: 3.67 minutes; LC method S.

Step 3: 5-(Cyclobutoxy)pyrimidine-2-carbaldehyde

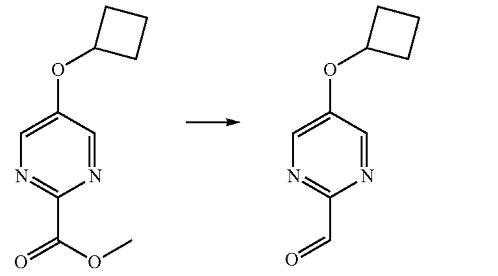

To a stirred solution of methyl 5-(cyclobutoxy)pyrimidine-2-carboxylate (30.1 g, 137.33 mmol) in THF (1 L) was added DIBAL in toluene (200 mL of 1 M, 200.00 mmol) at −78° C. over 30 minutes and the reaction was stirred for 1 h. The reaction mixture was quenched with methanol (200 mL) and water (200 mL). The dry ice bath was removed and the reaction mixture was allowed to warm to rt. The mixture was concentrated in vacuo to remove THF and methanol. DCM (1 L) was added and the mixture was filtered. The organic layer from the filtrate was separated and the aqueous layer was extracted with DCM (2×500 mL). The combined organic layer was dried over sodium sulfate, filtered and concentrated in vacuo. The resulting yellow solid was purified by flash chromatography ($SiO_2$, 220 g, loaded in DCM, eluted with 25% ethyl acetate in hexanes). The desired product fractions were combined and concentrated in vacuo to give 5-(cyclobutoxy)pyrimidine-2-carbaldehyde (21.5 g, 82%) as a white solid. $^1H$ NMR (500 MHz, DMSO-$d_6$) δ 9.88 (s, 1H), 8.67 (s, 2H), 5.08-4.92 (m, 1H), 2.58-2.48 (m, 2H), 2.18-2.03 (m, 2H), 1.88-1.77 (m, 1H), 1.74-1.59 (m, 1H). ESI-MS m z calc. 178.07423, found 179.2 $(M+1)^+$; Retention time: 1.38 minutes; LC method W.

Step 4: 3-[[4-[(3S)-3-[[5-(Cyclobutoxy)pyrimidin-2-yl]methylamino]-5,5-dimethyl-hexyl]-6-(2,6-dimethylphenyl)pyrimidin-2-yl]sulfamoyl]benzoic acid

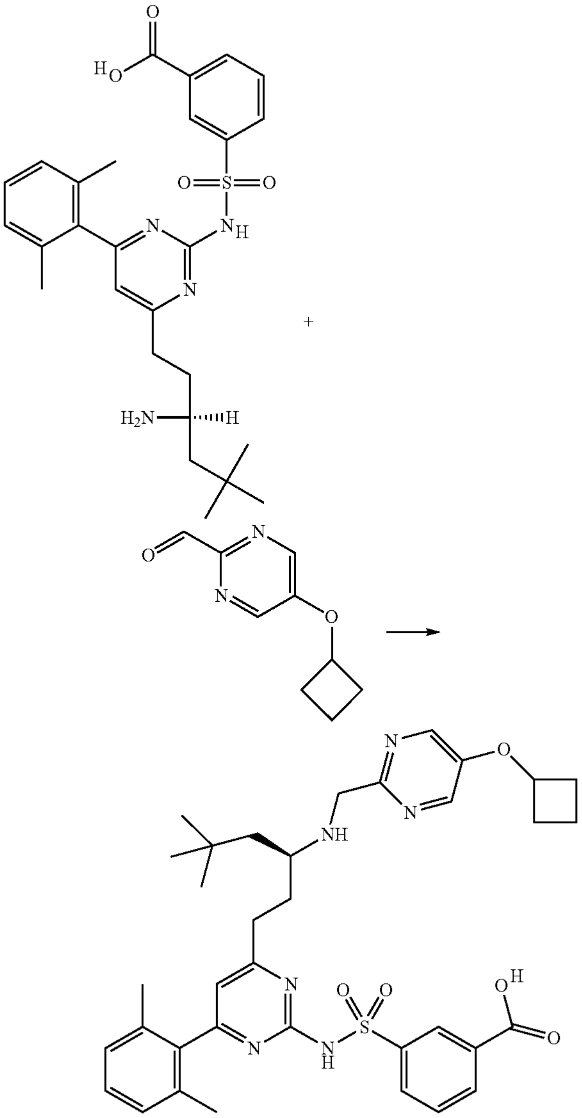

A 4 mL vial was charged under nitrogen with 3-[[4-[(3S)-3-amino-5,5-dimethyl-hexyl]-6-(2,6-dimethylphenyl)pyrimidin-2-yl]sulfamoyl]benzoic acid (hydrochloride salt) (58 mg, 0.1060 mmol), 5-(cyclobutoxy)pyrimidine-2-carbaldehyde (19.7 mg, 0.1106 mmol) and DCM (250 μL). The mixture was stirred at room temperature for 15 min. triacetoxyborohydride (Sodium salt) (35 mg, 0.1651 mmol) was added and the mixture was stirred at room temperature for 2.5 d. The reaction was quenched with a few drops of 1N aqueous HCl. Methanol and DMSO were added (2 mL total volume). After filtration, the product was subjected to reverse phase HPLC (1-99% acetonitrile/5 mM aqueous HCl over 15 min) to give 3-[[4-[(3S)-3-[[5-(cyclobutoxy)pyrimidin-2-yl]methylamino]-5,5-dimethyl-hexyl]-6-(2,6-dimethylphenyl)pyrimidin-2-yl]sulfamoyl]benzoic acid (Hydrochloride salt) (40.7 mg, 54%) as an off-white solid. ESI-MS m/z calc. 672.3094, found 673.62 $(M+1)^+$; Retention time: 1.51 minutes; LC method A.

Step 5: (11S)-12-[[5-(Cyclobutoxy)pyrimidin-2-yl]methyl]-6-(2,6-dimethylphenyl)-11-(2,2-dimethylpropyl)-2,2-dioxo-2λ6-thia-3,5,12,19-tetrazatricyclo[12.3.1.14,8]nonadeca-1(18),4(19),5,7,14,16-hexaen-13-one

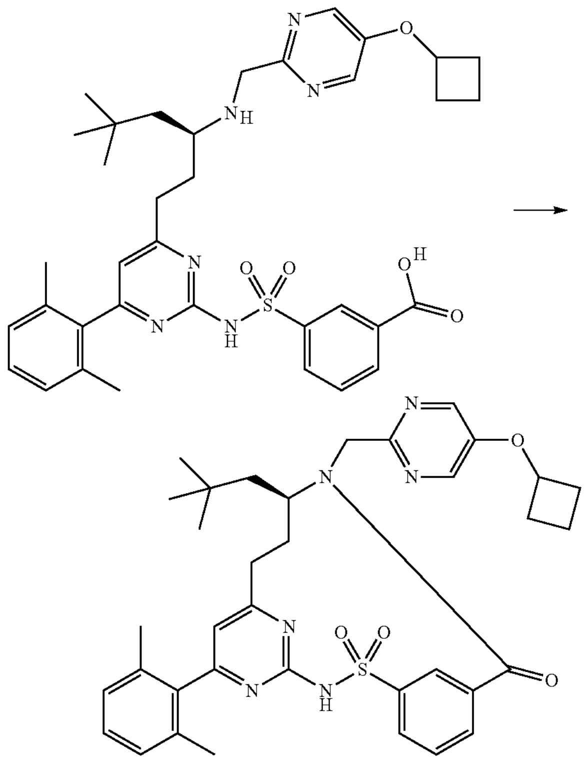

3-[[4-[(3S)-3-[[5-(Cyclobutoxy)pyrimidin-2-yl]methylamino]-5,5-dimethyl-hexyl]-6-(2,6-dimethylphenyl)pyrimidin-2-yl]sulfamoyl]benzoic acid (hydrochloride salt) (40.7 mg, 0.05738 mmol) was combined in a 4 mL vial under nitrogen with CDMT (16 mg, 0.09113 mmol) and DMF (1.3 mL). The solution was stirred at 0° C. 4-Methyl-morpholine (31 μL, 0.2820 mmol) was added and the mixture was stirred in the cooling bath that was allowed to warm to room temperature for 17 h. The reaction was diluted with DMSO and filtered. Purification by reverse phase HPLC (1-99% acetonitrile/5 mM aqueous HCl over 15 min) gave (11S)-12-[[5-(cyclobutoxy)pyrimidin-2-yl]methyl]-6-(2,6-dimethylphenyl)-11-(2,2-dimethylpropyl)-2,2-dioxo-2$\lambda^6$-thia-3,5,12,19-tetrazatricyclo[12.3.1.14,8]nonadeca-1(18),4(19),5,7,14,16-hexaen-13-one (27.4 mg, 73%) as a white solid. $^1$H NMR (400 MHz, DMSO-$d_6$) δ 11.76 (s, 1H), 8.74-8.63 (m, 1H), 8.45 (s, 2H), 8.06-7.95 (m, 1H), 7.79-7.65 (m, 2H), 7.21 (t, J=7.6 Hz, 1H), 7.09 (d, J=7.7 Hz, 3H), 4.94-4.76 (m, 2H), 4.54 (d, J=16.7 Hz, 1H), 3.79 (s, 1H), 3.10-2.95 (m, 1H), 2.95-2.77 (m, 2H), 2.47-2.44 (overlapped with DMSO, m, 1H), 2.14-2.00 (m, 3H), 2.02-1.72 (m, 8H), 1.71-1.52 (m, 2H), 1.34-1.20 (m, 1H), 0.48 (s, 9H). ESI-MS m/z calc. 654.2988, found 655.58 $(M+1)^+$; Retention time: 2.0 minutes; LC method A.

C. Characterization of Compounds 58-73

The compounds in Tables 9 and 10 below were prepared by procedures analogous to those disclosed in the specification, and the analytical data were consistent with the reported structure.

TABLE 9

LCMS Data for Compounds 58-73

| Compound Number | Structure | LCMS Rt (min) | Calc. Mass | M + 1 | LCMS Method |
|---|---|---|---|---|---|
| 58 | 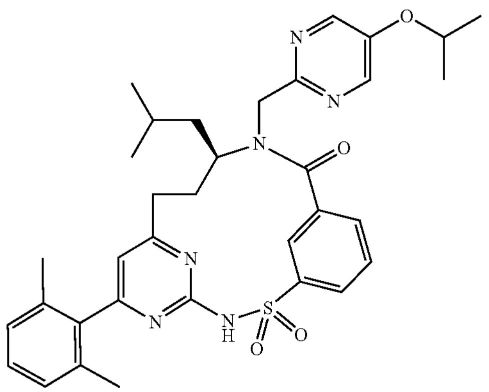 [SMILES: Cc1cccc(C)c1-c1cc2nc(n1)NS(=O)(=O)c1cccc(c1)C(=O)N(Cc1ncc(OC(C)C)cn1)[C@H](CC(C)C)CC2] | 1.9 | 628.283 | 629.5 | A |

TABLE 9-continued
| Compound Number | Structure | LCMS Rt (min) | Calc. Mass | M + 1 | LCMS Method |
|---|---|---|---|---|---|
| | LCMS Data for Compounds 58-73 | | | | |
| 59 | 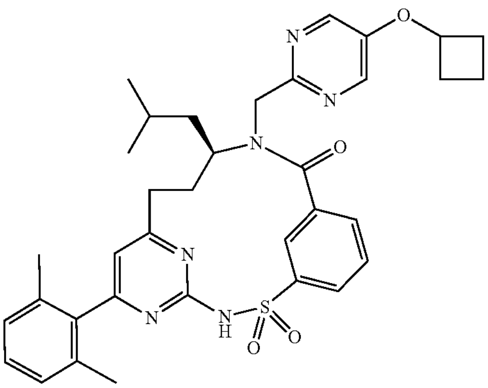 [SMILES: Cc1cccc(C)c1-c1cc2nc(n1)NS(=O)(=O)c1cccc(c1)C(=O)N(Cc1ncc(OC3CCC3)cn1)[C@H](CC(C)C)CC2] | 1.97 | 640.283 | 641.5 | A |
| 60 | 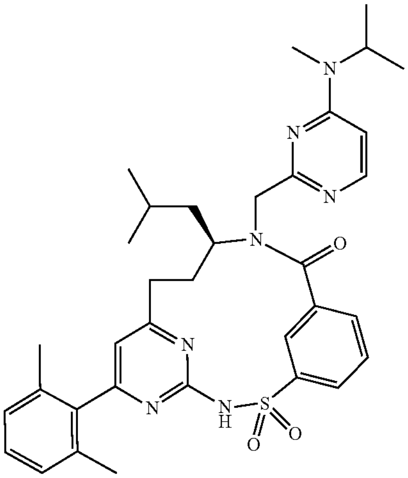 [SMILES: Cc1cccc(C)c1-c1cc2nc(n1)NS(=O)(=O)c1cccc(c1)C(=O)N(Cc1nccc(N(C)C(C)C)n1)[C@H](CC(C)C)CC2] | 1.4 | 641.315 | 642.6 | A |
| 61 | 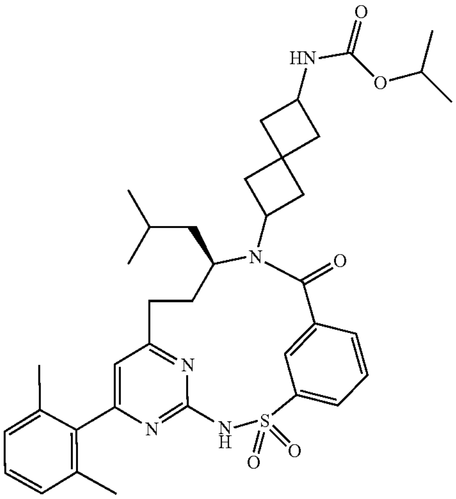 [SMILES: Cc1cccc(C)c1-c1cc2nc(n1)NS(=O)(=O)c1cccc(c1)C(=O)N(C1CC3(CC(NC(=O)OC(C)C)C3)C1)[C@H](CC(C)C)CC2] | 2.03 | 673.33 | 674.3 | A |

TABLE 9-continued
| LCMS Data for Compounds 58-73 | | | | | |
|---|---|---|---|---|---|
| Compound Number | Structure | LCMS Rt (min) | Calc. Mass | M + 1 | LCMS Method |
| 62 | 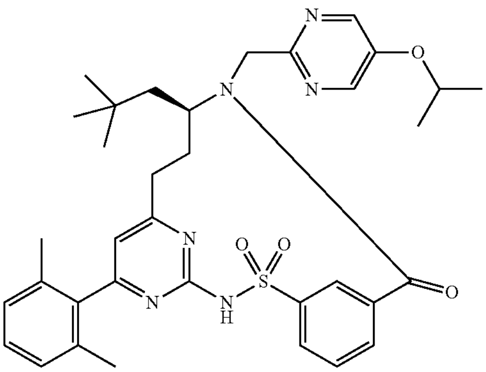 [SMILES: Cc1cccc(C)c1-c1cc2nc(n1)NS(=O)(=O)c1cccc(c1)C(=O)N(Cc1ncc(OC(C)C)cn1)[C@H](CC(C)(C)C)CC2] | 1.94 | 642.299 | 643.58 | A |
| 63 | 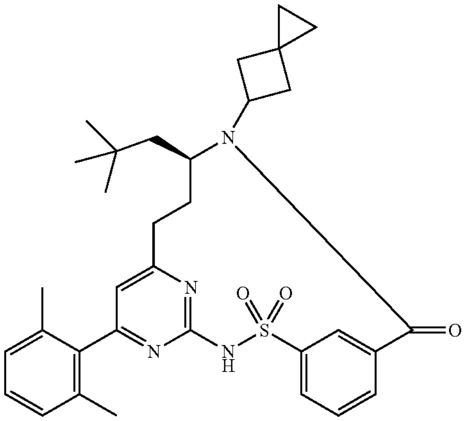 [SMILES: Cc1cccc(C)c1-c1cc2nc(n1)NS(=O)(=O)c1cccc(c1)C(=O)N(C1CC3(CC3)C1)[C@H](CC(C)(C)C)CC2] | 2.16 | 572.282 | 573.61 | A |
| 64 | 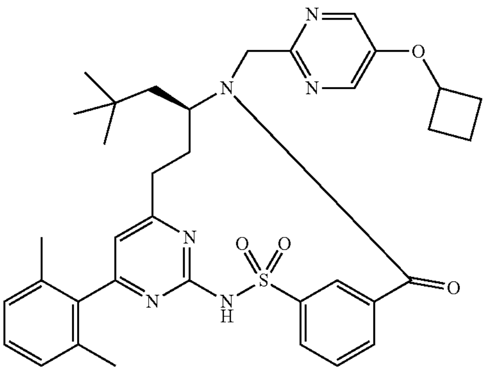 [SMILES: Cc1cccc(C)c1-c1cc2nc(n1)NS(=O)(=O)c1cccc(c1)C(=O)N(Cc1ncc(OC3CCC3)cn1)[C@H](CC(C)(C)C)CC2] | 2 | 654.299 | 655.58 | A |

TABLE 9-continued
LCMS Data for Compounds 58-73
| Compound Number | Structure | LCMS Rt (min) | Calc. Mass | M + 1 | LCMS Method |
|---|---|---|---|---|---|
| 65 | 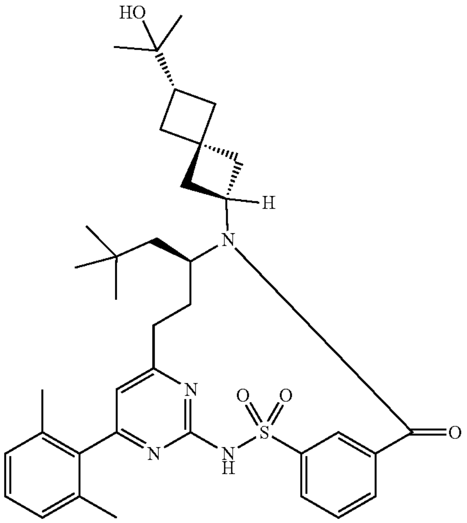 | 1.99 | 644.34 | 645.81 | A |
| 66 | 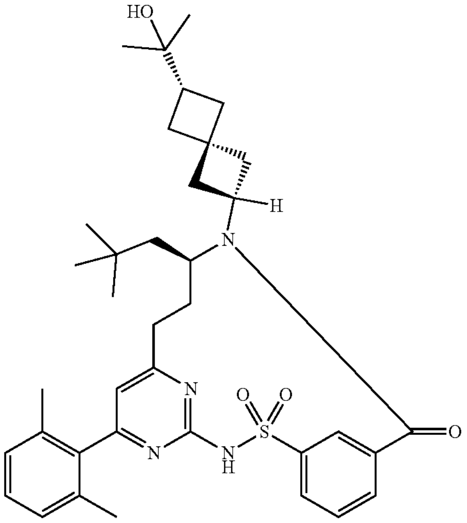 | 2.04 | 644.34 | 645.81 | A |
| 67 | 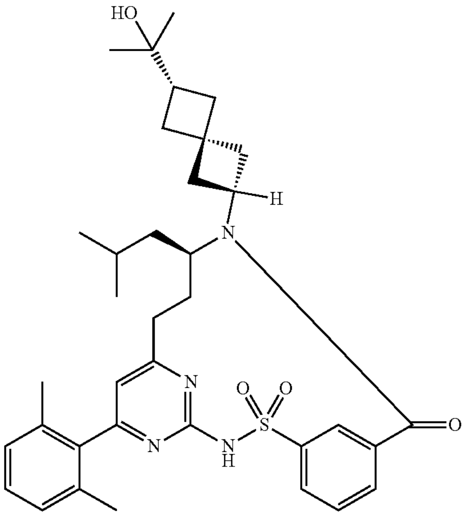 | 1.96 | 630.324 | 631.83 | A |

TABLE 9-continued
| LCMS Data for Compounds 58-73 | | | | | |
|---|---|---|---|---|---|
| Compound Number | Structure | LCMS Rt (min) | Calc. Mass | M + 1 | LCMS Method |
| 68 | 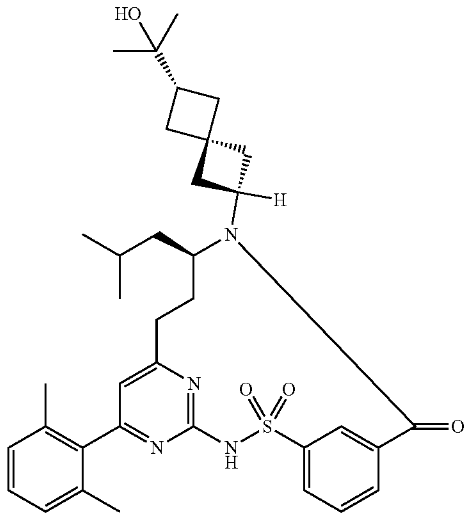 | 2 | 630.324 | 631.89 | A |
| 69 | 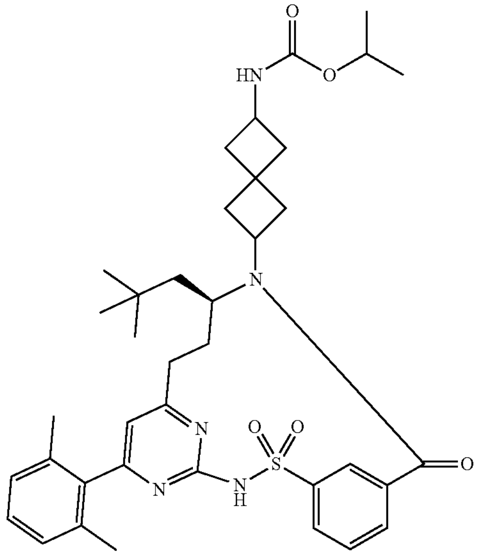 [SMILES: Cc1cccc(C)c1-c1cc2nc(n1)NS(=O)(=O)c1cccc(c1)C(=O)N(C1CC3(CC(NC(=O)OC(C)C)C3)C1)[C@H](CC(C)(C)C)CC2] | 2.04 | 687.345 | 688.3 | A |
| 70 | 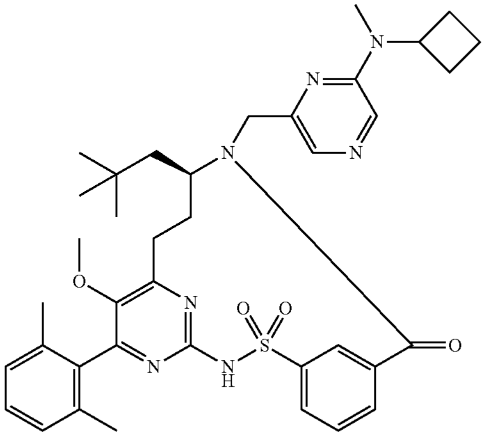 [SMILES: COc1c2nc(nc1-c1c(C)cccc1C)NS(=O)(=O)c1cccc(c1)C(=O)N(Cc1cncc(N(C)C3CCC3)n1)[C@H](CC(C)(C)C)CC2] | 1.915 | 697.341 | 698.2 | A |

TABLE 9-continued
| LCMS Data for Compounds 58-73 | | | | | |
|---|---|---|---|---|---|
| Compound Number | Structure | LCMS Rt (min) | Calc. Mass | M + 1 | LCMS Method |
| 71 | 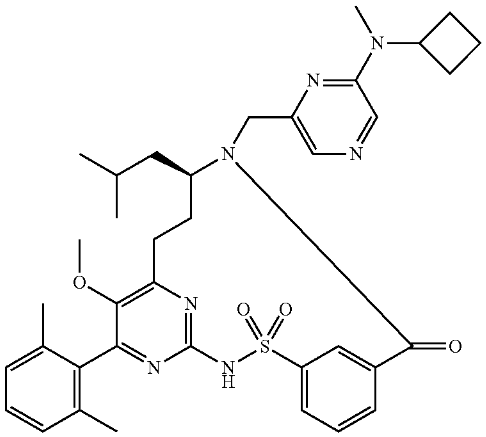 [SMILES: COc1c2nc(nc1-c1c(C)cccc1C)NS(=O)(=O)c1cccc(c1)C(=O)N(Cc1cncc(N(C)C3CCC3)n1)[C@H](CC(C)C)CC2] | 1.882 | 683.325 | 684.2 | A |
| 72 | 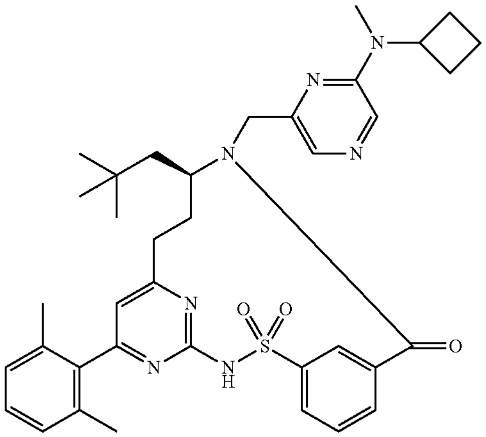 [SMILES: Cc1cccc(C)c1-c1cc2nc(n1)NS(=O)(=O)c1cccc(c1)C(=O)N(Cc1cncc(N(C)C3CCC3)n1)[C@H](CC(C)(C)C)CC2] | 1.82 | 667.33 | 668.3 | A |
| 73 | 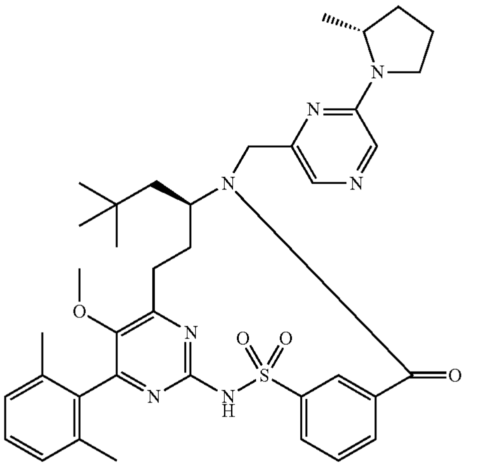 [SMILES: COc1c2nc(nc1-c1c(C)cccc1C)NS(=O)(=O)c1cccc(c1)C(=O)N(Cc1cncc(N3CCC[C@H]3C)n1)[C@H](CC(C)(C)C)CC2] | 1.89 | 697.341 | 698.2 | A |

TABLE 10

NMR Data for Compounds 58-73

| Compound Numbers | NMR |
|---|---|
| 58 | $^1$H NMR (400 MHz, Chloroform-d) δ 8.84 (t, J = 1.8 Hz, 1H), 8.46 (s, 2H), 8.05 (dt, J = 8.2, 1.4 Hz, 1H), 7.84 (dt, J = 7.7, 1.4 Hz, 1H), 7.61 (t, J = 7.8 Hz, 1H), 7.23-7.18 (m, 1H), 7.09-7.05 (m, 2H), 6.73 (s, 1H), 5.32 (d, J = 16.6 Hz, 1H), 4.64 (p, J = 6.1 Hz, 1H), 4.46 (d, J = 16.6 Hz, 1H), 3.90-3.80 (m, 1H), 3.19-3.10 (m, 1H), 3.08-2.96 (m, 1H), 2.76-2.65 (m, 1H), 1.96 (s, 6H), 1.85-1.75 (m, 1H), 1.57-1.48 (m, 1H), 1.44-1.37 (m, 7H), 1.06 (ddd, J = 13.9, 9.9, 3.8 Hz, 1H), 0.71 (d, J = 6.6 Hz, 3H), 0.17 (d, J = 6.4 Hz, 3H). |
| 59 | $^1$H NMR (400 MHz, $CDCl_3$) δ 8.85 (t, J = 1.8 Hz, 1H), 8.35 (s, 2H), 8.07-8.03 (m, 1H), 7.86-7.81 (m, 1H), 7.60 (t, J = 7.8 Hz, 1H), 7.23-7.17 (m, 1H), 7.10-7.04 (m, 2H), 6.72 (s, 1H), 5.28 (d, J = 16.5 Hz, 1H), 4.71 (p, J = 7.1 Hz, 1H), 4.41 (d, J = 16.5 Hz, 1H), 3.88-3.78 (m, 1H), 3.18-3.08 (m, 1H), 3.07-2.96 (m, 1H), 2.74-2.63 (m, 1H), 2.56-2.44 (m, 2H), 2.28-2.15 (m, 2H), 1.95 (s, 6H), 1.92-1.87 (m, 1H), 1.82-1.67 (m, 2H), 1.56-1.46 (m, 1H), 1.46-1.34 (m, 1H), 1.10-0.99 (m, 1H), 0.71 (d, J = 6.6 Hz, 3H), 0.17 (d, J = 6.4 Hz, 3H). |
| 61 | $^1$H NMR (400 MHz, DMSO-$d_6$) δ 11.67 (s, 1H), 8.28 (d, J = 5.0 Hz, 1H), 7.93 (t, J = 4.9 Hz, 1H), 7.72-7.62 (m, 2H), 7.32-7.23 (m, 1H), 7.20 (t, J = 7.6 Hz, 1H), 7.08 (d, J = 7.6 Hz, 2H), 7.01 (s, 1H), 4.72 (pd, J = 6.2, 1.5 Hz, 1H), 3.85 (p, J = 8.7 Hz, 2H), 3.31-3.20 (m, 2H), 3.17-3.04 (m, 2H), 2.99 (d, J = 15.3 Hz, 1H), 2.86-2.71 (m, 1H), 2.58-2.52 (m, 1H), 2.40 (p, J = 6.3 Hz, 1H), 2.28-2.00 (m, 4H), 2.00-1.94 (m, 2H), 1.90 (s, 6H), 1.42 (q, J = 11.9 Hz, 1H), 1.15 (d, J = 6.2 Hz, 6H), 1.06-0.94 (m, 1H), 0.68 (t, J = 7.0 Hz, 3H), 0.01 (d, J = 5.5 Hz, 3H). |
| 62 | $^1$H NMR (400 MHz, DMSO-$d_6$) δ 11.75 (s, 1H), 8.71-8.64 (m, 1H), 8.52 (s, 2H), 8.05-7.95 (m, 1H), 7.72 (s, 2H), 7.21 (t, J = 7.5 Hz, 1H), 7.09 (d, J = 7.9 Hz, 3H), 4.87-4.74 (m, 2H), 4.53 (d, J = 16.7 Hz, 1H), 3.86-3.70 (m, 1H), 3.04 (d, J = 14.5 Hz, 1H), 2.96-2.73 (m, 2H), 2.02-1.73 (m, 7H), 1.59 (dd, J = 15.2, 10.0 Hz, 1H), 1.31 (d, J = 3.2 Hz, 3H), 1.29 (d, J = 3.2 Hz, 3H), 1.26 (d, J = 14.5 Hz, 1H), 0.49 (s, 9H). |
| 63 | $^1$H NMR (400 MHz, DMSO-$d_6$) δ 11.74 (s, 1H), 8.44-8.36 (m, 1H), 7.95 (d, J = 6.2 Hz, 1H), 7.76-7.61 (m, 2H), 7.20 (t, J = 7.6 Hz, 1H), 7.08 (d, J = 7.6 Hz, 2H), 7.02 (s, 1H), 4.24 (p, J = 8.6 Hz, 1H), 3.61-3.38 (m, 2H), 3.06 (d, J = 17.3 Hz, 1H), 2.90 (t, J = 14.2 Hz, 1H), 2.58-2.50 (overlapped with DMSO, m, 2H), 2.20-2.11 (m, 1H), 2.10-2.03 (m, 2H), 2.00-1.63 (m, 6H), 1.45 (dd, J = 15.2, 9.5 Hz, 1H), 1.24 (d, J = 14.9 Hz, 1H), 0.58-0.30 (m, 13H). |
| 64 | $^1$H NMR (400 MHz, DMSO-$d_6$) δ 11.76 (s, 1H), 8.74-8.63 (m, 1H), 8.45 (s, 2H), 8.06-7.95 (m, 1H), 7.79-7.65 (m, 2H), 7.21 (t, J = 7.6 Hz, 1H), 7.09 (d, J = 7.7 Hz, 3H), 4.94-4.76 (m, 2H), 4.54 (d, J = 16.7 Hz, 1H), 3.79 (s, 1H), 3.10-2.95 (m, 1H), 2.95-2.77 (m, 2H), 2.47-2.44 (overlapped with DMSO, m, 1H), 2.14-2.00 (m, 3H), 2.02-1.72 (m, 8H), 1.71-1.52 (m, 2H), 1.34-1.20 (m, 1H), 0.48 (s, 9H). |
| 65 | $^1$H NMR (400 MHz, DMSO-$d_6$) δ 11.73 (s, 1H), 8.37 (s, 1H), 7.94 (d, J = 7.4 Hz, 1H), 7.76-7.58 (m, 2H), 7.19 (t, J = 7.6 Hz, 1H), 7.11-6.91 (m, 3H), 3.97 (s, 1H), 3.85 (p, J = 8.8 Hz, 1H), 3.46 (s, 1H), 3.14-2.96 (m, 3H), 2.88 (t, J = 15.0 Hz, 1H), 2.28-2.19 (m, 1H), 2.17-2.06 (m, 2H), 2.04-1.68 (m, 12H), 1.40 (dd, J = 15.2, 9.4 Hz, 1H), 1.28-1.16 (m, 1H), 0.97 (d, J = 2.3 Hz, 6H), 0.41 (s, 9H). |
| 66 | $^1$H NMR (400 MHz, DMSO-$d_6$) δ 11.73 (s, 1H), 8.36 (s, 1H), 7.94 (d, J = 7.1 Hz, 1H), 7.74-7.62 (m, 2H), 7.20 (t, J = 7.6 Hz, 1H), 7.12-6.91 (m, 3H), 3.98 (s, 1H), 3.85 (p, J = 8.8 Hz, 1H), 3.45 (s, 1H), 3.18 (t, J = 9.5 Hz, 1H), 3.10-2.80 (m, 3H), 2.24 (td, J = 9.5, 8.9, 3.8 Hz, 1H), 2.17-1.70 (m, 14H), 1.43 (dd, J = 15.1, 9.5 Hz, 1H), 1.22 (d, J = 15.0 Hz, 1H), 1.07-0.90 (m, 6H), 0.42 (s, 9H). |
| 67 | $^1$H NMR (400 MHz, DMSO-$d_6$) δ 11.67 (s, 1H), 8.28 (s, 1H), 7.97-7.87 (m, 1H), 7.72-7.60 (m, 2H), 7.19 (t, J = 7.5 Hz, 1H), 7.08 (d, J = 7.6 Hz, 2H), 7.00 (broad s, 1H), 3.97 (s, 1H), 3.81 (p, J = 8.7 Hz, 1H), 3.25 (overlapped with water, m, 1H), 3.09 (t, J = 9.6 Hz, 1H), 3.04-2.93 (m, 2H), 2.79 (t, J = 14.2 Hz, 1H), 2.59-2.52 (m, 1H), 2.23 (td, J = 9.7, 9.0, 3.6 Hz, 1H), 2.16-2.08 (m, 2H), 2.02-1.67 (m, 11H), 1.40 (t, J = 12.6 Hz, 1H), 1.24-1.08 (m, 1H), 1.03 (d, J = 11.5 Hz, 1H), 0.98-0.91 (m, 6H), 0.67 (d, J = 6.6 Hz, 3H), 0.01 (overlapped with TMS, d, J = 6.8 Hz, 3H) |
| 68 | $^1$H NMR (400 MHz, DMSO-$d_6$) δ 11.67 (s, 1H), 8.27 (s, 1H), 7.92 (dd, J = 6.4, 2.9 Hz, 1H), 7.76-7.60 (m, 2H), 7.20 (t, J = 7.6 Hz, 1H), 7.08 (d, J = 7.6 Hz, 2H), 7.01 (s, 1H), 3.98 (s, 1H), 3.81 (p, J = 8.8 Hz, 1H), 3.09 (t, J = 9.4 Hz, 1H), 3.05-2.91 (m, 2H), 2.79 (t, J = 12.9 Hz, 1H), 2.62-2.53 (overlapped with DMSO, m, 1H), 2.23-1.70 (m, 15H), 1.44 (t, J = 12.4 Hz, 1H), 1.26-1.10 (m, 1H), 1.07-0.88 (m, 7H), 0.69 (d, J = 6.6 Hz, 3H), 0.01 (d, J = 6.3 Hz, 3H) |

TABLE 10-continued

NMR Data for Compounds 58-73

| Compound Numbers | NMR |
|---|---|
| 69 | $^1$H NMR (400 MHz, DMSO) δ 11.74 (s, 1H), 8.37 (s, 1H), 7.95 (d, J = 7.2 Hz, 1H), 7.68 (s, 2H), 7.26 (d, J = 8.0 Hz, 1H), 7.20 (t, J = 7.6 Hz, 1H), 7.08 (d, J = 7.6 Hz, 2H), 7.02 (s, 1H), 4.72 (p, J = 6.2 Hz, 1H), 3.99-3.77 (m, 2H), 3.32-3.30 (m, 4H), 3.24-3.17 (m, 1H), 3.05 (t, J = 11.0 Hz, 2H), 2.88 (t, J = 15.0 Hz, 1H), 2.44-2.36 (m, 1H), 2.31-2.18 (m, 2H), 2.15-2.01 (m, 2H), 2.00-1.72 (m, 7H), 1.42 (dd, J = 15.2, 9.5 Hz, 1H), 1.15 (d, J = 6.2 Hz, 6H), 0.41 (s, 9H). |
| 70 | $^1$H NMR (400 MHz, $CDCl_3$) δ 8.92 (s, 1H), 8.08 (d, J = 1.6 Hz, 1H), 7.93-7.86 (m, 3H), 7.62 (t, J = 7.8 Hz, 1H), 7.22 (t, J = 7.6 Hz, 1H), 7.11 (d, J = 7.6 Hz, 1H), 7.05 (d, J = 7.6 Hz, 1H), 5.05 (d, J = 15.7 Hz, 1H), 4.68-4.58 (m, 1H), 4.17-4.03 (m, 2H), 3.32-3.21 (m, 4H), 3.11 (s, 3H), 3.08-3.01 (m, 1H), 2.86-2.79 (m, 1H), 2.32-2.13 (m, 4H), 2.10 (s, 3H), 2.08-1.95 (m, 2H), 1.88 (s, 3H), 1.76-1.66 (m, 2H), 1.30-1.24 (m, 1H), 0.55 (s, 9H). |
| 71 | $^1$H NMR (400 MHz, $CDCl_3$) δ 8.83 (s, 1H), 8.05 (d, J = 1.4 Hz, 1H), 7.93 (s, 1H), 7.89-7.84 (m, 2H), 7.61 (t, J = 7.8 Hz, 1H), 7.22 (t, J = 7.6 Hz, 1H), 7.11 (d, J = 7.6 Hz, 1H), 7.05 (d, J = 7.6 Hz, 1H), 5.07 (d, J = 15.7 Hz, 1H), 4.66 (p, J = 8.4 Hz, 1H), 4.15(d, J = 15.8 Hz, 1H), 3.94-3.85 (m, 1H), 3.27 (s, 3H), 3.22-3.15 (m, 1H), 3.10 (s, 3H), 3.03-2.92 (m, 1H), 2.84-2.75 (m, 1H), 2.33-2.21 (m, 3H), 2.10 (s, 3H), 2.04-1.94 (m, 2H), 1.87 (s, 3H), 1.78-1.67 (m, 3H), 1.37-1.29 (m, 1H), 1.14-1.05 (m, 1H), 0.69 (d, J = 6.6 Hz, 3H), 0.20 (d, J = 6.4 Hz, 3H). |
| 72 | $^1$H NMR (400 MHz, $CDCl_3$) δ 8.90 (s, 1H), 8.04 (d, J = 1.5 Hz, 1H), 7.94-7.87 (m, 3H), 7.61 (t, J = 7.8 Hz, 1H), 7.20 (t, J = 7.6 Hz, 1H), 7.07 (d, J = 7.6 Hz, 2H), 6.73 (s, 1H), 5.04 (d, J = 15.7 Hz, 1H), 4.68-4.58 (m, 1H), 4.13 (d, J = 15.8 Hz, 1H), 4.07-3.99 (m, 1H), 3.21-3.07 (m, 6H), 2.80-2.69 (m, 1H), 2.28-2.15 (m, 4H), 1.95 (s, 5H), 1.76-1.69 (m, 2H), 1.61-1.53 (m, 2H), 1.27-1.20 (m, 1H), 0.55 (s, 9H). |
| 73 | $^1$H NMR (400 MHz, $CDCl_3$) δ 8.94 (s, 1H), 8.08 (d, J = 8.0 Hz, 1H), 7.90 (d, J = 7.7 Hz, 1H), 7.84 (s, 1H), 7.75-7.67 (m, 2H), 7.63 (t, J = 7.8 Hz, 1H), 7.22 (t, J = 7.6 Hz, 1H), 7.11 (d, J = 7.6 Hz, 1H), 7.05 (d, J = 7.6 Hz, 1H), 5.02 (d, J = 15.5 Hz, 1H), 4.27-4.16 (m, 2H), 4.11-4.03 (m, 1H), 3.67-3.59 (m, 1H), 3.52-3.44 (m, 1H), 3.28 (s, 3H), 3.23-3.11 (m, 1H), 2.83 (d, J = 17.5 Hz, 1H), 2.13-2.02 (m, 7H), 1.88 (s, 3H), 1.81-1.76 (m, 1H), 1.56-1.48 (m, 1H), 1.32-1.26 (m, 4H), 0.56 (s, 9H). |

D. Biological Activity of Compounds 58-73

1. Assay Procedures (a) HBE Assay (1) Ussing Chamber Assay of CFTR-Mediated Short-Circuit Currents Ussing chamber experiments were performed using human bronchial epithelial (HBE) cells derived from CF subjects heterozygous for F508del and a minimal function CFTR mutation (F508del/MF-HBE) and cultured as previously described (Neuberger T, Burton B, Clark H, Van Goor F Methods Mol Biol 2011:741:39-54). After four days the apical media was removed, and the cells were grown at an air liquid interface for >14 days prior to use. This resulted in a monolayer of fully differentiated columnar cells that were ciliated, features that are characteristic of human bronchial airway epithelia.

To isolate the CFTR-mediated short-circuit ($I_{SC}$) current, F508del/MF-HBE grown on Costar® Snapwell™ cell culture inserts were mounted in an Ussing chamber and the transepithelial $I_{SC}$ was measured under voltage-clamp recording conditions ($V_{hold}$=0 mV) at 37° C. The basolateral solution contained (in mM) 145 NaCl, 0.83$K_2HPO_4$, 3.3 $KH_2PO_4$, 1.2 $MgCl_2$, 1.2 $CaCl_2$), 10 Glucose, 10 HEPES (pH adjusted to 7.4 with NaOH) and the apical solution contained (in mM) 145 NaGluconate, 1.2 $MgCl_2$, 1.2 $CaCl_2$), 10 glucose, 10 HEPES (pH adjusted to 7.4 with NaOH) and 30 μM amiloride to block the epithelial sodium channel. Forskolin (20 μM) was added to the apical surface to activate CFTR, followed by apical addition of a CFTR inhibitor cocktail consisting of BPO, GlyH-101, and CFTR inhibitor 172 (each at 20 μM final assay concentration) to specifically isolate CFTR currents. The CFTR-mediated $I_{SC}$ (μA/cm$^2$) for each condition was determined from the peak forskolin response to the steady-state current following inhibition.

(2) Identification of Corrector Compounds

The activity of the CFTR corrector compounds on the CFTR-mediated $I_{SC}$ was determined in Ussing chamber studies as described above. The F508del/MF-HBE cell cultures were either incubated with the corrector compounds at a range of concentrations in combination with 1 μM Ivacaftor or were incubated with the corrector compounds at a single fixed concentration of 10 μM in combination with 1 μM Ivacaftor for 18-24 hours at 37° C. and in the presence of 20% human serum. The concentration of corrector compounds with 1 μM Ivacaftor during the 18-24 hours incubations was kept constant throughout the Ussing chamber measurement of the CFTR-mediated $I_{SC}$ to ensure compounds were present throughout the entire experiment. The efficacy and potency of the putative F508del correctors was compared to that of the known Vertex corrector, (14S)-8-[3-(2-{Dispiro[2.0.2.1]heptan-7-yl}ethoxy)-1H-pyrazol-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione, in combination with 18 μM Tezacaftor and 1 μM Ivacaftor.

(b) HBE2 Assay (1) Ussing Chamber Assay of CFTR-Mediated Short-Circuit Currents

Ussing chamber experiments were performed using human bronchial epithelial (HBE) cells derived from CF subjects heterozygous for F508del and a minimal function CFTR mutation (F508del/MF-HBE) and cultured as previously described (Neuberger T, Burton B, Clark H, Van Goor F Methods Mol Biol 2011:741:39-54). After four days the apical media was removed, and the cells were grown at an air liquid interface for >14 days prior to use. This resulted in a monolayer of fully differentiated columnar cells that were ciliated, features that are characteristic of human bronchial airway epithelia.

To isolate the CFTR-mediated short-circuit ($I_{SC}$) current, F508del/MF-HBE grown on Costar® Snapwell™ cell culture inserts were mounted in an Ussing chamber and the transepithelial $I_{SC}$ was measured under voltage-clamp recording conditions ($V_{hold}$=0 mV) at 37° C. The basolateral solution contained (in mM) 145 NaCl, 0.83$K_2HPO_4$, 3.3 $KH_2PO_4$, 1.2 $MgCl_2$, 1.2 $CaCl_2$), 10 Glucose, 10 HEPES (pH adjusted to 7.4 with NaOH) and the apical solution contained (in mM) 145 NaGluconate, 1.2 $MgCl_2$, 1.2 $CaCl_2$), 10 glucose, 10 HEPES (pH adjusted to 7.4 with NaOH) and 30 μM amiloride to block the epithelial sodium channel. Forskolin (20 μM) was added to the apical surface to activate CFTR, followed by apical addition of a CFTR inhibitor cocktail consisting of BPO, GlyH-101, and CFTR inhibitor 172 (each at 20 μM final assay concentration) to specifically isolate CFTR currents. The CFTR-mediated $I_{SC}$ (μA/$cm^2$) for each condition was determined from the peak forskolin response to the steady-state current following inhibition.

(2) Identification of Corrector Compounds

The activity of the CFTR corrector compounds on the CFTR-mediated $I_{SC}$ was determined in Ussing chamber studies as described above. The F508del/MF-HBE cell cultures were either incubated with the corrector compounds at a range of concentrations in combination with 44 nM (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol or were incubated with the corrector compounds at a single fixed concentration of 1 and 3 μM in combination with 44 nM (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol for 18-24 hours at 37° C. and in the presence of 20% human serum. The concentration of corrector compounds with 44 nM (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol during the 18-24 hours incubations was kept constant throughout the Ussing chamber measurement of the CFTR-mediated $I_{SC}$ to ensure compounds were present throughout the entire experiment. The efficacy and potency of the putative F508del correctors was compared to that of the known Vertex corrector, (14S')-8-[3-(2-{Dispiro[2.0.2.1]heptan-7-yl}ethoxy)-1H-pyrazol-1-yl]-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione, in combination with 18 μM Tezacaftor and 1 μM Ivacaftor.

2. Biological Activity Data

Table 11 provides CFTR modulating activity for Compounds 58-71 generated using one or more of the assays disclosed herein ($EC_{50}$: +++ is <1 μM; ++ is 1-<3 μM; + is 3-<30 μM; and ND is "not detected in this assay." % Activity: +++ is >60%; ++ is 30-60%; + is <300%).

TABLE 11

Biological Data for Compounds 58-73

| Compound Number | Structure | HBE $EC_{50}$ (μM) | HBE Max. activity (%) | HBE Activity at 10 μM (%) | HBE2 Activity at 3 μM (%) |
|---|---|---|---|---|---|
| 58 | 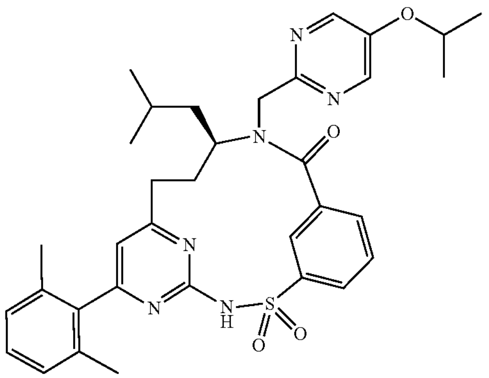 [SMILES: Cc1cccc(C)c1-c1cc2nc(n1)NS(=O)(=O)c1cccc(c1)C(=O)N(Cc1ncc(OC(C)C)cn1)[C@H](CC(C)C)CC2] | +++ | +++ | | |

TABLE 11-continued
| Biological Data for Compounds 58-73 | | | | | |
|---|---|---|---|---|---|
| Compound Number | Structure | HBE $EC_{50}$ (μM) | HBE Max. activity (%) | HBE Activity at 10 μM (%) | HBE2 Activity at 3 μM (%) |
| 59 | 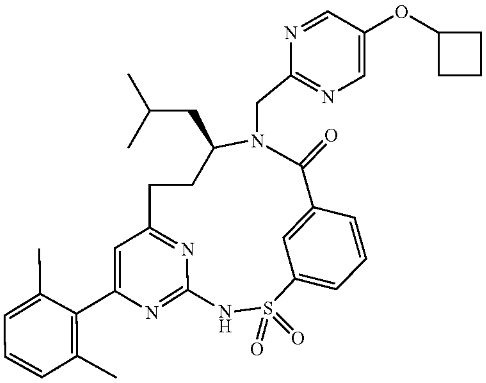 [SMILES: Cc1cccc(C)c1-c1cc2nc(n1)NS(=O)(=O)c1cccc(c1)C(=O)N(Cc1ncc(OC3CCC3)cn1)[C@H](CC(C)C)CC2] | +++ | +++ | | |
| 60 | 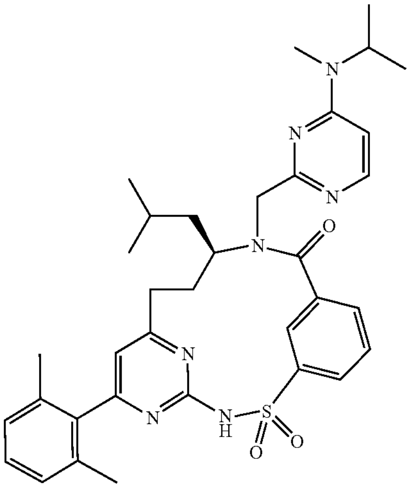 [SMILES: Cc1cccc(C)c1-c1cc2nc(n1)NS(=O)(=O)c1cccc(c1)C(=O)N(Cc1nccc(N(C)C(C)C)n1)[C@H](CC(C)C)CC2] | +++ | +++ | | |
| 61 | 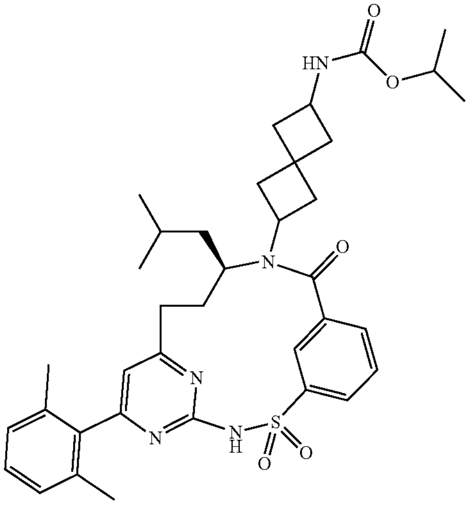 [SMILES: Cc1cccc(C)c1-c1cc2nc(n1)NS(=O)(=O)c1cccc(c1)C(=O)N(C1CC3(CC(NC(=O)OC(C)C)C3)C1)[C@H](CC(C)C)CC2] | | | | |

TABLE 11-continued
Biological Data for Compounds 58-73
| Compound Number | Structure | HBE $EC_{50}$ (μM) | HBE Max. activity (%) | HBE Activity at 10 μM (%) | HBE2 Activity at 3 μM (%) |
|---|---|---|---|---|---|
| 62 | 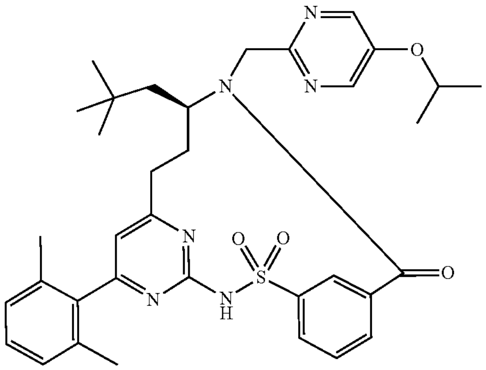 [SMILES: Cc1cccc(C)c1-c1cc2nc(n1)NS(=O)(=O)c1cccc(c1)C(=O)N(Cc1ncc(OC(C)C)cn1)[C@H](CC(C)(C)C)CC2] | +++ | +++ | | |
| 63 | 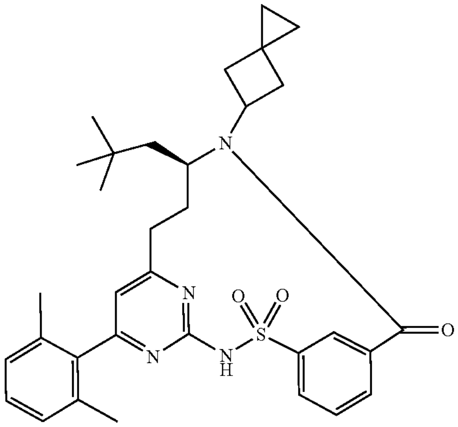 [SMILES: Cc1cccc(C)c1-c1cc2nc(n1)NS(=O)(=O)c1cccc(c1)C(=O)N(C1CC3(CC3)C1)[C@H](CC(C)(C)C)CC2] | | | +++ | |
| 64 | 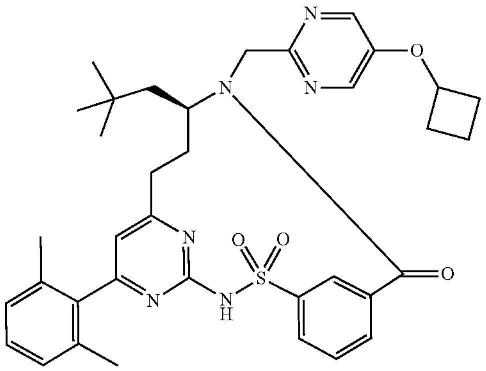 [SMILES: Cc1cccc(C)c1-c1cc2nc(n1)NS(=O)(=O)c1cccc(c1)C(=O)N(Cc1ncc(OC3CCC3)cn1)[C@H](CC(C)(C)C)CC2] | | | +++ | |

TABLE 11-continued
| Biological Data for Compounds 58-73 | | | | | |
|---|---|---|---|---|---|
| Compound Number | Structure | HBE $EC_{50}$ (μM) | HBE Max. activity (%) | HBE Activity at 10 μM (%) | HBE2 Activity at 3 μM (%) |
| 65 | 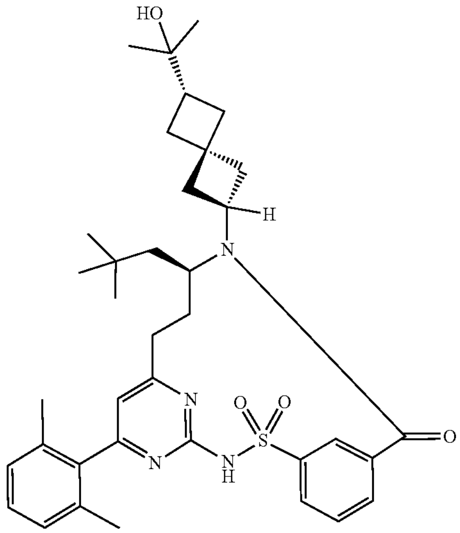 | | | +++ | |
| 66 | 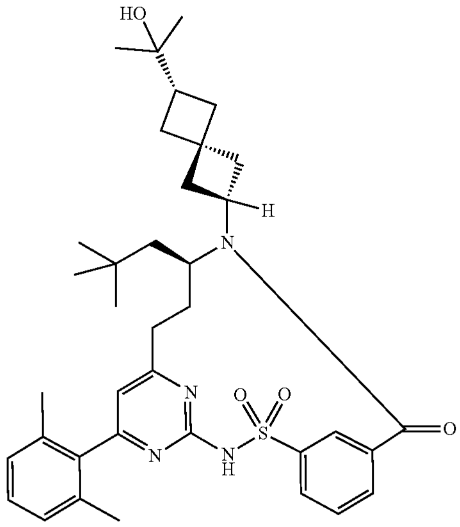 | | | +++ | |

TABLE 11-continued
| Biological Data for Compounds 58-73 | | | | | |
|---|---|---|---|---|---|
| Compound Number | Structure | HBE $EC_{50}$ (μM) | HBE Max. activity (%) | HBE Activity at 10 μM (%) | HBE2 Activity at 3 μM (%) |
| 67 | 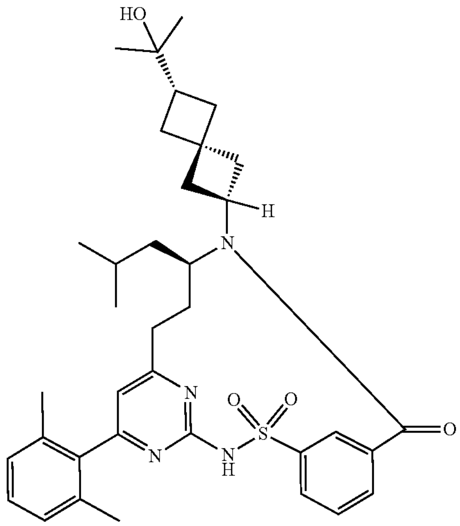 | | | | |
| 68 | 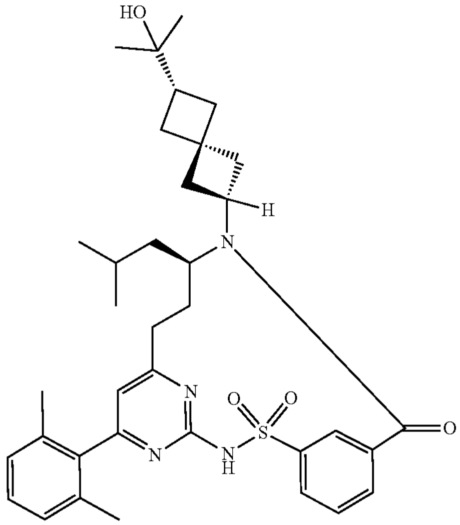 | | | | |

TABLE 11-continued
| Compound Number | Structure | HBE $EC_{50}$ (μM) | HBE Max. activity (%) | HBE Activity at 10 μM (%) | HBE2 Activity at 3 μM (%) |
|---|---|---|---|---|---|
| Biological Data for Compounds 58-73 | | | | | |
| 69 | 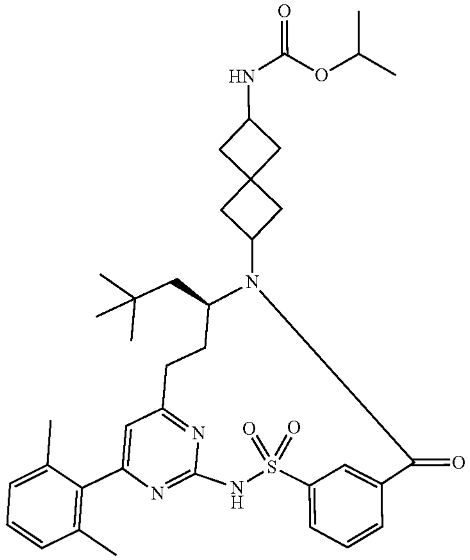 [SMILES: Cc1cccc(C)c1-c1cc2nc(n1)NS(=O)(=O)c1cccc(c1)C(=O)N(C1CC3(CC(NC(=O)OC(C)C)C3)C1)[C@H](CC(C)(C)C)CC2] | | | | +++ |
| 70 | 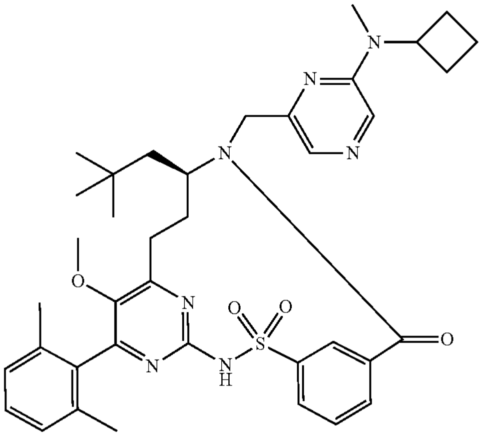 [SMILES: COc1c2nc(nc1-c1c(C)cccc1C)NS(=O)(=O)c1cccc(c1)C(=O)N(Cc1cncc(N(C)C3CCC3)n1)[C@H](CC(C)(C)C)CC2] | | | | |
| 71 | 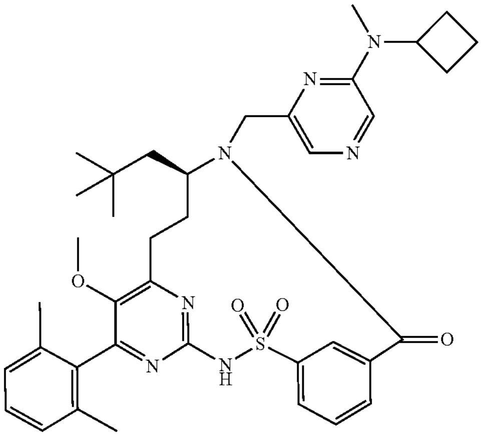 [SMILES: COc1c2nc(nc1-c1c(C)cccc1C)NS(=O)(=O)c1cccc(c1)C(=O)N(Cc1cncc(N(C)C3CCC3)n1)[C@H](CC(C)(C)C)CC2] | | | | |

TABLE 11-continued

| Compound Number | Structure | HBE $EC_{50}$ (μM) | HBE Max. activity (%) | HBE Activity at 10 μM (%) | HBE2 Activity at 3 μM (%) |
|---|---|---|---|---|---|
| Biological Data for Compounds 58-73 | | | | | |
| 72 | 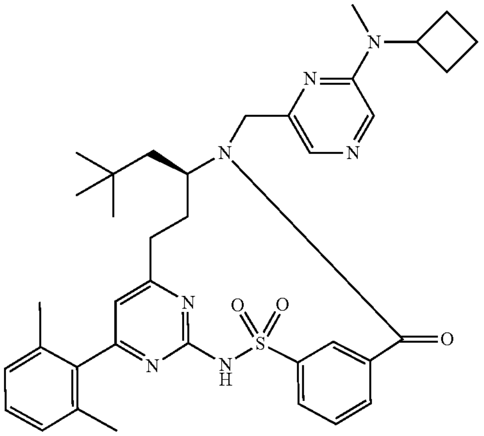 [SMILES: Cc1cccc(C)c1-c1cc2nc(n1)NS(=O)(=O)c1cccc(c1)C(=O)N(Cc1cncc(N(C)C3CCC3)n1)[C@H](CC(C)(C)C)CC2] | | | | +++ |
| 73 | 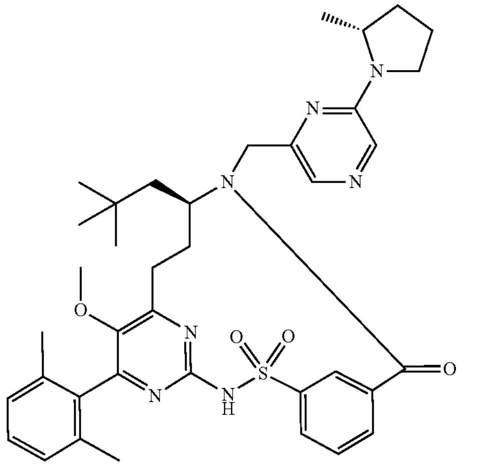 [SMILES: COc1c2nc(nc1-c1c(C)cccc1C)NS(=O)(=O)c1cccc(c1)C(=O)N(Cc1cncc(N3CCC[C@H]3C)n1)[C@H](CC(C)(C)C)CC2] | | | | |

VIII. Synthesis of (6R,12R)-17-amino-12-methyl-6, 15-bis(trifluoromethyl)-13,19-dioxa-3,4,18-triazatricyclo [12.3.1.12,5] nonadeca-1(18),2,4,14,16-pentaen-6-ol

A. General Methods

Reagents and starting materials were obtained by commercial sources unless otherwise stated and were used without purification.

Proton and carbon NMR spectra were acquired on either a Bruker Biospin DRX 400 MHz FTNMR spectrometer operating at a $^{1}H$ and $^{13}C$ resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution respectively. All proton and carbon spectra were acquired with temperature control at 30° C. using standard, previously published pulse sequences and routine processing parameters.

NMR (1D & 2D) spectra were also recorded on a Bruker AVNEO 400 MHz spectrometer operating at 400 MHz and 100 MHz respectively equipped with a 5 mm multinuclear Iprobe.

NMR spectra were also recorded on a Varian Mercury NMR instrument at 300 MHz for $^{1}H$ using a 45 degree pulse angle, a spectral width of 4800 Hz and 28860 points of acquisition. FID were zero-filled to 32 k points and a line broadening of 0.3 Hz was applied before Fourier transform. $^{19}F$ NMR spectra were recorded at 282 MHz using a 30 degree pulse angle, a spectral width of 100 kHz and 59202 points were acquired. FID were zero-filled to 64 k points and a line broadening of 0.5 Hz was applied before Fourier transform.

NMR spectra were also recorded on a Bruker Avance III HD NMR instrument at 400 MHz for $^{1}H$ using a 30 degree pulse angle, a spectral width of 8000 Hz and 128 k points of acquisition. FID were zero-filled to 256 k points and a line broadening of 0.3 Hz was applied before Fourier transform. $^{19}F$ NMR spectra were recorded at 377 MHz using a 30 deg pulse angle, a spectral width of 89286 Hz and 128 k points were acquired. FID were zero-filled to 256 k points and a line broadening of 0.3 Hz was applied before Fourier transform.

NMR spectra were also recorded on a Bruker AC 250 MHz instrument equipped with a: 5 mm QNP(H1/C13/F19/P31) probe (type: 250-SB, s #23055/0020) or on a Varian 500 MHz instrument equipped with a ID PFG, 5 mm, 50-202/500 MHz probe (model/part #99337300).

Unless stated to the contrary in the following examples, final purity of compounds was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 3.0 minutes. Mobile phase A=$H_2O$ (0.05% $CF_3CO_2H$). Mobile phase B═$CH_3CN$ (0.035% $CF_3CO_2H$). Flow rate=1.2 mL/min, injection volume=1.5 μL, and column temperature=60° C. Final purity was calculated by averaging the area under the curve (AUC) of two UV traces (220 nm, 254 nm). Low-resolution mass spectra were reported as $[M+1]^+$ species obtained using a single quadrupole mass spectrometer equipped with an electrospray ionization (ESI) source capable of achieving a mass accuracy of 0.1 Da and a minimum resolution of 1000 (no units on resolution) across the detection range.

Solid-state NMR (SSNMR) spectra were recorded on a Bruker-Biospin 400 MHz wide-bore spectrometer equipped with Bruker-Biospin 4 mm HFX probe. Samples were packed into 4 mm $ZrO_2$ rotors and spun under Magic Angle Spinning (MAS) condition with spinning speed typically set to 12.5 kHz. The proton relaxation time was measured using $^1H$ MAS Ti saturation recovery relaxation experiment in order to set up proper recycle delay of the $^{13}C$ cross-polarization (CP) MAS experiment. The fluorine relaxation time was measured using $^{19}F$ MAS Ti saturation recovery relaxation experiment in order to set up proper recycle delay of the $^{19}F$ MAS experiment. The CP contact time of carbon CPMAS experiment was set to 2 ms. A CP proton pulse with linear ramp (from 50% to 100%) was employed. The carbon Hartmann-Hahn match was optimized on external reference sample (glycine). Both carbon and fluorine spectra were recorded with proton decoupling using TPPM15 decoupling sequence with the field strength of approximately 100 kHz.

B. Procedures for the Synthesis of Intermediates

Intermediate 1: Preparation of methyl 3-[bis(tert-butoxycarbonyl)amino]-6-bromo-5-(trifluoromethyl) pyridine-2-carboxylate

Step 1: Methyl 3-(benzhydrylideneamino)-5-(trifluoromethyl)pyridine-2-carboxylate A mixture of methyl 3-chloro-5-(trifluoromethyl)pyridine-2-carboxylate (47.3 g, 197.43 mmol), diphenylmethanimine (47 g, 259.33 mmol), Xantphos (9.07 g, 15.675 mmol), and cesium carbonate (131 g, 402.06 mmol) in dioxane (800 mL) was degassed with bubbling nitrogen for 30 minutes. $Pd(OAc)_2$ (3.52 g, 15.679 mmol) was added and the system was purged with nitrogen three times. The reaction mixture was heated at 100° C. for 18 hours. The reaction was cooled to room temperature and filtered on a pad of Celite. The cake was washed with EtOAc and solvents were evaporated under reduced pressure to give methyl 3-(benzhydrylideneamino)-5-(trifluoromethyl)pyridine-2-carboxylate (90 g, 84%) as yellow solid. ESI-MS m/z calc. 384.10855, found 385.1 $(M+1)^+$; Retention time: 2.24 minutes. LCMS Method: Kinetex $C_{18}$ 4.6×50 mm 2.6 μM, 2.0 mL/min, 95% $H_2O$ (0.1% formic acid)+5% acetonitrile (0.1% formic acid) to 95% acetonitrile (0.1% formic acid) gradient (2.0 min) then held at 95% acetonitrile (0.1% formic acid) for 1.0 minute.

Step 2: Methyl 3-amino-5-(trifluoromethyl)pyridine-2-carboxylate

To a suspension of methyl 3-(benzhydrylideneamino)-5-(trifluoromethyl)pyridine-2-carboxylate (65 g, 124.30 mmol) in methanol (200 mL) was added HCl (3 M in methanol) (146 mL of 3 M, 438.00 mmol). The mixture was stirred at room temperature for 1.5 hours, then the solvent was removed under reduced pressure. The residue was taken up in ethyl acetate (2 L) and dichloromethane (500 mL). The organic phase was washed with 5% aqueous sodium bicarbonate solution (3×500 mL) and brine (2×500 mL), dried over anhydrous sodium sulfate, filtered and the solvent was removed under reduced pressure. The residue was triturated with heptanes (2×50 mL), and the mother liquors were discarded. The solid obtained was triturated with a mixture of dichloromethane and heptanes (1:1, 40 mL) and filtered to afford methyl 3-amino-5-(trifluoromethyl)pyridine-2-carboxylate (25.25 g, 91%) as yellow solid. $^1H$ NMR (300 MHz, $CDCl_3$) δ 8.24 (s, 1H), 7.28 (s, 1H), 5.98 (br. s, 2H), 4.00 (s, 3H) ppm. 19F NMR (282 MHz, $CDCl_3$) δ−63.23 (s, 3F) ppm. ESI-MS m/z calc. 220.046, found 221.1 $(M+1)^+$; Retention time: 1.62 minutes. LCMS Method: Kinetex Polar $C_{18}$ 3.0×50 mm 2.6 μm, 3 min, 5-95% acetonitrile in $H_2O$ (0.1% formic acid) 1.2 mL/min.

Step 3: Methyl 3-amino-6-bromo-5-(trifluoromethyl)pyridine-2-carboxylate

To a solution of methyl 3-amino-5-(trifluoromethyl)pyridine-2-carboxylate (18.75 g, 80.91 mmol) in acetonitrile (300 mL) at 0° C. was added portion wise N-bromosuccinimide (18.7 g, 105.3 mmol). The mixture was stirred overnight at 25° C. Ethyl acetate (1000 mL) was added. The organic layer was washed with 10% sodium thiosulfate solution (3×200 mL) which was back extracted with ethyl acetate (2×200 mL). The combined organic extracts were washed with saturated sodium bicarbonate solution (3×200 mL), brine (200 mL), dried over sodium sulfate and concentrated in vacuo to provide methyl 3-amino-6-bromo-5-(trifluoromethyl)pyridine-2-carboxylate (25.46 g, 98%). $^1H$ NMR (300 MHz, $CDCl_3$) δ 3.93-4.03 (m, 3H), 6.01 (br. s., 2H), 7.37 (s, 1H) ppm. $^{19}F$ NMR (282 MHz, $CDCl_3$) ppm −64.2 (s, 3F). ESI-MS m/z calc. 297.9565, found 299.0 $(M+1)^+$; Retention time: 2.55 minutes. LCMS Method: Kinetex $C_{18}$ 4.6×50 mm 2.6 μM. Temp: 45° C., Flow: 2.0 mL/min, Run Time: 6 minutes. Mobile Phase: Initial 95% $H_2O$ (0.1% formic acid) and 5% acetonitrile (0.1% formic acid) linear gradient to 95% acetonitrile (0.1% formic acid) for 4.0 minutes, then held at 95% acetonitrile (0.1% formic acid) for 2.0 minutes.

Step 4: Methyl 3-[bis(tert-butoxycarbonyl)amino]-6-bromo-5-(trifluoro methyl)pyridine-2-carboxylate A mixture of methyl 3-amino-6-bromo-5-(trifluoromethyl)pyridine-2-carboxylate (5 g, 15.549 mmol), $(Boc)_2O$ (11 g, 11.579 mL, 50.402 mmol), DMAP (310 mg, 2.5375 mmol) and $CH_2Cl_2$ (150 mL) was stirred at room temperature overnight. The reaction mixture was concentrated under reduced pressure, and purification by silica gel chromatography (0-15% ethyl acetate in heptane) provided methyl 3-[bis(tert-butoxycarbonyl)amino]-6-bromo-5-(trifluoromethyl)pyridine-2-carboxylate (6.73 g, 87%) as light yellow solid. $^1$H NMR (300 MHz, $CDCl_3$) δ 1.42 (s, 18H), 3.96 (s, 3H), 7.85 (s, 1H) ppm. $^{19}$F NMR (282 MHz, $CDCl_3$) δ−63.9 (s, 3F) ppm. ESI-MS m/z calc. 498.06134, Retention time: 2.34 minutes. LCMS Method: Kinetex $C_{18}$ 4.6×50 mm 2.6 μM. Temp: 45° C., Flow: 2.0 mL/min, Run Time: 3 minutes. Mobile Phase: Initial 95% $H_2O$ (0.1% formic acid) and 5% acetonitrile (0.1% formic acid) linear gradient to 95% acetonitrile (0.1% formic acid) for 2.0 minutes, then held at 95% acetonitrile (0.1% formic acid) for 1.0 minute.

Intermediate 2: Preparation of 6-bromo-3-(tert-butoxycarbonylamino)-5-(trifluoromethyl)pyridine-2-carboxylic acid

Step 1: 6-Bromo-3-(tert-butoxycarbonylamino)-5-(trifluoromethyl)pyridine-2-carboxylic acid To a mixture of methyl 3-[bis(tert-butoxycarbonyl)amino]-6-bromo-5-(trifluoromethyl)pyridine-2-carboxylate (247 g, 494.7 mmol) in THF (1.0 L) was added a solution of LiOH (47.2 g, 1.971 mol) in water (500 mL). The mixture was stirred at ambient temperature for 18 hours, affording a yellow slurry. The mixture was cooled with an ice-bath and slowly acidified with HCl (1000 mL of 2 M, 2.000 mol) keeping the reaction temperature <15° C. The mixture was diluted with heptane (1.5 L), mixed and the organic phase separated. The aqueous phase was extracted with heptane (500 mL). The combined organic phases were washed with brine, dried over $MgSO_4$, filtered and concentrated in vacuo. The crude oil was dissolved in heptane (600 mL), seeded and stirred at ambient temperature for 18 hours, affording a thick slurry. The slurry was diluted with cold heptane (500 mL) and the precipitate collected using a medium frit. The filter cake was washed with cold heptane and air dried for 1 hour, then in vacuo at 45° C. for 48 hours to afford 6-bromo-3-(tert-butoxycarbonylamino)-5-(trifluoromethyl)pyridine-2-carboxylic acid (158.3 g, 83%). $^1$H NMR (400 MHz, DMSO-$d_6$) δ 10.38 (s, 1H), 9.01 (s, 1H), 1.50 (s, 9H) ppm. ESI-MS m/z calc. 383.99326, found 384.9 $(M+1)^+$; Retention time: 2.55 minutes. LCMS Method Detail: Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=$H_2O$ (0.05% $CF_3CO_2H$). Mobile phase B=acetonitrile (0.035% $CF_3CO_2H$). Flow rate=1.2 mL/min, injection volume=1.5 μL, and column temperature=60° C.

Intermediate 3: Preparation of 2-Benzyloxy-2-(trifluoromethyl)hex-5-enoic acid

Step 1: Ethyl 2-hydroxy-2-(trifluoromethyl)hex-5-enoate

To a solution of ethyl 3,3,3-trifluoro-2-oxo-propanoate (25.15 g, 147.87 mmol) in $Et_2O$ (270 mL) at −78° C. was added bromo(but-3-enyl)magnesium in THF (190 mL of 0.817 M, 155.23 mmol) dropwise over a period of 1.5 hours (inner temperature −72° C. to −76° C.). The mixture was stirred at −78° C. for 20 minutes. The dry ice-acetone bath was removed. The mixture was slowly warm to 5° C. over 1 hour, added to a mixture of 1 N aqueous HCl (170 mL) and crushed ice (150 g) (pH=4). The two layers were separated. The organic layer was concentrated, and the residue was combined with aqueous phase and extracted with EtOAc (2×150 mL). The combined organic phase was washed with 5% aqueous $NaHCO_3$(50 mL) and brine (20 mL), and dried with $Na_2SO_4$. The mixture was filtered and concentrated, and co-evaporated with THF (2×40 mL) to give ethyl 2-hydroxy-2-(trifluoromethyl)hex-5-enoate (37.44 g, 96%) as colorless oil. $^1$H NMR (300 MHz, $CDCl_3$) δ 5.77 (ddt, J=17.0, 10.4, 6.4 Hz, 1H), 5.15-4.93 (m, 2H), 4.49-4.28 (m, 2H), 3.88 (s, 1H), 2.35-2.19 (m, 1H), 2.17-1.89 (m, 3H), 1.34 (t, J=7.0 Hz, 3H) ppm. $^{19}$F NMR (282 MHz, $CDCl_3$) δ−78.74 (s, 3F) ppm.

Step 2: Ethyl 2-benzyloxy-2-(trifluoromethyl)hex-5-enoate

To a solution of ethyl 2-hydroxy-2-(trifluoromethyl)hex-5-enoate (24.29 g, 87.6% purity, 94.070 mmol) in DMF (120 mL) at 0° C. was added NaH (60% in mineral oil, 5.64 g, 141.01 mmol) portion-wise. The mixture was stirred at 0° C. for 10 minutes. Benzyl bromide (24.13 g, 141.08 mmol) and TBAI (8.68 g, 23.500 mmol) were added. The mixture was stirred at room temperature overnight. $NH_4Cl$ (3 g, 0.6 eq) was added. The mixture was stirred for 10 minutes. 30 mL of EtOAc was added, then ice-water was added (400 g). The mixture was extracted with $CH_2Cl_2$ and the combined organic layers were concentrated. Purification by silica gel chromatography (0-20% $CH_2Cl_2$ in heptanes) provided ethyl 2-benzyloxy-2-(trifluoromethyl)hex-5-enoate (26.05 g, 88%) as pink oil. $^1$H NMR (300 MHz, $CDCl_3$) δ 1.34 (t, J=7.2 Hz, 3H), 2.00-2.19 (m, 3H), 2.22-2.38 (m, 1H), 4.33 (q, J=7.2 Hz, 2H), 4.64 (d, J=10.6 Hz, 1H), 4.84 (d, J=10.9 Hz, 1H), 4.91-5.11 (m, 2H), 5.62-5.90 (m, 1H), 7.36 (s, 5H) ppm. 19F NMR (282 MHz, $CDCl_3$) δ-70.5 (s, 3F) ppm. ESI-MS m/z calc. 316.12863, found 317.1 $(M+1)^+$; Retention time: 2.47 minutes. LCMS Method: Kinetex $C_{18}$ 4.6×50 mm 2.6 μM. Temp: 45° C., Flow: 2.0 mL/min, Run Time: 3 minutes. Mobile Phase: Initial 95% $H_2O$ (0.1% formic acid) and 5% acetonitrile (0.1% formic acid) linear gradient to 95% acetonitrile (0.1% formic acid) for 2.0 minutes, then held at 95% acetonitrile (0.1% formic acid) for 1.0 minute.

Step 3: 2-Benzyloxy-2-(trifluoromethyl)hex-5-enoic acid

A solution of sodium hydroxide (7.86 g, 196.51 mmol) in water (60 mL) was added to a solution of ethyl 2-benzyloxy-2-(trifluoromethyl)hex-5-enoate (24.86 g, 78.593 mmol) in methanol (210 mL). The reaction was heated at 50° C. overnight. The reaction was concentrated to remove methanol, diluted with water (150 mL) and the carboxylate sodium salt was washed with heptane (1×100 mL). The aqueous solution was acidified to pH=2 with aqueous 3N solution of HCl. The carboxylic acid was extracted with dichloromethane (3×100 mL) and dried over sodium sulfate. The solution was filtered and concentrated to give 2-benzyloxy-2-(trifluoromethyl)hex-5-enoic acid (22.57 g, 97%) as pale yellow oil. $^1$H NMR (300 MHz, DMSO-$d_6$) δ 14.31 (br. s., 1H), 7.55-7.20 (m, 5H), 5.93-5.70 (m, 1H), 5.17-4.91 (m, 2H), 4.85-4.68 (m, 1H), 4.67-4.55 (m, 1H), 2.32-1.94 (m, 4H) ppm. $^{19}$F NMR (282 MHz, DMSO-$d_6$) δ−70.29 (s, 3F) ppm. ESI-MS m/z calc. 288.09732, found 287.1 (M−1); Retention time: 3.1 minutes. LCMS Method: Kinetex Polar $C_{18}$ 3.0×50 mm 2.6 μm, 6 min, 5-95% acetonitrile in $H_2O$ (0.1% formic acid) 1.2 mL/min.

Intermediate 4: Preparation of (2R)-2-benzyloxy-2-(trifluoromethyl)hex-5-enoic acid Step-1: (2R)-2-Benzyloxy-2-(trifluoromethyl)hex-5-enoic acid; (R)-4-quinolyl-[(2S,4S)-5-vinylquinuclidin-2-yl]methanol To a $N_2$ purged jacketed reactor set to 20° C. was added isopropyl acetate (IPAC, 100 L, 0.173 M, 20 Vols), followed by previously melted 2-benzyloxy-2-(trifluoromethyl)hex-5-enoic acid (5.00 kg, 17.345 mol) and cinchonidine (2.553 kg, 8.67 mol) made into a slurry with minor amount of the reaction solvent. The reactor was set to ramp internal temperature to 80° C. over 1 hour, with solids going in solution upon heating to set temperature, then the solution was held at temperature for at least 10 minutes, then cooled to 70° C. held and seeded with chiral salt (50 g, 1.0% by wt). The mixture was stirred for 10 minutes, then ramped to 20° C. internal temperature over 4 hours, then held overnight at 20° C. The mixture was filtered, cake washed with isopropyl acetate (10.0 L, 2.0 vols) and dried under vacuum. The cake was then dried in vacuo (50° C., vacuum) to afford 4.7 kg of salt. The resulting solid salt was returned to the reactor by making a slurry with a portion of isopropyl acetate (94 L, 20 vol based on current salt wt), and pumped into reactor and stirred. The mixture was then heated to 80° C. internal, stirred hot slurry for at least 10 minutes, then ramped to 20° C. over 4-6 hours, then stirred overnight at 20° C. The material was then filtered and the cake washed with isopropyl acetate (9.4 L, 2.0 vol), pulled dry, cake scooped out and dried in vacuo (50° C., vacuum) to afford 3.1 kg of solid. The solid (3.1 kg) and isopropyl acetate (62 L, 20 vol based on salt solid wt) was slurried and added to a reactor, stirred under $N_2$ purge and heated to 80° C. and held at temperature at least 10 minutes, then ramped to 20° C. over 4-6 hours, then stirred overnight. The mixture was filtered, cake washed with isopropyl acetate (6.2 L, 2 vol), pulled dry, scooped out and dried in vacuo (50° C., vac) to afford 2.25 kg of solid salt. The solid (2.25 kg) and isopropyl acetate (45 L, 20 vol based on salt solid wt) was slurried and added to a reactor, stirred under $N_2$ purge and heated to 80° C., held at temperature at least 10 minutes, then ramped to 20° C. over 4-6 hours, then stirred overnight. The mixture was filtered, cake washed with isopropyl acetate (4.5 L, 2 vol), pulled dry, scooped out and dried in vacuo (50° C. to afford (2R)-2-benzyloxy-2-(trifluoromethyl)hex-5-enoic acid; (R)-4-quinolyl-[(2S,4S)-5-vinylquinuclidin-2-yl]methanol (1.886 kg, >98.0% ee) as an off-white to tan solid. Chiral purity was determined by Agilent 1200 HPLC instrument using Phenomenex Lux i-Amylose-3 column (3 μm, 150×4.6 mm) and a dual, isocratic gradient run 30% to 70% mobile phase B over 20.0 minutes. Mobile phase A=$H_2O$ (0.1% $CF_3CO_2H$). Mobile phase B=MeOH (0.1% $CF_3CO_2H$). Flow rate=1.0 mL/min, injection volume=2 μL, and column temperature=30° C., sample concentration: 1 mg/mL in 60% acetonitrile/40% water.

Step 2: (2R)-2-Benzyloxy-2-(trifluoromethyl)hex-5-enoic acid

A suspension of (2R)-2-benzyloxy-2-(trifluoromethyl)hex-5-enoic acid; (R)-4-quinolyl-[(2S,4S)-5-vinylquinuclidin-2-yl]methanol (50 g, 87.931 mmol) in ethyl acetate (500.00 mL) was treated with an aqueous solution of hydrochloric acid (200 mL of 1 M, 200.00 mmol). After stirring for 15 minutes at room temperature, the two phases were separated. The aqueous phase was extracted twice with ethyl acetate (200 mL). The combined organic layer was washed with 1 N HCl (100 mL). The organic layer was dried over sodium sulfate, filtered and concentrated. The material was dried over high vacuum overnight to give (2R)-2-benzyloxy-2-(trifluoromethyl)hex-5-enoic acid (26.18 g, 96%) as pale brown oil. $^1$H NMR (400 MHz, $CDCl_3$) δ 7.46-7.31 (m, 5H), 5.88-5.73 (m, 1H), 5.15-4.99 (m, 2H), 4.88 (d, J=10.3 Hz, 1H), 4.70 (d, J=10.3 Hz, 1H), 2.37-2.12 (m, 4H) ppm. $^{19}$F NMR (377 MHz, $CDCl_3$) δ−71.63 (br s, 3F) ppm. ESI-MS m/z calc. 288.0973, found 287.0 $(M-1)^-$; Retention time: 2.15 minutes. LCMS Method: Kinetex Polar $C_{18}$ 3.0×50 mm 2.6 μm, 3 min, 5-95% acetonitrile in $H_2O$ (0.1% formic acid) 1.2 mL/min.

Intermediate 5: Preparation of (2R)-2-benzyloxy-2-(trifluoromethyl)hex-5-enehydrazide Step 1: tert-Butyl N-[[(2R)-2-benzyloxy-2-(trifluoromethyl)hex-5-enoyl]amino]carbamate To a solution of (2R)-2-benzyloxy-2-(trifluoromethyl)hex-5-enoic acid (365 g, 1.266 mol) in DMF (2 L) was added HATU (612 g, 1.610 mol) and DIEA (450 mL, 2.584 mol) and the mixture was stirred at ambient temperature for 10 minutes. To the mixture was added tert-butyl N-aminocarbamate (200 g, 1.513 mol) (slight exotherm upon addition) and the mixture was stirred at ambient temperature for 16 hours. The reaction was poured into ice water (5 L). The resultant precipitate was collected by filtration and washed with water. The solid was dissolved in EtOAc (2 L) and washed with brine. The organic phase was dried over $MgSO_4$, filtered, and concentrated in vacuo. The oil was diluted with EtOAc (500 mL) followed by heptane (3 L) and stirred at ambient temperature for several hours affording a thick slurry. The slurry was diluted with additional heptane and filtered to collect fluffy white solid (343 g). The filtrate was concentrated and purification by silica gel chromatography (0-40% EtOAc/hexanes) provided tert-butyl N-[[(2R)-2-benzyloxy-2-(trifluoromethyl)hex-5-enoyl]amino]carbamate (464 g, 91%, combined with product from crystallization). ESI-MS m z calc. 402.17664, found 303.0 (M+1-Boc)*; Retention time: 2.68 minutes. Final purity was determined by reversed phase UPLC using an Acquity UPLC BEH $C_{18}$ column (50×2.1 mm, 1.7 μm particle) made by Waters (pn: 186002350) and a dual gradient run from 1-99% mobile phase B over 4.5 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

Step 2: (2R)-2-Benzyloxy-2-(trifluoromethyl)hex-5-enehydrazide

To a solution of tert-butyl N-[[(2R)-2-benzyloxy-2-(trifluoromethyl)hex-5-enoyl]amino]carbamate (464 g, 1.153 mol) in DCM (1.25 L) and was added HCl (925 mL of 4 M, 3.700 mol) and the mixture stirred at ambient temperature for 20 hours. The mixture was concentrated in vacuo removing most of the DCM. The mixture was diluted with isopropyl acetate (1 L) and basified to pH=6 with NaOH (140 g of 50% w/w, 1.750 mol) in 1 L of ice water. The organic phase was separated and washed with 1 L of brine and the combined aqueous phases were extracted with isopropyl acetate (1 L). The combined organic phases were dried over $MgSO_4$, filtered and concentrated in vacuo affording a dark yellow oil of (2R)-2-benzyloxy-2-(trifluoromethyl)hex-5-enehydrazide (358 g, quant.). $^1$H NMR (400 MHz, $CDCl_3$) δ 8.02 (s, 1H), 7.44-7.29 (m, 5H), 5.81 (ddt, J=16.8, 10.1, 6.4 Hz, 1H), 5.13-4.93 (m, 2H), 4.75 (dd, J=10.5, 1.5 Hz, 1H), 4.61 (d, J=10.5 Hz, 1H), 3.78 (s, 2H), 2.43 (ddd, J=14.3, 11.0, 5.9 Hz, 1H), 2.26-1.95 (m, 3H) ppm. ESI-MS m/z calc. 302.1242, found 303.0 $(M+1)^+$; Retention time: 2.0 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

Intermediate 6: Preparation of tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]carbamate

Step 1: tert-Butyl N-[2-[[[(2R)-2-benzyloxy-2-(trifluoromethyl)hex-5-enoyl]amino]carbamoyl]-6-bromo-5-(trifluoromethyl)-3-pyridyl]carbamate To a mixture of 6-bromo-3-(tert-butoxycarbonylamino)-5-(trifluoromethyl)pyridine-2-carboxylic acid (304 g, 789.3 mmol) and (2R)-2-benzyloxy-2-(trifluoromethyl)hex-5-enehydrazide (270 g, 893.2 mmol) in EtOAc (2.25 L) at ambient temperature was added DIEA (425 mL, 2.440 mol). To the mixture was slowly added $T_3P$ (622 g of 50% w/w, 977.4 mmol) using an ice-water bath to keep the temperature <35° C. (temperature rose to 34° C.) and the reaction mixture was stirred at ambient temperature for 18 hours. Additional DIEA (100 mL, 574.1 mmol) and $T_3P$ (95 g, 298.6 mmol) were added and stirred at ambient temperature for 2 days. Starting material was still observed and additional $T_3P$ (252 g, 792 mmol) was added and stirred for 5 days. The reaction was quenched with the slow addition of water (2.5 L) and the mixture stirred for 30 minutes. The organic phase was separated, and the aqueous phase extracted with EtOAc (2 L). The combined organic phases were washed with brine, dried over $MgSO_4$, filtered and concentrated in vacuo. The crude product was dissolved in MTBE (300 mL) and diluted with heptane (3 L), the mixture stirred at ambient temperature for 12 hours affording a light yellow slurry. The slurry was filtered, and the resultant solid was air dried for 2 hours, then in vacuo at 40° C. for 48 hours. The filtrate was concentrated in vacuo and purified by silica gel chromatography (0-20% EtOAc/hexanes) and combined with material obtained from crystallization providing tert-butyl N-[2-[[[(2R)-2-benzyloxy-2-(trifluoromethyl)hex-5-enoyl]amino]carbamoyl]-6-bromo-5-(trifluoromethyl)-3-pyridyl]carbamate (433 g, 82%). $^1$H NMR (400 MHz, DMSO) δ 11.07 (s, 1H), 10.91 (s, 1H), 10.32 (s, 1H), 9.15 (s, 1H), 7.53-7.45 (m, 2H), 7.45-7.28 (m, 3H), 5.87 (ddt, J=17.0, 10.2, 5.1 Hz, 1H), 5.09 (dq, J=17.1, 1.3 Hz, 1H), 5.02 (dd, J=10.3, 1.9 Hz, 1H), 4.84 (q, J=11.3 Hz, 2H), 2.37-2.13 (m, 4H), 1.49 (s, 9H) ppm. ESI-MS m/z calc. 668.1069, found 669.0 $(M+1)^+$; Retention time: 3.55 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

Step 2: tert-Butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]carbamate To a solution of tert-butyl N-[2-[[[(2R)-2-benzyloxy-2-(trifluoromethyl)hex-5-enoyl]amino]carbamoyl]-6-bromo-5-(trifluoromethyl)-3-pyridyl]carbamate (240 g, 358.5 mmol) in anhydrous acetonitrile (1.5 L) under nitrogen was added DIEA (230 mL, 1.320 mol) and the orange solution heated to 70° C. To the mixture was added p-toluenesulfonyl chloride (80.5 g, 422.2 mmol) in 3 equal portions over 1 hour. The mixture was stirred at 70° C. for 9 hours then additional p-toluenesulfonyl chloride (6.5 g, 34.09 mmol) was added. The mixture was stirred for a total of 24 hours then allowed to cool to ambient temperature. Acetonitrile was removed in vacuo affording a dark orange oil which was diluted with EtOAc (1.5 L) and water (1.5 L). The organic phase was separated and washed with 500 mL of 1M HCl, 500 mL of brine, dried over $MgSO_4$, filtered and concentrated in vacuo. Purification by silica gel chromatography (0-20% EtOAc/hexanes) provided tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]carbamate (200 g, 86%). $^1$H NMR (400 MHz, DMSO) δ 10.11 (s, 1H), 9.10 (s, 1H), 7.55-7.48 (m, 2H), 7.47-7.28 (m, 3H), 5.87 (ddt, J=16.7, 10.2, 6.4 Hz, 1H), 5.11 (dt, J=17.2, 1.7 Hz, 1H), 5.01 (dt, J=10.2, 1.5 Hz, 1H), 4.74 (d, J=10.6 Hz, 1H), 4.65 (d, J=10.6 Hz, 1H), 2.55-2.42 (m, 2H), 2.30 (qd, J=11.3, 10.3, 6.9 Hz, 2H), 1.52 (s, 9H) ppm. ESI-MS m/z calc. 650.0963, found 650.0 $(M+1)^+$; Retention time: 3.78 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

Intermediate 7: Preparation of tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate

Step 1: tert-Butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate To a solution of tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]carbamate (222 g, 340.8 mmol) in MTBE (1.333 L) was added DIPEA (65.3 mL, 374.9 mmol) followed DMAP (2.09 g, 17.11 mmol). A solution of di-tert-butyl dicarbonate (111.6 g, 511.3 mmol) in MTBE (250 mL) was added over approximately 8 minutes, and the resulting mixture was stirred for additional 30 minutes. 1 L of water was added and the layers separated. The organic layer was washed with $KHSO_4$ (886 mL of 0.5 M, 443.0 mmol), 300 mL brine, dried with $MgSO_4$ and most (>95%) of the MTBE was evaporated by rotary evaporation at 45° C., leaving a thick oil. 1.125 L of heptane was added, spun in the 45° C. rotovap bath until dissolved, then evaporated out 325 mL of solvent by rotary evaporation. The rotovap bath temp was allowed to drop to room temperature and product started crystallizing out during the evaporation. Then the flask was placed in a −20° C. freezer overnight. The resultant solid was filtered and washed with cold heptane and dried at room temperature for 3 days to give tert-butyl N-[2-[5-[(1R)-1-benzyloxy-1-(trifluoromethyl) pent-4-enyl]-1,3,4-oxadiazol-2-yl]-6-bromo-5-(trifluoromethyl)-3-pyridyl]-N-tert-butoxycarbonyl-carbamate (240.8 g, 94%). $^1$H NMR (400 MHz, Chloroform-d) δ 7.95 (s, 1H), 7.52-7.45 (m, 2H), 7.44-7.36 (m, 2H), 7.36-7.29 (m, 1H), 5.83-5.67 (m, 1H), 5.08-5.00 (m, 1H), 5.00-4.94 (m, 1H), 4.79 (d, J=10.4 Hz, 1H), 4.64 (d, J=10.4 Hz, 1H), 2.57-2.26 (m, 3H), 2.26-2.12 (m, 1H), 1.41 (s, 18H) ppm. ESI-MS m/z calc. 750.14874, found 751.1 (M+1)$^+$; Retention time: 3.76 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

Intermediate 8: Preparation of tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate Step 1: tert-Butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate tert-Butyl N-[2-[5-[(1R)-1-benzyloxy-1-(trifluoromethyl) pent-4-enyl]-1,3,4-oxadiazol-2-yl]-6-bromo-5-(trifluoromethyl)-3-pyridyl]-N-tert-butoxycarbonyl-carbamate (280 g, 372.6 mmol) was dissolved in DMSO (1.82 L) (yellow solution) and treated with cesium acetate (215 g, 1.120 mol) under stirring at room temperature. The yellow suspension was heated at 80° C. for 5 hours. The reaction mixture was cooled to room temperature and added to a stirred cold emulsion of water (5.5 L) with 1 kg ammonium chloride dissolved in it and a 1:1 mixture of MTBE and heptane (2 L) (in 20 L). The phases were separated and the organic phase washed with water (3×3 L) and with brine (1×2.5 L). The organic phase was dried with $MgSO_4$, filtered, and concentrated under reduced pressure. The resultant yellow solution was diluted with heptane (~1 L) and seeded with tert-butyl N-[2-[5-[(1R)-1-benzyloxy-1-(trifluoromethyl) pent-4-enyl]-1,3,4-oxadiazol-2-yl]-6-hydroxy-5-(trifluoromethyl)-3-pyridyl]-N-tert-butoxycarbonyl-carbamate and stirred on the rotovap at 100 mbar pressure at room temperature for 1.5 hours. The solid mass was stirred mechanically for 2 hours at room temperature, resultant thick fine suspension was filtered, washed with dry ice cold heptane and dried under vacuum at 45° C. with a nitrogen bleed for 16 hours to give tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate (220 g, 85%) as an off white solid. $^1$H NMR (400 MHz, DMSO-$d_6$) δ 13.28 (s, 1H), 8.43 (s, 1H), 7.58-7.26 (m, 5H), 5.85 (ddt, J=16.8, 10.3, 6.5 Hz, 1H), 5.10 (dq, J=17.2, 1.6 Hz, 1H), 5.01 (dq, J=10.2, 1.3 Hz, 1H), 4.76 (d, J=11.0 Hz, 1H), 4.65 (d, J=11.0 Hz, 1H), 2.55 (dd, J=9.6, 5.2 Hz, 2H), 2.23 (td, J=13.2, 10.0, 5.7 Hz, 2H), 1.27 (d, J=3.8 Hz, 18H) ppm. ESI-MS m/z calc. 688.23315, found 689.0 (M+1)$^+$; Retention time: 3.32 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

C. Preparation of (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol Step 1: tert-Butyl N-[2-[5-[(1R)-1-benzyloxy-1-(trifluoromethyl)pent-4-enyl]-1,3,4-oxadiazol-2-yl]-6-[(1R)-1-methylbut-3-enoxy]-5-(trifluoromethyl)-3-pyridyl]-N-tert-butoxycarbonyl-carbamate Dissolved tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate (159.3 g, 231.3 mmol) and triphenylphosphine (72.9 g, 277.9 mmol) in toluene (1 L), then added (2S)-pent-4-en-2-ol (28.7 mL, 278.9 mmol). Heated this mixture to 45° C., then added DIAD (58.3 mL, 296.1 mmol) (exotherm) slowly over 40 minutes. For the next approximately 2 hours, the mixture was cooled to room temperature. During this cooling period, after the first 10 minutes, triphenylphosphine (6.07 g, 23.14 mmol) was added. After a further 1 hour, additional triphenylphosphine (3.04 g, 11.59 mmol) was added. After a further 23 minutes, DIAD (2.24 mL, 11.57 mmol) was added. After the ~2 hour cooling to room temperature period, the mixture was cooled to 15° C., and seed crystals of DIAD-triphenylphosphine oxide complex were added which caused precipitation to occur, then added 1000 mL heptane. Stored the mixture at −20° C. for 3 days. Filtered out and discarded the precipitate and concentrated the filtrate to give a red residue/oil. Dissolved the residue in 613 mL heptane at 45° C., then cooled to 0° C., seeded with DIAD-triphenylphosphine oxide complex, stirred at 0° C. for 30 minutes, then filtered the solution. The filtrate was concentrated to a smaller volume, then loaded onto a 1.5 kg silica gel column (column volume=2400 mL, flow rate=600 mL/min). Ran a gradient of 1% to 6% EtOAc in hexanes over 32 minutes (8 column volumes), then held at 6% EtOAc in hexanes until the product finished eluting which gave tert-butyl N-[2-[5-[(1R)-1-benzyloxy-1-(trifluoromethyl)pent-4-enyl]-1,3,4-oxadiazol-2-yl]-6-[(1R)-1-methylbut-3-enoxy]-5-(trifluoromethyl)-3-pyridyl]-N-tert-butoxycarbonyl-carbamate (163.5 g, 93%). $^1$H NMR (400 MHz, Chloroform-d) δ 7.82 (s, 1H), 7.43-7.27 (m, 5H), 5.88-5.69 (m, 2H), 5.35 (h, J=6.2 Hz, 1H), 5.16-4.94 (m, 4H), 4.81 (d, J=10.7 Hz, 1H), 4.63 (d, J=10.7 Hz, 1H), 2.58-2.15 (m, 6H), 1.42 (s, 18H), 1.36 (d, J=6.2 Hz, 3H) ppm. ESI-MS m/z calc. 756.2958, found 757.3 (M+1)$^+$; Retention time: 4.0 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=water (0.05% $CF_3CO_2H$). Mobile phase B=acetonitrile (0.035% $CF_3CO_2H$). Flow rate=1.2 mL/min, injection volume=1.5 μL, and column temperature=60° C.

Step 2: tert-Butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]-N-tert-butoxycarbonyl-carbamate (E/Z Mixture)

The following reaction was run, split equally between two, 12 L reaction flasks run in parallel. Mechanical stirring was employed, and reactions were subjected to a constant nitrogen gas purge using a coarse porosity gas dispersion tube. To each flask was added tert-butyl N-[2-[5-[(1R)-1-benzyloxy-1-(trifluoromethyl)pent-4-enyl]-1,3,4-oxadiazol-2-yl]-6-[(1R)-1-methylbut-3-enoxy]-5-(trifluoromethyl)-3-pyridyl]-N-tert-butoxycarbonyl-carbamate (54 g, 71.36 mmol in each flask) dissolved in DCE (8 L in each flask) and both flasks were strongly purged with nitrogen at room temperature. Both flasks were heated to 62° C. and Grubbs 1st Generation Catalyst (9 g, 10.94 mmol in each flask) was added to each reaction and stirred at 400 rpm while setting an internal temperature control to 75° C. with strong nitrogen purging (both reactions reached ~75° C. after approximately 20 min). After 5 hours, 15 minutes, the internal temperature control was set to 45° C. After approximately 2 hours, 2-sulfanylpyridine-3-carboxylic acid (11 g, 70.89 mmol in each flask) was added to each flask, followed by triethylamine (10 mL, 71.75 mmol in each flask). On completion of addition, the nitrogen purge was turned off and both reaction flasks were stirred at 45° C. open to air overnight. The reactions were then removed from heat and 130 g of silica gel was added to each reaction and each was stirred at room temperature. After approximately 2 hours, the green mixtures were combined and filtered over Celite then concentrated by rotary evaporation at 43° C. The obtained residue was dissolved in dichloromethane/heptane 1:1 (400 mL) and the formed orange solid was removed by filtration. The greenish mother liquor was evaporated to give 115.5 g of a green foam. Dissolved this material in 500 mL of 1:1 dichloromethane/hexanes then loaded onto a 3 kg silica gel column (column volume=4800 mL, flow rate=900 mL/min). Ran a gradient of 2% to 9% EtOAc in hexanes over 43 minutes (8 column volumes), then ran at 9% EtOAc until the product finished eluting giving 77.8 g of impure product. This material was co-evaporated with methanol (~500 mL) then diluted with methanol (200 mL) to give 234.5 g of a methanolic solution, which was halved and each half was purified by reverse phase chromatography (3.8 kg $C_{18}$ column, column volume=3300 mL, flow rate=375 mL/min, loaded as solution in methanol). Ran the column at 55% acetonitrile for ~5 minutes (0.5 column volumes), then at a gradient of 55% to 100% acetonitrile in water over ~170 minutes (19-20 column volumes), then held at 100% acetonitrile until the product and impurities finished eluting. Clean product fractions from both columns were combined and concentrated by rotary evaporation then transferred with ethanol into 5 L flask, evaporated and carefully dried (becomes a foam) to give as a mixture of olefin isomers, tert-butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]-N-tert-butoxycarbonyl-carbamate (E/Z mixture) (55.5 g, 53%). ESI-MS m/z calc. 728.26447, found 729.0 $(M+1)^+$; Retention time: 3.82 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=water (0.05% $CF_3CO_2H$). Mobile phase B=acetonitrile (0.035% $CF_3CO_2H$). Flow rate=1.2 mL/min, injection volume=1.5 μL, and column temperature=60° C.

Step 3: tert-Butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate tert-Butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]-N-tert-butoxycarbonyl-carbamate (E/Z mixture) (11.7 g, 16.06 mmol) was dissolved in stirring ethanol (230 mL) and cycled the flask 3 times vacuum/nitrogen and treated with 10% Pd/C (50% water wet, 2.2 g of 5% w/w, 1.034 mmol). The mixture was cycled 3 times between vacuum/nitrogen and 3 times between vacuum/hydrogen. The mixture was then stirred strongly under hydrogen (balloon) for 7.5 hours. The catalyst was removed by filtration, replaced with fresh 10% Pd/C (50% water wet, 2.2 g of 5% w/w, 1.034 mmol) and stirred vigorously under hydrogen (balloon) overnight. Then, the catalyst was removed again by filtration, the filtrate evaporated and the residue (11.3 g, 1 g set aside) was dissolved in ethanol (230 mL), charged with fresh 10% Pd/C (50% water wet, 2.2 g of 5% w/w, 1.034 mmol) and stirred vigorously under hydrogen (balloon) for 6 hours, recharged again with fresh 10% Pd/C (50% water wet, 2.2 g of 5% w/w, 1.034 mmol) and stirred vigorously under hydrogen (balloon) overnight. The catalyst was removed by filtration and the filtrate was evaporated (10 g of residue obtained). This crude material (10 g+1 g set aside above) was purified by silica gel chromatography (330 g column, liquid load in dichloromethane) with a linear gradient of 0% to 15% ethyl acetate in hexane until the product eluted followed by 15% to 100% ethyl acetate in hexane to giving, as a colorless foam, tert-butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate (9.1 g, 78%). ESI-MS m/z calc. 730.2801, found 731.0 $(M+1)^+$; Retention time: 3.89 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=water (0.05% $CF_3CO_2H$). Mobile phase B=acetonitrile (0.035% $CF_3CO_2H$). Flow rate=1.2 mL/min, injection volume=1.5 μL, and column temperature=60° C.

Step 4: (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol tert-Butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate (8.6 g, 11.77 mmol) was dissolved in ethanol (172 mL) then the flask was cycled 3 times between vacuum/nitrogen. Treated the mixture with 10% Pd/C (50% water wet, 1.8 g of 5% w/w, 0.8457 mmol) then cycled 3 times between vacuum/nitrogen and 3 times between vacuum/hydrogen and then stirred vigorously under hydrogen (balloon) at room temperature for 18 hours. The mixture was cycled 3 times between vacuum/nitrogen, filtered over Celite, washing with ethanol, and then the filtrate was evaporated to give 7.3 g of tert-butyl N-tert-butoxycarbonyl-N-[(6R,12R)-6-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate an off-white solid. 1H NMR and MS confirmed the expected product. CFTR modulating activity was confirmed using a standard Ussing Chamber Assay for CFTR potentiator activity.

IX. Other Embodiments

The foregoing discussion discloses and describes merely exemplary embodiments of this disclosure. One skilled in the art will readily recognize from such discussion and from the accompanying drawings and claims, that various changes, modifications and variations can be made therein without departing from the spirit and scope of this disclosure as defined in the following claims.

The invention claimed is:

1. A compound of Formula I:

(I)

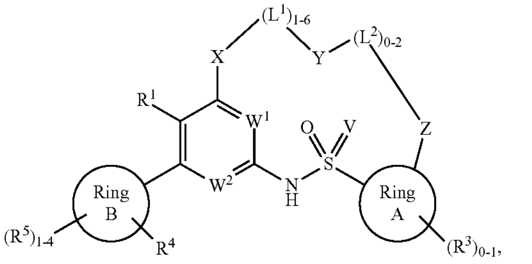

a tautomer thereof, a deuterated derivative of the compound or tautomer, or a pharmaceutically acceptable salt of any of the foregoing, wherein:

Ring A is selected from:
$C_6$-$C_{10}$ aryl,
$C_3$-$C_{10}$ cycloalkyl,
3- to 10-membered heterocyclyl, and
5- to 10-membered heteroaryl;

Ring B is selected from:
$C_6$-$C_{10}$ aryl,
$C_3$-$C_{10}$ cycloalkyl,
3- to 10-membered heterocyclyl, and
5- to 10-membered heteroaryl;

V is selected from O and NH;

$W^1$ is selected from N and CH;

$W^2$ is selected from N and CH; provided that at least one of $W^1$ and $W^2$ is N;

X is selected from $NR^{XN}$ and $C(R^{XC})_2$;

Y is selected from O, $NR^{YN}$, and $C(R^{YC})_2$;

Z is selected from O, $NR^{ZN}$, and $C(R^{ZC})_2$, provided that when $L^2$ is absent, either Y is $C(R^{YC})_2$ or Z is $C(R^{ZC})_2$;

each $L^1$ is independently selected from $C(R^{L1})_2$ and

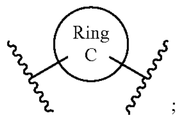

;

each $L^2$ is independently selected from $C(R^{L2})_2$;

Ring C is selected from $C_6$-$C_{10}$ aryl optionally substituted with 1-3 groups independently selected from:
halogen,
$C_1$-$C_6$ alkyl, and
$N(R^N)_2$;

$R^1$ is selected from:
hydrogen,
halogen,
cyano,
$C_1$-$C_6$ alkyl optionally substituted with 1-3 groups independently selected from hydroxyl, oxo, and $N(R^N)_2$,
C-$C_6$ alkoxy,
$C_1$-$C_6$ fluoroalkyl,
$C_6$-$C_{10}$ aryl optionally substituted with 1-3 groups independently selected from $C_1$-$C_6$ alkoxy,
3- to 10-membered heterocyclyl optionally substituted with 1-3 groups independently selected from $R^N$, and
5- to 10-membered heteroaryl optionally substituted with 1-3 groups independently selected from $C_1$-$C_6$ alkyl;

each $R^3$ is independently selected from:
halogen,
$C_1$-$C_6$ alkyl,
$C_1$-$C_6$ alkoxy,
$C_3$-$C_{10}$ cycloalkyl,
$C_6$-$C_{10}$ aryl optionally substituted with 1-3 groups independently selected from $C_1$-$C_6$ alkyl, and
3- to 10-membered heterocyclyl;

$R^4$ is selected from hydrogen and $C_1$-$C_6$ alkyl;

each $R^5$ is independently selected from:
hydrogen,
halogen,
hydroxyl,
$N(R^N)_2$,
—SO-Me,
—CH═C($R^{LC}$)$_2$, wherein both $R^{LC}$ are taken together to form a $C_3$-$C_{10}$ cycloalkyl,
$C_1$-$C_6$ alkyl optionally substituted with 1-3 groups independently selected from:
hydroxyl,
$C_1$-$C_6$ alkoxy optionally substituted with 1-3 groups independently selected from $C_1$-$C_6$ alkoxy and $C_6$-$C_{10}$ aryl,
$C_3$-$C_{10}$ cycloalkyl,
—$(O)_{0-1}$-($C_6$-$C_{10}$ aryl) optionally substituted with 1-3 groups independently selected from $C_1$-$C_6$ alkyl and $C_1$-$C_6$ alkoxy,
3- to 10-membered heterocyclyl, and
$N(R^N)_2$,
$C_1$-$C_6$ alkoxy optionally substituted with 1-3 groups independently selected from:
halogen,
$C_6$-$C_{10}$ aryl, and
$C_3$-$C_{10}$ cycloalkyl optionally substituted with 1-3 groups independently selected from $C_1$-$C_6$ fluoroalkyl,
$C_1$-$C_6$ fluoroalkyl,
$C_3$-$C_{10}$ cycloalkyl,
$C_6$-$C_{10}$ aryl, and
3- to 10-membered heterocyclyl;

each $R^{XN}$, $R^{YN}$, and $R^{ZN}$ is independently selected from:
hydrogen,
$C_1$-$C_9$ alkyl optionally substituted with 1-3 groups independently selected from:
hydroxyl,
oxo,
cyano,
$C_1$-$C_6$ alkoxy optionally substituted with 1-3 groups independently selected from halogen and $C_1$-$C_6$ alkoxy,
$N(R^N)_2$,
$SO_2Me$,
$C_3$-$C_{10}$ cycloalkyl optionally substituted with 1-3 groups independently selected from:
hydroxyl,
$C_1$-$C_6$ alkyl optionally substituted with 1-3 groups independently selected from hydroxyl, oxo, $C_1$-$C_6$ alkoxy, $C_6$-$C_{10}$ aryl, and $N(R^N)_2$,
$C_1$-$C_6$ fluoroalkyl,
$C_1$-$C_6$ alkoxy, COOH,
$N(R^N)_2$,
$C_6$-$C_{10}$ aryl, and
3- to 10-membered heterocyclyl optionally substituted with 1-3 groups independently selected from oxo and $C_1$-$C_6$ alkyl,
$C_6$-$C_{10}$ aryl optionally substituted with 1-3 groups independently selected from:
halogen,
hydroxyl,
cyano,
$SiMe_3$,
$SO_2Me$,
$SF_5$,
$N(R^N)_2$,
$P(O)Me_2$,
—$(O)_{0-1}$—($C_3$-$C_{10}$ cycloalkyl) optionally substituted with 1-3 groups independently selected from $C_1$-$C_6$ fluoroalkyl,
$C_1$-$C_6$ alkyl optionally substituted with 1-3 groups independently selected from hydroxyl, oxo, $C_1$-$C_6$ alkoxy, 5- to 10-membered heteroaryl, $SO_2Me$, and $N(R^N)_2$,
$C_1$-$C_6$ alkoxy optionally substituted with 1-3 groups independently selected from hydroxyl, oxo, $N(R^N)_2$, and $C_6$-$C_{10}$ aryl,
$C_1$-$C_6$ fluoroalkyl,
3- to 10-membered heterocyclyl optionally substituted with 1-3 groups independently selected from $C_1$-$C_6$ alkyl,
—$(O)_{0-1}$—($C_6$-$C_{10}$ aryl), and
—$(O)_{0-1}$-(5- to 10-heteroaryl) optionally substituted with hydroxyl, oxo, $N(R^N)_2$, $C_1$-$C_6$ alkyl, $C_1$-$C_6$ alkoxy, $C_1$-$C_6$ fluoroalkyl, and $C_3$-$C_{10}$ cycloalkyl,
3- to 10-membered heterocyclyl optionally substituted with 1-4 groups independently selected from:
hydroxyl,
oxo,
$N(R^N)_2$,
$C_1$-$C_6$ alkyl (optionally substituted with 1-3 groups independently selected from oxo and $C_1$-$C_6$ alkoxy),
$C_1$-$C_6$ alkoxy,
$C_1$-$C_6$ fluoroalkyl,
$C_6$-$C_{10}$ aryl optionally substituted with 1-3 groups independently selected from halogen, and
5- to 10-membered heteroaryl,
5- to 10-membered heteroaryl optionally substituted with 1-3 groups independently selected from:
hydroxyl,
cyano,
oxo,
halogen,
$B(OH)_2$,
$N(R^N)_2$,
$C_1$-$C_6$ alkyl optionally substituted with 1-3 groups independently selected from hydroxyl, oxo, $C_1$-$C_6$ alkoxy (optionally substituted with 1-3-$SiMe_3$), and $N(R^N)_2$,
$C_1$-$C_6$ alkoxy optionally substituted with 1-3 groups independently selected from hydroxyl, oxo, $C_1$-$C_6$ alkoxy, $N(R^N)_2$, and $C_3$-$C_{10}$ cycloalkyl,
$C_1$-$C_6$ fluoroalkyl,
—$(O)_{0-1}$-($C_3$-$C_{10}$ cycloalkyl) optionally substituted with 1-3 groups independently selected from $C_1$-$C_6$ alkyl,
—$(O)_{0-1}$—($C_6$-$C_{10}$ aryl),
—$(O)_{0-1}$-(3- to 10-membered heterocyclyl) optionally substituted with 1-4 groups independently selected from hydroxyl, oxo, halogen, cyano, $N(R^N)_2$, $C_1$-$C_6$ alkyl (optionally substituted with 1-3 groups independently selected from hydroxyl, oxo, $N(R^N)_2$, and $C_1$-$C_6$ alkoxy), $C_1$-$C_6$ alkoxy, $C_1$-$C_6$ fluoroalkyl, 3- to 10-membered heterocyclyl (optionally substituted with 1-3 groups independently selected from $C_1$-$C_6$ fluoroalkyl), and
5- to 10-membered heteroaryl optionally substituted with 1-4 groups independently selected from $C_1$-$C_6$ alkyl and $C_3$-$C_{10}$ cycloalkyl,
$C_1$-$C_6$ fluoroalkyl,
$C_3$-$C_{10}$ cycloalkyl optionally substituted with 1-3 groups independently selected from:
hydroxyl,
oxo,
halogen,
cyano,
$N(R^N)_2$,
$C_1$-$C_6$ alkyl optionally substituted with 1-3 groups independently selected from:
hydroxyl,
oxo,
$N(R^N)_2$,
$C_1$-$C_6$ alkoxy, and
$C_6$-$C_{10}$ aryl,
$C_1$-$C_6$ alkoxy optionally substituted with 1-3 groups independently selected from halogen, oxo, $C_6$-$C_{10}$ aryl, and $N(R^N)_2$,
halogen,
$C_3$-$C_{10}$ cycloalkyl,
3- to 10-member heterocyclyl optionally substituted with 1-3 groups independently selected from $C_1$-$C_6$ alkyl,
5- to 10-membered heteroaryl optionally substituted with 1-3 groups independently selected from:
hydroxyl,
cyano,
oxo,
halogen,
$N(R^N)_2$,
$C_1$-$C_6$ alkyl optionally substituted with 1-3 groups independently selected from hydroxyl, oxo, $C_1$-$C_6$ alkoxy, and $N(R^N)_2$,
$C_1$-$C_6$ alkoxy optionally substituted with 1-3 groups independently selected from hydroxyl, $C_1$-$C_6$ alkoxy, $N(R^N)_2$, and $C_3$-$C_{10}$ cycloalkyl,
$C_1$-$C_6$ fluoroalkyl,
—$(O)_{0-1}$—($C_3$-$C_{10}$ cycloalkyl) optionally substituted with 1-3 groups independently selected from $C_1$-$C_6$ alkyl,
$C_6$-$C_{10}$ aryl, and
3- to 10-membered heterocyclyl optionally substituted with 1-3 groups independently selected from $C_1$-$C_6$ alkyl,
$C_6$-$C_{10}$ aryl,
3- to 10-membered heterocyclyl optionally substituted with 1-3 groups independently selected from:
oxo,
$C_1$-$C_6$ alkyl optionally substituted with 1-3 groups independently selected from:

oxo,
hydroxyl,
$N(R^N)_2$,
$C_1$-$C_6$ alkoxy optionally substituted with 1-3 groups independently selected from halogen and $C_6$-$C_{10}$ aryl, and
—$(O)_{0-1}$—($C_3$-$C_{10}$ cycloalkyl),
$C_1$-$C_6$ fluoroalkyl,
$C_3$-$C_{10}$ cycloalkyl optionally substituted with 1-3 groups independently selected from halogen, and
3- to 10-membered heterocyclyl,
5- to 10-membered heteroaryl optionally substituted with 1-3 groups independently selected from:
halogen,
$C_1$-$C_6$ alkyl optionally substituted with 1-3 groups independently selected from oxo, $C_1$-$C_6$ alkoxy, and $N(R^N)_2$, and
3- to 10-membered heterocyclyl optionally substituted with 1-3 groups independently selected from $C_1$-$C_6$ alkyl (optionally substituted with 1-3 groups selected from oxo, $C_1$-$C_6$ alkoxy, and $C_6$-$C_{10}$ aryl), and
$R^F$;
each $R^{XC}$, $R^{YC}$, and $R^{ZC}$ is independently selected from:
hydrogen,
$C_1$-$C_6$ alkyl optionally substituted with 1-3 groups independently selected from $C_6$-$C_{10}$ aryl (optionally substituted with 1-3 groups independently selected from $C_1$-$C_6$ alkyl),
$C_6$-$C_{10}$ aryl optionally substituted with 1-3 groups independently selected from $C_1$-$C_6$ alkyl, and
$R^F$;
or two $R^{XC}$ are taken together to form a group selected from oxo and $C_3$-$C_{10}$ cycloalkyl;
or two $R^{YC}$ are taken together to form an oxo group;
or two $R^{ZC}$ are taken together to form an oxo group;
each $R^{L1}$ is independently selected from:
hydrogen,
$N(R^N)_2$, provided that two $N(R^N)_2$ are not bonded to the same carbon,
$C_1$-$C_9$ alkyl optionally substituted with 1-3 groups independently selected from:
halogen,
hydroxyl,
oxo,
$N(R^N)_2$,
$C_1$-$C_6$ alkoxy optionally substituted with 1-3 groups independently selected from $C_6$-$C_{10}$ aryl,
$C_3$-$C_{10}$ cycloalkyl optionally substituted with 1-3 groups independently selected from halogen and $C_1$-$C_6$ fluoroalkyl,
$C_6$-$C_{10}$ aryl optionally substituted with 1-3 groups independently selected from $C_1$-$C_6$ alkyl, and
3- to 10-membered heterocyclyl optionally substituted with 1-3 groups independently selected from $C_1$-$C_6$ alkyl (optionally substituted with 1-3 groups independently selected from hydroxyl and oxo),
$C_3$-$C_{10}$ cycloalkyl,
$C_6$-$C_{10}$ aryl optionally substituted with 1-4 groups independently selected from:
halogen,
cyano,
$SiMe_3$,
$POMe_2$,
$C_1$-$C_7$ alkyl optionally substituted with 1-3 groups independently selected from:

hydroxyl,
oxo,
cyano,
$SiMe_3$,
$N(R^N)_2$, and
$C_3$-$C_{10}$ cycloalkyl optionally substituted with 1-3 groups independently selected from $C_1$-$C_6$ fluoroalkyl,
$C_1$-$C_6$ alkoxy optionally substituted with 1-3 groups independently selected from:
$C_3$-$C_{10}$ cycloalkyl optionally substituted with 1-3 groups independently selected from $C_1$-$C_6$ fluoroalkyl, and
$C_1$-$C_6$ alkoxy,
$C_1$-$C_6$ fluoroalkyl,
$C_3$-$C_{10}$ cycloalkyl optionally substituted with 1-3 groups independently selected from $C_1$-$C_6$ alkyl and $C_1$-$C_6$ fluoroalkyl,
$C_6$-$C_{10}$ aryl,
3- to 10-membered heterocyclyl optionally substituted with 1-3 groups independently selected from $C_1$-$C_6$ alkyl, and
5- to 10-membered heteroaryl,
3- to 10-membered heterocyclyl optionally substituted with 1-3 groups independently selected from:
$C_1$-$C_6$ alkyl optionally substituted with 1-3 groups independently selected from:
oxo, and
$C_1$-$C_6$ alkoxy,
5- to 10-membered heteroaryl optionally substituted with 1-3 groups independently selected from:
$C_1$-$C_6$ alkyl optionally substituted with 1-3 groups independently selected from:
$C_3$-$C_{10}$ cycloalkyl optionally substituted with 1-3 groups independently selected from $C_1$-$C_6$ fluoroalkyl, and
$C_6$-$C_{10}$ aryl optionally substituted with 1-3 groups independently selected from $C_1$-$C_6$ alkyl, and
$R^F$;
or two $R^{L1}$ on the same carbon atom are taken together to form an oxo group;
each $R^{L2}$ is independently selected from hydrogen and $R^F$;
or two $R^{L2}$ on the same carbon atom are taken together to form an oxo group;
each $R^N$ is independently selected from:
hydrogen,
$C_1$-$C_8$alkyl optionally substituted with 1-3 groups independently selected from:
oxo,
halogen,
hydroxyl,
$NH_2$,
NHMe,
$NMe_2$,
$C_1$-$C_6$ alkoxy optionally substituted with 1-3 groups independently selected from $C_6$-$C_{10}$ aryl,
—$(O)_{0-1}$—($C_3$-$C_{10}$ cycloalkyl),
$C_6$-$C_{10}$ aryl optionally substituted with 1-3 groups independently selected from halogen and $C_1$-$C_6$ alkyl,
3- to 14-membered heterocyclyl optionally substituted with 1-4 groups independently selected from oxo and $C_1$-$C_6$ alkyl, and
5- to 14-membered heteroaryl optionally substituted with 1-4 groups independently selected from oxo and $C_1$-$C_6$ alkyl, $C_3$-$C_{10}$ cycloalkyl optionally substituted with 1-3 groups independently selected from:
hydroxyl,
$NH_2$,
NHMe, and
$C_1$-$C_6$ alkyl optionally substituted with 1-3 groups independently selected from hydroxyl,
$C_6$-$C_{10}$ aryl, and
3- to 10-membered heterocyclyl;

or two $R^N$ on the same nitrogen atom are taken together with the nitrogen to which they are bonded to form a 3- to 10-membered heterocyclyl optionally substituted with 1-3 groups selected from:
hydroxyl,
oxo,
cyano,
$C_1$-$C_6$ alkyl optionally substituted with 1-3 groups independently selected from oxo, hydroxyl, $C_1$-$C_6$ alkoxy, and $N(R^{N2})_2$, wherein each $R^{N2}$ is independently selected from hydrogen and $C_1$-$C_6$ alkyl,
$C_1$-$C_6$ alkoxy, and
$C_1$-$C_6$ fluoroalkyl;

or one $R^4$ and one $R^{L1}$ are taken together to form a $C_6$-$C_8$ alkylene;

when $R^F$ is present, two $R^F$ taken together with the atoms to which they are bonded form a group selected from:
$C_3$-$C_{10}$ cycloalkyl optionally substituted with 1-3 groups independently selected from $C_1$-$C_6$ alkyl,
$C_6$-$C_{10}$ aryl optionally substituted with 1-3 groups independently selected from:
halogen,
$C_1$-$C_6$ alkyl,
$N(R^N)_2$, and
3- to 10-membered heterocyclyl optionally substituted with 1-3 groups independently selected from hydroxyl,
3- to 11-membered heterocyclyl optionally substituted with 1-3 groups independently selected from:
oxo,
$N(R^N)_2$,
$C_1$-$C_9$ alkyl optionally substituted with 1-4 groups independently selected from:
oxo,
halogen,
hydroxyl,
$N(R^N)_2$,
—$SO_2$—($C_1$-$C_6$ alkyl),
$C_1$-$C_6$ alkoxy optionally substituted with 1-3 groups independently selected from halogen, $C_6$-$C_{10}$ aryl,
$C_6$-$C_{10}$ aryl optionally substituted with 1-3 groups independently selected from hydroxyl, halogen, cyano, $C_1$-$C_6$ alkyl (optionally substituted with 1-3 groups independently selected from oxo and $C_1$-$C_6$ alkoxy), $C_1$-$C_6$ alkoxy (optionally substituted with 1-3 groups independently selected from $C_6$-$C_{10}$ aryl), —$(O)_{0-1}$—($C_1$-$C_6$ fluoroalkyl), and $C_6$-$C_{10}$ aryl (optionally substituted with 1-3 groups independently selected from $C_1$-$C_6$ alkoxy),
—$(O)_{0-1}$—($C_3$-$C_{10}$ cycloalkyl) optionally substituted with 1-4 groups independently selected from hydroxyl, halogen, $N(R^N)_2$, $C_1$-$C_6$ alkyl (optionally substituted with 1-3 groups independently selected from oxo, hydroxyl, and $C_1$-$C_6$ alkoxy), $C_1$-$C_6$ fluoroalkyl, and $C_6$-$C_{10}$ aryl,
3- to 10-membered heterocyclyl optionally substituted with 1-3 groups independently selected from oxo, $C_1$-$C_6$ alkyl (optionally substituted with 1-3 groups independently selected from $C_6$-$C_{10}$ aryl (optionally substituted with 1-3 groups independently selected from halogens)), $C_1$-$C_6$ alkoxy, $C_3$-$C_{10}$ cycloalkyl, and $R^N$,
—O-(5- to 12-membered heteroaryl) optionally substituted with 1-3 groups independently selected from $C_6$-$C_{10}$ aryl (optionally substituted with 1-3 groups independently selected from halogen) and $C_1$-$C_6$ alkyl, and
5- to 10-membered heteroaryl optionally substituted with 1-3 groups independently selected from hydroxyl, oxo, $N(R^N)_2$, $C_1$-$C_6$ alkyl (optionally substituted with 1-3 groups independently selected from cyano), $C_1$-$C_6$ alkoxy, —$(O)_{0-1}$—($C_1$-$C_6$ fluoroalkyl), —O—($C_6$-$C_{10}$ aryl), and $C_3$-$C_{10}$ cycloalkyl,
$C_3$-$C_{12}$ cycloalkyl optionally substituted with 1-4 groups independently selected from halogen, $C_1$-$C_6$ alkyl, and $C_1$-$C_6$ fluoroalkyl,
$C_6$-$C_{10}$ aryl,
3- to 10-membered heterocyclyl, and
5- to 10-membered heteroaryl optionally substituted with 1-3 groups independently selected from $C_1$-$C_6$ alkoxy and $C_1$-$C_6$ fluoroalkyl, and
5- to 12-membered heteroaryl optionally substituted with 1-3 groups independently selected from $C_1$-$C_6$ alkyl and $C_1$-$C_6$ fluoroalkyl.

2. The compound, tautomer, deuterated derivative, or pharmaceutically acceptable salt according to claim 1, selected from compounds of Formula Ia:

(Ia)

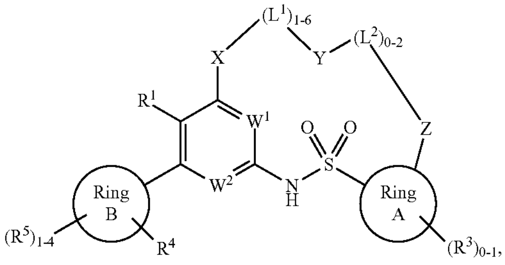

tautomers thereof, deuterated derivatives of those compounds or tautomers, and pharmaceutically acceptable salts of those compounds, tautomers, or deuterated derivatives, wherein Ring A, Ring B, $W^1$, $W^2$, X, Y, Z, $L^1$, $L^2$, $R^1$, $R^3$, $R^4$, and $R^5$ are defined as according to claim 1.

3. The compound, tautomer, deuterated derivative, or pharmaceutically acceptable salt according to claim 1, selected from compounds of Formula IIa:

(IIa)

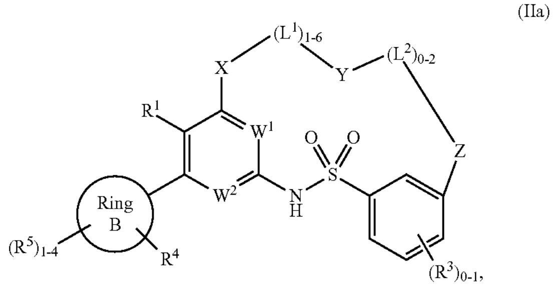

tautomers thereof, deuterated derivatives of those compounds or tautomers, and pharmaceutically acceptable salts of those compounds, tautomers, or deuterated derivatives, wherein Ring B, $W^1$, $W^2$, X, Y, Z, $L^1$, $L^2$, $R^1$, $R^3$, $R^4$, and $R^5$ are defined as according to claim 1.

4. The compound, tautomer, deuterated derivative, or pharmaceutically acceptable salt according to claim 1, selected from compounds of Formula IIb:

(IIb)

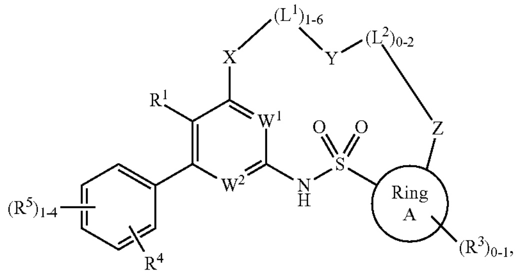

tautomers thereof, deuterated derivatives of those compounds or tautomers, and pharmaceutically acceptable salts of those compounds, tautomers, or deuterated derivatives, wherein Ring A, $W^1$, $W^2$, X, Y, Z, $L^1$, $L^2$, $R^1$, $R^3$, $R^4$, and $R^5$ are defined as according to claim 1.

5. The compound, tautomer, deuterated derivative, or pharmaceutically acceptable salt according to claim 1, selected from compounds of Formula III:

(III)

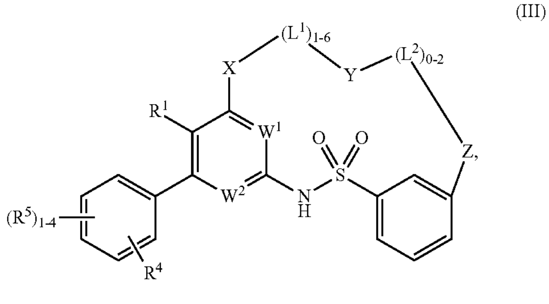

tautomers thereof, deuterated derivatives of those compounds or tautomers, and pharmaceutically acceptable salts of those compounds, tautomers, or deuterated derivatives, wherein $W^1$, $W^2$, X, Y, Z, $L^1$, $L^2$, $R^1$, $R^4$, and $R^5$ are defined as according to claim 1.

6. The compound, tautomer, deuterated derivative, or pharmaceutically acceptable salt according to claim 1, selected from compounds of Formula IV:

(IV)

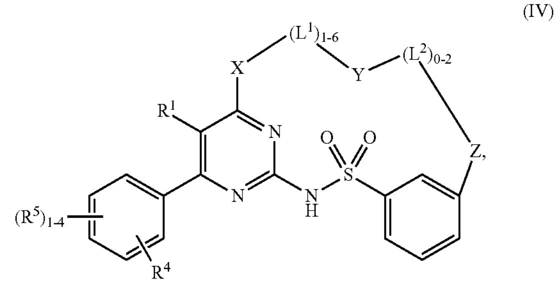

tautomers thereof, deuterated derivatives of those compounds or tautomers, and pharmaceutically acceptable salts of those compounds, tautomers, or deuterated derivatives, wherein X, Y, Z, $L^1$, $L^2$, $R^1$, $R^4$, and $R^5$ are defined as according to claim 1.

7. The compound, tautomer, deuterated derivative, or pharmaceutically acceptable salt according to claim 1, selected from compounds of Formula V:

(V)

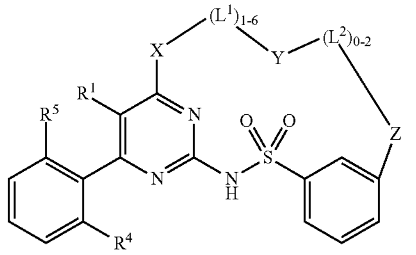

tautomers thereof, deuterated derivatives of those compounds or tautomers, and pharmaceutically acceptable salts of those compounds, tautomers, or deuterated derivatives, wherein X, Y, Z, $L^1$, $L^2$, $R^1$, $R^4$, and $R^5$ are defined as according to claim 1.

8. The compound, tautomer, deuterated derivative, or pharmaceutically acceptable salt according to claim 1, selected from compounds of Formula VIa:

(VIa)

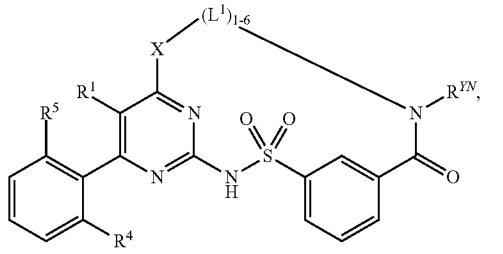

tautomers thereof, deuterated derivatives of those compounds or tautomers, and pharmaceutically acceptable salts of those compounds, tautomers, or deuterated derivatives, wherein X, $L^1$, $R^1$, $R^4$, $R^5$, and $R^{YN}$ are defined as according to claim 1.

9. The compound, tautomer, deuterated derivative, or pharmaceutically acceptable salt according to claim 1, selected from compounds of Formula VIb:

(VIb)

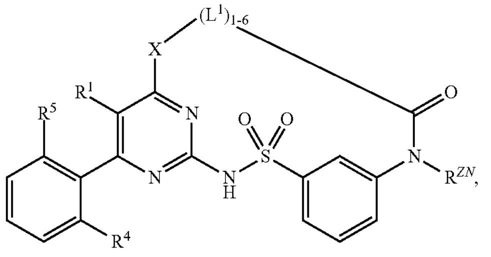

tautomers thereof, deuterated derivatives of those compounds or tautomers, and pharmaceutically acceptable salts of those compounds, tautomers, or deuterated derivatives, wherein X, $L^1$, $R^1$, $R^4$, $R^5$, and $R^{ZN}$ are defined as according to claim 1.

10. The compound, tautomer, deuterated derivative, or pharmaceutically acceptable salt according to claim 1, selected from compounds of Formula VIIa or Formula VIIb:

(VIIa)

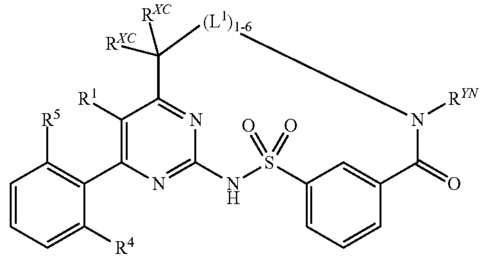

or (VIIb)

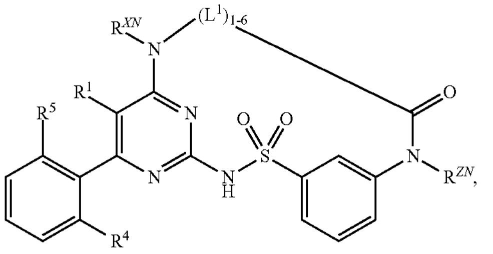

tautomers thereof, deuterated derivatives of those compounds or tautomers, and pharmaceutically acceptable salts of those compounds, tautomers, or deuterated derivatives, wherein X, $L^1$, $R^1$, $R^4$, $R^5$, $R^{XC}$, $R^{XN}$, $R^{YN}$, and $R^{ZN}$ are defined as according to claim 1.

11. The compound, tautomer, deuterated derivative, or pharmaceutically acceptable salt according to claim 1, selected from Compounds 1-41, 42-47, 58-71, 72, 73, and tautomers thereof, deuterated derivatives of those compounds or tautomers, and pharmaceutically acceptable salts of those compounds, tautomers, or deuterated derivatives.

12. A pharmaceutical composition comprising the compound, tautomer, deuterated derivative, or pharmaceutically acceptable salt according to claim 1, and a pharmaceutically acceptable carrier.

13. The pharmaceutical composition according to claim 12, further comprising one or more additional therapeutic agent(s).

14. The pharmaceutical composition according to claim 13, wherein the one or more additional therapeutic agent(s) is selected from CFTR modulators.

15. The pharmaceutical composition according to claim 14, wherein the CFTR modulator is a potentiator or a corrector.

16. The pharmaceutical composition according to claim 14, wherein the pharmaceutical composition comprises a CFTR corrector and a CFTR potentiator.

17. The pharmaceutical composition according to claim 13, wherein the one or more additional therapeutic agents are selected from tezacaftor, ivacaftor, deutivacaftor, lumacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts thereof.

18. A method of treating cystic fibrosis comprising administering to a patient in need thereof the compound, tautomer, deuterated derivative, or pharmaceutically acceptable salt according to claim 1.

19. The method according to claim 18, further comprising administering to the patient one or more additional therapeutic agents prior to, concurrent with, or subsequent to the compound, tautomer, deuterated derivative, or pharmaceutically acceptable salt according to claim 1.

20. The method according to claim 19, wherein the one or more additional therapeutic agent(s) is a CFTR modulator.

21. The method according to claim 20, wherein the CFTR modulator is a CFTR potentiator compound or a CFTR corrector compound.

22. The method according to claim 21, wherein the method comprises administering the compound, tautomer, deuterated derivative, or pharmaceutically acceptable salt according to claim 1 in combination with a CFTR potentiator compound and a CFTR corrector compound.

23. The method according to claim 21, wherein the CFTR potentiator and CFTR corrector compounds are selected from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, lumacaftor, tezacaftor, lumacaftor, and deuterated derivatives and pharmaceutically acceptable salts of any of the foregoing.

* * * * *